US011180455B2

(12) United States Patent
Wynn et al.

(10) Patent No.: US 11,180,455 B2
(45) Date of Patent: *Nov. 23, 2021

(54) COMPOUNDS FOR THE TREATMENT OF PAIN

(71) Applicant: Alkermes, Inc., Waltham, MA (US)

(72) Inventors: Thomas Andrew Wynn, Lexington, MA (US); Juan C. Alvarez, Lincoln, MA (US); Demetri Theodore Moustakas, Belmont, MA (US); Markus Haeberlein, Wellesley, MA (US); Lewis D. Pennington, Arlington, MA (US)

(73) Assignee: Alkermes, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 16/790,224

(22) Filed: Feb. 13, 2020

(65) Prior Publication Data
US 2020/0255383 A1 Aug. 13, 2020

Related U.S. Application Data

(63) Continuation of application No. 16/267,025, filed on Feb. 4, 2019, now Pat. No. 10,604,489.

(60) Provisional application No. 62/626,499, filed on Feb. 5, 2018.

(51) Int. Cl.
C07D 221/26 (2006.01)
A61K 31/439 (2006.01)
A61P 29/00 (2006.01)
C07D 453/02 (2006.01)
A61P 25/04 (2006.01)
C07D 401/04 (2006.01)
C07D 401/14 (2006.01)
C07D 405/04 (2006.01)
C07D 409/04 (2006.01)

(52) U.S. Cl.
CPC .......... C07D 221/26 (2013.01); A61K 31/439 (2013.01); A61P 25/04 (2018.01); A61P 29/00 (2018.01); C07D 401/04 (2013.01); C07D 401/14 (2013.01); C07D 405/04 (2013.01); C07D 409/04 (2013.01); C07D 453/02 (2013.01)

(58) Field of Classification Search
CPC ............... C07D 221/26; C07D 401/04; C07D 401/14; C07D 405/04; A61K 31/439
USPC ...................................................... 514/295
See application file for complete search history.

(56) References Cited

U.S. PATENT DOCUMENTS

| 3,167,562 A | 1/1965 | Iwai et al. |
| 3,196,154 A | 7/1965 | Steck |
| 3,475,439 A | 10/1969 | Iwai et al. |
| 3,502,669 A | 3/1970 | Nakanishi et al. |
| 3,812,134 A | 3/1974 | Iwai et al. |
| 3,829,427 A | 8/1974 | Curran |
| 5,539,119 A | 7/1996 | Nagase et al. |
| 5,541,217 A | 7/1996 | Carmosin et al. |
| 5,703,091 A | 12/1997 | Steiner et al. |
| 6,313,312 B1 | 11/2001 | Banks et al. |
| 7,056,930 B2 | 6/2006 | Coe et al. |
| 7,230,001 B1 | 6/2007 | Rudolf et al. |
| 7,241,887 B2 | 7/2007 | Coe et al. |
| 7,488,726 B2 | 2/2009 | Van Duzer et al. |
| RE40,838 E | 7/2009 | Coe et al. |
| 7,750,158 B2 | 7/2010 | Shankar et al. |
| 7,897,611 B2 | 3/2011 | Bhatti et al. |
| 7,902,220 B2 | 3/2011 | Saito et al. |
| 8,048,895 B2 | 11/2011 | Carroll et al. |
| 8,354,420 B2 | 1/2013 | Baker-Glenn et al. |
| 8,455,491 B2 | 6/2013 | Sanofi |
| 8,580,788 B2 | 11/2013 | Dolle et al. |
| 8,580,790 B2 | 11/2013 | Sanofi |
| 8,759,357 B2 | 6/2014 | Shipps, Jr. et al. |
| 9,156,811 B2 | 10/2015 | Brand et al. |
| 10,604,489 B2 * | 3/2020 | Wynn ............... C07D 401/04 |
| 2004/0204445 A1 | 10/2004 | Coe et al. |

FOREIGN PATENT DOCUMENTS

| EP | 0 013 138 A1 | 7/1980 | |
| EP | 0 483 403 A1 | 5/1992 | |
| GB | 952137 A | 3/1964 | |
| GB | 1142415 A | 2/1969 | |
| GB | 2498976 A | 8/2013 | |
| JP | 49061168 | 6/1974 | |
| WO | WO 2003/070728 A2 | 8/2003 | |
| WO | WO 2004/089908 A2 | 10/2004 | |
| WO | WO-2004089908 A2 * | 10/2004 | ........... C07D 405/06 |
| WO | WO 2007/029156 A2 | 3/2007 | |
| WO | WO 2007/103187 A2 | 9/2007 | |
| WO | WO 2009/029256 A1 | 3/2009 | |
| WO | WO 2011/147951 A1 | 12/2011 | |
| WO | WO 2012/075232 A1 | 6/2012 | |
| WO | WO 2012/129495 A1 | 9/2012 | |
| WO | WO 2013/047144 A1 | 4/2013 | |

(Continued)

OTHER PUBLICATIONS

Bhatia et al A review on Bioisosterism: A rational approach for Drug Design and Molecular modification. (Year: 2011).*
Todd A. Brugel et al. SAR development of a series of 8-azabicyclo[3.2.1]octan-3-yloxy-benzamides as kappa opioid receptor antagonists. Part2. (Year: 2010).*
Arjunan et al. (1981) "Syntheses and a Conformational Study of Certain Selected 3-Oxa-7-azabicyclo[3.3.1]nonan-9-ones. Single-Crystal X-ray Diffraction Analysis of 6,8-Bis(2-chlorophenyl)-3-oxa-7-azabicyclo[3.3.1]nonan-9-one," J. Org. Chem., 46(16):3196-3204.
Bagley et al. (1991) "New 1-(Heterocyclylalkyl)-4-(Propionanilido)-4-Piperidinyl Methyl Ester and Methylene Methyl Ether Analgesics," J. Med. Chem., 34:827-841.

(Continued)

Primary Examiner — Rita J Desai
(74) Attorney, Agent, or Firm — Lathrop GPM LLP; Brian C. Trinque

(57) ABSTRACT

Provided herein are compounds that are useful in the treatment of pain in a subject.

16 Claims, No Drawings

(56) References Cited

FOREIGN PATENT DOCUMENTS

| WO | WO 2013/122107 A1 | 8/2013 |
|---|---|---|
| WO | WO 2014/197345 A2 | 12/2014 |
| WO | WO 2015/091931 A1 | 6/2015 |
| WO | WO 2016/027195 A1 | 2/2016 |
| WO | WO 2018/045229 A1 | 3/2018 |
| WO | WO 2018/136546 A1 | 7/2018 |

OTHER PUBLICATIONS

Beckett et al. (1960) "Some N-Phenethyl-4-Heteroaryl-4-Piperidinols and Related Compounds," Journal of Medicinal and Pharmaceutical Chemistry, 2(3):245-261.
Brandt et al. (1993) "A new consistent model explaining structure (conformation)-activity relationships of opiates with μ-Selectivity," Drug Design and Discovery, 10:257-283.
Zhu You-cheng and Fang Su-nan (1982) "Studies on Potent Analgesics III. Synthesis of 3,5-propanepiperidine derivatives," Acta Pharmaceutica Sinica, vol. XVII, No. 3, 194-199.
Brugel et al. (2010) "SAR development of a series of 8-azabicyclo[3.2.1]octan-3-yloxy-benzamides as kappa opioid receptor antagonist. Part 2," Bioorganics and Medicinal Chemistry Letters, 20:5405-5410.
Buolamwini et al. (1990) "Synthesis and Antinociceptive Activity of 4-Pyridyl and -Dihydropyridyl analogues of Meperidine and Ketobemidone", Drug Design and Delivery, 1990, 7:19-31.
Chun et al. (1987) "Comparison between Scatchard and dose-response ratio equations and their application," Acta Pharmacologica Sinica, 8(1):6-10.
Codd et al. (2006) "The Novel, Orally Active, Delta Opioid RWJ-394674 IS Biotransformed to the Potent Mu Opioid RWJ-431216," The Journal of Pharmacology and Experimental Therapeutics, 318(3):1273-1279.
Del Bello et al. (2010) "Fruitful Adrenergic α2C-Agonism/α2A-Antagonism Combination to Prevent and Contrast Morphine Tolerance and Dependence1," J. Med. Chem., 53:7825-7835.
Diaz et al. (2005) "SAR and biological evaluation of novel trans-3,4-dimethyl-4-arylpiperidine derivatives as opioid antagonists," Bioorganic and Medicinal Chemistry Letters, 15:3844-3848.
Froimowitz, Mark et al. (1984) "Conformational Properties of 60 - and 62 -Azabicyclane Opiates. The Effect of Conformation on Pharmacological Activity," Journal of Computational Chemistry, 5(4):291-298.
Ge et al., (1989) "P-8502—a new μ selective opioid receptor ligand", Acta Pharmaceutica Sinica, 10(2):13-16.
GE; Band-lun, et al. (1989) "Preparation of [3H] 3-(β-phenethyl)-9β-methoxy-9α-( m -hydroxyphenyl )-3-azabicyclo [ 3,3,1 ]-nonane and characterization of its binding to opioid receptors of rat brain membrane," Chinese Journal of Pharmacology and Toxicology, 3(3):187-191.
Hersh et al. (1985) "Measurement of Meperidine-Induced Respiratory Depression Using a New Non-lnvasive Technique," Anesthesia Progress, 194-198.
Hite et al. (1984) "Stereochemical Aspects of Narcotic Action. II. *9-(m-Hydroxyphenyl)-9a-methoxy-3-methyl-3-azoniabicyclo[3.3.1]nonane p-Toluenesulfonate Monohydrate," Acta Cryst., C40:850-853.
Ho et al. (2009) "The discovery of tropane derivatives as nociceptin receptor ligands for the management of cough and anxiety," Bioorganic and Medicinal Chemistry Letters, 19:2519-2523.
International Search Report in related PCT Application No. PCT/US2019/016543 dated May 28, 2019 (4 pages).
Jiang et al. (2017) "Discovery of N-substituted-endo-3-(-8-azabicyclo[3.2.1]oct-3-yl)-phenol and -phenyl carboxamide series of μ-opioid receptor antagonists," Bioorganic and Medicinal Chemistry Letters, 27:2926-2930.
Kobayashi et al. (1970) "The Pharmacology of Azabicyclane, a New Analgesic Agent," Toxicology and Applied Pharmacology, 17:344-354.

Kormos et al. (2016) "Design, synthesis, and pharmacological evaluation of JDTic analogs to examine the significance of replacement of the 3-hydroxyphenyl group with pyridine or thiophene bioisosteres," Bioorganic and Medicinal Chemistry, 24:3842-3848.
Leander et al. (1979) "Effects of Propoxyphene, Ethoheptazine, and Azabicyclane on Schedule-Controlled Responding: Attenuation by Pentobarbital but not Naloxone," Psychopharmacology, 66:19-22.
Le Bourdonnec et al. (2003) "trans-3,4-Dimethyl-4-(3-carboxamidophenyl)piperidines: A Novel Class of μ-Selective Opioid Antagonists," Bioorganic and Medicinal Chemistry Letters, 13:4459-4462.
Le Bourdonnec et al. (2006) "Synthesis and structure-activity relationships of a new series of 2α-substituted trans-4,5-dimethyl-4-(3-hydroxyphenyl)piperidine as μ-selective opioid antagonists," Bioorganic and Medicinal Chemistry Letters, 16:864-868.
Li et al. (2006) "Conformational re-analysis of (+)-meptazinol: an opioid with mixed anal-gesic pharmacophores," Acta Pharmacologica Sinica, 27(9):1247-1252.
Li-Qun et al. (1991) "Characterization of 9 slowly dissociated opioid ligands azabicyclonanes compounds to μ, σ, and K receptors," Acta Pharmacologica Sinica, 12(3):245-249.
Loriga et al. (2015) "Novel diazabicycloalkane delta opioid agonists," Bioorganic and Medicinal Chemistry, 23:5527-5538.
Morikawa et al. (1970) "Clinical Experience and Cardiovascular and Respiratory Effects of Intravenous Use of Azabicyclane," Anesthesia, XIX, 9.
Neumeyer et al. (2003) "Receptor affinities of dopamine D1 receptor-selective novel phenylbenzazepines," European Journal of Pharmacology, 474:137-140.
Ohki et al. (1970) "3-Azabicyclo[3.3.1]nonane Derivatives as Potential Analgesics," Chem. Pharm. Bull., 18(10):2050-2057.
Ohki et al. (1974) "3,5-Propanopiperidine Derivates as Potential Analgesics," Chern. Pharm. Bull., 22(5): 1014-1021.
Oida et al. (1966) "Fragmentation Reaction of Azabicyclic Compounds," Chem. Pharm. Bull., 14(12): 1418-1424.
Salva et al. (1986) "Diazabicyclane: A New Narcotic Analgesic," Journal of Medicinal Chemistry, 29(10):2111-2113.
Schiller et al. (1999) "The Opioid μ Agonist/ σ, Antagonist DIPP-NH$_2$ [ψ] Produces a Potent Analgesic Effect, No Physical Dependence, and Less Tolerance than Morphine in Rats,".
Tecle et al. "Narcotic Antagonists-The 3-Azabicyclanes. 1. New Insights into the Molecular Modes of Receptor Interactions of Narcotic Analgesics and Narcotic Antagonists," Section of Medicinal Chemistry and Pharmacognosy, School of Pharmacy, University of Connecticut Storrs, Connecticut.
Tran et al. (2007) "Synthesis, Sterochemical, and Conformational Studies of Selected 3,7-Diheterabicyclo[3.3.1]nonan-9-ols:X-Ray, Diffraction Analyses of 7-Benzyl-9-phenyl-3-oxa-7-azabicylo[3.3.1]nonan-9-ol and 7-Benzyl-9-(4-N,N'dimethylaminophenyl)-3-thia-7-azabicyclo[3.3.1]nonan-9-ol, a Rare Stable Chair-Boat Form With Trigonal Nitrogen," Phosphorus, Sulfur, and Silicon, 182:99-119.
Wang et al. (1984) "Relationship between analgesic activity and opiate receptor binding affinity for 5 derivatives of 3-aza-bicyclo [3.3.1] Nonanes," Acta Pharmacologica Sinica, 5(3):158-163.
Wang et al. (1985) "Effects of 5 Derivatives of 3-azabicyclo[3,3,1]Nonanes on Isolated Guinea Pig Ileum Myenteric Plexus-Longitudinal Muscle," Acta Pharmacologica Sinica, 6(4):236-238.
Wen-Qiao et al. (1989) "P-7521—a new irreversible opioid ligand," Acta Pharmacologica Sinica, 10(3):205-210.
Wentland et al. (2005) "Synthesis and opioid receptor binding properties of a highly potent 4-hydroxy analogue of naltrexone," Bioorganic and Medicinal Chemistry Letters, 15:2107-2110.
Wentland et al. (2009) "Redefining the structure-activity relationships of 2,6-methano-3-benzazocines. Part 7: Syntheses and opioid receptor properties of cyclic variants of cyclazocine," Bioorganic and Medicinal Chemistry Letters, 365-368.
Wentland et al. (2009) "Syntheses and opioid receptor binding properties of carboxamido-substituted opioids," Bioorganic and Medicinal Chemistry Letters, 19:203-208.
Yang et al. (1988) "Antitumor activity of trewiasine in vitro and in vivo," Acta Pharmacologica Sinica, 9(6):508-511.

(56) References Cited

OTHER PUBLICATIONS

Zhang et al. (2004) "10-Ketomorphinan and 3-Substituted-3-desoxymorphinan Analogues as Mixed K and μ Opioid Ligands: Synthesis and Biological Evaluation of Their Binding Affinity at Opioid Receptors," J. Med. Chem., 2004, 47:165-174.
Zhao et al. (1988) "Effects of potent analgesic 3-(β- phenylethyl)-9β-methoxy-9α-(m-hydroxyphenyl)-3-azabicyclo [3,3,1]-nonane (P-7521) on electro-encephalography in rabbits," Acta Pharmacologica Sinica, 9(4):300-303.
Zhiqiang et al. (1990) "A Potent and Long-Lasting Ligand, Azabicyclononane (P-7521)", The International Narcotics Research Conference (INRC) '89, pp. 1-4.
Zhou et al., (1982) "Synthesis and Analgesic Activity of Derivatives of Azabicycloalkanes", Acta Pharmaceutica Sinica, 17(7):504-509.
Zhu et al., (1982) "Studies on Potent Analgesics", Acta Pharmceutica Sinica, 17(3):195-199.
Zimmerman et al. (1978) "New structural concepts for narcotic antagonists defined in a 4-phenylpiperidine series", Nature, 1978. vol. 275:332-334.

* cited by examiner

COMPOUNDS FOR THE TREATMENT OF PAIN

RELATED APPLICATION

This application is a continuation of U.S. patent application Ser. No. 16/267,025, filed Feb. 4, 2019, which application claims the benefit of U.S. Provisional Patent Application No. 62/626,499, filed Feb. 5, 2018. The entire contents of these applications are incorporated herein by reference in their entirety.

BACKGROUND

Pain is the most common reason for physician consultation, and can be caused by a variety of medical conditions and procedures. Both chronic and acute pain can lead to a significant reduction in the quality of life, with many individuals facing long term disablement and handicaps.

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) have been employed in human therapy. The actions of endogenous opioids and opiates are mediated by three receptor types ($\mu$, $\delta$, and $\kappa$ receptors), which are coupled to different intracellular effector systems. [Berrocoso E. et. al., Current Pharmaceutical Design, 15(14) 2009, 1612-22]. As such, agents that can modulate the actions of one or more of the opioid receptor types with selectivity and sensitivity are important to treat the various diseases and disorders regulated by the opioid system. Compounds that bind to opioid receptors are likely to be useful in the treatment of diseases and conditions modulated by opiate receptors.

Traditional opioid analgesics exert their pharmacological activity once they have passed into the central nervous system (CNS). But this can lead to undesirable CNS-mediated side effects, such as respiratory depression, increased drug tolerance, increased drug dependence, constipation and unwanted euphoria. There remains a continuing need for new drugs that can be used to treat or prevent pain, and that reduce or avoid one or more side effects associated with traditional opioid therapy.

While certain treatments for pain do exist, many commonly used analgesics suffer from significant drawbacks including inefficacy, tolerance, and chemical dependence. There is therefore a need for new compounds and methods of treatment for pain that may be used alone or in conjunction with existing therapeutic modalities.

SUMMARY

Provided herein are compounds useful for the treatment of pain in a subject in need thereof.

In an aspect, provided herein are compounds of the Formula I:

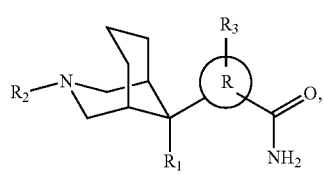

(I)

or a pharmaceutically acceptable salt thereof.

In another aspect, provided herein are compounds of Formula II, or pharmaceutically acceptable salts thereof. Examples of compounds of Formula II provided herein include compounds of Formulas IIa, IIb, IIc, IId, IIe, IIf, IIg, IIh, and IIi, or pharmaceutically acceptable salts thereof. In another aspect, provided herein are compounds of Formula III, or pharmaceutically acceptable salts thereof. Examples of compounds of Formula III provided herein include compounds of Formulas IIIa, IIIb, IIIc, IIId, IIIe, IIIf, IIIg, IIIh, and IIIi, or pharmaceutically acceptable salts thereof. In another aspect, provided herein are compounds of Formula IV, or pharmaceutically acceptable salts thereof. Examples of compounds of Formula IV provided herein include compounds of Formulas IVa, IVb, IVc, IVd, IVe, IVf, IVg, IVh, and IVi, or pharmaceutically acceptable salts thereof.

Also provided herein is a pharmaceutical composition comprising a compound of any of Formulas I, II, III, or IV, or pharmaceutically acceptable salts thereof, and a pharmaceutically acceptable carrier.

In an aspect, provided herein is a method of treating pain in a subject in need thereof comprising administering to the subject a compound of Formulas I, II, III, or IV, or pharmaceutically acceptable salts thereof. In an embodiment, the pain is inflammatory pain, thermal pain, acute pain, chronic pain, traumatic pain, chemical pain, ischemic pain, centrally mediated pain, peripherally mediated pain, prickling pain, visceral pain, progressive disease pain, musculoskeletal pain (e.g., back pain, neck pain), post-surgical pain, bone pain (e.g., osteoarthritis), nociceptive pain, or neuropathic pain. In another embodiment, the pain is inflammatory pain, thermal pain, acute pain, chronic pain, or neuropathic pain. In another embodiment, the pain is musculoskeletal pain (e.g., back pain, neck pain), post-surgical pain, or bone pain (e.g., osteoarthritis).

In another aspect, provided herein is a method of treating depression in a subject in need thereof comprising administering to the subject a compound of Formula I, II, III, or IV, or a pharmaceutically acceptable salt thereof.

In still another aspect, provided herein is a method of treating addiction in a subject in need thereof comprising administering to the subject a compound of Formula I, II, III, or IV, or a pharmaceutically acceptable salt thereof. In an embodiment, the addiction is drug addiction. In an embodiment, the addiction is opioid addiction. In another embodiment, the addiction is alcohol addiction.

DETAILED DESCRIPTION

Provided herein are compounds, e.g., the compounds of Formulas I, II, III or IV, or pharmaceutically acceptable salts thereof, that are useful in the treatment of pain in a subject.

In a non-limiting aspect, these compounds may modulate the $\mu$-opioid receptor. In a particular embodiment, the compounds provided herein are considered $\mu$-receptor agonists. As such, in one aspect, the compounds provided herein are useful in treatment of pain in a subject by acting as an agonist of the $\mu$-receptor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used to herein, the term "$EC_{50}$" refers to the concentration of a compound required to achieve an effect that is 50% of the maximal observed effect of a compound.

The term "agonist," as used herein, refers to a compound that, when contacted with a target of interest (e.g., the μ-opioid receptor) causes an increase in the magnitude of a certain activity or function of the target compared to the magnitude of the activity or function observed in the absence of the agonist.

As used herein, "pain" is generally defined as physical suffering or discomfort caused by illness or injury, and can be thought of as encompassing inflammatory pain, thermal pain, acute pain, chronic pain, musculoskeletal pain, post-surgical pain, nociceptive pain, neuropathic pain, and the like.

As used herein, the term "depression" can be generally defined as a mental condition characterized by feelings of severe despondency and dejection. "Depression" can also be referred to as major depression, clinical depression, major depressive illness, major affective disorder and unipolar mood disorder. The depressive condition can be an anxiety disorder, a mental condition, recurrent depression, and the like.

As used herein, addiction is generally defined as a chronic brain disease that causes compulsive drug seeking and use, or alcohol seeking and use. Drug addiction can be opioid addiction (i.e., opioid dependence), stimulant addiction, and the like.

The term "treat," "treated," "treating," or "treatment" includes the diminishment or alleviation of at least one symptom associated or caused by the state, disorder or disease being treated. In certain embodiments, the treatment comprises bringing into contact with the opioid receptor an effective amount of a compound of the invention for conditions related to pain, depression or addiction.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention.

Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_5$-alkyl include ethyl, methyl, isopropyl, isobutyl, n-pentyl, and n-hexyl.

As used herein, the term "alkylene" refers to divalent aliphatic hydrocarbyl groups, for example, having from 1 to 4 carbon atoms that are either straight-chained or branched. This term includes, by way of example, methylene (—$CH_2$—), ethylene (—$CH_2CH_2$—), n-propylene (—$CH_2CH_2CH_2$—), iso-propylene (—$CH_2CH(CH_3)$—), and the like.

As used herein, the term "alkenyl" denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "cycloalkylene" means a divalent cycloalkyl system, wherein cycloalkyl is defined above.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

As used herein, the term "heterocycloalkylene" means a divalent heterocycloalkyl system, wherein heterocycloalkyl is defined above.

As used herein, the term "oxo" and "oxo moiety" means a carbonyl group having the formula C=O, and can be used interchangeably with "keto."

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo

[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

Compounds of the Invention

Provided herein are compounds having the structure of Formula (I):

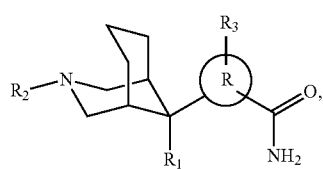

(I)

or a pharmaceutically acceptable salt thereof, wherein:
ring R is phenyl, pyridinyl, or thiophenyl;
$R_1$ is $C_{1-2}$ alkoxy, wherein the $C_{1-2}$ alkoxy is optionally substituted with 1, 2, or 3 halo substituents;
$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);
wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl);
further wherein the $C_{3-10}$ cycloalkyl, 5- to 14-membered heteroaryl, or 4- to 12-membered heterocycloalkyl of $R_2$ is optionally substituted with 1, 2, or 3 oxo moieties; and
$R_3$ is hydrogen, OH, halo, $C_{1-4}$ alkyl, or $C_{1-4}$ alkoxy.

In another embodiment of Formula (I), $R_1$ is unsubstituted $C_{1-2}$ alkoxy.
In another embodiment of Formula (I), $R_1$ is —OCH$_3$.
In another embodiment of Formula (I), $R_1$ is —OCH$_2$CF$_3$.
In another embodiment of Formula (I), ring R is phenyl or pyridinyl.

In another embodiment of Formula (I), ring R is phenyl or thiophenyl.
In another embodiment of Formula (I), ring R is pyridinyl or thiophenyl.
In another embodiment of Formula (I), ring R is phenyl.
In another embodiment of Formula (I), ring R is pyridinyl.
In another embodiment of Formula (I), ring R is thiophenyl.
In another embodiment of Formula (I), ring R is pyridin-2-yl.
In another embodiment of Formula (I), ring R is pyridin-3-yl.
In another embodiment of Formula (I), ring R is pyridin-4-yl.
In another embodiment of Formula (I), ring R is thiophen-2-yl.
In another embodiment of Formula (I), ring R is thiophen-3-yl.
In another embodiment of Formula (I), ring R is phenyl with the —C(=O)NH$_2$ group at the ortho position.
In another embodiment of Formula (I), ring R is phenyl with the —C(=O)NH$_2$ group at the meta position.
In another embodiment of Formula (I), ring R is phenyl with the —C(=O)NH$_2$ group at the para position.
In another embodiment of Formula (I), ring R is pyridin-2-yl with the —C(=O)NH$_2$ group at the 6-position.
In another embodiment of Formula (I), ring R is pyridin-2-yl with the —C(=O)NH$_2$ group at the 5-position.
In another embodiment of Formula (I), ring R is pyridin-2-yl with the —C(=O)NH$_2$ group at the 4-position.
In another embodiment of Formula (I), ring R is pyridin-2-yl with the —C(=O)NH$_2$ group at the 3-position.
In another embodiment of Formula (I), ring R is pyridin-3-yl with the —C(=O)NH$_2$ group at the 2-position.
In another embodiment of Formula (I), ring R is pyridin-3-yl with the —C(=O)NH$_2$ group at the 4-position.
In another embodiment of Formula (I), ring R is pyridin-3-yl with the —C(=O)NH$_2$ group at the 5-position.
In another embodiment of Formula (I), ring R is pyridin-3-yl with the —C(=O)NH$_2$ group at the 6-position.
In another embodiment of Formula (I), ring R is pyridin-4-yl with the —C(=O)NH$_2$ group at the 2-position.
In another embodiment of Formula (I), ring R is pyridin-4-yl with the —C(=O)NH$_2$ group at the 3-position.
In another embodiment of Formula (I), ring R is thiophen-3-yl with the —C(=O)NH$_2$ group at the 2-position.
In another embodiment of Formula (I), ring R is thiophen-3-yl with the —C(=O)NH$_2$ group at the 4-position.
In another embodiment of Formula (I), ring R is thiophen-3-yl with the —C(=O)NH$_2$ group at the 5-position.
In another embodiment of Formula (I), ring R is thiophen-2-yl with the —C(=O)NH$_2$ group at the 3-position.
In another embodiment of Formula (I), ring R is thiophen-2-yl with the —C(=O)NH$_2$ group at the 4-position.
In another embodiment of Formula (I), ring R is thiophen-2-yl with the —C(=O)NH$_2$ group at the 5-position.
In another embodiment of Formula (I), ring R is selected from the group consisting of:

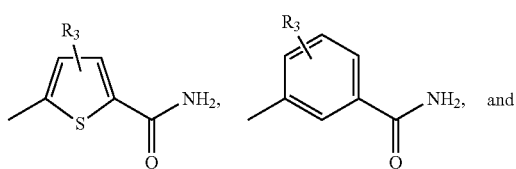

-continued

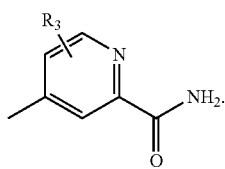

In another embodiment of Formula (I), ring R is selected from the group consisting of:

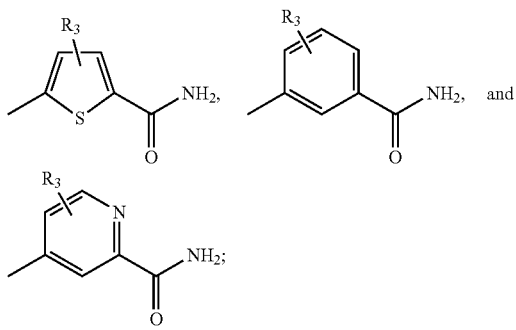

and R₃ is hydrogen.

In another embodiment of Formula (I), ring R is selected from the group consisting of:

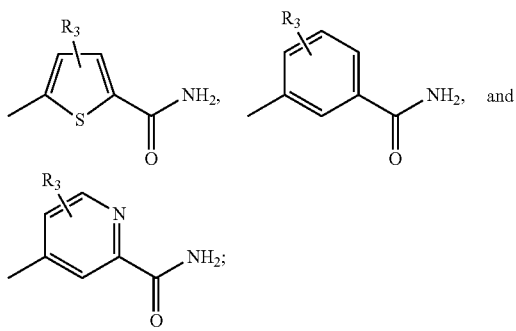

and $R^3$ is OH, halo, $C_{1-4}$ alkyl, or $C_{1-4}$ alkoxy.

In another embodiment of Formula (I), ring R is selected from the group consisting of:

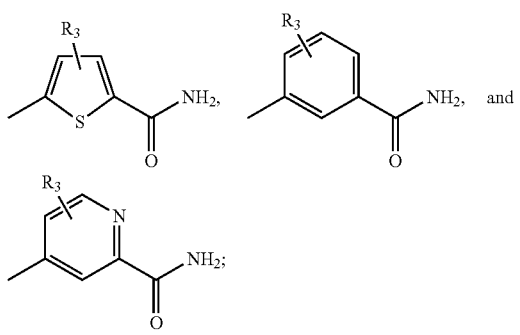

$R_3$ is hydrogen; and $R_2$ is hydrogen.

In another embodiment of Formula (I), ring R is selected from the group consisting of:

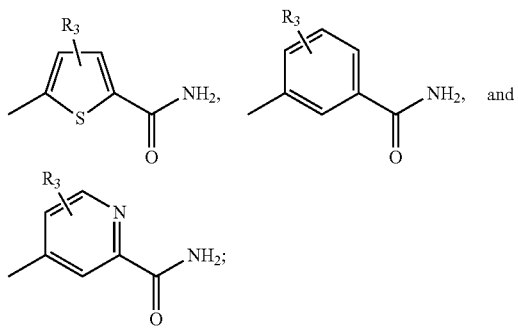

$R_3$ is OH, halo, $C_{1-4}$ alkyl, or $C_{1-4}$ alkoxy; and $R_2$ is hydrogen. In another embodiment of Formula (I), ring R is selected from the group consisting of:

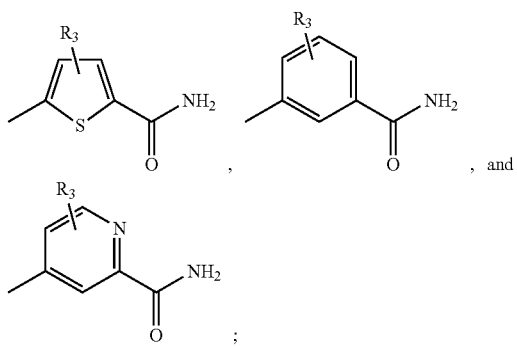

and $R_2$ is $C_{1-6}$ alkyl, $C_{3-10}$ cycloalkyl, 4- to 12-membered heterocycloalkyl, $C_{1-4}$ alkylene-CF₃, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{5-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl).

In another embodiment of Formula (I), ring R is selected from the group consisting of:

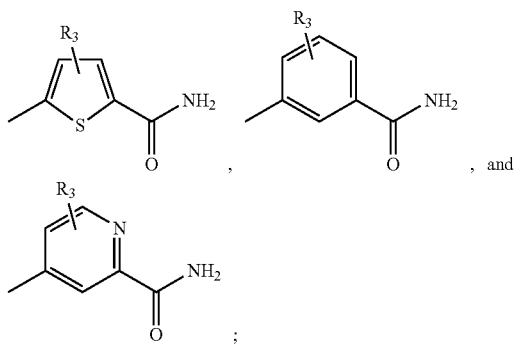

$R_3$ is hydrogen; and $R_2$ is $C_{1-6}$alkyl, $C_{3-10}$ cycloalkyl, 4- to 12-membered heterocycloalkyl, $C_{1-4}$alkylene-CF₃, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl).

In another embodiment of Formula (I), ring R is phenyl or pyridinyl, and $R_1$ is —$OCH_3$.

In another embodiment of Formula (I), ring R is phenyl or thiophenyl, and $R_1$ is —$OCH_3$.

In another embodiment of Formula (I), ring R is pyridinyl or thiophenyl, and $R_1$ is —$OCH_3$.

In another embodiment of Formula (I), ring R is phenyl and $R_1$ is —$OCH_3$.

In another embodiment of Formula (I), ring R is pyridinyl and $R_1$ is —$OCH_3$.

In another embodiment of Formula (I), ring R is thiophenyl and $R_1$ is —$OCH_3$.

In another embodiment of Formula (I), ring R is phenyl or pyridinyl, $R_1$ is —$OCH_3$, and $R_3$ is OH, halo, $C_{1-4}$ alkyl, or $C_{1-4}$ alkoxy.

In another embodiment of Formula (I), ring R is phenyl or thiophenyl, $R_1$ is —$OCH_3$, and $R_3$ is OH, halo, $C_{1-4}$ alkyl, or $C_{1-4}$ alkoxy.

In another embodiment of Formula (I), ring R is pyridinyl or thiophenyl, $R_1$ is —$OCH_3$, and $R_3$ is OH, halo, $C_{1-4}$ alkyl, or $C_{1-4}$ alkoxy.

In another embodiment of Formula (I), ring R is phenyl, $R_1$ is —$OCH_3$, and $R_3$ is OH, halo, $C_{1-4}$ alkyl, or $C_{1-4}$ alkoxy.

In another embodiment of Formula (I), ring R is pyridinyl, $R_1$ is —$OCH_3$, and $R_3$ is OH, halo, $C_{1-4}$ alkyl, or $C_{1-4}$ alkoxy.

In another embodiment of Formula (I), ring R is thiophenyl, $R_1$ is —$OCH_3$, and $R_3$ is OH, halo, $C_{1-4}$ alkyl, or $C_{1-4}$ alkoxy.

In another embodiment of Formula (I), $R_2$ is hydrogen.

In another embodiment of Formula (I), $R_3$ is OH, halo, $C_{1-4}$ alkyl, or $C_{1-4}$ alkoxy, and $R_2$ is hydrogen.

In another embodiment of Formula (I), $R_3$ is hydrogen and $R_2$ is hydrogen.

In another embodiment of Formula (I), $R_1$ is —$OCH_3$, $R_3$ is hydrogen, and $R_2$ is hydrogen.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is hydrogen.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is hydrogen.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is hydrogen.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{3-10}$ cycloalkyl.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{3-10}$ cycloalkyl.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{3-10}$ cycloalkyl.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{6-14}$ aryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{6-14}$ aryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-($C_{6-14}$ aryl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (I), ring R is phenyl or pyridinyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In another embodiment of Formula (I), ring R is pyridinyl or thiophenyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In another embodiment of Formula (I), ring R is phenyl or thiophenyl, $R_1$ is —$OCH_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In an embodiment, the compound of Formula (I) has the structure of Formula (II):

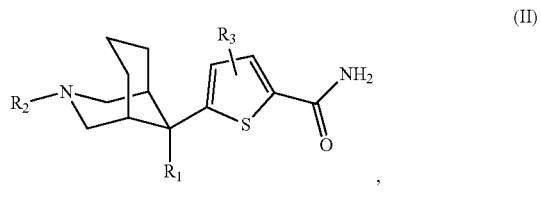

(II)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl);

further wherein the $C_{3-10}$ cycloalkyl, 5- to 14-membered heteroaryl, or 4- to 12-membered heterocycloalkyl of $R_2$ is optionally substituted with 1, 2, or 3 oxo moieties; and $R_3$ is hydrogen, OH, halo, $C_{1-4}$ alkyl, or $C_{1-4}$ alkoxy.

In another embodiment of Formula (II), $R_1$ is unsubstituted $C_{1-2}$ alkoxy.

In another embodiment of Formula (II), $R_1$ is —$OCH_3$.

In another embodiment of Formula (II), $R_1$ is —$OCH_2CF_3$.

In another embodiment of Formula (II), $R_1$ is —$OCH_3$, and $R_3$ is OH, halo, $C_{1-4}$ alkyl, or $C_{1-4}$ alkoxy.

In another embodiment of Formula (II), $R_1$ is unsubstituted $C_{1-2}$ alkoxy, and $R_3$ is OH, halo, $C_{1-4}$ alkyl, or $C_{1-4}$ alkoxy.

In another embodiment of Formula (II), $R_1$ is —$OCH_2CF_3$, and $R_3$ is OH, halo, $C_{1-4}$ alkyl, or $C_{1-4}$ alkoxy.

In another embodiment of Formula (II), $R_1$ is —$OCH_3$, $R_3$ is OH, halo, $C_{1-4}$ alkyl, or $C_{1-4}$ alkoxy, and $R_2$ is hydrogen.

In another embodiment of Formula (II), $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (II), $R_1$ is —$OCH_3$, $R_3$ is OH, halo, $C_{1-4}$ alkyl, or $C_{1-4}$ alkoxy, and $R_2$ is $C_{3-10}$ cycloalkyl.

In another embodiment of Formula (II), $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (II), $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (II), $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (II), $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (II), $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (II), $R_1$ is —$OCH_3$, $R_3$ is OH, halo, $C_{1-4}$ alkyl, or $C_{1-4}$ alkoxy, and $R_2$ is $C_{1-4}$ alkylene-($C_{5-14}$ aryl).

In another embodiment of Formula (II), $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (II), $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (II), $R_1$ is —OCH$_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (II), $R_1$ is —OCH$_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (II), $R_1$ is —OCH$_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In another embodiment of Formula (II), $R_3$ is halo.
In another embodiment of Formula (II), $R_3$ is fluoro.
In another embodiment of Formula (II), $R_3$ is OH.
In another embodiment of Formula (II), $R_3$ is hydrogen.

In an embodiment, the compound of Formula (II) has the structure of Formula (IIa):

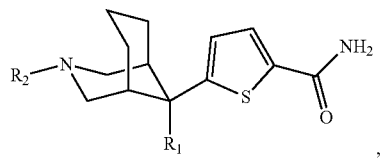

(IIa)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-CF$_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the $C_{3-10}$ cycloalkyl, 5- to 14-membered heteroaryl, or 4- to 12-membered heterocycloalkyl of $R_2$ is optionally substituted with 1, 2, or 3 oxo moieties.

In another embodiment of Formula (IIa), $R_1$ is unsubstituted $C_{1-2}$ alkoxy.

In another embodiment of Formula (IIa), $R_1$ is —OCH$_3$.

In another embodiment of Formula (IIa), $R_1$ is —OCH$_2$CF$_3$.

In another embodiment of Formula (IIa), $R_2$ is hydrogen, $C_{1-6}$ alkyl, $C_{3-10}$ cycloalkyl, or 4- to 12-membered heterocycloalkyl.

In another embodiment of Formula (IIa), $R_2$ is hydrogen, $C_{1-6}$ alkyl, $C_{3-7}$ cycloalkyl, or 4- to 10-membered heterocycloalkyl.

In another embodiment of Formula (IIa), $R_2$ is hydrogen, $C_{1-6}$ alkyl, $C_{3-7}$ cycloalkyl, or 4- to 7-membered heterocycloalkyl.

In another embodiment of Formula (IIa), $R_2$ is $C_{3-10}$ cycloalkyl, 4- to 12-membered heterocycloalkyl, $C_{1-4}$ alkylene-($C_{3-10}$cycloalkyl), or $C_{1-4}$ alkylene-(4- to 12-membered heterocycloalkyl).

In another embodiment of Formula (IIa), $R_2$ is $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IIa), $R_2$ is $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IIa), $R_2$ is hydrogen, $C_{1-6}$ alkyl, $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IIa), $R_2$ is hydrogen, $C_{1-6}$ alkyl, $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IIa), $R_2$ is $C_{1-4}$ alkylene-($C_{3-10}$ cycloalkyl) or $C_{1-4}$ alkylene-(4- to 12-membered heterocycloalkyl).

In another embodiment of Formula (IIa), $R_2$ is $C_{1-4}$ alkylene-($C_{3-7}$ cycloalkyl) or $C_{1-4}$ alkylene-(4- to 10-membered heterocycloalkyl).

In another embodiment of Formula (IIa), $R_2$ is $C_{1-4}$ alkylene-($C_{3-7}$ cycloalkyl) or $C_{1-4}$ alkylene-(4- to 7-membered heterocycloalkyl).

In another embodiment of Formula (IIa), $R_2$ is hydrogen or $C_{1-6}$ alkyl.

In another embodiment of Formula (IIa), $R_2$ is hydrogen, $C_{1-6}$ alkyl, $C_{1-4}$ alkylene-CF$_3$ or $C_{1-6}$ alkenyl.

In another embodiment of Formula (IIa), $R_2$ is hydrogen, $C_{1-4}$ alkylene-CF$_3$ or $C_{1-6}$ alkenyl.

In another embodiment of Formula (IIa), $R_2$ is $C_{3-10}$ cycloalkyl or 4- to 12-membered heterocycloalkyl.

In another embodiment of Formula (IIa), $R_2$ is $C_{3-7}$ cycloalkyl or 4- to 10-membered heterocycloalkyl.

In another embodiment of Formula (IIa), $R_2$ is $C_{3-7}$ cycloalkyl or 4- to 7-membered heterocycloalkyl.

In another embodiment of Formula (IIa), $R_2$ is hydrogen, $C_{1-6}$ alkyl, or $C_{1-4}$ alkylene-CF$_3$.

In another embodiment of Formula (IIa), $R_2$ is ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl).

In another embodiment of Formula (IIa), $R_2$ is ($C_{3-7}$ cycloalkylene)-($C_{6-10}$ aryl), ($C_{3-7}$ cycloalkylene)-(5- to 10-membered heteroaryl), (4- to 10-membered heterocycloalkylene)-($C_{6-10}$ aryl), or (4- to 10-membered heterocycloalkylene)-(5- to 10-membered heteroaryl).

In another embodiment of Formula (IIa), $R_2$ is ($C_{3-7}$ cycloalkylene)-($C_{6-10}$ aryl), ($C_{3-7}$ cycloalkylene)-(5- to 7-membered heteroaryl), (4- to 7-membered heterocycloalkylene)-($C_{6-10}$ aryl), or (4- to 7-membered heterocycloalkylene)-(5- to 7-membered heteroaryl).

In another embodiment of Formula (IIa), $R_2$ is ($C_{3-7}$ cycloalkylene)-($C_{6-10}$ aryl) or ($C_{3-7}$ cycloalkylene)-(5- to 7-membered heteroaryl).

In another embodiment of Formula (IIa), $R_2$ is (4- to 7-membered heterocycloalkylene)-($C_{6-10}$ aryl) or (4- to 7-membered heterocycloalkylene)-(5- to 7-membered heteroaryl).

In another embodiment of Formula (IIa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-(C$_{6-10}$ aryl), or (7- to 9-membered heterocycloalkylene)-(7- to 9-membered heteroaryl).

In another embodiment of Formula (IIa), R$_2$ is (C$_{3-7}$ cycloalkylene)-(C$_{6-10}$ aryl), (C$_{3-7}$ cycloalkylene)-(7- to 9-membered heteroaryl), (7- to 9-membered heterocycloalkylene)-(C$_{6-10}$ aryl), or (5- to 7-membered heterocycloalkylene)-(7- to 9-membered heteroaryl).

In another embodiment of Formula (IIa), R$_2$ is (C$_{3-7}$ cycloalkylene)-(C$_{6-10}$ aryl), (C$_{3-7}$ cycloalkylene)-(7- to 9-membered heteroaryl), (7- to 9-membered heterocycloalkylene)-(C$_{6-10}$ aryl), or (7- to 9-membered heterocycloalkylene)-(5- to 7-membered heteroaryl).

In another embodiment of Formula (IIa), R$_2$ is (C$_{3-7}$ cycloalkylene)-(C$_{6-10}$ aryl) or (C$_{3-7}$ cycloalkylene)-(7- to 9-membered heteroaryl).

In another embodiment of Formula (IIa), R$_2$ is (7- to 9-membered heterocycloalkylene)-(C$_{6-10}$ aryl) or (7- to 9-membered heterocycloalkylene)-(7- to 9-membered heteroaryl).

In another embodiment of Formula (IIa), R$_2$ is (7- to 9-membered heterocycloalkylene)-(C$_{6-10}$ aryl) or (5- to 7-membered heterocycloalkylene)-(7- to 9-membered heteroaryl).

In another embodiment of Formula (IIa), R$_2$ is (7- to 9-membered heterocycloalkylene)-(C$_{6-10}$ aryl) or (7- to 9-membered heterocycloalkylene)-(5- to 7-membered heteroaryl).

In another embodiment of Formula (IIa), R$_2$ is C$_{1-4}$ alkylene-(C$_{6-14}$ aryl), (C$_{3-10}$ cycloalkylene)-(C$_{6-14}$ aryl), or (4- to 12-membered heterocycloalkylene)-(C$_{6-14}$ aryl).

In another embodiment of Formula (IIa), R$_2$ is C$_{1-4}$ alkylene-(C$_{6-10}$ aryl), (C$_{3-7}$ cycloalkylene)-(C$_{6-10}$ aryl), or (4- to 7-membered heterocycloalkylene)-(C$_6$10 aryl).

In another embodiment of Formula (IIa), R$_2$ is C$_{1-4}$ alkylene-(C$_{6-14}$ aryl) or (C$_{3-10}$ cycloalkylene)-(C$_{6-14}$ aryl).

In another embodiment of Formula (IIa), R$_2$ is (C$_{3-10}$ cycloalkylene)-(C$_{6-14}$ aryl) or (4- to 12-membered heterocycloalkylene)-(C$_{6-14}$ aryl).

In another embodiment of Formula (IIa), R$_2$ is C$_{1-4}$ alkylene-(C$_{6-14}$ aryl) or (4- to 12-membered heterocycloalkylene)-(C$_{6-14}$ aryl).

In another embodiment of Formula (IIa), R$_2$ is C$_{1-4}$ alkylene-(C$_{6-10}$ aryl) or (C$_{3-7}$ cycloalkylene)-(C$_{6-10}$ aryl).

In another embodiment of Formula (IIa), R$_2$ is (C$_{3-7}$ cycloalkylene)-(C$_{6-10}$ aryl) or (4- to 7-membered heterocycloalkylene)-(C$_{6-10}$ aryl).

In another embodiment of Formula (IIa), R$_2$ is C$_{1-4}$ alkylene-(C$_{6-10}$ aryl) or (4- to 7-membered heterocycloalkylene)-(C$_{6-10}$ aryl).

In another embodiment of Formula (IIa), R$_2$ is C$_{1-4}$ alkylene-(5- to 14-membered heteroaryl), (C$_{3-10}$ cycloalkylene)-(5- to 14-membered heteroaryl), or (4- to 12-membered heterocycloalkylene)-(5- to 14-membered heteroaryl).

In another embodiment of Formula (IIa), R$_2$ is C$_{1-4}$ alkylene-(5- to 10-membered heteroaryl), (C$_{3-7}$ cycloalkylene)-(5- to 10-membered heteroaryl), or (4- to 7-membered heterocycloalkylene)-(5- to 10-membered heteroaryl).

In another embodiment of Formula (IIa), R$_2$ is C$_{1-4}$ alkylene-(5- to 7-membered heteroaryl), (C$_{3-7}$ cycloalkylene)-(5- to 7-membered heteroaryl), or (4- to 7-membered heterocycloalkylene)-(5- to 7-membered heteroaryl).

In an embodiment, the compound of Formula (II) has the structure of Formula (IIb):

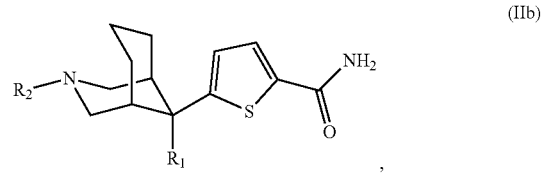

or a pharmaceutically acceptable salt thereof, wherein:
R$_1$ is C$_{1-2}$ alkoxy, wherein the C$_{1-2}$ alkoxy is optionally substituted with 1, 2, or 3 halo substituents;
R$_2$ is hydrogen, C$_{1-6}$ alkyl, C$_{1-4}$ alkylene-CF$_3$, or C$_{1-6}$ alkenyl; and
wherein each of the C$_{1-6}$ alkyl, C$_{1-6}$ alkenyl, and C$_{1-4}$ alkylene of R$_2$ is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIb), R$_1$ is unsubstituted C$_{1-2}$ alkoxy.

In another embodiment of Formula (IIb), R$_1$ is —OCH$_3$.

In another embodiment of Formula (IIb), R$_1$ is —OCH$_2$CF$_3$.

In another embodiment of Formula (IIb), R$_2$ is hydrogen, C$_{1-4}$ alkylene-CF$_3$, or C$_{1-6}$ alkenyl.

In another embodiment of Formula (IIb), R$_2$ is C$_{1-6}$ alkyl, C$_{1-4}$ alkylene-CF$_3$, or C$_{1-6}$ alkenyl.

In another embodiment of Formula (IIb), R$_2$ is hydrogen, C$_{1-6}$ alkyl, or C$_{1-6}$ alkenyl.

In another embodiment of Formula (IIb), R$_2$ is hydrogen, C$_{1-6}$ alkyl, or C$_{1-4}$ alkylene-CF$_3$.

In another embodiment of Formula (IIb), R$_2$ is hydrogen or C$_{1-6}$ alkyl.

In another embodiment of Formula (IIb), R$_2$ is hydrogen or C$_{1-4}$ alkylene-CF$_3$.

In another embodiment of Formula (IIb), R$_2$ is hydrogen or C$_{1-6}$ alkenyl.

In another embodiment of Formula (IIIb), R$_2$ is C$_{1-6}$ alkyl or C$_{1-4}$ alkylene-CF$_3$.

In another embodiment of Formula (IIIb), R$_2$ is C$_{1-6}$ alkyl or C$_{1-6}$ alkenyl.

In another embodiment of Formula (IIIb), R$_2$ is C$_{1-4}$ alkylene-CF$_3$ or C$_{1-6}$ alkenyl.

In another embodiment of Formula (IIb), R$_2$ is hydrogen.
In another embodiment of Formula (IIb), R$_2$ is C$_{1-6}$ alkyl.
In another embodiment of Formula (IIb), R$_2$ is C$_{1-4}$ alkylene-CF$_3$.
In another embodiment of Formula (IIb), R$_2$ is C$_{1-2}$ alkylene-CF$_3$.
In another embodiment of Formula (IIb), R$_2$ is C$_{1-6}$ alkenyl.
In another embodiment of Formula (IIb), R$_2$ is unsubstituted C$_{1-6}$ alkyl.
In another embodiment of Formula (IIb), R$_2$ is unsubstituted neopentyl.
In another embodiment of Formula (IIb), R$_2$ is unsubstituted sec-pentyl.
In another embodiment of Formula (IIb), R$_2$ is unsubstituted C$_{1-4}$ alkyl.
In another embodiment of Formula (IIb), R$_2$ is unsubstituted propyl.

In another embodiment of Formula (IIb), R$_2$ is unsubstituted isopropyl.

In another embodiment of Formula (IIb), R$_2$ is unsubstituted butyl.

In another embodiment of Formula (IIb), R$_2$ is unsubstituted isobutyl.

In another embodiment of Formula (IIb), R$_2$ is unsubstituted tert-butyl.

In another embodiment of Formula (IIb), R$_2$ is unsubstituted C$_{1-2}$ alkyl.

In another embodiment of Formula (IIb), R$_2$ is unsubstituted ethyl.

In another embodiment of Formula (IIb), R$_2$ is unsubstituted methyl.

In another embodiment of Formula (IIb), R$_2$ is deuterated C$_{1-6}$ alkyl.

In another embodiment of Formula (IIb), R$_2$ is —CD$_3$.

In another embodiment of Formula (IIb), R$_2$ is C$_{1-6}$ alkyl, wherein the C$_{1-6}$ alkyl is substituted with 1 or 2 substituents independently selected from the group consisting of —OH, halo, C$_{1-4}$ alkyl, and C$_{1-4}$ alkoxy.

In another embodiment of Formula (IIb), R$_2$ is C$_{1-4}$ alkyl, wherein the C$_{1-4}$ alkyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIb), R$_2$ is C$_{1-4}$ alkyl, wherein the C$_{1-4}$ alkyl is substituted with 1 or 2 substituents independently selected from the group consisting of —OH, halo, C$_{1-4}$ alkyl, and C$_{1-4}$ alkoxy.

In another embodiment of Formula (IIb), R$_2$ is C$_{1-4}$ alkyl, wherein the C$_{1-4}$ alkyl is substituted with —S(=O)$_2$—(C$_{1-4}$ alkyl).

In another embodiment of Formula (IIb), R$_2$ is C$_{1-4}$ alkyl, wherein the C$_{1-4}$ alkyl is substituted with C$_{1-4}$ alkoxy.

In another embodiment of Formula (IIb), R$_2$ is C$_{1-4}$ alkyl, wherein the C$_{1-4}$ alkyl is substituted with 1 or 2 halo.

In another embodiment of Formula (IIIb), R$_2$ is C$_{1-4}$ alkyl, wherein the C$_{1-4}$ alkyl is substituted with 1 or 2 fluoro.

In another embodiment of Formula (IIIb), R$_2$ is C$_{1-2}$ alkyl, wherein the C$_{1-2}$ alkyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIb), R$_2$ is C$_{1-2}$ alkyl, wherein the C$_{1-2}$ alkyl is substituted with 1 or 2 substituents independently selected from the group consisting of —OH, halo, C$_{1-4}$ alkyl, and C$_{1-4}$ alkoxy.

In another embodiment of Formula (IIb), R$_2$ is C$_{1-2}$ alkyl, wherein the C$_{1-2}$ alkyl is substituted with —S(=O)$_2$—(C$_{1-4}$ alkyl).

In another embodiment of Formula (IIb), R$_2$ is C$_{1-2}$ alkyl, wherein the C$_{1-2}$ alkyl is substituted with C$_{1-4}$ alkoxy.

In another embodiment of Formula (IIb), R$_2$ is C$_{1-2}$ alkyl, wherein the C$_{1-2}$ alkyl is substituted with 1 or 2 halo.

In another embodiment of Formula (IIb), R$_2$ is C$_{1-2}$ alkyl, wherein the C$_{1-2}$ alkyl is substituted with 1 or 2 fluoro.

In another embodiment of Formula (IIb), R$_2$ is unsubstituted C$_{1-4}$ alkylene-CF$_3$.

In another embodiment of Formula (IIb), R$_2$ is unsubstituted C$_{1-2}$ alkylene-CF$_3$.

In another embodiment of Formula (IIb), R$_2$ is C$_{1-4}$ alkylene-CF$_3$, wherein the C$_{1-4}$ alkylene-CF$_3$ is substituted with 1 or 2 substituents independently selected from the group consisting of —OH, halo, C$_{1-4}$ alkyl, and C$_{1-4}$ alkoxy.

In another embodiment of Formula (IIb), R$_2$ is C$_{1-2}$ alkylene-CF$_3$, wherein the C$_{1-2}$ alkylene-CF$_3$ is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIb), R$_2$ is ethylene-CF$_3$.

In another embodiment of Formula (IIb), R$_2$ is unsubstituted C$_{1-6}$ alkenyl.

In another embodiment of Formula (IIb), R$_2$ is unsubstituted C$_{1-4}$ alkenyl.

In another embodiment of Formula (IIb), R$_2$ is C$_{1-6}$ alkenyl, wherein the C$_{1-6}$ alkenyl is substituted with 1 or 2 substituents independently selected from the group consisting of —OH, halo, C$_{1-4}$ alkyl, and C$_{1-4}$ alkoxy.

In another embodiment of Formula (IIb), R$_2$ is C$_{1-4}$ alkenyl, wherein the C$_{1-4}$ alkenyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIb), R$_2$ is allyl.

In an embodiment, the compound of Formula (II) has the structure of Formula (IIc):

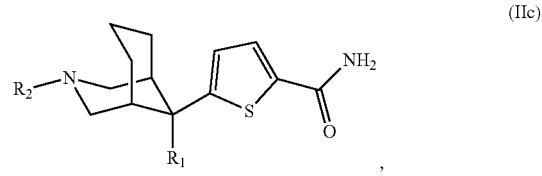

or a pharmaceutically acceptable salt thereof,
wherein:

R$_1$ is C$_{1-2}$ alkoxy, wherein the C$_{1-2}$ alkoxy is optionally substituted with 1, 2, or 3 halo substituents;

R$_2$ is C$_{3-10}$ cycloalkyl;

wherein the C$_{3-10}$ cycloalkyl is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and further wherein the C$_{3-10}$ cycloalkyl is optionally substituted with 1, 2, or 3 oxo moieties.

In another embodiment of Formula (IIc), R$_1$ is unsubstituted C$_{1-2}$ alkoxy.

In another embodiment of Formula (IIc), R$_1$ is —OCH$_3$.

In another embodiment of Formula (IIc), R$_1$ is —OCH$_2$CF$_3$.

In another embodiment of Formula (IIc), R$_2$ is C$_{3-10}$ cycloalkyl.

In another embodiment of Formula (IIc), R$_2$ is C$_{3-10}$ cycloalkyl, wherein the C$_{3-10}$ cycloalkyl is substituted with 1 or 2 substituents independently selected from the group consisting of —OH, halo, C$_{1-4}$ alkyl, and C$_{1-4}$ alkoxy.

In another embodiment of Formula (IIc), R$_2$ is unsubstituted C$_{3-10}$ cycloalkyl.

In another embodiment of Formula (IIc), R$_2$ is C$_{3-7}$ cycloalkyl.

In another embodiment of Formula (IIc), R$_2$ is C$_{3-7}$ cycloalkyl, wherein the C$_{3-7}$ cycloalkyl is substituted with 1 or 2 substituents independently selected from the group consisting of —OH, halo, C$_{1-4}$ alkyl, and C$_{1-4}$ alkoxy.

In another embodiment of Formula (IIc), R$_2$ is unsubstituted C$_{3-7}$ cycloalkyl.

In another embodiment of Formula (IIc), R$_2$ is cyclopropyl.

In another embodiment of Formula (IIc), R$_2$ is unsubstituted cyclopropyl.

In another embodiment of Formula (IIc), R$_2$ is cyclopropyl substituted with 1 or 2 substituents independently selected from the group consisting of —OH, halo, C$_{1-4}$ alkyl, and C$_{1-4}$ alkoxy.

In another embodiment of Formula (IIc), R$_2$ is cyclopropyl substituted with C$_{1-4}$ alkyl.

In another embodiment of Formula (IIc), R$_2$ is cyclobutyl.

In another embodiment of Formula (IIc), R$_2$ is unsubstituted cyclobutyl.

In another embodiment of Formula (IIc), R$_2$ is cyclobutyl substituted with 1 or 2 substituents independently selected from the group consisting of —OH, halo, C$_{1-4}$ alkyl, and C$_{1-4}$ alkoxy.

In another embodiment of Formula (IIc), R$_2$ is cyclobutyl substituted with 1 or 2 halo.

In another embodiment of Formula (IIc), R$_2$ is cyclobutyl substituted with C$_{1-4}$ alkyl.

In another embodiment of Formula (IIc), R$_2$ is cyclobutyl substituted with C$_{1-4}$ alkoxy.

In another embodiment of Formula (IIc), R$_2$ is cyclopentyl.

In another embodiment of Formula (IIc), R$_2$ is unsubstituted cyclopentyl.

In another embodiment of Formula (IIc), R$_2$ is cyclopentyl substituted with 1 or 2 substituents independently selected from the group consisting of —OH, halo, C$_{1-4}$ alkyl, and C$_{1-4}$ alkoxy.

In another embodiment of Formula (IIc), R$_2$ is cyclohexyl.

In another embodiment of Formula (IIc), R$_2$ is unsubstituted cyclohexyl.

In another embodiment of Formula (IIc), R$_2$ is cyclohexyl substituted with 1 or 2 substituents independently selected from the group consisting of —OH, halo, C$_{1-4}$ alkyl, and C$_{1-4}$ alkoxy.

In another embodiment of Formula (IIc), R$_2$ is cyclohexyl substituted with 1 or 2 halo.

In another embodiment of Formula (IIc), R$_2$ is bicyclo[3.1.0]hexyl.

In another embodiment of Formula (IIc), R$_2$ is unsubstituted bicyclo[3.1.0]hexyl.

In another embodiment of Formula (IIc), R$_2$ is bicyclo[3.1.0]hexyl substituted with 1 or 2 substituents independently selected from the group consisting of —OH, halo, C$_{1-4}$ alkyl, and C$_{1-4}$ alkoxy.

In another embodiment of Formula (IIc), R$_2$ is bicyclo[3.1.0]hexyl substituted with 1 or 2 halo.

In another embodiment of Formula (IIc), R$_2$ is spiro[3.3]heptanyl.

In another embodiment of Formula (IIc), R$_2$ is unsubstituted spiro[3.3]heptanyl.

In another embodiment of Formula (IIc), R$_2$ is spiro[3.3]heptanyl substituted with 1 or 2 substituents independently selected from the group consisting of —OH, halo, C$_{1-4}$ alkyl, and C$_{1-4}$ alkoxy.

In another embodiment of Formula (IIc), R$_2$ is bicyclo[1.1.1]pentyl.

In another embodiment of Formula (IIc), R$_2$ is unsubstituted bicyclo[1.1.1]pentyl.

In another embodiment of Formula (IIc), R$_2$ is bicyclo[1.1.1]pentyl substituted with 1 or 2 substituents independently selected from the group consisting of —OH, halo, C$_{1-4}$ alkyl, and C$_{1-4}$ alkoxy.

In an embodiment, the compound of Formula (II) has the structure of Formula (IIId):

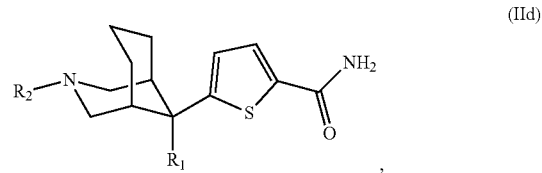

(IId)

or a pharmaceutically acceptable salt thereof, wherein:
R$_1$ is C$_{1-2}$ alkoxy, wherein the C$_{1-2}$ alkoxy is optionally substituted with 1, 2, or 3 halo substituents;
R$_2$ is 4- to 12-membered heterocycloalkyl;
wherein the 4- to 12-membered heterocycloalkyl is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and
further wherein the 4- to 12-membered heterocycloalkyl is optionally substituted with 1, 2, or 3 oxo moieties.

In another embodiment of Formula (IIId), R$_1$ is unsubstituted C$_{1-2}$ alkoxy.

In another embodiment of Formula (IIId), R$_1$ is —OCH$_3$.

In another embodiment of Formula (IIId), R$_1$ is —OCH$_2$CF$_3$.

In another embodiment of Formula (IIId), R$_2$ is 4- to 12-membered heterocycloalkyl, wherein the 4- to 12-membered heterocycloalkyl is substituted with 1 or 2 substituents independently selected from the group consisting of —OH, halo, C$_{1-4}$ alkyl, and C$_{1-4}$ alkoxy.

In another embodiment of Formula (IIId), R$_2$ is unsubstituted 4- to 12-membered heterocycloalkyl.

In another embodiment of Formula (IIId), R$_2$ is 4- to 9-membered heterocycloalkyl.

In another embodiment of Formula (IIId), R$_2$ is 4- to 9-membered heterocycloalkyl, wherein the 4- to 9-membered heterocycloalkyl is substituted with 1 or 2 substituents independently selected from the group consisting of —OH, halo, C$_{1-4}$ alkyl, and C$_{1-4}$ alkoxy.

In another embodiment of Formula (IIId), R$_2$ is unsubstituted 4- to 9-membered heterocycloalkyl.

In another embodiment of Formula (IIId), R$_2$ is 4- to 6-membered heterocycloalkyl.

In another embodiment of Formula (IIId), R$_2$ is 4- to 6-membered heterocycloalkyl, wherein the 4- to 6-membered heterocycloalkyl is substituted with 1 or 2 substituents independently selected from the group consisting of —OH, halo, C$_{1-4}$ alkyl, and C$_{1-4}$ alkoxy.

In another embodiment of Formula (IIId), R$_2$ is unsubstituted 4- to 6-membered heterocycloalkyl.

In another embodiment of Formula (IIId), R$_2$ is 7- to 9-membered heterocycloalkyl.

In another embodiment of Formula (IIId), R$_2$ is 7- to 9-membered heterocycloalkyl, wherein the 7- to 9-membered heterocycloalkyl is substituted with 1 or 2 substituents independently selected from the group consisting of —OH, halo, C$_{1-4}$ alkyl, and C$_{1-4}$ alkoxy.

In another embodiment of Formula (IIId), R$_2$ is unsubstituted 7- to 9-membered heterocycloalkyl.

In another embodiment of Formula (IIId), R$_2$ is 4-membered heterocycloalkyl.

In another embodiment of Formula (IIId), R$_2$ is 4-membered heterocycloalkyl, wherein the 4-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 4-membered heterocycloalkyl.

In another embodiment of Formula (IIId), $R_2$ is 5-membered heterocycloalkyl.

In another embodiment of Formula (IIId), $R_2$ is 5-membered heterocycloalkyl, wherein the 5-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 5-membered heterocycloalkyl.

In another embodiment of Formula (IIId), $R_2$ is 6-membered heterocycloalkyl.

In another embodiment of Formula (IIId), $R_2$ is 6-membered heterocycloalkyl, wherein the 6-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 6-membered heterocycloalkyl.

In another embodiment of Formula (IIId), $R_2$ is 7-membered heterocycloalkyl.

In another embodiment of Formula (IIId), $R_2$ is 7-membered heterocycloalkyl, wherein the 7-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 7-membered heterocycloalkyl.

In another embodiment of Formula (IIId), $R_2$ is 8-membered heterocycloalkyl.

In another embodiment of Formula (IIId), $R_2$ is 8-membered heterocycloalkyl, wherein the 8-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 8-membered heterocycloalkyl.

In another embodiment of Formula (IIId), $R_2$ is 9-membered heterocycloalkyl.

In another embodiment of Formula (IIId), $R_2$ is 9-membered heterocycloalkyl, wherein the 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 9-membered heterocycloalkyl.

In another embodiment of Formula (IIId), $R_2$ is 4- to 9-membered heterocycloalkyl, wherein the 4- to 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 9-membered heterocycloalkyl is optionally substituted with 1, 2, or 3 oxo moieties.

In another embodiment of Formula (IIId), $R_2$ is 4- to 6-membered heterocycloalkyl, wherein the 4- to 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 6-membered heterocycloalkyl is optionally substituted with 1, 2, or 3 oxo moieties.

In another embodiment of Formula (IIId), $R_2$ is 4-membered heterocycloalkyl, wherein the 4-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4-membered heterocycloalkyl is optionally substituted with 1, 2, or 3 oxo moieties.

In another embodiment of Formula (IIId), $R_2$ is 5-membered heterocycloalkyl, wherein the 5-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5-membered heterocycloalkyl is optionally substituted with 1, 2, or 3 oxo moieties.

In another embodiment of Formula (IIId), $R_2$ is 6-membered heterocycloalkyl, wherein the 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 6-membered heterocycloalkyl is optionally substituted with 1, 2, or 3 oxo moieties.

In another embodiment of Formula (IIId), $R_2$ is 7-membered heterocycloalkyl, wherein the 7-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 7-membered heterocycloalkyl is optionally substituted with 1, 2, or 3 oxo moieties.

In another embodiment of Formula (IIId), $R_2$ is 8-membered heterocycloalkyl, wherein the 8-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 8-membered heterocycloalkyl is optionally substituted with 1, 2, or 3 oxo moieties.

In another embodiment of Formula (IIId), $R_2$ is 9-membered heterocycloalkyl, wherein the 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 9-membered heterocycloalkyl is optionally substituted with 1, 2, or 3 oxo moieties.

In another embodiment of Formula (IIId), $R_2$ is oxetanyl.

In another embodiment of Formula (IIId), $R_2$ is unsubstituted oxetanyl.

In another embodiment of Formula (IIId), $R_2$ is oxetanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is azetidinyl.

In another embodiment of Formula (IIId), $R_2$ is unsubstituted azetidinyl.

In another embodiment of Formula (IIId), $R_2$ is azetidinyl substituted with 1 or 2 substituents independently selected from the group consisting of —OH, halo, $C_{1-4}$ alkyl, and $C_{1-4}$ alkoxy.

In another embodiment of Formula (IIId), $R_2$ is azetidinyl substituted with 1 or 2 substituents independently selected from the group consisting of —OH, halo, $C_{1-4}$ alkyl, $C_{1-4}$ alkoxy, and —C(=O)—($C_{1-4}$ alkyl).

In another embodiment of Formula (IIId), $R_2$ is azetidinyl substituted with 1 or 2 substituents independently selected from the group consisting of halo, $C_{1-4}$ alkyl and —C(=O)—($C_{1-4}$ alkyl).

In another embodiment of Formula (IIId), $R_2$ is azetidinyl substituted with —C(=O)—($C_{1-4}$ alkyl).

In another embodiment of Formula (IIId), $R_2$ is tetrahydrofuranyl.

In another embodiment of Formula (IIId), $R_2$ is unsubstituted tetrahydrofuranyl.

In another embodiment of Formula (IIId), $R_2$ is tetrahydrofuranyl substituted with 1 or 2 substituents independently selected from the group consisting of —OH, halo, $C_{1-4}$ alkyl, and $C_{1-4}$ alkoxy.

In another embodiment of Formula (IIId), $R_2$ is oxanyl.

In another embodiment of Formula (IIId), $R_2$ is unsubstituted oxanyl.

In another embodiment of Formula (IIId), $R_2$ is oxan-2-yl.
In another embodiment of Formula (IIId), $R_2$ is oxan-3-yl.
In another embodiment of Formula (IIId), $R_2$ is oxan-4-yl.
In another embodiment of Formula (IIId), $R_2$ is oxanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 2-oxaspiro[3.5]nonanyl.

In another embodiment of Formula (IIId), $R_2$ is unsubstituted 2-oxaspiro[3.5]nonanyl.

In another embodiment of Formula (IIId), $R_2$ is 2-oxaspiro[3.5]nonanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 3-oxaspiro[5.3]nonanyl.

In another embodiment of Formula (IIId), $R_2$ is unsubstituted 3-oxaspiro[5.3]nonanyl.

In another embodiment of Formula (IIId), $R_2$ is 3-oxaspiro[5.3]nonanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 8-oxabicyclo[3.2.1]octanyl.

In another embodiment of Formula (IIId), $R_2$ is unsubstituted 8-oxabicyclo[3.2.1]octanyl.

In another embodiment of Formula (IIId), $R_2$ is 8-oxabicyclo[3.2.1]octanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 2-oxaspiro[3.3]heptanyl.

In another embodiment of Formula (IIId), $R_2$ is unsubstituted 2-oxaspiro[3.3]heptanyl.

In another embodiment of Formula (IIId), $R_2$ is 2-oxaspiro[3.3]heptanyl substituted with 1 or 2 substituents independently selected from the group consisting of —OH, halo, $C_{1-4}$ alkyl, and $C_{1-4}$ alkoxy.

In an embodiment, the compound of Formula (ii) has the structure of Formula (IIIe):

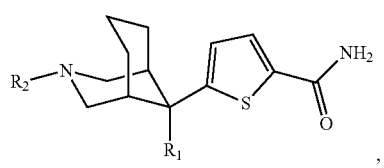

(IIe)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents; $R_2$ is $C_{1-4}$ alkylene-($C_{6-10}$ cycloalkyl) or $C_{1-4}$ alkylene-($C_{6-14}$ aryl);

wherein each of the $C_{3-10}$ cycloalkyl, $C_{6-14}$ aryl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the $C_{3-10}$ cycloalkyl of $R_2$ is optionally substituted with 1, 2, or 3 oxo moieties.

In another embodiment of Formula (IIIe), $R_1$ is unsubstituted $C_{1-2}$ alkoxy.

In another embodiment of Formula (IIIe), $R_1$ is —OCH$_3$.

In another embodiment of Formula (IIIe), $R_1$ is —OCH$_2$CF$_3$.

In another embodiment of Formula (IIIe), $R_2$ is $C_{1-4}$ alkylene-($C_{3-10}$ cycloalkyl).

In another embodiment of Formula (IIIe), $R_2$ is unsubstituted $C_{1-4}$ alkylene-($C_{3-10}$ cycloalkyl).

In another embodiment of Formula (IIIe), $R_2$ is $C_{1-4}$ alkylene-($C_{3-10}$ cycloalkyl), wherein the $C_{3-10}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-10}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-10}$ cycloalkyl), wherein each of the $C_{1-4}$ alkylene and $C_{3-10}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl).

In another embodiment of Formula (IIIe), $R_2$ is unsubstituted $C_{1-4}$ alkylene-($C_{3-7}$ cycloalkyl).

In another embodiment of Formula (IIIe), $R_2$ is $C_{1-4}$ alkylene-($C_{3-7}$ cycloalkyl), wherein the $C_{3-7}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl), wherein each of the $C_{1-4}$ alkylene and $C_{3-7}$ cycloalkyl is substituted with 1 or 2 substituents independently selected from the group consisting of —OH, halo, $C_{1-4}$ alkyl, and $C_{1-4}$ alkoxy.

In another embodiment of Formula (IIe), $R_2$ is $C_{1-4}$ alkylene-(cyclopropyl).

In another embodiment of Formula (IIe), $R_2$ is $C_{1-4}$ alkylene-(cyclopropyl), wherein the cyclopropyl is substituted with 1 or 2 substituents independently selected from the group consisting of —OH, halo, $C_{1-4}$ alkyl, and $C_{1-4}$ alkoxy.

In another embodiment of Formula (IIe), $R_2$ is $C_{1-4}$ alkylene-(cyclopropyl), wherein the cyclopropyl is substituted with —OH.

In another embodiment of Formula (IIe), $R_2$ is $C_{1-4}$ alkylene-(cyclopropyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIe), $R_2$ is $C_{1-4}$ alkylene-(cyclopropyl), wherein each of the $C_{1-4}$ alkylene and cyclopropyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(cyclopropyl).

In another embodiment of Formula (IIe), $R_2$ is $C_{1-4}$ alkylene-(cyclobutyl), wherein the cyclobutyl is substituted with 1 or 2 substituents independently selected from the group consisting of —OH, halo, $C_{1-4}$ alkyl, and $C_{1-4}$ alkoxy.

In another embodiment of Formula (IIe), $R_2$ is $C_{1-4}$ alkylene-(cyclobutyl).

In another embodiment of Formula (IIe), $R_2$ is $C_{1-4}$ alkylene-(cyclobutyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIe), $R_2$ is $C_{1-4}$ alkylene-(cyclobutyl), wherein each of the $C_{1-4}$ alkylene and cyclobutyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(cyclobutyl).

In another embodiment of Formula (IIIe), $R_2$ is $C_{1-4}$ alkylene-(bicyclo[3.1.0]hexyl).

In another embodiment of Formula (IIIe), $R_2$ is $C_{1-4}$ alkylene-(bicyclo[3.1.0]hexyl), wherein the bicyclo[3.1.0]hexyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(bicyclo[3.1.0]hexyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(bicyclo[3.1.0]hexyl), wherein each of the $C_{1-4}$ alkylene and bicyclo[3.1.0]hexyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(bicyclo[3.1.0]hexyl).

In another embodiment of Formula (IIIe), $R_2$ is $C_{1-4}$ alkylene-($C_{1-4}$ aryl).

In another embodiment of Formula (IIIe), $R_2$ is unsubstituted $C_{1-4}$ alkylene-($C_{1-4}$ aryl).

In another embodiment of Formula (IIIe), $R_2$ is $C_{1-4}$ alkylene-($C_{6-14}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-14}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{1-4}$ aryl), wherein each of the $C_{1-4}$ alkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl).

In another embodiment of Formula (IIIe), $R_2$ is unsubstituted $C_{1-4}$ alkylene-($C_{6-10}$ aryl).

In another embodiment of Formula (IIIe), $R_2$ is $C_{1-4}$ alkylene-($C_{6-10}$ aryl), wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl), wherein each of the $C_{1-4}$ alkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl).

In another embodiment of Formula (IIIe), $R_2$ is unsubstituted $C_{1-4}$ alkylene-(phenyl).

In another embodiment of Formula (IIIe), $R_2$ is $C_{1-4}$ alkylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl), wherein each of the $C_{1-4}$ alkylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl).

In another embodiment of Formula (IIIe), $R_2$ is unsubstituted methylene-(phenyl).

In another embodiment of Formula (IIIe), $R_2$ is methylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl), wherein the methylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl), wherein each of the methylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl).

In another embodiment of Formula (IIIe), $R_2$ is unsubstituted ethylene-(phenyl).

In another embodiment of Formula (IIIe), $R_2$ is ethylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl), wherein the ethylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl), wherein each of the ethylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl).

In another embodiment of Formula (IIIe), $R_2$ is unsubstituted $C_{1-4}$ alkylene-(indanyl).

In another embodiment of Formula (IIIe), $R_2$ is $C_{1-4}$ alkylene-(indanyl), wherein the indanyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl), wherein the indanyl is substituted with —OH.

In another embodiment of Formula (IIIe), $R_2$ is $C_{1-4}$ alkylene-(indanyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl), wherein each of the $C_{1-4}$ alkylene and indanyl is substituted with 1 or 2 substituents independently selected from the group consisting of —OH, halo, $C_{1-4}$ alkyl, and $C_{1-4}$ alkoxy.

In an embodiment, the compound of Formula (II) has the structure of Formula (IIf):

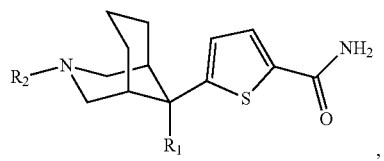

(IIf)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-(4- to 12-membered heterocycloalkyl);
wherein each of the 4- to 12-membered heterocycloalkyl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the 4- to 12-membered heterocycloalkyl of $R_2$ is optionally substituted with 1, 2, or 3 oxo moieties.

In another embodiment of Formula (IIIf), $R_1$ is unsubstituted $C_{1-2}$ alkoxy.

In another embodiment of Formula (IIIf), $R_1$ is —OCH$_3$.

In another embodiment of Formula (IIIf), $R_1$ is —OCH$_2$CF$_3$.

In another embodiment of Formula (IIIf), $R_2$ is unsubstituted $C_{1-4}$ alkylene-(4- to 12-membered heterocycloalkyl).

In another embodiment of Formula (IIIf), $R_2$ is $C_{1-4}$ alkylene-(4- to 9-membered heterocycloalkyl).

In another embodiment of Formula (IIIf), $R_2$ is unsubstituted $C_{1-4}$ alkylene-(4- to 9-membered heterocycloalkyl).

In another embodiment of Formula (IIf), $R_2$ is $C_{1-4}$ alkylene-(4- to 6-membered heterocycloalkyl).

In another embodiment of Formula (IIf), $R_2$ is unsubstituted $C_{1-4}$ alkylene-(4- to 6-membered heterocycloalkyl).

In another embodiment of Formula (IIf), $R_2$ is $C_{1-4}$ alkylene-(4-membered heterocycloalkyl).

In another embodiment of Formula (IIIf), $R_2$ is unsubstituted $C_{1-4}$ alkylene-(4-membered heterocycloalkyl).

In another embodiment of Formula (IIf), $R_2$ is $C_{1-4}$ alkylene-(5-membered heterocycloalkyl).

In another embodiment of Formula (IIIf), $R_2$ is unsubstituted $C_{1-4}$ alkylene-(5-membered heterocycloalkyl).

In another embodiment of Formula (IIf), $R_2$ is $C_{1-4}$ alkylene-(6-membered heterocycloalkyl).

In another embodiment of Formula (IIIf), $R_2$ is unsubstituted $C_{1-4}$ alkylene-(6-membered heterocycloalkyl).

In another embodiment of Formula (IIf), $R_2$ is $C_{1-4}$ alkylene-(7-membered heterocycloalkyl).

In another embodiment of Formula (IIIf), $R_2$ is unsubstituted $C_{1-4}$ alkylene-(7-membered heterocycloalkyl).

In another embodiment of Formula (IIf), $R_2$ is $C_{1-4}$ alkylene-(8-membered heterocycloalkyl).

In another embodiment of Formula (IIIf), $R_2$ is unsubstituted $C_{1-4}$ alkylene-(8-membered heterocycloalkyl).

In another embodiment of Formula (IIf), $R_2$ is $C_{1-4}$ alkylene-(9-membered heterocycloalkyl).

In another embodiment of Formula (IIIf), $R_2$ is unsubstituted $C_{1-4}$ alkylene-(9-membered heterocycloalkyl).

In another embodiment of Formula (IIf), $R_2$ is $C_{1-4}$ alkylene-(4- to 12-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IIf), $R_2$ is $C_{1-4}$ alkylene-(4- to 12-membered heterocycloalkyl), wherein the 4- to 12-membered heterocycloalkyl is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IIIf), $R_2$ is $C_{1-4}$ alkylene-(4- to 12-membered heterocycloalkyl), wherein the 4- to 12-membered heterocycloalkyl is optionally substituted with 1, 2, or 3 oxo moieties.

In another embodiment of Formula (IIIf), $R_2$ is $C_{1-4}$ alkylene-(4- to 9-membered heterocycloalkyl), wherein the 4- to 9-membered heterocycloalkyl is substituted with 1 or 2 substituents independently selected from the group consisting of —OH, halo, $C_{1-4}$ alkyl, and $C_{1-4}$ alkoxy; and
further wherein the 4- to 9-membered heterocycloalkyl is optionally substituted with 1, 2, or 3 oxo moieties.

In another embodiment of Formula (IIIf), $R_2$ is $C_{1-4}$ alkylene-(4- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 9-membered heterocycloalkyl is optionally substituted with 1, 2, or 3 oxo moieties.

In another embodiment of Formula (IIf), $R_2$ is $C_{1-4}$ alkylene-(4- to 9-membered heterocycloalkyl), wherein the 4- to 9-membered heterocycloalkyl is optionally substituted with 1, 2, or 3 oxo moieties.

In another embodiment of Formula (IIIf), $R_2$ is $C_{1-4}$ alkylene-(4- to 6-membered heterocycloalkyl), wherein the 4- to 6-membered heterocycloalkyl is substituted with 1 or 2 substituents independently selected from the group consisting of —OH, halo, $C_{1-4}$ alkyl, and $C_{1-4}$ alkoxy; and
further wherein the 4- to 6-membered heterocycloalkyl is optionally substituted with 1, 2, or 3 oxo moieties.

In another embodiment of Formula (IIIf), $R_2$ is $C_{1-4}$ alkylene-(4- to 6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4- to 6-membered heterocycloalkyl is optionally substituted with 1, 2, or 3 oxo moieties.

In another embodiment of Formula (IIf), $R_2$ is $C_{1-4}$ alkylene-(4- to 6-membered heterocycloalkyl), wherein the 4- to 6-membered heterocycloalkyl is optionally substituted with 1, 2, or 3 oxo moieties.

In another embodiment of Formula (IIf), $R_2$ is $C_{1-4}$ alkylene-(7- to 9-membered heterocycloalkyl), wherein the 7- to 9-membered heterocycloalkyl is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IIIf), $R_2$ is $C_{1-4}$ alkylene-(7- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IIf), $R_2$ is $C_{1-4}$ alkylene-(7- to 9-membered heterocycloalkyl), wherein the 7- to 9-membered heterocycloalkyl is optionally substituted with 1, 2, or 3 oxo moieties.

In another embodiment of Formula (IIf), $R_2$ is $C_{1-4}$ alkylene-(4-membered heterocycloalkyl), wherein the 4-membered heterocycloalkyl is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IIf), $R_2$ is $C_{1-4}$ alkylene-(4-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IIf), $R_2$ is $C_{1-4}$ alkylene-(4-membered heterocycloalkyl), wherein the 4-membered heterocycloalkyl is optionally substituted with 1 or 2 oxo moieties.

In another embodiment of Formula (IIf), $R_2$ is $C_{1-4}$ alkylene-(5-membered heterocycloalkyl), wherein the 5-membered heterocycloalkyl is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IIf), $R_2$ is $C_{1-4}$ alkylene-(5-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IIIf), $R_2$ is $C_{1-4}$ alkylene-(5-membered heterocycloalkyl), wherein the 5-membered heterocycloalkyl is optionally substituted with 1, 2 or 3 oxo moieties.

In another embodiment of Formula (IIf), $R_2$ is $C_{1-4}$ alkylene-(6-membered heterocycloalkyl), wherein the 6-membered heterocycloalkyl is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IIf), $R_2$ is $C_{1-4}$ alkylene-(6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IIf), $R_2$ is $C_{1-4}$ alkylene-(6-membered heterocycloalkyl), wherein the 6-membered heterocycloalkyl is optionally substituted with 1, 2 or 3 oxo moieties.

In another embodiment of Formula (IIf), $R_2$ is $C_{1-4}$ alkylene-(7-membered heterocycloalkyl), wherein the 7-membered heterocycloalkyl is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IIf), $R_2$ is $C_{1-4}$ alkylene-(7-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IIf), $R_2$ is $C_{1-4}$ alkylene-(7-membered heterocycloalkyl), wherein the 7-membered heterocycloalkyl is optionally substituted with 1, 2 or 3 oxo moieties.

In another embodiment of Formula (IIIf), $R_2$ is $C_{1-4}$ alkylene-(8-membered heterocycloalkyl), wherein the 8-membered heterocycloalkyl is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IIf), $R_2$ is $C_{1-4}$ alkylene-(8-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IIf), $R_2$ is $C_{1-4}$ alkylene-(8-membered heterocycloalkyl), wherein the 8-membered heterocycloalkyl is optionally substituted with 1, 2 or 3 oxo moieties.

In another embodiment of Formula (IIf), $R_2$ is $C_{1-4}$ alkylene-(9-membered heterocycloalkyl), wherein the 9-membered heterocycloalkyl is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IIf), $R_2$ is $C_{1-4}$ alkylene-(9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IIf), $R_2$ is $C_{1-4}$ alkylene-(9-membered heterocycloalkyl), wherein the 9-membered heterocycloalkyl is optionally substituted with 1, 2 or 3 oxo moieties.

In another embodiment of Formula (IIf), $R_2$ is $C_{1-4}$ alkylene-(oxetanyl).

In another embodiment of Formula (IIf), $R_2$ is $C_{1-4}$ alkylene-(oxetan-2-yl).

In another embodiment of Formula (IIf), $R_2$ is $C_{1-4}$ alkylene-(oxetan-3-yl).

In another embodiment of Formula (IIf), $R_2$ is $C_{1-4}$ alkylene-(oxetanyl), wherein the oxetanyl is optionally substituted with 1, 2 or 3 oxo moieties.

In another embodiment of Formula (IIIf), $R_2$ is $C_{1-2}$ alkylene-(oxetanyl), wherein the oxetanyl is optionally substituted with 1, 2 or 3 oxo moieties.

In another embodiment of Formula (IIIf), $R_2$ is unsubstituted $C_{1-2}$ alkylene-(oxetanyl).

In another embodiment of Formula (IIIf), $R_2$ is $C_{1-4}$ alkylene-(pyrrolidinyl).

In another embodiment of Formula (IIf), $R_2$ is $C_{1-4}$ alkylene-(pyrrolidin-2-yl).

In another embodiment of Formula (IIf), $R_2$ is $C_{1-4}$ alkylene-(pyrrolidin-3-yl).

In another embodiment of Formula (IIf), $R_2$ is $C_{1-4}$ alkylene-(pyrrolidinyl), wherein the pyrrolidinyl is optionally substituted with 1, 2 or 3 oxo moieties.

In another embodiment of Formula (IIf), $R_2$ is $C_{1-2}$ alkylene-(pyrrolidinyl), wherein the pyrrolidinyl is optionally substituted with 1, 2 or 3 oxo moieties.

In another embodiment of Formula (IIf), $R_2$ is $C_{1-2}$ alkylene-(pyrrolidinyl), wherein the pyrrolidinyl is substituted with 2 oxo moieties.

In another embodiment of Formula (IIf), $R_2$ is $C_{1-4}$ alkylene-(imidazolidinyl), wherein the imidazolidinyl is optionally substituted with 1, 2 or 3 oxo moieties.

In another embodiment of Formula (IIf), $R_2$ is $C_{1-2}$ alkylene-(imidazolidinyl), wherein the imidazolidinyl is optionally substituted with 1, 2 or 3 oxo moieties.

In another embodiment of Formula (IIf), $R_2$ is $C_{1-2}$ alkylene-(imidazolidinyl), wherein the imidazolidinyl is substituted with 1 oxo moiety.

In another embodiment of Formula (IIf), $R_2$ is $C_{1-4}$ alkylene-(oxazolidinyl), wherein the oxazolidinyl is optionally substituted with 1, 2 or 3 oxo moieties.

In another embodiment of Formula (IIf), $R_2$ is $C_{1-2}$ alkylene-(oxazolidinyl), wherein the oxazolidinyl is optionally substituted with 1, 2 or 3 oxo moieties.

In another embodiment of Formula (IIf), $R_2$ is $C_{1-2}$ alkylene-(oxazolidinyl), wherein the oxazolidinyl is substituted with 1 oxo moiety.

In another embodiment of Formula (IIf), $R_2$ is $C_{1-4}$ alkylene-(isothiazolidinyl), wherein the isothiazolidinyl is optionally substituted with 1, 2 or 3 oxo moieties.

In another embodiment of Formula (IIf), $R_2$ is $C_{1-2}$ alkylene-(isothiazolidinyl), wherein the isothiazolidinyl is optionally substituted with 1, 2 or 3 oxo moieties.

In another embodiment of Formula (IIf), $R_2$ is $C_{1-2}$ alkylene-(isothiazolidinyl), wherein the isothiazolidinyl is substituted with 2 oxo moieties.

In another embodiment of Formula (IIf), $R_2$ is $C_{1-4}$ alkylene-(tetrahydrofuranyl).

In another embodiment of Formula (IIf), $R_2$ is $C_{1-4}$ alkylene-(tetrahydrofuran-2-yl).

In another embodiment of Formula (IIf), $R_2$ is $C_{1-4}$ alkylene-(tetrahydrofuran-3-yl).

In another embodiment of Formula (IIf), $R_2$ is $C_{1-4}$ alkylene-(tetrahydrofuranyl), wherein the tetrahydrofuranyl is optionally substituted with 1, 2 or 3 oxo moieties.

In another embodiment of Formula (IIf), $R_2$ is $C_{1-2}$ alkylene-(tetrahydrofuranyl), wherein the tetrahydrofuranyl is optionally substituted with 1, 2 or 3 oxo moieties.

In another embodiment of Formula (IIIf), $R_2$ is unsubstituted $C_{1-2}$ alkylene-(tetrahydrofuranyl).

In another embodiment of Formula (IIIf), $R_2$ is $C_{1-4}$ alkylene-(thianyl).

In another embodiment of Formula (IIIf), $R_2$ is $C_{1-4}$ alkylene-(thian-2-yl).

In another embodiment of Formula (IIf), $R_2$ is $C_{1-4}$ alkylene-(thian-3-yl).

In another embodiment of Formula (IIf), $R_2$ is $C_{1-4}$ alkylene-(thian-4-yl).

In another embodiment of Formula (IIf), $R_2$ is $C_{1-4}$ alkylene-(thianyl), wherein the thianyl is optionally substituted with 1, 2 or 3 oxo moieties.

In another embodiment of Formula (IIf), $R_2$ is $C_{1-2}$ alkylene-(thianyl), wherein the thianyl is optionally substituted with 1, 2 or 3 oxo moieties.

In another embodiment of Formula (IIf), $R_2$ is $C_{1-2}$ alkylene-(thianyl), wherein the thianyl is substituted with 2 oxo moieties.

In another embodiment of Formula (IIf), $R_2$ is unsubstituted $C_{1-4}$ alkylene-(oxanyl).

In another embodiment of Formula (IIf), $R_2$ is unsubstituted $C_{1-4}$ alkylene-(oxan-2-yl).

In another embodiment of Formula (IIf), $R_2$ is unsubstituted $C_{1-4}$ alkylene-(oxan-3-yl).

In another embodiment of Formula (IIf), $R_2$ is unsubstituted $C_{1-4}$ alkylene-(oxan-4-yl).

In another embodiment of Formula (IIf), $R_2$ is unsubstituted $C_{1-2}$ alkylene-(oxanyl).

In another embodiment of Formula (IIf), $R_2$ is unsubstituted $C_{1-2}$ alkylene-(oxan-2-yl).

In another embodiment of Formula (IIf), $R_2$ is unsubstituted $C_{1-2}$ alkylene-(oxan-3-yl).

In another embodiment of Formula (IIf), $R_2$ is unsubstituted $C_{1-2}$ alkylene-(oxan-4-yl).

In another embodiment of Formula (IIf), $R_2$ is $C_{1-4}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IIf), $R_2$ is $C_{1-2}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IIf), $R_2$ is $C_{1-2}$ alkylene-(oxanyl), wherein the oxanyl is substituted with 1 or 2 halo.

In another embodiment of Formula (IIf), $R_2$ is $C_{1-4}$ alkylene-(pyridinon-2(1H)-yl).

In another embodiment of Formula (IIf), $R_2$ is unsubstituted $C_{1-4}$ alkylene-(pyridinon-2(1H)-yl).

In another embodiment of Formula (IIf), $R_2$ is $C_{1-4}$ alkylene-(pyridinon-2(1H)-yl), wherein one or both of the $C_{1-4}$ alkylene and pyridinon-2(1H)-yl is substituted with 1 or 2 substituents independently selected from the group consisting of —OH, halo, $C_{1-4}$ alkyl, and $C_{1-4}$ alkoxy.

In an embodiment, the compound of Formula (II) has the structure of Formula (IIg):

(IIg)

[Chemical structure showing R$_2$—N bicyclic system connected to thiophene ring with C(=O)NH$_2$ group and R$_1$ substituent]

or a pharmaceutically acceptable salt thereof,
wherein:
R$_1$ is C$_{1-2}$ alkoxy, wherein the C$_{1-2}$ alkoxy is optionally substituted with 1, 2, or 3 halo substituents;
R$_2$ is C$_{1-4}$ alkylene-(5- to 14-membered heteroaryl);
wherein each of the 5- to 14-membered heteroaryl and C$_{1-4}$ alkylene of R$_2$ is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and
further wherein the 5- to 14-membered heteroaryl of R$_2$ is optionally substituted with 1, 2, or 3 oxo moieties.

In another embodiment of Formula (IIg), R$_1$ is unsubstituted C$_{1-2}$ alkoxy.

In another embodiment of Formula (IIg), R$_1$ is —OCH$_3$.

In another embodiment of Formula (IIg), R$_1$ is —OCH$_2$CF$_3$.

In another embodiment of Formula (IIg), R$_2$ is unsubstituted C$_{1-4}$ alkylene-(5- to 14-membered heteroaryl).

In another embodiment of Formula (IIg), R$_2$ is C$_{1-4}$ alkylene-(5- to 14-membered heteroaryl), wherein the 5- to 14-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 14-membered heteroaryl), wherein the C$_{1-4}$ alkylene is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 14-membered heteroaryl), wherein each of the C$_{1-4}$ alkylene and 5- to 14-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 10-membered heteroaryl).

In another embodiment of Formula (IIg), R$_2$ is unsubstituted C$_{1-4}$ alkylene-(5- to 10-membered heteroaryl).

In another embodiment of Formula (IIg), R$_2$ is C$_{1-4}$ alkylene-(5- to 10-membered heteroaryl), wherein the 5- to 10-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 10-membered heteroaryl), wherein the C$_{1-4}$ alkylene is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 10-membered heteroaryl), wherein each of the C$_{1-4}$ alkylene and 5- to 10-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 7-membered heteroaryl).

In another embodiment of Formula (IIg), R$_2$ is unsubstituted C$_{1-4}$ alkylene-(5- to 7-membered heteroaryl).

In another embodiment of Formula (IIg), R$_2$ is C$_{1-4}$ alkylene-(5- to 7-membered heteroaryl), wherein the 5- to 7-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 7-membered heteroaryl), wherein the C$_{1-4}$ alkylene is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5- to 7-membered heteroaryl), wherein each of the C$_{1-4}$ alkylene and 5- to 7-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5-membered heteroaryl).

In another embodiment of Formula (IIg), R$_2$ is unsubstituted C$_{1-4}$ alkylene-(5-membered heteroaryl).

In another embodiment of Formula (IIg), R$_2$ is C$_{1-4}$ alkylene-(5-membered heteroaryl), wherein the 5-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5-membered heteroaryl), wherein the C$_{1-4}$ alkylene is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(5-membered heteroaryl), wherein each of the C$_{1-4}$ alkylene and 5-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(6-membered heteroaryl).

In another embodiment of Formula (IIg), R$_2$ is unsubstituted C$_{1-4}$ alkylene-(6-membered heteroaryl).

In another embodiment of Formula (IIg), R$_2$ is C$_{1-4}$ alkylene-(6-membered heteroaryl), wherein the 6-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(6-membered heteroaryl), wherein the C$_{1-4}$ alkylene is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(6-membered heteroaryl), wherein each of the C$_{1-4}$ alkylene and 6-membered heteroaryl is substituted with 1 or 2 substituents independently selected from the group consisting of —OH, halo, C$_{1-4}$ alkyl, and C$_{1-4}$ alkoxy.

In another embodiment of Formula (IIg), R$_2$ is C$_{1-4}$ alkylene-(7-membered heteroaryl).

In another embodiment of Formula (IIg), R$_2$ is unsubstituted C$_{1-4}$ alkylene-(7-membered heteroaryl).

In another embodiment of Formula (IIg), R$_2$ is C$_{1-4}$ alkylene-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(7-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(7-membered heteroaryl), wherein each of the $C_{1-4}$ alkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(8-membered heteroaryl).

In another embodiment of Formula (IIg), $R_2$ is unsubstituted $C_{1-4}$ alkylene-(8-membered heteroaryl).

In another embodiment of Formula (IIg), $R_2$ is $C_{1-4}$ alkylene-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(8-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(8-membered heteroaryl), wherein each of the $C_{1-4}$ alkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(9-membered heteroaryl).

In another embodiment of Formula (IIg), $R_2$ is unsubstituted $C_{1-4}$ alkylene-(9-membered heteroaryl).

In another embodiment of Formula (IIg), $R_2$ is $C_{1-4}$ alkylene-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(9-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(9-membered heteroaryl), wherein each of the $C_{1-4}$ alkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(imidazolyl).

In another embodiment of Formula (IIg), $R_2$ is unsubstituted $C_{1-4}$ alkylene-(imidazolyl).

In another embodiment of Formula (IIg), $R_2$ is $C_{1-4}$ alkylene-(imidazolyl), wherein one or both of the $C_{1-4}$ alkylene and imidazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(1-methyl-imidazolyl).

In another embodiment of Formula (IIg), $R_2$ is unsubstituted $C_{1-4}$ alkylene-(1-methyl-imidazolyl).

In another embodiment of Formula (IIg), $R_2$ is $C_{1-4}$ alkylene-(1-methyl-imidazolyl), wherein one or both of the $C_{1-4}$ alkylene and 1-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(2-methyl-imidazolyl).

In another embodiment of Formula (IIg), $R_2$ is unsubstituted $C_{1-4}$ alkylene-(2-methyl-imidazolyl).

In another embodiment of Formula (IIg), $R_2$ is $C_{1-4}$ alkylene-(2-methyl-imidazolyl), wherein one or both of the $C_{1-4}$ alkylene and 2-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(3-methyl-imidazolyl).

In another embodiment of Formula (IIg), $R_2$ is unsubstituted $C_{1-4}$ alkylene-(3-methyl-imidazolyl).

In another embodiment of Formula (IIg), $R_2$ is $C_{1-4}$ alkylene-(3-methyl-imidazolyl), wherein one or both of the $C_{1-4}$ alkylene and 3-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(pyrazolyl).

In another embodiment of Formula (IIg), $R_2$ is unsubstituted $C_{1-4}$ alkylene-(pyrazolyl).

In another embodiment of Formula (IIg), $R_2$ is $C_{1-4}$ alkylene-(pyrazolyl), wherein one or both of the $C_{1-4}$ alkylene and pyrazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(oxazolyl).

In another embodiment of Formula (IIg), $R_2$ is unsubstituted $C_{1-4}$ alkylene-(oxazolyl).

In another embodiment of Formula (IIg), $R_2$ is $C_{1-4}$ alkylene-(oxazolyl), wherein one or both of the $C_{1-4}$ alkylene and oxazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(isoxazolyl).

In another embodiment of Formula (IIg), $R_2$ is unsubstituted $C_{1-4}$ alkylene-(isoxazolyl).

In another embodiment of Formula (IIg), $R_2$ is $C_{1-4}$ alkylene-(isoxazolyl), wherein one or both of the $C_{1-4}$ alkylene and isoxazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(triazolyl).

In another embodiment of Formula (IIg), $R_2$ is unsubstituted $C_{1-4}$ alkylene-(triazolyl).

In another embodiment of Formula (IIg), $R_2$ is $C_{1-4}$ alkylene-(triazolyl), wherein one or both of the $C_{1-4}$ alkylene and triazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(1-methyl-triazolyl).

In another embodiment of Formula (IIg), $R_2$ is unsubstituted $C_{1-4}$ alkylene-(1-methyl-triazolyl).

In another embodiment of Formula (IIg), $R_2$ is $C_{1-4}$ alkylene-(1-methyl-triazolyl), wherein one or both of the $C_{1-4}$ alkylene and 1-methyl-triazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(3-methyl-triazolyl).

In another embodiment of Formula (IIg), $R_2$ is unsubstituted $C_{1-4}$ alkylene-(3-methyl-triazolyl).

In another embodiment of Formula (IIg), $R_2$ is $C_{1-4}$ alkylene-(3-methyl-triazolyl), wherein one or both of the $C_{1-4}$ alkylene and 3-methyl-triazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(pyridinyl).

In another embodiment of Formula (IIg), $R_2$ is unsubstituted $C_{1-4}$ alkylene-(pyridinyl).

In another embodiment of Formula (IIg), $R_2$ is $C_{1-4}$ alkylene-(pyridinyl), wherein one or both of the $C_{1-4}$ alkylene and pyridinyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is unsubstituted $C_{1-4}$ alkylene-(pyridin-2-yl).

In another embodiment of Formula (IIg), $R_2$ is unsubstituted $C_{1-4}$ alkylene-(pyridin-3-yl).

In another embodiment of Formula (IIg), $R_2$ is unsubstituted $C_{1-4}$ alkylene-(pyridin-4-yl).

In another embodiment of Formula (IIg), $R_2$ is $C_{1-4}$ alkylene-(indazolyl).

In another embodiment of Formula (IIg), $R_2$ is unsubstituted $C_{1-4}$ alkylene-(indazolyl).

In another embodiment of Formula (IIg), $R_2$ is $C_{1-4}$ alkylene-(indazolyl), wherein one or both of the $C_{1-4}$ alkylene and indazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(benzimidazolyl).

In another embodiment of Formula (IIg), $R_2$ is unsubstituted $C_{1-4}$ alkylene-(benzimidazolyl).

In another embodiment of Formula (IIg), $R_2$ is $C_{1-4}$ alkylene-(benzimidazolyl), wherein one or both of the $C_{1-4}$ alkylene and benzimidazolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(indolyl).

In another embodiment of Formula (IIg), $R_2$ is unsubstituted $C_{1-4}$ alkylene-(indolyl).

In another embodiment of Formula (IIg), $R_2$ is $C_{1-4}$ alkylene-(indolyl), wherein one or both of the $C_{1-4}$ alkylene and indolyl is substituted with 1 or 2 substituents independently selected from the group consisting of —OH, halo, $C_{1-4}$ alkyl, and $C_{1-4}$ alkoxy.

In another embodiment of Formula (IIg), $R_2$ is $C_{1-4}$ alkylene-(isoindolyl).

In another embodiment of Formula (IIg), $R_2$ is unsubstituted $C_{1-4}$ alkylene-(isoindolyl).

In another embodiment of Formula (IIg), $R_2$ is $C_{1-4}$ alkylene-(isoindolyl), wherein one or both of the $C_{1-4}$ alkylene and isoindolyl is substituted with 1 or 2 substituents independently selected from the group consisting of —OH, halo, $C_{1-4}$ alkyl, and $C_{1-4}$ alkoxy.

In an embodiment, the compound of Formula (II) has the structure of Formula (IIh):

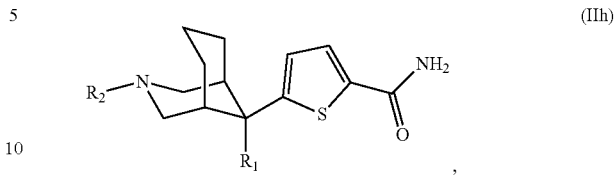

(IIh)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $(C_{3-10}$ cycloalkylene)-$(C_{6-14}$ aryl) or $(C_{3-10}$ cycloalkylene)-(5- to 14-membered heteroaryl);
wherein each of the $C_{3-10}$ cycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the 5- to 14-membered heteroaryl of $R_2$ is optionally substituted with 1, 2, or 3 oxo moieties.

In another embodiment of Formula (IIh), $R_1$ is unsubstituted $C_{1-2}$ alkoxy.

In another embodiment of Formula (IIh), $R_1$ is —OCH$_3$.

In another embodiment of Formula (IIh), $R_1$ is —OCH$_2$CF$_3$.

In another embodiment of Formula (IIh), $R_2$ is $(C_{3-10}$ cycloalkylene)-$(C_{6-14}$ aryl).

In another embodiment of Formula (IIh), $R_2$ is unsubstituted $(C_{3-10}$ cycloalkylene)-$(C_{6-14}$ aryl).

In another embodiment of Formula (IIh), $R_2$ is $(C_{3-7}$ cycloalkylene)-$(C_{1-4}$ aryl).

In another embodiment of Formula (IIh), $R_2$ is unsubstituted $(C_{3-7}$ cycloalkylene)-$(C_{1-4}$ aryl).

In another embodiment of Formula (IIh), $R_2$ is $(C_{3-7}$ cycloalkylene)-$(C_{1-4}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-$(C_{1-4}$ aryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-$(C_{1-4}$ aryl), wherein each of the $C_{3-7}$ cycloalkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-$(C_{6-10}$ aryl).

In another embodiment of Formula (IIh), $R_2$ is unsubstituted $(C_{3-7}$ cycloalkylene)-$(C_{6-10}$ aryl).

In another embodiment of Formula (IIh), $R_2$ is $(C_{3-7}$ cycloalkylene)-$(C_{6-10}$ aryl) wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-$(C_{6-10}$ aryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-$(C_{6-10}$ aryl), wherein each of the $C_{3-7}$ cycloalkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(phenyl).

In another embodiment of Formula (IIh), $R_2$ is unsubstituted $(C_{3-7}$ cycloalkylene)-(phenyl).

In another embodiment of Formula (IIh), $R_2$ is $(C_{3-7}$ cycloalkylene)-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(phenyl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(phenyl), wherein each of the $C_{3-7}$ cycloalkylene and phenyl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-10}$ cycloalkylene)-(5- to 14-membered heteroaryl).

In another embodiment of Formula (IIh), $R_2$ is unsubstituted $(C_{3-10}$ cycloalkylene)-(5- to 14-membered heteroaryl).

In another embodiment of Formula (IIh), $R_2$ is $(C_{3-7}$ cycloalkylene)-(5- to 14-membered heteroaryl).

In another embodiment of Formula (IIh), $R_2$ is unsubstituted $(C_{3-7}$ cycloalkylene)-(5- to 14-membered heteroaryl).

In another embodiment of Formula (IIh), $R_2$ is $(C_{3-7}$ cycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 14-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 14-membered heteroaryl), wherein each of the $C_{3-7}$ cycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 10-membered heteroaryl).

In another embodiment of Formula (IIh), $R_2$ is unsubstituted $(C_{3-7}$ cycloalkylene)-(5- to 10-membered heteroaryl).

In another embodiment of Formula (IIh), $R_2$ is $(C_{3-7}$ cycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 10-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 10-membered heteroaryl), wherein each of the $C_{3-7}$ cycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 7-membered heteroaryl).

In another embodiment of Formula (IIh), $R_2$ is unsubstituted $(C_{3-7}$ cycloalkylene)-(5- to 7-membered heteroaryl).

In another embodiment of Formula (IIh), $R_2$ is $(C_{3-7}$ cycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 7-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5- to 7-membered heteroaryl), wherein each of the $C_{3-7}$ cycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5-membered heteroaryl).

In another embodiment of Formula (IIh), $R_2$ is unsubstituted $(C_{3-7}$ cycloalkylene)-(5-membered heteroaryl).

In another embodiment of Formula (IIh), $R_2$ is $(C_{3-7}$ cycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(5-membered heteroaryl), wherein each of the $C_{3-7}$ cycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(6-membered heteroaryl).

In another embodiment of Formula (IIh), $R_2$ is unsubstituted $(C_{3-7}$ cycloalkylene)-(6-membered heteroaryl).

In another embodiment of Formula (IIh), $R_2$ is $(C_{3-7}$ cycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(6-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(6-membered heteroaryl), wherein each of the $C_{3-7}$ cycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIh), $R_2$ is $(C_{3-7}$ cycloalkylene)-(7-membered heteroaryl).

In another embodiment of Formula (IIh), $R_2$ is unsubstituted $(C_{3-7}$ cycloalkylene)-(7-membered heteroaryl).

In another embodiment of Formula (IIh), R$_2$ is (C$_{3-7}$ cycloalkylene)-(7-membered heteroaryl), wherein the 7-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(7-membered heteroaryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(7-membered heteroaryl), wherein each of the C$_{3-7}$ cycloalkylene and 7-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(8-membered heteroaryl).

In another embodiment of Formula (IIh), R$_2$ is unsubstituted (C$_{3-7}$ cycloalkylene)-(8-membered heteroaryl).

In another embodiment of Formula (IIh), R$_2$ is (C$_{3-7}$ cycloalkylene)-(8-membered heteroaryl), wherein the 8-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(8-membered heteroaryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(8-membered heteroaryl), wherein each of the C$_{3-7}$ cycloalkylene and 8-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(9-membered heteroaryl).

In another embodiment of Formula (IIh), R$_2$ is unsubstituted (C$_{3-7}$ cycloalkylene)-(9-membered heteroaryl).

In another embodiment of Formula (IIh), R$_2$ is (C$_{3-7}$ cycloalkylene)-(9-membered heteroaryl), wherein the 9-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(9-membered heteroaryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IIh), R$_2$ is (C$_{3-7}$ cycloalkylene)-(9-membered heteroaryl), wherein each of the C$_{3-7}$ cycloalkylene and 9-membered heteroaryl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (cyclobutyl)-(phenyl).

In another embodiment of Formula (IIh), R$_2$ is unsubstituted (cyclobutyl)-(phenyl).

In another embodiment of Formula (IIh), R$_2$ is (cyclobutyl)-(phenyl), wherein one or both of the cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (cyclobutyl)-2-(phenyl).

In another embodiment of Formula (IIh), R$_2$ is unsubstituted (cyclobutyl)-2-(phenyl).

In another embodiment of Formula (IIh), R$_2$ is (cyclobutyl)-2-(phenyl), wherein one or both of the 2-cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (cyclobutyl)-3-(phenyl).

In another embodiment of Formula (IIh), R$_2$ is unsubstituted (cyclobutyl)-3-(phenyl).

In another embodiment of Formula (IIh), R$_2$ is (cyclobutyl)-3-(phenyl), wherein one or both of the 3-cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IIh), R$_2$ is (bicyclo[1.1.1]pentyl)-(phenyl).

In another embodiment of Formula (IIh), R$_2$ is unsubstituted (bicyclo[1.1.1]pentyl)-(phenyl).

In another embodiment of Formula (IIh), R$_2$ is (bicyclo[1.1.1]pentyl)-(phenyl), wherein one or both of the bicyclo[1.1.1]pentyl and phenyl is substituted with 1 or 2 substituents independently selected from the group consisting of —OH, halo, C$_{1-4}$ alkyl, and C$_{1-4}$ alkoxy.

In an embodiment, the compound of Formula (II) has the structure of Formula (IIi):

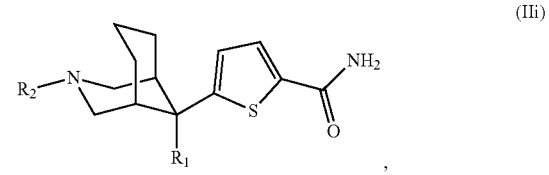

(IIi)

or a pharmaceutically acceptable salt thereof, wherein:

R$_1$ is C$_{1-2}$ alkoxy, wherein the C$_{1-2}$ alkoxy is optionally substituted with 1, 2, or 3 halo substituents;

R$_2$ is (4- to 12-membered heterocycloalkylene)-(C$_{6-14}$ aryl) or (4- to 12-membered heterocycloalkylene)-(5- to 14-membered heteroaryl);

wherein each of the 4- to 12-membered heterocycloalkylene, C$_{6-14}$ aryl, and 5- to 14-membered heteroaryl of R$_2$ is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and further wherein the 5- to 14-membered heteroaryl of R$_2$ is optionally substituted with 1, 2, or 3 oxo moieties.

In another embodiment of Formula (IIi), R$_1$ is unsubstituted C$_{1-2}$ alkoxy.

In another embodiment of Formula (IIi), R$_1$ is —OCH$_3$.

In another embodiment of Formula (IIi), R$_1$ is —OCH$_2$CF$_3$.

In another embodiment of Formula (IIi), R$_2$ is (4- to 12-membered heterocycloalkylene)-(C$_{1-4}$ aryl).

In another embodiment of Formula (IIi), R$_2$ is unsubstituted (4- to 12-membered heterocycloalkylene)-(C$_{1-4}$ aryl).

In another embodiment of Formula (IIi), R$_2$ is (4- to 7-membered heterocycloalkylene)-(C$_{6-14}$ aryl).

In another embodiment of Formula (IIi), R$_2$ is unsubstituted (4- to 7-membered heterocycloalkylene)-(C$_{1-4}$ aryl).

In another embodiment of Formula (IIi), $R_2$ is (4- to 7-membered heterocycloalkylene)-($C_{6-14}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-($C_{6-14}$ aryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-($C_{6-14}$ aryl), wherein each of the 4- to 7-membered heterocycloalkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-($C_{6-10}$ aryl).

In another embodiment of Formula (IIi), $R_2$ is unsubstituted (4- to 7-membered heterocycloalkylene)-($C_{6-10}$ aryl).

In another embodiment of Formula (IIi), $R_2$ is (4- to 7-membered heterocycloalkylene)-($C_{6-10}$ aryl) wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-($C_{6-10}$ aryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-($C_{6-10}$ aryl), wherein each of the 4- to 7-membered heterocycloalkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(phenyl).

In another embodiment of Formula (IIi), $R_2$ is unsubstituted (4- to 7-membered heterocycloalkylene)-(phenyl).

In another embodiment of Formula (IIi), $R_2$ is (4- to 7-membered heterocycloalkylene)-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(phenyl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(phenyl), wherein each of the 4- to 7-membered heterocycloalkylene and phenyl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 12-membered heterocycloalkylene)-(5- to 14-membered heteroaryl).

In another embodiment of Formula (IIi), $R_2$ is unsubstituted (4- to 12-membered heterocycloalkylene)-(5- to 14-membered heteroaryl).

In another embodiment of Formula (IIi), $R_2$ is (4- to 7-membered heterocycloalkylene)-(5- to 14-membered heteroaryl).

In another embodiment of Formula (IIi), $R_2$ is unsubstituted (4- to 7-membered heterocycloalkylene)-(5- to 14-membered heteroaryl).

In another embodiment of Formula (IIi), $R_2$ is (4- to 7-membered heterocycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 14-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 14-membered heteroaryl), wherein each of the 4- to 7-membered heterocycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 10-membered heteroaryl).

In another embodiment of Formula (IIi), $R_2$ is unsubstituted (4- to 7-membered heterocycloalkylene)-(5- to 10-membered heteroaryl).

In another embodiment of Formula (IIi), $R_2$ is (4- to 7-membered heterocycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 10-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 10-membered heteroaryl), wherein each of the 4- to 7-membered heterocycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 7-membered heteroaryl).

In another embodiment of Formula (IIi), $R_2$ is unsubstituted (4- to 7-membered heterocycloalkylene)-(5- to 7-membered heteroaryl).

In another embodiment of Formula (IIi), $R_2$ is (4- to 7-membered heterocycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5- to 7-membered heteroaryl), wherein each of the 4- to 7-membered heterocycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5-membered heteroaryl).

In another embodiment of Formula (IIi), $R_2$ is unsubstituted (4- to 7-membered heterocycloalkylene)-(5-membered heteroaryl).

In another embodiment of Formula (IIi), $R_2$ is (4- to 7-membered heterocycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(5-membered heteroaryl), wherein each of the 4- to 7-membered heterocycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(6-membered heteroaryl).

In another embodiment of Formula (IIi), $R_2$ is unsubstituted (4- to 7-membered heterocycloalkylene)-(6-membered heteroaryl).

In another embodiment of Formula (IIi), $R_2$ is (4- to 7-membered heterocycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(6-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(6-membered heteroaryl), wherein each of the 4- to 7-membered heterocycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(7-membered heteroaryl).

In another embodiment of Formula (IIi), $R_2$ is unsubstituted (4- to 7-membered heterocycloalkylene)-(7-membered heteroaryl).

In another embodiment of Formula (IIi), $R_2$ is (4- to 7-membered heterocycloalkylene)-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(7-membered heteroaryl), wherein each of the 4- to 7-membered heterocycloalkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(8-membered heteroaryl).

In another embodiment of Formula (IIi), $R_2$ is unsubstituted (4- to 7-membered heterocycloalkylene)-(8-membered heteroaryl).

In another embodiment of Formula (IIi), $R_2$ is (4- to 7-membered heterocycloalkylene)-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(8-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(8-membered heteroaryl), wherein each of the 4- to 7-membered heterocycloalkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(9-membered heteroaryl).

In another embodiment of Formula (IIi), $R_2$ is unsubstituted (4- to 7-membered heterocycloalkylene)-(9-membered heteroaryl).

In another embodiment of Formula (IIi), $R_2$ is (4- to 7-membered heterocycloalkylene)-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(9-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4- to 7-membered heterocycloalkylene)-(9-membered heteroaryl), wherein each of the 4- to 7-membered heterocycloalkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (4-membered heterocycloalkylene)-($C_{6-10}$ aryl).

In another embodiment of Formula (IIi), $R_2$ is unsubstituted (4-membered heterocycloalkylene)-($C_{6-10}$ aryl).

In another embodiment of Formula (IIi), $R_2$ is (5-membered heterocycloalkylene)-($C_{6-10}$ aryl).

In another embodiment of Formula (IIi), $R_2$ is unsubstituted (5-membered heterocycloalkylene)-($C_{6-10}$ aryl).

In another embodiment of Formula (IIi), $R_2$ is (6-membered heterocycloalkylene)-($C_{6-10}$ aryl).

In another embodiment of Formula (IIi), $R_2$ is unsubstituted (6-membered heterocycloalkylene)-($C_{6-10}$ aryl).

In another embodiment of Formula (IIi), $R_2$ is (7-membered heterocycloalkylene)-($C_{6-10}$ aryl).

In another embodiment of Formula (IIi), $R_2$ is unsubstituted (7-membered heterocycloalkylene)-($C_{6-10}$ aryl).

In another embodiment of Formula (IIi), $R_2$ is (8-membered heterocycloalkylene)-($C_{6-10}$ aryl).

In another embodiment of Formula (IIi), $R_2$ is unsubstituted (8-membered heterocycloalkylene)-($C_{6-10}$ aryl).

In another embodiment of Formula (IIi), $R_2$ is (9-membered heterocycloalkylene)-($C_{6-10}$ aryl).

In another embodiment of Formula (IIi), $R_2$ is unsubstituted (9-membered heterocycloalkylene)-($C_{6-10}$ aryl).

In another embodiment of Formula (IIi), $R_2$ is (4-membered heterocycloalkylene)-(phenyl).

In another embodiment of Formula (IIi), $R_2$ is unsubstituted (4-membered heterocycloalkylene)-(phenyl).

In another embodiment of Formula (IIi), $R_2$ is (azetidinyl)-(phenyl).

In another embodiment of Formula (IIi), $R_2$ is unsubstituted (azetidinyl)-(phenyl).

In another embodiment of Formula (IIIi), $R_2$ is (azetidinyl)-(phenyl), wherein one or both of the azetidinyl and phenyl is substituted with 1 or 2 substituents independently selected from the group consisting of —OH, halo, $C_{1-4}$ alkyl, and $C_{1-4}$ alkoxy.

In another embodiment of Formula (IIi), $R_2$ is (azetidinyl)-(N-phenyl).

In another embodiment of Formula (IIi), $R_2$ is unsubstituted (azetidinyl)-(N-phenyl).

In another embodiment of Formula (IIi), $R_2$ is (azetidinyl)-(N-phenyl), wherein one or both of the azetidinyl and N-phenyl is substituted with 1 or 2 substituents independently selected from the group consisting of —OH, halo, $C_{1-4}$ alkyl, and $C_{1-4}$ alkoxy.

In an embodiment, the compound of Formula (I) has the structure of Formula (III):

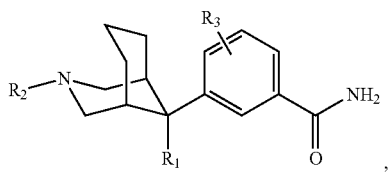

(III)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl);

further wherein the $C_{3-10}$ cycloalkyl, 5- to 14-membered heteroaryl, or 4- to 12-membered heterocycloalkyl of $R_2$ is optionally substituted with 1, 2, or 3 oxo moieties; and $R_3$ is hydrogen, OH, halo, $C_{1-4}$ alkyl, or $C_{1-4}$ alkoxy.

In another embodiment of Formula (III), $R_1$ is unsubstituted $C_{1-2}$ alkoxy.

In another embodiment of Formula (III), $R_1$ is —$OCH_3$.

In another embodiment of Formula (III), $R_1$ is —$OCH_2CF_3$.

In another embodiment of Formula (III), $R_1$ is —$OCH_3$, and $R_3$ is OH, halo, $C_{1-4}$ alkyl, or $C_{1-4}$ alkoxy.

In another embodiment of Formula (III), $R_1$ is unsubstituted $C_{1-2}$ alkoxy, and $R_3$ is OH, halo, $C_{1-4}$ alkyl, or $C_{1-4}$ alkoxy.

In another embodiment of Formula (III), $R_1$ is —$OCH_2CF_3$, and $R_3$ is OH, halo, $C_{1-4}$ alkyl, or $C_{1-4}$ alkoxy.

In another embodiment of Formula (III), $R_1$ is $C_{1-2}$ alkoxy, $R_2$ is hydrogen, and $R_3$ is hydrogen.

In another embodiment of Formula (III), $R_1$ is —$OCH_2CH_3$, $R_2$ is hydrogen, and $R_3$ is hydrogen.

In another embodiment of Formula (III), $R_1$ is —$OCH_3$, $R_3$ is OH, halo, $C_{1-4}$ alkyl, or $C_{1-4}$ alkoxy, and $R_2$ is hydrogen.

In another embodiment of Formula (III), $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (III), $R_1$ is —$OCH_3$, $R_3$ is OH, halo, $C_{1-4}$ alkyl, or $C_{1-4}$ alkoxy, and $R_2$ is $C_{3-10}$ cycloalkyl.

In another embodiment of Formula (III), $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (III), $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (III), $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (III), $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (III), $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (III), $R_1$ is —$OCH_3$, $R_3$ is OH, halo, $C_{1-4}$ alkyl, or $C_{1-4}$ alkoxy, and $R_2$ is $C_{1-4}$ alkylene-($C_{1-4}$ aryl).

In another embodiment of Formula (III), $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (III), $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (III), $R_1$ is —$OCH_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (III), $R_1$ is —$OCH_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (III), $R_1$ is —$OCH_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In another embodiment of Formula (III), $R_3$ is halo.

In another embodiment of Formula (III), $R_3$ is fluoro.

In another embodiment of Formula (III), $R_3$ is OH.

In another embodiment of Formula (III), $R_3$ is hydrogen.

In an embodiment, the compound of Formula (III) has the structure of Formula (IIIa):

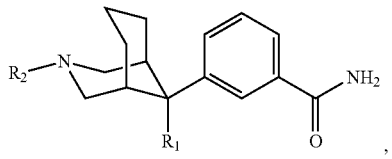

(IIIa)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the $C_{3-10}$ cycloalkyl, 5- to 14-membered heteroaryl, or 4- to 12-membered heterocycloalkyl of $R_2$ is optionally substituted with 1, 2, or 3 oxo moieties.

In another embodiment of Formula (IIIa), $R_1$ is unsubstituted $C_{1-2}$ alkoxy.

In another embodiment of Formula (IIIa), $R_1$ is —$OCH_3$.

In another embodiment of Formula (IIIa), $R_1$ is —$OCH_2CH_3$.

In another embodiment of Formula (IIIa), $R_1$ is —$OCH_2CF_3$.

In another embodiment of Formula (IIIa), $R_2$ is hydrogen, $C_{1-6}$ alkyl, $C_{3-10}$ cycloalkyl, or 4- to 12-membered heterocycloalkyl.

In another embodiment of Formula (IIIa), $R_2$ is hydrogen, $C_{1-6}$ alkyl, $C_{3-7}$ cycloalkyl, or 4- to 10-membered heterocycloalkyl.

In another embodiment of Formula (IIIa), $R_2$ is hydrogen, $C_{1-6}$ alkyl, $C_{3-7}$ cycloalkyl, or 4- to 7-membered heterocycloalkyl.

In another embodiment of Formula (IIIa), $R_2$ is $C_{3-10}$ cycloalkyl, 4- to 12-membered heterocycloalkyl, $C_{1-4}$ alkylene-($C_{3-10}$ cycloalkyl), or $C_{1-4}$ alkylene-(4- to 12-membered heterocycloalkyl).

In another embodiment of Formula (IIIa), $R_2$ is $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IIIa), $R_2$ is $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IIIa), $R_2$ is hydrogen, $C_{1-6}$ alkyl, $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IIIa), $R_2$ is hydrogen, $C_{1-6}$ alkyl, $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IIIa), $R_2$ is $C_{1-4}$ alkylene-($C_{3-10}$ cycloalkyl) or $C_{1-4}$ alkylene-(4- to 12-membered heterocycloalkyl).

In another embodiment of Formula (IIIa), $R_2$ is $C_{1-4}$ alkylene-($C_{3-7}$ cycloalkyl) or $C_{1-4}$ alkylene-(4- to 10-membered heterocycloalkyl).

In another embodiment of Formula (IIIa), $R_2$ is $C_{1-4}$ alkylene-($C_{3-7}$ cycloalkyl) or $C_{1-4}$ alkylene-(4- to 7-membered heterocycloalkyl).

In another embodiment of Formula (IIIa), $R_2$ is hydrogen or $C_{1-6}$ alkyl.

In another embodiment of Formula (IIIa), $R_2$ is hydrogen, $C_{1-6}$ alkyl, $C_{1-4}$ alkylene-$CF_3$ or $C_{1-6}$ alkenyl.

In another embodiment of Formula (IIIa), $R_2$ is hydrogen, $C_{1-4}$ alkylene-$CF_3$ or $C_{1-6}$ alkenyl.

In another embodiment of Formula (IIIa), $R_2$ is $C_{3-10}$ cycloalkyl or 4- to 12-membered heterocycloalkyl.

In another embodiment of Formula (IIIa), $R_2$ is $C_{3-7}$ cycloalkyl or 4- to 10-membered heterocycloalkyl.

In another embodiment of Formula (IIIa), $R_2$ is $C_{3-7}$ cycloalkyl or 4- to 7-membered heterocycloalkyl.

In another embodiment of Formula (IIIa), $R_2$ is hydrogen, $C_{1-6}$ alkyl, or $C_{1-4}$ alkylene-$CF_3$.

In another embodiment of Formula (IIIa), $R_1$ is $C_{1-2}$ alkoxy and $R_2$ is hydrogen.

In another embodiment of Formula (IIIa), $R_1$ is —$OCH_2CH_3$ and $R_2$ is hydrogen.

In another embodiment of Formula (IIIa), $R_2$ is ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl).

In another embodiment of Formula (IIIa), $R_2$ is ($C_{3-7}$ cycloalkylene)-($C_{6-10}$ aryl), ($C_{3-7}$ cycloalkylene)-(5- to 10-membered heteroaryl), (4- to 10-membered heterocycloalkylene)-($C_{5-10}$ aryl), or (4- to 10-membered heterocycloalkylene)-(5- to 10-membered heteroaryl).

In another embodiment of Formula (IIIa), $R_2$ is ($C_{3-7}$ cycloalkylene)-($C_{6-10}$ aryl), ($C_{3-7}$ cycloalkylene)-(5- to 7-membered heteroaryl), (4- to 7-membered heterocycloalkylene)-($C_{6-10}$ aryl), or (4- to 7-membered heterocycloalkylene)-(5- to 7-membered heteroaryl).

In another embodiment of Formula (IIIa), $R_2$ is ($C_{3-7}$ cycloalkylene)-($C_{6-10}$ aryl) or ($C_{3-7}$ cycloalkylene)-(5- to 7-membered heteroaryl).

In another embodiment of Formula (IIIa), $R_2$ is (4- to 7-membered heterocycloalkylene)-($C_{6-10}$ aryl) or (4- to 7-membered heterocycloalkylene)-(5- to 7-membered heteroaryl).

In another embodiment of Formula (IIIa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (7- to 9-membered heterocycloalkylene)-(7- to 9-membered heteroaryl).

In another embodiment of Formula (IIIa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (5- to 7-membered heterocycloalkylene)-(7- to 9-membered heteroaryl).

In another embodiment of Formula (IIIa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (7- to 9-membered heterocycloalkylene)-(5- to 7-membered heteroaryl).

In another embodiment of Formula (IIIa), $R_2$ is ($C_{3-7}$ cycloalkylene)-($C_{6-10}$ aryl) or ($C_{3-7}$ cycloalkylene)-(7- to 9-membered heteroaryl).

In another embodiment of Formula (IIIa), $R_2$ is (7- to 9-membered heterocycloalkylene)-($C_{6-10}$ aryl) or (7- to 9-membered heterocycloalkylene)-(7- to 9-membered heteroaryl).

In another embodiment of Formula (IIIa), $R_2$ is (7- to 9-membered heterocycloalkylene)-($C_{6-10}$ aryl) or (5- to 7-membered heterocycloalkylene)-(7- to 9-membered heteroaryl).

In another embodiment of Formula (IIIa), $R_2$ is (7- to 9-membered heterocycloalkylene)-($C_{6-10}$ aryl) or (7- to 9-membered heterocycloalkylene)-(5- to 7-membered heteroaryl).

In another embodiment of Formula (IIIa), $R_2$ is $C_{1-4}$ alkylene-($C_{6-14}$ aryl), ($C_{3-10}$ cycloalkylene)-($C_{6-14}$ aryl), or (4- to 12-membered heterocycloalkylene)-($C_{6-14}$ aryl).

In another embodiment of Formula (IIIa), $R_2$ is $C_{1-4}$ alkylene-($C_{6-10}$ aryl), ($C_{3-7}$ cycloalkylene)-($C_{6-10}$ aryl), or (4- to 7-membered heterocycloalkylene)-($C_{6-10}$ aryl).

In another embodiment of Formula (IIIa), $R_2$ is $C_{1-4}$ alkylene-($C_{6-14}$ aryl) or ($C_{3-10}$ cycloalkylene)-($C_{6-14}$ aryl).

In another embodiment of Formula (IIIa), $R_2$ is ($C_{3-10}$ cycloalkylene)-($C_{1-4}$ aryl) or (4- to 12-membered heterocycloalkylene)-($C_{6-14}$ aryl).

In another embodiment of Formula (IIIa), $R_2$ is $C_{1-4}$ alkylene-($C_{6-14}$ aryl) or (4- to 12-membered heterocycloalkylene)-($C_{6-14}$ aryl).

In another embodiment of Formula (IIIa), $R_2$ is $C_{1-4}$ alkylene-($C_{6-10}$ aryl) or ($C_{3-7}$ cycloalkylene)-($C_{6-10}$ aryl).

In another embodiment of Formula (IIIa), $R_2$ is ($C_{3-7}$ cycloalkylene)-($C_{6-10}$ aryl) or (4- to 7-membered heterocycloalkylene)-($C_{6-10}$ aryl).

In another embodiment of Formula (IIIa), $R_2$ is $C_{1-4}$ alkylene-($C_{6-10}$ aryl) or (4- to 7-membered heterocycloalkylene)-($C_{6-10}$ aryl).

In another embodiment of Formula (IIIa), $R_2$ is $C_{1-4}$ alkylene-(5- to 14-membered heteroaryl), ($C_{3-10}$ cycloalkylene)-(5- to 14-membered heteroaryl), or (4- to 12-membered heterocycloalkylene)-(5- to 14-membered heteroaryl).

In another embodiment of Formula (IIIa), $R_2$ is $C_{1-4}$ alkylene-(5- to 10-membered heteroaryl), ($C_{3-7}$ cycloalkylene)-(5- to 10-membered heteroaryl), or (4- to 7-membered heterocycloalkylene)-(5- to 10-membered heteroaryl).

In another embodiment of Formula (IIIa), $R_2$ is $C_{1-4}$ alkylene-(5- to 7-membered heteroaryl), ($C_{3-7}$ cycloalkylene)-(5- to 7-membered heteroaryl), or (4- to 7-membered heterocycloalkylene)-(5- to 7-membered heteroaryl).

In an embodiment, the compound of Formula (III) has the structure of Formula (IIIb):

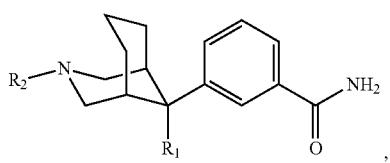

(IIIb)

or a pharmaceutically acceptable salt thereof, wherein:
$R_1$ is $C_{1-2}$ alkoxy, wherein the $C_{1-2}$ alkoxy is optionally substituted with 1, 2, or 3 halo substituents;
$R_2$ is hydrogen, $C_{1-6}$ alkyl, $C_{1-4}$ alkylene-$CF_3$, or $C_{1-6}$ alkenyl; and
wherein each of the $C_{1-6}$ alkyl, $C_{1-6}$ alkenyl, and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IIIb), $R_1$ is unsubstituted $C_{1-2}$ alkoxy.

In another embodiment of Formula (IIIb), $R_1$ is —OCH$_3$.

In another embodiment of Formula (IIIb), $R_1$ is —OCH$_2$CH$_3$.

In another embodiment of Formula (IIIb), $R_1$ is —OCH$_2$CF$_3$.

In another embodiment of Formula (IIIb), $R_1$ is $C_{1-2}$ alkoxy and $R_2$ is hydrogen.

In another embodiment of Formula (IIIb), $R_1$ is —OCH$_2$CH$_3$ and $R_2$ is hydrogen.

In another embodiment of Formula (IIIb), $R_2$ is hydrogen, $C_{1-4}$ alkylene-$CF_3$, or $C_{1-6}$ alkenyl.

In another embodiment of Formula (IIIb), $R_2$ is $C_{1-6}$ alkyl, $C_{1-4}$ alkylene-$CF_3$, or $C_{1-6}$ alkenyl.

In another embodiment of Formula (IIIb), $R_2$ is hydrogen, $C_{1-6}$ alkyl, or $C_{1-6}$ alkenyl.

In another embodiment of Formula (IIIb), $R_2$ is hydrogen, $C_{1-6}$ alkyl, or $C_{1-4}$ alkylene-$CF_3$.

In another embodiment of Formula (IIIb), $R_2$ is hydrogen or $C_{1-6}$ alkyl.

In another embodiment of Formula (IIIb), $R_2$ is hydrogen or $C_{1-4}$ alkylene-$CF_3$.

In another embodiment of Formula (IIIb), $R_2$ is hydrogen or $C_{1-6}$ alkenyl.

In another embodiment of Formula (IIIb), $R_2$ is $C_{1-6}$ alkyl or $C_{1-4}$ alkylene-$CF_3$.

In another embodiment of Formula (IIIb), $R_2$ is $C_{1-6}$ alkyl or $C_{1-6}$ alkenyl.

In another embodiment of Formula (IIIb), $R_2$ is $C_{1-4}$ alkylene-$CF_3$ or $C_{1-6}$ alkenyl.

In another embodiment of Formula (IIIb), $R_2$ is hydrogen.

In another embodiment of Formula (IIIb), $R_2$ is $C_{1-6}$ alkyl.

In another embodiment of Formula (IIIb), $R_2$ is $C_{1-4}$ alkylene-$CF_3$.

In another embodiment of Formula (IIIb), $R_2$ is $C_{1-2}$ alkylene-$CF_3$.

In another embodiment of Formula (IIIb), $R_2$ is $C_{1-6}$ alkenyl.

In another embodiment of Formula (IIIb), $R_2$ is unsubstituted $C_{1-6}$ alkyl.

In another embodiment of Formula (IIIb), $R_2$ is unsubstituted neopentyl.

In another embodiment of Formula (IIIb), $R_2$ is unsubstituted sec-pentyl.

In another embodiment of Formula (IIIb), $R_2$ is unsubstituted $C_{1-4}$ alkyl.

In another embodiment of Formula (IIIb), $R_2$ is unsubstituted propyl.

In another embodiment of Formula (IIIb), $R_2$ is unsubstituted isopropyl.

In another embodiment of Formula (IIIb), $R_2$ is unsubstituted butyl.

In another embodiment of Formula (IIIb), $R_2$ is unsubstituted isobutyl.

In another embodiment of Formula (IIIb), R$_2$ is unsubstituted tert-butyl.

In another embodiment of Formula (IIIb), R$_2$ is unsubstituted C$_{1-2}$ alkyl.

In another embodiment of Formula (IIIb), R$_2$ is unsubstituted ethyl.

In another embodiment of Formula (IIIb), R$_2$ is unsubstituted methyl.

In another embodiment of Formula (IIIb), R$_2$ is deuterated C$_{1-6}$ alkyl.

In another embodiment of Formula (IIIb), R$_2$ is —CD$_3$.

In another embodiment of Formula (IIIb), R$_2$ is C$_{1-6}$ alkyl, wherein the C$_{1-6}$ alkyl is substituted with 1 or 2 substituents independently selected from the group consisting of —OH, halo, C$_{1-4}$ alkyl, and C$_{1-4}$ alkoxy.

In another embodiment of Formula (IIIb), R$_2$ is C$_{1-4}$ alkyl, wherein the C$_{1-4}$ alkyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIIb), R$_2$ is C$_{1-4}$ alkyl, wherein the C$_{1-4}$ alkyl is substituted with 1 or 2 substituents independently selected from the group consisting of —OH, halo, C$_{1-4}$ alkyl, and C$_{1-4}$ alkoxy.

In another embodiment of Formula (IIIb), R$_2$ is C$_{1-4}$ alkyl, wherein the C$_{1-4}$ alkyl is substituted with —S(=O)$_2$—(C$_{1-4}$ alkyl).

In another embodiment of Formula (IIIb), R$_2$ is C$_{1-4}$ alkyl, wherein the C$_{1-4}$ alkyl is substituted with C$_{1-4}$ alkoxy.

In another embodiment of Formula (IIIb), R$_2$ is C$_{1-4}$ alkyl, wherein the C$_{1-4}$ alkyl is substituted with 1 or 2 halo.

In another embodiment of Formula (IIIb), R$_2$ is C$_{1-4}$ alkyl, wherein the C$_{1-4}$ alkyl is substituted with 1 or 2 fluoro.

In another embodiment of Formula (IIIb), R$_2$ is C$_{1-2}$ alkyl, wherein the C$_{1-2}$ alkyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIIb), R$_2$ is C$_{1-2}$ alkyl, wherein the C$_{1-2}$ alkyl is substituted with 1 or 2 substituents independently selected from the group consisting of —OH, halo, C$_{1-4}$ alkyl, and C$_{1-4}$ alkoxy.

In another embodiment of Formula (IIIb), R$_2$ is C$_{1-2}$ alkyl, wherein the C$_{1-2}$ alkyl is substituted with —S(=O)$_2$—(C$_{1-4}$ alkyl).

In another embodiment of Formula (IIIb), R$_2$ is C$_{1-2}$ alkyl, wherein the C$_{1-2}$ alkyl is substituted with C$_{1-4}$ alkoxy.

In another embodiment of Formula (IIIb), R$_2$ is C$_{1-2}$ alkyl, wherein the C$_{1-2}$ alkyl is substituted with 1 or 2 halo.

In another embodiment of Formula (IIIb), R$_2$ is C$_{1-2}$ alkyl, wherein the C$_{1-2}$ alkyl is substituted with 1 or 2 fluoro.

In another embodiment of Formula (IIIb), R$_2$ is unsubstituted C$_{1-4}$ alkylene-CF$_3$.

In another embodiment of Formula (IIIb), R$_2$ is unsubstituted C$_{1-2}$ alkylene-CF$_3$.

In another embodiment of Formula (IIIb), R$_2$ is C$_{1-4}$ alkylene-CF$_3$, wherein the C$_{1-4}$ alkylene-CF$_3$ is substituted with 1 or 2 substituents independently selected from the group consisting of —OH, halo, C$_{1-4}$ alkyl, and C$_{1-4}$ alkoxy.

In another embodiment of Formula (IIIb), R$_2$ is C$_{1-2}$ alkylene-CF$_3$, wherein the C$_{1-2}$ alkylene-CF$_3$ is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIIb), R$_2$ is ethylene-CF$_3$.

In another embodiment of Formula (IIIb), R$_2$ is unsubstituted C$_{1-6}$ alkenyl.

In another embodiment of Formula (IIIb), R$_2$ is unsubstituted C$_{1-4}$ alkenyl.

In another embodiment of Formula (IIIb), R$_2$ is C$_{1-6}$ alkenyl, wherein the C$_{1-6}$ alkenyl is substituted with 1 or 2 substituents independently selected from the group consisting of —OH, halo, C$_{1-4}$ alkyl, and C$_{1-4}$ alkoxy.

In another embodiment of Formula (IIIb), R$_2$ is C$_{1-4}$ alkenyl, wherein the C$_{1-4}$ alkenyl is substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl).

In another embodiment of Formula (IIIb), R$_2$ is allyl.

In an embodiment, the compound of Formula (III) has the structure of Formula (IIIc):

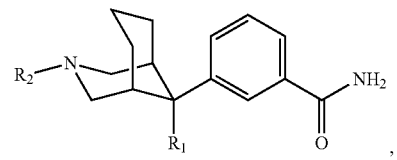

(IIIc)

or a pharmaceutically acceptable salt thereof, wherein:

R$_1$ is C$_{1-2}$ alkoxy, wherein the C$_{1-2}$ alkoxy is optionally substituted with 1, 2, or 3 halo substituents;

R$_2$ is C$_{3-10}$ cycloalkyl;

wherein the C$_{3-10}$ cycloalkyl is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and further wherein the C$_{3-10}$ cycloalkyl is optionally substituted with 1, 2, or 3 oxo moieties.

In another embodiment of Formula (IIIc), R$_1$ is unsubstituted C$_{1-2}$ alkoxy.

In another embodiment of Formula (IIIc), R$_1$ is —OCH$_3$.

In another embodiment of Formula (IIIc), R$_1$ is —OCH$_2$CF$_3$.

In another embodiment of Formula (IIIc), R$_2$ is C$_{3-10}$ cycloalkyl.

In another embodiment of Formula (IIIc), R$_2$ is C$_{3-10}$ cycloalkyl, wherein the C$_{3-10}$ cycloalkyl is substituted with 1 or 2 substituents independently selected from the group consisting of —OH, halo, C$_{1-4}$ alkyl, and C$_{1-4}$ alkoxy.

In another embodiment of Formula (IIIc), R$_2$ is unsubstituted C$_{3-10}$ cycloalkyl.

In another embodiment of Formula (IIIc), R$_2$ is C$_{3-7}$ cycloalkyl.

In another embodiment of Formula (IIIc), R$_2$ is C$_{3-7}$ cycloalkyl, wherein the C$_{3-7}$ cycloalkyl is substituted with 1 or 2 substituents independently selected from the group consisting of —OH, halo, C$_{1-4}$ alkyl, and C$_{1-4}$ alkoxy.

In another embodiment of Formula (IIIc), R$_2$ is unsubstituted C$_{3-7}$ cycloalkyl.

In another embodiment of Formula (IIIc), R$_2$ is cyclopropyl.

In another embodiment of Formula (IIIc), R$_2$ is unsubstituted cyclopropyl.

In another embodiment of Formula (IIIc), R$_2$ is cyclopropyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is cyclopropyl substituted with $C_{1-4}$ alkyl.

In another embodiment of Formula (IIIc), $R_2$ is cyclobutyl.

In another embodiment of Formula (IIIc), $R_2$ is unsubstituted cyclobutyl.

In another embodiment of Formula (IIIc), $R_2$ is cyclobutyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is cyclobutyl substituted with 1 or 2 halo.

In another embodiment of Formula (IIIc), $R_2$ is cyclobutyl substituted with $C_{1-4}$ alkyl.

In another embodiment of Formula (IIIc), $R_2$ is cyclobutyl substituted with $C_{1-4}$ alkoxy.

In another embodiment of Formula (IIIc), $R_2$ is cyclopentyl.

In another embodiment of Formula (IIIc), $R_2$ is unsubstituted cyclopentyl.

In another embodiment of Formula (IIIc), $R_2$ is cyclopentyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is cyclohexyl.

In another embodiment of Formula (IIIc), $R_2$ is unsubstituted cyclohexyl.

In another embodiment of Formula (IIIc), $R_2$ is cyclohexyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is cyclohexyl substituted with 1 or 2 halo.

In another embodiment of Formula (IIIc), $R_2$ is bicyclo[3.1.0]hexyl.

In another embodiment of Formula (IIIc), $R_2$ is unsubstituted bicyclo[3.1.0]hexyl.

In another embodiment of Formula (IIIc), $R_2$ is bicyclo[3.1.0]hexyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is bicyclo[3.1.0]hexyl substituted with 1 or 2 halo.

In another embodiment of Formula (IIIc), $R_2$ is spiro[3.3]heptanyl.

In another embodiment of Formula (IIIc), $R_2$ is unsubstituted spiro[3.3]heptanyl.

In another embodiment of Formula (IIIc), $R_2$ is spiro[3.3]heptanyl substituted with 1 or 2 substituents independently selected from the group consisting of —OH, halo, $C_{1-4}$ alkyl, and $C_{1-4}$ alkoxy.

In another embodiment of Formula (IIIc), $R_2$ is bicyclo[1.1.1]pentyl.

In another embodiment of Formula (IIIc), $R_2$ is unsubstituted bicyclo[1.1.1]pentyl.

In another embodiment of Formula (IIIc), $R_2$ is bicyclo[1.1.1]pentyl substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIId):

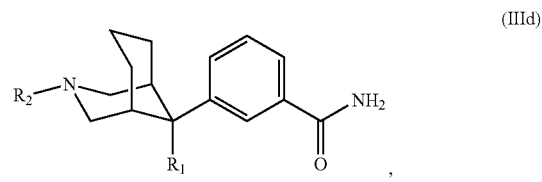

(IIId)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is 4- to 12-membered heterocycloalkyl;
wherein the 4- to 12-membered heterocycloalkyl is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the 4- to 12-membered heterocycloalkyl is optionally substituted with 1, 2, or 3 oxo moieties.

In another embodiment of Formula (IIId), $R_1$ is unsubstituted $C_{1-2}$ alkoxy.

In another embodiment of Formula (IIId), $R_1$ is —OCH$_3$.

In another embodiment of Formula (IIId), $R_1$ is —OCH$_2$CF$_3$.

In another embodiment of Formula (IIId), $R_2$ is 4- to 12-membered heterocycloalkyl, wherein the 4- to 12-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 4- to 12-membered heterocycloalkyl.

In another embodiment of Formula (IIId), $R_2$ is 4- to 9-membered heterocycloalkyl.

In another embodiment of Formula (IIId), $R_2$ is 4- to 9-membered heterocycloalkyl, wherein the 4- to 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 4- to 9-membered heterocycloalkyl.

In another embodiment of Formula (IIId), $R_2$ is 4- to 6-membered heterocycloalkyl.

In another embodiment of Formula (IIId), $R_2$ is 4- to 6-membered heterocycloalkyl, wherein the 4- to 6-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 4- to 6-membered heterocycloalkyl.

In another embodiment of Formula (IIId), $R_2$ is 7- to 9-membered heterocycloalkyl.

In another embodiment of Formula (IIId), $R_2$ is 7- to 9-membered heterocycloalkyl, wherein the 7- to 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 7- to 9-membered heterocycloalkyl.

In another embodiment of Formula (IIId), $R_2$ is 4-membered heterocycloalkyl.

In another embodiment of Formula (IIId), $R_2$ is 4-membered heterocycloalkyl, wherein the 4-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 4-membered heterocycloalkyl.

In another embodiment of Formula (IIId), $R_2$ is 5-membered heterocycloalkyl.

In another embodiment of Formula (IIId), $R_2$ is 5-membered heterocycloalkyl, wherein the 5-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 5-membered heterocycloalkyl.

In another embodiment of Formula (IIId), $R_2$ is 6-membered heterocycloalkyl.

In another embodiment of Formula (IIId), $R_2$ is 6-membered heterocycloalkyl, wherein the 6-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 6-membered heterocycloalkyl.

In another embodiment of Formula (IIId), $R_2$ is 7-membered heterocycloalkyl.

In another embodiment of Formula (IIId), $R_2$ is 7-membered heterocycloalkyl, wherein the 7-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 7-membered heterocycloalkyl.

In another embodiment of Formula (IIId), $R_2$ is 8-membered heterocycloalkyl.

In another embodiment of Formula (IIId), $R_2$ is 8-membered heterocycloalkyl, wherein the 8-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 8-membered heterocycloalkyl.

In another embodiment of Formula (IIId), $R_2$ is 9-membered heterocycloalkyl.

In another embodiment of Formula (IIId), $R_2$ is 9-membered heterocycloalkyl, wherein the 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IIId), $R_2$ is unsubstituted 9-membered heterocycloalkyl.

In another embodiment of Formula (IIId), $R_2$ is 4- to 9-membered heterocycloalkyl, wherein the 4- to 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 9-membered heterocycloalkyl is optionally substituted with 1, 2, or 3 oxo moieties.

In another embodiment of Formula (IIId), $R_2$ is 4- to 6-membered heterocycloalkyl, wherein the 4- to 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 6-membered heterocycloalkyl is optionally substituted with 1, 2, or 3 oxo moieties.

In another embodiment of Formula (IIId), $R_2$ is 4-membered heterocycloalkyl, wherein the 4-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4-membered heterocycloalkyl is optionally substituted with 1, 2, or 3 oxo moieties.

In another embodiment of Formula (IIId), $R_2$ is 5-membered heterocycloalkyl, wherein the 5-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5-membered heterocycloalkyl is optionally substituted with 1, 2, or 3 oxo moieties.

In another embodiment of Formula (IIId), $R_2$ is 6-membered heterocycloalkyl, wherein the 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 6-membered heterocycloalkyl is optionally substituted with 1, 2, or 3 oxo moieties.

In another embodiment of Formula (IIId), $R_2$ is 7-membered heterocycloalkyl, wherein the 7-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 7-membered heterocycloalkyl is optionally substituted with 1, 2, or 3 oxo moieties.

In another embodiment of Formula (IIId), $R_2$ is 8-membered heterocycloalkyl, wherein the 8-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 8-membered heterocycloalkyl is optionally substituted with 1, 2, or 3 oxo moieties.

In another embodiment of Formula (IIId), $R_2$ is 9-membered heterocycloalkyl, wherein the 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 9-membered heterocycloalkyl is optionally substituted with 1, 2, or 3 oxo moieties.

In another embodiment of Formula (IIId), $R_2$ is oxetanyl.

In another embodiment of Formula (IIId), $R_2$ is unsubstituted oxetanyl.

In another embodiment of Formula (IIId), $R_2$ is oxetanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is azetidinyl.

In another embodiment of Formula (IIId), $R_2$ is unsubstituted azetidinyl.

In another embodiment of Formula (IIId), $R_2$ is azetidinyl substituted with 1 or 2 substituents independently selected from the group consisting of —OH, halo, $C_{1-4}$ alkyl, and $C_{1-4}$ alkoxy.

In another embodiment of Formula (IIId), $R_2$ is azetidinyl substituted with 1 or 2 substituents independently selected from the group consisting of —OH, halo, $C_{1-4}$ alkyl, $C_{1-4}$ alkoxy, and —C(=O)—($C_{1-4}$ alkyl).

In another embodiment of Formula (IIId), $R_2$ is azetidinyl substituted with 1 or 2 substituents independently selected from the group consisting of halo, $C_{1-4}$ alkyl and —C(=O)—($C_{1-4}$ alkyl).

In another embodiment of Formula (IIId), $R_2$ is azetidinyl substituted with —C(=O)—($C_{1-4}$ alkyl).

In another embodiment of Formula (IIId), $R_2$ is tetrahydrofuranyl.

In another embodiment of Formula (IIId), $R_2$ is unsubstituted tetrahydrofuranyl.

In another embodiment of Formula (IIId), $R_2$ is tetrahydrofuranyl substituted with 1 or 2 substituents independently selected from the group consisting of —OH, halo, $C_{1-4}$ alkyl, and $C_{1-4}$ alkoxy.

In another embodiment of Formula (IIId), $R_2$ is oxanyl.

In another embodiment of Formula (IIId), $R_2$ is unsubstituted oxanyl.

In another embodiment of Formula (IIId), $R_2$ is oxan-2-yl.

In another embodiment of Formula (IIId), $R_2$ is oxan-3-yl.

In another embodiment of Formula (IIId), $R_2$ is oxan-4-yl.

In another embodiment of Formula (IIId), $R_2$ is oxanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 2-oxaspiro[3.5]nonanyl.

In another embodiment of Formula (IIId), $R_2$ is unsubstituted 2-oxaspiro[3.5]nonanyl.

In another embodiment of Formula (IIId), $R_2$ is 2-oxaspiro[3.5]nonanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 3-oxaspiro[5.3]nonanyl.

In another embodiment of Formula (IIId), $R_2$ is unsubstituted 3-oxaspiro[5.3]nonanyl.

In another embodiment of Formula (IIId), $R_2$ is 3-oxaspiro[5.3]nonanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 8-oxabicyclo[3.2.1]octanyl.

In another embodiment of Formula (IIId), $R_2$ is unsubstituted 8-oxabicyclo[3.2.1]octanyl.

In another embodiment of Formula (IIId), $R_2$ is 8-oxabicyclo[3.2.1]octanyl substituted with 1 or 2 substituents independently selected from the group consisting of —OH, halo, $C_{1-4}$ alkyl, and $C_{1-4}$ alkoxy.

In another embodiment of Formula (IIId), $R_2$ is 2-oxaspiro[3.3]heptanyl.

In another embodiment of Formula (IIId), $R_2$ is unsubstituted 2-oxaspiro[3.3]heptanyl.

In another embodiment of Formula (IIId), $R_2$ is 2-oxaspiro[3.3]heptanyl substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIIe):

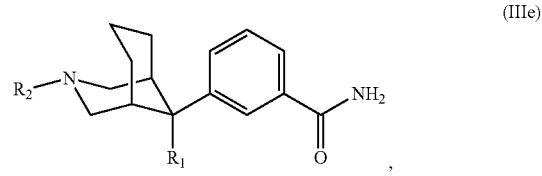

(IIIe)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-($C_{3-10}$ cycloalkyl) or $C_{1-4}$ alkylene-($C_{6-14}$ aryl);
wherein each of the $C_{3-10}$ cycloalkyl, $C_{6-14}$ aryl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the $C_{3-10}$ cycloalkyl of $R_2$ is optionally substituted with 1, 2, or 3 oxo moieties.

In another embodiment of Formula (IIIe), $R_1$ is unsubstituted $C_{1-2}$ alkoxy.

In another embodiment of Formula (IIIe), $R_1$ is —OCH$_3$.

In another embodiment of Formula (IIIe), $R_1$ is —OCH$_2$CF$_3$.

In another embodiment of Formula (IIIe), $R_2$ is $C_{1-4}$ alkylene-($C_{3-10}$ cycloalkyl).

In another embodiment of Formula (IIIe), $R_2$ is unsubstituted $C_{1-4}$ alkylene-($C_{3-10}$ cycloalkyl).

In another embodiment of Formula (IIIe), $R_2$ is $C_{1-4}$ alkylene-($C_{3-10}$ cycloalkyl), wherein the $C_{3-10}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-10}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-10}$ cycloalkyl), wherein each of the $C_{1-4}$ alkylene and $C_{3-10}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl).

In another embodiment of Formula (IIIe), $R_2$ is unsubstituted $C_{1-4}$ alkylene-($C_{3-7}$ cycloalkyl).

In another embodiment of Formula (IIIe), $R_2$ is $C_{1-4}$ alkylene-($C_{3-7}$ cycloalkyl), wherein the $C_{3-7}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{3-7}$ cycloalkyl), wherein each of the $C_{1-4}$ alkylene and $C_{3-7}$ cycloalkyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(cyclopropyl).

In another embodiment of Formula (IIIe), $R_2$ is $C_{1-4}$ alkylene-(cyclopropyl), wherein the cyclopropyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(cyclopropyl), wherein the cyclopropyl is substituted with —OH.

In another embodiment of Formula (IIIe), $R_2$ is $C_{1-4}$ alkylene-(cyclopropyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(cyclopropyl), wherein each of the $C_{1-4}$ alkylene and cyclopropyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(cyclopropyl).

In another embodiment of Formula (IIIe), $R_2$ is $C_{1-4}$ alkylene-(cyclobutyl), wherein the cyclobutyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(cyclobutyl).

In another embodiment of Formula (IIIe), $R_2$ is $C_{1-4}$ alkylene-(cyclobutyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(cyclobutyl), wherein each of the $C_{1-4}$ alkylene and cyclobutyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(cyclobutyl).

In another embodiment of Formula (IIIe), $R_2$ is $C_{1-4}$ alkylene-(bicyclo[3.1.0]hexyl).

In another embodiment of Formula (IIIe), $R_2$ is $C_{1-4}$ alkylene-(bicyclo[3.1.0]hexyl), wherein the bicyclo[3.1.0]hexyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(bicyclo[3.1.0]hexyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(bicyclo[3.1.0]hexyl), wherein each of the $C_{1-4}$ alkylene and bicyclo[3.1.0]hexyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is unsubstituted $C_{1-4}$ alkylene-(bicyclo[3.1.0]hexyl).

In another embodiment of Formula (IIIe), $R_2$ is $C_{1-4}$ alkylene-($C_{6-14}$ aryl).

In another embodiment of Formula (IIIe), $R_2$ is unsubstituted $C_{1-4}$ alkylene-($C_{6-14}$ aryl).

In another embodiment of Formula (IIIe), $R_2$ is $C_{1-4}$ alkylene-($C_{6-14}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-14}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-14}$ aryl), wherein each of the $C_{1-4}$ alkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl).

In another embodiment of Formula (IIIe), $R_2$ is unsubstituted $C_{1-4}$ alkylene-($C_{6-10}$ aryl).

In another embodiment of Formula (IIIe), $R_2$ is $C_{1-4}$ alkylene-($C_{6-10}$ aryl), wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-($C_{6-10}$ aryl), wherein each of the $C_{1-4}$ alkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl).

In another embodiment of Formula (IIIe), $R_2$ is unsubstituted $C_{1-4}$ alkylene-(phenyl).

In another embodiment of Formula (IIIe), $R_2$ is $C_{1-4}$ alkylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(phenyl), wherein each of the $C_{1-4}$ alkylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl).

In another embodiment of Formula (IIIe), $R_2$ is unsubstituted methylene-(phenyl).

In another embodiment of Formula (IIIe), $R_2$ is methylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl), wherein the methylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is methylene-(phenyl), wherein each of the methylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl).

In another embodiment of Formula (IIIe), $R_2$ is unsubstituted ethylene-(phenyl).

In another embodiment of Formula (IIIe), $R_2$ is ethylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl), wherein the ethylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is ethylene-(phenyl), wherein each of the ethylene and phenyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl).

In another embodiment of Formula (IIIe), $R_2$ is unsubstituted $C_{1-4}$ alkylene-(indanyl).

In another embodiment of Formula (IIIe), $R_2$ is $C_{1-4}$ alkylene-(indanyl), wherein the indanyl is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl), wherein the indanyl is substituted with —OH.

In another embodiment of Formula (IIIe), $R_2$ is $C_{1-4}$ alkylene-(indanyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIe), $R_2$ is $C_{1-4}$ alkylene-(indanyl), wherein each of the $C_{1-4}$ alkylene and indanyl is substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIIf):

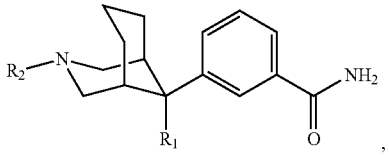

(IIIf)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-(4- to 12-membered heterocycloalkyl);
wherein each of the 4- to 12-membered heterocycloalkyl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(═O)—($C_{1-4}$ alkyl), —S(═O)—($C_{1-4}$ alkyl) and —S(═O)$_2$—($C_{1-4}$ alkyl); and
further wherein the 4- to 12-membered heterocycloalkyl of $R_2$ is optionally substituted with 1, 2, or 3 oxo moieties.

In another embodiment of Formula (IIIf), $R_1$ is unsubstituted $C_{1-2}$ alkoxy.

In another embodiment of Formula (IIIf), $R_1$ is —OCH$_3$.

In another embodiment of Formula (IIIf), $R_1$ is —OCH$_2$CF$_3$.

In another embodiment of Formula (IIIf), $R_2$ is unsubstituted $C_{1-4}$ alkylene-(4- to 12-membered heterocycloalkyl).

In another embodiment of Formula (IIIf), $R_2$ is $C_{1-4}$ alkylene-(4- to 9-membered heterocycloalkyl).

In another embodiment of Formula (IIIf), $R_2$ is unsubstituted $C_{1-4}$ alkylene-(4- to 9-membered heterocycloalkyl).

In another embodiment of Formula (IIIf), $R_2$ is $C_{1-4}$ alkylene-(4- to 6-membered heterocycloalkyl).

In another embodiment of Formula (IIIf), $R_2$ is unsubstituted $C_{1-4}$ alkylene-(4- to 6-membered heterocycloalkyl).

In another embodiment of Formula (IIIf), $R_2$ is $C_{1-4}$ alkylene-(4-membered heterocycloalkyl).

In another embodiment of Formula (IIIf), $R_2$ is unsubstituted $C_{1-4}$ alkylene-(4-membered heterocycloalkyl).

In another embodiment of Formula (IIIf), $R_2$ is $C_{1-4}$ alkylene-(5-membered heterocycloalkyl).

In another embodiment of Formula (IIIf), $R_2$ is unsubstituted $C_{1-4}$ alkylene-(5-membered heterocycloalkyl).

In another embodiment of Formula (IIIf), $R_2$ is $C_{1-4}$ alkylene-(6-membered heterocycloalkyl).

In another embodiment of Formula (IIIf), $R_2$ is unsubstituted $C_{1-4}$ alkylene-(6-membered heterocycloalkyl).

In another embodiment of Formula (IIIf), $R_2$ is $C_{1-4}$ alkylene-(7-membered heterocycloalkyl).

In another embodiment of Formula (IIIf), $R_2$ is unsubstituted $C_{1-4}$ alkylene-(7-membered heterocycloalkyl).

In another embodiment of Formula (IIIf), $R_2$ is $C_{1-4}$ alkylene-(8-membered heterocycloalkyl).

In another embodiment of Formula (IIIf), $R_2$ is unsubstituted $C_{1-4}$ alkylene-(8-membered heterocycloalkyl).

In another embodiment of Formula (IIIf), $R_2$ is $C_{1-4}$ alkylene-(9-membered heterocycloalkyl).

In another embodiment of Formula (IIIf), $R_2$ is unsubstituted $C_{1-4}$ alkylene-(9-membered heterocycloalkyl).

In another embodiment of Formula (IIIf), $R_2$ is $C_{1-4}$ alkylene-(4- to 12-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IIIf), $R_2$ is $C_{1-4}$ alkylene-(4- to 12-membered heterocycloalkyl), wherein the 4- to 12-membered heterocycloalkyl is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IIIf), $R_2$ is $C_{1-4}$ alkylene-(4- to 12-membered heterocycloalkyl), wherein the 4- to 12-membered heterocycloalkyl is optionally substituted with 1, 2, or 3 oxo moieties.

In another embodiment of Formula (IIIf), $R_2$ is $C_{1-4}$ alkylene-(4- to 9-membered heterocycloalkyl), wherein the 4- to 9-membered heterocycloalkyl is substituted with 1 or 2 substituents independently selected from the group consisting of —OH, halo, $C_{1-4}$ alkyl, and $C_{1-4}$ alkoxy; and
further wherein the 4- to 9-membered heterocycloalkyl is optionally substituted with 1, 2, or 3 oxo moieties.

In another embodiment of Formula (IIIf), $R_2$ is $C_{1-4}$ alkylene-(4- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4- to 9-membered heterocycloalkyl is optionally substituted with 1, 2, or 3 oxo moieties.

In another embodiment of Formula (IIIf), $R_2$ is $C_{1-4}$ alkylene-(4- to 9-membered heterocycloalkyl), wherein the 4- to 9-membered heterocycloalkyl is optionally substituted with 1, 2, or 3 oxo moieties.

In another embodiment of Formula (IIIf), $R_2$ is $C_{1-4}$ alkylene-(4- to 6-membered heterocycloalkyl), wherein the 4- to 6-membered heterocycloalkyl is substituted with 1 or 2 substituents independently selected from the group consisting of —OH, halo, $C_{1-4}$ alkyl, and $C_{1-4}$ alkoxy; and further wherein the 4- to 6-membered heterocycloalkyl is optionally substituted with 1, 2, or 3 oxo moieties.

In another embodiment of Formula (IIIf), $R_2$ is $C_{1-4}$ alkylene-(4- to 6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4- to 6-membered heterocycloalkyl is optionally substituted with 1, 2, or 3 oxo moieties.

In another embodiment of Formula (IIIf), $R_2$ is $C_{1-4}$ alkylene-(4- to 6-membered heterocycloalkyl), wherein the 4- to 6-membered heterocycloalkyl is optionally substituted with 1, 2, or 3 oxo moieties.

In another embodiment of Formula (IIIf), $R_2$ is $C_{1-4}$ alkylene-(7- to 9-membered heterocycloalkyl), wherein the 7- to 9-membered heterocycloalkyl is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IIIf), $R_2$ is $C_{1-4}$ alkylene-(7- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IIIf), $R_2$ is $C_{1-4}$ alkylene-(7- to 9-membered heterocycloalkyl), wherein the 7- to 9-membered heterocycloalkyl is optionally substituted with 1, 2, or 3 oxo moieties.

In another embodiment of Formula (IIIf), $R_2$ is $C_{1-4}$ alkylene-(4-membered heterocycloalkyl), wherein the 4-membered heterocycloalkyl is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IIIf), $R_2$ is $C_{1-4}$ alkylene-(4-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IIIf), $R_2$ is $C_{1-4}$ alkylene-(4-membered heterocycloalkyl), wherein the 4-membered heterocycloalkyl is optionally substituted with 1 or 2 oxo moieties.

In another embodiment of Formula (IIIf), $R_2$ is $C_{1-4}$ alkylene-(5-membered heterocycloalkyl), wherein the 5-membered heterocycloalkyl is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IIIf), $R_2$ is $C_{1-4}$ alkylene-(5-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IIIf), $R_2$ is $C_{1-4}$ alkylene-(5-membered heterocycloalkyl), wherein the 5-membered heterocycloalkyl is optionally substituted with 1, 2 or 3 oxo moieties.

In another embodiment of Formula (IIIf), $R_2$ is $C_{1-4}$ alkylene-(6-membered heterocycloalkyl), wherein the 6-membered heterocycloalkyl is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IIIf), $R_2$ is $C_{1-4}$ alkylene-(6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IIIf), $R_2$ is $C_{1-4}$ alkylene-(6-membered heterocycloalkyl), wherein the 6-membered heterocycloalkyl is optionally substituted with 1, 2 or 3 oxo moieties.

In another embodiment of Formula (IIIf), $R_2$ is $C_{1-4}$ alkylene-(7-membered heterocycloalkyl), wherein the 7-membered heterocycloalkyl is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IIIf), $R_2$ is $C_{1-4}$ alkylene-(7-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IIIf), $R_2$ is $C_{1-4}$ alkylene-(7-membered heterocycloalkyl), wherein the 7-membered heterocycloalkyl is optionally substituted with 1, 2 or 3 oxo moieties.

In another embodiment of Formula (IIIf), $R_2$ is $C_{1-4}$ alkylene-(8-membered heterocycloalkyl), wherein the 8-membered heterocycloalkyl is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IIIf), $R_2$ is $C_{1-4}$ alkylene-(8-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IIIf), $R_2$ is $C_{1-4}$ alkylene-(8-membered heterocycloalkyl), wherein the 8-membered heterocycloalkyl is optionally substituted with 1, 2 or 3 oxo moieties.

In another embodiment of Formula (IIIf), $R_2$ is $C_{1-4}$ alkylene-(9-membered heterocycloalkyl), wherein the 9-membered heterocycloalkyl is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IIIf), $R_2$ is $C_{1-4}$ alkylene-(9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IIIf), $R_2$ is $C_{1-4}$ alkylene-(9-membered heterocycloalkyl), wherein the 9-membered heterocycloalkyl is optionally substituted with 1, 2 or 3 oxo moieties.

In another embodiment of Formula (IIIf), $R_2$ is $C_{1-4}$ alkylene-(oxetanyl).

In another embodiment of Formula (IIIf), $R_2$ is $C_{1-4}$ alkylene-(oxetan-2-yl).

In another embodiment of Formula (IIIf), $R_2$ is $C_{1-4}$ alkylene-(oxetan-3-yl).

In another embodiment of Formula (IIIf), $R_2$ is $C_{1-4}$ alkylene-(oxetanyl), wherein the oxetanyl is optionally substituted with 1, 2 or 3 oxo moieties.

In another embodiment of Formula (IIIf), $R_2$ is $C_{1-2}$ alkylene-(oxetanyl), wherein the oxetanyl is optionally substituted with 1, 2 or 3 oxo moieties.

In another embodiment of Formula (IIIf), $R_2$ is unsubstituted $C_{1-2}$ alkylene-(oxetanyl).

In another embodiment of Formula (IIIf), $R_2$ is $C_{1-4}$ alkylene-(pyrrolidinyl).

In another embodiment of Formula (IIIf), $R_2$ is $C_{1-4}$ alkylene-(pyrrolidin-2-yl).

In another embodiment of Formula (IIIf), $R_2$ is $C_{1-4}$ alkylene-(pyrrolidin-3-yl).

In another embodiment of Formula (IIIf), $R_2$ is $C_{1-4}$ alkylene-(pyrrolidinyl), wherein the pyrrolidinyl is optionally substituted with 1, 2 or 3 oxo moieties.

In another embodiment of Formula (IIIf), $R_2$ is $C_{1-2}$ alkylene-(pyrrolidinyl), wherein the pyrrolidinyl is optionally substituted with 1, 2 or 3 oxo moieties.

In another embodiment of Formula (IIIf), $R_2$ is $C_{1-2}$ alkylene-(pyrrolidinyl), wherein the pyrrolidinyl is substituted with 2 oxo moieties.

In another embodiment of Formula (IIIf), $R_2$ is $C_{1-4}$ alkylene-(imidazolidinyl), wherein the imidazolidinyl is optionally substituted with 1, 2 or 3 oxo moieties.

In another embodiment of Formula (IIIf), $R_2$ is $C_{1-2}$ alkylene-(imidazolidinyl), wherein the imidazolidinyl is optionally substituted with 1, 2 or 3 oxo moieties.

In another embodiment of Formula (IIIf), $R_2$ is $C_{1-2}$ alkylene-(imidazolidinyl), wherein the imidazolidinyl is substituted with 1 oxo moiety.

In another embodiment of Formula (IIIf), $R_2$ is $C_{1-4}$ alkylene-(oxazolidinyl), wherein the oxazolidinyl is optionally substituted with 1, 2 or 3 oxo moieties.

In another embodiment of Formula (IIIf), $R_2$ is $C_{1-2}$ alkylene-(oxazolidinyl), wherein the oxazolidinyl is optionally substituted with 1, 2 or 3 oxo moieties.

In another embodiment of Formula (IIIf), $R_2$ is $C_{1-2}$ alkylene-(oxazolidinyl), wherein the oxazolidinyl is substituted with 1 oxo moiety.

In another embodiment of Formula (IIIf), $R_2$ is $C_{1-4}$ alkylene-(isothiazolidinyl), wherein the isothiazolidinyl is optionally substituted with 1, 2 or 3 oxo moieties.

In another embodiment of Formula (IIIf), $R_2$ is $C_{1-2}$ alkylene-(isothiazolidinyl), wherein the isothiazolidinyl is optionally substituted with 1, 2 or 3 oxo moieties.

In another embodiment of Formula (IIIf), $R_2$ is $C_{1-2}$ alkylene-(isothiazolidinyl), wherein the isothiazolidinyl is substituted with 2 oxo moieties.

In another embodiment of Formula (IIIf), $R_2$ is $C_{1-4}$ alkylene-(tetrahydrofuranyl).

In another embodiment of Formula (IIIf), $R_2$ is $C_{1-4}$ alkylene-(tetrahydrofuran-2-yl).

In another embodiment of Formula (IIIf), $R_2$ is $C_{1-4}$ alkylene-(tetrahydrofuran-3-yl).

In another embodiment of Formula (IIIf), $R_2$ is $C_{1-4}$ alkylene-(tetrahydrofuranyl), wherein the tetrahydrofuranyl is optionally substituted with 1, 2 or 3 oxo moieties.

In another embodiment of Formula (IIIf), $R_2$ is $C_{1-2}$ alkylene-(tetrahydrofuranyl), wherein the tetrahydrofuranyl is optionally substituted with 1, 2 or 3 oxo moieties.

In another embodiment of Formula (IIIf), $R_2$ is unsubstituted $C_{1-2}$ alkylene-(tetrahydrofuranyl).

In another embodiment of Formula (IIIf), $R_2$ is $C_{1-4}$ alkylene-(thianyl).

In another embodiment of Formula (IIIf), $R_2$ is $C_{1-4}$ alkylene-(thian-2-yl).

In another embodiment of Formula (IIIf), $R_2$ is $C_{1-4}$ alkylene-(thian-3-yl).

In another embodiment of Formula (IIIf), $R_2$ is $C_{1-4}$ alkylene-(thian-4-yl).

In another embodiment of Formula (IIIf), $R_2$ is $C_{1-4}$ alkylene-(thianyl), wherein the thianyl is optionally substituted with 1, 2 or 3 oxo moieties.

In another embodiment of Formula (IIIf), $R_2$ is $C_{1-2}$ alkylene-(thianyl), wherein the thianyl is optionally substituted with 1, 2 or 3 oxo moieties.

In another embodiment of Formula (IIIf), $R_2$ is $C_{1-2}$ alkylene-(thianyl), wherein the thianyl is substituted with 2 oxo moieties.

In another embodiment of Formula (IIIf), $R_2$ is unsubstituted $C_{1-4}$ alkylene-(oxanyl).

In another embodiment of Formula (IIIf), $R_2$ is unsubstituted $C_{1-4}$ alkylene-(oxan-2-yl).

In another embodiment of Formula (IIIf), $R_2$ is unsubstituted $C_{1-4}$ alkylene-(oxan-3-yl).

In another embodiment of Formula (IIIf), $R_2$ is unsubstituted $C_{1-4}$ alkylene-(oxan-4-yl).

In another embodiment of Formula (IIIf), $R_2$ is unsubstituted $C_{1-2}$ alkylene-(oxanyl).

In another embodiment of Formula (IIIf), $R_2$ is unsubstituted $C_{1-2}$ alkylene-(oxan-2-yl).

In another embodiment of Formula (IIIf), $R_2$ is unsubstituted $C_{1-2}$ alkylene-(oxan-3-yl).

In another embodiment of Formula (IIIf), $R_2$ is unsubstituted $C_{1-2}$ alkylene-(oxan-4-yl).

In another embodiment of Formula (IIIf), $R_2$ is $C_{1-4}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IIIf), $R_2$ is $C_{1-2}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IIIf), $R_2$ is $C_{1-2}$ alkylene-(oxanyl), wherein the oxanyl is substituted with 1 or 2 halo.

In another embodiment of Formula (IIIf), $R_2$ is $C_{1-4}$ alkylene-(pyridinon-2(1H)-yl).

In another embodiment of Formula (IIIf), $R_2$ is unsubstituted $C_{1-4}$ alkylene-(pyridinon-2(1H)-yl).

In another embodiment of Formula (IIIf), $R_2$ is $C_{1-4}$ alkylene-(pyridinon-2(1H)-yl), wherein one or both of the $C_{1-4}$ alkylene and pyridinon-2(1H)-yl is substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIIg):

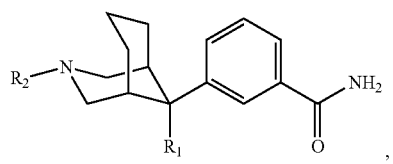

(IIIg)

or a pharmaceutically acceptable salt thereof,
wherein:

$R_1$ is $C_{1-2}$ alkoxy, wherein the $C_{1-2}$ alkoxy is optionally substituted with 1, 2, or 3 halo substituents;

$R_2$ is $C_{1-4}$ alkylene-(5- to 14-membered heteroaryl);

wherein each of the 5- to 14-membered heteroaryl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5- to 14-membered heteroaryl of $R_2$ is optionally substituted with 1, 2, or 3 oxo moieties.

In another embodiment of Formula (IIIg), $R_1$ is unsubstituted $C_{1-2}$ alkoxy.

In another embodiment of Formula (IIIg), $R_1$ is —OCH$_3$.

In another embodiment of Formula (IIIg), $R_1$ is —OCH$_2$CF$_3$.

In another embodiment of Formula (IIIg), $R_2$ is unsubstituted $C_{1-4}$ alkylene-(5- to 14-membered heteroaryl).

In another embodiment of Formula (IIIg), $R_2$ is $C_{1-4}$ alkylene-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 14-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 14-membered heteroaryl), wherein each of the $C_{1-4}$ alkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 10-membered heteroaryl).

In another embodiment of Formula (IIIg), $R_2$ is unsubstituted $C_{1-4}$ alkylene-(5- to 10-membered heteroaryl).

In another embodiment of Formula (IIIg), $R_2$ is $C_{1-4}$ alkylene-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 10-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 10-membered heteroaryl), wherein each of the $C_{1-4}$ alkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 7-membered heteroaryl).

In another embodiment of Formula (IIIg), $R_2$ is unsubstituted $C_{1-4}$ alkylene-(5- to 7-membered heteroaryl).

In another embodiment of Formula (IIIg), $R_2$ is $C_{1-4}$ alkylene-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 7-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5- to 7-membered heteroaryl), wherein each of the $C_{1-4}$ alkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5-membered heteroaryl).

In another embodiment of Formula (IIIg), $R_2$ is unsubstituted $C_{1-4}$ alkylene-(5-membered heteroaryl).

In another embodiment of Formula (IIIg), $R_2$ is $C_{1-4}$ alkylene-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(5-membered heteroaryl), wherein each of the $C_{1-4}$ alkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(6-membered heteroaryl).

In another embodiment of Formula (IIIg), $R_2$ is unsubstituted $C_{1-4}$ alkylene-(6-membered heteroaryl).

In another embodiment of Formula (IIIg), $R_2$ is $C_{1-4}$ alkylene-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(6-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(6-membered heteroaryl), wherein each of the $C_{1-4}$ alkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(7-membered heteroaryl).

In another embodiment of Formula (IIIg), $R_2$ is unsubstituted $C_{1-4}$ alkylene-(7-membered heteroaryl).

In another embodiment of Formula (IIIg), $R_2$ is $C_{1-4}$ alkylene-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(7-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(7-membered heteroaryl), wherein each of the $C_{1-4}$ alkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(8-membered heteroaryl).

In another embodiment of Formula (IIIg), $R_2$ is unsubstituted $C_{1-4}$ alkylene-(8-membered heteroaryl).

In another embodiment of Formula (IIIg), $R_2$ is $C_{1-4}$ alkylene-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(8-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(8-membered heteroaryl), wherein each of the $C_{1-4}$ alkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(9-membered heteroaryl).

In another embodiment of Formula (IIIg), $R_2$ is unsubstituted $C_{1-4}$ alkylene-(9-membered heteroaryl).

In another embodiment of Formula (IIIg), $R_2$ is $C_{1-4}$ alkylene-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(9-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(9-membered heteroaryl), wherein each of the $C_{1-4}$ alkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(imidazolyl).

In another embodiment of Formula (IIIg), $R_2$ is unsubstituted $C_{1-4}$ alkylene-(imidazolyl).

In another embodiment of Formula (IIIg), $R_2$ is $C_{1-4}$ alkylene-(imidazolyl), wherein one or both of the $C_{1-4}$ alkylene and imidazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(1-methyl-imidazolyl).

In another embodiment of Formula (IIIg), $R_2$ is unsubstituted $C_{1-4}$ alkylene-(1-methyl-imidazolyl).

In another embodiment of Formula (IIIg), $R_2$ is $C_{1-4}$ alkylene-(1-methyl-imidazolyl), wherein one or both of the $C_{1-4}$ alkylene and 1-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(2-methyl-imidazolyl).

In another embodiment of Formula (IIIg), $R_2$ is unsubstituted $C_{1-4}$ alkylene-(2-methyl-imidazolyl).

In another embodiment of Formula (IIIg), $R_2$ is $C_{1-4}$ alkylene-(2-methyl-imidazolyl), wherein one or both of the $C_{1-4}$ alkylene and 2-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(3-methyl-imidazolyl).

In another embodiment of Formula (IIIg), $R_2$ is unsubstituted $C_{1-4}$ alkylene-(3-methyl-imidazolyl).

In another embodiment of Formula (IIIg), $R_2$ is $C_{1-4}$ alkylene-(3-methyl-imidazolyl), wherein one or both of the $C_{1-4}$ alkylene and 3-methyl-imidazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(pyrazolyl).

In another embodiment of Formula (IIIg), $R_2$ is unsubstituted $C_{1-4}$ alkylene-(pyrazolyl).

In another embodiment of Formula (IIIg), $R_2$ is $C_{1-4}$ alkylene-(pyrazolyl), wherein one or both of the $C_{1-4}$ alkylene and pyrazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(oxazolyl).

In another embodiment of Formula (IIIg), $R_2$ is unsubstituted $C_{1-4}$ alkylene-(oxazolyl).

In another embodiment of Formula (IIIg), $R_2$ is $C_{1-4}$ alkylene-(oxazolyl), wherein one or both of the $C_{1-4}$ alkylene and oxazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(isoxazolyl).

In another embodiment of Formula (IIIg), $R_2$ is unsubstituted $C_{1-4}$ alkylene-(isoxazolyl).

In another embodiment of Formula (IIIg), $R_2$ is $C_{1-4}$ alkylene-(isoxazolyl), wherein one or both of the $C_{1-4}$ alkylene and isoxazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(triazolyl).

In another embodiment of Formula (IIIg), $R_2$ is unsubstituted $C_{1-4}$ alkylene-(triazolyl).

In another embodiment of Formula (IIIg), $R_2$ is $C_{1-4}$ alkylene-(triazolyl), wherein one or both of the $C_{1-4}$ alkylene and triazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(1-methyl-triazolyl).

In another embodiment of Formula (IIIg), $R_2$ is unsubstituted $C_{1-4}$ alkylene-(1-methyl-triazolyl).

In another embodiment of Formula (IIIg), $R_2$ is $C_{1-4}$ alkylene-(1-methyl-triazolyl), wherein one or both of the $C_{1-4}$ alkylene and 1-methyl-triazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(3-methyl-triazolyl).

In another embodiment of Formula (IIIg), $R_2$ is unsubstituted $C_{1-4}$ alkylene-(3-methyl-triazolyl).

In another embodiment of Formula (IIIg), $R_2$ is $C_{1-4}$ alkylene-(3-methyl-triazolyl), wherein one or both of the $C_{1-4}$ alkylene and 3-methyl-triazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(pyridinyl).

In another embodiment of Formula (IIIg), $R_2$ is unsubstituted $C_{1-4}$ alkylene-(pyridinyl).

In another embodiment of Formula (IIIg), $R_2$ is $C_{1-4}$ alkylene-(pyridinyl), wherein one or both of the $C_{1-4}$ alkylene and pyridinyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is unsubstituted $C_{1-4}$ alkylene-(pyridin-2-yl).

In another embodiment of Formula (IIIg), $R_2$ is unsubstituted $C_{1-4}$ alkylene-(pyridin-3-yl).

In another embodiment of Formula (IIIg), $R_2$ is unsubstituted $C_{1-4}$ alkylene-(pyridin-4-yl).

In another embodiment of Formula (IIIg), $R_2$ is $C_{1-4}$ alkylene-(indazolyl).

In another embodiment of Formula (IIIg), $R_2$ is unsubstituted $C_{1-4}$ alkylene-(indazolyl).

In another embodiment of Formula (IIIg), $R_2$ is $C_{1-4}$ alkylene-(indazolyl), wherein one or both of the $C_{1-4}$ alkylene and indazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(benzimidazolyl).

In another embodiment of Formula (IIIg), $R_2$ is unsubstituted $C_{1-4}$ alkylene-(benzimidazolyl).

In another embodiment of Formula (IIIg), $R_2$ is $C_{1-4}$ alkylene-(benzimidazolyl), wherein one or both of the $C_{1-4}$ alkylene and benzimidazolyl is substituted with 1 or 2 substituents independently selected from the group consisting of —OH, halo, $C_{1-4}$ alkyl, and $C_{1-4}$ alkoxy.

In another embodiment of Formula (IIIg), $R_2$ is $C_{1-4}$ alkylene-(indolyl).

In another embodiment of Formula (IIIg), $R_2$ is unsubstituted $C_{1-4}$ alkylene-(indolyl).

In another embodiment of Formula (IIIg), $R_2$ is $C_{1-4}$ alkylene-(indolyl), wherein one or both of the $C_{1-4}$ alkylene and indolyl is substituted with 1 or 2 substituents independently selected from the group consisting of —OH, $C_{1-4}$ alkyl, and $C_{1-4}$ alkoxy.

In another embodiment of Formula (IIIg), $R_2$ is $C_{1-4}$ alkylene-(isoindolyl).

In another embodiment of Formula (IIIg), $R_2$ is unsubstituted $C_{1-4}$ alkylene-(isoindolyl).

In another embodiment of Formula (IIIg), $R_2$ is $C_{1-4}$ alkylene-(isoindolyl), wherein one or both of the $C_{1-4}$ alkylene and isoindolyl is substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIIh):

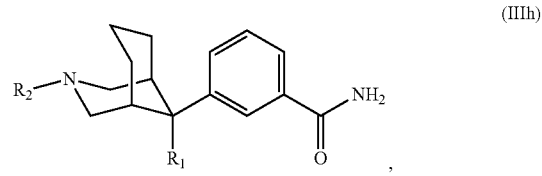

(IIIh)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is $(C_{3-10}$ cycloalkylene)-$(C_{1-4}$ aryl) or $(C_{3-10}$ cycloalkylene)-(5- to 14-membered heteroaryl);

wherein each of the $C_{3-10}$ cycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—$(C_{1-4}$ alkyl), —S(=O)—$(C_{1-4}$ alkyl) and —S(=O)$_2$—$(C_{1-4}$ alkyl); and further wherein the 5- to 14-membered heteroaryl of $R_2$ is optionally substituted with 1, 2, or 3 oxo moieties.

In another embodiment of Formula (IIIh), $R_1$ is unsubstituted $C_{1-2}$ alkoxy.

In another embodiment of Formula (IIIh), $R_1$ is —OCH$_3$.

In another embodiment of Formula (IIIh), $R_1$ is —OCH$_2$CF$_3$.

In another embodiment of Formula (IIIh), $R_2$ is $(C_{3-10}$ cycloalkylene)-$(C_{6-14}$ aryl).

In another embodiment of Formula (IIIh), $R_2$ is unsubstituted $(C_{3-10}$ cycloalkylene)-$(C_{6-14}$ aryl).

In another embodiment of Formula (IIIh), $R_2$ is $(C_{3-7}$ cycloalkylene)-$(C_{6-14}$ aryl).

In another embodiment of Formula (IIIh), $R_2$ is unsubstituted $(C_{3-7}$ cycloalkylene)-$(C_{6-14}$ aryl).

In another embodiment of Formula (IIIh), $R_2$ is $(C_{3-7}$ cycloalkylene)-$(C_{6-14}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is $(C_{3-7}$ cycloalkylene)-$(C_{6-14}$ aryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is $(C_{3-7}$ cycloalkylene)-$(C_{6-14}$ aryl), wherein each of the $C_{3-7}$ cycloalkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is $(C_{3-7}$ cycloalkylene)-$(C_{6-10}$ aryl).

In another embodiment of Formula (IIIh), $R_2$ is unsubstituted $(C_{3-7}$ cycloalkylene)-$(C_{6-10}$ aryl).

In another embodiment of Formula (IIIh), $R_2$ is $(C_{3-7}$ cycloalkylene)-$(C_{6-10}$ aryl) wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is $(C_{3-7}$ cycloalkylene)-$(C_{6-10}$ aryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-($C_{6-10}$ aryl), wherein each of the $C_{3-7}$ cycloalkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(phenyl).

In another embodiment of Formula (IIIh), $R_2$ is unsubstituted ($C_{3-7}$ cycloalkylene)-(phenyl).

In another embodiment of Formula (IIIh), $R_2$ is ($C_{3-7}$ cycloalkylene)-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(phenyl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(phenyl), wherein each of the $C_{3-7}$ cycloalkylene and phenyl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-10}$ cycloalkylene)-(5- to 14-membered heteroaryl).

In another embodiment of Formula (IIIh), $R_2$ is unsubstituted ($C_{3-10}$ cycloalkylene)-(5- to 14-membered heteroaryl).

In another embodiment of Formula (IIIh), $R_2$ is ($C_{3-7}$ cycloalkylene)-(5- to 14-membered heteroaryl).

In another embodiment of Formula (IIIh), $R_2$ is unsubstituted ($C_{3-7}$ cycloalkylene)-(5- to 14-membered heteroaryl).

In another embodiment of Formula (IIIh), $R_2$ is ($C_{3-7}$ cycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 14-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 14-membered heteroaryl), wherein each of the $C_{3-7}$ cycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 10-membered heteroaryl).

In another embodiment of Formula (IIIh), $R_2$ is unsubstituted ($C_{3-7}$ cycloalkylene)-(5- to 10-membered heteroaryl).

In another embodiment of Formula (IIIh), $R_2$ is ($C_{3-7}$ cycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 10-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 10-membered heteroaryl), wherein each of the $C_{3-7}$ cycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 7-membered heteroaryl).

In another embodiment of Formula (IIIh), $R_2$ is unsubstituted ($C_{3-7}$ cycloalkylene)-(5- to 7-membered heteroaryl).

In another embodiment of Formula (IIIh), $R_2$ is ($C_{3-7}$ cycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 7-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5- to 7-membered heteroaryl), wherein each of the $C_{3-7}$ cycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5-membered heteroaryl).

In another embodiment of Formula (IIIh), $R_2$ is unsubstituted ($C_{3-7}$ cycloalkylene)-(5-membered heteroaryl).

In another embodiment of Formula (IIIh), $R_2$ is ($C_{3-7}$ cycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(5-membered heteroaryl), wherein each of the $C_{3-7}$ cycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(6-membered heteroaryl).

In another embodiment of Formula (IIIh), $R_2$ is unsubstituted ($C_{3-7}$ cycloalkylene)-(6-membered heteroaryl).

In another embodiment of Formula (IIIh), $R_2$ is ($C_{3-7}$ cycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(6-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(6-membered heteroaryl), wherein each of the $C_{3-7}$ cycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(7-membered heteroaryl).

In another embodiment of Formula (IIIh), $R_2$ is unsubstituted ($C_{3-7}$ cycloalkylene)-(7-membered heteroaryl).

In another embodiment of Formula (IIIh), $R_2$ is ($C_{3-7}$ cycloalkylene)-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(7-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(7-membered heteroaryl), wherein each of the $C_{3-7}$ cycloalkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(8-membered heteroaryl).

In another embodiment of Formula (IIIh), $R_2$ is unsubstituted ($C_{3-7}$ cycloalkylene)-(8-membered heteroaryl).

In another embodiment of Formula (IIIh), $R_2$ is ($C_{3-7}$ cycloalkylene)-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(8-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(8-membered heteroaryl), wherein each of the $C_{3-7}$ cycloalkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(9-membered heteroaryl).

In another embodiment of Formula (IIIh), $R_2$ is unsubstituted ($C_{3-7}$ cycloalkylene)-(9-membered heteroaryl).

In another embodiment of Formula (IIIh), $R_2$ is ($C_{3-7}$ cycloalkylene)-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(9-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IIIh), $R_2$ is ($C_{3-7}$ cycloalkylene)-(9-membered heteroaryl), wherein each of the $C_{3-7}$ cycloalkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is (cyclobutyl)-(phenyl).

In another embodiment of Formula (IIIh), $R_2$ is unsubstituted (cyclobutyl)-(phenyl).

In another embodiment of Formula (IIIh), $R_2$ is (cyclobutyl)-(phenyl), wherein one or both of the cyclobutyl and phenyl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is (cyclobutyl)-2-(phenyl).

In another embodiment of Formula (IIIh), $R_2$ is unsubstituted (cyclobutyl)-2-(phenyl).

In another embodiment of Formula (IIIh), $R_2$ is (cyclobutyl)-2-(phenyl), wherein one or both of the 2-cyclobutyl and phenyl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is (cyclobutyl)-3-(phenyl).

In another embodiment of Formula (IIIh), $R_2$ is unsubstituted (cyclobutyl)-3-(phenyl).

In another embodiment of Formula (IIIh), $R_2$ is (cyclobutyl)-3-(phenyl), wherein one or both of the 3-cyclobutyl and phenyl is substituted with 1 or 2 substituents independently selected from the group consisting of —OH, halo, $C_{1-4}$ alkyl, and $C_{1-4}$ alkoxy.

In another embodiment of Formula (IIIh), $R_2$ is (bicyclo[1.1.1]pentyl)-(phenyl).

In another embodiment of Formula (IIIh), $R_2$ is unsubstituted (bicyclo[1.1.1]pentyl)-(phenyl).

In another embodiment of Formula (IIIh), $R_2$ is (bicyclo[1.1.1]pentyl)-(phenyl), wherein one or both of the bicyclo[1.1.1]pentyl and phenyl is substituted with 1 or 2 substituents independently selected from the group consisting of —OH, halo, $C_{1-4}$ alkyl, and $C_{1-4}$ alkoxy.

In an embodiment, the compound of Formula (III) has the structure of Formula (IIIi):

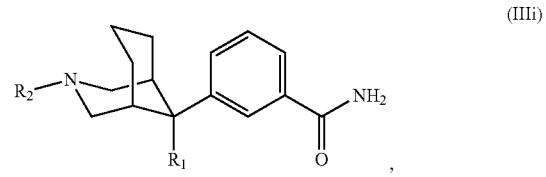

(IIIi)

or a pharmaceutically acceptable salt thereof,
wherein:

$R_1$ is $C_{1-2}$ alkoxy, wherein the $C_{1-2}$ alkoxy is optionally substituted with 1, 2, or 3 halo substituents;

$R_2$ is (4- to 12-membered heterocycloalkylene)-($C_{1-4}$ aryl) or (4- to 12-membered heterocycloalkylene)-(5- to 14-membered heteroaryl);

wherein each of the 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5- to 14-membered heteroaryl of $R_2$ is optionally substituted with 1, 2, or 3 oxo moieties.

In another embodiment of Formula (IIIi), $R_1$ is unsubstituted $C_{1-2}$ alkoxy.

In another embodiment of Formula (IIIi), $R_1$ is —OCH$_3$.

In another embodiment of Formula (IIIi), $R_1$ is —OCH$_2$CF$_3$.

In another embodiment of Formula (IIIi), $R_2$ is (4- to 12-membered heterocycloalkylene)-($C_{1-4}$ aryl).

In another embodiment of Formula (IIIi), $R_2$ is unsubstituted (4- to 12-membered heterocycloalkylene)-($C_{6-14}$ aryl).

In another embodiment of Formula (IIIi), $R_2$ is (4- to 7-membered heterocycloalkylene)-($C_{1-4}$ aryl).

In another embodiment of Formula (IIIi), $R_2$ is unsubstituted (4- to 7-membered heterocycloalkylene)-($C_{1-4}$ aryl).

In another embodiment of Formula (IIIi), $R_2$ is (4- to 7-membered heterocycloalkylene)-($C_{1-4}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-($C_{1-4}$ aryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-($C_{1-4}$ aryl), wherein each of the 4- to 7-membered heterocycloalkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-($C_{6-10}$ aryl).

In another embodiment of Formula (IIIi), $R_2$ is unsubstituted (4- to 7-membered heterocycloalkylene)-($C_{6-10}$ aryl).

In another embodiment of Formula (IIIi), $R_2$ is (4- to 7-membered heterocycloalkylene)-($C_{6-10}$ aryl) wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-($C_{6-10}$ aryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-($C_{6-10}$ aryl), wherein each of the 4- to 7-membered heterocycloalkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(phenyl).

In another embodiment of Formula (IIIi), $R_2$ is unsubstituted (4- to 7-membered heterocycloalkylene)-(phenyl).

In another embodiment of Formula (IIIi), $R_2$ is (4- to 7-membered heterocycloalkylene)-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(phenyl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(phenyl), wherein each of the 4- to 7-membered heterocycloalkylene and phenyl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 12-membered heterocycloalkylene)-(5- to 14-membered heteroaryl).

In another embodiment of Formula (IIIi), $R_2$ is unsubstituted (4- to 12-membered heterocycloalkylene)-(5- to 14-membered heteroaryl).

In another embodiment of Formula (IIIi), $R_2$ is (4- to 7-membered heterocycloalkylene)-(5- to 14-membered heteroaryl).

In another embodiment of Formula (IIIi), $R_2$ is unsubstituted (4- to 7-membered heterocycloalkylene)-(5- to 14-membered heteroaryl).

In another embodiment of Formula (IIIi), $R_2$ is (4- to 7-membered heterocycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 14-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 14-membered heteroaryl), wherein each of the 4- to 7-membered heterocycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 10-membered heteroaryl).

In another embodiment of Formula (IIIi), $R_2$ is unsubstituted (4- to 7-membered heterocycloalkylene)-(5- to 10-membered heteroaryl).

In another embodiment of Formula (IIIi), $R_2$ is (4- to 7-membered heterocycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 10-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 10-membered heteroaryl), wherein each of the 4- to 7-membered heterocycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 7-membered heteroaryl).

In another embodiment of Formula (IIIi), $R_2$ is unsubstituted (4- to 7-membered heterocycloalkylene)-(5- to 7-membered heteroaryl).

In another embodiment of Formula (IIIi), $R_2$ is (4- to 7-membered heterocycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5- to 7-membered heteroaryl), wherein each of the 4- to 7-membered heterocycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5-membered heteroaryl).

In another embodiment of Formula (IIIi), $R_2$ is unsubstituted (4- to 7-membered heterocycloalkylene)-(5-membered heteroaryl).

In another embodiment of Formula (IIIi), $R_2$ is (4- to 7-membered heterocycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(5-membered heteroaryl), wherein each of the 4- to 7-membered heterocycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(6-membered heteroaryl).

In another embodiment of Formula (IIIi), $R_2$ is unsubstituted (4- to 7-membered heterocycloalkylene)-(6-membered heteroaryl).

In another embodiment of Formula (IIIi), $R_2$ is (4- to 7-membered heterocycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(6-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(6-membered heteroaryl), wherein each of the 4- to 7-membered heterocycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(7-membered heteroaryl).

In another embodiment of Formula (IIIi), $R_2$ is unsubstituted (4- to 7-membered heterocycloalkylene)-(7-membered heteroaryl).

In another embodiment of Formula (IIIi), $R_2$ is (4- to 7-membered heterocycloalkylene)-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(7-membered heteroaryl), wherein each of the 4- to 7-membered heterocycloalkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(8-membered heteroaryl).

In another embodiment of Formula (IIIi), $R_2$ is unsubstituted (4- to 7-membered heterocycloalkylene)-(8-membered heteroaryl).

In another embodiment of Formula (IIIi), $R_2$ is (4- to 7-membered heterocycloalkylene)-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(8-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(8-membered heteroaryl), wherein each of the 4- to 7-membered heterocycloalkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(9-membered heteroaryl).

In another embodiment of Formula (IIIi), $R_2$ is unsubstituted (4- to 7-membered heterocycloalkylene)-(9-membered heteroaryl).

In another embodiment of Formula (IIIi), $R_2$ is (4- to 7-membered heterocycloalkylene)-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(9-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4- to 7-membered heterocycloalkylene)-(9-membered heteroaryl), wherein each of the 4- to 7-membered heterocycloalkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (4-membered heterocycloalkylene)-($C_{6-10}$ aryl).

In another embodiment of Formula (IIIi), $R_2$ is unsubstituted (4-membered heterocycloalkylene)-($C_{6-10}$ aryl).

In another embodiment of Formula (IIIi), $R_2$ is (5-membered heterocycloalkylene)-($C_{6-10}$ aryl).

In another embodiment of Formula (IIIi), $R_2$ is unsubstituted (5-membered heterocycloalkylene)-($C_{6-10}$ aryl).

In another embodiment of Formula (IIIi), $R_2$ is (6-membered heterocycloalkylene)-($C_{6-10}$ aryl).

In another embodiment of Formula (IIIi), $R_2$ is unsubstituted (6-membered heterocycloalkylene)-($C_{6-10}$ aryl).

In another embodiment of Formula (IIIi), $R_2$ is (7-membered heterocycloalkylene)-($C_{6-10}$ aryl).

In another embodiment of Formula (IIIi), $R_2$ is unsubstituted (7-membered heterocycloalkylene)-($C_{6-10}$ aryl).

In another embodiment of Formula (IIIi), $R_2$ is (8-membered heterocycloalkylene)-($C_6$. 10 aryl).

In another embodiment of Formula (IIIi), $R_2$ is unsubstituted (8-membered heterocycloalkylene)-($C_{6-10}$ aryl).

In another embodiment of Formula (IIIi), $R_2$ is (9-membered heterocycloalkylene)-($C_6$. 10 aryl).

In another embodiment of Formula (IIIi), $R_2$ is unsubstituted (9-membered heterocycloalkylene)-($C_{6-10}$ aryl).

In another embodiment of Formula (IIIi), $R_2$ is (4-membered heterocycloalkylene)-(phenyl).

In another embodiment of Formula (IIIi), $R_2$ is unsubstituted (4-membered heterocycloalkylene)-(phenyl).

In another embodiment of Formula (IIIi), $R_2$ is (azetidinyl)-(phenyl).

In another embodiment of Formula (IIIi), $R_2$ is unsubstituted (azetidinyl)-(phenyl).

In another embodiment of Formula (IIIi), $R_2$ is (azetidinyl)-(phenyl), wherein one or both of the azetidinyl and phenyl is substituted with 1 or 2 substituents independently selected from the group consisting of —OH, halo, $C_{1-4}$ alkyl, and $C_{1-4}$ alkoxy.

In another embodiment of Formula (IIIi), $R_2$ is (azetidinyl)-(N-phenyl).

In another embodiment of Formula (IIIi), $R_2$ is unsubstituted (azetidinyl)-(N-phenyl).

In another embodiment of Formula (IIIi), $R_2$ is (azetidinyl)-(N-phenyl), wherein one or both of the azetidinyl and N-phenyl is substituted with 1 or 2 substituents independently selected from the group consisting of —OH, halo, $C_{1-4}$ alkyl, and $C_{1-4}$ alkoxy.

In an embodiment, the compound of Formula (I) has the structure of Formula (IV):

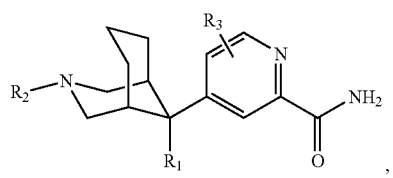

(IV)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); further wherein the $C_{3-10}$ cycloalkyl, 5- to 14-membered heteroaryl, or 4- to 12-membered heterocycloalkyl of $R_2$ is optionally substituted with 1, 2, or 3 oxo moieties; and $R_3$ is hydrogen, OH, halo, $C_{1-4}$ alkyl, or $C_{1-4}$ alkoxy.

In another embodiment of Formula (IV), $R_1$ is unsubstituted $C_{1-2}$ alkoxy.

In another embodiment of Formula (IV), $R_1$ is —$OCH_3$.

In another embodiment of Formula (IV), $R_1$ is —$OCH_2CF_3$.

In another embodiment of Formula (IV), $R_1$ is —$OCH_3$, and $R_3$ is OH, halo, $C_{1-4}$ alkyl, or $C_{1-4}$ alkoxy.

In another embodiment of Formula (IV), $R_1$ is unsubstituted $C_{1-2}$ alkoxy, and $R_3$ is OH, halo, $C_{1-4}$ alkyl, or $C_{1-4}$ alkoxy.

In another embodiment of Formula (IV), $R_1$ is —$OCH_2CF_3$, and $R_3$ is OH, halo, $C_{1-4}$ alkyl, or $C_{1-4}$ alkoxy.

In another embodiment of Formula (IV), $R_1$ is —$OCH_3$, $R_3$ is OH, halo, $C_{1-4}$ alkyl, or $C_{1-4}$alkoxy, and $R_2$ is hydrogen.

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-6}$ alkyl.

In another embodiment of Formula (IV), $R_1$ is —$OCH_3$, $R_3$ is OH, halo, $C_{1-4}$ alkyl, or $C_{1-4}$alkoxy, and $R_2$ is $C_{3-10}$ cycloalkyl.

In another embodiment of Formula (IV), $R_1$ is —$OCH_3$, $R_3$ is OH, halo, $C_{1-4}$ alkyl, or $C_{1-4}$ alkoxy, and $R_2$ is 4- to 12-membered heterocycloalkyl.

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-4}$ alkylene-$CF_3$.

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-4}$ alkylene-($C_{3-10}$ cycloalkyl).

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-4}$ alkylene-(4- to 12-membered heterocycloalkyl).

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-6}$ alkenyl.

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-4}$ alkylene-($C_{6-14}$ aryl).

In another embodiment of Formula (IV), $R_1$ is —$OCH_3$, $R_3$ is OH, halo, $C_{1-4}$ alkyl, or $C_{1-4}$ alkoxy, and $R_2$ is $C_{1-4}$ alkylene-(5- to 14-membered heteroaryl).

In another embodiment of Formula (IV), $R_1$ is —$OCH_3$, $R_3$ is OH, halo, $C_{1-4}$ alkyl, or $C_{1-4}$ alkoxy, and $R_2$ is ($C_{3-10}$ cycloalkylene)-($C_{6-14}$ aryl).

In another embodiment of Formula (IV), $R_1$ is —$OCH_3$, $R_3$ is OH, halo, $C_{1-4}$ alkyl, or $C_{1-4}$ alkoxy, and $R_2$ is ($C_{3-10}$ cycloalkylene)-(5- to 14-membered heteroaryl).

In another embodiment of Formula (IV), $R_1$ is —$OCH_3$, $R_3$ is OH, halo, $C_{1-4}$ alkyl, or $C_{1-4}$ alkoxy, and $R_2$ is (4- to 12-membered heterocycloalkylene)-($C_{6-14}$ aryl).

In another embodiment of Formula (IV), $R_1$ is —$OCH_3$, $R_3$ is OH, halo, $C_{1-4}$ alkyl, or $C_{1-4}$ alkoxy, and $R_2$ is (4- to 12-membered heterocycloalkylene)-(5- to 14-membered heteroaryl).

In another embodiment of Formula (IV), $R_3$ is halo.

In another embodiment of Formula (IV), $R_3$ is fluoro.

In another embodiment of Formula (IV), $R_3$ is OH.

In another embodiment of Formula (IV), $R_3$ is hydrogen.

In an embodiment, the compound of Formula (IV) has the structure of Formula (IVa):

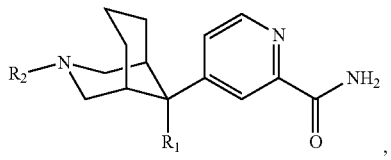

(IVa)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-6}$ alkenyl, $C_{1-4}$ alkylene-($C_{6-14}$ aryl), $C_{1-4}$ alkylene-(5- to 14-membered heteroaryl), ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl);

wherein each of the $C_{1-6}$ alkyl, $C_{3-10}$ cycloalkyl, 4- to 12-membered heterocycloalkyl, $C_{1-4}$ alkylene, $C_{1-6}$ alkenyl, $C_{3-10}$ cycloalkylene, 4- to 12-membered heterocycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the $C_{3-10}$ cycloalkyl, 5- to 14-membered heteroaryl, or 4- to 12-membered heterocycloalkyl of $R_2$ is optionally substituted with 1, 2, or 3 oxo moieties.

In another embodiment of Formula (IVa), $R_1$ is unsubstituted $C_{1-2}$ alkoxy.

In another embodiment of Formula (IVa), $R_1$ is —$OCH_3$.

In another embodiment of Formula (IVa), $R_1$ is —$OCH_2CF_3$.

In another embodiment of Formula (IVa), $R_2$ is hydrogen, $C_{1-6}$ alkyl, $C_{3-10}$ cycloalkyl, or 4- to 12-membered heterocycloalkyl.

In another embodiment of Formula (IVa), $R_2$ is hydrogen, $C_{1-6}$ alkyl, $C_{3-7}$ cycloalkyl, or 4- to 10-membered heterocycloalkyl.

In another embodiment of Formula (IVa), $R_2$ is hydrogen, $C_{1-6}$ alkyl, $C_{3-7}$ cycloalkyl, or 4- to 7-membered heterocycloalkyl.

In another embodiment of Formula (IVa), $R_2$ is $C_{3-10}$ cycloalkyl, 4- to 12-membered heterocycloalkyl, $C_{1-4}$ alkylene-($C_{3-10}$ cycloalkyl), or $C_{1-4}$ alkylene-(4- to 12-membered heterocycloalkyl).

In another embodiment of Formula (IVa), $R_2$ is $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IVa), $R_2$ is $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IVa), $R_2$ is hydrogen, $C_{1-6}$ alkyl, $C_{3-7}$ cycloalkyl, 4- to 10-membered heterocycloalkyl, $C_{1-4}$ alkylene-($C_{3-7}$ cycloalkyl), or $C_{1-4}$ alkylene-(4- to 10-membered heterocycloalkyl).

In another embodiment of Formula (IVa), $R_2$ is hydrogen, $C_{1-6}$ alkyl, $C_{3-7}$ cycloalkyl, 4- to 7-membered heterocycloalkyl, $C_{1-4}$ alkylene-($C_{3-7}$ cycloalkyl), or $C_{1-4}$ alkylene-(4- to 7-membered heterocycloalkyl).

In another embodiment of Formula (IVa), $R_2$ is $C_{1-4}$ alkylene-($C_{3-10}$ cycloalkyl) or $C_{1-4}$ alkylene-(4- to 12-membered heterocycloalkyl).

In another embodiment of Formula (IVa), $R_2$ is $C_{1-4}$ alkylene-($C_{3-7}$ cycloalkyl) or $C_{1-4}$ alkylene-(4- to 10-membered heterocycloalkyl).

In another embodiment of Formula (IVa), $R_2$ is $C_{1-4}$ alkylene-($C_{3-7}$ cycloalkyl) or $C_{1-4}$ alkylene-(4- to 7-membered heterocycloalkyl).

In another embodiment of Formula (IVa), $R_2$ is hydrogen or $C_{1-6}$ alkyl.

In another embodiment of Formula (IVa), $R_2$ is hydrogen, $C_{1-6}$ alkyl, $C_{1-4}$ alkylene-$CF_3$ or $C_{1-6}$ alkenyl.

In another embodiment of Formula (IVa), $R_2$ is hydrogen, $C_{1-4}$ alkylene-$CF_3$ or $C_{1-6}$ alkenyl.

In another embodiment of Formula (IVa), $R_2$ is $C_{3-10}$ cycloalkyl or 4- to 12-membered heterocycloalkyl.

In another embodiment of Formula (IVa), $R_2$ is $C_{3-7}$ cycloalkyl or 4- to 10-membered heterocycloalkyl.

In another embodiment of Formula (IVa), $R_2$ is $C_{3-7}$ cycloalkyl or 4- to 7-membered heterocycloalkyl.

In another embodiment of Formula (IVa), $R_2$ is hydrogen, $C_{1-6}$ alkyl, or $C_{1-4}$ alkylene-$CF_3$.

In another embodiment of Formula (IVa), $R_2$ is ($C_{3-10}$ cycloalkylene)-($C_{6-14}$ aryl), ($C_{3-10}$ cycloalkylene)-(5- to 14-membered heteroaryl), (4- to 12-membered heterocycloalkylene)-($C_{6-14}$ aryl), or (4- to 12-membered heterocycloalkylene)-(5- to 14-membered heteroaryl).

In another embodiment of Formula (IVa), $R_2$ is ($C_{3-7}$ cycloalkylene)-($C_{6-10}$ aryl), ($C_{3-7}$ cycloalkylene)-(5- to 10-membered heteroaryl), (4- to 10-membered heterocycloalkylene)-($C_{6-10}$ aryl), or (4- to 10-membered heterocycloalkylene)-(5- to 10-membered heteroaryl).

In another embodiment of Formula (IVa), $R_2$ is ($C_{3-7}$ cycloalkylene)-($C_{6-10}$ aryl), ($C_{3-7}$ cycloalkylene)-(5- to 7-membered heteroaryl), (4- to 7-membered heterocycloalkylene)-($C_{6-10}$ aryl), or (4- to 7-membered heterocycloalkylene)-(5- to 7-membered heteroaryl).

In another embodiment of Formula (IVa), $R_2$ is ($C_{3-7}$ cycloalkylene)-($C_{6-10}$ aryl) or ($C_{3-7}$ cycloalkylene)-(5- to 7-membered heteroaryl).

In another embodiment of Formula (IVa), $R_2$ is (4- to 7-membered heterocycloalkylene)-($C_{6-10}$ aryl) or (4- to 7-membered heterocycloalkylene)-(5- to 7-membered heteroaryl).

In another embodiment of Formula (IVa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (7- to 9-membered heterocycloalkylene)-(7- to 9-membered heteroaryl).

In another embodiment of Formula (IVa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (5- to 7-membered heterocycloalkylene)-(7- to 9-membered heteroaryl).

In another embodiment of Formula (IVa), $R_2$ is ($C_{3-7}$ cycloalkylene)-($C_{6-10}$ aryl), ($C_{3-7}$ cycloalkylene)-(7- to 9-membered heteroaryl), (7- to 9-membered heterocycloalkylene)-($C_{6-10}$ aryl), or (7- to 9-membered heterocycloalkylene)-(5- to 7-membered heteroaryl).

In another embodiment of Formula (IVa), $R_2$ is ($C_{3-7}$ cycloalkylene)-($C_{6-10}$ aryl) or ($C_{3-7}$ cycloalkylene)-(7- to 9-membered heteroaryl).

In another embodiment of Formula (IVa), $R_2$ is (7- to 9-membered heterocycloalkylene)-($C_{6-10}$ aryl) or (7- to 9-membered heterocycloalkylene)-(7- to 9-membered heteroaryl).

In another embodiment of Formula (IVa), $R_2$ is (7- to 9-membered heterocycloalkylene)-($C_{6-10}$ aryl) or (5- to 7-membered heterocycloalkylene)-(7- to 9-membered heteroaryl).

In another embodiment of Formula (IVa), $R_2$ is (7- to 9-membered heterocycloalkylene)-($C_{6-10}$ aryl) or (7- to 9-membered heterocycloalkylene)-(5- to 7-membered heteroaryl).

In another embodiment of Formula (IVa), $R_2$ is $C_{1-4}$ alkylene-($C_{6-14}$ aryl), ($C_{3-10}$ cycloalkylene)-($C_{6-14}$ aryl), or (4- to 12-membered heterocycloalkylene)-($C_{6-14}$ aryl).

In another embodiment of Formula (IVa), $R_2$ is $C_{1-4}$ alkylene-($C_{6-10}$ aryl), ($C_{3-7}$ cycloalkylene)-($C_{6-10}$ aryl), or (4- to 7-membered heterocycloalkylene)-($C_{6-10}$ aryl).

In another embodiment of Formula (IVa), $R_2$ is $C_{1-4}$ alkylene-($C_{6-14}$ aryl) or ($C_{3-10}$ cycloalkylene)-($C_{6-14}$ aryl).

In another embodiment of Formula (IVa), $R_2$ is ($C_{3-10}$ cycloalkylene)-($C_{1-4}$ aryl) or (4- to 12-membered heterocycloalkylene)-($C_{6-14}$ aryl).

In another embodiment of Formula (IVa), $R_2$ is $C_{1-4}$ alkylene-($C_{6-14}$ aryl) or (4- to 12-membered heterocycloalkylene)-($C_{6-14}$ aryl).

In another embodiment of Formula (IVa), $R_2$ is $C_{1-4}$ alkylene-($C_{6-10}$ aryl) or ($C_{3-7}$ cycloalkylene)-($C_{6-10}$ aryl).

In another embodiment of Formula (IVa), $R_2$ is ($C_{3-7}$ cycloalkylene)-($C_{6-10}$ aryl) or (4- to 7-membered heterocycloalkylene)-($C_{6-10}$ aryl).

In another embodiment of Formula (IVa), $R_2$ is $C_{1-4}$ alkylene-($C_{6-10}$ aryl) or (4- to 7-membered heterocycloalkylene)-($C_{6-10}$ aryl).

In another embodiment of Formula (IVa), $R_2$ is $C_{1-4}$ alkylene-(5- to 14-membered heteroaryl), ($C_{3-10}$ cycloalkylene)-(5- to 14-membered heteroaryl), or (4- to 12-membered heterocycloalkylene)-(5- to 14-membered heteroaryl).

In another embodiment of Formula (IVa), $R_2$ is $C_{1-4}$ alkylene-(5- to 10-membered heteroaryl), ($C_{3-7}$ cycloalkylene)-(5- to 10-membered heteroaryl), or (4- to 7-membered heterocycloalkylene)-(5- to 10-membered heteroaryl).

In another embodiment of Formula (IVa), $R_2$ is $C_{1-4}$ alkylene-(5- to 7-membered heteroaryl), ($C_{3-7}$ cycloalkylene)-(5- to 7-membered heteroaryl), or (4- to 7-membered heterocycloalkylene)-(5- to 7-membered heteroaryl).

In an embodiment, the compound of Formula (IV) has the structure of Formula (IVb):

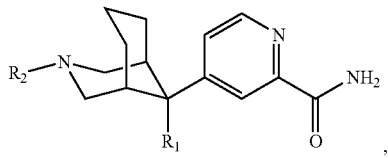

(IVb)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is hydrogen, $C_{1-6}$ alkyl, $C_{1-4}$ alkylene-$CF_3$, or $C_{1-6}$ alkenyl;

wherein each of the $C_{1-6}$ alkyl, $C_{1-6}$ alkenyl, and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IVb), $R_1$ is unsubstituted $C_{1-2}$ alkoxy.

In another embodiment of Formula (IVb), $R_1$ is —$OCH_3$.

In another embodiment of Formula (IVb), $R_1$ is —$OCH_2CF_3$.

In another embodiment of Formula (IVb), $R_2$ is hydrogen, $C_{1-4}$ alkylene-$CF_3$, or $C_{1-6}$ alkenyl.

In another embodiment of Formula (IVb), $R_2$ is $C_{1-6}$ alkyl, $C_{1-4}$ alkylene-$CF_3$, or $C_{1-6}$ alkenyl.

In another embodiment of Formula (IVb), $R_2$ is hydrogen, $C_{1-6}$ alkyl, or $C_{1-6}$ alkenyl.

In another embodiment of Formula (IVb), $R_2$ is hydrogen, $C_{1-6}$ alkyl, or $C_{1-4}$ alkylene-$CF_3$.

In another embodiment of Formula (IVb), $R_2$ is hydrogen or $C_{1-6}$ alkyl.

In another embodiment of Formula (IVb), $R_2$ is hydrogen or $C_{1-4}$ alkylene-$CF_3$.

In another embodiment of Formula (IVb), $R_2$ is hydrogen or $C_{1-6}$ alkenyl.

In another embodiment of Formula (IVb), $R_2$ is $C_{1-6}$ alkyl or $C_{1-4}$ alkylene-$CF_3$.

In another embodiment of Formula (IVb), $R_2$ is $C_{1-6}$ alkyl or $C_{1-6}$ alkenyl.

In another embodiment of Formula (IVb), $R_2$ is $C_{1-4}$ alkylene-$CF_3$ or $C_{1-6}$ alkenyl.

In another embodiment of Formula (IVb), $R_2$ is hydrogen.

In another embodiment of Formula (IVb), $R_2$ is $C_{1-6}$ alkyl.

In another embodiment of Formula (IVb), $R_2$ is $C_{1-4}$ alkylene-$CF_3$.

In another embodiment of Formula (IVb), $R_2$ is $C_{1-2}$ alkylene-$CF_3$.

In another embodiment of Formula (IVb), $R_2$ is $C_{1-6}$ alkenyl.

In another embodiment of Formula (IVb), $R_2$ is unsubstituted $C_{1-6}$ alkyl.

In another embodiment of Formula (IVb), $R_2$ is unsubstituted neopentyl.

In another embodiment of Formula (IVb), $R_2$ is unsubstituted sec-pentyl.

In another embodiment of Formula (IVb), $R_2$ is unsubstituted $C_{1-4}$ alkyl.

In another embodiment of Formula (IVb), $R_2$ is unsubstituted propyl.

In another embodiment of Formula (IVb), $R_2$ is unsubstituted isopropyl.

In another embodiment of Formula (IVb), $R_2$ is unsubstituted butyl.

In another embodiment of Formula (IVb), $R_2$ is unsubstituted isobutyl.

In another embodiment of Formula (IVb), $R_2$ is unsubstituted tert-butyl.

In another embodiment of Formula (IVb), $R_2$ is unsubstituted $C_{1-2}$ alkyl.

In another embodiment of Formula (IVb), $R_2$ is unsubstituted ethyl.

In another embodiment of Formula (IVb), $R_2$ is unsubstituted methyl.

In another embodiment of Formula (IVb), $R_2$ is deuterated $C_{1-6}$ alkyl.

In another embodiment of Formula (IVb), $R_2$ is —$CD_3$.

In another embodiment of Formula (IVb), $R_2$ is $C_{1-6}$ alkyl, wherein the $C_{1-6}$ alkyl is substituted with 1 or 2 substituents independently selected from the group consisting of —OH, halo, $C_{1-4}$ alkyl, and $C_{1-4}$ alkoxy.

In another embodiment of Formula (IVb), $R_2$ is $C_{1-4}$ alkyl, wherein the $C_{1-4}$ alkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IVb), $R_2$ is $C_{1-4}$ alkyl, wherein the $C_{1-4}$ alkyl is substituted with 1 or 2 substituents independently selected from the group consisting of —OH, halo, $C_{1-4}$ alkyl, and $C_{1-4}$ alkoxy.

In another embodiment of Formula (IVb), $R_2$ is $C_{1-4}$ alkyl, wherein the $C_{1-4}$ alkyl is substituted with —S(=O)$_2$—($C_{1-4}$ alkyl).

In another embodiment of Formula (IVb), $R_2$ is $C_{1-4}$ alkyl, wherein the $C_{1-4}$ alkyl is substituted with $C_{1-4}$ alkoxy.

In another embodiment of Formula (IVb), $R_2$ is $C_{1-4}$ alkyl, wherein the $C_{1-4}$ alkyl is substituted with 1 or 2 halo.

In another embodiment of Formula (IVb), $R_2$ is $C_{1-4}$ alkyl, wherein the $C_{1-4}$ alkyl is substituted with 1 or 2 fluoro.

In another embodiment of Formula (IVb), $R_2$ is $C_{1-2}$ alkyl, wherein the $C_{1-2}$ alkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IVb), $R_2$ is $C_{1-2}$ alkyl, wherein the $C_{1-2}$ alkyl is substituted with 1 or 2 substituents independently selected from the group consisting of —OH, halo, $C_{1-4}$ alkyl, and $C_{1-4}$ alkoxy.

In another embodiment of Formula (IVb), $R_2$ is $C_{1-2}$ alkyl, wherein the $C_{1-2}$ alkyl is substituted with —S(=O)$_2$—($C_{1-4}$ alkyl).

In another embodiment of Formula (IVb), $R_2$ is $C_{1-2}$ alkyl, wherein the $C_{1-2}$ alkyl is substituted with $C_{1-4}$ alkoxy.

In another embodiment of Formula (IVb), $R_2$ is $C_{1-2}$ alkyl, wherein the $C_{1-2}$ alkyl is substituted with 1 or 2 halo.

In another embodiment of Formula (IVb), $R_2$ is $C_{1-2}$ alkyl, wherein the $C_{1-2}$ alkyl is substituted with 1 or 2 fluoro.

In another embodiment of Formula (IVb), $R_2$ is unsubstituted $C_{1-4}$ alkylene-$CF_3$.

In another embodiment of Formula (IVb), $R_2$ is unsubstituted $C_{1-2}$ alkylene-$CF_3$.

In another embodiment of Formula (IVb), $R_2$ is $C_{1-4}$ alkylene-$CF_3$, wherein the $C_{1-4}$ alkylene-$CF_3$ is substituted with 1 or 2 substituents independently selected from the group consisting of —OH, halo, $C_{1-4}$ alkyl, and $C_{1-4}$ alkoxy.

In another embodiment of Formula (IVb), $R_2$ is $C_{1-2}$ alkylene-$CF_3$, wherein the $C_{1-2}$ alkylene-$CF_3$ is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IVb), $R_2$ is ethylene-$CF_3$.

In another embodiment of Formula (IVb), $R_2$ is unsubstituted $C_{1-6}$ alkenyl.

In another embodiment of Formula (IVb), $R_2$ is unsubstituted $C_{1-4}$ alkenyl.

In another embodiment of Formula (IVb), $R_2$ is $C_{1-6}$ alkenyl, wherein the $C_{1-6}$ alkenyl is substituted with 1 or 2 substituents independently selected from the group consisting of —OH, halo, $C_{1-4}$ alkyl, and $C_{1-4}$ alkoxy.

In another embodiment of Formula (IVb), $R_2$ is $C_{1-4}$ alkenyl, wherein the $C_{1-4}$ alkenyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl).

In another embodiment of Formula (IVb), $R_2$ is allyl.

In an embodiment, the compound of Formula (IV) has the structure of Formula (IVc):

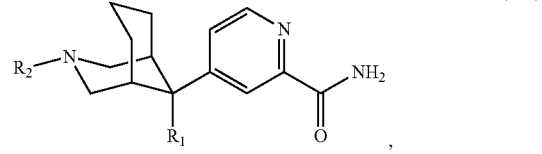

(IVc)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{3-10}$ cycloalkyl;
wherein the $C_{3-10}$ cycloalkyl is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the $C_{3-10}$ cycloalkyl is optionally substituted with 1, 2, or 3 oxo moieties.

In another embodiment of Formula (IVc), $R_1$ is unsubstituted $C_{1-2}$ alkoxy.

In another embodiment of Formula (IVc), $R_1$ is —$OCH_3$.

In another embodiment of Formula (IVc), $R_1$ is —$OCH_2CF_3$.

In another embodiment of Formula (IVc), $R_2$ is $C_{3-10}$ cycloalkyl.

In another embodiment of Formula (IVc), $R_2$ is $C_{3-10}$ cycloalkyl, wherein the $C_{3-10}$ cycloalkyl is substituted with 1 or 2 substituents independently selected from the group consisting of —OH, halo, $C_{1-4}$ alkyl, and $C_{1-4}$ alkoxy.

In another embodiment of Formula (IVc), $R_2$ is unsubstituted $C_{3-10}$ cycloalkyl.

In another embodiment of Formula (IVc), $R_2$ is $C_{3-7}$ cycloalkyl.

In another embodiment of Formula (IVc), $R_2$ is $C_{3-7}$ cycloalkyl, wherein the $C_{3-7}$ cycloalkyl is substituted with 1 or 2 substituents independently selected from the group consisting of —OH, halo, $C_{1-4}$ alkyl, and $C_{1-4}$ alkoxy.

In another embodiment of Formula (IVc), $R_2$ is unsubstituted $C_{3-7}$ cycloalkyl.

In another embodiment of Formula (IVc), $R_2$ is cyclopropyl.

In another embodiment of Formula (IVc), $R_2$ is unsubstituted cyclopropyl.

In another embodiment of Formula (IVc), $R_2$ is cyclopropyl substituted with 1 or 2 substituents independently selected from the group consisting of —OH, halo, $C_{1-4}$ alkyl, and $C_{1-4}$ alkoxy.

In another embodiment of Formula (IVc), $R_2$ is cyclopropyl substituted with $C_{1-4}$ alkyl.

In another embodiment of Formula (IVc), $R_2$ is cyclobutyl.

In another embodiment of Formula (IVc), $R_2$ is unsubstituted cyclobutyl.

In another embodiment of Formula (IVc), $R_2$ is cyclobutyl substituted with 1 or 2 substituents independently selected from the group consisting of —OH, halo, $C_{1-4}$ alkyl, and $C_{1-4}$ alkoxy.

In another embodiment of Formula (IVc), $R_2$ is cyclobutyl substituted with 1 or 2 halo.

In another embodiment of Formula (IVc), $R_2$ is cyclobutyl substituted with $C_{1-4}$ alkyl.

In another embodiment of Formula (IVc), $R_2$ is cyclobutyl substituted with $C_{1-4}$ alkoxy.

In another embodiment of Formula (IVc), $R_2$ is cyclopentyl.

In another embodiment of Formula (IVc), $R_2$ is unsubstituted cyclopentyl.

In another embodiment of Formula (IVc), $R_2$ is cyclopentyl substituted with 1 or 2 substituents independently selected from the group consisting of —OH, halo, $C_{1-4}$ alkyl, and $C_{1-4}$ alkoxy.

In another embodiment of Formula (IVc), $R_2$ is cyclohexyl.

In another embodiment of Formula (IVc), $R_2$ is unsubstituted cyclohexyl.

In another embodiment of Formula (IVc), $R_2$ is cyclohexyl substituted with 1 or 2 substituents independently selected from the group consisting of —OH, halo, $C_{1-4}$ alkyl, and $C_{1-4}$ alkoxy.

In another embodiment of Formula (IVc), $R_2$ is cyclohexyl substituted with 1 or 2 halo.

In another embodiment of Formula (IVc), $R_2$ is bicyclo[3.1.0]hexyl.

In another embodiment of Formula (IVc), $R_2$ is unsubstituted bicyclo[3.1.0]hexyl.

In another embodiment of Formula (IVc), $R_2$ is bicyclo[3.1.0]hexyl substituted with 1 or 2 substituents independently selected from the group consisting of —OH, halo, $C_{1-4}$ alkyl, and $C_{1-4}$ alkoxy.

In another embodiment of Formula (IVc), $R_2$ is bicyclo[3.1.0]hexyl substituted with 1 or 2 halo.

In another embodiment of Formula (IVc), $R_2$ is spiro[3.3]heptanyl.

In another embodiment of Formula (IVc), $R_2$ is unsubstituted spiro[3.3]heptanyl.

In another embodiment of Formula (IVc), $R_2$ is spiro[3.3]heptanyl substituted with 1 or 2 substituents independently selected from the group consisting of —OH, halo, $C_{1-4}$ alkyl, and $C_{1-4}$ alkoxy.

In another embodiment of Formula (IVc), $R_2$ is bicyclo[1.1.1]pentyl.

In another embodiment of Formula (IVc), $R_2$ is unsubstituted bicyclo[1.1.1]pentyl.

In another embodiment of Formula (IVc), $R_2$ is bicyclo[1.1.1]pentyl substituted with 1 or 2 substituents independently selected from the group consisting of —OH, halo, $C_{1-4}$ alkyl, and $C_{1-4}$ alkoxy.

In an embodiment, the compound of Formula (IV) has the structure of Formula (IVd):

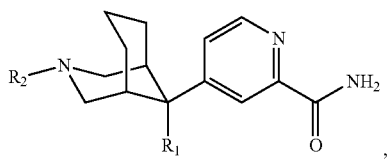

(IVd)

or a pharmaceutically acceptable salt thereof, wherein:

$R_1$ is $C_{1-2}$ alkoxy, wherein the $C_{1-2}$ alkoxy is optionally substituted with 1, 2, or 3 halo substituents;

$R_2$ is 4- to 12-membered heterocycloalkyl;

wherein the 4- to 12-membered heterocycloalkyl is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 12-membered heterocycloalkyl is optionally substituted with 1, 2, or 3 oxo moieties.

In another embodiment of Formula (IVd), $R_1$ is unsubstituted $C_{1-2}$ alkoxy.

In another embodiment of Formula (IVd), $R_1$ is —OCH$_3$.

In another embodiment of Formula (IVd), $R_1$ is —OCH$_2$CF$_3$.

In another embodiment of Formula (IVd), $R_2$ is 4- to 12-membered heterocycloalkyl, wherein the 4- to 12-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 4- to 12-membered heterocycloalkyl.

In another embodiment of Formula (IVd), $R_2$ is 4- to 9-membered heterocycloalkyl.

In another embodiment of Formula (IVd), $R_2$ is 4- to 9-membered heterocycloalkyl, wherein the 4- to 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 4- to 9-membered heterocycloalkyl.

In another embodiment of Formula (IVd), $R_2$ is 4- to 6-membered heterocycloalkyl.

In another embodiment of Formula (IVd), $R_2$ is 4- to 6-membered heterocycloalkyl, wherein the 4- to 6-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 4- to 6-membered heterocycloalkyl.

In another embodiment of Formula (IVd), $R_2$ is 7- to 9-membered heterocycloalkyl.

In another embodiment of Formula (IVd), $R_2$ is 7- to 9-membered heterocycloalkyl, wherein the 7- to 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 7- to 9-membered heterocycloalkyl.

In another embodiment of Formula (IVd), $R_2$ is 4-membered heterocycloalkyl.

In another embodiment of Formula (IVd), $R_2$ is 4-membered heterocycloalkyl, wherein the 4-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 4-membered heterocycloalkyl.

In another embodiment of Formula (IVd), $R_2$ is 5-membered heterocycloalkyl.

In another embodiment of Formula (IVd), $R_2$ is 5-membered heterocycloalkyl, wherein the 5-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 5-membered heterocycloalkyl.

In another embodiment of Formula (IVd), $R_2$ is 6-membered heterocycloalkyl.

In another embodiment of Formula (IVd), $R_2$ is 6-membered heterocycloalkyl, wherein the 6-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 6-membered heterocycloalkyl.

In another embodiment of Formula (IVd), $R_2$ is 7-membered heterocycloalkyl.

In another embodiment of Formula (IVd), $R_2$ is 7-membered heterocycloalkyl, wherein the 7-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 7-membered heterocycloalkyl.

In another embodiment of Formula (IVd), $R_2$ is 8-membered heterocycloalkyl.

In another embodiment of Formula (IVd), $R_2$ is 8-membered heterocycloalkyl, wherein the 8-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 8-membered heterocycloalkyl.

In another embodiment of Formula (IVd), $R_2$ is 9-membered heterocycloalkyl.

In another embodiment of Formula (IVd), $R_2$ is 9-membered heterocycloalkyl, wherein the 9-membered heterocycloalkyl is substituted with 1 or 2 substituents independently selected from the group consisting of —OH, halo, $C_{1-4}$ alkyl, and $C_{1-4}$ alkoxy.

In another embodiment of Formula (IVd), $R_2$ is unsubstituted 9-membered heterocycloalkyl.

In another embodiment of Formula (IVd), $R_2$ is 4- to 9-membered heterocycloalkyl, wherein the 4- to 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 9-membered heterocycloalkyl is optionally substituted with 1, 2, or 3 oxo moieties.

In another embodiment of Formula (IVd), $R_2$ is 4- to 6-membered heterocycloalkyl, wherein the 4- to 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4- to 6-membered heterocycloalkyl is optionally substituted with 1, 2, or 3 oxo moieties.

In another embodiment of Formula (IVd), $R_2$ is 4-membered heterocycloalkyl, wherein the 4-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 4-membered heterocycloalkyl is optionally substituted with 1, 2, or 3 oxo moieties.

In another embodiment of Formula (IVd), $R_2$ is 5-membered heterocycloalkyl, wherein the 5-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5-membered heterocycloalkyl is optionally substituted with 1, 2, or 3 oxo moieties.

In another embodiment of Formula (IVd), $R_2$ is 6-membered heterocycloalkyl, wherein the 6-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 6-membered heterocycloalkyl is optionally substituted with 1, 2, or 3 oxo moieties.

In another embodiment of Formula (IVd), $R_2$ is 7-membered heterocycloalkyl, wherein the 7-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 7-membered heterocycloalkyl is optionally substituted with 1, 2, or 3 oxo moieties.

In another embodiment of Formula (IVd), $R_2$ is 8-membered heterocycloalkyl, wherein the 8-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 8-membered heterocycloalkyl is optionally substituted with 1, 2, or 3 oxo moieties.

In another embodiment of Formula (IVd), $R_2$ is 9-membered heterocycloalkyl, wherein the 9-membered heterocycloalkyl is substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 9-membered heterocycloalkyl is optionally substituted with 1, 2, or 3 oxo moieties.

In another embodiment of Formula (IVd), $R_2$ is oxetanyl.

In another embodiment of Formula (IVd), $R_2$ is unsubstituted oxetanyl.

In another embodiment of Formula (IVd), $R_2$ is oxetanyl substituted with 1 or 2 substituents independently selected from the group consisting of —OH, halo, $C_{1-4}$ alkyl, and $C_{1-4}$ alkoxy.

In another embodiment of Formula (IVd), $R_2$ is azetidinyl.

In another embodiment of Formula (IVd), $R_2$ is unsubstituted azetidinyl.

In another embodiment of Formula (IVd), $R_2$ is azetidinyl substituted with 1 or 2 substituents independently selected from the group consisting of —OH, halo, $C_{1-4}$ alkyl, and $C_{1-4}$ alkoxy.

In another embodiment of Formula (IVd), $R_2$ is azetidinyl substituted with 1 or 2 substituents independently selected from the group consisting of —OH, halo, $C_{1-4}$ alkyl, $C_{1-4}$ alkoxy, and —C(=O)—($C_{1-4}$ alkyl).

In another embodiment of Formula (IVd), $R_2$ is azetidinyl substituted with 1 or 2 substituents independently selected from the group consisting of halo, $C_{1-4}$ alkyl and —C(=O)—($C_{1-4}$ alkyl).

In another embodiment of Formula (IVd), $R_2$ is azetidinyl substituted with —C(=O)—($C_{1-4}$alkyl).

In another embodiment of Formula (IVd), $R_2$ is tetrahydrofuranyl.

In another embodiment of Formula (IVd), $R_2$ is unsubstituted tetrahydrofuranyl.

In another embodiment of Formula (IVd), $R_2$ is tetrahydrofuranyl substituted with 1 or 2 substituents independently selected from the group consisting of —OH, halo, $C_{1-4}$ alkyl, and $C_{1-4}$ alkoxy.

In another embodiment of Formula (IVd), $R_2$ is oxanyl.

In another embodiment of Formula (IVd), $R_2$ is unsubstituted oxanyl.

In another embodiment of Formula (IVd), $R_2$ is oxan-2-yl.
In another embodiment of Formula (IVd), $R_2$ is oxan-3-yl.
In another embodiment of Formula (IVd), $R_2$ is oxan-4-yl.
In another embodiment of Formula (IVd), $R_2$ is oxanyl substituted with 1 or 2 substituents independently selected from the group consisting of —OH, halo, $C_{1-4}$ alkyl, and $C_{1-4}$ alkoxy.
In another embodiment of Formula (IVd), $R_2$ is 2-oxaspiro[3.5]nonanyl.
In another embodiment of Formula (IVd), $R_2$ is unsubstituted 2-oxaspiro[3.5]nonanyl.
In another embodiment of Formula (IVd), $R_2$ is 2-oxaspiro[3.5]nonanyl substituted with 1 or 2 substituents independently selected from the group consisting of —OH, halo, $C_{1-4}$ alkyl, and $C_{1-4}$ alkoxy.
In another embodiment of Formula (IVd), $R_2$ is 3-oxaspiro[5.3]nonanyl.
In another embodiment of Formula (IVd), $R_2$ is unsubstituted 3-oxaspiro[5.3]nonanyl.
In another embodiment of Formula (IVd), $R_2$ is 3-oxaspiro[5.3]nonanyl substituted with 1 or 2 substituents independently selected from the group consisting of —OH, halo, $C_{1-4}$ alkyl, and $C_{1-4}$ alkoxy.
In another embodiment of Formula (IVd), $R_2$ is 8-oxabicyclo[3.2.1]octanyl.
In another embodiment of Formula (IVd), $R_2$ is unsubstituted 8-oxabicyclo[3.2.1]octanyl.
In another embodiment of Formula (IVd), $R_2$ is 8-oxabicyclo[3.2.1]octanyl substituted with 1 or 2 substituents independently selected from the group consisting of —OH, halo, $C_{1-4}$ alkyl, and $C_{1-4}$ alkoxy.
In another embodiment of Formula (IVd), $R_2$ is 2-oxaspiro[3.3]heptanyl.
In another embodiment of Formula (IVd), $R_2$ is unsubstituted 2-oxaspiro[3.3]heptanyl.
In another embodiment of Formula (IVd), $R_2$ is 2-oxaspiro[3.3]heptanyl substituted with 1 or 2 substituents independently selected from the group consisting of —OH, halo, $C_{1-4}$ alkyl, and $C_{1-4}$ alkoxy.
In an embodiment, the compound of Formula (IV) has the structure of Formula (IVe):

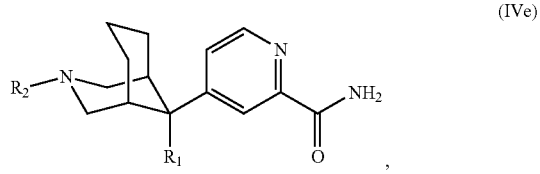

(IVe)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-($C_{3-10}$ cycloalkyl) or $C_{1-4}$ alkylene-($C_{6-14}$ aryl);
wherein each of the $C_{3-10}$ cycloalkyl, $C_{6-14}$ aryl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the $C_{3-10}$ cycloalkyl of $R_2$ is optionally substituted with 1, 2, or 3 oxo moieties.

In another embodiment of Formula (IVe), $R_1$ is unsubstituted $C_{1-2}$ alkoxy.
In another embodiment of Formula (IVe), $R_1$ is —OCH$_3$.
In another embodiment of Formula (IVe), $R_1$ is —OCH$_2$CF$_3$.
In another embodiment of Formula (IVe), $R_2$ is $C_{1-4}$ alkylene-($C_{3-10}$ cycloalkyl).
In another embodiment of Formula (IVe), $R_2$ is unsubstituted $C_{1-4}$ alkylene-($C_{3-10}$ cycloalkyl).
In another embodiment of Formula (IVe), $R_2$ is $C_{1-4}$ alkylene-($C_{3-10}$cycloalkyl), wherein the $C_{3-10}$ cycloalkyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-($C_{3-10}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-($C_{3-10}$ cycloalkyl), wherein each of the $C_{1-4}$ alkylene and $C_{3-10}$ cycloalkyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-($C_{3-7}$ cycloalkyl).
In another embodiment of Formula (IVe), $R_2$ is unsubstituted $C_{1-4}$ alkylene-($C_{3-7}$ cycloalkyl).
In another embodiment of Formula (IVe), $R_2$ is $C_{1-4}$ alkylene-($C_{3-7}$ cycloalkyl), wherein the $C_{3-7}$ cycloalkyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-($C_{3-7}$ cycloalkyl), wherein the $C_{1-4}$ alkylene is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-($C_{3-7}$ cycloalkyl), wherein each of the $C_{1-4}$ alkylene and $C_{3-7}$ cycloalkyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-(cyclopropyl).
In another embodiment of Formula (IVe), $R_2$ is $C_{1-4}$ alkylene-(cyclopropyl), wherein the cyclopropyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-(cyclopropyl), wherein the cyclopropyl is substituted with —OH.
In another embodiment of Formula (IVe), $R_2$ is $C_{1-4}$ alkylene-(cyclopropyl), wherein the $C_{1-4}$ alkylene is substituted with 1 or 2 substituents independently selected from the group consisting of —OH, halo, $C_{1-4}$ alkyl, and $C_{1-4}$ alkoxy.
In another embodiment of Formula (IVe), $R_2$ is $C_{1-4}$ alkylene-(cyclopropyl), wherein each of the $C_{1-4}$ alkylene and cyclopropyl is substituted with 1 or 2 substituents independently selected from the group consisting of —OH, halo, $C_{1-4}$ alkyl, and $C_{1-4}$ alkoxy.
In another embodiment of Formula (IVe), $R_2$ is unsubstituted $C_{1-4}$ alkylene-(cyclopropyl).
In another embodiment of Formula (IVe), $R_2$ is $C_{1-4}$ alkylene-(cyclobutyl), wherein the cyclobutyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(cyclobutyl).

In another embodiment of Formula (IVe), $R_2$ is $C_{1-4}$ alkylene-(cyclobutyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(cyclobutyl), wherein each of the $C_{1-4}$ alkylene and cyclobutyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is unsubstituted $C_{1-4}$ alkylene-(cyclobutyl).

In another embodiment of Formula (IVe), $R_2$ is $C_{1-4}$ alkylene-(bicyclo[3.1.0]hexyl).

In another embodiment of Formula (IVe), $R_2$ is $C_{1-4}$ alkylene-(bicyclo[3.1.0]hexyl), wherein the bicyclo[3.1.0] hexyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(bicyclo[3.1.0]hexyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(bicyclo[3.1.0]hexyl), wherein each of the $C_{1-4}$ alkylene and bicyclo[3.1.0]hexyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is unsubstituted $C_{1-4}$ alkylene-(bicyclo[3.1.0]hexyl).

In another embodiment of Formula (IVe), $R_2$ is $C_{1-4}$ alkylene-($C_{6-14}$ aryl).

In another embodiment of Formula (IVe), $R_2$ is unsubstituted $C_{1-4}$ alkylene-($C_{6-14}$ aryl).

In another embodiment of Formula (IVe), $R_2$ is $C_{1-4}$ alkylene-($C_{6-14}$ aryl), wherein the $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-($C_{6-14}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-($C_{6-14}$ aryl), wherein each of the $C_{1-4}$ alkylene and $C_{6-14}$ aryl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-($C_{6-10}$ aryl).

In another embodiment of Formula (IVe), $R_2$ is unsubstituted $C_{1-4}$ alkylene-($C_{6-10}$ aryl).

In another embodiment of Formula (IVe), $R_2$ is $C_{1-4}$ alkylene-($C_{6-10}$ aryl), wherein the $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-($C_{6-10}$ aryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-($C_{6-10}$ aryl), wherein each of the $C_{1-4}$ alkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(phenyl).

In another embodiment of Formula (IVe), $R_2$ is unsubstituted $C_{1-4}$ alkylene-(phenyl).

In another embodiment of Formula (IVe), $R_2$ is $C_{1-4}$ alkylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(phenyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(phenyl), wherein each of the $C_{1-4}$ alkylene and phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is methylene-(phenyl).

In another embodiment of Formula (IVe), $R_2$ is unsubstituted methylene-(phenyl).

In another embodiment of Formula (IVe), $R_2$ is methylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is methylene-(phenyl), wherein the methylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is methylene-(phenyl), wherein each of the methylene and phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is ethylene-(phenyl).

In another embodiment of Formula (IVe), $R_2$ is unsubstituted ethylene-(phenyl).

In another embodiment of Formula (IVe), $R_2$ is ethylene-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is ethylene-(phenyl), wherein the ethylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is ethylene-(phenyl), wherein each of the ethylene and phenyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(indanyl).

In another embodiment of Formula (IVe), $R_2$ is unsubstituted $C_{1-4}$ alkylene-(indanyl).

In another embodiment of Formula (IVe), $R_2$ is $C_{1-4}$ alkylene-(indanyl), wherein the indanyl is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(indanyl), wherein the indanyl is substituted with —OH.

In another embodiment of Formula (IVe), $R_2$ is $C_{1-4}$ alkylene-(indanyl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVe), $R_2$ is $C_{1-4}$ alkylene-(indanyl), wherein each of the $C_{1-4}$ alkylene and indanyl is substituted with 1 or 2 substituents independently selected from the group consisting of —OH, halo, $C_{1-4}$ alkyl, and $C_{1-4}$ alkoxy.

In an embodiment, the compound of Formula (IV) has the structure of Formula (IVf):

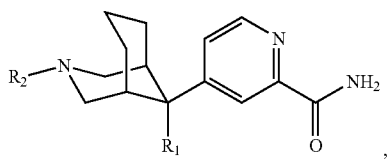

(IVf)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-(4- to 12-membered heterocycloalkyl);
wherein each of the 4- to 12-membered heterocycloalkyl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and
further wherein the 4- to 12-membered heterocycloalkyl of $R_2$ is optionally substituted with 1, 2, or 3 oxo moieties.

In another embodiment of Formula (IVf), $R_1$ is unsubstituted $C_{1-2}$ alkoxy.

In another embodiment of Formula (IVf), $R_1$ is —OCH$_3$.
In another embodiment of Formula (IVf), $R_1$ is —OCH$_2$CF$_3$.

In another embodiment of Formula (IVf), $R_2$ is unsubstituted $C_{1-4}$ alkylene-(4- to 12-membered heterocycloalkyl).

In another embodiment of Formula (IVf), $R_2$ is $C_{1-4}$ alkylene-(4- to 9-membered heterocycloalkyl).

In another embodiment of Formula (IVf), $R_2$ is unsubstituted $C_{1-4}$ alkylene-(4- to 9-membered heterocycloalkyl).

In another embodiment of Formula (IVf), $R_2$ is $C_{1-4}$ alkylene-(4- to 6-membered heterocycloalkyl).

In another embodiment of Formula (IVf), $R_2$ is unsubstituted $C_{1-4}$ alkylene-(4- to 6-membered heterocycloalkyl).

In another embodiment of Formula (IVf), $R_2$ is $C_{1-4}$ alkylene-(4-membered heterocycloalkyl).

In another embodiment of Formula (IVf), $R_2$ is unsubstituted $C_{1-4}$ alkylene-(4-membered heterocycloalkyl).

In another embodiment of Formula (IVf), $R_2$ is $C_{1-4}$ alkylene-(5-membered heterocycloalkyl).

In another embodiment of Formula (IVf), $R_2$ is unsubstituted $C_{1-4}$ alkylene-(5-membered heterocycloalkyl).

In another embodiment of Formula (IVf), $R_2$ is $C_{1-4}$ alkylene-(6-membered heterocycloalkyl).

In another embodiment of Formula (IVf), $R_2$ is unsubstituted $C_{1-4}$ alkylene-(6-membered heterocycloalkyl).

In another embodiment of Formula (IVf), $R_2$ is $C_{1-4}$ alkylene-(7-membered heterocycloalkyl).

In another embodiment of Formula (IVf), $R_2$ is unsubstituted $C_{1-4}$ alkylene-(7-membered heterocycloalkyl).

In another embodiment of Formula (IVf), $R_2$ is $C_{1-4}$ alkylene-(8-membered heterocycloalkyl).

In another embodiment of Formula (IVf), $R_2$ is unsubstituted $C_{1-4}$ alkylene-(8-membered heterocycloalkyl).

In another embodiment of Formula (IVf), $R_2$ is $C_{1-4}$ alkylene-(9-membered heterocycloalkyl).

In another embodiment of Formula (IVf), $R_2$ is unsubstituted $C_{1-4}$ alkylene-(9-membered heterocycloalkyl).

In another embodiment of Formula (IVf), $R_2$ is $C_{1-4}$ alkylene-(4- to 12-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IVf), $R_2$ is $C_{1-4}$ alkylene-(4- to 12-membered heterocycloalkyl), wherein the 4- to 12-membered heterocycloalkyl is substituted with 1 or 2 substituents independently selected from the group consisting of —OH, halo, $C_{1-4}$ alkyl, and $C_{1-4}$ alkoxy; and
further wherein the 4- to 12-membered heterocycloalkyl is optionally substituted with 1, 2, or 3 oxo moieties.

In another embodiment of Formula (IVf), $R_2$ is $C_{1-4}$ alkylene-(4- to 12-membered heterocycloalkyl), wherein the 4- to 12-membered heterocycloalkyl is optionally substituted with 1, 2, or 3 oxo moieties.

In another embodiment of Formula (IVf), $R_2$ is $C_{1-4}$ alkylene-(4- to 9-membered heterocycloalkyl), wherein the 4- to 9-membered heterocycloalkyl is substituted with 1 or 2 substituents independently selected from the group consisting of —OH, halo, $C_{1-4}$ alkyl, and $C_{1-4}$ alkoxy; and
further wherein the 4- to 9-membered heterocycloalkyl is optionally substituted with 1, 2, or 3 oxo moieties.

In another embodiment of Formula (IVf), $R_2$ is $C_{1-4}$ alkylene-(4- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 9-membered heterocycloalkyl is optionally substituted with 1, 2, or 3 oxo moieties.

In another embodiment of Formula (IVf), $R_2$ is $C_{1-4}$ alkylene-(4- to 9-membered heterocycloalkyl), wherein the 4- to 9-membered heterocycloalkyl is optionally substituted with 1, 2, or 3 oxo moieties.

In another embodiment of Formula (IVf), $R_2$ is $C_{1-4}$ alkylene-(4- to 6-membered heterocycloalkyl), wherein the 4- to 6-membered heterocycloalkyl is substituted with 1 or 2 substituents independently selected from the group consisting of —OH, halo, $C_{1-4}$ alkyl, and $C_{1-4}$ alkoxy; and
further wherein the 4- to 6-membered heterocycloalkyl is optionally substituted with 1, 2, or 3 oxo moieties.

In another embodiment of Formula (IVf), $R_2$ is $C_{1-4}$ alkylene-(4- to 6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and
further wherein the 4- to 6-membered heterocycloalkyl is optionally substituted with 1, 2, or 3 oxo moieties.

In another embodiment of Formula (IVf), $R_2$ is $C_{1-4}$ alkylene-(4- to 6-membered heterocycloalkyl), wherein the 4- to 6-membered heterocycloalkyl is optionally substituted with 1, 2, or 3 oxo moieties.

In another embodiment of Formula (IVf), $R_2$ is $C_{1-4}$ alkylene-(7- to 9-membered heterocycloalkyl), wherein the 7- to 9-membered heterocycloalkyl is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IVf), $R_2$ is $C_{1-4}$ alkylene-(7- to 9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7- to 9-membered heterocycloalkyl is optionally substituted with 1, 2, or 3 oxo moieties.

In another embodiment of Formula (IVf), $R_2$ is $C_{1-4}$ alkylene-(7- to 9-membered heterocycloalkyl), wherein the 7- to 9-membered heterocycloalkyl is optionally substituted with 1, 2, or 3 oxo moieties.

In another embodiment of Formula (IVf), $R_2$ is $C_{1-4}$ alkylene-(4-membered heterocycloalkyl), wherein the 4-membered heterocycloalkyl is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IVf), $R_2$ is $C_{1-4}$ alkylene-(4-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 4-membered heterocycloalkyl is optionally substituted with 1 or 2 oxo moieties.

In another embodiment of Formula (IVf), $R_2$ is $C_{1-4}$ alkylene-(4-membered heterocycloalkyl), wherein the 4-membered heterocycloalkyl is optionally substituted with 1 or 2 oxo moieties.

In another embodiment of Formula (IVf), $R_2$ is $C_{1-4}$ alkylene-(5-membered heterocycloalkyl), wherein the 5-membered heterocycloalkyl is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IVf), $R_2$ is $C_{1-4}$ alkylene-(5-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 5-membered heterocycloalkyl is optionally substituted with 1, 2 or 3 oxo moieties.

In another embodiment of Formula (IVf), $R_2$ is $C_{1-4}$ alkylene-(5-membered heterocycloalkyl), wherein the 5-membered heterocycloalkyl is optionally substituted with 1, 2 or 3 oxo moieties.

In another embodiment of Formula (IVf), $R_2$ is $C_{1-4}$ alkylene-(6-membered heterocycloalkyl), wherein the 6-membered heterocycloalkyl is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IVf), $R_2$ is $C_{1-4}$ alkylene-(6-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 6-membered heterocycloalkyl is optionally substituted with 1, 2 or 3 oxo moieties.

In another embodiment of Formula (IVf), $R_2$ is $C_{1-4}$ alkylene-(6-membered heterocycloalkyl), wherein the 6-membered heterocycloalkyl is optionally substituted with 1, 2 or 3 oxo moieties.

In another embodiment of Formula (IVf), $R_2$ is $C_{1-4}$ alkylene-(7-membered heterocycloalkyl), wherein the 7-membered heterocycloalkyl is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IVf), $R_2$ is $C_{1-4}$ alkylene-(7-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 7-membered heterocycloalkyl is optionally substituted with 1, 2 or 3 oxo moieties.

In another embodiment of Formula (IVf), $R_2$ is $C_{1-4}$ alkylene-(7-membered heterocycloalkyl), wherein the 7-membered heterocycloalkyl is optionally substituted with 1, 2 or 3 oxo moieties.

In another embodiment of Formula (IVf), $R_2$ is $C_{1-4}$ alkylene-(8-membered heterocycloalkyl), wherein the 8-membered heterocycloalkyl is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IVf), $R_2$ is $C_{1-4}$ alkylene-(8-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 8-membered heterocycloalkyl is optionally substituted with 1, 2 or 3 oxo moieties.

In another embodiment of Formula (IVf), $R_2$ is $C_{1-4}$ alkylene-(8-membered heterocycloalkyl), wherein the 8-membered heterocycloalkyl is optionally substituted with 1, 2 or 3 oxo moieties.

In another embodiment of Formula (IVf), $R_2$ is $C_{1-4}$ alkylene-(9-membered heterocycloalkyl), wherein the 9-membered heterocycloalkyl is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IVf), $R_2$ is $C_{1-4}$ alkylene-(9-membered heterocycloalkyl), wherein the $C_{1-4}$ alkylene is substituted with 1 or 2 substituents independently selected from the group consisting of —OH, halo, $C_{1-4}$ alkyl, and $C_{1-4}$ alkoxy; and further wherein the 9-membered heterocycloalkyl is optionally substituted with 1, 2 or 3 oxo moieties.

In another embodiment of Formula (IVf), $R_2$ is $C_{1-4}$ alkylene-(9-membered heterocycloalkyl), wherein the 9-membered heterocycloalkyl is optionally substituted with 1, 2 or 3 oxo moieties.

In another embodiment of Formula (IVf), $R_2$ is $C_{1-4}$ alkylene-(oxetanyl).

In another embodiment of Formula (IVf), $R_2$ is $C_{1-4}$ alkylene-(oxetan-2-yl).

In another embodiment of Formula (IVf), $R_2$ is $C_{1-4}$ alkylene-(oxetan-3-yl).

In another embodiment of Formula (IVf), $R_2$ is $C_{1-4}$ alkylene-(oxetanyl), wherein the oxetanyl is optionally substituted with 1, 2 or 3 oxo moieties.

In another embodiment of Formula (IVf), $R_2$ is $C_{1-2}$ alkylene-(oxetanyl), wherein the oxetanyl is optionally substituted with 1, 2 or 3 oxo moieties.

In another embodiment of Formula (IVf), $R_2$ is unsubstituted $C_{1-2}$ alkylene-(oxetanyl).

In another embodiment of Formula (IVf), $R_2$ is $C_{1-4}$ alkylene-(pyrrolidinyl).

In another embodiment of Formula (IVf), $R_2$ is $C_{1-4}$ alkylene-(pyrrolidin-2-yl).

In another embodiment of Formula (IVf), $R_2$ is $C_{1-4}$ alkylene-(pyrrolidin-3-yl).

In another embodiment of Formula (IVf), $R_2$ is $C_{1-4}$ alkylene-(pyrrolidinyl), wherein the pyrrolidinyl is optionally substituted with 1, 2 or 3 oxo moieties.

In another embodiment of Formula (IVf), $R_2$ is $C_{1-2}$ alkylene-(pyrrolidinyl), wherein the pyrrolidinyl is optionally substituted with 1, 2 or 3 oxo moieties.

In another embodiment of Formula (IVf), $R_2$ is $C_{1-2}$ alkylene-(pyrrolidinyl), wherein the pyrrolidinyl is substituted with 2 oxo moieties.

In another embodiment of Formula (IVf), $R_2$ is $C_{1-4}$ alkylene-(imidazolidinyl), wherein the imidazolidinyl is optionally substituted with 1, 2 or 3 oxo moieties.

In another embodiment of Formula (IVf), $R_2$ is $C_{1-2}$ alkylene-(imidazolidinyl), wherein the imidazolidinyl is optionally substituted with 1, 2 or 3 oxo moieties.

In another embodiment of Formula (IVf), $R_2$ is $C_{1-2}$ alkylene-(imidazolidinyl), wherein the imidazolidinyl is substituted with 1 oxo moiety.

In another embodiment of Formula (IVf), $R_2$ is $C_{1-4}$ alkylene-(oxazolidinyl), wherein the oxazolidinyl is optionally substituted with 1, 2 or 3 oxo moieties.

In another embodiment of Formula (IVf), $R_2$ is $C_{1-2}$ alkylene-(oxazolidinyl), wherein the oxazolidinyl is optionally substituted with 1, 2 or 3 oxo moieties.

In another embodiment of Formula (IVf), $R_2$ is $C_{1-2}$ alkylene-(oxazolidinyl), wherein the oxazolidinyl is substituted with 1 oxo moiety.

In another embodiment of Formula (IVf), $R_2$ is $C_{1-4}$ alkylene-(isothiazolidinyl), wherein the isothiazolidinyl is optionally substituted with 1, 2 or 3 oxo moieties.

In another embodiment of Formula (IVf), $R_2$ is $C_{1-2}$ alkylene-(isothiazolidinyl), wherein the isothiazolidinyl is optionally substituted with 1, 2 or 3 oxo moieties.

In another embodiment of Formula (IVf), $R_2$ is $C_{1-2}$ alkylene-(isothiazolidinyl), wherein the isothiazolidinyl is substituted with 2 oxo moieties.

In another embodiment of Formula (IVf), $R_2$ is $C_{1-4}$ alkylene-(tetrahydrofuranyl).

In another embodiment of Formula (IVf), $R_2$ is $C_{1-4}$ alkylene-(tetrahydrofuran-2-yl).

In another embodiment of Formula (IVf), $R_2$ is $C_{1-4}$ alkylene-(tetrahydrofuran-3-yl).

In another embodiment of Formula (IVf), $R_2$ is $C_{1-4}$ alkylene-(tetrahydrofuranyl), wherein the tetrahydrofuranyl is optionally substituted with 1, 2 or 3 oxo moieties.

In another embodiment of Formula (IVf), $R_2$ is $C_{1-2}$ alkylene-(tetrahydrofuranyl), wherein the tetrahydrofuranyl is optionally substituted with 1, 2 or 3 oxo moieties.

In another embodiment of Formula (IVf), $R_2$ is unsubstituted $C_{1-2}$ alkylene-(tetrahydrofuranyl).

In another embodiment of Formula (IVf), $R_2$ is $C_{1-4}$ alkylene-(thianyl).

In another embodiment of Formula (IVf), $R_2$ is $C_{1-4}$ alkylene-(thian-2-yl).

In another embodiment of Formula (IVf), $R_2$ is $C_{1-4}$ alkylene-(thian-3-yl).

In another embodiment of Formula (IVf), $R_2$ is $C_{1-4}$ alkylene-(thian-4-yl).

In another embodiment of Formula (IVf), $R_2$ is $C_{1-4}$ alkylene-(thianyl), wherein the thianyl is optionally substituted with 1, 2 or 3 oxo moieties.

In another embodiment of Formula (IVf), $R_2$ is $C_{1-2}$ alkylene-(thianyl), wherein the thianyl is optionally substituted with 1, 2 or 3 oxo moieties.

In another embodiment of Formula (IVf), $R_2$ is $C_{1-2}$ alkylene-(thianyl), wherein the thianyl is substituted with 2 oxo moieties.

In another embodiment of Formula (IVf), $R_2$ is unsubstituted $C_{1-4}$ alkylene-(oxanyl).

In another embodiment of Formula (IVf), $R_2$ is unsubstituted $C_{1-4}$ alkylene-(oxan-2-yl).

In another embodiment of Formula (IVf), $R_2$ is unsubstituted $C_{1-4}$ alkylene-(oxan-3-yl).

In another embodiment of Formula (IVf), $R_2$ is unsubstituted $C_{1-4}$ alkylene-(oxan-4-yl).

In another embodiment of Formula (IVf), $R_2$ is unsubstituted $C_{1-2}$ alkylene-(oxanyl).

In another embodiment of Formula (IVf), $R_2$ is unsubstituted $C_{1-2}$ alkylene-(oxan-2-yl).

In another embodiment of Formula (IVf), $R_2$ is unsubstituted $C_{1-2}$ alkylene-(oxan-3-yl).

In another embodiment of Formula (IVf), $R_2$ is unsubstituted $C_{1-2}$ alkylene-(oxan-4-yl).

In another embodiment of Formula (IVf), $R_2$ is $C_{1-4}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IVf), $R_2$ is $C_{1-2}$ alkylene-(oxanyl), wherein the oxanyl is optionally substituted with 1 or 2 substituents independently selected from the group consisting of —OH, halo, $C_{1-4}$ alkyl, and $C_{1-4}$ alkoxy.

In another embodiment of Formula (IVf), $R_2$ is $C_{1-2}$ alkylene-(oxanyl), wherein the oxanyl is substituted with 1 or 2 halo.

In another embodiment of Formula (IVf), $R_2$ is $C_{1-4}$ alkylene-(pyridinon-2(1H)-yl).

In another embodiment of Formula (IVf), $R_2$ is unsubstituted $C_{1-4}$ alkylene-(pyridinon-2(1H)-yl).

In another embodiment of Formula (IVf), $R_2$ is $C_{1-4}$ alkylene-(pyridinon-2(1H)-yl), wherein one or both of the $C_{1-4}$ alkylene and pyridinon-2(1H)-yl is substituted with 1 or 2 substituents independently selected from the group consisting of —OH, halo, $C_{1-4}$ alkyl, and $C_{1-4}$ alkoxy.

In an embodiment, the compound of Formula (IV) has the structure of Formula (IVg):

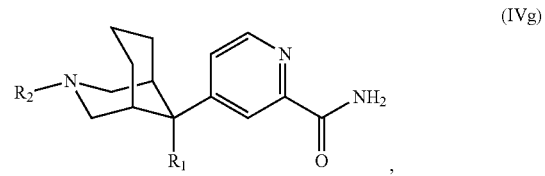

(IVg)

or a pharmaceutically acceptable salt thereof,
wherein:
$R_1$ is $C_{1-2}$ alkoxy, wherein the $C_{1-2}$ alkoxy is optionally substituted with 1, 2, or 3 halo substituents;
$R_2$ is $C_{1-4}$ alkylene-(5- to 14-membered heteroaryl);
wherein each of the 5- to 14-membered heteroaryl and $C_{1-4}$ alkylene of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), —S(=O)—($C_{1-4}$ alkyl) and —S(=O)$_2$—($C_{1-4}$ alkyl); and further wherein the 5- to 14-membered heteroaryl of $R_2$ is optionally substituted with 1, 2, or 3 oxo moieties.

In another embodiment of Formula (IVg), $R_1$ is unsubstituted $C_{1-2}$ alkoxy.

In another embodiment of Formula (IVg), $R_1$ is —OCH$_3$.

In another embodiment of Formula (IVg), $R_1$ is —OCH$_2$CF$_3$.

In another embodiment of Formula (IVg), $R_2$ is unsubstituted $C_{1-4}$ alkylene-(5- to 14-membered heteroaryl).

In another embodiment of Formula (IVg), $R_2$ is $C_{1-4}$ alkylene-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 14-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 14-membered heteroaryl), wherein each of the $C_{1-4}$ alkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 10-membered heteroaryl).

In another embodiment of Formula (IVg), $R_2$ is unsubstituted $C_{1-4}$ alkylene-(5- to 10-membered heteroaryl).

In another embodiment of Formula (IVg), $R_2$ is $C_{1-4}$ alkylene-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 10-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 10-membered heteroaryl), wherein each of the $C_{1-4}$ alkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 7-membered heteroaryl).

In another embodiment of Formula (IVg), $R_2$ is unsubstituted $C_{1-4}$ alkylene-(5- to 7-membered heteroaryl).

In another embodiment of Formula (IVg), $R_2$ is $C_{1-4}$ alkylene-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 7-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5- to 7-membered heteroaryl), wherein each of the $C_{1-4}$ alkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5-membered heteroaryl).

In another embodiment of Formula (IVg), $R_2$ is unsubstituted $C_{1-4}$ alkylene-(5-membered heteroaryl).

In another embodiment of Formula (IVg), $R_2$ is $C_{1-4}$ alkylene-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(5-membered heteroaryl), wherein each of the $C_{1-4}$ alkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(6-membered heteroaryl).

In another embodiment of Formula (IVg), $R_2$ is unsubstituted $C_{1-4}$ alkylene-(6-membered heteroaryl).

In another embodiment of Formula (IVg), $R_2$ is $C_{1-4}$ alkylene-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(6-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(6-membered heteroaryl), wherein each of the $C_{1-4}$ alkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(7-membered heteroaryl).

In another embodiment of Formula (IVg), $R_2$ is unsubstituted $C_{1-4}$ alkylene-(7-membered heteroaryl).

In another embodiment of Formula (IVg), $R_2$ is $C_{1-4}$ alkylene-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(7-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(7-membered heteroaryl), wherein each of the $C_{1-4}$ alkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(8-membered heteroaryl).

In another embodiment of Formula (IVg), $R_2$ is unsubstituted $C_{1-4}$ alkylene-(8-membered heteroaryl).

In another embodiment of Formula (IVg), $R_2$ is $C_{1-4}$ alkylene-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(8-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(8-membered heteroaryl), wherein each of the $C_{1-4}$ alkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(9-membered heteroaryl).

In another embodiment of Formula (IVg), $R_2$ is unsubstituted $C_{1-4}$ alkylene-(9-membered heteroaryl).

In another embodiment of Formula (IVg), $R_2$ is $C_{1-4}$ alkylene-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(9-membered heteroaryl), wherein the $C_{1-4}$ alkylene is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(9-membered heteroaryl), wherein each of the $C_{1-4}$ alkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(imidazolyl).

In another embodiment of Formula (IVg), $R_2$ is unsubstituted $C_{1-4}$ alkylene-(imidazolyl).

In another embodiment of Formula (IVg), $R_2$ is $C_{1-4}$ alkylene-(imidazolyl), wherein one or both of the $C_{1-4}$ alkylene and imidazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(1-methyl-imidazolyl).

In another embodiment of Formula (IVg), $R_2$ is unsubstituted $C_{1-4}$ alkylene-(1-methyl-imidazolyl).

In another embodiment of Formula (IVg), $R_2$ is $C_{1-4}$ alkylene-(1-methyl-imidazolyl), wherein one or both of the $C_{1-4}$ alkylene and 1-methyl-imidazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(2-methyl-imidazolyl).

In another embodiment of Formula (IVg), $R_2$ is unsubstituted $C_{1-4}$ alkylene-(2-methyl-imidazolyl).

In another embodiment of Formula (IVg), $R_2$ is $C_{1-4}$ alkylene-(2-methyl-imidazolyl), wherein one or both of the $C_{1-4}$ alkylene and 2-methyl-imidazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(3-methyl-imidazolyl).

In another embodiment of Formula (IVg), $R_2$ is unsubstituted $C_{1-4}$ alkylene-(3-methyl-imidazolyl).

In another embodiment of Formula (IVg), $R_2$ is $C_{1-4}$ alkylene-(3-methyl-imidazolyl), wherein one or both of the $C_{1-4}$ alkylene and 3-methyl-imidazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(pyrazolyl).

In another embodiment of Formula (IVg), $R_2$ is unsubstituted $C_{1-4}$ alkylene-(pyrazolyl).

In another embodiment of Formula (IVg), $R_2$ is $C_{1-4}$ alkylene-(pyrazolyl), wherein one or both of the $C_{1-4}$ alkylene and pyrazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(oxazolyl).

In another embodiment of Formula (IVg), $R_2$ is unsubstituted $C_{1-4}$ alkylene-(oxazolyl).

In another embodiment of Formula (IVg), $R_2$ is $C_{1-4}$ alkylene-(oxazolyl), wherein one or both of the $C_{1-4}$ alkylene and oxazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(isoxazolyl).

In another embodiment of Formula (IVg), $R_2$ is unsubstituted $C_{1-4}$ alkylene-(isoxazolyl).

In another embodiment of Formula (IVg), $R_2$ is $C_{1-4}$ alkylene-(isoxazolyl), wherein one or both of the $C_{1-4}$ alkylene and isoxazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(triazolyl).

In another embodiment of Formula (IVg), $R_2$ is unsubstituted $C_{1-4}$ alkylene-(triazolyl).

In another embodiment of Formula (IVg), $R_2$ is $C_{1-4}$ alkylene-(triazolyl), wherein one or both of the $C_{1-4}$ alkylene and triazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(1-methyl-triazolyl).

In another embodiment of Formula (IVg), $R_2$ is unsubstituted $C_{1-4}$ alkylene-(1-methyl-triazolyl).

In another embodiment of Formula (IVg), $R_2$ is $C_{1-4}$ alkylene-(1-methyl-triazolyl), wherein one or both of the $C_{1-4}$ alkylene and 1-methyl-triazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(3-methyl-triazolyl).

In another embodiment of Formula (IVg), $R_2$ is unsubstituted $C_{1-4}$ alkylene-(3-methyl-triazolyl).

In another embodiment of Formula (IVg), $R_2$ is $C_{1-4}$ alkylene-(3-methyl-triazolyl), wherein one or both of the $C_{1-4}$ alkylene and 3-methyl-triazolyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is $C_{1-4}$ alkylene-(pyridinyl).

In another embodiment of Formula (IVg), $R_2$ is unsubstituted $C_{1-4}$ alkylene-(pyridinyl).

In another embodiment of Formula (IVg), $R_2$ is $C_{1-4}$ alkylene-(pyridinyl), wherein one or both of the $C_{1-4}$ alkylene and pyridinyl is substituted with 1 or 2 substituents independently selected from the group consisting of —OH, halo, $C_{1-4}$ alkyl, and $C_{1-4}$ alkoxy.

In another embodiment of Formula (IVg), $R_2$ is unsubstituted $C_{1-4}$ alkylene-(pyridin-2-yl).

In another embodiment of Formula (IVg), $R_2$ is unsubstituted $C_{1-4}$ alkylene-(pyridin-3-yl).

In another embodiment of Formula (IVg), R$_2$ is unsubstituted C$_{1-4}$ alkylene-(pyridin-4-yl).

In another embodiment of Formula (IVg), R$_2$ is C$_{1-4}$ alkylene-(indazolyl).

In another embodiment of Formula (IVg), R$_2$ is unsubstituted C$_{1-4}$ alkylene-(indazolyl).

In another embodiment of Formula (IVg), R$_2$ is C$_{1-4}$ alkylene-(indazolyl), wherein one or both of the C$_{1-4}$ alkylene and indazolyl is substituted with 1 or 2 substituents independently selected from the group consisting of —OH, halo, C$_{1-4}$ alkyl, and C$_{1-4}$ alkoxy.

In another embodiment of Formula (IVg), R$_2$ is C$_{1-4}$ alkylene-(benzimidazolyl).

In another embodiment of Formula (IVg), R$_2$ is unsubstituted C$_{1-4}$ alkylene-(benzimidazolyl).

In another embodiment of Formula (IVg), R$_2$ is C$_{1-4}$ alkylene-(benzimidazolyl), wherein one or both of the C$_{1-4}$ alkylene and benzimidazolyl is substituted with 1 or 2 substituents independently selected from the group consisting of —OH, halo, C$_{1-4}$ alkyl, and C$_{1-4}$ alkoxy.

In another embodiment of Formula (IVg), R$_2$ is C$_{1-4}$ alkylene-(indolyl).

In another embodiment of Formula (IVg), R$_2$ is unsubstituted C$_{1-4}$ alkylene-(indolyl).

In another embodiment of Formula (IVg), R$_2$ is C$_{1-4}$ alkylene-(indolyl), wherein one or both of the C$_{1-4}$ alkylene and indolyl is substituted with 1 or 2 substituents independently selected from the group consisting of —OH, halo, C$_{1-4}$ alkyl, and C$_{1-4}$ alkoxy.

In another embodiment of Formula (IVg), R$_2$ is C$_{1-4}$ alkylene-(isoindolyl).

In another embodiment of Formula (IVg), R$_2$ is unsubstituted C$_{1-4}$ alkylene-(isoindolyl).

In another embodiment of Formula (IVg), R$_2$ is C$_{1-4}$ alkylene-(isoindolyl), wherein one or both of the C$_{1-4}$ alkylene and isoindolyl is substituted with 1 or 2 substituents independently selected from the group consisting of —OH, halo, C$_{1-4}$ alkyl, and C$_{1-4}$ alkoxy.

In an embodiment, the compound of Formula (IV) has the structure of Formula (IVh):

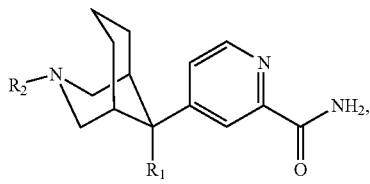

(IVh)

or a pharmaceutically acceptable salt thereof,
wherein:
R$_1$ is C$_{1-2}$ alkoxy, wherein the C$_{1-2}$ alkoxy is optionally substituted with 1, 2, or 3 halo substituents;

R$_2$ is (C$_{3-10}$ cycloalkylene)-(C$_{6-14}$ aryl) or (C$_{3-10}$ cycloalkylene)-(5- to 14-membered heteroaryl);

wherein each of the C$_{3-10}$ cycloalkylene, C$_{6-14}$ aryl, and 5- to 14-membered heteroaryl of R$_2$ is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and further wherein the 5- to 14-membered heteroaryl of R$_2$ is optionally substituted with 1, 2, or 3 oxo moieties.

In another embodiment of Formula (IVh), R$_1$ is unsubstituted C$_{1-2}$ alkoxy.

In another embodiment of Formula (IVh), R$_1$ is —OCH$_3$.

In another embodiment of Formula (IVh), R$_1$ is —OCH$_2$CF$_3$.

In another embodiment of Formula (IVh), R$_2$ is (C$_{3-10}$ cycloalkylene)-(C$_{1-4}$ aryl).

In another embodiment of Formula (IVh), R$_2$ is unsubstituted (C$_{3-10}$ cycloalkylene)-(C$_{6-14}$ aryl).

In another embodiment of Formula (IVh), R$_2$ is (C$_{3-7}$ cycloalkylene)-(C$_{6-14}$ aryl).

In another embodiment of Formula (IVh), R$_2$ is unsubstituted (C$_{3-7}$ cycloalkylene)-(C$_{6-14}$ aryl).

In another embodiment of Formula (IVh), R$_2$ is (C$_{3-7}$ cycloalkylene)-(C$_{6-14}$ aryl), wherein the C$_{6-14}$ aryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(C$_{6-14}$ aryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(C$_{6-14}$ aryl), wherein each of the C$_{3-7}$ cycloalkylene and C$_{6-14}$ aryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(C$_{6-10}$ aryl).

In another embodiment of Formula (IVh), R$_2$ is unsubstituted (C$_{3-7}$ cycloalkylene)-(C$_{6-10}$ aryl).

In another embodiment of Formula (IVh), R$_2$ is (C$_{3-7}$ cycloalkylene)-(C$_{6-10}$ aryl) wherein the C$_{6-10}$ aryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(C$_{6-10}$ aryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(C$_{6-10}$ aryl), wherein each of the C$_{3-7}$ cycloalkylene and C$_{6-10}$ aryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(phenyl).

In another embodiment of Formula (IVh), R$_2$ is unsubstituted (C$_{3-7}$ cycloalkylene)-(phenyl).

In another embodiment of Formula (IVh), R$_2$ is (C$_{3-7}$ cycloalkylene)-(phenyl), wherein the phenyl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(phenyl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(phenyl), wherein each of the C$_{3-7}$ cycloalkylene and phenyl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-10}$ cycloalkylene)-(5- to 14-membered heteroaryl).

In another embodiment of Formula (IVh), $R_2$ is unsubstituted ($C_{3-10}$ cycloalkylene)-(5- to 14-membered heteroaryl).

In another embodiment of Formula (IVh), $R_2$ is ($C_{3-7}$ cycloalkylene)-(5- to 14-membered heteroaryl).

In another embodiment of Formula (IVh), $R_2$ is unsubstituted ($C_{3-7}$ cycloalkylene)-(5- to 14-membered heteroaryl).

In another embodiment of Formula (IVh), $R_2$ is ($C_{3-7}$ cycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 14-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 14-membered heteroaryl), wherein each of the $C_{3-7}$ cycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 10-membered heteroaryl).

In another embodiment of Formula (IVh), $R_2$ is unsubstituted ($C_{3-7}$ cycloalkylene)-(5- to 10-membered heteroaryl).

In another embodiment of Formula (IVh), $R_2$ is ($C_{3-7}$ cycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 10-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 10-membered heteroaryl), wherein each of the $C_{3-7}$ cycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 7-membered heteroaryl).

In another embodiment of Formula (IVh), $R_2$ is unsubstituted ($C_{3-7}$ cycloalkylene)-(5- to 7-membered heteroaryl).

In another embodiment of Formula (IVh), $R_2$ is ($C_{3-7}$ cycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 7-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5- to 7-membered heteroaryl), wherein each of the $C_{3-7}$ cycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5-membered heteroaryl).

In another embodiment of Formula (IVh), $R_2$ is unsubstituted ($C_{3-7}$ cycloalkylene)-(5-membered heteroaryl).

In another embodiment of Formula (IVh), $R_2$ is ($C_{3-7}$ cycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(5-membered heteroaryl), wherein each of the $C_{3-7}$ cycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(6-membered heteroaryl).

In another embodiment of Formula (IVh), $R_2$ is unsubstituted ($C_{3-7}$ cycloalkylene)-(6-membered heteroaryl).

In another embodiment of Formula (IVh), $R_2$ is ($C_{3-7}$ cycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(6-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(6-membered heteroaryl), wherein each of the $C_{3-7}$ cycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(7-membered heteroaryl).

In another embodiment of Formula (IVh), $R_2$ is unsubstituted ($C_{3-7}$ cycloalkylene)-(7-membered heteroaryl).

In another embodiment of Formula (IVh), $R_2$ is ($C_{3-7}$ cycloalkylene)-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(7-membered heteroaryl), wherein the $C_{3-7}$ cycloalkylene is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(7-membered heteroaryl), wherein each of the $C_{3-7}$ cycloalkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), $R_2$ is ($C_{3-7}$ cycloalkylene)-(8-membered heteroaryl).

In another embodiment of Formula (IVh), $R_2$ is unsubstituted ($C_{3-7}$ cycloalkylene)-(8-membered heteroaryl).

In another embodiment of Formula (IVh), $R_2$ is ($C_{3-7}$ cycloalkylene)-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IVh), R$_2$ is (C$_{3-7}$ cycloalkylene)-(8-membered heteroaryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(8-membered heteroaryl), wherein each of the C$_{3-7}$ cycloalkylene and 8-membered heteroaryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(9-membered heteroaryl).

In another embodiment of Formula (IVh), R$_2$ is unsubstituted (C$_{3-7}$ cycloalkylene)-(9-membered heteroaryl).

In another embodiment of Formula (IVh), R$_2$ is (C$_{3-7}$ cycloalkylene)-(9-membered heteroaryl), wherein the 9-membered heteroaryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(9-membered heteroaryl), wherein the C$_{3-7}$ cycloalkylene is substituted with 1 or 2 substituents independently selected from the group consisting of —OH, halo, C$_{1-4}$ alkyl, and C$_{1-4}$ alkoxy.

In another embodiment of Formula (IVh), R$_2$ is (C$_{3-7}$ cycloalkylene)-(9-membered heteroaryl), wherein each of the C$_{3-7}$ cycloalkylene and 9-membered heteroaryl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (cyclobutyl)-(phenyl).

In another embodiment of Formula (IVh), R$_2$ is unsubstituted (cyclobutyl)-(phenyl).

In another embodiment of Formula (IVh), R$_2$ is (cyclobutyl)-(phenyl), wherein one or both of the cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (cyclobutyl)-2-(phenyl).

In another embodiment of Formula (IVh), R$_2$ is unsubstituted (cyclobutyl)-2-(phenyl).

In another embodiment of Formula (IVh), R$_2$ is (cyclobutyl)-2-(phenyl), wherein one or both of the 2-cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (cyclobutyl)-3-(phenyl).

In another embodiment of Formula (IVh), R$_2$ is unsubstituted (cyclobutyl)-3-(phenyl).

In another embodiment of Formula (IVh), R$_2$ is (cyclobutyl)-3-(phenyl), wherein one or both of the 3-cyclobutyl and phenyl is substituted with 1 or 2 substituents independently selected from the group consisting of —OH, halo, C$_{1-4}$ alkyl, and C$_{1-4}$ alkoxy.

In another embodiment of Formula (IVh), R$_2$ is (bicyclo[1.1.1]pentyl)-(phenyl).

In another embodiment of Formula (IVh), R$_2$ is unsubstituted (bicyclo[1.1.1]pentyl)-(phenyl).

In another embodiment of Formula (IVh), R$_2$ is (bicyclo[1.1.1]pentyl)-(phenyl), wherein one or both of the bicyclo[1.1.1]pentyl and phenyl is substituted with 1 or 2 substituents independently selected from the group consisting of —OH, halo, C$_{1-4}$ alkyl, and C$_{1-4}$ alkoxy.

In an embodiment, the compound of Formula (IV) has the structure of Formula (IVi):

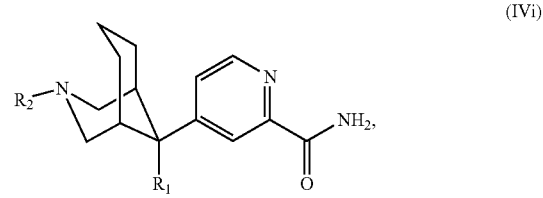

(IVi)

or a pharmaceutically acceptable salt thereof, wherein:

R$_1$ is C$_{1-2}$ alkoxy, wherein the C$_{1-2}$ alkoxy is optionally substituted with 1, 2, or 3 halo substituents;

R$_2$ is (4- to 12-membered heterocycloalkylene)-(C$_{6-14}$ aryl) or (4- to 12-membered heterocycloalkylene)-(5- to 14-membered heteroaryl);

wherein each of the 4- to 12-membered heterocycloalkylene, C$_{6-14}$ aryl, and 5- to 14-membered heteroaryl of R$_2$ is unsubstituted or substituted with 1 or 2 substituents independently selected from the group consisting of —OH, halo, C$_{1-4}$ alkyl, C$_{1-4}$ alkoxy, —C(=O)—(C$_{1-4}$ alkyl), —S(=O)—(C$_{1-4}$ alkyl) and —S(=O)$_2$—(C$_{1-4}$ alkyl); and further wherein the 5- to 14-membered heteroaryl of R$_2$ is optionally substituted with 1, 2, or 3 oxo moieties.

In another embodiment of Formula (IVi), R$_1$ is unsubstituted C$_{1-2}$ alkoxy.

In another embodiment of Formula (IVi), R$_1$ is —OCH$_3$.

In another embodiment of Formula (IVi), R$_1$ is —OCH$_2$CF$_3$.

In another embodiment of Formula (IVi), R$_2$ is (4- to 12-membered heterocycloalkylene)-(C$_{6-14}$ aryl).

In another embodiment of Formula (IVi), R$_2$ is unsubstituted (4- to 12-membered heterocycloalkylene)-(C$_{6-14}$ aryl).

In another embodiment of Formula (IVi), R$_2$ is (4- to 7-membered heterocycloalkylene)-(C$_{6-14}$ aryl).

In another embodiment of Formula (IVi), R$_2$ is unsubstituted (4- to 7-membered heterocycloalkylene)-(C$_{6-14}$ aryl).

In another embodiment of Formula (IVi), R$_2$ is (4- to 7-membered heterocycloalkylene)-(C$_{6-14}$ aryl), wherein the C$_{6-14}$ aryl is substituted with 1 or 2 substituents independently selected from the group consisting of —OH, halo, C$_{1-4}$ alkyl, and C$_{1-4}$ alkoxy.

In another embodiment of Formula (IVi), R$_2$ is (4- to 7-membered heterocycloalkylene)-(C$_{6-14}$ aryl), wherein the 4- to 7-membered heterocycloalkylene is substituted with 1 or 2 substituents independently selected from the group consisting of —OH, halo, C$_{1-4}$ alkyl, and C$_{1-4}$ alkoxy.

In another embodiment of Formula (IVi), R$_2$ is (4- to 7-membered heterocycloalkylene)-(C$_{5-14}$ aryl), wherein each of the 4- to 7-membered heterocycloalkylene and C$_{6-14}$ aryl is substituted with 1 or 2 substituents independently selected from the group consisting of —OH, halo, C$_{1-4}$ alkyl, and C$_{1-4}$ alkoxy.

In another embodiment of Formula (IVi), R$_2$ is (4- to 7-membered heterocycloalkylene)-(C$_{6-10}$ aryl).

In another embodiment of Formula (IVi), R$_2$ is unsubstituted (4- to 7-membered heterocycloalkylene)-(C$_{6-10}$ aryl).

In another embodiment of Formula (IVi), R$_2$ is (4- to 7-membered heterocycloalkylene)-(C$_{6-10}$ aryl) wherein the C$_{6-10}$ aryl is substituted with 1 or 2 substituents independently selected from the group consisting of —OH, halo, C$_{1-4}$ alkyl, and C$_{1-4}$ alkoxy.

In another embodiment of Formula (IVi), $R_2$ is (4- to 7-membered heterocycloalkylene)-($C_{6-10}$ aryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-($C_{6-10}$ aryl), wherein each of the 4- to 7-membered heterocycloalkylene and $C_{6-10}$ aryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(phenyl).

In another embodiment of Formula (IVi), $R_2$ is unsubstituted (4- to 7-membered heterocycloalkylene)-(phenyl).

In another embodiment of Formula (IVi), $R_2$ is (4- to 7-membered heterocycloalkylene)-(phenyl), wherein the phenyl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(phenyl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(phenyl), wherein each of the 4- to 7-membered heterocycloalkylene and phenyl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 12-membered heterocycloalkylene)-(5- to 14-membered heteroaryl).

In another embodiment of Formula (IVi), $R_2$ is unsubstituted (4- to 12-membered heterocycloalkylene)-(5- to 14-membered heteroaryl).

In another embodiment of Formula (IVi), $R_2$ is (4- to 7-membered heterocycloalkylene)-(5- to 14-membered heteroaryl).

In another embodiment of Formula (IVi), $R_2$ is unsubstituted (4- to 7-membered heterocycloalkylene)-(5- to 14-membered heteroaryl).

In another embodiment of Formula (IVi), $R_2$ is (4- to 7-membered heterocycloalkylene)-(5- to 14-membered heteroaryl), wherein the 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 14-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 14-membered heteroaryl), wherein each of the 4- to 7-membered heterocycloalkylene and 5- to 14-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 10-membered heteroaryl).

In another embodiment of Formula (IVi), $R_2$ is unsubstituted (4- to 7-membered heterocycloalkylene)-(5- to 10-membered heteroaryl).

In another embodiment of Formula (IVi), $R_2$ is (4- to 7-membered heterocycloalkylene)-(5- to 10-membered heteroaryl), wherein the 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 10-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 10-membered heteroaryl), wherein each of the 4- to 7-membered heterocycloalkylene and 5- to 10-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 7-membered heteroaryl).

In another embodiment of Formula (IVi), $R_2$ is unsubstituted (4- to 7-membered heterocycloalkylene)-(5- to 7-membered heteroaryl).

In another embodiment of Formula (IVi), $R_2$ is (4- to 7-membered heterocycloalkylene)-(5- to 7-membered heteroaryl), wherein the 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5- to 7-membered heteroaryl), wherein each of the 4- to 7-membered heterocycloalkylene and 5- to 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5-membered heteroaryl).

In another embodiment of Formula (IVi), $R_2$ is unsubstituted (4- to 7-membered heterocycloalkylene)-(5-membered heteroaryl).

In another embodiment of Formula (IVi), $R_2$ is (4- to 7-membered heterocycloalkylene)-(5-membered heteroaryl), wherein the 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(5-membered heteroaryl), wherein each of the 4- to 7-membered heterocycloalkylene and 5-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(6-membered heteroaryl).

In another embodiment of Formula (IVi), $R_2$ is unsubstituted (4- to 7-membered heterocycloalkylene)-(6-membered heteroaryl).

In another embodiment of Formula (IVi), $R_2$ is (4- to 7-membered heterocycloalkylene)-(6-membered heteroaryl), wherein the 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(6-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(6-membered heteroaryl), wherein each of the 4- to 7-membered heterocycloalkylene and 6-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(7-membered heteroaryl).

In another embodiment of Formula (IVi), $R_2$ is unsubstituted (4- to 7-membered heterocycloalkylene)-(7-membered heteroaryl).

In another embodiment of Formula (IVi), $R_2$ is (4- to 7-membered heterocycloalkylene)-(7-membered heteroaryl), wherein the 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(7-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(7-membered heteroaryl), wherein each of the 4- to 7-membered heterocycloalkylene and 7-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(8-membered heteroaryl).

In another embodiment of Formula (IVi), $R_2$ is unsubstituted (4- to 7-membered heterocycloalkylene)-(8-membered heteroaryl).

In another embodiment of Formula (IVi), $R_2$ is (4- to 7-membered heterocycloalkylene)-(8-membered heteroaryl), wherein the 8-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(8-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(8-membered heteroaryl), wherein each of the 4- to 7-membered heterocycloalkylene and 8-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(9-membered heteroaryl).

In another embodiment of Formula (IVi), $R_2$ is unsubstituted (4- to 7-membered heterocycloalkylene)-(9-membered heteroaryl).

In another embodiment of Formula (IVi), $R_2$ is (4- to 7-membered heterocycloalkylene)-(9-membered heteroaryl), wherein the 9-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(9-membered heteroaryl), wherein the 4- to 7-membered heterocycloalkylene is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4- to 7-membered heterocycloalkylene)-(9-membered heteroaryl), wherein each of the 4- to 7-membered heterocycloalkylene and 9-membered heteroaryl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (4-membered heterocycloalkylene)-($C_{6-10}$ aryl).

In another embodiment of Formula (IVi), $R_2$ is unsubstituted (4-membered heterocycloalkylene)-($C_{6-10}$ aryl).

In another embodiment of Formula (IVi), $R_2$ is (5-membered heterocycloalkylene)-($C_{6-10}$ aryl).

In another embodiment of Formula (IVi), $R_2$ is unsubstituted (5-membered heterocycloalkylene)-($C_{6-10}$ aryl).

In another embodiment of Formula (IVi), $R_2$ is (6-membered heterocycloalkylene)-($C_{6-10}$ aryl).

In another embodiment of Formula (IVi), $R_2$ is unsubstituted (6-membered heterocycloalkylene)-($C_{6-10}$ aryl).

In another embodiment of Formula (IVi), $R_2$ is (7-membered heterocycloalkylene)-($C_{6-10}$ aryl).

In another embodiment of Formula (IVi), $R_2$ is unsubstituted (7-membered heterocycloalkylene)-($C_{6-10}$ aryl).

In another embodiment of Formula (IVi), $R_2$ is (8-membered heterocycloalkylene)-($C_{6-10}$ aryl).

In another embodiment of Formula (IVi), $R_2$ is unsubstituted (8-membered heterocycloalkylene)-($C_{6-10}$ aryl).

In another embodiment of Formula (IVi), $R_2$ is (9-membered heterocycloalkylene)-($C_{6-10}$ aryl).

In another embodiment of Formula (IVi), $R_2$ is unsubstituted (9-membered heterocycloalkylene)-($C_{6-10}$ aryl).

In another embodiment of Formula (IVi), $R_2$ is (4-membered heterocycloalkylene)-(phenyl).

In another embodiment of Formula (IVi), $R_2$ is unsubstituted (4-membered heterocycloalkylene)-(phenyl).

In another embodiment of Formula (IVi), $R_2$ is (azetidinyl)-(phenyl).

In another embodiment of Formula (IVi), $R_2$ is unsubstituted (azetidinyl)-(phenyl).

In another embodiment of Formula (IVi), $R_2$ is (azetidinyl)-(phenyl), wherein one or both of the azetidinyl and phenyl is substituted with 1 or 2 substituents independently selected from the group consisting of —OH, halo, $C_{1-4}$ alkyl, and $C_{1-4}$ alkoxy.

In another embodiment of Formula (IVi), $R_2$ is (azetidinyl)-(N-phenyl).

In another embodiment of Formula (IVi), $R_2$ is unsubstituted (azetidinyl)-(N-phenyl).

In another embodiment of Formula (IVi), R$_2$ is (azetidinyl)-(N-phenyl), wherein one or both of the azetidinyl and N-phenyl is substituted with 1 or 2 substituents independently selected from the group consisting of —OH, halo, C$_{1-4}$ alkyl, and C$_{1-4}$ alkoxy.

In another embodiment of Formula I, II, III or IV, the 4- to 12-membered heterocycloalkyl is selected from the group consisting of: epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

In another embodiment of Formula I, II, III or IV, the 4-membered heterocycloalkyl is selected from azetidinyl and oxetanyl.

In another embodiment of Formula I, II, III or IV, the 5-membered heterocycloalkyl is selected from the group consisting of: pyrrolidinyl, 2,5-dihydro-1H-pyrrolyl, tetrahydrofuranyl, oxazolidinyl, and thiazolidinyl.

In another embodiment of Formula I, II, III or IV, the 6-membered heterocycloalkyl is selected from the group consisting of: piperidinyl, oxanyl, pyranyl, dioxanyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 3-azabicyclo[3.1.0]hexanyl, and 2-azabicyclo[3.1.0]hexanyl.

In another embodiment of Formula I, II, III or IV, the 7-membered heterocycloalkyl is selected from the group consisting of: 6-azabicyclo[3.1.1]heptanyl, 2-azabicyclo[2.2.1]heptanyl, 3-azabicyclo[3.1.1]heptanyl, 2-azabicyclo[3.1.1]heptanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, and 2-oxaspiro[3.3]heptanyl.

In another embodiment of Formula I, II, III or IV, the 8-membered heterocycloalkyl is selected from the group consisting of: 3-azabicyclo[3.2.1]octanyl, 8-azabicyclo[3.2.1]octanyl, and 8-oxabicyclo[3.2.1]octanyl.

In another embodiment of Formula I, II, III or IV, the 9-membered heterocycloalkyl is selected from the group consisting of: 3-oxa-7-azabicyclo[3.3.1]nonanyl, 3-oxa-9-azabicyclo[3.3.1]nonanyl, 2-oxaspiro[3.5]nonanyl, and 3-oxaspiro[5.3]nonanyl.

In another embodiment of Formula I, II, III or IV, the 4- to 12-membered heterocycloalkylene is selected from the group consisting of: epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl In another embodiment of Formula I, II, III or IV, the 4-membered heterocycloalkylene is selected from azetidinyl and oxetanyl.

In another embodiment of Formula I, II, III or IV, the 5-membered heterocycloalkylene is selected from the group consisting of: pyrrolidinyl, 2,5-dihydro-1H-pyrrolyl, tetrahydrofuranyl, oxazolidinyl, and thiazolidinyl.

In another embodiment of Formula I, II, III or IV, the 6-membered heterocycloalkylene is selected from the group consisting of: piperidinyl, oxanyl, pyranyl, dioxanyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 3-azabicyclo[3.1.0]hexanyl, and 2-azabicyclo[3.1.0]hexanyl.

In another embodiment of Formula I, II, III or IV, the 7-membered heterocycloalkylene is selected from the group consisting of: 6-azabicyclo[3.1.1]heptanyl, 2-azabicyclo[2.2.1]heptanyl, 3-azabicyclo[3.1.1]heptanyl, 2-azabicyclo[3.1.1]heptanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, and 2-oxaspiro[3.3]heptanyl.

In another embodiment of Formula I, II, III or IV, the 8-membered heterocycloalkylene is selected from the group consisting of: 3-azabicyclo[3.2.1]octanyl, 8-azabicyclo[3.2.1]octanyl, and 8-oxabicyclo[3.2.1]octanyl.

In another embodiment of Formula I, II, III or IV, the 9-membered heterocycloalkylene is selected from the group consisting of: 3-oxa-7-azabicyclo[3.3.1]nonanyl, 3-oxa-9-azabicyclo[3.3.1]nonanyl, 2-oxaspiro[3.5]nonanyl, and 3-oxaspiro[5.3]nonanyl.

In another embodiment of Formula I, II, III or IV, the 5- to 14-membered heteroaryl is selected from the group consisting of: furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

In another embodiment of Formula I, II, III or IV, the 5-membered heteroaryl is selected from the group consisting of: furanyl, thiophenyl, oxazolyl, thiazolyl, imidazolyl, pyrazolyl, triazolyl, tetrazolyl, isoxazolyl, isothiazolyl, oxadiazolyl, and thiadiazolyl.

In another embodiment of Formula I, II, III or IV, the 6-membered heteroaryl is selected from the group consisting of: pyridinyl, pyridazinyl, pyrimidinyl, and pyrazinyl.

In another embodiment of Formula I, II, III or IV, the 8-membered heteroaryl is selected from the group consisting of: 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, and 6,7-dihydro-5H-pyrrolo[1,2-b][1,2,4]triazolyl, In another embodiment of Formula I, II, III or IV, the 9-membered heteroaryl is selected from the group consisting of: imidazo[1,2-a]pyridinyl, pyrazolo[1,5-a]pyridinyl, 6,7-dihydro-5H-cyclopenta[b]pyridinyl, 6,7-dihydro-5H-cyclopenta[c]pyridinyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

In another embodiment of Formula I, II, III or IV, the 9-membered heteroaryl is selected from 5,6,7,8-tetrahydroisoquinolinyl and 5,6,7,8-tetrahydroquinolinyl.

Certain embodiments of compounds of Formulas I, II, III or IV, or pharmaceutically acceptable salts thereof, are shown below in Table 1. Compounds of Formulas I, II, III or IV, or pharmaceutically acceptable salts thereof, and compounds of Table 1, or pharmaceutically acceptable salts thereof, are sometimes referred to herein as "compounds of the invention," or "compounds provided herein."

TABLE 1

| Structure | Compound No. | µ EC$_{50}$ (nM) | µ K$_i$ (nM) |
|---|---|---|---|
| 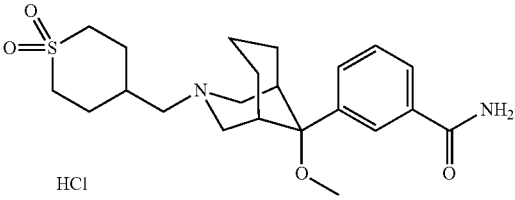 [SMILES: COC1(c2cccc(C(N)=O)c2)C2CCCC1CN(CC1CCS(=O)(=O)CC1)C2 ; Cl] | 1 | /\ | ** |
| 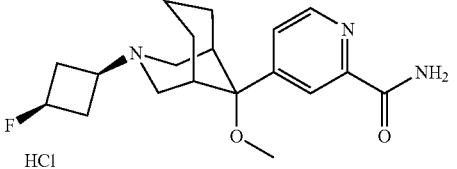 [SMILES: COC1(c2ccnc(C(N)=O)c2)C2CCCC1CN([C@H]1C[C@@H](F)C1)C2 ; Cl] | 2 | /\/\ | *** |
| 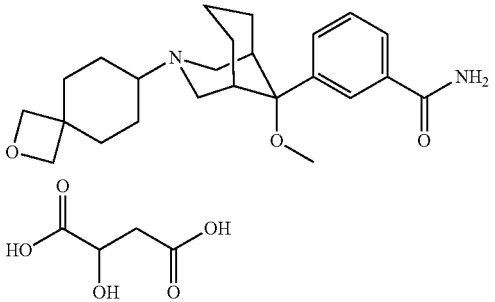 | 3 | /\/\/\ | *** |
| 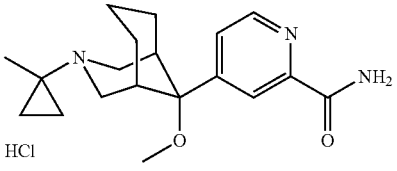 [SMILES: COC1(c2ccnc(C(N)=O)c2)C2CCCC1CN(C1(C)CC1)C2 ; Cl] | 4 | /\ | * |
| 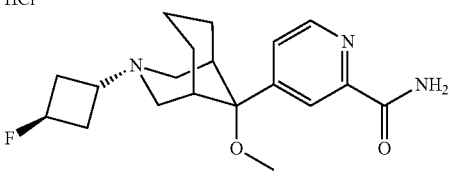 | 5 | NT | NT |
| 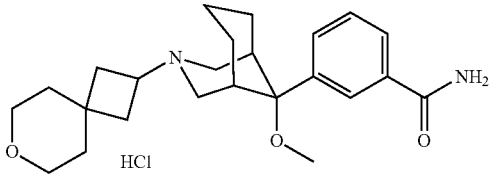 [SMILES: COC1(c2cccc(C(N)=O)c2)C2CCCC1CN(C1CC3(CCOCC3)C1)C2 ; Cl] | 6 | /\/\/\ | *** |

TABLE 1-continued
| Structure | Compound No. | μ EC$_{50}$ (nM) | μ K$_i$ (nM) |
|---|---|---|---|
| 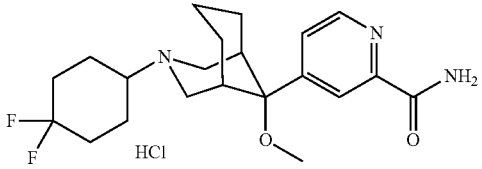 [SMILES: COC1(c2ccnc(C(N)=O)c2)C2CCCC1CN(C1CCC(F)(F)CC1)C2 ; Cl] | 7 | ∧ | ** |
| 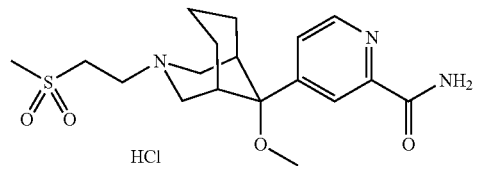 [SMILES: COC1(c2ccnc(C(N)=O)c2)C2CCCC1CN(CCS(C)(=O)=O)C2 ; Cl] | 8 | NT | * |
| 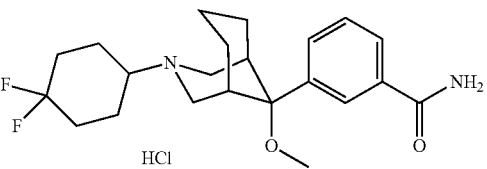 [SMILES: COC1(c2cccc(C(N)=O)c2)C2CCCC1CN(C1CCC(F)(F)CC1)C2 ; Cl] | 9 | ∧∧ | *** |
| 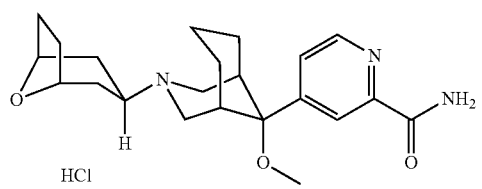 [SMILES: COC1(c2ccnc(C(N)=O)c2)C2CCCC1CN(C1CC3CCC(C1)O3)C2 ; Cl] | 10 | ∧ | * |
| 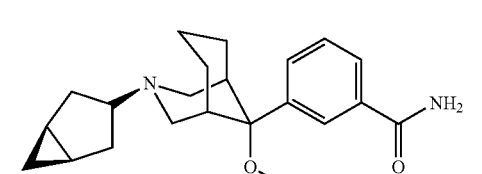 | 11 | ∧∧∧ | *** |
| 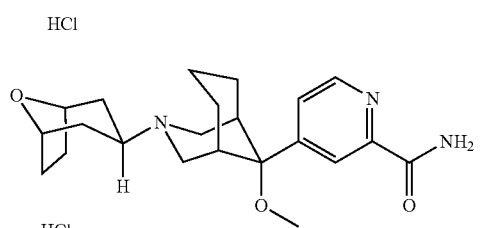 | 12 | ∧∧ | *** |
| 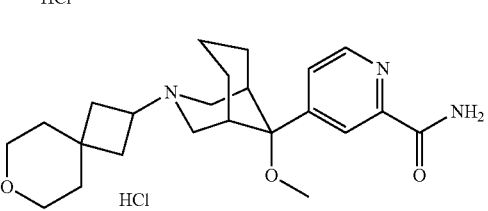 | 13 | ∧∧∧ | *** |
| 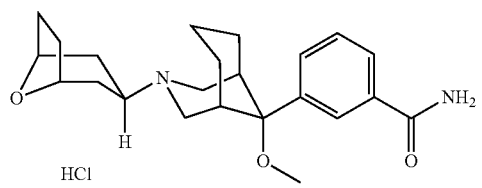 [SMILES: COC1(c2cccc(C(N)=O)c2)C2CCCC1CN(C1CC3CCC(C1)O3)C2 ; Cl] | 14 | ∧ | ** |

TABLE 1-continued
| Structure | Compound No. | μ EC$_{50}$ (nM) | μ K$_i$ (nM) |
|---|---|---|---|
| 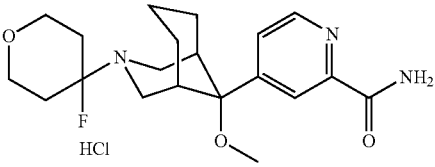 [SMILES: COC1(c2ccnc(C(N)=O)c2)C2CCCC1CN(C1(F)CCOCC1)C2 ; Cl] HCl | 15 | NT | * |
| 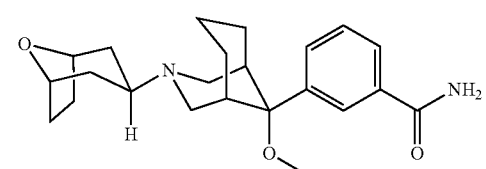 HCl | 16 | /\/\/\ | *** |
| 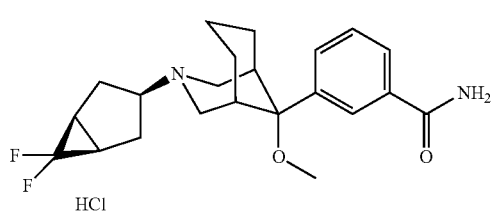 [SMILES: COC1(c2cccc(C(N)=O)c2)C2CCCC1CN([C@H]1C[C@@H]3[C@H](C1)C3(F)F)C2 ; Cl] HCl | 17 | /\/\/\ | *** |
| 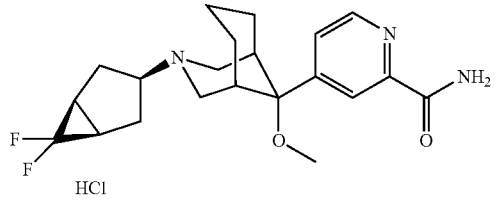 [SMILES: COC1(c2ccnc(C(N)=O)c2)C2CCCC1CN([C@H]1C[C@@H]3[C@H](C1)C3(F)F)C2 ; Cl] HCl | 18 | /\/\/\ | *** |
| 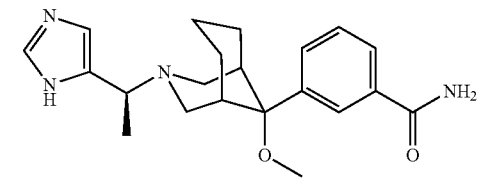 HCl | 19 | /\/\/\ | *** |
| 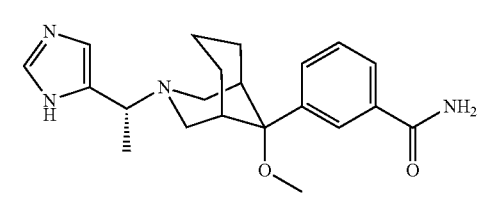 HCl | 20 | /\/\ | ** |
| 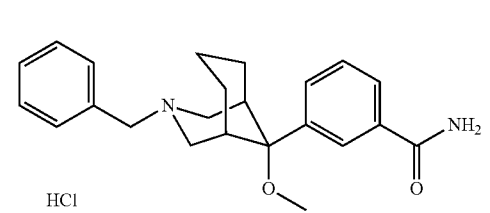 [SMILES: COC1(c2cccc(C(N)=O)c2)C2CCCC1CN(Cc1ccccc1)C2 ; Cl] HCl | 21 | /\/\/\ | *** |

TABLE 1-continued
| Structure | Compound No. | μ EC$_{50}$ (nM) | μ K$_i$ (nM) |
|---|---|---|---|
| 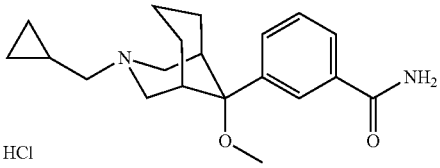 [SMILES: COC1(c2cccc(C(N)=O)c2)C2CCCC1CN(CC1CC1)C2 ; Cl] | 22 | /\/\/\ | *** |
| 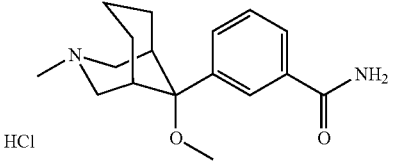 [SMILES: Cl ; COC1(c2cccc(C(N)=O)c2)C2CCCC1CN(C)C2] | 23 | /\/\/\ | *** |
| 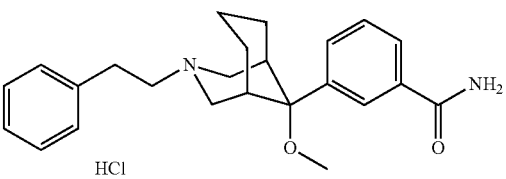 [SMILES: COC1(c2cccc(C(N)=O)c2)C2CCCC1CN(CCc1ccccc1)C2 ; Cl] | 24 | /\/\/\ | *** |
| 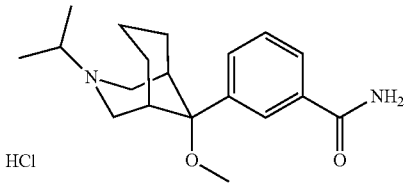 [SMILES: Cl ; COC1(c2cccc(C(N)=O)c2)C2CCCC1CN(C(C)C)C2] | 25 | NT | *** |
| 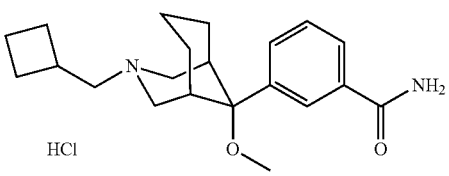 [SMILES: COC1(c2cccc(C(N)=O)c2)C2CCCC1CN(CC1CCC1)C2 ; Cl] | 26 | /\/\/\ | *** |
| 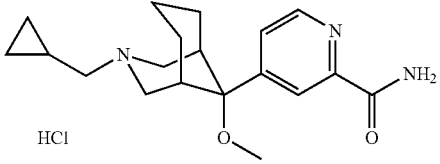 [SMILES: COC1(c2ccnc(C(N)=O)c2)C2CCCC1CN(CC1CC1)C2 ; Cl] | 27 | /\/\ | ** |
| 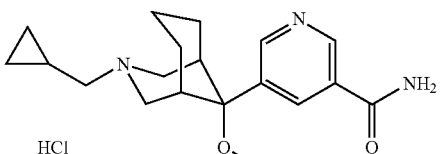 | 28 | NT | * |
| 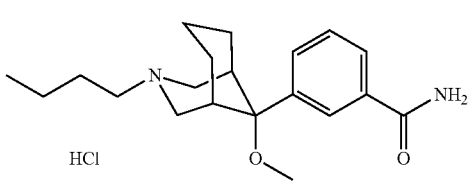 [SMILES: CCCCN1CC2CCCC(C1)C2(OC)c1cccc(C(N)=O)c1 ; Cl] | 29 | /\/\/\ | *** |

TABLE 1-continued
| Structure | Compound No. | μ EC$_{50}$ (nM) | μ K$_i$ (nM) |
|---|---|---|---|
| 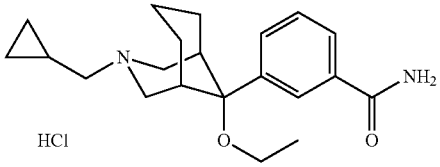 [SMILES: CCOC1(c2cccc(C(N)=O)c2)C2CCCC1CN(CC1CC1)C2 ; Cl] | 30 | /\/\/\ | *** |
| 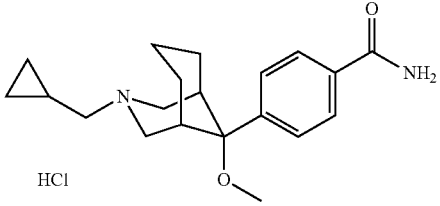 [SMILES: COC1(c2ccc(C(N)=O)cc2)C2CCCC1CN(CC1CC1)C2 ; Cl] | 31 | NT | * |
| 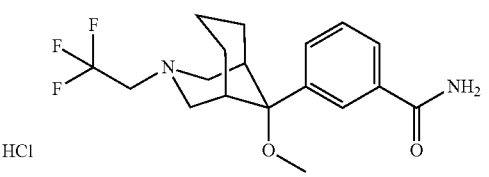 [SMILES: Cl ; COC1(c2cccc(C(N)=O)c2)C2CCCC1CN(CC(F)(F)F)C2] | 32 | NT | * |
| 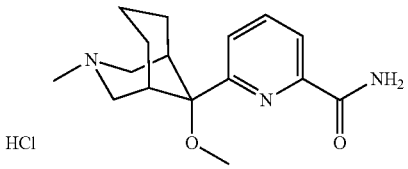 [SMILES: Cl ; COC1(c2cccc(C(N)=O)n2)C2CCCC1CN(C)C2] | 33 | NT | * |
| 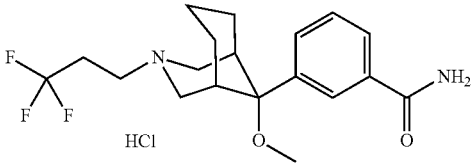 [SMILES: COC1(c2cccc(C(N)=O)c2)C2CCCC1CN(CCC(F)(F)F)C2 ; Cl] | 34 | /\/\/\ | *** |
| 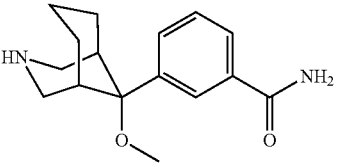 | 35 | /\/\ | *** |
| 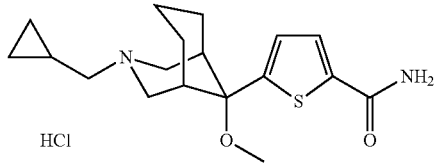 [SMILES: COC1(c2ccc(C(N)=O)s2)C2CCCC1CN(CC1CC1)C2 ; Cl] | 36 | /\/\ | *** |
| 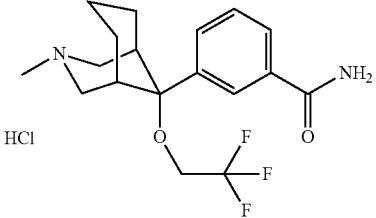 [SMILES: Cl ; CN1CC2CCCC(C1)C2(OCC(F)(F)F)c1cccc(C(N)=O)c1] | 37 | /\/\ | ** |

TABLE 1-continued
| Structure | Compound No. | μ EC₅₀ (nM) | μ Kᵢ (nM) |
|---|---|---|---|
| 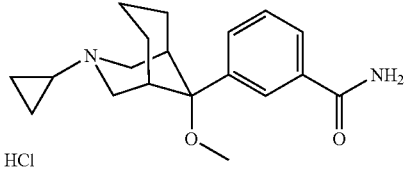 [SMILES: Cl ; COC1(c2cccc(C(N)=O)c2)C2CCCC1CN(C1CC1)C2] | 38 | /\/\ | *** |
| 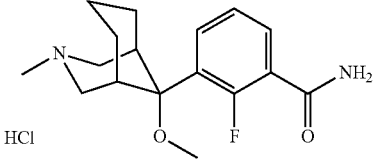 [SMILES: Cl ; COC1(c2cccc(C(N)=O)c2F)C2CCCC1CN(C)C2] | 39 | /\/\ | ** |
| 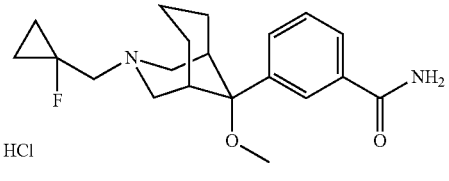 [SMILES: Cl ; COC1(c2cccc(C(N)=O)c2)C2CCCC1CN(CC1(F)CC1)C2] | 40 | /\/\ | *** |
| 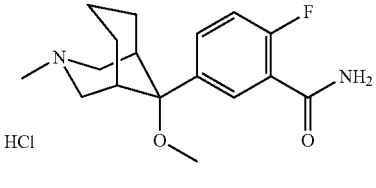 [SMILES: Cl ; COC1(c2ccc(F)c(C(N)=O)c2)C2CCCC1CN(C)C2] | 41 | NT | * |
| 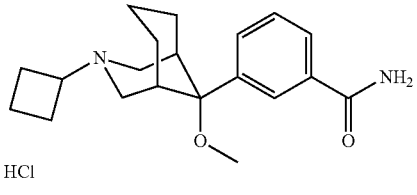 [SMILES: COC1(c2cccc(C(N)=O)c2)C2CCCC1CN(C1CCC1)C2 ; Cl] | 42 | /\/\/\ | *** |
| 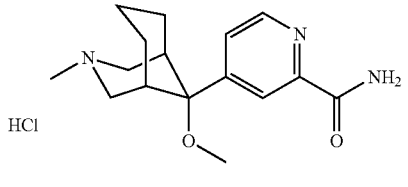 [SMILES: Cl ; COC1(c2ccnc(C(N)=O)c2)C2CCCC1CN(C)C2] | 43 | /\/\ | *** |
| 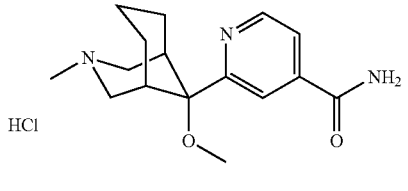 [SMILES: Cl ; COC1(c2cc(C(N)=O)ccn2)C2CCCC1CN(C)C2] | 44 | NT | ** |
| 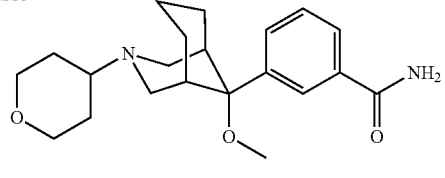 | 45 | /\/\ | ** |

TABLE 1-continued

| Structure | Compound No. | μ EC$_{50}$ (nM) | μ K$_i$ (nM) |
|---|---|---|---|
| (structure) HCl | 46 | /\/\ | *** |
| (structure) HCl | 47 | /\/\/\ | *** |
| (structure) HCl | 48 | /\/\ | *** |
| (structure) HCl | 49 | /\/\/\ | *** |
| (structure) with malic acid | 50 | /\/\ | ** |
| (structure) with malic acid | 51 | /\/\ | *** |
| (structure) HCl | 52 | NT | * |

TABLE 1-continued

| Structure | Compound No. | μ EC$_{50}$ (nM) | μ K$_i$ (nM) |
|---|---|---|---|
| (structure 53) HCl | 53 | ∧ | ** |
| (structure 54) HCl | 54 | ∧∧∧ | *** |
| (structure 55) HCl | 55 | ∧∧ | *** |
| (structure 56) HCl | 56 | ∧ | * |
| (structure 57) HCl | 57 | ∧ | * |
| (structure 58) HCl | 58 | ∧∧∧ | *** |
| (structure 59) HCl | 59 | NT | ** |
| (structure 60) HCl | 60 | ∧ | ** |

TABLE 1-continued
| Structure | Compound No. | μ EC$_{50}$ (nM) | μ K$_i$ (nM) |
|---|---|---|---|
| 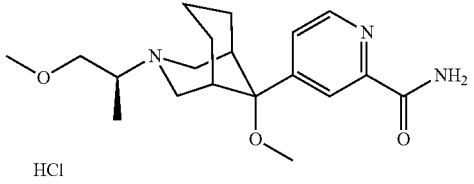 [SMILES: COC[C@H](C)N1CC2CCCC(C1)C2(OC)c1ccnc(C(N)=O)c1 ; Cl] HCl | 61 | ∧∧ | ** |
|  HCl | 62 | ∧ | * |
| 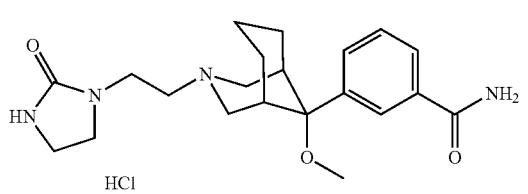 [SMILES: COC1(c2cccc(C(N)=O)c2)C2CCCC1CN(CCN1CCNC1=O)C2 ; Cl] HCl | 63 | ∧∧ | *** |
| 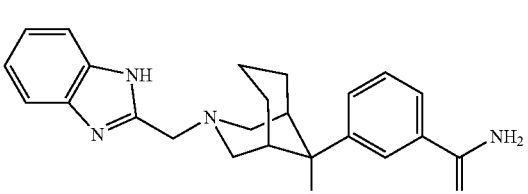 HCl | 64 | ∧∧∧ | *** |
| 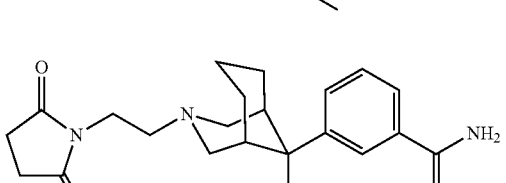 HCl | 65 | ∧∧∧ | *** |
| 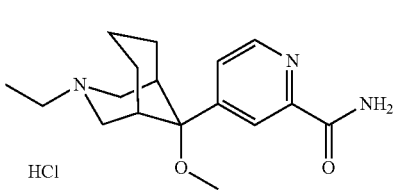 [SMILES: CCN1CC2CCCC(C1)C2(OC)c1ccnc(C(N)=O)c1 ; Cl] HCl | 66 | ∧∧ | ** |
| 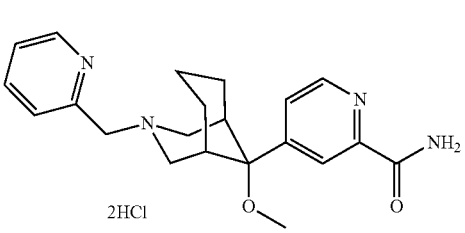 [SMILES: COC1(c2ccnc(C(N)=O)c2)C2CCCC1CN(Cc1ccccn1)C2 ; "2HCl"] 2HCl | 67 | ∧∧ | ** |

TABLE 1-continued
| Structure | Compound No. | μ EC$_{50}$ (nM) | μ K$_i$ (nM) |
|---|---|---|---|
| 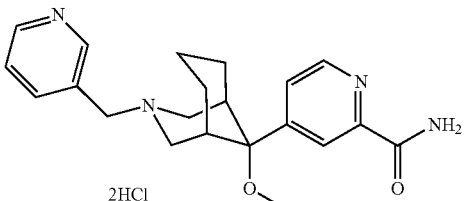 2HCl | 68 | ∧∧ | ** |
| 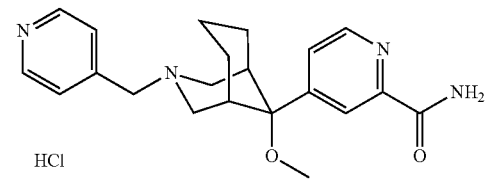 [SMILES: COC1(c2ccnc(C(N)=O)c2)C2CCCC1CN(Cc1ccncc1)C2 ; Cl] HCl | 69 | ∧ | * |
| 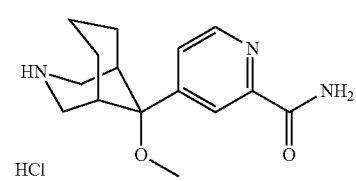 [SMILES: Cl ; COC1(c2ccnc(C(N)=O)c2)C2CCCC1CNC2] HCl HCl | 70 | ∧ | ** |
| 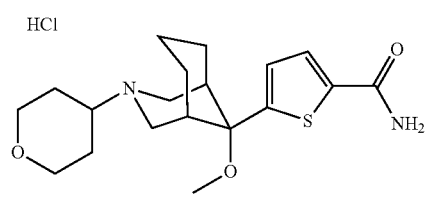 [SMILES: Cl ; COC1(c2ccc(C(N)=O)s2)C2CCCC1CN(C1CCOCC1)C2] | 71 | ∧ | * |
| 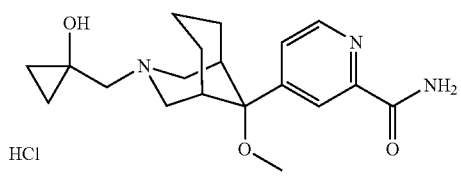 [SMILES: Cl ; COC1(c2ccnc(C(N)=O)c2)C2CCCC1CN(CC1(O)CC1)C2] HCl | 72 | ∧ | ** |
| 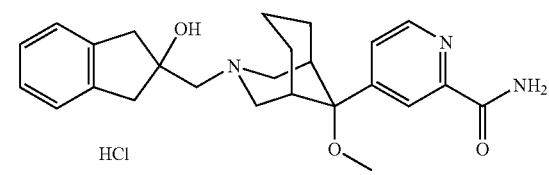 [SMILES: COC1(c2ccnc(C(N)=O)c2)C2CCCC1CN(CC1(O)Cc3ccccc3C1)C2 ; Cl] HCl | 73 | ∧∧∧ | *** |
| 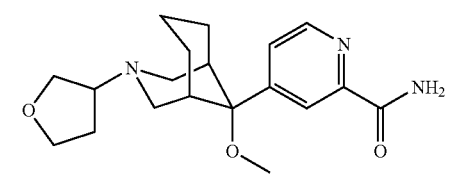 HCl | 74 | ∧∧ | ** |
| 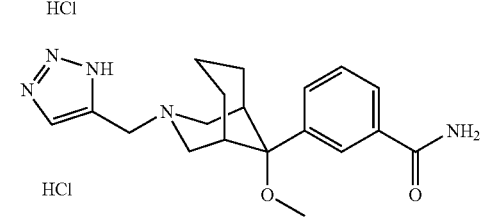 HCl | 75 | ∧∧∧ | *** |

TABLE 1-continued

| Structure | Compound No. | μ EC₅₀ (nM) | μ Kᵢ (nM) |
|---|---|---|---|
| (structure, HCl salt) | 76 | ∧∧ | ** |
| (structure, HCl salt) | 77 | ∧∧∧ | *** |
| (structure, HCl salt) | 78 | ∧∧ | ** |
| (structure, HCl salt) | 79 | ∧∧ | ** |
| (structure, HCl salt) | 80 | NT | * |
| (structure, malate salt) | 81 | ∧∧ | *** |
| (structure, HCl salt) | 82 | ∧∧ | ** |

TABLE 1-continued
| Structure | Compound No. | µ EC$_{50}$ (nM) | µ K$_i$ (nM) |
|---|---|---|---|
| 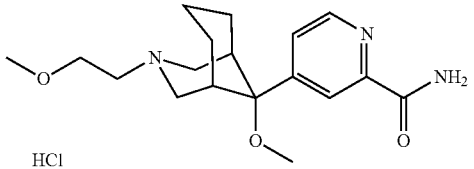 [SMILES: COCCN1CC2CCCC(C1)C2(OC)c1ccnc(C(N)=O)c1 ; Cl] | 83 | /\/\ | ** |
| 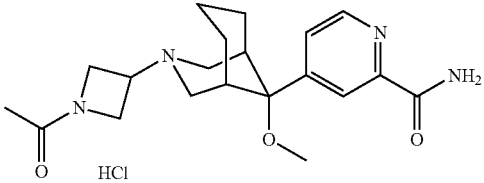 [SMILES: COC1(c2ccnc(C(N)=O)c2)C2CCCC1CN(C1CN(C(C)=O)C1)C2 ; Cl] | 84 | NT | * |
| 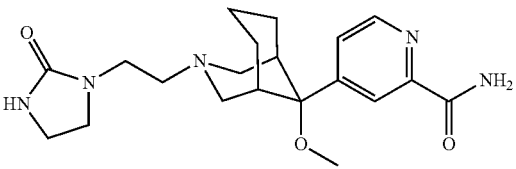 | 85 | /\/\ | ** |
| 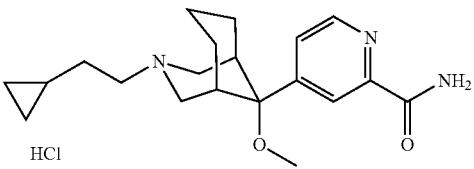 [SMILES: COC1(c2ccnc(C(N)=O)c2)C2CCCC1CN(CCC1CC1)C2 ; Cl] | 86 | /\/\ | ** |
| 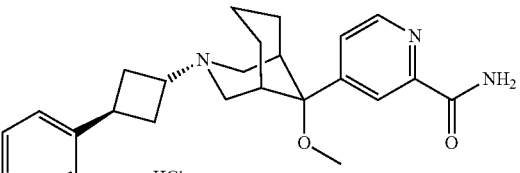 | 87 | /\/\/\ | *** |
| 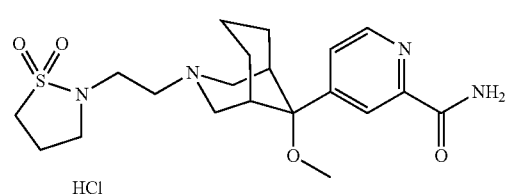 [SMILES: COC1(c2ccnc(C(N)=O)c2)C2CCCC1CN(CCN1CCCS1(=O)=O)C2 ; Cl] | 88 | /\ | ** |
| 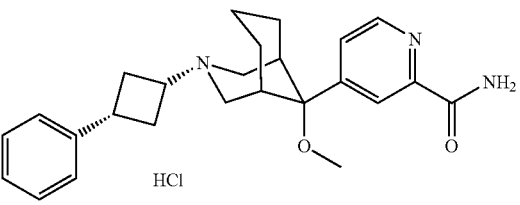 | 89 | /\/\/\ | *** |
| 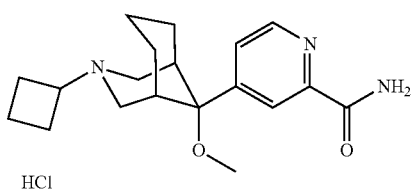 [SMILES: COC1(c2ccnc(C(N)=O)c2)C2CCCC1CN(C1CCC1)C2 ; Cl] | 90 | /\/\ | ** |

TABLE 1-continued

| Structure | Compound No. | μ EC$_{50}$ (nM) | μ K$_i$ (nM) |
|---|---|---|---|
| 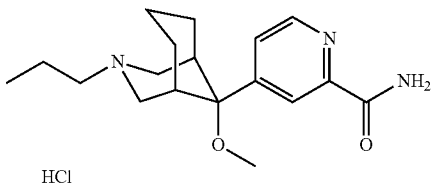 [SMILES: CCCN1CC2CCCC(C1)C2(OC)c1ccnc(C(N)=O)c1 ; Cl] | 91 | /\/\ | ** |
| 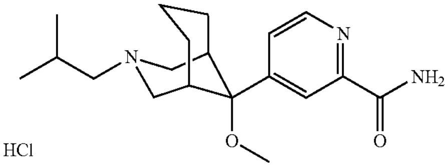 [SMILES: Cl ; COC1(c2ccnc(C(N)=O)c2)C2CCCC1CN(CC(C)C)C2] | 92 | /\ | * |
| 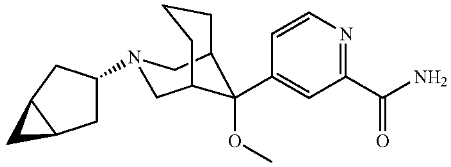 | 93 | /\/\ | ** |
| 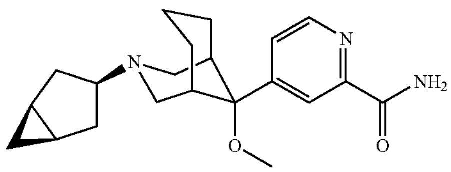 | 94 | /\/\ | *** |
| | 95 | /\ | ** |
| 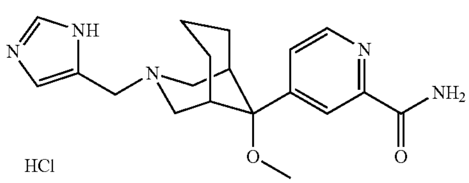 [SMILES: COC1(c2ccnc(C(N)=O)c2)C2CCCC1CN(Cc1cnc[nH]1)C2 ; Cl] | 96 | /\/\ | *** |
| | 97 | /\/\ | *** |

TABLE 1-continued

| Structure | Compound No. | μ EC$_{50}$ (nM) | μ K$_i$ (nM) |
|---|---|---|---|
| 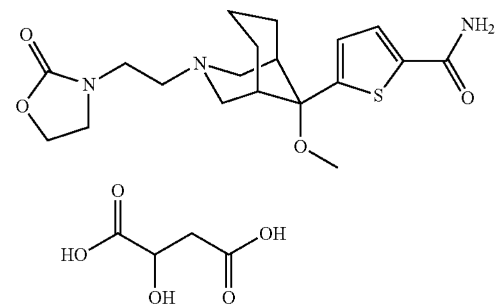 [SMILES: COC1(c2ccc(C(N)=O)s2)C2CCCC1CN(CCN1CCOC1=O)C2 ; O=C(O)CC(O)C(=O)O] | 98 | /\/\ | * |
| 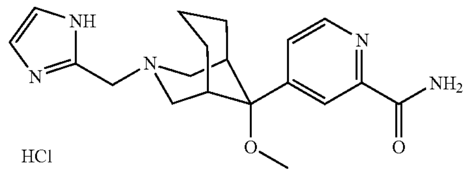 [SMILES: COC1(c2ccnc(C(N)=O)c2)C2CCCC1CN(Cc1ncc[nH]1)C2 ; Cl] | 99 | /\/\ | ** |
| 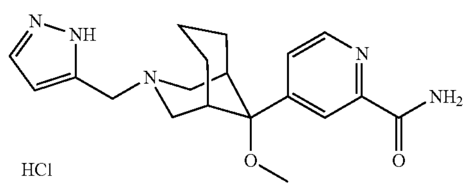 [SMILES: COC1(c2ccnc(C(N)=O)c2)C2CCCC1CN(Cc1ccn[nH]1)C2 ; Cl] | 100 | /\/\ | *** |
| 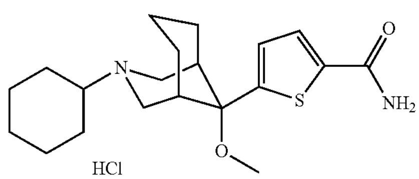 [SMILES: COC1(c2ccc(C(N)=O)s2)C2CCCC1CN(C1CCCCC1)C2 ; Cl] | 101 | /\ | ** |
| 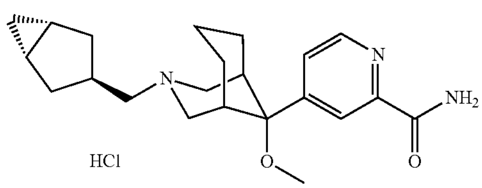 [SMILES: COC1(c2ccnc(C(N)=O)c2)C2CCCC1CN(C[C@H]1C[C@@H]3C[C@@H]3C1)C2 ; Cl] | 102 | /\/\ | *** |
| 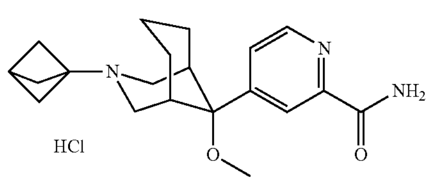 [SMILES: COC1(c2ccnc(C(N)=O)c2)C2CCCC1CN(C13CC(C1)C3)C2 ; Cl] | 103 | /\ | ** |
| 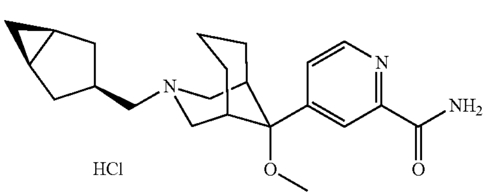 [SMILES: COC1(c2ccnc(C(N)=O)c2)C2CCCC1CN(C[C@@H]1C[C@@H]3C[C@@H]3C1)C2 ; Cl] | 104 | /\/\ | *** |

TABLE 1-continued

| Structure | Compound No. | μ EC$_{50}$ (nM) | μ K$_i$ (nM) |
|---|---|---|---|
| 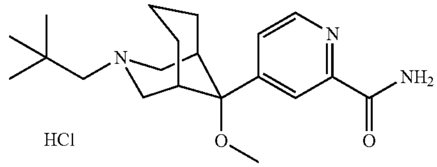 [SMILES: COC1(c2ccnc(C(N)=O)c2)C2CCCC1CN(CC(C)(C)C)C2 ; Cl] | 105 | NT | * |
| 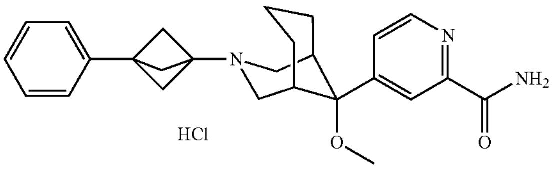 [SMILES: COC1(c2ccnc(C(N)=O)c2)C2CCCC1CN(C13CC(c4ccccc4)(C1)C3)C2 ; Cl] | 106 | /\/\/\ | *** |
| 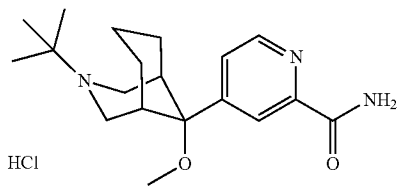 [SMILES: COC1(c2ccnc(C(N)=O)c2)C2CCCC1CN(C(C)(C)C)C2 ; Cl] | 107 | /\ | ** |
| 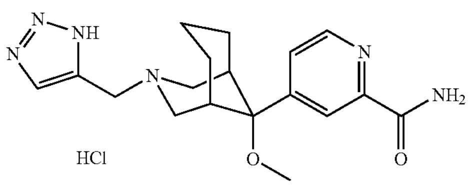 [SMILES: COC1(c2ccnc(C(N)=O)c2)C2CCCC1CN(Cc1cnn[nH]1)C2 ; Cl] | 108 | /\/\ | ** |
| 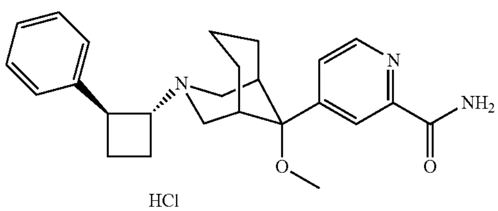 [SMILES: COC1(c2ccnc(C(N)=O)c2)C2CCCC1CN([C@@H]1CC[C@H]1c1ccccc1)C2 ; Cl] | 109 | /\/\/\ | *** |
| 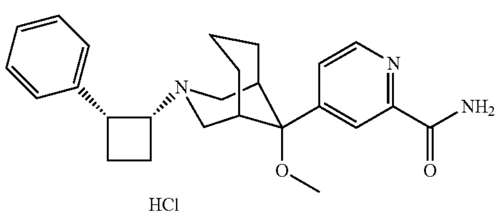 [SMILES: COC1(c2ccnc(C(N)=O)c2)C2CCCC1CN([C@@H]1CC[C@@H]1c1ccccc1)C2 ; Cl] | 110 | NT | * |
| 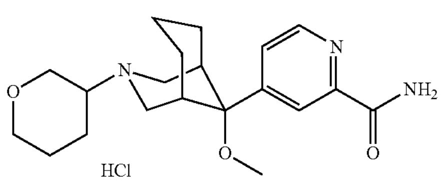 [SMILES: COC1(c2ccnc(C(N)=O)c2)C2CCCC1CN(C1CCCOC1)C2 ; Cl] | 111 | /\ | * |
| 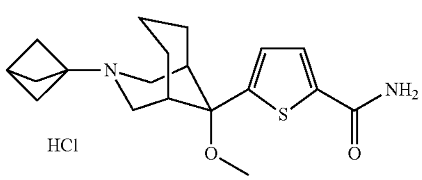 [SMILES: COC1(c2ccc(C(N)=O)s2)C2CCCC1CN(C13CC(C1)C3)C2 ; Cl] | 112 | /\ | ** |

TABLE 1-continued

| Structure | Compound No. | μ EC$_{50}$ (nM) | μ K$_i$ (nM) |
|---|---|---|---|
| 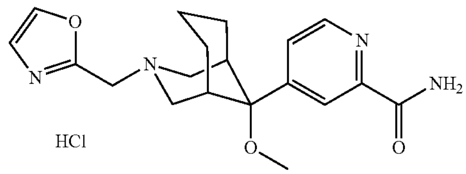 [SMILES: COC1(c2ccnc(C(N)=O)c2)C2CCCC1CN(Cc1ncco1)C2 ; Cl] | 113 | /\ | * |
| 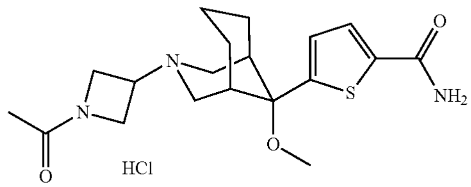 [SMILES: COC1(c2ccc(C(N)=O)s2)C2CCCC1CN(C1CN(C(C)=O)C1)C2 ; Cl] | 114 | /\ | * |
| 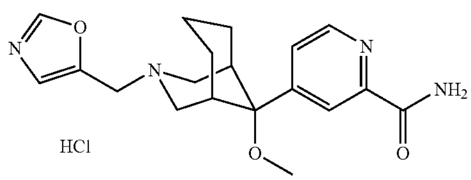 [SMILES: COC1(c2ccnc(C(N)=O)c2)C2CCCC1CN(Cc1cnco1)C2 ; Cl] | 115 | /\/\ | ** |
| 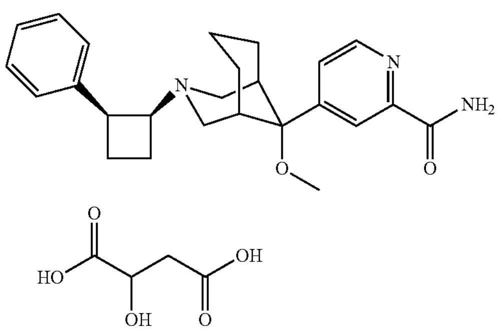 | 116 | NT | * |
| 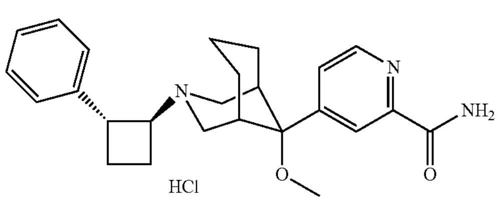 [SMILES: COC1(c2ccnc(C(N)=O)c2)C2CCCC1CN([C@H]1CC[C@@H]1c1ccccc1)C2 ; Cl] | 117 | /\/\ | ** |
| 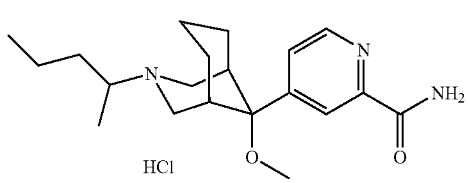 [SMILES: CCCC(C)N1CC2CCCC(C1)C2(OC)c1ccnc(C(N)=O)c1 ; Cl] | 118 | /\/\ | ** |

TABLE 1-continued

| Structure | Compound No. | μ EC$_{50}$ (nM) | μ K$_i$ (nM) |
|---|---|---|---|
| 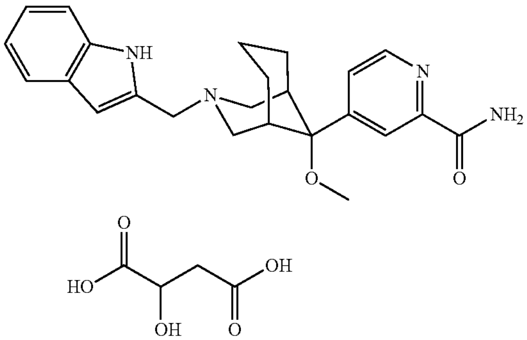 [SMILES: COC1(c2ccnc(C(N)=O)c2)C2CCCC1CN(Cc1cc3ccccc3[nH]1)C2 ; O=C(O)CC(O)C(=O)O] | 119 | /\/\/\ | *** |
| 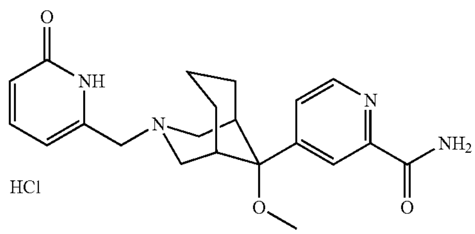 [SMILES: COC1(c2ccnc(C(N)=O)c2)C2CCCC1CN(Cc1cccc(=O)[nH]1)C2 ; Cl] | 120 | NT | * |
| 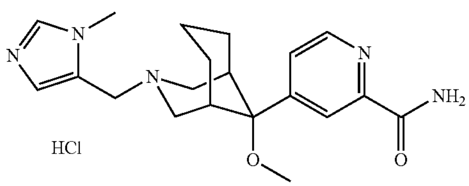 [SMILES: COC1(c2ccnc(C(N)=O)c2)C2CCCC1CN(Cc1cncn1C)C2 ; Cl] | 121 | /\ | ** |
| 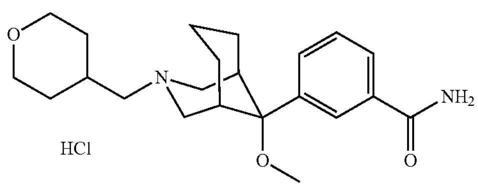 [SMILES: COC1(c2cccc(C(N)=O)c2)C2CCCC1CN(CC1CCOCC1)C2 ; Cl] | 122 | /\/\ | ** |
| 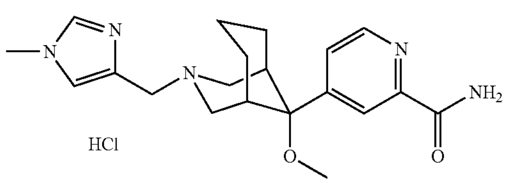 [SMILES: COC1(c2ccnc(C(N)=O)c2)C2CCCC1CN(Cc1cn(C)cn1)C2 ; Cl] | 123 | /\/\ | ** |
| 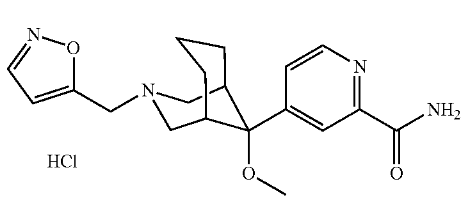 [SMILES: COC1(c2ccnc(C(N)=O)c2)C2CCCC1CN(Cc1ccno1)C2 ; Cl] | 124 | /\ | * |
| 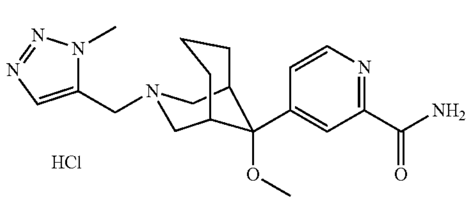 [SMILES: COC1(c2ccnc(C(N)=O)c2)C2CCCC1CN(Cc1cnnn1C)C2 ; Cl] | 125 | NT | * |

TABLE 1-continued

| Structure | Compound No. | μ EC$_{50}$ (nM) | μ K$_i$ (nM) |
|---|---|---|---|
| 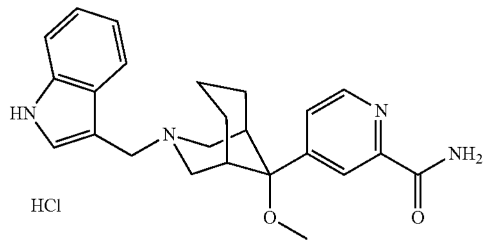 [SMILES: COC1(c2ccnc(C(N)=O)c2)C2CCCC1CN(Cc1c[nH]c3ccccc13)C2 ; Cl] | 126 | /\/\/\ | *** |
| 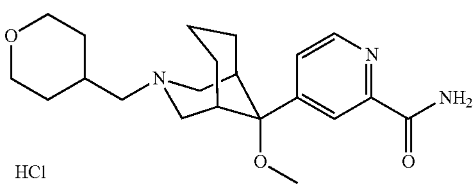 [SMILES: COC1(c2ccnc(C(N)=O)c2)C2CCCC1CN(CC1CCOCC1)C2 ; Cl] | 127 | /\/\ | ** |
| 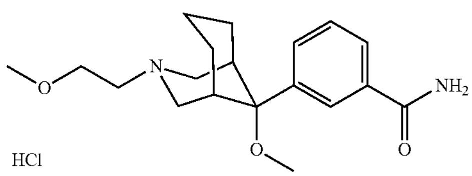 [SMILES: COCCN1CC2CCCC(C1)C2(OC)c1cccc(C(N)=O)c1 ; Cl] | 128 | /\/\ | *** |
| 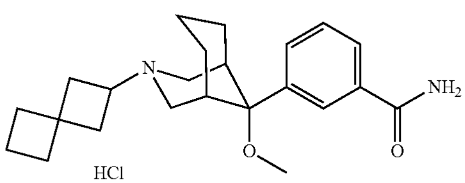 [SMILES: COC1(c2cccc(C(N)=O)c2)C2CCCC1CN(C1CC3(CCC3)C1)C2 ; Cl] | 129 | /\/\/\ | *** |
| 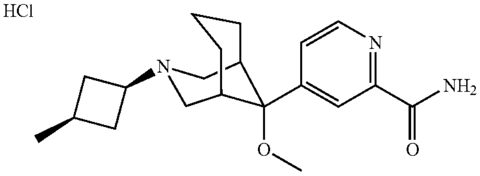 [SMILES: Cl ; COC1(c2ccnc(C(N)=O)c2)C2CCCC1CN([C@H]1C[C@@H](C)C1)C2] | 130 | /\/\ | *** |
| 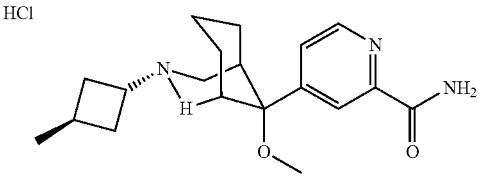 | 131 | /\/\ | ** |
| 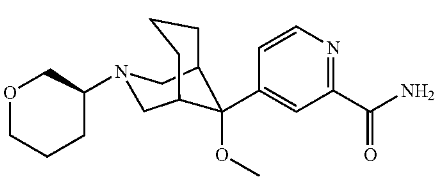 | 132 | /\ | ** |

TABLE 1-continued
| Structure | Compound No. | μ EC$_{50}$ (nM) | μ K$_i$ (nM) |
|---|---|---|---|
| 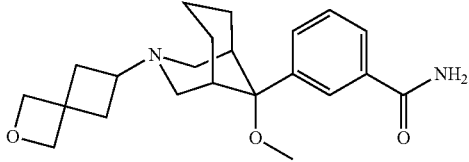 | 133 | /\/\/\ | *** |
| 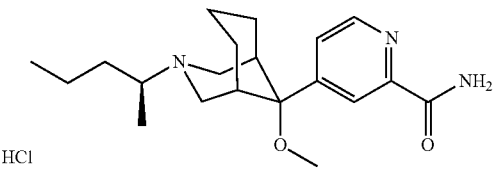 [SMILES: Cl ; CCC[C@H](C)N1CC2CCCC(C1)C2(OC)c1ccnc(C(N)=O)c1] | 134 | /\/\ | *** |
| 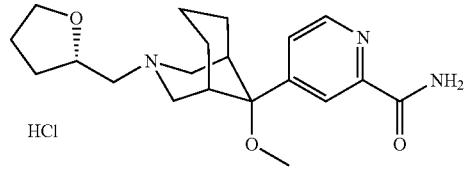 [SMILES: COC1(c2ccnc(C(N)=O)c2)C2CCCC1CN(C[C@@H]1CCCO1)C2 ; Cl] | 135 | /\/\ | ** |
| 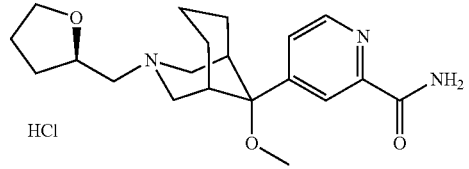 [SMILES: COC1(c2ccnc(C(N)=O)c2)C2CCCC1CN(C[C@H]1CCCO1)C2 ; Cl] | 136 | /\/\ | * |
| 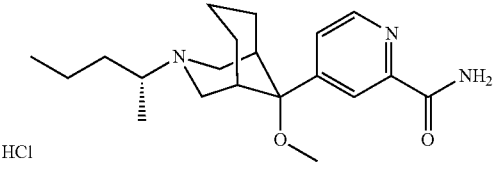 [SMILES: Cl ; CCC[C@@H](C)N1CC2CCCC(C1)C2(OC)c1ccnc(C(N)=O)c1] | 137 | /\/\ | ** |
| 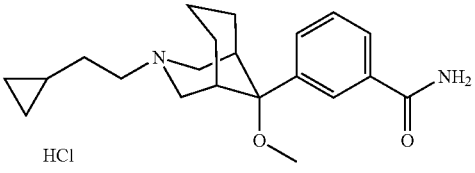 [SMILES: COC1(c2cccc(C(N)=O)c2)C2CCCC1CN(CCC1CC1)C2 ; Cl] | 138 | /\/\/\ | *** |
| 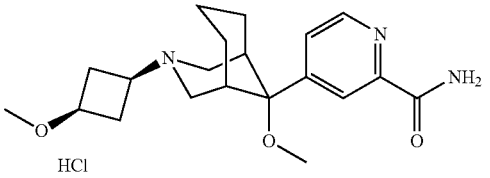 [SMILES: COC1(c2ccnc(C(N)=O)c2)C2CCCC1CN([C@H]1C[C@@H](OC)C1)C2 ; Cl] | 139 | /\/\ | *** |

TABLE 1-continued

| Structure | Compound No. | µ EC$_{50}$ (nM) | µ K$_i$ (nM) |
|---|---|---|---|
| (structure) HCl | 140 | /\/\ | *** |
| (structure) HCl | 141 | /\/\ | *** |
| (structure) HCl | 142 | /\/\/\ | *** |
| (structure) HCl | 143 | /\/\/\ | *** |
| (structure) HCl | 144 | /\/\ | *** |
| (structure) HCl | 145 | NT | NT |
| (structure) HCl | 146 | NT | NT |

TABLE 1-continued

| Structure | Compound No. | μ EC$_{50}$ (nM) | μ K$_i$ (nM) |
|---|---|---|---|
| (structure) HCl | 147 | /\/\ | ** |
| (structure) HCl | 148 | /\/\/\ | *** |
| (structure) HCl | 149 | /\/\/\ | *** |
| (structure) HCl | 150 | /\ | ** |
| (structure) HCl | 151 | /\/\/\ | *** |
| (structure) HCl | 152 | /\/\/\ | *** |
| (structure) HCl | 153 | /\/\ | *** |
| (structure) HCl | 154 | /\/\/\ | *** |

TABLE 1-continued

| Structure | Compound No. | μ EC$_{50}$ (nM) | μ K$_i$ (nM) |
|---|---|---|---|
| 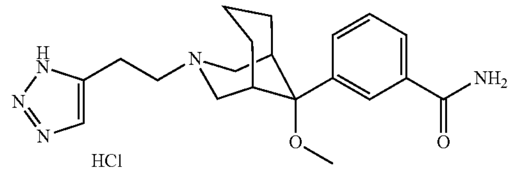 [SMILES: COC1(c2cccc(C(N)=O)c2)C2CCCC1CN(CCc1cnn[nH]1)C2 ; Cl] | 155 | /\/\/\ | *** |
| 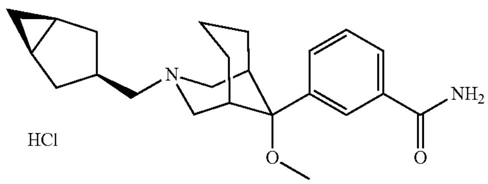 [SMILES: COC1(c2cccc(C(N)=O)c2)C2CCCC1CN(C[C@@H]1C[C@@H]3C[C@@H]3C1)C2 ; Cl] | 156 | /\/\/\ | *** |
| 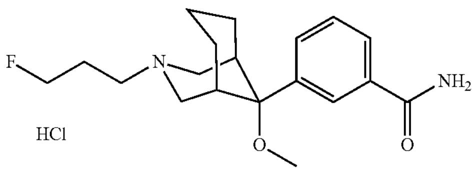 [SMILES: COC1(c2cccc(C(N)=O)c2)C2CCCC1CN(CCCF)C2 ; Cl] | 157 | /\/\ | *** |
| 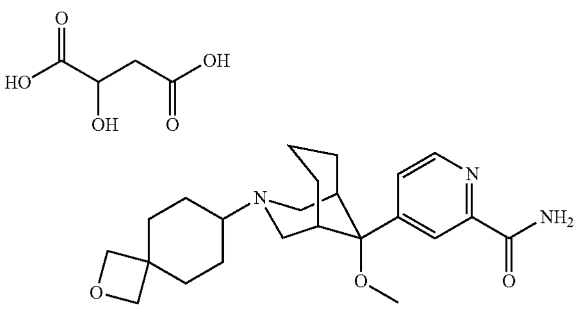 [SMILES: O=C(O)CC(O)C(=O)O ; COC1(c2ccnc(C(N)=O)c2)C2CCCC1CN(C1CCC3(CC1)COC3)C2] | 158 | /\/\ | ** |
| 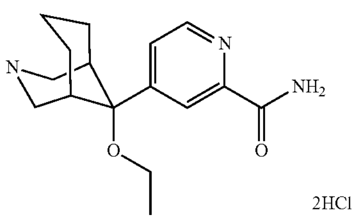 [SMILES: CCOC1(c2ccnc(C(N)=O)c2)C2CCCC1CNC2] | 161 | /\/\ | NT |
| 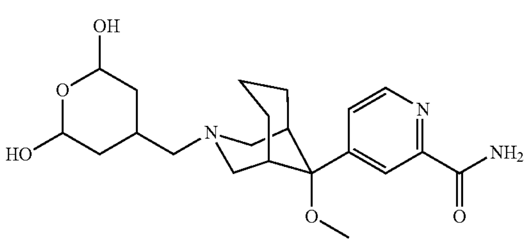 [SMILES: COC1(c2ccnc(C(N)=O)c2)C2CCCC1CN(CC1CC(O)OC(O)C1)C2] | 162 | NT | NT |
| 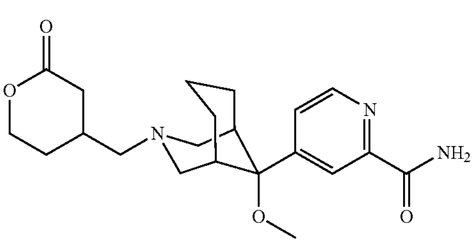 [SMILES: COC1(c2ccnc(C(N)=O)c2)C2CCCC1CN(CC1CCOC(=O)C1)C2] | 163 | NT | NT |

TABLE 1-continued

| Structure | Compound No. | μ EC$_{50}$ (nM) | μ K$_i$ (nM) |
|---|---|---|---|
| 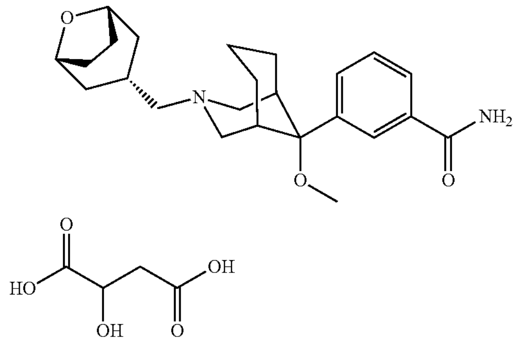 [SMILES: COC1(c2cccc(C(N)=O)c2)C2CCCC1CN(C[C@@H]1C[C@H]3CC[C@@H](C1)O3)C2 ; O=C(O)CC(O)C(=O)O] | 167 | /\/\/\ | NT |
| 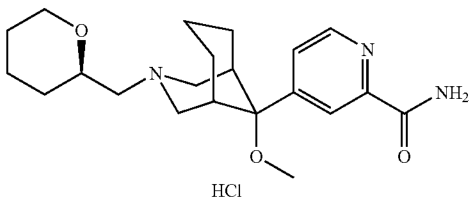 [SMILES: COC1(c2ccnc(C(N)=O)c2)C2CCCC1CN(C[C@H]1CCCCO1)C2 ; Cl] | 168 | /\/\ | NT |
| 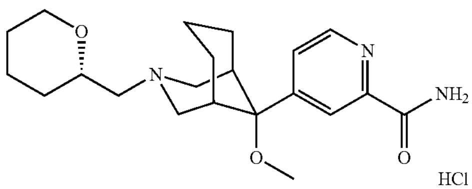 [SMILES: COC1(c2ccnc(C(N)=O)c2)C2CCCC1CN(C[C@@H]1CCCCO1)C2 ; Cl] | 169 | /\/\ | NT |
| 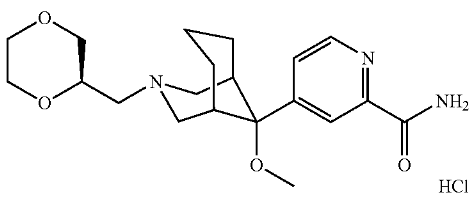 [SMILES: COC1(c2ccnc(C(N)=O)c2)C2CCCC1CN(C[C@@H]1COCCO1)C2 ; Cl] | 170 | NT | NT |
| 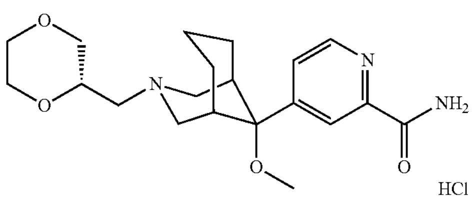 [SMILES: COC1(c2ccnc(C(N)=O)c2)C2CCCC1CN(C[C@H]1COCCO1)C2 ; Cl] | 171 | NT | NT |
| 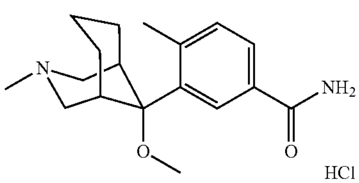 [SMILES: COC1(c2cc(C(N)=O)ccc2C)C2CCCC1CN(C)C2 ; Cl] | 172 | /\ | NT |
| 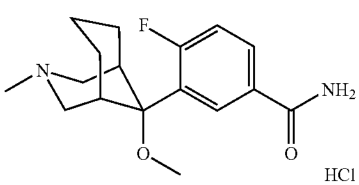 [SMILES: COC1(c2cc(C(N)=O)ccc2F)C2CCCC1CN(C)C2 ; Cl] | 173 | /\/\ | NT |

TABLE 1-continued
| Structure | Compound No. | µ EC$_{50}$ (nM) | µ K$_i$ (nM) |
|---|---|---|---|
| 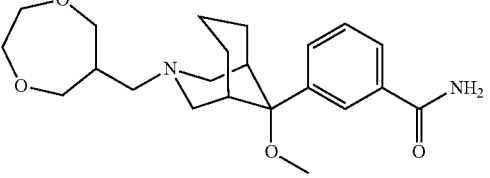 | 174 | NT | NT |
| 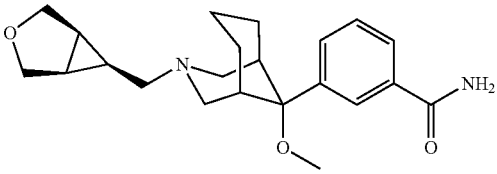 HCl | 175 | /\/\/\ | *** |
| 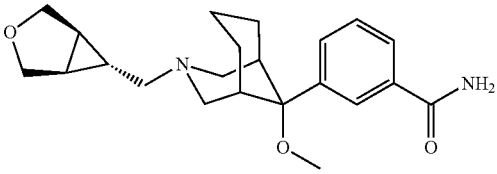 HCl | 176 | /\/\/\ | *** |
| 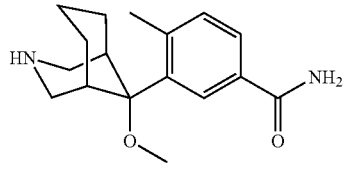 [SMILES: COC1(c2cc(C(N)=O)ccc2C)C2CCCC1CNC2] | 177 | NT | NT |
| 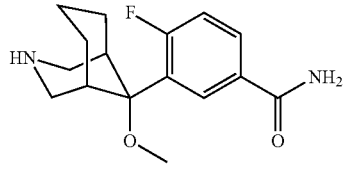 [SMILES: COC1(c2cc(C(N)=O)ccc2F)C2CCCC1CNC2] | 178 | NT | NT |
| 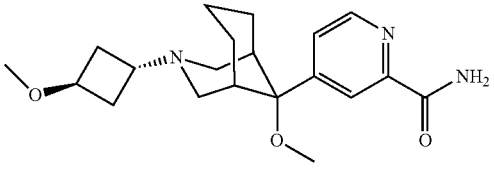 [SMILES: COC1(c2ccnc(C(N)=O)c2)C2CCCC1CN([C@H]1C[C@H](OC)C1)C2] | 179 | NT | NT |
| 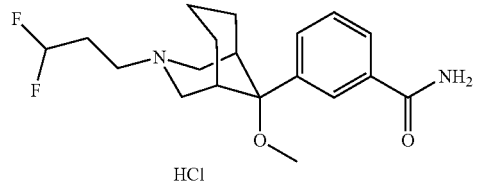 [SMILES: COC1(c2cccc(C(N)=O)c2)C2CCCC1CN(CCC(F)F)C2 ; Cl] HCl | 159 | /\/\/\ | *** |

TABLE 1-continued
| Structure | Compound No. | μ EC$_{50}$ (nM) | μ K$_i$ (nM) |
|---|---|---|---|
| 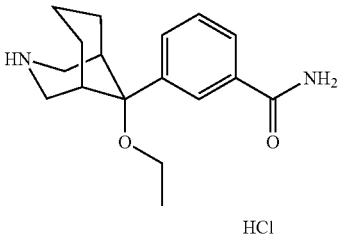 [SMILES: CCOC1(c2cccc(C(N)=O)c2)C2CCCC1CNC2 ; Cl] | 160 | ∧∧ | ** |
| 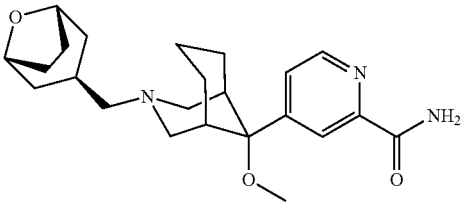 | 164 | ∧∧ | NT |
| 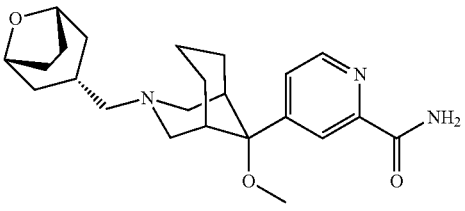 | 165 | ∧∧ | NT |
| 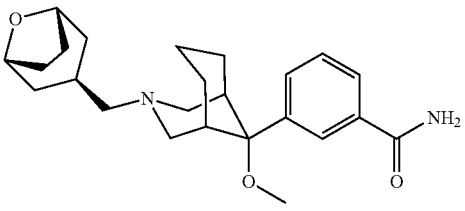 | 166 | ∧∧∧ | NT |
| 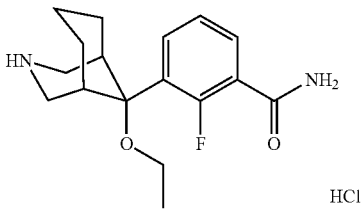 [SMILES: CCOC1(c2cccc(C(N)=O)c2F)C2CCCC1CNC2 ; Cl] | 180 | ∧ | * |

TABLE 1-continued

| Structure | Compound No. | μ EC$_{50}$ (nM) | μ K$_i$ (nM) |
|---|---|---|---|
| 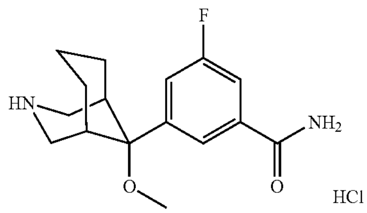 [SMILES: COC1(c2cc(F)cc(C(N)=O)c2)C2CCCC1CNC2 ; Cl] | 181 | ∧∧ | NT |
| 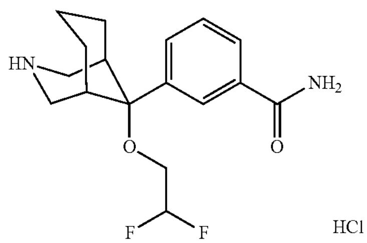 [SMILES: NC(=O)c1cccc(C2(OCC(F)F)C3CCCC2CNC3)c1 ; Cl] | 182 | ∧∧ | * |
| 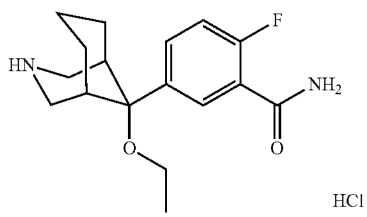 [SMILES: CCOC1(c2ccc(F)c(C(N)=O)c2)C2CCCC1CNC2 ; Cl] | 183 | ∧ | * |
| 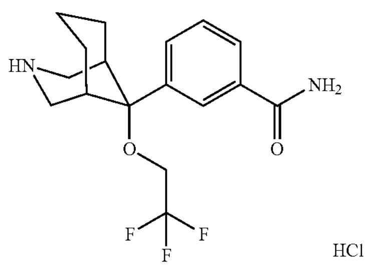 [SMILES: NC(=O)c1cccc(C2(OCC(F)(F)F)C3CCCC2CNC3)c1 ; Cl] | 184 | ∧∧ | NT |
| 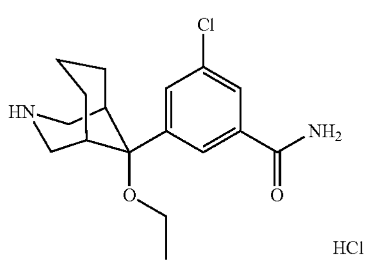 | 185 | ∧ | NT |
| 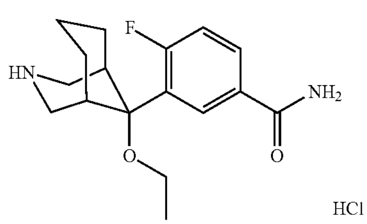 [SMILES: CCOC1(c2cc(C(N)=O)ccc2F)C2CCCC1CNC2 ; Cl] | 186 | ∧∧ | NT |

TABLE 1-continued
| Structure | Compound No. | μ EC$_{50}$ (nM) | μ K$_i$ (nM) |
|---|---|---|---|
| 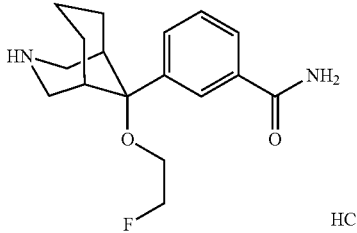 | 187 | ∧∧ | * |
| 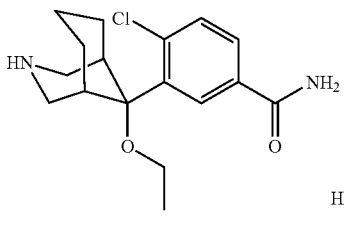 | 188 | ∧ | * |
| 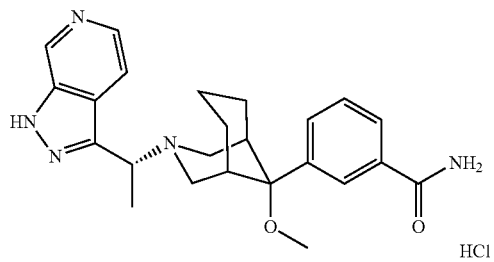 [SMILES: COC1(c2cccc(C(N)=O)c2)C2CCCC1CN([C@H](C)c1n[nH]c3cnccc13)C2 ; Cl] | 189 | ∧∧ | NT |
| 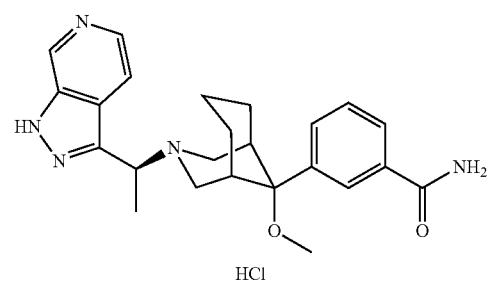 [SMILES: COC1(c2cccc(C(N)=O)c2)C2CCCC1CN([C@@H](C)c1n[nH]c3cnccc13)C2 ; Cl] | 190 | ∧∧∧ | NT |
| 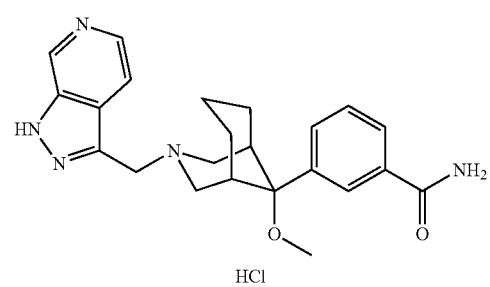 [SMILES: COC1(c2cccc(C(N)=O)c2)C2CCCC1CN(Cc1n[nH]c3cnccc13)C2 ; Cl] | 191 | ∧∧ | NT |
| 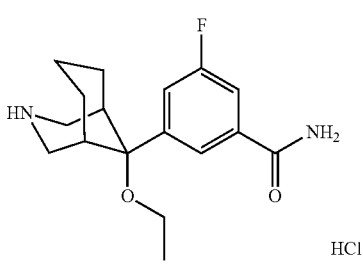 [SMILES: CCOC1(c2cc(F)cc(C(N)=O)c2)C2CCCC1CNC2 ; Cl] | 192 | ∧∧ | NT |

TABLE 1-continued
| Structure | Compound No. | µ EC$_{50}$ (nM) | µ K$_i$ (nM) |
|---|---|---|---|
| 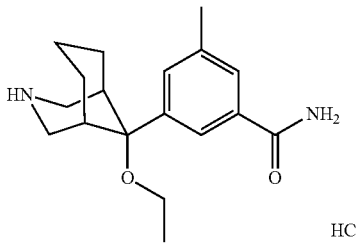 | 193 | ∧ | NT |
| 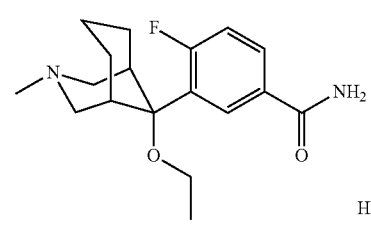 | 194 | ∧∧∧ | NT |
| 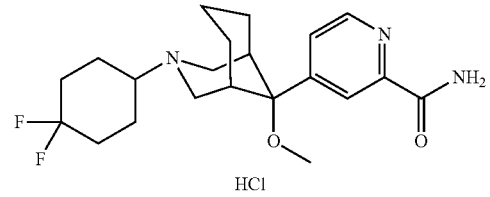 [SMILES: COC1(c2ccnc(C(N)=O)c2)C2CCCC1CN(C1CCC(F)(F)CC1)C2 ; Cl] | 195 | ∧ | ** |
| 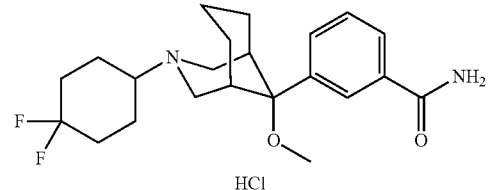 [SMILES: COC1(c2cccc(C(N)=O)c2)C2CCCC1CN(C1CCC(F)(F)CC1)C2 ; Cl] | 196 | ∧∧ | *** |
| 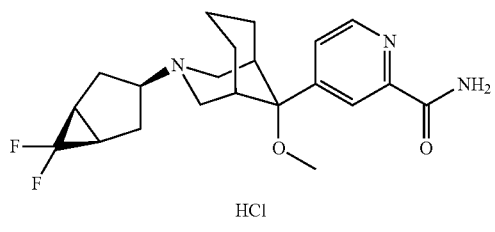 [SMILES: COC1(c2ccnc(C(N)=O)c2)C2CCCC1CN([C@H]1C[C@@H]3[C@H](C1)C3(F)F)C2 ; Cl] | 197 | ∧∧∧ | *** |
| 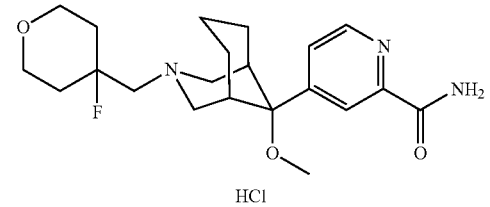 [SMILES: COC1(c2ccnc(C(N)=O)c2)C2CCCC1CN(CC1(F)CCOCC1)C2 ; Cl] | 198 | NT | * |
| 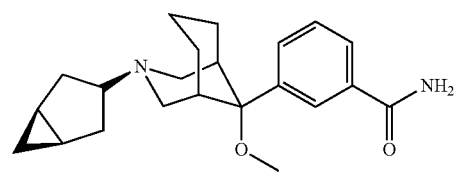 | 199 | ∧∧∧ | *** |

TABLE 1-continued

| Structure | Compound No. | μ EC$_{50}$ (nM) | μ K$_i$ (nM) |
|---|---|---|---|
| (structure 200) HCl | 200 | /\/\/\ | *** |
| (structure 201) HCl | 201 | /\/\ | NT |
| (structure 202) HCl | 202 | /\ | * |
| (structure 203) HCl | 203 | /\ | ** |
| (structure 204) HCl | 204 | /\/\ | NT |
| (structure 205) HCl | 205 | /\/\/\ | NT |
| (structure 206) HCl | 206 | /\ | NT |

TABLE 1-continued

| Structure | Compound No. | μ EC$_{50}$ (nM) | μ K$_i$ (nM) |
|---|---|---|---|
| 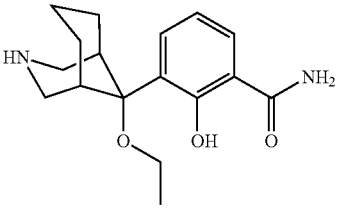 HCl | 207 | /\ | NT |

NT = not tested
* K$_i$ >5 nM;
** K$_i$ 1-5 nM (inclusive);
*** K$_i$ <1 nM
/\ EC$_{50}$ >75 nM;
/\/\ EC$_{50}$ 10-75 nM (inclusive);
/\/\/\ EC$_{50}$ <10 nM The disclosed compounds may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of two or more isomers is utilized as the disclosed compound described herein. In another embodiment, a pure isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^2$H (i.e., deuterium) isotope.

In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention.

The compounds of the invention can be used to treat a disease or condition selected from the group consisting of pain, depression, or addiction in a subject in need thereof.

In one embodiment, the compounds of the invention can be used to treat pain in the subject.

In another embodiment, the pain is selected from inflammatory pain, thermal pain, acute pain, chronic pain, traumatic pain, chemical pain, ischemic pain, centrally mediated pain, peripherally mediated pain, prickling pain, visceral pain, progressive disease pain, musculoskeletal pain (e.g., back pain, neck pain), post-surgical pain, bone pain (e.g., osteoarthritis), nociceptive pain, or neuropathic pain. In another embodiment, the pain is inflammatory pain, thermal pain, acute pain, chronic pain, or neuropathic pain. In another embodiment, the pain is musculoskeletal pain (e.g., back pain, neck pain), post-surgical pain, or bone pain (e.g., osteoarthritis).

In another embodiment, the pain is inflammatory pain, thermal pain, acute pain, chronic pain, traumatic pain, chemical pain, ischemic pain, centrally mediated pain, peripherally mediated pain, prickling pain, visceral pain, progressive disease pain, musculoskeletal pain and neuropathic pain.

In yet another embodiment, the pain can be chronic pain, wherein the pain is chronic pain from headache, chronic pain from neuropathic conditions, chronic pain from post-stroke conditions or chronic pain from migraine.

In still another embodiment, the pain can be acute pain, wherein the pain is acute pain from acute injury, acute pain from trauma, or acute pain from surgery.

In a particular embodiment, the pain is inflammatory pain, thermal pain, acute pain, chronic pain, musculoskeletal pain, and neuropathic pain. In another embodiment, the pain is chromic pain. In another embodiment, the pain is musculoskeletal pain.

In one embodiment, the pain can be neuropathic pain, wherein the pain is neuropathic pain from alcoholic polyneuropathy, phantom limb pain, chemotherapy, diabetic pain, pain from HIV infection or AIDS, multiple sclerosis, shingles, Parkinson's disease, spine surgery, or postherpetic neuralgia.

In one embodiment, the pain can be inflammatory pain, wherein the pain is pain associated with arthritis such as rheumatoid arthritis, rheumatoid spondylitis, osteoarthritis, gouty arthritis, juvenile arthritis, or scapulohumeral periarthritis.

In one embodiment, the compounds of the invention can be used to treat depression in a subject in need thereof. As used herein, the term "depression" refers to "clinical depression" or "major depressive disorder."

In another embodiment, the compounds of the invention can be used to treat a depressive condition in a subject in need thereof. In an embodiment, the depressive condition is depressed mood, diminished concentration, insomnia, fatigue, loss of appetite, excessive guilt, and suicidal thoughts. The depressive condition can be an anxiety disorder, wherein the anxiety disorder is generalized anxiety disorder, panic, or agoraphobia. The depressive condition can be associated with a mental condition, wherein the mental condition is schizoaffective disorder, or seasonal affective disorder. The depressive condition can be associated with chronic or recurrent depression. The depressive condition can be depressed mood, loss of pleasure, loss of appetite, sleep disturbance, psychomotor changes, fatigue, or post-partum depression. The depressive condition can be adjustment disorders with depressed mood, Asperger syndrome, attention deficit, bereavement, bipolar I disorder, bipolar II disorder, borderline and personality disorder, cyclothymia and dysthymia, Dysthymic disorder, hyperactivity disorder, impulse control disorder, mixed mania, obsessive-compulsive personality disorder (OCD), paranoid, seasonal affective disorder, self-injury separation, sleep disorder, substance-induced mood disorder, Tourette syndrome, tic disorder, or Trichotillomania.

In another embodiment, the compounds of the invention can be used to treat addiction in a subject in need thereof. The addiction can be drug addiction or alcohol addiction.

The drug addiction can be one or more of opioid addiction (i.e., opioid dependence) or stimulant addiction. The opioid can be one or more of fentanyl, morphine, oxymorphone, buprenorphine, hydromorphone, oxycodone, hydrocodone, or the like. The drug addiction can also be one or more of diamorphine (i.e., heroin), cocaine, nicotine, and amphetamine.

In one embodiment, compounds of the invention can be used to treat a disease or condition in a subject, wherein the subject has a tolerance to opioid medication, the subject has a history of opioid dependency or abuse, the subject is at risk of opioid dependency or abuse, or in circumstances wherein it is desirable that the risk of opioid dependence, opioid addiction, or symptoms of opioid withdrawal in the subject is minimized.

The compounds of the invention can also be used to treat alcohol addiction, which can also be referred to as alcoholism. "Alcoholism" refers to an addictive disease or disorder characterized by an inability to control the intake of alcohol, i.e., a continued excessive or compulsive use of alcoholic drinks. Alcoholism may involve changes an individual's ability to metabolize alcohol as well. Diagnosis of alcoholism can be made by psychiatric examination.

In one aspect, the compounds provided herein are useful in treatment of pain by acting as an agonist of the µ-opioid receptor.

In one embodiment of the methods described herein, the subject is human.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 1,000 mg. In some embodiments, a dose of a disclosed compound used in compositions described herein is less than about 1,000 mg, or less than about 800 mg, or less than about 600 mg, or less than about 500 mg, or less than about 300 mg, or less than about 200 mg, or less than about 100 mg, or less than about 50 mg, or less than about 20 mg, or less than about 10 mg. For example, a dose is about 10 mg, 20 mg, 25 mg, 30 mg, 40 mg, 50 mg, 60 mg, 70 mg, 80 mg, 90 mg, 100 mg, 120 mg, 140 mg, 160 mg, 180 mg, 200 mg, 220 mg, 240, 260 mg, 280 mg, 300 mg, 350 mg, 400 mg, 450 mg, 500 mg, 550 mg, or about 600 mg.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

General Procedures

Pyridinyl Carboxamide Analogues—Reductive Aminations

A suspension of 4-((1R,5S,9r)-9-methoxy-3-azabicyclo[3.3.1]nonan-9-yl)picolinamide hydrochloride (1 eq) and the desired aldehyde or ketone (2 eq) in dichloromethane (10 mL/mmol) and acetic acid (2 eq) is stirred at room temperature for 30 minutes before the addition of sodium triacetoxyborohydride (2 eq). The reaction is stirred at room temperature overnight. The reaction is quenched with saturated sodium hydrogen carbonate solution and extracted with dichloromethane (×3). The dichloromethane phases are combined, washed (brine), dried over $MgSO_4$, filtered and concentrated under reduced pressure. The residue is purified by silica column chromatography or reverse phase C18 chromatography to give the desired product.

Phenyl Carboxamide Analogues—Reductive Aminations

To 3-((1R,5S,9r)-9-methoxy-3-azabicyclo[3.3.1]nonan-9-yl)benzamide hydrochloride (1 eq) in dichloromethane (10 mL/mmol) is added the desired aldehyde or ketone (2 eq) followed by triethylamine (3 eq). The reaction is stirred at room temperature for 5 minutes before the addition of sodium triacetoxyborohydride (3 eq). The reaction is stirred at room temperature overnight. The reaction is quenched with saturated sodium hydrogen carbonate solution and extracted with dichloromethane (×3). The dichloromethane phases are combined, washed (brine), dried over $MgSO_4$, filtered and concentrated under reduced pressure. The residue is purified by silica column chromatography or reverse phase C18 chromatography to give the desired product.

The thiophenyl carboxamide analogues of the present invention (compounds of Formula II) are synthesized in a similar manner to the pyridinyl and phenyl analogues described above.

Example 1: Synthesis Procedure

Synthesis procedures for preparation of the compounds of the invention are readily available to the ordinary skilled artisan.

Compound 26

Synthesis of 3-benzyl-1,5,3-dioxazepane

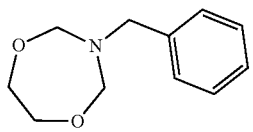

A mixture of benzylamine (88.0 g, 0.82 mol), paraformaldehyde (61.6 g, 2.05 mol) and ethylene glycol (55.0 mL, 0.98 mol) in toluene (350 mL) was heated at reflux for 2 hours with a Dean Stark trap. The mixture was cooled, and then partitioned between ethyl acetate and brine. The aqueous phase was extracted with ethyl acetate and the combined organic phases were dried over MgSO$_4$, filtered and concentrated under reduced pressure to give 3-benzyl-1,5,3-dioxazepane (100.0 g, 68% yield); $^1$H NMR (300 MHz, CDCl$_3$): 7.20-7.43 (m, 5H), 4.48 (s, 4H), 4.02 (s, 2H), 3.89 (s, 4H).

Synthesis of (1R,5S)-3-benzyl-3-azabicyclo[3.3.1] nonan-9-one

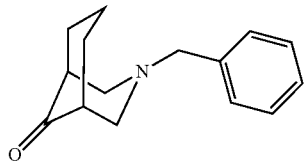 [SMILES: O=C1C2CCCC1CN(Cc1ccccc1)C2]

To a solution of 3-benzyl-1,5,3-dioxazepane (100 g, 0.52 mol) in methanol (600 mL) at 5° C. was added acetyl chloride (111 mL, 1.55 mol) over 10 minutes. After stirring for 5 minutes, a solution of cyclohexanone (51 g, 0.52 mol) in methanol (60 mL) was added. The mixture was stirred for 10 minutes, then allowed to warm to room temperature and stirred for 4 hours. The mixture was poured into concentrated aqueous ammonia and extracted with ethyl acetate (×2). The combined organic phases were washed with brine, dried over MgSO$_4$, filtered and concentrated under reduced pressure. The residue was dissolved in 4.4 M aqueous hydrochloric acid (500 mL) and heated at 50° C. for 3 hours. The reaction mixture was cooled and poured into ice/concentrated aqueous ammonia. The mixture was extracted with ethyl acetate (×2) and the combined organic phases were dried over MgSO$_4$, filtered and concentrated under reduced pressure. The residue was purified by silica chromatography, eluting with 40-100% dichloromethane in heptane, to give (1R,5S)-3-benzyl-3-azabicyclo[3.3.1]nonan-9-one (95 g, 50% yield); [M+H]$^+$ 230.13.

Synthesis of (1R,5S,9s)-3-benzyl-9-(3-iodophenyl)-3-azabicyclo[3.3.1]nonan-9-ol and (1R,5S,9r)-3-benzyl-9-(3-iodophenyl)-3-azabicyclo[3.3.1]nonan-9-ol

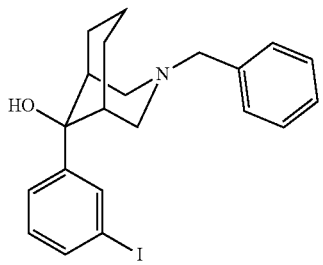

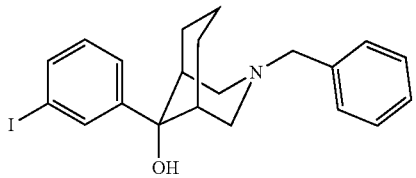 [SMILES: OC1(c2cccc(I)c2)C2CCCC1CN(Cc1ccccc1)C2]

n-Butyl lithium (1.5 M in hexanes, 49.9 mL, 74.8 mmol) was added drop wise to a solution of 1,3-diiodobenzene (41.2 g, 124.7 mmol) in diethyl ether (300 mL) at −78° C. under argon. After 40 minutes at −78° C., a solution of (1R,5S)-3-benzyl-3-azabicyclo[3.3.1]nonan-9-one (14.3 g, 62.4 mmol) in diethyl ether (50 mL) was added drop wise. The reaction mixture was allowed to warm to room temperature over 1 hour. The reaction was quenched with water and then poured into a mixture of 2 M aqueous hydrochloric acid and diethyl ether. The phases were separated and the organic phase washed with 2 M aqueous hydrochloric acid. The acidic phases were combined, basified with concentrated ammonium hydroxide and extracted with dichloromethane (×3). The combined dichloromethane layers were washed with brine, dried over MgSO$_4$, filtered and concentrated under reduced pressure to give a 1:2 ratio of (1R,5S,9r)-3-benzyl-9-(3-iodophenyl)-3-azabicyclo[3.3.1]nonan-9-ol, and (1R,5S,9s)-3-benzyl-9-(3-iodophenyl)-3-azabicyclo[3.3.1]nonan-9-ol (24.3 g, 90% yield); [M+H]$^+$ 434.28.

Epimerisation of (1R,5S,9s)-3-benzyl-9-(3-iodophenyl)-3-azabicyclo[3.3.1]nonan-9-ol to (1R,5S,9r)-3-benzyl-9-(3-iodophenyl)-3-azabicyclo[3.3.1]nonan-9-ol

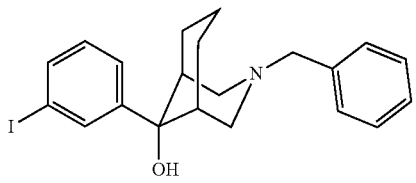

To a stirred solution of (1R,5S,9s)-3-benzyl-9-(3-iodophenyl)-3-azabicyclo[3.3.1]nonan-9-ol and (1R,5S,9r)-3-benzyl-9-(3-iodophenyl)-3-azabicyclo[3.3.1]nonan-9-ol (24.1 g, 55.6 mmol), in a 2:1 ratio, in 1,4-dioxane (150 mL) was added water (80 mL) followed by 6 M aqueous sulfuric acid (300 mL) and the mixture was stirred at 100° C. for 16 hours. Further 6 M aqueous sulfuric acid (100 mL) was added and the reaction stirred for 1 hour at 100° C. The reaction was poured onto ice/concentrated aqueous ammonia and extracted with dichloromethane (×3). The combined organic phases were washed with brine, dried over MgSO$_4$, filtered and concentrated under reduced pressure to give a 9:2 ratio of (1R,5S,9r)-3-benzyl-9-(3-iodophenyl)-3-azabicyclo[3.3.1]nonan-9-ol:(1R,5S,9s)-3-benzyl-9-(3-iodophenyl)-3-azabicyclo[3.3.1]nonan-9-ol (26.8 g, 100% yield). Purification of 16.5 g of this material by silica chromatography, eluting with 0-10% ethyl acetate in toluene:heptane (1:1) gave (1R,5S,9r)-3-benzyl-9-(3-iodophenyl)-3-azabicyclo[3.3.1]nonan-9-ol (9.3 g); [M+H]$^+$ 434.54; and (1R,5S,9s)-3-benzyl-9-(3-iodophenyl)-3-azabicyclo[3.3.1]nonan-9-ol (1.9 g); [M+H]$^+$ 434.29.

Synthesis of (1R,5S,9r)-3-benzyl-9-(3-iodophenyl)-9-methoxy-3-azabicyclo[3.3.1]nonane

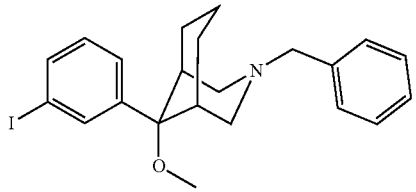 [SMILES: COC1(c2cccc(I)c2)C2CCCC1CN(Cc1ccccc1)C2]

To an ice cold solution of (1R,5S,9r)-3-benzyl-9-(3-iodophenyl)-3-azabicyclo[3.3.1]nonan-9-ol (3.99 g, 9.21 mmol) in dimethyl sulfoxide (20 mL) was added sodium hydride (60% dispersion in oil, 0.66 g, 16.58 mmol) portion wise. After 10 minutes, iodomethane (0.86 mL, 13.81 mmol) was added. The reaction mixture was allowed to warm to room temperature, and stirred for 1 hour. A further portion of sodium hydride (60% dispersion in oil, 110 mg, 2.75 mmol) was added, followed by iodomethane (0.17 mL, 2.75 mmol) and the reaction mixture was stirred for 1 hour. The reaction was quenched by pouring into ice/water and extracted with ethyl acetate (×3). The combined organic phases were washed with brine, dried over MgSO$_4$, filtered and concentrated under reduced pressure. The crude material was purified by silica chromatography, eluting with 5-7% ethyl acetate in heptane, to give (1R,5S,9r)-3-benzyl-9-(3-iodophenyl)-9-methoxy-3-azabicyclo[3.3.1]nonane (3.24 g, 78% yield); [M+H]$^+$ 448.30.

Synthesis of 3-((1R,5S,9r)-3-benzyl-9-methoxy-3-azabicyclo[3.3.1]nonan-9-yl)benzonitrile

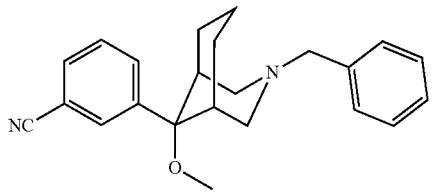 [SMILES: COC1(c2cccc(C#N)c2)C2CCCC1CN(Cc1ccccc1)C2]

To a solution of (1R,5S,9r)-3-benzyl-9-(3-iodophenyl)-9-methoxy-3-azabicyclo[3.3.1]nonane (3.24 g, 7.20 mmol) in degassed N,N-dimethylformamide (35 mL) was added tris(dibenzylideneacetone)dipalladium (0) (0.66 g, 0.72 mmol) and 1,1'bis(diphenylphosphino)ferrocene (0.80 g, 1.50 mmol). After heating to 50° C., zinc cyanide (0.51 g, 4.34 mmol) was added and the reaction mixture heated at 110° C. for 2 hours. The reaction mixture was cooled to room temperature, quenched with sodium hydrogen carbonate solution, diluted with ethyl acetate and filtered through a pad of Celite. The product was extracted with ethyl acetate (×3). The combined organic phases were washed with water (×2), brine (×1), dried over MgSO$_4$, filtered and concentrated under reduced pressure. The crude material was purified by silica chromatography, eluting with 0-20% ethyl acetate in heptane, to give 3-((1R,5S,9r)-3-benzyl-9-methoxy-3-azabicyclo[3.3.1]nonan-9-yl)benzonitrile (1.89 g); [M+H]$^+$ 347.36.

Synthesis of 3-((1R,5S,9r)-3-benzyl-9-methoxy-3-azabicyclo[3.3.1]nonan-9-yl)benzamide

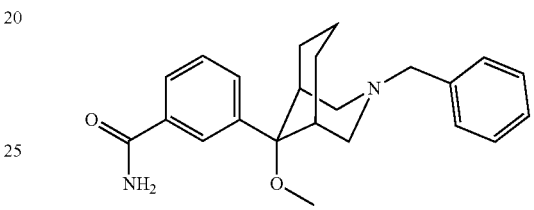

To 3-((1R,5S,9r)-3-benzyl-9-methoxy-3-azabicyclo[3.3.1]nonan-9-yl)benzonitrile (1.89 g, 5.50 mmol) was added tert-butanol (55 mL), followed by potassium hydroxide (1.53 g, 27.3 mmol) and the reaction was heated at reflux for 2 hours. The mixture was cooled to room temperature, diluted with water and extracted with ethyl acetate (×3). The combined organic phases were washed with water (×2), then brine (×1), dried over MgSO$_4$, filtered and concentrated under reduced pressure. The crude material was purified by silica chromatography, eluting with 50-66% ethyl acetate in heptane, to give 3-((1R,5S,9r)-3-benzyl-9-methoxy-3-azabicyclo[3.3.1]nonan-9-yl)benzamide (1.03 g, 39% yield over 2 steps); [M+H]$^+$ 365.38.

Synthesis of 3-((1R,5S,9r)-9-methoxy-3-azabicyclo[3.3.1]nonan-9-yl)benzamide

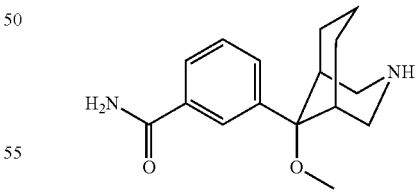

A mixture of 3-((1R,5S,9r)-3-benzyl-9-methoxy-3-azabicyclo[3.3.1]nonan-9-yl)benzamide (980 mg, 2.70 mmol), 20% palladium hydroxide on carbon (98 mg), and ammonium formate (1.70 g, 27.00 mmol) in methanol (25 mL) was heated at reflux for 30 minutes. Further ammonium formate (1.70 g, 27.00 mmol) and 20% palladium hydroxide on carbon (49 mg) were added and the mixture heated at reflux for 30 minutes. The mixture was cooled to room temperature and filtered through a pad of Celite washing thoroughly with methanol. The filtrate was concentrated under reduced pressure. The residue was taken up in dichloromethane and concentrated aqueous ammonia/water (1:1) and extracted with dichloromethane (×3). The combined organic phases were washed with brine, dried over MgSO₄, filtered and concentrated under reduced pressure. The residue was purified by reverse phase chromatography (C18) to give 3-((1R,5S,9r)-9-methoxy-3-azabicyclo[3.3.1]nonan-9-yl)benzamide (273 mg, 37% yield); [M+H]⁺ 275.18.

Synthesis of 3-((1R,5S,9r)-3-(cyclobutylmethyl)-9-methoxy-3-azabicyclo[3.3.1]nonan-9-yl)benzamide Hydrochloride

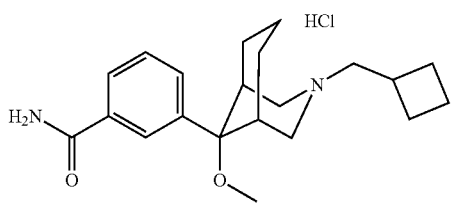 [SMILES: COC1(c2cccc(C(N)=O)c2)C2CCCC1CN(CC1CCC1)C2 ; Cl]

To an aqueous solution of 3-((1R,5S,9r)-9-methoxy-3-azabicyclo[3.3.1]nonan-9-yl)benzamide (100 mg, 0.36 mmol) diluted with tetrahydrofuran (10 mL) was added cyclobutane carboxaldehyde (0.19 mL, 3.9 M in dichloromethane, 0.74 mmol), followed by sodium triacetoxyborohydride (155 mg, 0.73 mmol), and the reaction mixture was stirred at room temperature for 18 hours. The reaction was quenched by the addition of aqueous sodium hydrogen carbonate solution and extracted with dichloromethane (×3). The aqueous phase was diluted with tetrahydrofuran (10 mL) then cyclobutane carboxaldehyde (0.19 mL, 3.9 M in dichloromethane, 0.74 mmol) followed by sodium triacetoxyborohydride (155 mg, 0.73 mmol) were added, and the reaction mixture was stirred at room temperature for 18 hours. Further cyclobutyl carboxaldehyde (0.38 mL, 3.9 M in dichloromethane, 1.48 mmol) and sodium triacetoxyborohydride (310 mg, 1.47 mmol) were added and the reaction mixture stirred at room temperature for a further 18 hours. The mixture was quenched by the addition of aqueous sodium hydrogen carbonate solution and extracted with dichloromethane (×3). The combined organic phases were washed with brine, dried over MgSO₄, filtered and concentrated under reduced pressure. The crude residue was purified by reverse phase chromatography (C18) to give 3-((1R,5S,9r)-3-(cyclobutylmethyl)-9-methoxy-3-azabicyclo[3.3.1]nonan-9-yl)benzamide (18 mg, 14% yield). To a solution of 3-((1R,5S,9r)-3-(cyclobutylmethyl)-9-methoxy-3-azabicyclo[3.3.1]nonan-9-yl)benzamide (18 mg, 0.05 mmol) in ethyl acetate (6 mL) was added 2 M hydrochloric acid in diethyl ether (30 µL, 0.06 mmol). After 10 minutes, the mixture was concentrated under reduced pressure, and the residue freeze dried from water to give 3-((1R,5S,9r)-3-(cyclobutylmethyl)-9-methoxy-3-azabicyclo[3.3.1]nonan-9-yl)benzamide hydrochloride (20 mg, 100% yield); [M+H]⁺ 343.21; ¹H NMR (300 MHz, D₂O): 7.75 (s, 1H), 7.70 (d, 1H), 7.60 (d, 1H), 7.48 (t, 1H), 3.44 (br s, 4H), 3.10 (d, 2H), 2.86 (br s, 2H), 2.76-2.59 (m, 4H), 2.09-1.96 (m, 2H), 1.94-1.54 (m, 8H), 1.53-1.31 (m, 2H).

Compound 33

Synthesis of (1R,5S,9s)-9-(6-bromopyridin-2-yl)-3-methyl-3-azabicyclo[3.3.1]nonan-9-ol and (1R,5S,9r)-9-(6-bromopyridin-2-yl)-3-methyl-3-azabicyclo[3.3.1]nonan-9-ol

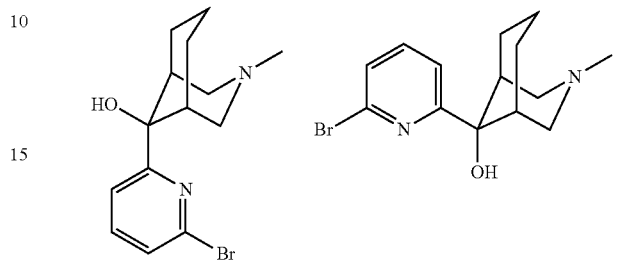

A solution of 2,6-dibromopyridine (928 mg, 3.92 mmol) in tetrahydrofuran (8 mL) was cooled to −78° C. n-Butyl lithium (1.6 M in hexanes, 2.61 mL, 3.92 mmol) was added and the mixture stirred for 1 hour. A solution of (1R,5S)-3-methyl-3-azabicyclo[3.3.1]nonan-9-one (500 mg, 3.26 mmol) in tetrahydrofuran (2 mL) was added drop wise. After 15 minutes, the reaction mixture was allowed to warm to room temperature and stirred for 1 hour. Saturated ammonium chloride solution was added and the mixture was extracted with ethyl acetate (×2). The combined organic phases were washed with brine, dried over MgSO₄, filtered and concentrated under reduced pressure. The residue was purified by silica chromatography, eluting with 3% ammonia/methanol in dichloromethane, to give a mixture of (1R,5S,9s)-9-(6-bromopyridin-2-yl)-3-methyl-3-azabicyclo[3.3.1]nonan-9-ol and (1R,5S,9r)-9-(6-bromopyridin-2-yl)-3-methyl-3-azabicyclo[3.3.1]nonan-9-ol (306 mg) and (1R,5S,9r)-9-(6-bromopyridin-2-yl)-3-methyl-3-azabicyclo[3.3.1]nonan-9-ol (341 mg); [M+H]⁺ 311.15, 313.15.

Epimerisation of (1R,5S,9s)-9-(6-bromopyridin-2-yl)-3-methyl-3-azabicyclo[3.3.1]nonan-9-ol to (1R,5S,9r)-9-(6-bromopyridin-2-yl)-3-methyl-3-azabicyclo[3.3.1]nonan-9-ol

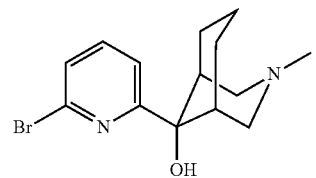 [SMILES: CN1CC2CCCC(C1)C2(O)c1cccc(Br)n1]

A solution of (1R,5S,9s)-9-(6-bromopyridin-2-yl)-3-methyl-3-azabicyclo[3.3.1]nonan-9-ol and (1R,5S,9r)-9-(6-bromopyridin-2-yl)-3-methyl-3-azabicyclo[3.3.1]nonan-9-ol (341 mg, 1.10 mmol) in 6 M sulfuric acid (10 mL) was heated at 100° C. for 40 hours. The mixture was cooled to room temperature then poured into ice/concentrated aqueous ammonia and extracted with ethyl acetate (×2). The combined organic phases were dried over MgSO₄, filtered and concentrated under reduced pressure. The residue was combined with the mixed fractions from the previous step and purified by silica chromatography, eluting with 3% ammonia/methanol in dichloromethane, to give (1R,5S,9r)-9-(6- bromopyridin-2-yl)-3-methyl-3-azabicyclo[3.3.1]nonan-9-ol (421 mg, 41% yield over 2 steps); [M+H]+ 311.20, 313.20.

Synthesis of (1R,5S,9r)-9-(6-bromopyridin-2-yl)-9-methoxy-3-methyl-3-azabicyclo[3.3.1]nonane

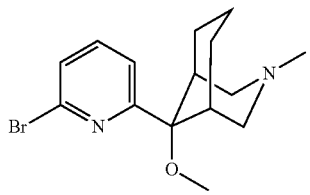 [SMILES: COC1(c2cccc(Br)n2)C2CCCC1CN(C)C2]

To an ice cold solution of (1R,5S,9r)-9-(6-bromopyridin-2-yl)-3-methyl-3-azabicyclo[3.3.1]nonan-9-ol (421 mg, 1.35 mmol) in N,N-dimethylformamide (10 mL) was added sodium hydride (60% dispersion in oil, 108 mg, 2.71 mmol) and the reaction mixture was stirred for 30 minutes. Iodomethane (0.10 mL, 1.62 mmol) was added and the reaction mixture was stirred at room temperature for 1 hour. The mixture was diluted with water and extracted with ethyl acetate (×2). The combined organic phases were washed with water (×3), then brine, dried over MgSO4, filtered and concentrated under reduced pressure. The residue was purified by silica chromatography, eluting with 5-10% methanol in dichloromethane, to give (1R,5S,9r)-9-(6-bromopyridin-2-yl)-9-methoxy-3-methyl-3-azabicyclo[3.3.1]nonane (413 mg, 94% yield); [M+H]+ 325.15, 327.10.

Synthesis of 6-((1R,5S,9r)-9-methoxy-3-methyl-3-azabicyclo[3.3.1]nonan-9-yl)picolinonitrile

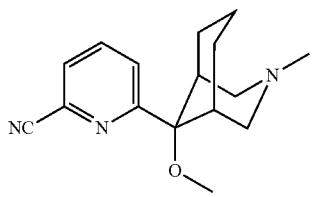 [SMILES: COC1(c2cccc(C#N)n2)C2CCCC1CN(C)C2]

A solution of (1R,5S,9r)-9-(6-bromopyridin-2-yl)-9-methoxy-3-methyl-3-azabicyclo[3.3.1]nonane (360 mg, 1.11 mmol) in N,N-dimethylformamide (5 mL) was degassed under argon for 10 minutes. Tetrakis(triphenylphosphine)palladium(0) (256 mg, 0.22 mmol) was added followed by zinc cyanide (156 mg, 1.33 mmol) and the reaction mixture was heated at 110° C. for 90 minutes. The reaction mixture was cooled to room temperature, diluted with water then extracted with ethyl acetate (×2). The combined organic phases were washed with water (×3), then brine, dried over MgSO4, filtered and concentrated under reduced pressure. The residue was purified by silica chromatography, eluting with 5% methanol in dichloromethane, to give 6-((1R,5S,9r)-9-methoxy-3-methyl-3-azabicyclo[3.3.1]nonan-9-yl)picolinonitrile as an off white solid (175 mg 52% yield); [M+H]+ 272.22.

Synthesis of 6-((1R,5S,9r)-9-methoxy-3-methyl-3-azabicyclo[3.3.1]nonan-9-yl)picolinamide Hydrochloride

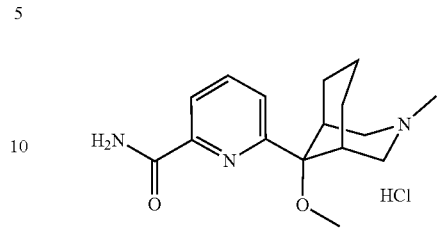

To a solution of 6-((1R,5S,9r)-9-methoxy-3-methyl-3-azabicyclo[3.3.1]nonan-9-yl)picolinonitrile (175 mg, 0.65 mmol) in tert-butanol (5 mL) was added potassium hydroxide (181 mg, 3.22 mmol), and the reaction was heated at 100° C. for 90 minutes. The mixture was cooled to room temperature, diluted with water and extracted with ethyl acetate (×3). The combined organic phases were washed with brine, dried over MgSO4, filtered and concentrated under reduced pressure. The crude material was purified by silica chromatography, eluting with 4-5% ammonia/methanol in dichloromethane, to give 6-((1R,5S,9r)-9-methoxy-3-methyl-3-azabicyclo[3.3.1]nonan-9-yl)picolinamide (141 mg, 75% yield). To a solution of 6-((1R,5S,9r)-9-methoxy-3-methyl-3-azabicyclo[3.3.1]nonan-9-yl)picolinamide (141 mg, 0.49 mmol) in ethyl acetate (5 mL) was added 2 M hydrochloric acid in diethyl ether (0.47 mL, 0.95 mmol) drop wise and the mixture was stirred for 30 minutes. The solvent was removed under reduced pressure and the solid dissolved in water and freeze dried to give 6-((1R,5S,9r)-9-methoxy-3-methyl-3-azabicyclo[3.3.1]nonan-9-yl)picolinamide hydrochloride (159 mg, 100% yield); [M+H]+ 290.12; 1H NMR (300 MHz, d6-DMSO): 8.44 (br s, 1H), 8.09-7.97 (m, 2H), 7.92 (br s, 1H), 7.75 (d, 1H), 7.57 (br s, 1H), 3.56 (dd, 2H), 3.49-3.34 (m, 2H), 3.17 (s, 2H), 2.81 (d, 3H), 2.79 (s, 3H), 2.01-1.71 (m, 3H), 1.71-1.51 (m, 2H) 1.33-1.19 (m, 1H).
Compound 37

Synthesis of (1R,5S,9r)-9-(3-iodophenyl)-3-methyl-9-(2,2,2-trifluoroethoxy)-3-azabicyclo[3.3.1]nonane

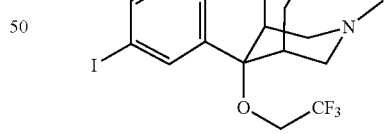

A mixture of (1R,5S,9r)-9-(3-iodophenyl)-9-methoxy-3-methyl-3-azabicyclo[3.3.1]nonane (300 mg, 0.81 mmol) and 3 M sulfuric acid in 2,2,2-trifluoroethanol (5 mL) was stirred at room temperature for 4 hours. The mixture was poured into ice/concentrated aqueous ammonia and extracted with ethyl acetate (×2). The combined organic phases were washed with brine, dried over MgSO4, and concentrated under reduced pressure. The residue was purified by silica chromatography, eluting with 20% ethyl acetate in heptane then 10% methanol in dichloromethane. The resulting oil was further purified by silica chromatography, eluting with 50% ethyl acetate in dichloromethane then 10% methanol in dichloromethane, to give (1R,5S,9r)-9-(3-iodophenyl)-3-methyl-9-(2,2,2-trifluoroethoxy)-3-azabicyclo[3.3.1]nonane (269 mg, 76% yield); [M+H]+ 440.25.

Synthesis of 3-((1R,5S,9r)-3-methyl-9-(2,2,2-trifluoroethoxy)-3-azabicyclo[3.3.1]nonan-9-yl)benzonitrile

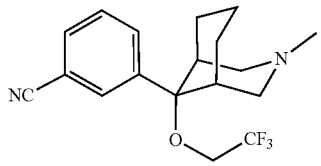 [SMILES: CN1CC2CCCC(C1)C2(OCC(F)(F)F)c1cccc(C#N)c1]

To a solution of (1R,5S,9r)-9-(3-iodophenyl)-3-methyl-9-(2,2,2-trifluoroethoxy)-3-azabicyclo[3.3.1]nonane (230 mg, 0.52 mmol) in degassed N,N-dimethylformamide (5 mL) was added tetrakis(triphenylphosphine)palladium(0) (121 mg, 0.11 mmol), followed by zinc cyanide (74 g, 0.63 mmol) and the reaction mixture was heated at 110° C. for 90 minutes. The reaction mixture was cooled to room temperature, diluted with water and extracted with ethyl acetate (×2). The combined organic phases were washed with water (×3), then brine, dried over MgSO4, filtered and concentrated under reduced pressure to give 3-((1R,5S,9r)-3-methyl-9-(2,2,2-trifluoroethoxy)-3-azabicyclo[3.3.1]nonan-9-yl)benzonitrile (300 mg); [M+H]+ 339.26.

Synthesis of 3-((1R,5S,9r)-3-methyl-9-(2,2,2-trifluoroethoxy)-3-azabicyclo[3.3.1]nonan-9-yl)benzamide Hydrochloride

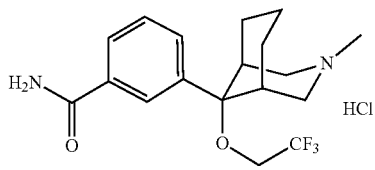 [SMILES: CN1CC2CCCC(C1)C2(OCC(F)(F)F)c1cccc(C(N)=O)c1 ; Cl]

To a solution of 3-((1R,5S,9r)-3-methyl-9-(2,2,2-trifluoroethoxy)-3-azabicyclo[3.3.1]nonan-9-yl)benzonitrile (177 mg, 0.54 mmol) in tert-butanol (5 mL) was added potassium hydroxide (147 mg, 2.62 mmol), and the reaction mixture was heated at 100° C. for 90 minutes. The mixture was cooled to room temperature, combined with a second batch, poured into water and extracted with ethyl acetate (×3). The combined organic phases were dried over MgSO4, filtered and concentrated under reduced pressure. The residue was purified by preparative HPLC, the product extracted with ethyl acetate, and the combined organic phases dried over MgSO4, filtered and concentrated under reduced pressure to give 3-((1R,5S,9r)-3-methyl-9-(2,2,2-trifluoroethoxy)-3-azabicyclo[3.3.1]nonan-9-yl)benzamide (93 mg, 47% over 2 steps). To a solution of 3-((1R,5S,9r)-3-methyl-9-(2,2,2-trifluoroethoxy)-3-azabicyclo[3.3.1]nonan-9-yl)benzamide (93 mg, 0.26 mmol) in ethyl acetate (5 mL) was added 2 M hydrochloric acid in diethyl ether (0.15 mL, 0.30 mmol) and the reaction mixture was stirred for 10 minutes. The mixture was concentrated under reduced pressure and the residue freeze dried from water to give 3-((1R,5S,9r)-3-methyl-9-(2,2,2-trifluoroethoxy)-3-azabicyclo[3.3.1]nonan-9-yl)benzamide hydrochloride (102 mg, 100%); [M+H]+ 357.15; 1H NMR (300 MHz, d6-DMSO): 8.44 (br s, 1H), 8.09 (s, 1H), 7.97 (s, 1H), 7.90 (d, 1H), 7.66 (d, 1H), 7.55 (t, 1H), 7.49 (s, 1H), 3.66 (d, 2H), 3.60-3.44 (m, 2H), 3.43-3.26 (m, 2H), 3.04 (br s, 2H), 2.77 (d, 3H), 2.01-1.72 (m, 3H), 1.66-1.44 (m, 2H), 1.40-1.17 (m, 1H).

Compound 39

Synthesis of 2-fluoro-3-((1R,5S,9r)-9-methoxy-3-methyl-3-azabicyclo[3.3.1]nonan-9-yl)phenyl Trifluoromethanesulfonate

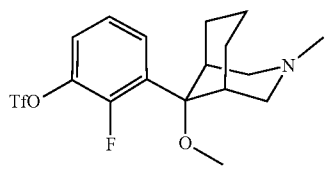 [SMILES: COC1(c2cccc(OS(=O)(=O)C(F)(F)F)c2F)C2CCCC1CN(C)C2]

To a solution of 2-fluoro-3-((1R,5S,9r)-9-methoxy-3-methyl-3-azabicyclo[3.3.1]nonan-9-yl)phenol (144 mg, 0.52 mmol) in dichloromethane (15 mL) was added N-phenyl-bis(trifluoromethanesulfonimide) (240 mg, 0.67 mmol) and triethylamine (93 µL, 0.67 mmol) and the reaction mixture was stirred for 20 hours at room temperature. The reaction mixture was washed with concentrated aqueous ammonia and the aqueous phase back extracted with dichloromethane. The combined organic phases were dried over MgSO4, filtered and concentrated under reduced pressure. The residue was purified by silica chromatography, eluting with 0-5% methanol in dichloromethane, to give 2-fluoro-3-((1R,5S,9r)-9-methoxy-3-methyl-3-azabicyclo[3.3.1]nonan-9-yl)phenyl trifluoromethanesulfonate (185 mg, 87% yield); [M+H]+ 412.29.

Synthesis of 2-fluoro-3-((1R,5S,9r)-9-methoxy-3-methyl-3-azabicyclo[3.3.1]nonan-9-yl)benzonitrile

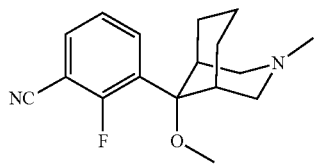 [SMILES: COC1(c2cccc(C#N)c2F)C2CCCC1CN(C)C2]

To a solution of 2-fluoro-3-((1R,5S,9r)-9-methoxy-3-methyl-3-azabicyclo[3.3.1]nonan-9-yl)phenyl trifluoromethanesulfonate (180 mg, 0.44 mmol) in degassed N,N-dimethylformamide (10 mL) was added tetrakis(triphenylphosphine)palladium(0) (100 mg, 0.09 mmol), followed by zinc cyanide (51 mg, 0.44 mmol) and the reaction mixture was heated at 100° C. for 90 minutes. The reaction mixture was cooled, diluted with brine and extracted with ethyl acetate (×2). The combined organic phases were washed with dilute brine (×3), dried over MgSO4, filtered and concentrated under reduced pressure. The residue was purified by silica chromatography, eluting with 0-10% methanol in dichloromethane, to give 2-fluoro-3-((1R,5S,9r)-9-methoxy-3-methyl-3-azabicyclo[3.3.1]nonan-9-yl)benzonitrile (84 mg, 67% yield); [M+H]+ 289.26.

Synthesis of 2-fluoro-3-((1R,5S,9r)-9-methoxy-3-methyl-3-azabicyclo[3.3.1]nonan-9-yl)benzamide Hydrochloride

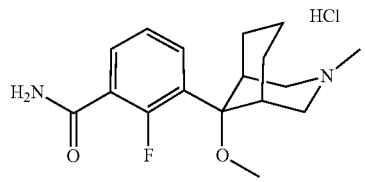 [SMILES: Cl ; COC1(c2cccc(C(N)=O)c2F)C2CCCC1CN(C)C2]

To a solution of 2-fluoro-3-((1R,5S,9r)-9-methoxy-3-methyl-3-azabicyclo[3.3.1]nonan-9-yl)benzonitrile (84 mg, 0.29 mmol) in industrial methylated spirits (10 mL) was added dimethyl sulfoxide (2 mL), potassium hydroxide (122 mg, 2.20 mmol) and hydrogen peroxide (37% aqueous solution, 0.20 mL). The reaction mixture was stirred vigorously for 2 hours, diluted with water and brine, and extracted with ethyl acetate (×2). The combined organic phases were washed with brine, dried over MgSO$_4$, filtered and concentrated under reduced pressure. The residue was purified by silica chromatography, eluting with 10% methanol in dichloromethane, then further purified by reverse phase chromatography (C18) to give 2-fluoro-3-((1R,5S,9r)-9-methoxy-3-methyl-3-azabicyclo[3.3.1]nonan-9-yl)benzamide (21 mg, 24% yield). To a solution of 2-fluoro-3-((1R,5S,9r)-9-methoxy-3-methyl-3-azabicyclo[3.3.1]nonan-9-yl)benzamide (21 mg, 0.07 mmol) in dichloromethane (5 mL) was added 2 M hydrochloric acid in diethyl ether (38 µL, 0.08 mmol). The mixture was concentrated under reduced pressure and the residue freeze dried from water to give 2-fluoro-3-((1R,5S,9r)-9-methoxy-3-methyl-3-azabicyclo[3.3.1]nonan-9-yl)benzamide hydrochloride (24 mg, 93% yield); [M+H]$^+$ 307.11; $^1$H NMR (300 MHz, D$_2$O): 7.62 (d, 1H), 7.57 (d, 1H), 7.25 (t, 1H), 3.50-3.37 (m, 4H), 3.10 (s, 1H), 2.89 (s, 1H), 2.83 (s, 3H), 2.74 (s, 3H), 1.94-1.69 (m, 3H), 1.61-1.38 (m, 3H).
Compound 44

Synthesis of (1R,5S,9r)-9-(4-bromopyridin-2-yl)-3-methyl-3-azabicyclo[3.3.1]nonan-9-ol

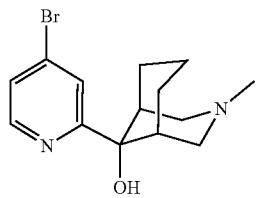 [SMILES: CN1CC2CCCC(C1)C2(O)c1cc(Br)ccn1]

A solution of 2,4-dibromopyridine (1.16 g, 4.89 mmol) in toluene (10 mL) was cooled to −78° C. n-Butyl lithium (1.5 M in hexanes, 3.26 mL, 4.89 mmol) was added drop wise and the reaction mixture stirred for 30 minutes. A solution of (1R,5S)-3-methyl-3-azabicyclo[3.3.1]nonan-9-one (0.75 g, 4.89 mmol) in toluene (2 mL) was added and the reaction was allowed to warm to room temperature. Water was added and the mixture extracted with ethyl acetate (×2). The combined organic phases were dried over MgSO$_4$, filtered and concentrated under reduced pressure. The residue was purified by silica chromatography, eluting with 2-5% ammonia/methanol in dichloromethane, then further purified by silica chromatography, eluting with 4% ammonia/methanol in dichloromethane, to give (1R,5S,9r)-9-(4-bromopyridin-2-yl)-3-methyl-3-azabicyclo[3.3.1]nonan-9-ol (0.24 g, 15% yield); [M+H]$^+$ 319.98.

Synthesis of (1R,5S,9r)-9-(4-bromopyridin-2-yl)-9-methoxy-3-methyl-3-azabicyclo[3.3.1]nonane

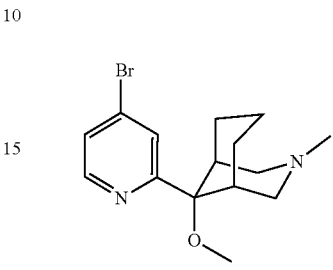

To an ice cold solution of (1R,5S,9r)-9-(4-bromopyridin-2-yl)-3-methyl-3-azabicyclo[3.3.1]nonan-9-ol (235 mg, 0.76 mmol) in N,N-dimethylformamide (4 mL) was added sodium hydride (60% dispersion in oil, 60 mg, 1.51 mmol) and the mixture was stirred for 20 minutes. Iodomethane (56 µL, 0.91 mmol) was added and the reaction mixture was stirred for 3 hours at room temperature. The mixture was quenched with water and extracted with ethyl acetate (×2). The combined organic phases were washed with water (×3), then brine (×2), dried over MgSO$_4$, filtered and concentrated under reduced pressure. The residue was purified by silica chromatography, eluting with 5% methanol in dichloromethane, to give (1R,5S,9r)-9-(4-bromopyridin-2-yl)-9-methoxy-3-methyl-3-azabicyclo[3.3.1]nonane (133 mg, 54% yield); [M+H]$^+$ 327.19.

Synthesis of 2-((1R,5S,9r)-9-methoxy-3-methyl-3-azabicyclo[3.3.1]nonan-9-yl)isonicotinonitrile

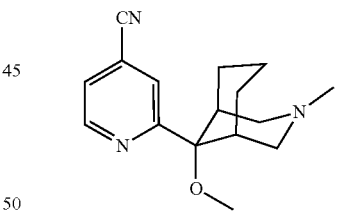

To a solution of (1R,5S,9r)-9-(4-bromopyridin-2-yl)-9-methoxy-3-methyl-3-azabicyclo[3.3.1]nonane (130 mg, 0.40 mmol) in degassed N,N-dimethylformamide (3 mL) was added tetrakis(triphenylphosphine)palladium(0) (92 mg, 0.08 mmol), followed by zinc cyanide (57 mg, 0.49 mmol) and the reaction mixture was heated at 110° C. for 3 hours. The reaction mixture was cooled to room temperature and quenched with water. The mixture was extracted with ethyl acetate (×2). The combined organic phases were washed with water (×3), then brine (×2), dried over MgSO$_4$, filtered and concentrated under reduced pressure. The residue was purified by silica chromatography, eluting with 5% methanol in dichloromethane, to give 2-((1R,5S,9r)-9-methoxy-3-methyl-3-azabicyclo[3.3.1]nonan-9-yl)isonicotinonitrile (74 mg, 81% yield); [M+H]$^+$ 272.24.

Synthesis of 2-((1R,5S,9r)-9-methoxy-3-methyl-3-azabicyclo[3.3.1]nonan-9-yl)isonicotinamide Hydrochloride

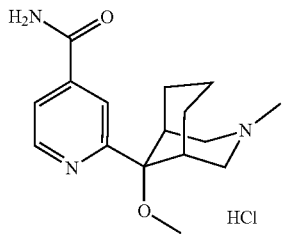 [SMILES: COC1(c2cc(C(N)=O)ccn2)C2CCCC1CN(C)C2 ; Cl]

To a solution of 2-((1R,5S,9r)-9-methoxy-3-methyl-3-azabicyclo[3.3.1]nonan-9-yl)isonicotinonitrile (70 mg, 0.26 mmol) in dimethyl sulfoxide (1 mL) was added potassium carbonate (107 mg, 0.77 mmol). Hydrogen peroxide (35%, 0.10 mL) was added drop wise and the reaction stirred for 1 hour. The reaction mixture was partitioned between water and ethyl acetate and the aqueous phase re-extracted with ethyl acetate. The combined organic phases were washed with water then aqueous sodium hydrogen carbonate solution, dried over MgSO$_4$, filtered and concentrated under reduced pressure. The residue was purified by silica chromatography, eluting with 3% ammonia/methanol in dichloromethane, to give 2-((1R,5S,9r)-9-methoxy-3-methyl-3-azabicyclo[3.3.1]nonan-9-yl)isonicotinamide (66 mg, 88% yield). To a solution of 2-((1R,5S,9r)-9-methoxy-3-methyl-3-azabicyclo[3.3.1]nonan-9-yl)isonicotinamide (66 mg, 0.23 mmol) in ethyl acetate (3 mL) was added 2 M hydrochloric acid in diethyl ether (0.23 mL, 0.46 mmol). The mixture was stirred for 20 minutes, then concentrated under reduced pressure and the residue freeze dried from water to give 2-((1R,5S,9r)-9-methoxy-3-methyl-3-azabicyclo[3.3.1]nonan-9-yl)isonicotinamide hydrochloride (69 mg, 93% yield); [M+H]$^+$ 290.19; $^1$H NMR (300 MHz, de-DMSO): 8.76 (d, 1H), 8.51 (brs, 1H), 8.36 (s, 1H), 7.95 (d, 1H), 7.85-7.31 (m, 2H), 3.56 (dd, 2H), 3.45-3.33 (m, 2H), 2.98 (s, 2H), 2.78 (d, 6H), 2.04-1.53 (m, 5H), 1.33-1.88 (m, 1H).

Compound 24

3-((1R,5S,9r)-9-methoxy-3-phenethyl-3-azabicyclo[3.3.1]nonan-9-yl)benzamide Hydrochloride

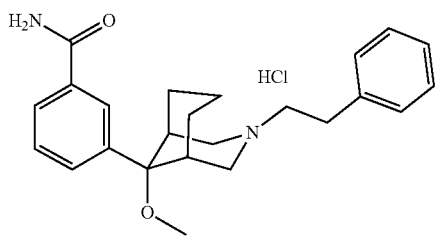 [SMILES: COC1(c2cccc(C(N)=O)c2)C2CCCC1CN(CCc1ccccc1)C2 ; Cl]

[M+H]$^+$ 379.10; $^1$H NMR (300 MHz, D$_2$O): 7.77 (s, 1H), 7.71 (d, 1H), 7.61 (d, 1H), 7.49 (t, 1H), 7.33-7.17 (m, 5H), 3.66-3.50 (m, 4H), 3.35-3.26 (m, 2H), 3.08-3.98 (m, 2H), 2.91 (s, 2H), 2.71 (s, 3H), 1.81-1.55 (m, 4H), 1.48-1.32 (m, 2H).

Compound 28

Synthesis of (1R,5S,9r)-9-(5-bromopyridin-3-yl)-3-(cyclopropylmethyl)-3-azabicyclo[3.3.1]nonan-9-ol and (1R,5S,9s)-9-(5-bromopyridin-3-yl)-3-(cyclopropylmethyl)-3-azabicyclo[3.3.1]nonan-9-ol

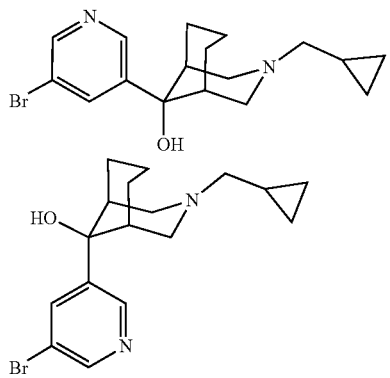

To a suspension of 3,5-dibromopyridine (14.70 g, 62.0 mmol) in toluene (220 mL) at −78° C. under argon, was added n-butyl lithium (1.5 M in hexanes, 42.00 mL, 63.0 mmol) drop wise over 10 minutes, and the reaction mixture was stirred for 1.5 hours. A solution of (1R,5S)-3-(cyclopropylmethyl)-3-azabicyclo[3.3.1]nonan-9-one (4.00 g, 20.6 mmol) in toluene (60 mL) was added over 15 minutes. The reaction mixture was warmed to −10° C. and stirred for 1.5 hours. The mixture was quenched with aqueous ammonium chloride solution and water then extracted with ethyl acetate (×3). The combined organic phases were dried over MgSO$_4$, filtered and concentrated under reduced pressure. The residue was purified by silica chromatography, eluting with 20-50% ethyl acetate in toluene, to give (1R,5S,9s)-9-(5-bromopyridin-3-yl)-3-(cyclopropylmethyl)-3-azabicyclo[3.3.1]nonan-9-ol (1.80 g, 25% yield); [M+H]$^+$ 351.19 and (1R,5S,9r)-9-(5-bromopyridin-3-yl)-3-(cyclopropylmethyl)-3-azabicyclo[3.3.1]nonan-9-ol. The (1R,5S,9r)-9-(5-bromopyridin-3-yl)-3-(cyclopropylmethyl)-3-azabicyclo[3.3.1]nonan-9-ol was further purified by silica chromatography, eluting with 20-40% ethyl acetate in toluene, to give (1R,5S,9r)-9-(5-bromopyridin-3-yl)-3-(cyclopropylmethyl)-3-azabicyclo[3.3.1]nonan-9-ol (0.88 g, 12% yield); [M+H]$^+$ 351.16.

Synthesis of (1R,5S,9r)-9-(5-bromopyridin-3-yl)-3-(cyclopropylmethyl)-9-methoxy-3-azabicyclo[3.3.1]nonane

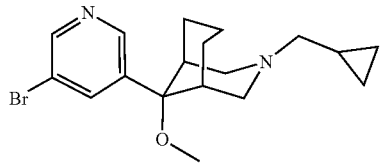 [SMILES: COC1(c2cncc(Br)c2)C2CCCC1CN(CC1CC1)C2]

To an ice cold solution of (1R,5S,9r)-9-(5-bromopyridin-3-yl)-3-(cyclopropylmethyl)-3-azabicyclo[3.3.1]nonan-9-ol (450 mg, 1.28 mmol) in N,N-dimethylformamide (15 mL) was added sodium hydride (60% dispersion in oil, 102 mg, 2.56 mmol) and the reaction mixture stirred for 30 minutes. Iodomethane (80 µL, 1.28 mmol) was added and the mixture was stirred for 45 minutes. Further iodomethane (10.0 µL, 0.16 mmol) was added and the mixture stirred for 30 minutes. The mixture was quenched with methanol and water then extracted with ethyl acetate (×3). The combined organic phases were washed with water (×3), dried over MgSO₄, filtered and concentrated under reduced pressure. The residue was purified by reverse phase chromatography (C18) to give (1R,5S,9r)-9-(5-bromopyridin-3-yl)-3-(cyclopropylmethyl)-9-methoxy-3-azabicyclo[3.3.1]nonane (300 mg, 64% yield); [M+H]⁺ 365.15.

Synthesis of 5-((1R,5S,9r)-3-(cyclopropylmethyl)-9-methoxy-3-azabicyclo[3.3.1]nonan-9-yl)nicotinonitrile

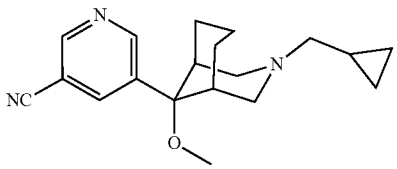 [SMILES: COC1(c2cncc(C#N)c2)C2CCCC1CN(CC1CC1)C2]

To a solution of (1R,5S,9r)-9-(5-bromopyridin-3-yl)-3-(cyclopropylmethyl)-9-methoxy-3-azabicyclo[3.3.1]nonane (244 mg, 0.67 mmol) in degassed N,N-dimethylformamide (5 mL) was added tetrakis(triphenylphosphine)palladium(0) (77 mg, 0.07 mmol) and the mixture heated to 80° C. Zinc cyanide (155 mg, 1.33 mmol) was added and the reaction mixture was heated at 110° C. for 18 hours. The reaction was cooled to room temperature, quenched with water and extracted with ethyl acetate (×3). The combined organic phases were washed with water (×2), dried over MgSO₄, filtered and concentrated under reduced pressure. The residue was purified by reverse phase chromatography (C18), then further purified by silica chromatography, eluting with 10% methanol in dichloromethane, to give 5-((1R,5S,9r)-3-(cyclopropylmethyl)-9-methoxy-3-azabicyclo[3.3.1]nonan-9-yl)nicotinonitrile (148 mg, 70% yield); [M+H]⁺ 312.25.

Synthesis of 5-((1R,5S,9r)-3-(cyclopropylmethyl)-9-methoxy-3-azabicyclo[3.3.1]nonan-9-yl)nicotinamide Hydrochloride

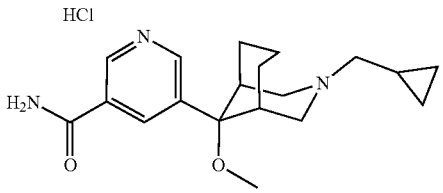 [SMILES: Cl ; COC1(c2cncc(C(N)=O)c2)C2CCCC1CN(CC1CC1)C2]

To a solution of 5-((1R,5S,9r)-3-(cyclopropylmethyl)-9-methoxy-3-azabicyclo[3.3.1]nonan-9-yl)nicotinonitrile (148 mg, 0.48 mmol) in tert-butanol (10 mL) was added potassium hydroxide (135 mg, 2.41 mmol) and the reaction mixture was heated at 100° C. for 2 hours. The mixture was cooled, quenched with water and extracted with ethyl acetate (×3). The combined organic phases were dried over MgSO₄, filtered and concentrated under reduced pressure. The residue was purified by reverse phase chromatography (C18) to give 5-((1R,5S,9r)-3-(cyclopropylmethyl)-9-methoxy-3-azabicyclo[3.3.1]nonan-9-yl)nicotinamide (102 mg, 65% yield). To a solution of 5-((1R,5S,9r)-3-(cyclopropylmethyl)-9-methoxy-3-azabicyclo[3.3.1]nonan-9-yl)nicotinamide (34 mg, 0.10 mmol) in ethyl acetate (10 mL) was added 2 M hydrochloric acid in diethyl ether (52 µL, 0.10 mmol) slowly at 0° C., and the reaction mixture was stirred for 30 minutes. The reaction was concentrated under reduced pressure and the residue freeze dried from water to give 5-((1R,5S,9r)-3-(cyclopropylmethyl)-9-methoxy-3-azabicyclo[3.3.1]nonan-9-yl)nicotinamide hydrochloride (38 mg, quant.); [M+H]⁺ 330.11; ¹H NMR (300 MHz, d₆-DMSO): 9.02 (d, 1H), 8.85 (d, 1H), 8.28 (s, 1H), 3.60 (d, 2H), 3.54-3.41 (m, 2H), 3.08-2.98 (m, 4H), 2.74 (s, 3H), 1.96-1.76 (m, 3H), 1.62-1.29 (m, 3H), 1.25-1.11 (m, 1H), 0.64 (dd, 2H), 0.43 (dd, 2H).

Compound 27

Synthesis of 4-((1R,5S,9r)-3-(cyclopropylmethyl)-9-methoxy-3-azabicyclo[3.3.1]nonan-9-yl)picolinonitrile

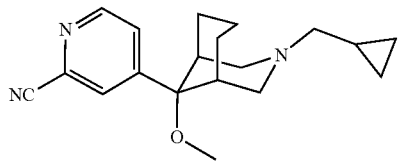 [SMILES: COC1(c2ccnc(C#N)c2)C2CCCC1CN(CC1CC1)C2]

To a solution of (1R,5S,9r)-9-(2-chloropyridin-4-yl)-3-(cyclopropylmethyl)-9-methoxy-3-azabicyclo[3.3.1]nonane (275 mg, 0.86 mmol) in degassed N,N-dimethylformamide (5 mL) was added tris(dibenzylideneacetone)dipalladium (0) (78 mg, 0.09 mmol) and 1,1'bis(diphenylphosphino)ferrocene (48 mg, 0.09 mmol). After heating to 80° C., zinc cyanide (200 mg, 1.71 mmol) was added and the reaction mixture heated at 120° C. for 18 hours. The reaction mixture was cooled to room temperature and filtered through a pad of Celite, washing with ethyl acetate. The filtrate was washed with water (×2), dried over MgSO₄, filtered and concentrated under reduced pressure. The crude residue was purified by silica chromatography, eluting with 15-20% ethyl acetate in toluene, to give 4-((1R,5S,9r)-3-(cyclopropylmethyl)-9-methoxy-3-azabicyclo[3.3.1]nonan-9-yl)picolinonitrile (150 mg, 56% yield); [M+H]⁺ 312.25.

Synthesis of 4-((1R,5S,9r)-3-(cyclopropylmethyl)-9-methoxy-3-azabicyclo[3.3.1]nonan-9-yl)picolinamide Hydrochloride

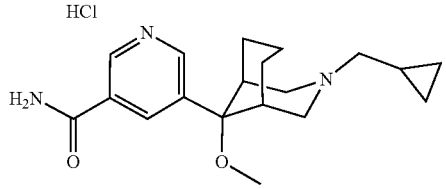 [SMILES: Cl ; COC1(c2cncc(C(N)=O)c2)C2CCCC1CN(CC1CC1)C2]

To a solution of 4-((1R,5S,9r)-3-(cyclopropylmethyl)-9-methoxy-3-azabicyclo[3.3.1]nonan-9-yl)picolinonitrile (150 mg, 0.48 mmol) in tert-butanol (5 mL) was added potassium hydroxide (135 mg, 2.40 mmol) and the reaction mixture was heated at 100° C. for 2.5 hours. The mixture was quenched with water and extracted with ethyl acetate (×3). The combined organic phases were dried over MgSO$_4$, filtered and concentrated under reduced pressure. The residue was purified by reverse phase chromatography (C18) to give 4-((1R,5S,9r)-3-(cyclopropylmethyl)-9-methoxy-3-azabicyclo[3.3.1]nonan-9-yl)picolinamide (110 mg, 69% yield). To a solution of 4-((1R,5S,9r)-3-(cyclopropylmethyl)-9-methoxy-3-azabicyclo[3.3.1]nonan-9-yl)picolinamide (110 mg, 0.33 mmol) in ethyl acetate (15 mL) was added 2 M hydrochloric acid in diethyl ether (0.20 mL, 0.40 mmol) slowly at 0° C., and the reaction mixture was stirred for 30 minutes. The reaction was concentrated under reduced pressure and the residue freeze dried from water to give 4-((1R,5S,9r)-3-(cyclopropylmethyl)-9-methoxy-3-azabicyclo[3.3.1]nonan-9-yl)picolinamide hydrochloride (117 mg, 96% yield); [M+H]$^+$ 330.11; $^1$H NMR (300 MHz, D$_2$O): 8.65 (d, 1H), 8.10 (s, 1H), 7.75 (d, 1H), 3.67 (d, 2H), 3.54 (d, 2H), 2.99 (d, 2H), 2.91 (br s, 2H), 2.75 (s, 3H), 1.90-1.70 (m, 2H), 1.68-1.34 (m, 4H), 1.11-0.94 (m, 1H), 0.63 (dd, 2H), 0.31 (dd, 2H).

Compound 30

Synthesis of (1R,5S,9r)-3-(cyclopropylmethyl)-9-ethoxy-9-(3-iodophenyl)-3-azabicyclo[3.3.1]nonane

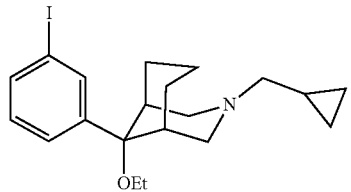 [SMILES: CCOC1(c2cccc(I)c2)C2CCCC1CN(CC1CC1)C2]

To an ice cold solution of (1R,5S,9r)-3-(cyclopropylmethyl)-9-(3-iodophenyl)-3-azabicyclo[3.3.1]nonan-9-ol (688 mg, 1.73 mmol) in N,N-dimethylformamide (10 mL) was added sodium hydride (60% dispersion in oil, 140 mg, 3.46 mmol) and the reaction mixture stirred for 30 minutes. Iodoethane (0.28 mL, 3.46 mmol) was added and the mixture was stirred at room temperature for 96 hours. Further sodium hydride (60% dispersion in oil, 140 mg, 3.46 mmol) was added, followed by iodoethane (0.28 mL, 3.46 mmol) and the reaction mixture was stirred for 72 hours. The mixture was quenched with water and extracted with ethyl acetate (×3). The combined organic phases were washed with brine (×3), dried over MgSO$_4$, filtered and concentrated under reduced pressure. The residue was purified by silica chromatography, eluting with 40% ethyl acetate in toluene, to give (1R,5S,9r)-3-(cyclopropylmethyl)-9-ethoxy-9-(3-iodophenyl)-3-azabicyclo[3.3.1]nonane (500 mg, 68% yield); [M+H]$^+$ 426.22.

Synthesis of 3-((1R,5S,9r)-3-(cyclopropylmethyl)-9-ethoxy-3-azabicyclo[3.3.1]nonan-9-yl)benzonitrile

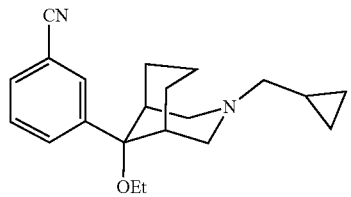 [SMILES: CCOC1(c2cccc(C#N)c2)C2CCCC1CN(CC1CC1)C2]

To a solution of (1R,5S,9r)-3-(cyclopropylmethyl)-9-ethoxy-9-(3-iodophenyl)-3-azabicyclo[3.3.1]nonane (500 mg, 1.17 mmol) in degassed N,N-dimethylformamide (10 mL) was added tetrakis(triphenylphosphine)palladium(0) (203 mg, 0.18 mmol) and the mixture was heated to 80° C., then zinc cyanide (138 mg, 1.17 mmol) was added. The reaction mixture was heated at 110° C. for 18 hours, cooled to room temperature, quenched with water and extracted with ethyl acetate (×3). The combined organic phases were washed with water (×2), then brine, dried over MgSO$_4$, filtered and concentrated under reduced pressure. The residue was purified by silica chromatography, eluting with 20% ethyl acetate in heptane, then further purified by silica chromatography, eluting with 10-20% ethyl acetate in heptane, to give 3-((1R,5S,9r)-3-(cyclopropylmethyl)-9-ethoxy-3-azabicyclo[3.3.1]nonan-9-yl)benzonitrile (80 mg, 20% yield); [M+H]$^+$ 325.27.

Synthesis of 3-((1R,5S,9r)-3-(cyclopropylmethyl)-9-ethoxy-3-azabicyclo[3.3.1]nonan-9-yl)benzamide Hydrochloride

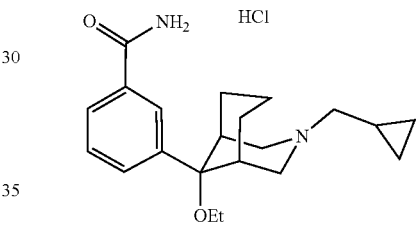

To a solution of 3-((1R,5S,9r)-3-(cyclopropylmethyl)-9-ethoxy-3-azabicyclo[3.3.1]nonan-9-yl)benzonitrile (80 mg, 0.25 mmol) in tert-butanol (6 mL) was added potassium hydroxide (70 mg, 1.23 mmol). The reaction mixture was heated at 100° C. for 2 hours, cooled, quenched with water and extracted with ethyl acetate (×3). The combined organic phases were dried over MgSO$_4$, filtered and concentrated under reduced pressure. The residue was purified by reverse phase chromatography (C18), then further purified by preparative HPLC to give 3-((1R,5S,9r)-3-(cyclopropylmethyl)-9-ethoxy-3-azabicyclo[3.3.1]nonan-9-yl)benzamide (43 mg, 51% yield). To a solution of 3-((1R,5S,9r)-3-(cyclopropylmethyl)-9-ethoxy-3-azabicyclo[3.3.1]nonan-9-yl)benzamide (43 mg, 0.13 mmol) in ethyl acetate (10 mL) was added 2 M hydrochloric acid in diethyl ether (75 μL, 0.15 mmol) at 0° C., and the reaction mixture was stirred for 30 minutes. The reaction was concentrated under reduced pressure and the residue freeze dried from water to give 3-((1R,5S,9r)-3-(cyclopropylmethyl)-9-ethoxy-3-azabicyclo[3.3.1]nonan-9-yl)benzamide hydrochloride (40 mg, 84% yield); [M+H]$^+$ 343.14; $^1$H NMR (300 MHz, D$_2$O): 7.83 (s, 1H), 7.75 (d, 1H), 7.67 (d, 1H), 7.54 (t, 1H), 3.72-3.58 (m, 4H), 3.04 (d, 2H), 3.01-2.91 (m, 4H), 1.90-1.34 (m, 6H), 1.18-0.98 (m, 1H), 0.87 (t, 3H), 0.70 (dd, 2H), 0.38 (dd, 2H).

Compound 31

Synthesis of (1R,5S,9r)-9-(4-(benzyloxy)phenyl)-3-(cyclopropylmethyl)-3-azabicyclo[3.3.1]nonan-9-ol and (1R,5S,9s)-9-(4-(benzyloxy)phenyl)-3-(cyclopropylmethyl)-3-azabicyclo[3.3.1]nonan-9-ol

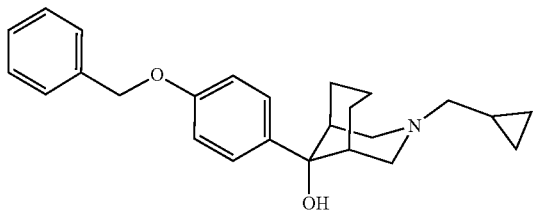

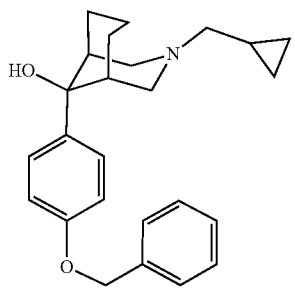

To a solution of 1-(benzyloxy)-4-iodobenzene (2.88 g, 9.29 mmol) in tetrahydrofuran (54 mL) at −78° C. under argon, was added n-butyl lithium (1.7 M in hexanes, 4.80 mL, 8.11 mmol) drop wise, and the reaction was stirred for 1 hour. A solution of (1R,5S)-3-(cyclopropylmethyl)-3-azabicyclo[3.3.1]nonan-9-one (1.12 g, 5.79 mmol) in tetrahydrofuran (6 mL) was added drop wise, and the reaction was stirred for 10 minutes, then warmed to room temperature. The mixture was quenched with water and poured into 2 M aqueous hydrochloric acid and diethyl ether. The resulting precipitate was collected by filtration. Concentrated aqueous ammonia was added to the precipitate and the mixture extracted with dichloromethane (×2). The combined dichloromethane phases were washed with brine, dried over MgSO$_4$, filtered and concentrated under reduced pressure to give (1R,5S,9r)-9-(4-(benzyloxy)phenyl)-3-(cyclopropylmethyl)-3-azabicyclo[3.3.1]nonan-9-ol (550 mg, 25% yield); [M+H]$^+$ 378.33. The phases of the filtrate were separated and the ether phase extracted with 2 M aqueous hydrochloric acid. The combined acidic phases were basified by the addition of concentrated aqueous ammonia and extracted with dichloromethane (×3). The combined dichloromethane phases were washed with brine, dried over MgSO$_4$, filtered and concentrated under reduced pressure. The residue was purified by silica chromatography, eluting with 20% ethyl acetate in heptane, to give (1R,5S,9s)-9-(4-(benzyloxy)phenyl)-3-(cyclopropylmethyl)-3-azabicyclo[3.3.1]nonan-9-ol (1.10 g, 50% yield); [M+H]$^+$ 378.33.

Synthesis of (1R,5S,9r)-9-(4-(benzyloxy)phenyl)-3-(cyclopropylmethyl)-9-methoxy-3-azabicyclo[3.3.1]nonane

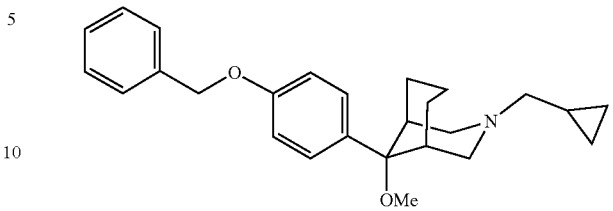

To an ice cold solution of (1R,5S,9r)-9-(4-(benzyloxy)phenyl)-3-(cyclopropylmethyl)-3-azabicyclo[3.3.1]nonan-9-ol (650 mg, 1.75 mmol) in N,N-dimethylformamide (6 mL) was added sodium hydride (60% dispersion in oil, 80 mg, 2.00 mmol) and the reaction mixture stirred for 5 minutes. Iodomethane (0.17 mL, 2.74 mmol) was added and the mixture stirred for 1 hour at room temperature. Further sodium hydride (60% dispersion in oil, 100 mg, 2.50 mmol) was added, followed by iodomethane (0.17 mL, 2.74 mmol) and the reaction was stirred for 1 hour. The mixture was quenched by pouring into ice/water and extracted with ethyl acetate (×3). The combined organic phases were washed with brine, dried over MgSO$_4$, filtered and concentrated under reduced pressure to give (1R,5S,9r)-9-(4-(benzyloxy)phenyl)-3-(cyclopropylmethyl)-9-methoxy-3-azabicyclo[3.3.1]nonane (650 mg, 96% yield); [M+H]$^+$ 392.12.

Synthesis of 4-((1R,5S,9r)-3-(cyclopropylmethyl)-9-methoxy-3-azabicyclo[3.3.1]nonan-9-yl)phenol

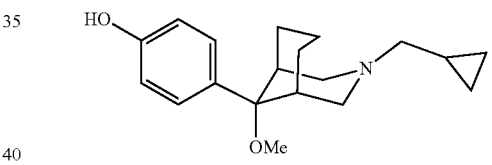

To a stirred solution of (1R,5S,9r)-9-(4-(benzyloxy)phenyl)-3-(cyclopropylmethyl)-9-methoxy-3-azabicyclo[3.3.1]nonane (540 mg, 1.38 mmol) in tetrahydrofuran (18 mL) and industrial methylated spirits (18 mL) under argon was added 20% palladium hydroxide on carbon (162 mg) and the reaction mixture was stirred for 18 hours under an atmosphere of hydrogen. The mixture was filtered through a pad of Celite, washed with dichloromethane and the filtrate concentrated under reduced pressure to give 4-((1R,5S,9r)-3-(cyclopropylmethyl)-9-methoxy-3-azabicyclo[3.3.1]nonan-9-yl)phenol (500 mg) which was used without purification; [M+H]$^+$ 302.24.

Synthesis of 4-((1R,5S,9r)-3-(cyclopropylmethyl)-9-methoxy-3-azabicyclo[3.3.1]nonan-9-yl)phenyl Trifluoromethanesulfonate

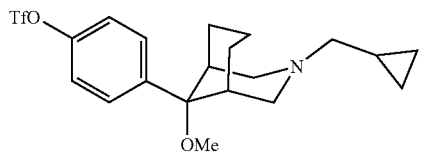 [SMILES: COC1(c2ccc(OS(=O)(=O)C(F)(F)F)cc2)C2CCCC1CN(CC1CC1)C2]

To a solution of 4-((1R,5S,9r)-3-(cyclopropylmethyl)-9-methoxy-3-azabicyclo[3.3.1]nonan-9-yl)phenol (300 mg, 1.00 mmol) in dichloromethane (8 mL) was added N-phenyl-bis(trifluoromethanesulfonimide) (355 mg, 1.00 mmol), followed by triethylamine (0.40 mL, 2.98 mmol) and the reaction mixture was stirred for 4 hours at room temperature. The reaction mixture was concentrated under reduced pressure and the residue taken up in ethyl acetate. The solution was washed with a 1:1 mixture of concentrated aqueous ammonia:water (×3), then brine, dried over MgSO$_4$, filtered and concentrated under reduced pressure. The residue was purified by silica chromatography, eluting with 10-50% ethyl acetate in heptane, to give 4-((1R,5S,9r)-3-(cyclopropylmethyl)-9-methoxy-3-azabicyclo[3.3.1]nonan-9-yl)phenyl trifluoromethanesulfonate (268 mg, 45% yield over 2 steps); [M+H]$^+$ 434.26.

Synthesis of 4-((1R,5S,9r)-3-(cyclopropylmethyl)-9-methoxy-3-azabicyclo[3.3.1]nonan-9-yl)benzonitrile

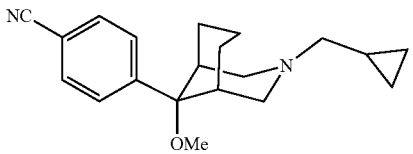 [SMILES: COC1(c2ccc(C#N)cc2)C2CCCC1CN(CC1CC1)C2]

To a solution of 4-((1R,5S,9r)-3-(cyclopropylmethyl)-9-methoxy-3-azabicyclo[3.3.1]nonan-9-yl)phenyl trifluoromethanesulfonate (214 mg, 0.49 mmol) in degassed N,N-dimethylformamide (6.5 mL) was added tetrakis(triphenylphosphine)palladium(0) (57 mg, 0.05 mmol) and the mixture was heated to 50° C. until complete dissolution occurred. Zinc cyanide (58 mg, 0.49 mmol) was added and the reaction mixture was heated at 110° C. for 2.5 hours. The reaction mixture was cooled to room temperature, quenched with water and extracted with ethyl acetate (×3). The combined organic phases were washed with brine (×3), dried over MgSO$_4$, filtered and concentrated under reduced pressure. The residue was purified by silica chromatography, eluting with 40-50% ethyl acetate in heptane, to give 4-((1R,5S,9r)-3-(cyclopropylmethyl)-9-methoxy-3-azabicyclo[3.3.1]nonan-9-yl)benzonitrile (76 mg, 49% yield); [M+H]$^+$ 311.23.

Synthesis of 4-((1R,5S,9r)-3-(cyclopropylmethyl)-9-methoxy-3-azabicyclo[3.3.1]nonan-9-yl)benzamide Hydrochloride

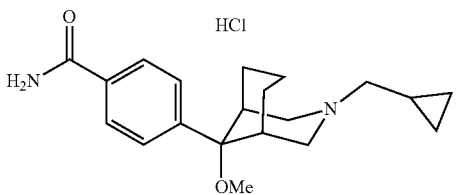 [SMILES: COC1(c2ccc(C(N)=O)cc2)C2CCCC1CN(CC1CC1)C2 ; Cl]

To a solution of 4-((1R,5S,9r)-3-(cyclopropylmethyl)-9-methoxy-3-azabicyclo[3.3.1]nonan-9-yl)benzonitrile (90 mg, 0.29 mmol) in tert-butanol (8 mL) was added potassium hydroxide (80 mg, 1.44 mmol). The reaction mixture was heated at 100° C. for 2 hours, cooled, quenched with water and extracted with ethyl acetate (×3). The combined organic phases were dried over MgSO$_4$, filtered and concentrated under reduced pressure. The residue was purified by preparative HPLC to give 4-((1R,5S,9r)-3-(cyclopropylmethyl)-9-methoxy-3-azabicyclo[3.3.1]nonan-9-yl)benzonitrile (60 mg, 67% yield). To a solution of 4-((1R,5S,9r)-3-(cyclopropylmethyl)-9-methoxy-3-azabicyclo[3.3.1]nonan-9-yl)benzonitrile (60 mg, 0.19 mmol) in dichloromethane (10 mL) was added 2 M hydrochloric acid in diethyl ether (0.11 mL, 0.22 mmol) at 0° C., and the reaction mixture was stirred for 15 minutes. The reaction was concentrated under reduced pressure and the residue freeze dried from water to give 4-((1R,5S,9r)-3-(cyclopropylmethyl)-9-methoxy-3-azabicyclo[3.3.1]nonan-9-yl)benzamide (69 mg, 98% yield); [M+H]$^+$ 329.12; $^1$H NMR (300 MHz, D$_2$O): 7.84 (d, 2H), 7.58 (d, 2H), 3.69 (d, 2H), 3.59 (d, 2H), 3.04 (d, 2H), 2.95 (br s, 2H), 2.78 (s, 3H), 1.91-1.39 (m, 6H), 1.15-1.00 (m, 1H), 0.77-0.63 (m, 2H), 0.43-0.32 (m, 2H).

Compound 36

5-((1R,5S,9r)-3-(cyclopropylmethyl)-9-methoxy-3-azabicyclo[3.3.1]nonan-9-yl)thiophene-2-carboxamide Hydrochloride

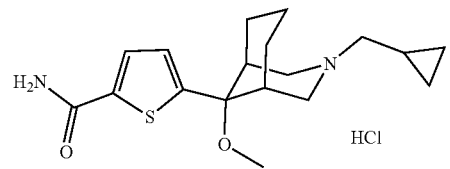 [SMILES: COC1(c2ccc(C(N)=O)s2)C2CCCC1CN(CC1CC1)C2 ; Cl]

[M+H]$^+$ 335.14; $^1$H NMR (300 MHz, D$_2$O): 7.51 (d, 1H), 7.15 (d, 1H), 3.54 (d, 2H), 3.44 (d, 2H), 2.92 (d, 2H), 2.08 (s, 3H), 2.65 (s, 2H), 1.93-1.67 (m, 4H), 1.61-1.35 (m, 2H), 1.03-0.88 (m, 1H), 0.59 (dd, 2H), 0.26 (dd, 2H).

Compound 35

Synthesis of (1R,5S,9r)-tert-butyl 9-(3-hydroxyphenyl)-9-methoxy-3-azabicyclo[3.3.1]nonane-3-carboxylate

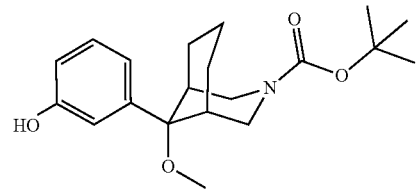 [SMILES: COC1(c2cccc(O)c2)C2CCCC1CN(C(=O)OC(C)(C)C)C2]

To a solution of 3-((1R,5S,9r)-3-benzyl-9-methoxy-3-azabicyclo[3.3.1]nonan-9-yl)phenol (2.46 g, 7.30 mmol) in ethyl acetate (75 mL) was added di-tert-butyl dicarbonate (1.75 g, 8.02 mmol), followed by 20% palladium hydroxide on carbon (740 mg) and the reaction mixture was stirred for 18 hours at room temperature under an atmosphere of hydrogen. The suspension was filtered through a pad of Celite, and washed with ethyl acetate and methanol. The filtrate was concentrated under reduced pressure and the residue was purified by silica chromatography, eluting with 0-40% ethyl acetate in heptane, to give (1R,5S,9r)-tert-butyl 9-(3-hydroxyphenyl)-9-methoxy-3-azabicyclo[3.3.1]

nonane-3-carboxylate (1.54 g, 61% yield); [M+H]⁺ 348.3 and (1R,5S,9r)-tert-butyl 9-(3-((tert-butoxycarbonyl)oxy)phenyl)-9-methoxy-3-azabicyclo[3.3.1]nonane-3-carboxylate (0.98 g, 30% yield); [M+H]⁺ 448.5. To a solution of (1R,5S,9r)-tert-butyl 9-(3-((tert-butoxycarbonyl)oxy)phenyl)-9-methoxy-3-azabicyclo[3.3.1]nonane-3-carboxylate (0.98 g, 2.20 mmol) in methanol (20 mL) was added 2 M aqueous sodium hydroxide (2.50 mL, 5.00 mmol) and the reaction was heated at reflux for 1 hour. The mixture was cooled to room temperature, quenched and neutralised to pH 7 by the addition of 0.5 M aqueous hydrochloric acid. The volatiles were removed under reduced pressure, the mixture diluted with aqueous sodium hydrogen carbonate solution and extracted with ethyl acetate (×3). The combined organic phases were washed with brine, dried over MgSO₄, filtered and concentrated under reduced pressure to give (1R,5S,9r)-tert-butyl 9-(3-hydroxyphenyl)-9-methoxy-3-azabicyclo[3.3.1]nonane-3-carboxylate (0.68 g, 89% yield). Overall yield (2.22 g, 88%); [M+H]⁺ 348.4.

Synthesis of (1R,5S,9r)-tert-butyl 9-methoxy-9-(3-(((trifluoromethyl)sulfonyl)oxy)phenyl)-3-azabicyclo[3.3.1]nonane-3-carboxylate

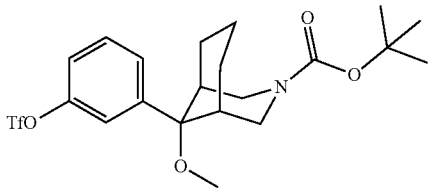 [SMILES: COC1(c2cccc(OS(=O)(=O)C(F)(F)F)c2)C2CCCC1CN(C(=O)OC(C)(C)C)C2]

To a solution of (1R,5S,9r)-tert-butyl 9-(3-hydroxyphenyl)-9-methoxy-3-azabicyclo[3.3.1]nonane-3-carboxylate (0.68 g, 1.96 mmol) in dichloromethane (20 mL) was added N-phenyl-bis(trifluoromethanesulfonimide) (0.72 g, 2.02 mmol) and triethylamine (0.82 mL, 5.88 mmol) and the reaction mixture was stirred for 6 hours at room temperature. The reaction was concentrated under reduced pressure and the residue taken up in ethyl acetate. The solution was washed with a 1:1 mixture of concentrated aqueous ammonia and water (×3), then brine, dried over MgSO₄, filtered and concentrated under reduced pressure. The residue was combined with a second batch and was purified by silica chromatography, eluting with 20% ethyl acetate in heptane, to give (1R,5S,9r)-tert-butyl 9-methoxy-9-(3-(((trifluoromethyl)sulfonyl)oxy)phenyl)-3-azabicyclo[3.3.1]nonane-3-carboxylate (2.81 g, 92% yield); [M+H]⁺ 480.3.

Synthesis of (1R,5S,9r)-tert-butyl 9-(3-cyanophenyl)-9-methoxy-3-azabicyclo[3.3.1]nonane-3-carboxylate

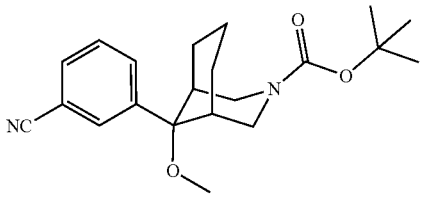 [SMILES: COC1(c2cccc(C#N)c2)C2CCCC1CN(C(=O)OC(C)(C)C)C2]

To a solution of (1R,5S,9r)-tert-butyl 9-methoxy-9-(3-(((trifluoromethyl)sulfonyl)oxy)phenyl)-3-azabicyclo[3.3.1]nonane-3-carboxylate (2.81 g, 5.86 mmol) in degassed N,N-dimethylformamide (35 mL) was added tetrakis(triphenylphosphine)palladium(0) (1.35 g, 1.17 mmol). The reaction mixture was heated to 50° C., then zinc cyanide (0.69 g, 5.86 mmol) was added and the reaction heated at 110° C. for 1.5 hours. The mixture was cooled to room temperature, quenched with aqueous sodium hydrogen carbonate solution and filtered through a pad of Celite. The filtrate was extracted with ethyl acetate (×3), and the combined organic phases were washed with 1:1 brine-water (×2), dried over MgSO₄, filtered and concentrated under reduced pressure. The residue was purified by silica chromatography, eluting with 0-30% ethyl acetate in heptane, to give (1R,5S,9r)-tert-butyl 9-(3-cyanophenyl)-9-methoxy-3-azabicyclo[3.3.1]nonane-3-carboxylate (2.24 g); [M+H]⁺ 357.4.

Synthesis of (1R,5S,9r)-tert-butyl 9-(3-carbamoylphenyl)-9-methoxy-3-azabicyclo[3.3.1]nonane-3-carboxylate

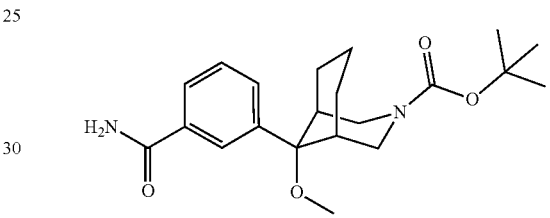

To a mixture of (1R,5S,9r)-tert-butyl 9-(3-cyanophenyl)-9-methoxy-3-azabicyclo[3.3.1]nonane-3-carboxylate (2.24 g, 6.29 mmol) in tert-butanol (60 mL) was added potassium hydroxide (1.76 g, 31.4 mmol), and the reaction mixture was heated at reflux for 1 hour. The mixture was cooled, poured into water and extracted with ethyl acetate (×3). The combined organic phases were dried over MgSO₄, filtered and concentrated under reduced pressure. The residue was purified by silica chromatography, eluting with 75-100% ethyl acetate in heptane, to give (1R,5S,9r)-tert-butyl 9-(3-carbamoylphenyl)-9-methoxy-3-azabicyclo[3.3.1]nonane-3-carboxylate (2.02 g, 92% over 2 steps); [M−H]⁻ 373.4.

Synthesis of 3-((1R,5S,9r)-9-methoxy-3-azabicyclo[3.3.1]nonan-9-yl)benzamide Hydrochloride

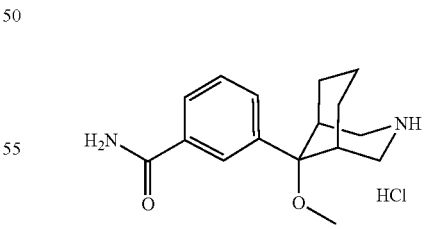

A mixture of (1R,5S,9r)-tert-butyl 9-(3-carbamoylphenyl)-9-methoxy-3-azabicyclo[3.3.1]nonane-3-carboxylate (189 mg, 0.51 mmol) in 2 M hydrochloric acid in diethyl ether (10 mL) was stirred for 24 hours at room temperature. The mixture was diluted with diethyl ether and the liquors decanted. The mixture was concentrated under reduced pressure, and freeze dried from water to give 3-((1R,5S,9r)-9-methoxy-3-azabicyclo[3.3.1]nonan-9-yl)benzamide hydrochloride (135 mg, 86% yield); [M+H]+ 275.19; 1H NMR (300 MHz, D2O): 7.75 (s, 1H), 7.68 (d, 1H), 7.60 (d, 1H), 7.46 (t, 1H), 3.56 (dd, 2H), 3.30 (d, 2H), 2.82 (s, 2H), 2.69 (s, 3H), 1.79-1.29 (m, 6H).

Compound 46

Synthesis of 1-((tetrahydro-2H-pyran-2-yl)oxy)cyclopropanecarboxylic Acid

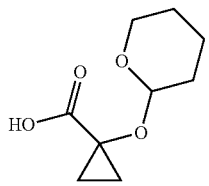 [SMILES: O=C(O)C1(OC2CCCCO2)CC1]

To a solution of 3,4-dihydro-2H-pyran (0.61 mL, 6.68 mmol) in dichloromethane (10 mL) was added 1-hydroxylcyclopropane carboxylic acid (620 mg, 6.07 mmol) and the reaction mixture was stirred for 24 hours at room temperature. The mixture was concentrated under reduced pressure. The residue was dissolved in dichloromethane (10 mL) and para-toluene sulfonic acid monohydrate (5 mg) was added and the reaction mixture was stirred for 72 hours at room temperature. The mixture was concentrated under reduced pressure and purified by silica chromatography, eluting with dichloromethane, to give 1-((tetrahydro-2H-pyran-2-yl)oxy)cyclopropanecarboxylic acid (402 mg, 35% yield); 1H NMR (300 MHz, CDCl3): 4.64 (dd, 1H), 4.15-4.06 (m, 1H), 3.66-3.55 (m, 1H), 1.91-1.81 (m, 1H), 1.77-1.68 (m, 1H), 1.64-1.46 (m, 4H), 1.41 (dd, 1H), 1.34 (dd, 1H), 1.28 (dd, 1H), 1.23-1.13 (m, 1H).

Synthesis of (1-((tetrahydro-2H-pyran-2-yl)oxy)cyclopropyl)methanol

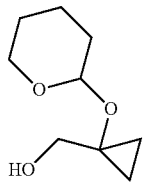 [SMILES: OCC1(OC2CCCCO2)CC1]

To an ice cooled solution of 1-((tetrahydro-2H-pyran-2-yl)oxy)cyclopropanecarboxylic acid (400 mg, 2.15 mmol) in tetrahydrofuran (5 mL) was added lithium aluminium hydride (2 M in tetrahydrofuran) (2.15 mL, 4.29 mmol) drop wise and the reaction mixture was stirred for 30 minutes. Water was added, followed by ethyl acetate and saturated sodium potassium tartrate and the mixture stirred for 20 minutes. The organic phase was separated, washed with water, dried over MgSO4, filtered and concentrated under reduced pressure. The residue was purified by silica chromatography, eluting with 20% ethyl acetate in heptane, to give (1-((tetrahydro-2H-pyran-2-yl)oxy)cyclopropyl)methanol (160 mg, 43% yield); 1H NMR (300 MHz, CDCl3): 4.68 (dd, 1H), 4.15 (dd, 1H), 4.12-4.00 (m, 2H), 3.68-3.58 (m, 1H), 3.10 (dd, 1H), 1.90-1.75 (m, 1H), 1.73-1.62 (m, 1H), 1.62-1.43 (m, 4H), 0.98-0.58 (m, 4H).

Synthesis of 1-((tetrahydro-2H-pyran-2-yl)oxy)cyclopropanecarbaldehyde

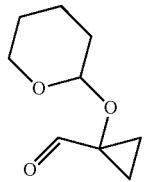 [SMILES: O=CC1(OC2CCCCO2)CC1]

A solution of oxalyl chloride (0.08 mL, 0.32 mmol) in dichloromethane (1.8 mL) was cooled to −60° C. Dimethyl sulfoxide (0.14 mL) in dichloromethane (0.30 mL) was added drop wise. After 5 minutes, a solution of (1-((tetrahydro-2H-pyran-2-yl)oxy)cyclopropyl)methanol (50 mg, 0.29 mmol) in dichloromethane (1 mL) was added and the mixture stirred for 15 minutes. Triethylamine (0.20 mL, 1.45 mmol) was added and the mixture warmed slowly to room temperature. The reaction was diluted with dichloromethane, washed with water then brine, dried over MgSO4, filtered and concentrated under reduced pressure to give 1-((tetrahydro-2H-pyran-2-yl)oxy)cyclopropanecarbaldehyde (55 mg, quantitative yield) which was used directly without purification; 1H NMR (300 MHz, CDCl3): 9.65 (s, 1H), 4.68 (dd, 1H), 4.01-3.92 (m, 1H), 3.56-3.44 (m, 1H), 1.92-1.72 (m, 2H), 1.70-1.34 (m, 6H), 1.30-1.19 (m, 2H).

Synthesis of 3-((1R,5S,9r)-9-methoxy-3-((1-((tetrahydro-2H-pyran-2-yl)oxy)cyclopropyl)-methyl)-3-azabicyclo[3.3.1]nonan-9-yl)benzamide

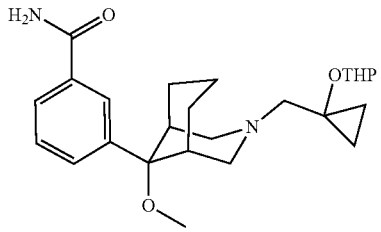

To a solution of 1-((tetrahydro-2H-pyran-2-yl)oxy)cyclopropanecarbaldehyde (50 mg, 0.29 mmol) in dichloromethane (2 mL) was added triethylamine (27 µL, 0.20 mmol), followed by 3-((1R,5S,9r)-9-methoxy-3-azabicyclo[3.3.1]nonan-9-yl)benzamide hydrochloride (61 mg, 0.20 mmol) and the suspension was stirred for 1 hour at room temperature. Sodium triacetoxyborohydride (187 mg, 0.88 mmol) was added and the reaction stirred for 1 hour. The mixture was diluted with dichloromethane and washed with saturated aqueous sodium hydrogen carbonate solution followed by brine. The organic phase was dried over MgSO4, filtered, and concentrated under reduced pressure. The residue was purified by silica chromatography, eluting with 4% methanol in dichloromethane, to give 3-((1R,5S,9r)-9-methoxy-3-((1-((tetrahydro-2H-pyran-2-yl)oxy)cyclopropyl)methyl)-3-azabicyclo[3.3.1]nonan-9-yl)benzamide (62 mg, 74% yield); [M+H]+ 429.46.

Synthesis of 3-((1R,5S,9r)-3-((1-hydroxycyclopropyl)methyl)-9-methoxy-3-azabicyclo[3.3.1]nonan-9-yl)benzamide Hydrochloride

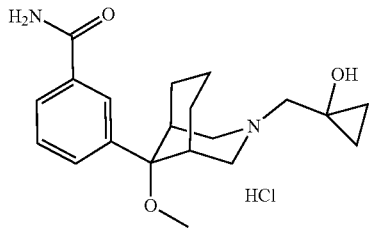 [SMILES: COC1(c2cccc(C(N)=O)c2)C2CCCC1CN(CC1(O)CC1)C2 ; Cl]

To a solution of 3-((1R,5S,9r)-9-methoxy-3-((1-((tetrahydro-2H-pyran-2-yl)oxy)cyclopropyl)methyl)-3-azabicyclo[3.3.1]nonan-9-yl)benzamide (133 mg, 0.31 mmol) in methanol (5 mL) was added 2 M hydrochloric acid in diethyl ether (0.50 mL, 1.00 mmol) and the reaction mixture was stirred for 90 minutes. The mixture was poured into ice/concentrated aqueous ammonia and extracted with dichloromethane (×2). The combined organic phases were dried over MgSO$_4$, filtered and concentrated under reduced pressure. The residue was purified by silica chromatography, eluting with 4% ammonia/methanol in dichloromethane, to give 3-((1R,5S,9r)-3-((1-hydroxycyclopropyl)methyl)-9-methoxy-3-azabicyclo[3.3.1]nonan-9-yl)benzamide (106 mg, 99% yield). To a solution of 3-((1R,5S,9r)-3-((1-hydroxycyclopropyl)methyl)-9-methoxy-3-azabicyclo[3.3.1]nonan-9-yl)benzamide (106 mg, 0.31 mmol) in ethyl acetate (5 mL) was added 2 M hydrochloric acid in diethyl ether (0.17 mL, 0.34 mmol). The mixture was stirred for 15 minutes, then concentrated under reduced pressure and the residue freeze dried from water to give 3-((1R,5S,9r)-3-((1-hydroxycyclopropyl)methyl)-9-methoxy-3-azabicyclo[3.3.1]nonan-9-yl)benzamide hydrochloride (101 mg, 86% yield); [M+H]$^+$ 345.26; $^1$H NMR (300 MHz, D$_2$O): 7.77 (s, 1H), 7.70 (d, 1H), 7.62 (d, 1H), 7.48 (t, 1H), 3.61 (d, 2H), 3.51 (d, 2H), 3.14 (s, 2H), 2.90 (br s, 2H), 2.71 (s, 3H), 1.85-1.43 (m, 6H), 0.85 (dd, 2H), 0.65 (dd, 2H).

Compound 32

3-((1R,5S,9r)-9-methoxy-3-(2,2,2-trifluoroethyl)-3-azabicyclo[3.3.1]nonan-9-yl)benzamide Hydrochloride

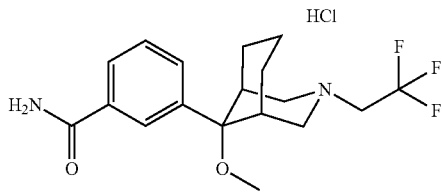 [SMILES: Cl ; COC1(c2cccc(C(N)=O)c2)C2CCCC1CN(CC(F)(F)F)C2]

[M+H]$^+$ 357.08; $^1$H NMR (300 MHz, d$_6$-DMSO): 8.03 (s, 1H), 7.92 (s, 1H), 7.80 (d, 1H), 7.59 (d, 1H), 7.45 (t, 1H), 7.38 (s, 1H), 3.20-2.99 (m, 4H), 2.82 (d, 2H), 2.65 (s, 3H), 2.67-2.54 (m, 2H), 2.54-2.36 (m, 2H), 1.77-1.41 (m, 4H), 1.23-1.06 (m, 1H).

Compound 34

3-((1R,5S,9r)-9-methoxy-3-(3,3,3-trifluoropropyl)-3-azabicyclo[3.3.1]nonan-9-yl)benzamide Hydrochloride

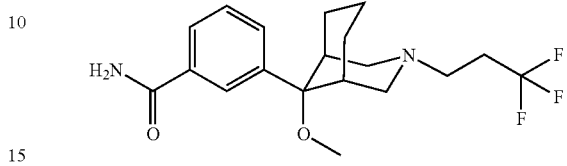

[M+H]$^+$ 371.17; $^1$H NMR (300 MHz, D$_2$O): 7.76 (s, 1H), 7.70 (d, 1H), 7.61 (d, 1H), 7.48 (t, 1H), 3.61 (d, 2H), 3.54 (d, 2H), 3.43-3.31 (m, 2H), 2.91 (br s, 2H), 2.80-2.65 (m, 2H), 2.70 (s, 3H), 1.82-1.32 (m, 6H).

Compound 47

3-((1R,5S,9r)-9-methoxy-3-propyl-3-azabicyclo[3.3.1]nonan-9-yl)benzamide Hydrochloride

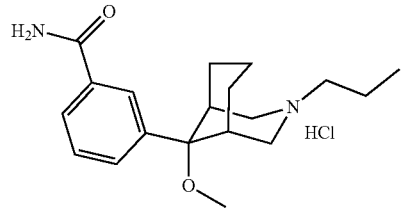 [SMILES: CCCN1CC2CCCC(C1)C2(OC)c1cccc(C(N)=O)c1 ; Cl]

[M+H]$^+$ 317.16; $^1$H NMR (300 MHz, D$_2$O): 7.77 (s, 1H), 7.70 (d, 1H), 7.61 (d, 1H), 7.49 (dd, 1H), 3.60-3.47 (m, 2H), 3.46-3.33 (m, 3H), 2.93 (br s, 2H), 2.72 (s, 3H), 1.80-1.15 (m, 12H).

Compound 45

Synthesis of 3-((1R,5S,9r)-9-methoxy-3-(tetrahydro-2H-pyran-4-yl)-3-azabicyclo[3.3.1]nonan-9-yl)benzamide Hydrochloride

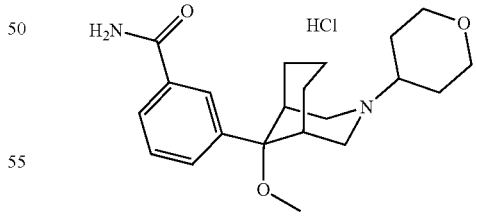

To a solution of 3-((1R,5S,9r)-9-methoxy-3-azabicyclo[3.3.1]nonan-9-yl)benzamide hydrochloride (50 mg, 0.16 mmol) in dichloromethane (4 mL) was added triethylamine (67 µL, 0.48 mmol), followed by tetrahydropyran (0.10 mL, 1.13 mmol) and the mixture was stirred for 20 minutes at room temperature. Sodium triacetoxyborohydride (102 mg, 0.48 mmol) was added and the reaction stirred for 18 hours at room temperature. The mixture was quenched with saturated aqueous sodium hydrogen carbonate solution and extracted with dichloromethane (×3). The combined organic phases were washed with brine, dried over MgSO₄, filtered, and concentrated under reduced pressure. The residue was purified by silica chromatography, eluting with 0-10% ammonia/methanol in dichloromethane to give 3-((1R,5S,9r)-9-methoxy-3-(tetrahydro-2H-pyran-4-yl)-3-azabicyclo[3.3.1]nonan-9-yl)benzamide (54 mg, 93% yield). To a solution of 3-((1R,5S,9r)-9-methoxy-3-(tetrahydro-2H-pyran-4-yl)-3-azabicyclo[3.3.1]nonan-9-yl)benzamide (83 mg, 0.23 mmol) in ethyl acetate (5 mL) and dichloromethane (7 mL) was added 2 M hydrochloric acid in diethyl ether (0.13 mL, 0.26 mmol) and the reaction was stirred for 10 minutes. The mixture was concentrated under reduced pressure, triturated with diethyl ether and ethyl acetate and the residue freeze dried from water to give 3-((1R,5S,9r)-9-methoxy-3-(tetrahydro-2H-pyran-4-yl)-3-azabicyclo[3.3.1]nonan-9-yl)benzamide hydrochloride (84 mg, 92% yield); [M+H]⁺ 359.21; ¹H NMR (300 MHz, D₂O): 7.78 (s, 1H), 7.71 (d, 1H), 7.62 (d, 1H), 7.49 (dd, 1H), 4.01 (d, 2H), 3.56 (s, 4H), 3.37 (t, 3H), 2.95 (s, 2H), 2.72 (s, 3H), 2.07 (d, 2H), 1.89-1.28 (m, 8H).

Compound 42 Synthesis of 3-((1R,5S,9r)-3-cyclobutyl-9-methoxy-3-azabicyclo[3.3.1]nonan-9-yl)benzamide Hydrochloride

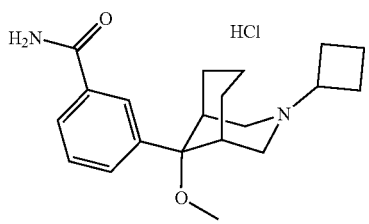 [SMILES: COC1(c2cccc(C(N)=O)c2)C2CCCC1CN(C1CCC1)C2 ; Cl]

To a solution of 3-((1R,5S,9r)-9-methoxy-3-azabicyclo[3.3.1]nonan-9-yl)benzamide hydrochloride (100 mg, 0.32 mmol) in dichloromethane (7 mL) was added triethylamine (0.13 mL, 0.97 mmol), followed by cyclobutanone (0.48 mL, 6.43 mmol) and the mixture was stirred for 20 minutes at room temperature. Sodium triacetoxyborohydride (205 mg, 0.97 mmol) was added and the reaction stirred for 18 hours at room temperature. The mixture was quenched with saturated aqueous sodium hydrogen carbonate solution and extracted with dichloromethane (×3). The combined organic phases were washed with brine, dried over MgSO₄, filtered, and concentrated under reduced pressure. The residue was purified by silica chromatography, eluting with 0-10% ammonia/methanol in dichloromethane to give 3-((1R,5S,9r)-3-cyclobutyl-9-methoxy-3-azabicyclo[3.3.1]nonan-9-yl)benzamide (78 mg, 74% yield). To a solution of 3-((1R,5S,9r)-3-cyclobutyl-9-methoxy-3-azabicyclo[3.3.1]nonan-9-yl)benzamide (73 mg, 0.22 mmol) in ethyl acetate (45 mL) and dichloromethane (5 mL) was added 2 M hydrochloric acid in diethyl ether (0.12 mL, 0.24 mmol) and the reaction was stirred for 10 minutes. The mixture was concentrated under reduced pressure, triturated with diethyl ether and the residue freeze dried from water to give 3-((1R,5S,9r)-3-cyclobutyl-9-methoxy-3-azabicyclo[3.3.1]nonan-9-yl)benzamide hydrochloride (78 mg, 96% yield); [M+H]⁺ 329.19; ¹H NMR (300 MHz, D₂O): 7.76 (s, 1H), 7.71 (d, 1H), 7.62 (d, 1H), 7.49 (dd, 1H), 3.77-3.63 (m, 1H), 3.59-3.27 (m, 4H), 2.90 (s, 2H), 2.71 (s, 3H), 2.34-2.07 (m, 4H), 1.82-1.27 (m, 8H).

Compound 50

3-((1R,5S,9r)-9-methoxy-3-(oxetan-3-yl)-3-azabicyclo[3.3.1]nonan-9-yl)benzamide (S)-2-hydroxysuccinate

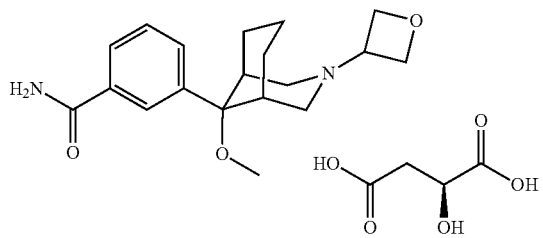

[M+H]⁺ 331.33; ¹H NMR (300 MHz, d₆-DMSO): 12.35 (br s, 1H), 8.04 (s, 1H), 7.92 (s, 1H), 7.80 (d, 1H), 7.59 (d, 1H), 7.45 (t, 1H), 7.38 (s, 1H), 5.56 (br s, 1H), 4.55-4.41 (m, 4H), 4.21 (dd, 1H), 3.47-3.21 (m, 2H), 2.71-2.52 (m, 11H), 2.44-2.33 (m, 1H), 1.77-1.63 (m, 2H), 1.62-1.43 (m, 2H), 1.21-1.06 (m, 1H).

Compound 51

Synthesis of 3-((1R,5S,9r)-9-methoxy-3-(oxetan-3-ylmethyl)-3-azabicyclo[3.3.1]nonan-9-yl)benzamide (S)-2-hydroxysuccinate

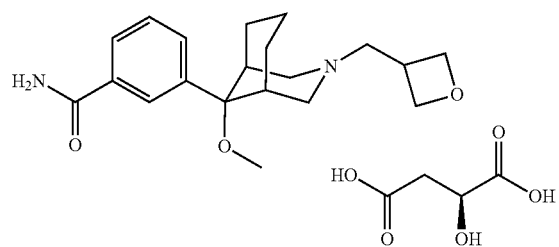

To a ice cold solution of oxetan-3-yl methanol (52 μL, 0.64 mmol) in dichloromethane (2 mL) was added Dess-Martin periodinane (273 mg, 0.64 mmol) and the reaction mixture was stirred for 15 minutes then warmed to room temperature and stirred for 3 hours to give a solution of oxetane-3-carbaldehyde which was used directly. To a mixture of 3-((1R,5S,9r)-9-methoxy-3-azabicyclo[3.3.1]nonan-9-yl)benzamide hydrochloride (100 mg, 0.32 mmol) in dichloromethane (3 mL) was added triethylamine (45 μL, 0.32 mmol), followed by a solution of oxetane-3-carbaldehyde (0.64 mmol) in dichloromethane (2 mL) and the reaction mixture was stirred for 30 minutes at room temperature. Sodium triacetoxyborohydride (205 mg, 0.97 mmol) was added and the reaction mixture was stirred for 18 hours at room temperature. The mixture was diluted with dichloromethane and washed with aqueous sodium hydrogen carbonate solution. The organic phase was dried over MgSO₄, filtered and concentrated under reduced pressure. The residue was purified by silica chromatography, eluting with 4% ammonia/methanol in dichloromethane and then further purified by preparative HPLC. The acetonitrile was removed under reduced pressure and the aqueous phase freeze dried to give 3-((1R,5S,9r)-9-methoxy-3-(oxetan-3-ylmethyl)-3-azabicyclo[3.3.1]nonan-9-yl)benzamide (50 mg, 45% yield).

To a solution of 3-((1R,5S,9r)-9-methoxy-3-(oxetan-3-ylmethyl)-3-azabicyclo[3.3.1]nonan-9-yl)benzamide (50 mg, 0.15 mmol) in ethyl acetate (3 mL) and dichloromethane (2 mL) was added L-malic acid (19 mg, 0.15 mmol) and the reaction mixture was stirred for 30 minutes at room temperature. The mixture was concentrated under reduced pressure and the residue freeze dried from water to give 3-((1R,5S,9r)-9-methoxy-3-(oxetan-3-ylmethyl)-3-azabicyclo[3.3.1]nonan-9-yl)benzamide (S)-2-hydroxysuccinate (61 mg, 88% yield); [M+H]$^+$ 345.19; $^1$H NMR (300 MHz, de-DMSO): 12.45 (br s, 1H), 8.03 (s, 1H), 7.91 (s, 1H), 7.79 (d, 1H), 7.57 (d, 1H), 7.44 (t, 1H), 7.34 (s, 1H), 7.07 (br s, 2H), 4.63 (dd, 2H), 4.24 (dd, 2H), 3.92-3.83 (m, 1H), 3.24-3.10 (m, 1H), 2.75 (d, 2H), 2.68-2.61 (m, 5H), 2.60-2.24 (m, 7H), 1.69-1.41 (m, 4H), 1.14-1.05 (m, 1H).

Compound 54

3-((1R,5S,9r)-9-methoxy-3-(trideuteriomethyl)-3-azabicyclo[3.3.1]nonan-9-yl)benzamide Hydrochloride

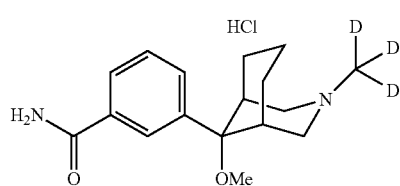 [SMILES: Cl ; [2H]C([2H])([2H])N1CC2CCCC(C1)C2(OC)c1cccc(C(N)=O)c1]

[M+H]$^+$ 292.17; $^1$H NMR (300 MHz, de-DMSO): 8.62 (br s, 1H), 8.09 (s, 1H), 7.94 (s, 1H), 7.87 (d, 1H), 7.61 (d, 1H), 7.50 (t, 1H), 7.44 (s, 1H), 3.55 (dd, 2H), 3.45-3.33 (m, 2H), 2.93 (s, 2H), 2.70 (s, 3H), 2.12-1.93 (m, 1H), 1.83-1.70 (m, 2H), 1.63-1.45 (m, 2H), 1.36-1.19 (m, 1H).

Compound 40

3-((1R,5S,9r)-3-((1-fluorocyclopropyl)methyl)-9-methoxy-3-azabicyclo[3.3.1]nonan-9-yl)benzamide Hydrochloride

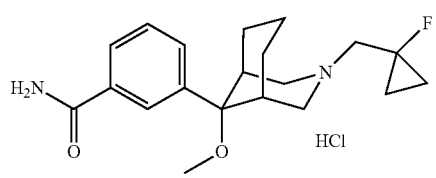 [SMILES: COC1(c2cccc(C(N)=O)c2)C2CCCC1CN(CC1(F)CC1)C2 ; Cl]

[M+H]$^+$ 347.17; $^1$H NMR (300 MHz, D$_2$O): 7.79 (s, 1H), 7.72 (d, 1H), 7.63 (d, 1H), 7.50 (dd, 1H), 3.81-3.49 (m, 6H), 2.95 (br s, 2H), 2.73 (s, 3H), 1.88-1.37 (m, 6H), 1.30-1.14 (m, 2H), 0.86 (dd, 2H).

Compound 41

2-fluoro-5-((1R,5S,9r)-9-methoxy-3-methyl-3-azabicyclo[3.3.1]nonan-9-yl)benzamide Hydrochloride

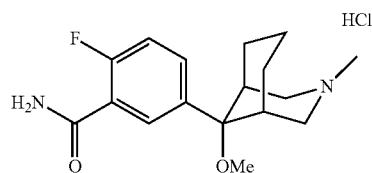 [SMILES: Cl ; COC1(c2ccc(F)c(C(N)=O)c2)C2CCCC1CN(C)C2]

[M+H]$^+$ 307.18; $^1$H NMR (300 MHz, de-DMSO): 8.21 (br s, 1H), 7.80-7.56 (m, 4H), 7.34 (dd, 1H), 3.54 (dd, 2H), 3.45-3.27 (m, 2H), 2.87 (br s, 2H), 2.78 (d, 3H), 2.72 (s, 3H), 1.97-1.67 (m, 3H), 1.63-1.44 (m, 2H), 1.40-1.26 (m, 1H).

Compound 43

Synthesis of 4-((1R,5S,9r)-9-methoxy-3-methyl-3-azabicyclo[3.3.1]nonan-9-yl)picolinonitrile

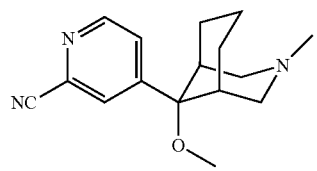 [SMILES: COC1(c2ccnc(C#N)c2)C2CCCC1CN(C)C2]

To a solution of (1R,5S,9r)-9-(2-chloropyridin-4-yl)-9-methoxy-3-methyl-3-azabicyclo[3.3.1]nonane (376 mg, 1.34 mmol) in degassed N,N-dimethylformamide (8 mL) was added tris(dibenzylideneacetone)dipalladium (0) (367 mg, 0.40 mmol) and 1,1'bis(diphenylphosphino)ferrocene (223 mg, 0.40 mmol). After heating to 80° C., zinc cyanide (314 mg, 2.67 mmol) was added and the reaction mixture heated at 120° C. for 18 hours. The reaction mixture was cooled to room temperature and filtered through a pad of Celite washing with ethyl acetate. The filtrate was washed with water (×2), then brine (×1), filtered through a second pad of Celite, dried over Na$_2$SO$_4$, filtered and concentrated under reduced pressure. The crude residue was purified by silica chromatography, eluting with 3% methanol in dichloromethane, to give 4-((1R,5S,9r)-9-methoxy-3-methyl-3-azabicyclo[3.3.1]nonan-9-yl)picolinonitrile (276 mg, 76% yield); [M+H]$^+$ 272.38.

Synthesis of 4-((1R,5S,9r)-9-methoxy-3-methyl-3-azabicyclo[3.3.1]nonan-9-yl)picolinamide Hydrochloride

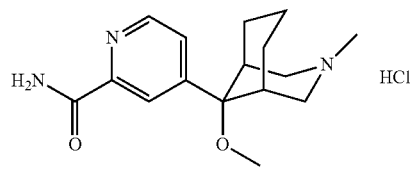 [SMILES: COC1(c2ccnc(C(N)=O)c2)C2CCCC1CN(C)C2 ; Cl]

To a solution of 4-((1R,5S,9r)-9-methoxy-3-methyl-3-azabicyclo[3.3.1]nonan-9-yl)picolinonitrile (276 mg, 1.02 mmol) in tert-butanol (8.5 mL) was added potassium hydroxide (285 mg, 5.09 mmol). The reaction mixture was heated at reflux for 1 hour, cooled, diluted with water and extracted with ethyl acetate (×3). The combined organic phases were washed with brine, dried over MgSO$_4$, filtered and concentrated under reduced pressure. The residue was purified by silica chromatography, eluting with 3% ammonia/methanol in dichloromethane, then further purified by reverse phase chromatography (C18) to give 4-((1R,5S,9r)-9-methoxy-3-methyl-3-azabicyclo[3.3.1]nonan-9-yl)picolinamide (103 mg, 35% yield).

To a solution of 4-((1R,5S,9r)-9-methoxy-3-methyl-3-azabicyclo[3.3.1]nonan-9-yl)picolinamide (103 mg, 0.36 mmol) in ethyl acetate (5 mL) was added 2 M hydrochloric acid in diethyl ether (0.27 mL, 0.54 mmol) and the reaction mixture was stirred for 15 minutes. The mixture was concentrated under reduced pressure and the residue freeze dried from water to give 4-((1R,5S,9r)-9-methoxy-3-methyl-3-azabicyclo[3.3.1]nonan-9-yl)picolinamide hydrochloride (107 mg, 92% yield); [M+H]$^+$ 290.19; $^1$H NMR (300 MHz, de-DMSO): 8.70 (d, 2H), 8.21 (s, 1H), 8.05 (s, 1H), 7.77 (s, 1H), 7.70 (dd, 1H), 3.56 (dd, 2H), 3.48-3.30 (m, 2H), 2.92 (s, 2H), 2.79 (d, 3H), 2.74 (s, 3H), 2.19-1.99 (m, 1H), 1.81 (dd, 2H), 1.56-1.38 (m, 2H), 1.35-1.21 (m, 1H). Compound 48

Synthesis of (1R,5S,9r)-9-(5-bromothiophen-2-yl)-3-methyl-3-azabicyclo[3.3.1]nonan-9-ol and (1R,5S,9s)-9-(5-bromothiophen-2-yl)-3-methyl-3-azabicyclo[3.3.1]nonan-9-ol

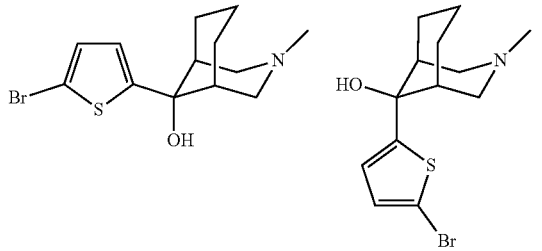 [SMILES: CN1CC2CCCC(C1)C2(O)c1ccc(Br)s1 ; CN1CC2CCCC(C1)C2(O)c1ccc(Br)s1]

To a solution of 2-bromo-5-iodothiophene (6.08 g, 21.1 mmol) in tetrahydrofuran (100 mL) at −78° C. under argon, was added n-butyl lithium (2.4 M in hexanes, 7.70 mL, 18.5 mmol) drop wise, and the mixture was stirred for 1 hour. A solution of (1R,5S)-3-methyl-3-azabicyclo[3.3.1]nonan-9-one (2.02 g, 13.2 mmol) in tetrahydrofuran (20 mL) was added drop wise, and the reaction was stirred for 15 minutes, then warmed to room temperature. The reaction mixture was quenched with water and poured into 2 M aqueous hydrochloric acid and diethyl ether. The phases were separated and the ether phase extracted with 2 M aqueous hydrochloric acid. The combined acidic phases were basified by the addition of concentrated aqueous ammonia and extracted with dichloromethane (×3). The combined dichloromethane phases were washed with brine, dried over MgSO$_4$, filtered and concentrated under reduced pressure. The residue was purified by silica chromatography, eluting with 15% ethyl acetate in heptane, to give (1R,5S,9s)-9-(5-bromothiophen-2-yl)-3-methyl-3-azabicyclo[3.3.1]nonan-9-ol (2.30 g, 55% yield); [M+H]$^+$ 316.15, 318.13; and (1R,5S,9r)-9-(5-bromothiophen-2-yl)-3-methyl-3-azabicyclo[3.3.1]nonan-9-ol (1.04 g, 25% yield); [M+H]$^+$ 316.15, 318.13.

Synthesis of 5-((1R,5S,9r)-9-hydroxy-3-methyl-3-azabicyclo[3.3.1]nonan-9-yl)thiophene-2-carbonitrile

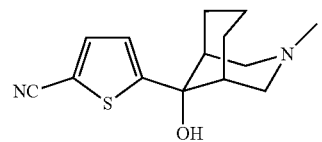 [SMILES: CN1CC2CCCC(C1)C2(O)c1ccc(C#N)s1]

To a solution of (1R,5S,9r)-9-(5-bromothiophen-2-yl)-3-methyl-3-azabicyclo[3.3.1]nonan-9-ol (1.04 g, 3.30 mmol) in degassed N,N-dimethylformamide (25 mL) was added tetrakis(triphenylphosphine)palladium(0) (0.76 g, 0.66 mmol) and the mixture was heated to 50° C. Zinc cyanide (0.59 g, 3.30 mmol) was added and the reaction was heated at 90° C. for 1.5 hours. The reaction mixture was cooled to room temperature, quenched with aqueous sodium hydrogen carbonate solution, filtered through a pad of Celite and extracted with ethyl acetate (×2). The combined organic phases were washed with brine, dried over MgSO$_4$, filtered and concentrated under reduced pressure. The residue was purified by silica chromatography, eluting with 15% ethyl acetate in heptane followed by 100% ethyl acetate, to give 5-((1R,5S,9r)-9-hydroxy-3-methyl-3-azabicyclo[3.3.1]nonan-9-yl)thiophene-2-carbonitrile (0.65 g); [M+H]$^+$ 263.16.

Synthesis of 5-((1R,5S,9r)-9-methoxy-3-methyl-3-azabicyclo[3.3.1]nonan-9-yl)thiophene-2-carbonitrile

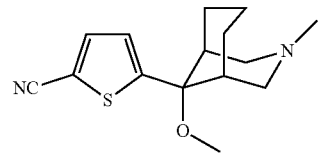 [SMILES: COC1(c2ccc(C#N)s2)C2CCCC1CN(C)C2]

To a water cooled solution of 5-((1R,5S,9r)-9-hydroxy-3-methyl-3-azabicyclo[3.3.1]nonan-9-yl)thiophene-2-carbonitrile (648 mg, 2.47 mmol) in N,N-dimethylformamide (25 mL) was added sodium hydride (60% dispersion in oil, 119 mg, 2.96 mmol). After 15 minutes at room temperature, iodomethane (0.15 mL, 2.47 mmol) was added and the reaction mixture was stirred for 2 hours. The mixture was quenched by pouring into ice/water and extracted with ethyl acetate (×3). The combined organic phases were washed with brine, dried over MgSO$_4$, filtered and concentrated under reduced pressure. The residue was purified by silica chromatography, eluting with 50-100% ethyl acetate in heptane, to give 5-((1R,5S,9r)-9-methoxy-3-methyl-3-azabicyclo[3.3.1]nonan-9-yl)thiophene-2-carbonitrile (439 mg); [M+H]$^+$ 277.05.

Synthesis of 5-((1R,5S,9r)-9-methoxy-3-methyl-3-azabicyclo[3.3.1]nonan-9-yl)thiophene-2-carboxamide Hydrochloride

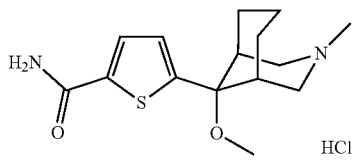 [SMILES: COC1(c2ccc(C(N)=O)s2)C2CCCC1CN(C)C2 ; Cl]

To a solution of 5-((1R,5S,9r)-9-methoxy-3-methyl-3-azabicyclo[3.3.1]nonan-9-yl)thiophene-2-carbonitrile (439 mg, 1.59 mmol) in tert-butanol (16 mL) was added potassium hydroxide (446 mg, 7.94 mmol). The reaction mixture was heated at reflux for 1 hour, cooled, diluted with water and extracted with ethyl acetate (×3). The combined organic phases were dried over MgSO$_4$, filtered and concentrated under reduced pressure. The residue was purified by silica chromatography, eluting with 0-10% ammonia/methanol in dichloromethane to give 5-((1R,5S,9r)-9-methoxy-3-methyl-3-azabicyclo[3.3.1]nonan-9-yl)thiophene-2-carboxamide (307 mg, 32% over 3 steps). To a solution of 5-((1R,5S,9r)-9-methoxy-3-methyl-3-azabicyclo[3.3.1]nonan-9-yl)thiophene-2-carboxamide (307 mg, 1.09 mmol) in ethyl acetate (10 mL) was added 2 M hydrochloric acid in diethyl ether (0.66 mL, 1.32 mmol) and the reaction was stirred for 10 minutes at room temperature. The mixture was concentrated under reduced pressure and the residue freeze dried from water to give 5-((1R,5S,9r)-9-methoxy-3-methyl-3-azabicyclo[3.3.1]nonan-9-yl)thiophene-2-carboxamide hydrochloride (291 mg, 84% yield); [M+H]$^+$ 295.29; $^1$H NMR (300 MHz, D$_2$O): 7.52 (d, 1H), 7.16 (d, 1H), 3.41 (s, 4H), 2.82 (s, 3H), 2.72 (s, 3H), 2.63 (s, 2H), 1.93-1.70 (m, 4H), 1.63-1.34 (m, 2H).

Compound 52

3-hydroxy-5-((1R,5S,9r)-9-methoxy-3-methyl-3-azabicyclo[3.3.1]nonan-9-yl)benzamide Hydrochloride

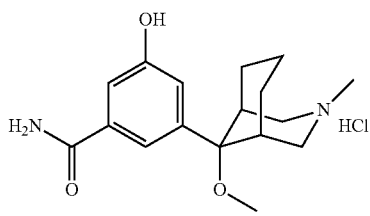 [SMILES: COC1(c2cc(O)cc(C(N)=O)c2)C2CCCC1CN(C)C2 ; Cl]

[M+H]$^+$ 305.20; $^1$H NMR (400 MHz, de-DMSO): 9.78 (s, 1H), 8.40 (br s, 1H), 7.95 (s, 1H), 7.36 (s, 1H), 7.34 (s, 1H), 7.21 (s, 1H), 6.96 (s, 1H), 3.53 (dd, 2H), 3.42-3.26 (m, 2H), 2.88-2.73 (m, 5H), 2.71 (s, 3H), 2.00-1.83 (m, 1H), 1.74 (dd, 2H), 1.65-1.50 (m, 2H), 1.36-1.24 (m, 1H).

Compound 49

2-hydroxy-3-((1R,5S,9r)-9-methoxy-3-methyl-3-azabicyclo[3.3.1]nonan-9-yl)benzamide Hydrochloride

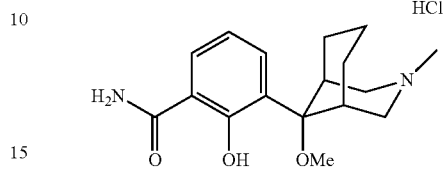

[M+H]$^+$ 305.20; $^1$H NMR (300 MHz, d$_3$-MeOD): 7.80 (dd, 1H), 7.59 (dd, 1H), 6.94 (t, 1H), 3.92 (br s, 1H), 3.69-3.45 (m, 4H), 2.96 (s, 3H), 2.93-2.83 (m, 1H), 2.87 (s, 3H), 2.08-1.82 (m, 3H), 1.82-1.66 (m, 2H), 1.64-1.49 (m, 1H).

Compound 25

3-((1R,5S,9r)-3-isopropyl-9-methoxy-3-azabicyclo[3.3.1]nonan-9-yl)benzamide Hydrochloride

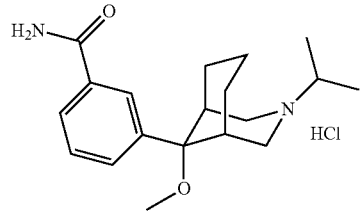 [SMILES: COC1(c2cccc(C(N)=O)c2)C2CCCC1CN(C(C)C)C2 ; Cl]

[M+H]$^+$ 317.16; $^1$H NMR (300 MHz, D$_2$O): 7.76 (s, 1H), 7.70 (d, 1H), 7.61 (d, 1H), 7.48 (t, 1H), 3.53 (dd, 2H), 3.47-3.34 (m, 3H), 2.92 (s, 2H), 2.71 (s, 3H), 1.79-1.42 (m, 5H), 1.42-1.32 (m, 1H), 1.27 (d, 6H).

Compound 38

3-((1R,5S,9r)-3-cyclopropyl-9-methoxy-3-azabicyclo[3.3.1]nonan-9-yl)benzamide

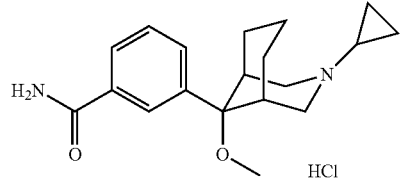 [SMILES: COC1(c2cccc(C(N)=O)c2)C2CCCC1CN(C1CC1)C2 ; Cl]

[M+H]$^+$ 315.18; $^1$H NMR (300 MHz, de-DMSO): 8.32 (br s, 1H), 8.10 (br s, 1H), 7.95 (s, 1H), 7.87 (d, 1H), 7.62 (d, 1H), 7.51 (t, 1H), 7.47 (br s, 1H), 3.68-3.38 (m, 4H), 2.97 (s, 2H), 2.90-2.79 (m, 1H), 2.73 (s, 3H), 2.16-2.95 (m, 1H), 1.74 (d, 2H), 1.57-1.38 (m, 2H), 1.35-1.25 (m, 2H), 1.25-1.09 (m, 1H), 0.72 (dd, 2H).

Compound 53

3-fluoro-4-((1R,5S,9r)-9-methoxy-3-methyl-3-azabicyclo[3.3.1]nonan-9-yl)picolinamide Hydrochloride

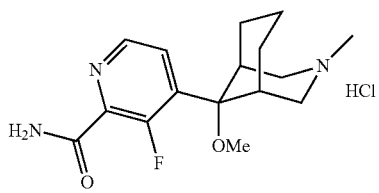 [SMILES: COC1(c2ccnc(C(N)=O)c2F)C2CCCC1CN(C)C2 ; Cl]

[M+H]⁺ 305.17; ¹H NMR (300 MHz, d6-DMSO): 8.76 (br s, 1H), 8.47 (d, 1H), 8.07 (s, 1H), 7.79-7.63 (m, 2H), 3.63-3.47 (m, 2H), 3.43-3.26 (m, 2H), 3.00 (d, 2H), 2.55 (s, 3H), 2.76 (d, 3H), 2.23-2.01 (m, 1H), 1.95-1.79 (m, 2H), 1.73-1.54 (m, 1H), 1.49-1.24 (m, 2H).

Compound 57

4-((1R,5S,9r)-3-cyclopropyl-9-methoxy-3-azabicyclo[3.3.1]nonan-9-yl)-3-fluoropicolinamide Hydrochloride

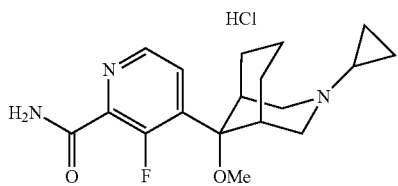 [SMILES: Cl ; COC1(c2ccnc(C(N)=O)c2F)C2CCCC1CN(C1CC1)C2]

[M+H]⁺ 334.15; ¹H NMR (300 MHz, d6-DMSO): 8.47 (d, 1H), 8.27 (br s, 1H), 8.07 (s, 1H), 7.78-7.61 (m, 2H), 3.63-3.43 (m, 3H), 3.17-2.71 (m, 7H), 2.56-2.42 (m, 2H), 2.21-1.98 (m, 1H), 1.90-1.77 (m, 1H), 1.69-1.47 (m, 1H), 1.45-1.17 (m, 3H), 0.71 (d, 2H).

Compound 55

Synthesis of (1R,5S)-3-cyclopentyl-3-azaspiro[bicyclo[3.3.1]nonane-9,2'-[1,3]dioxolane]

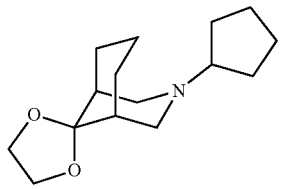 [SMILES: C1CCC(N2CC3CCCC(C2)C32OCCO2)C1]

To a solution of (1R,5S)-3-azaspiro[bicyclo[3.3.1]nonane-9,2'-[1,3]dioxolane] (1.90 g, 10.4 mmol) in dichloromethane (100 mL) was added cyclopentanone (6.42 mL, 72.6 mmol), and the reaction was stirred for 20 minutes. Sodium triacetoxyborohydride (6.59 g, 31.1 mmol) was added portion wise and the reaction mixture was stirred for 4 hours at room temperature. The mixture was quenched by the addition of aqueous sodium hydrogen carbonate solution and extracted with dichloromethane (×3). The combined organic phases were washed with brine, dried over MgSO₄, filtered and concentrated under reduced pressure to give (1R,5S)-3-cyclopentyl-3-azaspiro[bicyclo[3.3.1]nonane-9,2'-[1,3]dioxolane] (4.97 g) which was used without purification; [M+H]⁺ 252.08.

Synthesis of (1R,5S)-3-cyclopentyl-3-azabicyclo[3.3.1]nonan-9-one

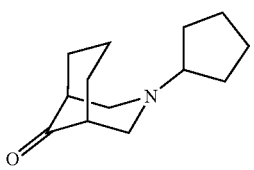 [SMILES: O=C1C2CCCC1CN(C1CCCC1)C2]

To a solution of (1R,5S)-3-cyclopentyl-3-azaspiro[bicyclo[3.3.1]nonane-9,2'-[1,3]dioxolane](2.61 g, 10.4 mmol) in 1,4-dioxane (8.50 mL) was added 2 M hydrochloric acid in diethyl ether (8.50 mL) and the reaction mixture was heated to 80° C. for 4 hours. Further 1,4-dioxane (10 mL) was added and the reaction mixture was heated at 80° C. for 18 hours. 4 M aqueous hydrochloric acid (60 mL) was added and the reaction was stirred for 5 hours at 60° C. The mixture was cooled to room temperature, poured into ice/concentrated aqueous ammonia and extracted with dichloromethane (×3). The combined organic phases were washed with brine, dried over MgSO₄, filtered and concentrated under reduced pressure. The residue was purified by silica chromatography, eluting with 0-15% ethyl acetate in heptane, to give (1R,5S)-3-cyclopentyl-3-azabicyclo[3.3.1]nonan-9-one (1.59 g, 74% yield over 2 steps); [M+H]⁺ 208.30.

Synthesis of (1R,5S,9r)-9-(2-chloropyridin-4-yl)-3-cyclopentyl-3-azabicyclo[3.3.1]nonan-9-ol and (1R,5S,9s)-9-(2-chloropyridin-4-yl)-3-cyclopentyl-3-azabicyclo[3.3.1]nonan-9-ol

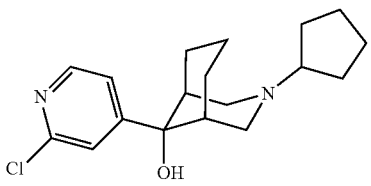

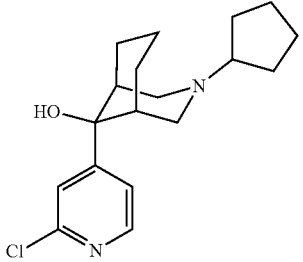

To a solution of 2-chloro-4-iodopyridine (1.14 g, 4.80 mmol) in diethyl ether (20 mL) at −78° C. under argon was added n-butyl lithium (2.0 M in hexanes, 2.40 mL, 4.80 mmol) drop wise and the reaction mixture was stirred for 30 minutes. A solution of (1R,5S)-3-cyclopentyl-3-azabicyclo[3.3.1]nonan-9-one (0.90 g, 4.34 mmol) in diethyl ether (10 mL) was added and the reaction mixture was stirred for 30 minutes then warmed to 0° C. The mixture was quenched with water and extracted with ethyl acetate (×3). The combined organic phases were washed with brine, dried over MgSO₄, filtered and concentrated under reduced pressure. The residue was purified by silica chromatography, eluting with 20-50% ethyl acetate in heptane, to give (1R,5S,9r)-9-(2-chloropyridin-4-yl)-3-cyclopentyl-3-azabicyclo[3.3.1]nonan-9-ol (0.22 g, 16% yield); [M+H]⁺ 321.29; and a mixture of (1R,5S,9s)-9-(2-chloropyridin-4-yl)-3-cyclopentyl-3-azabicyclo[3.3.1]nonan-9-ol and (1R,5S,9r)-9-(2-chloropyridin-4-yl)-3-cyclopentyl-3-azabicyclo[3.3.1]nonan-9-ol (0.60 g, 43% yield); [M+H]⁺ 321.28.

Synthesis of (1R,5S,9r)-9-(2-chloropyridin-4-yl)-3-cyclopentyl-9-methoxy-3-azabicyclo[3.3.1]nonane

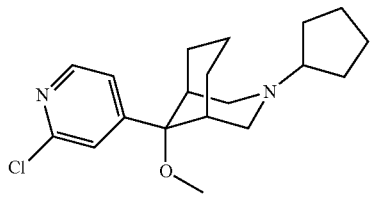 [SMILES: COC1(c2ccnc(Cl)c2)C2CCCC1CN(C1CCCC1)C2]

To a solution of (1R,5S,9r)-9-(2-chloropyridin-4-yl)-3-cyclopentyl-3-azabicyclo[3.3.1]nonan-9-ol (278 mg, 0.87 mmol) in N,N-dimethylformamide (10 mL) was added sodium hydride (60% dispersion in oil, 70 mg, 1.74 mmol) portion wise. The reaction mixture was stirred for 10 minutes at room temperature, then iodomethane (62 µL, 1.00 mmol) was added and the reaction was stirred for 3 hours. Further iodomethane (20 µL, 0.32 mmol) was added and the reaction mixture was stirred for 2 hours. The mixture was quenched by pouring into ice/water and extracted with ethyl acetate (×3). The combined organic phases were washed with water (×2), then brine, dried over MgSO₄, filtered and concentrated under reduced pressure. The residue was purified by silica chromatography, eluting with 20-30% ethyl acetate in heptane, to give (1R,5S,9r)-9-(2-chloropyridin-4-yl)-3-cyclopentyl-9-methoxy-3-azabicyclo[3.3.1]nonane (197 mg, 68% yield); [M+H]⁺ 335.29.

Synthesis of 4-((1R,5S,9r)-3-cyclopentyl-9-methoxy-3-azabicyclo[3.3.1]nonan-9-yl)picolinonitrile

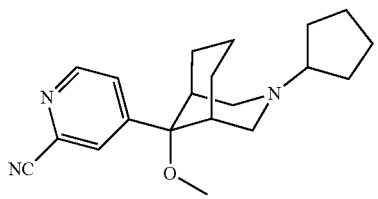 [SMILES: COC1(c2ccnc(C#N)c2)C2CCCC1CN(C1CCCC1)C2]

To a solution of (1R,5S,9r)-9-(2-chloropyridin-4-yl)-3-cyclopentyl-9-methoxy-3-azabicyclo[3.3.1]nonane (197 mg, 0.59 mmol) in degassed N,N-dimethylformamide (10 mL) was added tris(dibenzylideneacetone)dipalladium (0) (54 mg, 0.06 mmol) and 1,1'bis(diphenylphosphino)ferrocene (33 mg, 0.06 mmol). After heating to 60° C., zinc cyanide (138 mg, 1.18 mmol) was added and the reaction mixture was heated at 110° C. for 1.5 hours. The reaction mixture was cooled to room temperature, quenched with aqueous sodium hydrogen carbonate solution, diluted with ethyl acetate, filtered through a pad of Celite and the filtrate was extracted with ethyl acetate (×3). The combined organic phases were washed with water (×3), then brine, dried over MgSO₄, filtered and concentrated under reduced pressure. The crude residue was purified by silica chromatography, eluting with 0-40% ethyl acetate in heptane, to give 4-((1R,5S,9r)-3-cyclopentyl-9-methoxy-3-azabicyclo[3.3.1]nonan-9-yl)picolinonitrile (166 mg, 87% yield); [M+H]⁺ 326.34.

Synthesis of 4-((1R,5S,9r)-3-cyclopentyl-9-methoxy-3-azabicyclo[3.3.1]nonan-9-yl)picolinamide Hydrochloride

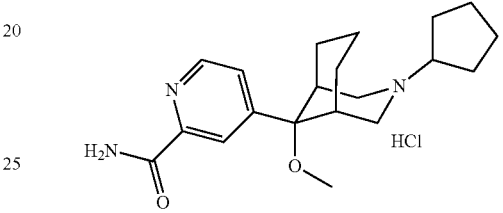

To a solution of 4-((1R,5S,9r)-3-cyclopentyl-9-methoxy-3-azabicyclo[3.3.1]nonan-9-yl)picolinonitrile (166 mg, 0.51 mmol) in tert-butanol (5 mL) was added potassium hydroxide (143 mg, 2.55 mmol). The reaction mixture was heated at reflux for 1 hour, cooled, quenched with water and extracted with ethyl acetate (×3). The combined organic phases were washed with brine, dried over MgSO₄, filtered and concentrated under reduced pressure. The residue was purified by silica chromatography, eluting with 4-10% methanol in dichloromethane, to give 4-((1R,5S,9r)-3-cyclopentyl-9-methoxy-3-azabicyclo[3.3.1]nonan-9-yl)picolinamide (95 mg, 54% yield). To a solution of 4-((1R,5S,9r)-3-cyclopentyl-9-methoxy-3-azabicyclo[3.3.1]nonan-9-yl)picolinamide (95 mg, 0.28 mmol) in ethyl acetate (10 mL) was added 2 M hydrochloric acid in diethyl ether (0.15 mL, 0.30 mmol) and the reaction was stirred for 10 minutes. The mixture was concentrated under reduced pressure and the residue triturated in diethyl ether (×2), then freeze dried from water to give 4-((1R,5S,9r)-3-cyclopentyl-9-methoxy-3-azabicyclo[3.3.1]nonan-9-yl)picolinamide hydrochloride (105 mg, quant.); [M+H]⁺ 344.20; ¹H NMR (300 MHz, D₂O): 8.60 (d, 1H), 8.02 (s, 1H), 7.64 (dd, 1H), 3.62-3.41 (m, 5H), 2.89 (s, 2H), 2.75 (s, 3H), 2.12-1.94 (m, 2H), 1.82-1.28 (m, 12H).

Compound 66

Synthesis of (1R,5S,9r)-3-benzyl-9-(2-chloropyridin-4-yl)-3-azabicyclo[3.3.1]nonan-9-ol and (1R,5S,9s)-3-benzyl-9-(2-chloropyridin-4-yl)-3-azabicyclo[3.3.1]nonan-9-ol

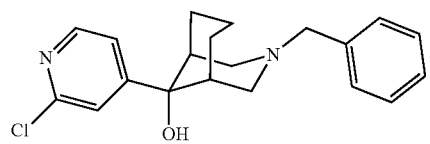

-continued

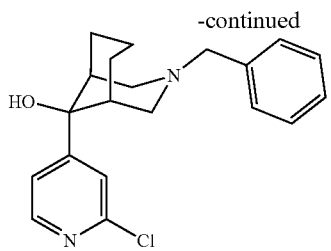

A mixture of 2-chloro-4-iodopyridine (13.6 g, 56.8 mmol) and (1R,5S)-3-benzyl-3-azabicyclo[3.3.1]nonan-9-one (8.70 g, 37.9 mmol) in tetrahydrofuran (200 mL) was cooled to −78° C. under argon. n-Butyl lithium (2.0 M in hexanes, 28.5 mL, 57.0 mmol) was added drop wise over 30 minutes and the reaction mixture was stirred for 15 minutes, then warmed to room temperature over 1 hour. The mixture was quenched with water and extracted with ethyl acetate (×2). The combined organic phases were dried over MgSO$_4$, filtered and concentrated under reduced pressure. The residue was purified by silica chromatography, eluting with 0-15% ethyl acetate in dichloromethane, to give a mixture of (1R,5S,9r)-3-benzyl-9-(2-chloropyridin-4-yl)-3-azabicyclo[3.3.1]nonan-9-ol and (1R,5S,9s)-3-benzyl-9-(2-chloropyridin-4-yl)-3-azabicyclo[3.3.1]nonan-9-ol (7.62 g, 59%); [M+H]$^+$ 343.3, 345.3.

Synthesis of (1R,5S,9r)-3-benzyl-9-(2-chloropyridin-4-yl)-9-methoxy-3-azabicyclo[3.3.1]nonane and (1R,5S,9s)-3-benzyl-9-(2-chloropyridin-4-yl)-9-methoxy-3-azabicyclo[3.3.1]nonane

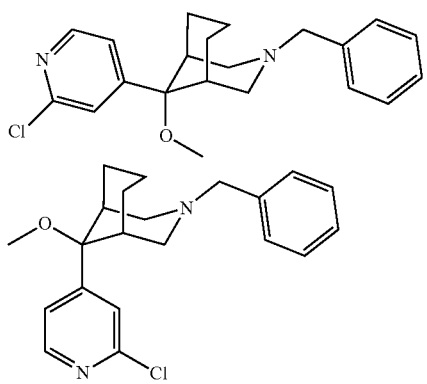

To a solution of (1R,5S,9r)-3-benzyl-9-(2-chloropyridin-4-yl)-3-azabicyclo[3.3.1]nonan-9-ol and (1R,5S,9s)-3-benzyl-9-(2-chloropyridin-4-yl)-3-azabicyclo[3.3.1]nonan-9-ol (7.70 g, 22.5 mmol) in N,N-dimethylformamide (120 mL) was added iodomethane (1.50 mL, 24.7 mmol), followed by sodium hydride (60% dispersion in oil, 1.35 g, 33.7 mmol) maintaining the temperature below 30° C. The reaction mixture was stirred for 30 minutes at room temperature, then quenched by pouring into ice/water and extracted with ethyl acetate (×2). The combined organic phases were washed with dilute brine (×3), dried over MgSO$_4$, filtered and concentrated under reduced pressure. The residue was passed through a plug of silica, eluting with 4:1 heptane: ethyl acetate, to give (1R,5S,9r)-3-benzyl-9-(2-chloropyridin-4-yl)-9-methoxy-3-azabicyclo[3.3.1]nonane and (1R,5S,9s)-3-benzyl-9-(2-chloropyridin-4-yl)-9-methoxy-3-azabicyclo[3.3.1]nonane (7.07 g, 88%); [M+H]$^+$ 359.3.

Synthesis of 4-((1R,5S,9r)-3-benzyl-9-methoxy-3-azabicyclo[3.3.1]nonan-9-yl)picolinonitrile and 4-((1R,5S,9s)-3-benzyl-9-methoxy-3-azabicyclo[3.3.1]nonan-9-yl)picolinonitrile

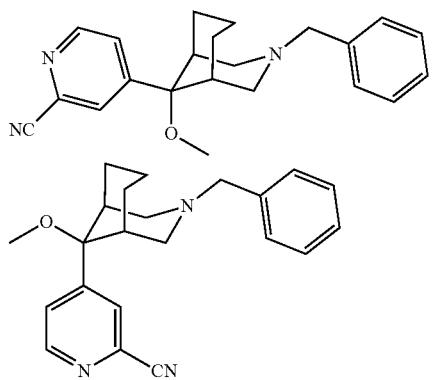

To a solution of (1R,5S,9r)-3-benzyl-9-(2-chloropyridin-4-yl)-9-methoxy-3-azabicyclo[3.3.1]nonane and (1R,5S,9s)-3-benzyl-9-(2-chloropyridin-4-yl)-9-methoxy-3-azabicyclo[3.3.1]nonane (7.07 g, 19.6 mmol) in degassed N,N-dimethylformamide (70 mL) was added tris(dibenzylideneacetone)dipalladium (0) (1.14 g, 1.98 mmol) and 1,1'bis(diphenylphosphino)ferrocene (1.10 g, 1.98 mmol). After heating to 60° C., zinc cyanide (4.70 g, 39.6 mmol) was added and the reaction mixture heated at 130° C. for 1 hour. The reaction mixture was cooled to room temperature, diluted with ethyl acetate and washed with dilute aqueous ammonia (150 mL). The aqueous phase was re-extracted with ethyl acetate. The combined organic phases were washed with brine, dried over MgSO$_4$, filtered and concentrated under reduced pressure. The crude residue was purified by silica chromatography, eluting with 0-50% dichloromethane in ethyl acetate, to give 4-((1R,5S,9r)-3-benzyl-9-methoxy-3-azabicyclo[3.3.1]nonan-9-yl)picolinonitrile (0.75 g, 11% yield); [M+H]$^+$ 348.22 and a mixture of 4-((1R,5S,9s)-3-benzyl-9-methoxy-3-azabicyclo[3.3.1]nonan-9-yl)picolinonitrile and 4-((1R,5S,9r)-3-benzyl-9-methoxy-3-azabicyclo[3.3.1]nonan-9-yl)picolinonitrile (4.06 g, 60% yield); [M+H]$^+$ 348.22.

Synthesis of 4-((1R,5S,9r)-3-benzyl-9-methoxy-3-azabicyclo[3.3.1]nonan-9-yl)picolinamide

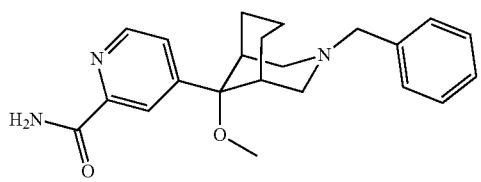 [SMILES: COC1(c2ccnc(C(N)=O)c2)C2CCCC1CN(Cc1ccccc1)C2]

To a solution of 4-((1R,5S,9r)-3-benzyl-9-methoxy-3-azabicyclo[3.3.1]nonan-9-yl)picolinonitrile (750 mg, 2.16 mmol) in tert-butanol (20 mL) was added potassium hydroxide (700 mg, 12.5 mmol). The reaction mixture was heated at reflux for 1 hour, cooled, diluted with water and extracted with ethyl acetate (×2). The combined organic phases were dried over MgSO₄, filtered and concentrated under reduced pressure. The residue was purified by silica chromatography, eluting with 0-100% ethyl acetate in dichloromethane, to give 4-((1R,5S,9r)-3-benzyl-9-methoxy-3-azabicyclo[3.3.1]nonan-9-yl)picolinamide (680 mg, 86% yield); [M+H]⁺ 366.32.

Synthesis of 4-((1R,5S,9r)-9-methoxy-3-azabicyclo[3.3.1]nonan-9-yl)picolinamide

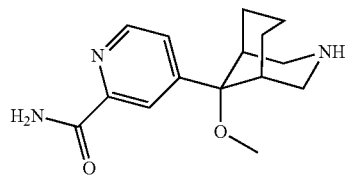 [SMILES: COC1(c2ccnc(C(N)=O)c2)C2CCCC1CNC2]

To a solution of 4-((1R,5S,9r)-3-benzyl-9-methoxy-3-azabicyclo[3.3.1]nonan-9-yl)picolinamide (680 mg, 1.86 mmol) in methanol (17 mL) and tetrahydrofuran (3 mL) was added 20% palladium hydroxide on carbon (400 mg) and the reaction mixture was stirred for 3 hours at room temperature under an atmosphere of hydrogen. The mixture was filtered through a pad of Celite and the filtrate concentrated under reduced pressure. The residue was purified by silica chromatography, eluting with 0-10% methanol in dichloromethane then 15% ammonia/methanol in dichloromethane, to give the desired product 4-((1R,5S,9r)-9-methoxy-3-azabicyclo[3.3.1]nonan-9-yl)picolinamide (300 mg, 59% yield); [M+H]⁺ 276.25.

Synthesis of 4-((1R,5S,9r)-3-ethyl-9-methoxy-3-azabicyclo[3.3.1]nonan-9-yl)picolinamide Hydrochloride

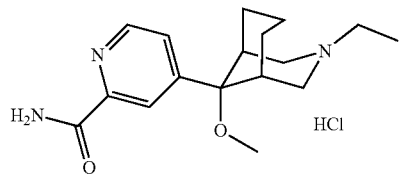 [SMILES: CCN1CC2CCCC(C1)C2(OC)c1ccnc(C(N)=O)c1 ; Cl]

To a solution of 4-((1R,5S,9r)-9-methoxy-3-azabicyclo[3.3.1]nonan-9-yl)picolinamide (94 mg, 0.34 mmol) in acetonitrile (10 mL) was added bromoethane (27 µL, 0.34 mmol) and potassium carbonate (143 mg, 1.03 mmol) and the reaction mixture was heated at 40° C. for 3.5 hours. The mixture was quenched with water and extracted with ethyl acetate (×3). The combined organic phases were washed with brine, dried over MgSO₄, filtered and concentrated under reduced pressure. The residue was purified by silica chromatography, eluting with 2.5% methanol in ethyl acetate, then further purified by preparative HPLC to give 4-((1R,5S,9r)-3-ethyl-9-methoxy-3-azabicyclo[3.3.1]nonan-9-yl)picolinamide (24 mg). To a solution of 4-((1R,5S,9r)-3-ethyl-9-methoxy-3-azabicyclo[3.3.1]nonan-9-yl)picolinamide (24 mg, 0.08 mmol) in ethyl acetate (5 mL) was added 2 M hydrochloric acid in diethyl ether (47 µL, 0.09 mmol) and the reaction mixture was stirred for 10 minutes. The mixture was concentrated under reduced pressure and the residue was freeze dried from water to give 4-((1R,5S,9r)-3-ethyl-9-methoxy-3-azabicyclo[3.3.1]nonan-9-yl)picolinamide hydrochloride (46 mg, 40% yield over 2 steps); [M+H]⁺ 304.21; ¹H NMR (400 MHz, D₂O): 8.60 (d, 1H), 8.29 (d, 1H), 7.66 (dd, 1H), 3.55 (d, 2H), 3.44 (dd, 2H), 3.10 (q, 2H), 2.88 (s, 2H), 2.73 (d, 3H), 1.81-1.71 (m, 2H), 1.63-1.32 (m, 4H), 1.21 (t, 3H).

Compound 68

Synthesis of (1R,5S)-3-(pyridin-3-ylmethy)-3-azabicyclo[3.3.1]nonan-9-one

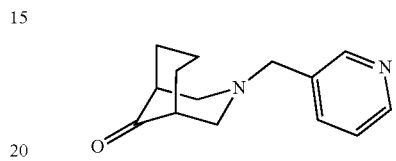

To a solution of (1R,5S)-3-azaspiro[bicyclo[3.3.1]nonane-9,2'-[1,3]dioxolane] (1.70 g, 9.28 mmol) in dichloromethane (100 mL) was added pyridine-3-carboxaldehyde (6.08 mL, 64.77 mmol) and the reaction mixture was stirred for 20 minutes. Sodium triacetoxyborohydride (5.90 g, 27.84 mmol) was added and the reaction mixture was stirred at room temperature for 18 hours. The mixture was quenched with aqueous sodium hydrogen carbonate solution and the phases separated. The aqueous phase was re-extracted with dichloromethane (×2). The combined organic phases were washed with brine, dried over MgSO₄, filtered and concentrated under reduced pressure to give (1R,5S)-3-(pyridin-3-ylmethyl)-3-azaspiro[bicyclo[3.3.1]nonane-9,2'-[1,3]dioxolane]. To a solution of (1R,5S)-3-(pyridin-3-ylmethyl)-3-azaspiro[bicyclo[3.3.1]nonane-9,2'-[1,3]dioxolane] (2.55 g, 9.28 mmol) in 1,4-dioxane (10 mL) was added 4 M aqueous hydrochloric acid (60 mL) and the reaction mixture was stirred at 50° C. for 24 hours, then at 70° C. for 1 hour. After cooling to room temperature, the mixture was poured into ice/concentrated aqueous ammonia and extracted with ethyl acetate (×3). The combined organic phases were washed with brine, dried over MgSO₄, filtered and concentrated under reduced pressure. The residue was purified by silica chromatography, eluting with 0-10% ethyl acetate in dichloromethane, then further purified by reverse phase chromatography (C18) to give (1R,5S)-3-(pyridin-3-ylmethyl)-3-azabicyclo[3.3.1]nonan-9-one (1.60 g, 75% yield over 2 steps); [M+H]⁺ 231.21.

Synthesis of (1R,5S,9r)-9-(2-chloropyridin-4-yl)-3-(pyridin-3-ylmethyl)-3-azabicyclo[3.3.1]nonan-9-ol

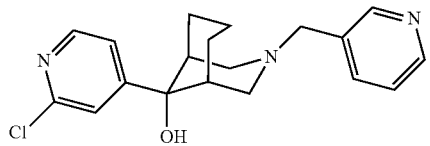 [SMILES: OC1(c2ccnc(Cl)c2)C2CCCC1CN(Cc1cccnc1)C2]

To a suspension of 2-chloro-4-iodopyridine (2.50 g, 10.44 mmol) and (1R,5S)-3-(pyridin-3-ylmethyl)-3-azabicyclo[3.3.1]nonan-9-one (1.60 g, 6.95 mmol) in diethyl ether (30 mL) at −78° C. under argon was added n-butyl lithium (2.1 M in hexanes, 4.96 mL, 10.44 mmol) drop wise over 10 minutes. The reaction mixture was stirred for 1 hour then warmed to room temperature. The mixture was quenched with water and extracted with ethyl acetate (×3). The combined organic phases were washed with brine, dried over MgSO$_4$, filtered and concentrated under reduced pressure. The residue was purified twice by reverse phase chromatography (C18) to give (1R,5S,9r)-9-(2-chloropyridin-4-yl)-3-(pyridin-3-ylmethyl)-3-azabicyclo[3.3.1]nonan-9-ol (0.44 g, 18% yield); [M+H]$^+$ 344.24.

Synthesis of (1R,5S,9r)-9-(2-chloropyridin-4-yl)-9-methoxy-3-(pyridin-3-ylmethyl)-3-azabicyclo[3.3.1]nonane

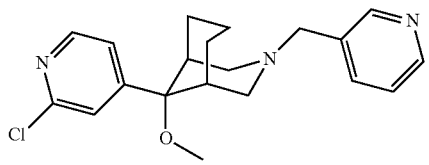 [SMILES: COC1(c2ccnc(Cl)c2)C2CCCC1CN(Cc1cccnc1)C2]

To a solution of (1R,5S,9r)-9-(2-chloropyridin-4-yl)-3-(pyridin-3-ylmethyl)-3-azabicyclo[3.3.1]nonan-9-ol (435 mg, 1.27 mmol) in N,N-dimethylformamide (10 mL) was added sodium hydride (60% dispersion in oil, 101 mg, 2.53 mmol) portion wise. The reaction mixture was stirred for 20 minutes at room temperature, then iodomethane (0.12 mL, 1.89 mmol) was added and the reaction stirred for 90 minutes. The mixture was quenched with water and extracted with ethyl acetate (×2). The combined organic phases were washed with water (×3), then brine (×2), dried over MgSO$_4$, filtered and concentrated under reduced pressure. The residue was purified by silica chromatography, eluting with 5% methanol in dichloromethane, to give (1R,5S,9r)-9-(2-chloropyridin-4-yl)-9-methoxy-3-(pyridin-3-ylmethyl)-3-azabicyclo[3.3.1]nonane (540 mg); [M+H]$^+$ 358.28.

Synthesis of 4-((1R,5S,9r)-9-methoxy-3-(pyridin-3-ylmethyl)-3-azabicyclo[3.3.1]nonan-9-yl)picolinonitrile

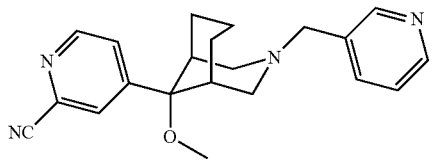 [SMILES: COC1(c2ccnc(C#N)c2)C2CCCC1CN(Cc1cccnc1)C2]

To a solution of (1R,5S,9r)-9-(2-chloropyridin-4-yl)-9-methoxy-3-(pyridin-3-ylmethyl)-3-azabicyclo[3.3.1]nonane (455 mg, 1.27 mmol) in degassed N,N-dimethylformamide (10 mL) was added tris(dibenzylideneacetone)dipalladium (0) (116 mg, 0.13 mmol) and 1,1'bis(diphenylphosphino)ferrocene (70 mg, 0.13 mmol). After heating to 80° C., zinc cyanide (297 mg, 2.53 mmol) was added and the reaction mixture heated at 120° C. for 1 hour. The reaction mixture was cooled to room temperature, quenched with water and extracted with ethyl acetate (×2). The combined organic phases were washed with water (×3), then brine (×2), dried over MgSO$_4$, filtered and concentrated under reduced pressure. The crude residue was purified by silica chromatography, eluting with 0-5% methanol in dichloromethane, to give 4-((1R,5S,9r)-9-methoxy-3-(pyridin-3-ylmethyl)-3-azabicyclo[3.3.1]nonan-9-yl)picolinonitrile (328 mg, 74% yield over 2 steps); [M+H]$^+$ 349.34.

Synthesis of 4-((1R,5S,9r)-9-methoxy-3-(pyridin-3-ylmethyl)-3-azabicyclo[3.3.1]nonan-9-yl)picolinamide Dihydrochloride

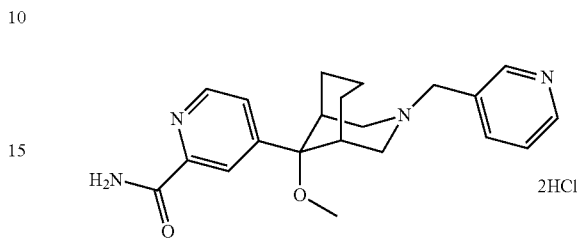

To a solution of 4-((1R,5S,9r)-9-methoxy-3-(pyridin-3-ylmethyl)-3-azabicyclo[3.3.1]nonan-9-yl)picolinonitrile (328 mg, 0.94 mmol) in tert-butanol (10 mL) was added potassium hydroxide (246 mg, 4.71 mmol). The reaction mixture was heated at 100° C. for 1 hour, cooled to room temperature, and partitioned between water and ethyl acetate. The aqueous phase was re-extracted with ethyl acetate (×2). The combined organic phases were washed with brine, dried over MgSO$_4$, filtered and concentrated under reduced pressure. The residue was purified by silica chromatography, eluting with 4% methanol in dichloromethane, then further purified by preparative HPLC to give 4-((1R,5S,9r)-9-methoxy-3-(pyridin-3-ylmethyl)-3-azabicyclo[3.3.1]nonan-9-yl)picolinamide (167 mg, 48% yield). To a solution of 4-((1R,5S,9r)-9-methoxy-3-(pyridin-3-ylmethyl)-3-azabicyclo[3.3.1]nonan-9-yl)picolinamide (167 mg, 0.46 mmol) in ethyl acetate (5 mL) was added 2 M hydrochloric acid in diethyl ether (0.50 mL, 1.04 mmol) and the reaction mixture was stirred for 30 minutes. The mixture was concentrated under reduced pressure and the residue was freeze dried from water to give 4-((1R,5S,9r)-9-methoxy-3-(pyridin-3-ylmethyl)-3-azabicyclo[3.3.1]nonan-9-yl)picolinamide dihydrochloride (200 mg, quant.); [M+H]$^+$ 367.21; $^1$H NMR (400 MHz, d$_6$-DMSO): 9.37 (br s, 2H), 8.93 (d, 2H), 8.69 (d, 1H), 8.21 (s, 1H), 8.05-7.95 (m, 2H), 7.76 (s, 1H), 7.68 (dd, 1H), 6.22 (br s, 1H), 4.53 (d, 2H), 3.53 (d, 4H), 2.96 (s, 2H), 2.73 (s, 3H), 2.26-2.07 (m, 1H), 1.86-1.75 (m, 2H), 1.49-1.34 (m, 2H), 1.29-1.16 (m, 1H).

Compound 67

4-((1R,5S,9r)-9-methoxy-3-(pyridin-2-ylmethyl)-3-azabicyclo[3.3.1]nonan-9-yl)picolinamide Dihydrochloride

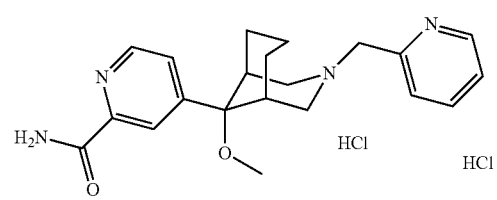 [SMILES: COC1(c2ccnc(C(N)=O)c2)C2CCCC1CN(Cc1ccccn1)C2 ; Cl ; Cl]

[M+H]$^+$ 367.13; $^1$H NMR (400 MHz, d$_6$, DMSO): 9.34 (br s, 2H), 8.74-8.66 (m, 2H), 8.22 (br s, 1H), 8.04 (s, 1H), 7.98-8.03 (td, 1H), 7.77 (br s, 1H), 7.73 (d, 1H), 7.70-7.63 (m, 1H), 7.56-7.51 (dd, 1H), 4.51 (s, 2H), 3.61 (d, 2H), 3.53 (d, 2H), 2.96 (s, 2H), 2.67 (s, 3H), 2.12-1.98 (m, 1H), 1.78-1.89 (m, 2H), 1.54-1.34 (m, 3H).

Compound 69

4-((1R,5S,9r)-9-methoxy-3-(pyridin-4-ylmethyl)-3-azabicyclo[3.3.1]nonan-9-yl)picolinamide Hydrochloride

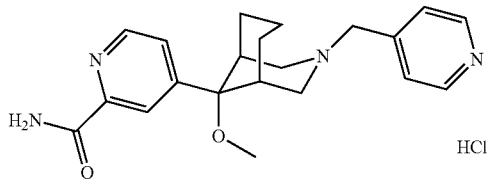 [SMILES: COC1(c2ccnc(C(N)=O)c2)C2CCCC1CN(Cc1ccncc1)C2 ; Cl]

[M+H]$^+$ 367.21; $^1$H NMR (400 MHz, D$_2$O): 8.72 (d, 2H), 8.56 (d, 1H), 8.03 (d, 2H), 7.96 (s, 1H), 7.58 (dd, 1H), 4.52 (s, 2H), 3.64 (d, 2H), 3.51 (d, 2H), 2.90 (s, 2H), 2.70 (s, 3H), 1.75 (d, 2H), 1.63-1.44 (m, 3H), 1.43-1.34 (m, 1H).

Compound 56

Synthesis of (1R,5S)-3-(tetrahydro-2H-pyran-4-yl)-3-azabicyclo[3.3.1]nonan-9-one

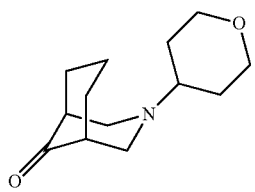 [SMILES: O=C1C2CCCC1CN(C1CCOCC1)C2]

To a solution of (1R,5S)-3-azaspiro[bicyclo[3.3.1]nonane-9,2'-[1,3]dioxolane] (1.10 g, 6.00 mmol) in dichloromethane (60 mL) was added tetrahydro-4H-pyran-4-one (3.88 mL, 42.00 mmol) and the reaction mixture was stirred for 10 minutes. Sodium triacetoxyborohydride (3.82 g, 18.00 mmol) was added and the reaction mixture was stirred at room temperature for 4 hours. The mixture was quenched with sodium hydrogen carbonate solution and extracted with dichloromethane (×3). The combined organic phases were washed with brine, dried over MgSO$_4$, filtered and concentrated under reduced pressure to give (1R,5S)-3-(tetrahydro-2H-pyran-4-yl)-3-azaspiro[bicyclo[3.3.1]nonane-9,2'-[1,3]dioxolane]. To a solution of (1R,5S)-3-(tetrahydro-2H-pyran-4-yl)-3-azaspiro[bicyclo[3.3.1]nonane-9,2'-[1,3]dioxolane](1.60 g, 6.00 mmol) in 1,4-dioxane (8 mL) was added 4 M aqueous hydrochloric acid (45 mL) and the reaction mixture was stirred at 70° C. for 3 hours. After cooling to room temperature, the mixture was poured into ice/concentrated aqueous ammonia and extracted with ethyl acetate (×2). The combined organic phases were washed with brine, dried over MgSO$_4$, filtered and concentrated under reduced pressure to give (1R,5S)-3-(tetrahydro-2H-pyran-4-yl)-3-azabicyclo[3.3.1]nonan-9-one (1.26 g, 94% yield over two steps); [M+H]$^+$ 224.12.

Synthesis of (1R,5S,9r)-9-(2-chloropyridin-4-yl)-3-(tetrahydro-2H-pyran-4-yl)-3-azabicyclo[3.3.1]nonan-9-ol

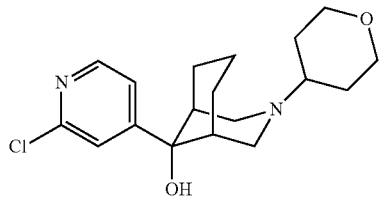 [SMILES: OC1(c2ccnc(Cl)c2)C2CCCC1CN(C1CCOCC1)C2]

To a solution of 2-chloro-4-iodopyridine (1.45 g, 6.04 mmol) and (1R,5S)-3-(tetrahydro-2H-pyran-4-yl)-3-azabicyclo[3.3.1]nonan-9-one (0.77 g, 3.45 mmol) in tetrahydrofuran (23 mL) at −78° C. under argon was added n-butyl lithium (2.0 M in hexanes, 3.00 mL, 6.04 mmol) drop wise and the reaction mixture was stirred for 15 minutes. The cooling bath was removed and the reaction mixture stirred for 15 minutes. The mixture was quenched with water and extracted with ethyl acetate (×3). The combined organic phases were washed with brine, dried over Na$_2$SO$_4$, filtered and concentrated under reduced pressure. The residue was purified by reverse phase chromatography (C18) to give (1R,5S,9r)-9-(2-chloropyridin-4-yl)-3-(tetrahydro-2H-pyran-4-yl)-3-azabicyclo[3.3.1]nonan-9-ol (0.14 g, 11% yield); [M+H]$^+$ 337.33.

Synthesis of (1R,5S,9r)-9-(2-chloropyridin-4-yl)-9-methoxy-3-(tetrahydro-2H-pyran-4-yl)-3-azabicyclo[3.3.1]nonane

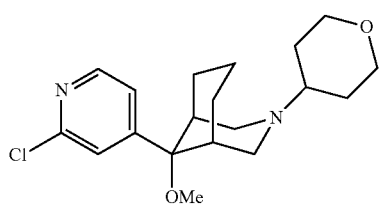 [SMILES: COC1(c2ccnc(Cl)c2)C2CCCC1CN(C1CCOCC1)C2]

To a solution of (1R,5S,9r)-9-(2-chloropyridin-4-yl)-3-(tetrahydro-2H-pyran-4-yl)-3-azabicyclo[3.3.1]nonan-9-ol (138 mg, 0.41 mmol) in N,N-dimethylformamide (1.5 mL) was added sodium hydride (60% dispersion in oil, 29 mg, 0.74 mmol) portion wise. The reaction mixture was stirred for 15 minutes at room temperature, then iodomethane (28 μL, 0.45 mmol) was added and the reaction stirred for 90 minutes. The mixture was quenched with water and extracted with ethyl acetate (×2). The combined organic phases were washed with water (×4), then brine, dried over Na$_2$SO$_4$, filtered and concentrated under reduced pressure. The residue was passed through a pad of silica, eluting with 2% methanol in dichloromethane, to give (1R,5S,9r)-9-(2-chloropyridin-4-yl)-9-methoxy-3-(tetrahydro-2H-pyran-4-yl)-3-azabicyclo[3.3.1]nonane (100 mg, 70% yield); [M+H]$^+$ 351.32.

Synthesis of 4-((1R,5S,9r)-9-methoxy-3-(tetrahydro-2H-pyran-4-yl)-3-azabicyclo[3.3.1]nonan-9-yl)picolinonitrile

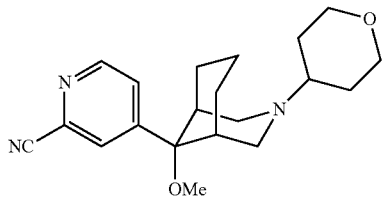 [SMILES: COC1(c2ccnc(C#N)c2)C2CCCC1CN(C1CCOCC1)C2]

To a solution of (1R,5S,9r)-9-(2-chloropyridin-4-yl)-9-methoxy-3-(tetrahydro-2H-pyran-4-yl)-3-azabicyclo[3.3.1]nonane (100 mg, 0.29 mmol) in degassed N,N-dimethylformamide (2.5 mL) was added tris(dibenzylideneacetone)dipalladium (0) (78 mg, 0.09 mmol) and 1,1'bis(diphenylphosphino)ferrocene (48 mg, 0.09 mmol). After heating to 80° C., zinc cyanide (67 mg, 0.57 mmol) was added and the reaction mixture heated at 120° C. for 90 minutes. The reaction mixture was cooled to room temperature, quenched with water and ethyl acetate and filtered through a pad of Celite. The phases of the filtrate were separated and the aqueous re-extracted with ethyl acetate. The combined organic phases were washed with water (×4), then brine, dried over $Na_2SO_4$, filtered and concentrated under reduced pressure. The crude residue was purified by reverse phase chromatography (C18) to give 4-((1R,5S,9r)-9-methoxy-3-(tetrahydro-2H-pyran-4-yl)-3-azabicyclo[3.3.1]nonan-9-yl)picolinonitrile (57 mg, 59% yield); [M+H]$^+$ 342.38.

Synthesis of 4-((1R,5S,9r)-9-methoxy-3-(tetrahydro-2H-pyran-4-yl)-3-azabicyclo[3.3.1]nonan-9-yl)picolinamide Hydrochloride

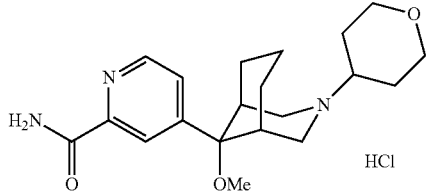 [SMILES: COC1(c2ccnc(C(N)=O)c2)C2CCCC1CN(C1CCOCC1)C2 ; Cl]

To a solution of 4-((1R,5S,9r)-9-methoxy-3-(tetrahydro-2H-pyran-4-yl)-3-azabicyclo[3.3.1]nonan-9-yl)picolinonitrile (57 mg, 0.17 mmol) in tert-butanol (1.7 mL) was added potassium hydroxide (47 mg, 0.84 mmol). The reaction mixture was heated at reflux for 1 hour, cooled to room temperature then partitioned between ethyl acetate and water.

The phases were separated and the aqueous phase re-extracted with ethyl acetate (×3). The combined organic phases were dried over $Na_2SO_4$, filtered and concentrated under reduced pressure. The residue was purified by reverse phase chromatography (C18) to give 4-((1R,5S,9r)-9-methoxy-3-(tetrahydro-2H-pyran-4-yl)-3-azabicyclo[3.3.1]nonan-9-yl)picolinamide (28 mg, 47% yield). To a solution of 4-((1R,5S,9r)-9-methoxy-3-(tetrahydro-2H-pyran-4-yl)-3-azabicyclo[3.3.1]nonan-9-yl)picolinamide (28 mg, 0.08 mmol) in tetrahydrofuran (5 mL) was added 2 M hydrochloric acid in diethyl ether (58 μL, 0.12 mmol) and the reaction mixture was stirred for 30 minutes. The mixture was concentrated under reduced pressure and the residue was freeze dried from water to give 4-((1R,5S,9r)-9-methoxy-3-(tetrahydro-2H-pyran-4-yl)-3-azabicyclo[3.3.1]nonan-9-yl)picolinamide hydrochloride (23 mg, 75% yield); [M+H]$^+$ 360.13; $^1$H NMR (300 MHz, d$_6$-DMSO): 8.70 (d, 1H), 8.74-8.55 (m, 1H), 8.20 (s, 1H), 8.04 (s, 1H), 7.75 (s, 1H), 7.71 (d, 1H), 3.95 (dd, 2H), 3.59-3.44 (m, 7H), 2.97 (s, 2H), 2.75 (s, 3H), 2.19-1.72 (m, 7H), 1.52-1.33 (m, 2H), 1.32-1.18 (m, 1H).

Compound 58

3-((1R,5S,9r)-3-((2-hydroxy-2,3-dihydro-1H-inden-2-yl)methyl)-9-methoxy-3-azabicyclo[3.3.1]nonan-9-yl)benzamide Hydrochloride

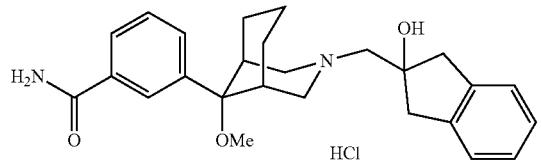 [SMILES: COC1(c2cccc(C(N)=O)c2)C2CCCC1CN(CC1(O)Cc3ccccc3C1)C2 ; Cl]

[M+H]$^+$ 421.22; $^1$H NMR (400 MHz, d$_3$-MeOD): 8.03 (s, 1H), 7.90 (d, 1H), 7.72 (d, 1H), 7.58 (dd, 1H), 7.29-7.14 (m, 4H), 3.94-3.73 (m, 4H), 3.59 (s, 2H), 3.34-3.24 (m, 2H), 3.24-3.14 (m, 2H), 3.05 (br s, 2H), 2.85 (s, 3H), 2.07-1.94 (m, 2H), 1.94-1.79 (m, 2H), 1.74-1.57 (m, 2H).

Compound 65

Synthesis of 3-((1R,5S,9r)-3-(2-(2,5-dioxopyrrolidin-1-yl)ethyl)-9-methoxy-3-azabicyclo[3.3.1]nonan-9-yl)benzamide Hydrochloride

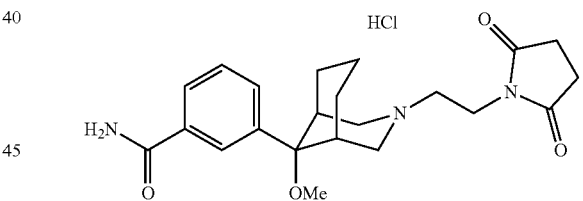

To a 0° C. solution of (2-hydroxyethyl)succinimide (86 mg, 0.60 mmol) in dichloromethane (10 mL) was added N,N-diisopropylethylamine (0.15 mL, 0.86 mmol), followed by methanesulfonyl chloride (50 μL, 0.65 mmol) and the reaction mixture was stirred at room temperature for 18 hours, then concentrated under reduced pressure. The residue was dissolved in acetonitrile (10 mL) and 3-((1R,5S,9r)-9-methoxy-3-azabicyclo[3.3.1]nonan-9-yl)benzamide hydrochloride (110 mg, 0.35 mmol) was added, followed by N,N-diisopropylethylamine (0.15 mL, 0.86 mmol) and the reaction mixture was stirred for 48 hours. The mixture was partitioned between ethyl acetate and sodium hydroxide. The organic phase was washed with brine, dried over MgSO$_4$, filtered and concentrated under reduced pressure. The residue was combined with a second batch and purified by reverse phase chromatography (C18), then recrystallised from acetonitrile to give 3-((1R,5S,9r)-3-(2-(2,5-dioxopyrrolidin-1-yl)ethyl)-9-methoxy-3-azabicyclo[3.3.1]nonan-9-yl)benzamide. The residue was dissolved in dichloromethane (2 mL) and 2 M hydrochloric acid in diethyl ether (0.10 mL, 0.20 mmol) was added. The mixture was stirred for 10 minutes then concentrated under reduced pressure. The residue was freeze dried from water to give 3-((1R,5S,9r)-3-(2-(2,5-dioxopyrrolidin-1-yl)ethyl)-9-methoxy-3-azabicyclo[3.3.1]nonan-9-yl)benzamide hydrochloride (37 mg, 12% yield over 2 steps); [M+H]$^+$ 400.19; $^1$H NMR (300 MHz, d$_6$-DMSO): 8.01 (s, 1H), 7.93 (s, 2H), 7.85 (d, 1H), 7.62 (d, 1H), 7.52 (t, 1H), 7.45 (s, 1H), 3.91-3.73 (m, 4H), 3.44 (t, 2H), 3.24-3.17 (m, 2H), 2.98 (br s, 2H), 2.70 (s, 3H), 2.65 (s, 4H), 2.84-1.69 (m, 3H), 1.64-1.46 (m, 2H), 1.39-1.22 (m, 1H).

Compound 59

5-((1R,5S,9r)-3-(cyclopropylmethyl)-9-methoxy-3-azabicyclo[3.3.1]nonan-9-yl)thiophene-3-carboxamide Hydrochloride

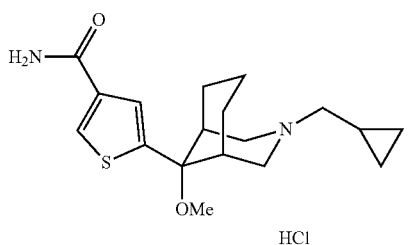 [SMILES: COC1(c2cc(C(N)=O)cs2)C2CCCC1CN(CC1CC1)C2 ; Cl]

[M+H]$^+$ 335.14; $^1$H NMR (300 MHz, D$_2$O): 8.03 (s, 1H), 7.41 (s, 1H), 3.57 (d, 2H), 3.45 (dd, 2H), 2.93 (d, 2H), 2.79 (s, 3H), 2.63 (br s, 2H), 1.94-1.71 (m, 4H), 1.61-1.38 (m, 2H), 1.04-0.88 (m, 1H), 0.64-0.54 (m, 2H), 0.26 (dd, 2H).

Compound 70

Synthesis of 4-((1R,5S,9r)-9-methoxy-3-azabicyclo[3.3.1]nonan-9-yl)picolinamide Hydrochloride

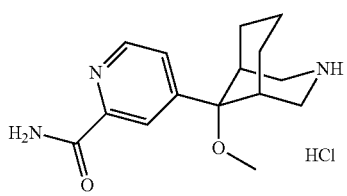 [SMILES: COC1(c2ccnc(C(N)=O)c2)C2CCCC1CNC2 ; Cl]

To a solution of 4-((1R,5S,9r)-9-methoxy-3-azabicyclo[3.3.1]nonan-9-yl)picolinamide (120 mg, 0.32 mmol) in dichloromethane (3 mL) was added 2 M hydrochloric acid in diethyl ether (8.0 mL, 16.0 mmol) and the reaction mixture was stirred for 90 minutes. The mixture was concentrated under reduced pressure and the residue freeze dried from water to give 4-((1R,5S,9r)-9-methoxy-3-azabicyclo[3.3.1]nonan-9-yl)picolinamide hydrochloride (112 mg, quant.); [M+H]$^+$ 276.18; $^1$H NMR (300 MHz, de-DMSO): 9.76 (br s, 1H), 8.69 (d, 1H), 8.20 (s, 1H), 8.04 (s, 1H), 7.95 (br s, 1H), 7.75 (s, 1H), 7.69 (dd, 1H), 3.47-3.30 (m, 2H), 3.30-3.20 (m, 2H), 2.88-2.80 (m, 2H), 2.72 (s, 3H), 1.95-1.73 (m, 3H), 1.52-1.39 (m, 2H), 1.39-1.23 (m, 1H).

Compound 72

4-((1R,5S,9r)-3-((1-hydroxycyclopropyl)methyl)-9-methoxy-3-azabicyclo[3.3.1]nonan-9-yl)picolinamide Hydrochloride

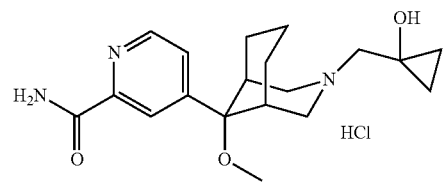 [SMILES: COC1(c2ccnc(C(N)=O)c2)C2CCCC1CN(CC1(O)CC1)C2 ; Cl]

[M+H]$^+$ 346.14; $^1$H NMR (300 MHz, de-DMSO): 8.70 (d, 1H), 8.20 (d, 1H), 8.05 (s, 1H), 7.75 (d, 1H), 7.72-7.59 (m, 2H), 6.02 (br s, 1H), 3.74-3.64 (m, 2H), 3.63-3.48 (m, 2H), 3.44-3.22 (d, 2H), 2.99 (br s, 2H), 2.74 (s, 3H), 1.97-1.72 (m, 3H), 1.30-1.31 (m, 3H), 0.78 (dd, 4H).

Compound 73

4-((1R,5S,9r)-3-((2-hydroxy-2,3-dihydro-1H-inden-2-yl)methyl)-9-methoxy-3-azabicyclo[3.3.1]nonan-9-yl)picolinamide Hydrochloride

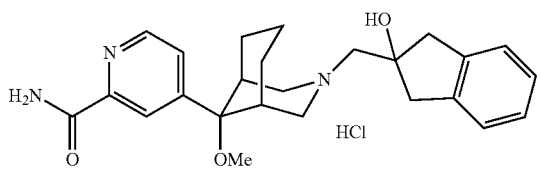 [SMILES: COC1(c2ccnc(C(N)=O)c2)C2CCCC1CN(CC1(O)Cc3ccccc3C1)C2 ; Cl]

[M+H]$^+$ 422.24; $^1$H NMR (300 MHz, d$_6$-DMSO): 8.72 (d, 1H), 8.21 (br s, 1H), 8.05 (s, 1H), 7.77 (br s, 1H), 7.70 (d, 1H), 7.45 (br s, 1H), 7.26-7.11 (m, 4H), 6.01 (s, 1H), 3.75 (d, 2H), 3.69-3.52 (m, 4H), 3.21 (d, 2H), 3.12-2.96 (m, 4H), 2.79-2.71 (m, 3H), 1.99-1.82 (m, 2H), 1.74-1.42 (m, 4H).

Compounds 87 and 89

4-((1R,5S,9R)-9-methoxy-3-((1 r,3R)-3-phenylcyclobutyl)-3-azabicyclo[3.3.1]nonan-9-yl)picolinamide hydrochloride and 4-((1R,5S,9R)-9-methoxy-3-((1s,3S)-3-phenylcyclobutyl)-3-azabicyclo[3.3.1]nonan-9-yl)picolinamide Hydrochloride

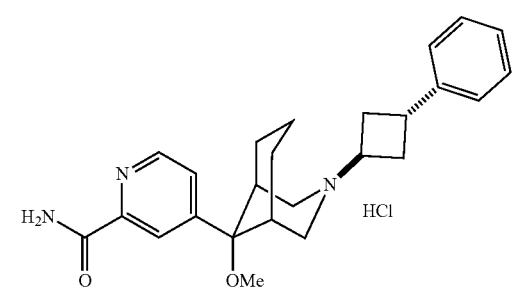

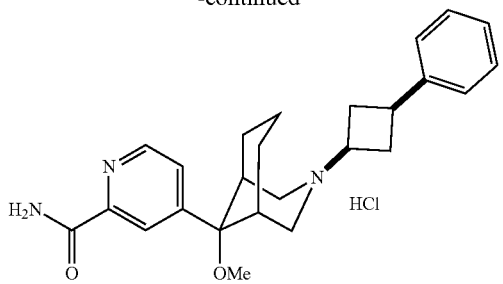

[M+H]+ 406.17. ¹H NMR (300 MHz, D₂O): 8.61 (d, 1H), 8.02 (s, 1H), 7.64 (d, 1H), 7.35-7.18 (m, 5H), 3.95 (quintuplet, 1H), 3.59-3.52 (m, 3H), 3.48-3.39 (m, 2H), 2.94 (s, 2H), 2.84 (d, 2H), 2.76 (s, 3H), 2.50-2.41 (m, 2H), 1.83-1.75 (m, 2H), 1.64-1.56 (m, 3H), 1.43-1.38 (m, 1H). [M+H]+ 406.29. ¹H NMR (300 MHz, DMSO-d₆): 8.76 (br s, 1H), 8.70 (d, 1H), 8.17 (s, 1H), 8.05 (s, 1H), 7.73-7.69 (m, 2H), 7.35-7.29 (m, 4H), 7.22-7.18 (m, 2H), 3.71 (sextuplet, 1H), 3.55 (d, 2H), 3.52 (d, 1H), 3.36-3.32 (quintuplet, 1H), 2.96 (s, 2H), 2.75 (s, 3H), 2.65-2.60 (m, 4H), 2.13-1.99 (m, 1H), 1.87-1.76 (m, 2H), 1.48-1.37 (m, 2H), 1.31-1.24 (m, 1H).

Compound 90

4-((1R,5S,9r)-3-cyclobutyl-9-methoxy-3-azabicyclo[3.3.1]nonan-9-yl)picolinamide Hydrochloride

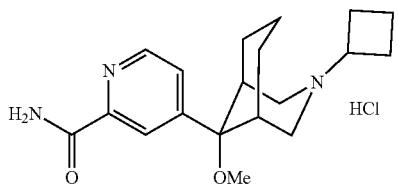 [SMILES: COC1(c2ccnc(C(N)=O)c2)C2CCCC1CN(C1CCC1)C2 ; Cl]

[M+H]+ 330.14. ¹H NMR (300 MHz, D₂O): 8.64 (d, 1H), 8.07 (s, 1H), 7.70 (d, 1H), 3.72 (quintuplet, 1H), 3.50 (d, 2H), 3.38 (d, 2H), 2.92 (s, 2H), 2.77 (s, 3H), 2.33-2.14 (m, 4H), 1.84-1.68 (m, 4H), 1.63-1.52 (m, 3H), 1.44-1.34 (m, 1H).

Compound 91

Synthesis of 4-((1R,5S,9r)-9-methoxy-3-propyl-3-azabicyclo[3.3.1]nonan-9-yl)picolinamide Hydrochloride

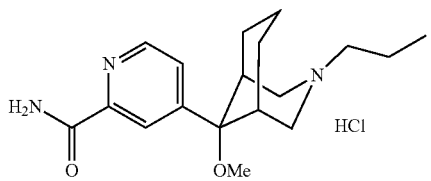 [SMILES: CCCN1CC2CCCC(C1)C2(OC)c1ccnc(C(N)=O)c1 ; Cl]

A suspension of 4-((1R,5S,9r)-9-methoxy-9-azabicyclo[3.3.1]nonan-9-yl)picolinamide hydrochloride (150 mg, 0.48 mmol) and propionaldehyde (0.10 mL, 1.44 mmol) in dichloromethane (10 mL) and acetic acid (0.06 mL, 0.96 mmol) was stirred at room temperature for 30 minutes before the addition of sodium triacetoxyborohydride (210 mg, 0.99 mmol). After stirring at room temperature under an atmosphere of argon for 2 hours, the mixture was quenched with an aqueous solution of sodium hydrogen carbonate and extracted with dichloromethane (×3). The combined organic phases were dried over MgSO₄ and the solvent evaporated under reduced pressure. The crude reaction was purified by silica column chromatography, eluting with 4% methanol in dichloromethane to give 4-((1R,5S,9r)-9-methoxy-3-propyl-3-azabicyclo[3.3.1]nonan-9-yl)picolinamide (135 mg, 88% yield). To 4-((1R,5S,9r)-9-methoxy-3-propyl-3-azabicyclo[3.3.1]nonan-9-yl)picolinamide (135 mg, 0.42 mmol) in acetonitrile/dichloromethane (3 mL/2 mL) was added 2M HCl in diethyl ether (0.25 mL, 0.51 mmol). After 30 minutes, the solvent was removed under reduced pressure and the product was dissolved in water and freeze dried overnight to give 4-((1R,5S,9r)-9-methoxy-3-propyl-3-azabicyclo[3.3.1]nonan-9-yl)picolinamide hydrochloride (118 mg, 79% yield); [M+H]+ 318.11. ¹H NMR (300 MHz, D₂O): 8.65 (d, 1H), 8.07 (s, 1H), 7.71 (dd, 1H), 3.61-3.48 (m, 4H), 3.05-2.99 (m, 2H), 2.91 (s, 2H), 2.77 (s, 3H), 1.83-1.42 (m, 8H), 0.85 (t, 3H).

Compound 92

4-((1R,5S,9r)-3-isobutyl-9-methoxy-3-azabicyclo[3.3.1]nonan-9-yl)picolinamide Hydrochloride

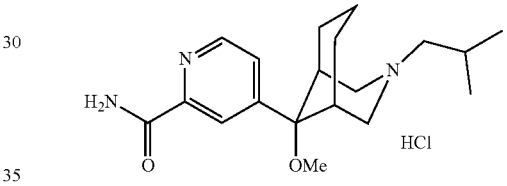

[M+H]+ 332.12. ¹H NMR (300 MHz, D₂O): 8.62 (d, 1H), 8.04 (s, 1H), 7.66 (d, 1H), 3.62-3.51 (m, 4H), 2.96-2.90 (m, 4H), 2.76 (s, 3H), 2.18-2.08 (m, 1H), 1.89-1.80 (m, 2H), 1.68-1.44 (m, 4H), 0.90 (d, 6H).

Compounds 109, 117, 116 and 110

Synthesis of (cyclopropylidenemethyl)benzene

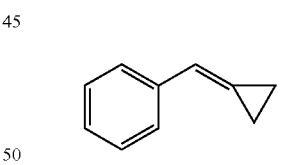

To a suspension of (3-bromopropyl)triphenylphosphonium (19.8 g, 42.6 mmol) in dry tetrahydrofuran (130 mL) was added a solution of potassium tert-butoxide (9.3 g, 82.8 mmol) in dry tetrahydrofuran (85 mL) slowly at room temperature. The mixture was heated to 70° C. before the dropwise addition of benzaldehyde (4.0 g, 37.6 mmol). The reaction was heated at 70° C. for 5 hours before cooling to room temperature. To the resulting suspension, hexane was added and the mixture was filtered through a pad of celite, rinsed with hexane and the filtrate was evaporated under reduced pressure. The residue was purified by dry flash chromatography on silica, eluting with 0-2% ethyl acetate in heptanes to give (cyclopropylidenemethyl)benzene (2.95 g, 60% yield). ¹H NMR (400 MHz, CDCl₃): 7.52 (d, 2H), 7.32 (t, 2H), 7.20 (t, 1H), 6.74 (s, 1H), 1.44-1.39 (td, 2H), 1.19-1.15 (td, 2H).

Synthesis of 2-phenylcyclobutanone

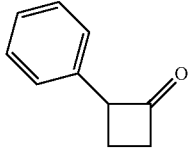

To a solution of (cyclopropylidenemethyl)benzene (2.3 g, 17.6 mmol) in dichloromethane (70 mL) was added 75% meta-chloroperoxybenzoic acid (7.2 g, 30.9 mmol) at 0° C. and stirred for 1.5 hours. The reaction was successively washed with saturated aqueous solutions of sodium hydrogen carbonate, sodium bisulfite and sodium hydrogen carbonate, dried over MgSO$_4$ and the solvent evaporated under reduced pressure. The residue was purified by silica column chromatography, eluting with 30% heptane in dichloromethane to give 2-phenylcyclobutanone (0.80 g, 32% yield). $^1$H NMR (300 MHz, CDCl$_3$): 7.36-7.24 (m, 5H), 4.54 (t, 1H), 3.30-3.17 (m, 1H), 3.09-2.97 (m, 1H), 2.54 (dq, 1H), 2.25 (dt, 1H).

Synthesis of 4-((1R,5S,9R)-9-methoxy-3-((1R,2S)-2-phenylcyclobutyl)-3-azabicyclo[3.3.1]nonan-9-yl)picolinamide hydrochloride, 4-((1R,5S,9S)-9-methoxy-3-((1S,2R)-2-phenylcyclobutyl)-3-azabicyclo[3.3.1]nonan-9-yl)picolinamide hydrochloride, 4-((1R,5S,9S)-9-methoxy-3-((1S,2S)-2-phenylcyclobutyl)-3-azabicyclo[3.3.1]nonan-9-yl)picolinamide (S)-2-hydroxysuccinate and 4-((1R,5S,9R)-9-methoxy-3-((1R,2R)-2-phenylcyclobutyl)-3-azabicyclo[3.3.1]nonan-9-yl)picolinamide Hydrochloride

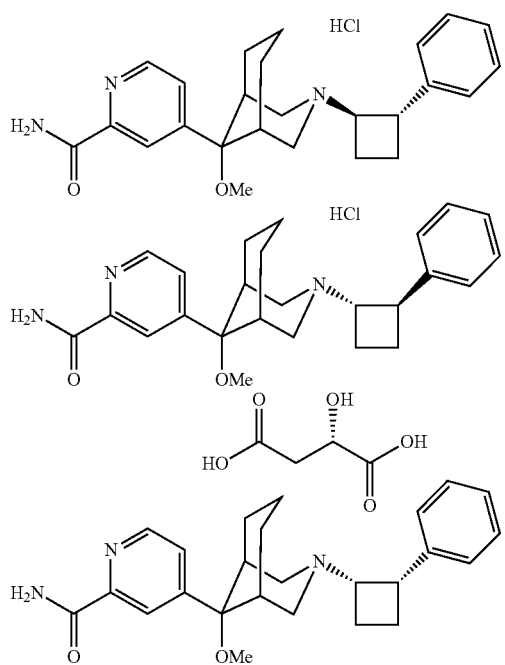

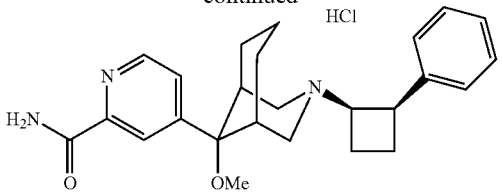

To a suspension of 4-((1R,5S,9r)-9-methoxy-9-azabicyclo[3.3.1]nonan-9-yl)picolinamide hydrochloride (500 mg, 1.60 mmol) and 2-phenylcyclobutanone (470 mg, 3.21 mmol) in dry dichloromethane (6 mL) was added titanium isopropoxide (1.23 mL, 4.15 mmol) dropwise at room temperature under an atmosphere of argon. After stirring for 1.5 hours, sodium cyanoborohydride (200 mg, 3.18 mmol) in ethanol (6 mL) was added and the solution was stirred at room temperature for 16 hours. The reaction was quenched with water, filtered through a pad of celite and rinsed with dichloromethane. The filtrate was washed with brine, extracted with dichloromethane (×3), dried over MgSO$_4$ and the solvent evaporated under reduced pressure. The crude reaction was purified by silica column chromatography eluting with 4% methanol in dichloromethane followed by C18 reverse phase chromatography to give 4-((1R,5S,9r)-9-methoxy-3-(2-phenylcyclobutyl)-3-azabicyclo[3.3.1]nonan-9-yl)picolinamide (170 mg, 26% yield, cis:trans 1:1 ratio). The 4 enantiomers were separated by supercritical fluid chromatography to give 4-((1R,5S,9R)-9-methoxy-3-((1R,2S)-2-phenylcyclobutyl)-3-azabicyclo[3.3.1]nonan-9-yl)picolinamide (47.1 mg), 4-((1R,5S,9S)-9-methoxy-3-((1S,2R)-2-phenylcyclobutyl)-3-azabicyclo[3.3.1]nonan-9-yl)picolinamide (52.3 mg), 4-((1R,5S,9S)-9-methoxy-3-((1S,2S)-2-phenylcyclobutyl)-3-azabicyclo[3.3.1]nonan-9-yl)picolinamide (21.5 mg) and 4-((1R,5S,9R)-9-methoxy-3-((1R,2R)-2-phenylcyclobutyl)-3-azabicyclo[3.3.1]nonan-9-yl)picolinamide (21.7 mg). Diastereomeric configuration determined by $^1$H NMR, enantiomeric configuration arbitrarily assigned.

To 4-((1R,5S,9R)-9-methoxy-3-((1R,2S)-2-phenylcyclobutyl)-3-azabicyclo[3.3.1]nonan-9-yl)picolinamide (47.1 mg, 0.11 mmol) in dichloromethane (2 mL) was added 2M HCl in diethyl ether (69 µL, 0.14 mmol). After 30 minutes, the solvent was removed under reduced pressure and the product was dissolved in water and freeze dried overnight to give 4-((1R,5S,9R)-9-methoxy-3-((1R,2S)-2-phenylcyclobutyl)-3-azabicyclo[3.3.1]nonan-9-yl)picolinamide hydrochloride (45.6 mg, 88% yield); [M+H]$^+$ 406.18. $^1$H NMR (300 MHz, D$_2$O): 8.53 (d, 1H), 7.91 (d, 1H), 7.53 (d, 1H), 7.34-7.20 (m, 5H), 3.97-3.87 (m, 1H), 3.77-3.66 (m, 1H), 3.50-3.43 (m, 1H), 3.38-3.26 (m, 2H), 3.14-3.04 (m, 1H), 2.83 (br s, 1H), 2.69 (br s, 1H), 2.65 (s, 1H), 2.62 (s, 3H), 2.26-2.17 (m, 3H), 1.82-1.62 (m, 3H), 1.58-1.48 (m, 3H).

To 4-((1R,5S,9S)-9-methoxy-3-((1S,2R)-2-phenylcyclobutyl)-3-azabicyclo[3.3.1]nonan-9-yl)picolinamide (52.3 mg, 0.13 mmol) in dichloromethane (2 mL) was added 2M HCl in diethyl ether (77 µL, 0.15 mmol). After 30 minutes, the solvent was removed under reduced pressure and the product was dissolved in water and freeze dried overnight to give 4-((1R,5S,9S)-9-methoxy-3-((1S,2R)-2-phenylcyclobutyl)-3-azabicyclo[3.3.1]nonan-9-yl)picolinamide hydrochloride (57.2 mg, 100% yield); [M+H]$^+$ 406.18. $^1$H NMR (300 MHz, D$_2$O): 8.53 (d, 1H), 7.91 (d, 1H), 7.53 (d, 1H), 7.34-7.20 (m, 5H), 3.97-3.87 (m, 1H), 3.77-3.66 (m, 1H), 3.50-3.43 (m, 1H), 3.38-3.26 (m, 2H), 3.14-3.04 (m, 1H), 2.83 (br s, 1H), 2.69 (br s, 1H), 2.65 (s, 1H), 2.62 (s, 3H), 2.26-2.17 (m, 3H), 1.82-1.62 (m, 3H), 1.58-1.48 (m, 3H).

To 4-((1R,5S,9S)-9-methoxy-3-((1 S,2S)-2-phenylcyclobutyl)-3-azabicyclo[3.3.1]nonan-9-yl)picolinamide (14 mg, 0.03 mmol) in dichloromethane (2 mL) was added L-malic acid (4.7 mg, 0.03 mmol). After 30 minutes, the solvent was removed under reduced pressure and the product was dissolved in water and freeze dried overnight to give 4-((1R,5S,9S)-9-methoxy-3-((1S,2S)-2-phenylcyclobutyl)-3-azabicyclo[3.3.1]nonan-9-yl)picolinamide (S)-2-hydroxysuccinate (16.6 mg, 87% yield); [M+H]⁺ 406.18. ¹H NMR (300 MHz, D₂O): 8.57 (d, 1H), 7.90 (s, 1H), 7.58-7.38 (m, 6H), 4.27-4.23 (m, 1H), 4.16-4.06 (m, 1H), 4.03-3.95 (m, 1H), 3.48-3.37 (m, 3H), 3.20-3.16 (m, 1H), 2.86-2.66 (m, 7H), 2.54-2.36 (m, 3H), 2.19-2.14 (m, 1H), 1.73-1.64 (m, 1H), 1.56-1.32 (m, 2H), 1.24-1.13 (m, 1H), 1.06-0.97 (m, 1H), 0.28-0.12 (m, 1H).

To 4-((1R,5S,9R)-9-methoxy-3-((1R,2R)-2-phenylcyclobutyl)-3-azabicyclo[3.3.1]nonan-9-yl)picolinamide (21.7 mg, 0.05 mmol) in dichloromethane (2 mL) was added 2M HCl in diethyl ether (32 µL, 0.06 mmol). After 30 minutes, the solvent was removed under reduced pressure and the product was dissolved in water and freeze dried overnight to give 4-((1R,5S,9R)-9-methoxy-3-((1R,2R)-2-phenylcyclobutyl)-3-azabicyclo[3.3.1]nonan-9-yl)picolinamide hydrochloride (17.7 mg, 75% yield); [M+H]⁺ 406.18. ¹H NMR (300 MHz, D₂O): 8.57 (d, 1H), 7.91 (s, 1H), 7.58-7.35 (m, 6H), 4.14-4.05 (m, 1H), 4.02-3.95 (m, 1H), 3.48-3.37 (m, 3H), 3.17 (d, 1H), 2.84-2.66 (m, 3H), 2.70 (s, 3H), 2.51-2.36 (m, 2H), 2.19-2.14 (m, 1H), 1.73-1.64 (m, 1H), 1.54-1.30 (m, 2H), 1.24-1.12 (m, 1H), 1.05-0.96 (m, 1H), 0.27-0.10 (m, 1H).

Compound 126

Synthesis of 4-((1R,5S,9r)-3-((1H-indol-3-yl)methyl)-9-methoxy-3-azabicyclo[3.3.1]nonan-9-yl)picolinamide Hydrochloride

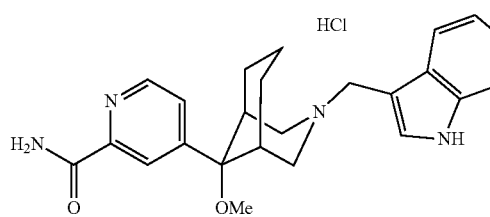

A suspension of 4-((1R,5S,9r)-9-methoxy-9-azabicyclo[3.3.1]nonan-9-yl)picolinamide hydrochloride (150 mg, 0.48 mmol) and indole-3-carboxaldehyde (210 mg, 1.44 mmol) in dichloromethane (10 mL) and acetic acid (0.06 mL, 0.96 mmol) was stirred at room temperature for 30 minutes before the addition of sodium triacetoxyborohydride (210 mg, 0.99 mmol). After stirring at room temperature under an atmosphere of argon for 19 hours, the mixture was quenched with an aqueous solution of sodium hydrogen carbonate and extracted with dichloromethane (×3). The combined organic phases were dried over MgSO₄ and the solvent evaporated under reduced pressure. The crude reaction was purified by C18 reverse phase chromatography and by preparative HPLC to give 4-((1R,5S,9r)-3-((1H-indol-3-yl)methyl)-9-methoxy-3-azabicyclo[3.3.1]nonan-9-yl)picolinamide (70 mg, 36% yield).

To 4-((1R,5S,9r)-3-((1H-indol-3-yl)methyl)-9-methoxy-3-azabicyclo[3.3.1]nonan-9-yl)picolinamide (70 mg, 0.17 mmol) in dichloromethane (5 mL) was added 2M HCl in diethyl ether (0.19 mL, 0.37 mmol). After 30 minutes, the solvent was removed under reduced pressure and the product was dissolved in water and freeze dried overnight to give 4-((1R,5S,9r)-3-((1H-indol-3-yl)methyl)-9-methoxy-3-azabicyclo[3.3.1]nonan-9-yl)picolinamide hydrochloride (63 mg, 82% yield); [M+H]⁺ 405.12. ¹H NMR (300 MHz, DMSO-d6): 11.54 (s, 1H), 8.64 (d, 1H), 8.55 (br s, 1H), 8.14 (s, 1H), 7.96 (s, 1H), 7.77-7.70 (m, 3H), 7.60 (d, 1H), 7.43 (d, 1H), 7.17-7.08 (m, 2H), 4.48 (s, 2H), 3.57-3.41 (m, 5H), 2.88 (s, 2H), 2.50-2.42 (m, 2H), 2.07-1.90 (m, 1H), 1.84-1.76 (m, 2H), 1.49-1.27 (m, 3H).

Compound 111

4-((1R,5S,9r)-9-methoxy-3-(tetrahydro-2H-pyran-3-yl)-3-azabicyclo[3.3.1]nonan-9-yl)picolinamide Hydrochloride

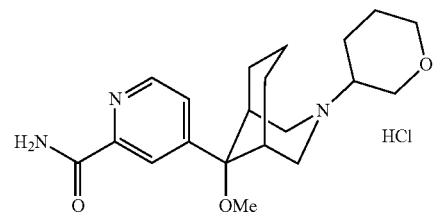 [SMILES: COC1(c2ccnc(C(N)=O)c2)C2CCCC1CN(C1CCCOC1)C2 ; Cl]

[M+H]⁺ 360.10. ¹H NMR (300 MHz, D₂O): 8.61 (s, 1H), 8.01 (s, 1H), 7.63 (s, 1H), 4.18 (d, 1H), 3.79 (d, 1H), 3.69-3.51 (m, 5H), 3.41-3.26 (m, 2H), 2.95 (s, 2H), 2.77 (s, 3H), 3.30-2.21 (m, 1H), 1.86-1.72 (m, 4H), 1.66-1.39 (m, 5H).

Compounds 60 and 132

Synthesis of 4-((1R,5S,9R)-9-methoxy-3-((R)-tetrahydro-2H-pyran-3-yl)-3-azabicyclo[3.3.1]nonan-9-yl)picolinamide hydrochloride and 4-((1R,5S,9S)-9-methoxy-3-((S)-tetrahydro-2H-pyran-3-yl)-3-azabicyclo[3.3.1]nonan-9-yl)picolinamide Hydrochloride

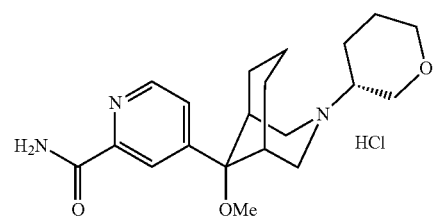

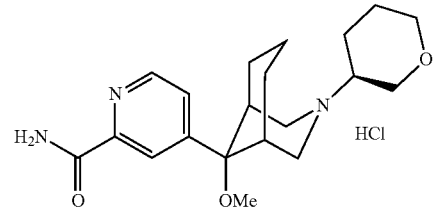

The 2 enantiomers of 4-((1R,5S,9r)-9-methoxy-3-(tetrahydro-2H-pyran-3-yl)-3-azabicyclo[3.3.1]nonan-9-yl)picolinamide hydrochloride were separated by supercritical fluid chromatography to give 4-((1R,5S,9R)-9-methoxy-3-((R)-tetrahydro-2H-pyran-3-yl)-3-azabicyclo[3.3.1]nonan-9-yl)picolinamide (142 mg) and 4-((1R,5S,9S)-9-methoxy-3-((S)-tetrahydro-2H-pyran-3-yl)-3-azabicyclo[3.3.1]nonan-9-yl)picolinamide (155 mg), which was Further purified by preparative HPLC to give 4-((1R,5S,9S)-9-methoxy-3-((S)-tetrahydro-2H-pyran-3-yl)-3-azabicyclo[3.3.1]nonan-9-yl)picolinamide (95 mg). The stereochemistry was arbitrary assigned.

To 4-((1R,5S,9R)-9-methoxy-3-((R)-tetrahydro-2H-pyran-3-yl)-3-azabicyclo[3.3.1]nonan-9-yl)picolinamide (142 mg, 0.39 mmol) in ethyl acetate (5 mL) was added 2M HCl in diethyl ether (0.24 mL, 0.47 mmol). After 30 minutes, the solvent was removed under reduced pressure and the product was dissolved in water and freeze dried overnight to give 4-((1R,5S,9R)-9-methoxy-3-((R)-tetrahydro-2H-pyran-3-yl)-3-azabicyclo[3.3.1]nonan-9-yl)picolinamide hydrochloride (133 mg, 85% yield); [M+H]$^+$ 360.10. $^1$H NMR (300 MHz, D$_2$O): 8.67 (d, 1H), 8.13 (s, 1H), 7.79 (d, 1H), 4.17 (d, 1H), 3.78 (d, 1H), 3.69-3.51 (m, 5H), 3.40-3.24 (m, 2H), 2.95 (s, 2H), 2.77 (s, 3H), 2.25 (br d, 1H), 1.83-1.72 (m, 4H), 1.65-1.39 (m, 5H).

To 4-((1R,5S,9S)-9-methoxy-3-((S)-tetrahydro-2H-pyran-3-yl)-3-azabicyclo[3.3.1]nonan-9-yl)picolinamide (95 mg, 0.26 mmol) in ethyl acetate (10 mL) was added 2M HCl in diethyl ether (0.16 mL, 0.31 mmol). After 30 minutes, the solvent was removed under reduced pressure and the product was dissolved in water and freeze dried overnight to give 4-((1R,5S,9S)-9-methoxy-3-((S)-tetrahydro-2H-pyran-3-yl)-3-azabicyclo[3.3.1]nonan-9-yl)picolinamide hydrochloride (103 mg, 99% yield); [M+H]$^+$ 360.10. $^1$H NMR (300 MHz, D$_2$O): 8.67 (d, 1H), 8.13 (s, 1H), 7.79 (d, 1H), 4.17 (d, 1H), 3.78 (d, 1H), 3.69-3.51 (m, 5H), 3.40-3.24 (m, 2H), 2.95 (s, 2H), 2.77 (s, 3H), 2.25 (br d, 1H), 1.83-1.72 (m, 4H), 1.65-1.39 (m, 5H).

Compound 142

4-((1R,5S,9r)-3-((1H-indazol-3-yl)methyl)-9-methoxy-3-azabicyclo[3.3.1]nonan-9-yl)picolinamide Hydrochloride

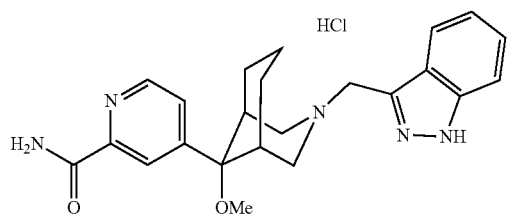 [SMILES: COC1(c2ccnc(C(N)=O)c2)C2CCCC1CN(Cc1n[nH]c3ccccc13)C2 ; Cl]

[M+H]$^+$ 406.11. $^1$H NMR (300 MHz, D$_2$O): 8.54 (d, 1H), 7.89 (s, 1H), 7.79 (d, 1H), 7.57 (d, 1H), 7.52 (d, 1H), 7.41 (t, 1H), 7.23 (t, 1H), 4.70 (s, 2H), 3.70 (d, 2H), 3.58 (d, 2H), 2.80 (s, 2H), 2.32 (s, 3H), 1.84-1.74 (m, 2H), 1.63-1.41 (m, 4H).

Compound 107

Synthesis of 3-(tert-butyl)-1,5,3-dioxazepane

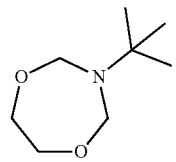

A mixture of tert-butylamine (18.2 mL, 174 mmol), paraformaldehyde (12.9 g, 432 mmol) and ethylene glycol (11.5 mL, 207 mmol) in toluene (125 mL) was heated at reflux for 18 hours with a Dean Stark trap attached. The mixture was cooled, washed with water, then brine and the solvent evaporated under reduced pressure. The residue was distilled under reduced pressure to give 3-(tert-butyl)-1,5,3-dioxazepane (20.0 g, 72% yield); $^1$H NMR (300 MHz, CDCl$_3$): 4.62 (s, 4H), 3.85 (s, 4H), 1.25 (s, 9H).

Synthesis of (1R,5S)-3-(tert-butyl)-3-azabicyclo[3.3.1]nonan-9-one

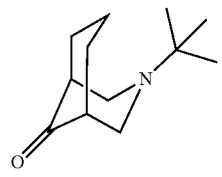

To a solution of 3-(tert-butyl)-1,5,3-dioxazepane (1.60 g, 10.0 mmol) in methanol (10 mL) at 0° C., was added acetyl chloride (2.10 mL, 29.5 mmol) over 10 minutes. After stirring for 10 minutes, a solution of cyclohexanone (1.00 mL, 9.7 mmol) in methanol (1 mL) was added. The reaction was stirred for 10 minutes, then warmed to room temperature and stirred for 18 hours. The mixture was quenched by the addition of concentrated aqueous ammonia and the volatiles removed under reduced pressure. Concentrated aqueous ammonia, brine, water and ethyl acetate were added and the phases separated. The organic phase was washed with brine, dried over MgSO$_4$, filtered and concentrated under reduced pressure. The residue was suspended in 2 M hydrochloric acid (10 mL) and the reaction heated to 50° C. for 3 hours. The mixture was cooled, diluted with concentrated aqueous ammonia, brine and ethyl acetate and the phases separated. The organic phase was washed with brine, dried over MgSO$_4$, filtered and concentrated under reduced pressure. The residue was purified by silica chromatography, eluting with 0-25% ethyl acetate in heptane, to give (1R,5S)-3-(tert-butyl)-3-azabicyclo[3.3.1]nonan-9-one (0.78 g, 56% yield); $^1$H NMR (300 MHz, CDCl$_3$): 3.27 (d, 2H), 2.79 (m, 1H), 2.64 (d, 2H), 2.30 (s, 2H), 2.15-2.08 (m, 2H), 2.06-1.94 (m, 2H), 1.43-1.33 (m, 1H), 1.07 (s, 9H).

Synthesis of (1R,5S,9r)-3-(tert-butyl)-9-(2-chloro-pyridin-4-yl)-3-azabicyclo[3.3.1]nonan-9-ol and (1R,5S,9s)-3-(tert-butyl)-9-(2-chloropyridin-4-yl)-3-azabicyclo[3.3.1]nonan-9-ol

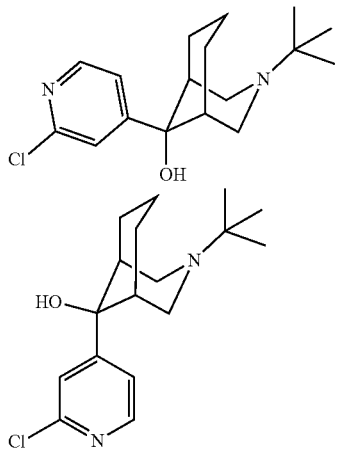

To a solution of 2-chloro-4-iodopyridine (4.80 g, 20.0 mmol) and (1R,5S)-3-(tert-butyl)-3-azabicyclo[3.3.1]nonan-9-one (3.50 g, 2.3 mmol) in diethyl ether (20 mL) at −78° C. under argon was added n-butyl lithium (2.2 M in hexanes, 9.10 mL, 20.0 mmol) drop wise over 10 minutes and the reaction mixture was stirred for 1 hour. The mixture was allowed to warm to 0° C. The mixture was quenched with concentrated aqueous ammonia and partitioned between brine and ethyl acetate. The organic phase was washed with brine, dried over MgSO$_4$, filtered and concentrated under reduced pressure. The residue was purified by silica chromatography, eluting with a gradient of 0-100% ethyl acetate in dichloromethane to give (1R,5S,9r)-3-(tert-butyl)-9-(2-chloropyridin-4-yl)-3-azabicyclo[3.3.1]nonan-9-ol (1.25 g, 22% yield); [M+H]$^+$ 309.1 and 311.1; and (1R,5S,9s)-3-(tert-butyl)-9-(2-chloropyridin-4-yl)-3-azabicyclo[3.3.1]nonan-9-ol (3.50 g, 63% yield); [M+H]$^+$ 309.1 and 311.1.

Synthesis of (1R,5S,9r)-3-(tert-butyl)-9-(2-chloro-pyridin-4-yl)-9-methoxy-3-azabicyclo[3.3.1]nonane

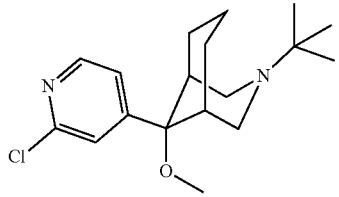 [SMILES: COC1(c2ccnc(Cl)c2)C2CCCC1CN(C(C)(C)C)C2]

To a solution of (1R,5S,9r)-3-(tert-butyl)-9-(2-chloropyridin-4-yl)-3-azabicyclo[3.3.1]nonan-9-ol (700 mg, 2.10 mmol) in N,N-dimethylformamide (7 mL) was added sodium hydride (60% dispersion in oil, 168 mg, 4.20 mmol) and the mixture stirred for 1 hour. Iodomethane (175 µL, 2.80 mmol) was added and the reaction mixture was stirred for 18 hours at room temperature. The mixture was quenched with concentrated aqueous ammonia, diluted with water and brine then extracted with diethyl ether. The organic phase was washed with brine, dried over MgSO$_4$, filtered and concentrated under reduced pressure. The residue was purified by trituration in heptanes, to give (1R,5S,9r)-3-(tert-butyl)-9-(2-chloropyridin-4-yl)-9-methoxy-3-azabicyclo[3.3.1]nonane (610 mg, 90% yield); [M+H]$^+$ 323.2 and 325.2.

Synthesis of 4-((1R,5S,9r)-3-(tert-butyl)-9-methoxy-3-azabicyclo[3.3.1]nonan-9-yl)picolinonitrile

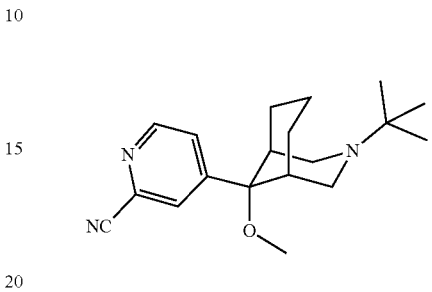

To a degassed solution of (1R,5S,9r)-3-(tert-butyl)-9-(2-chloropyridin-4-yl)-9-methoxy-3-azabicyclo[3.3.1]nonane (525 mg, 1.6 mmol) in dry N,N-dimethylformamide (20 mL) was added tetrakis(triphenylphosphine)palladium(0) (470 mg, 0.4 mmol). The solution was heated to 70° C. before the addition of zinc cyanide (228 mg, 1.9 mmol) and heated to 110° C. under an atmosphere of argon for 1 hour. The mixture was cooled down to room temperature, filtered through a pad of celite and rinsed with ethyl acetate. The filtrate was partitioned with water and extracted with ethyl acetate (×2). The combined organic phases were washed with water (×2), dried over MgSO$_4$, filtered and the solvent evaporated under reduced pressure. The residue was purified by silica column chromatography, eluting with 4% methanol in dichloromethane to give 4-((1R,5S,9r)-3-(tert-butyl)-9-methoxy-3-azabicyclo[3.3.1]nonan-9-yl)picolinonitrile (415 mg, 81% yield); [M+H]$^+$ 314.17.

Synthesis of 4-((1R,5S,9r)-3-(tert-butyl)-9-methoxy-3-azabicyclo[3.3.1]nonan-9-yl)picolinamide Hydrochloride

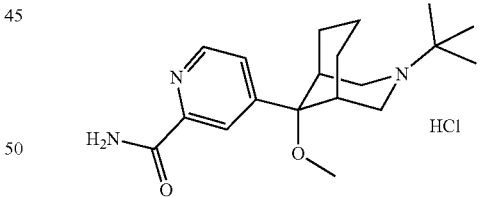

A solution of 4-((1R,5S,9r)-3-(tert-butyl)-9-methoxy-3-azabicyclo[3.3.1]nonan-9-yl)picolinonitrile (415 mg, 1.32 mmol) and potassium hydroxide (370 mg, 6.60 mmol) in tert-butanol (35 mL) was heated at 100° C. for 1 hour, cooled down to room temperature and partitioned between water and ethyl acetate. The mixture was extracted with ethyl acetate (×3), dried over MgSO$_4$, filtered and the solvent evaporated under reduced pressure. The residue was purified by silica column chromatography, eluting with 10% methanol in dichloromethane to give 4-((1R,5S,9r)-3-(tert-butyl)-9-methoxy-3-azabicyclo[3.3.1]nonan-9-yl)picolinamide (148 mg, 33%). To 4-((1R,5S,9r)-3-(tert-butyl)-9-methoxy-3-azabicyclo-[3.3.1]nonan-9-yl)picolinamide (143 mg, 0.45 mmol) in dichloromethane (20 mL) was added 2M HCl in diethyl ether (0.25 mL, 0.54 mmol). After 30 minutes, the solvent was removed under reduced pressure and the product was dissolved in water and freeze dried overnight to give 4-((1R,5S,9r)-3-(tert-butyl)-9-methoxy-3-azabicyclo[3.3.1]nonan-9-yl)picolinamide hydrochloride (128 mg, 77% yield); [M+H]$^+$ 332.15. $^1$H NMR (300 MHz, D$_2$O): 8.67 (d, 1H), 8.12 (s, 1H), 7.76 (d, 1H), 3.64 (d, 2H), 3.45 (d, 2H), 2.98 (s, 2H), 2.80 (s, 3H), 1.83-1.75 (m, 2H), 1.67-1.45 (m, 4H), 1.37 (s, 9H).
Compound 4

4-((1R,5S,9r)-9-methoxy-3-(1-methylcyclopropyl)-3-azabicyclo[3.3.1]nonan-9-yl)picolinamide Hydrochloride

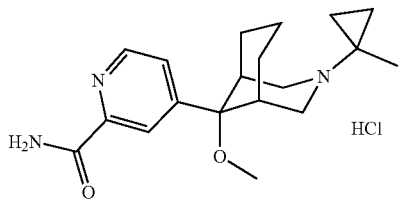 [SMILES: COC1(c2ccnc(C(N)=O)c2)C2CCCC1CN(C1(C)CC1)C2 ; Cl]

[M+H]$^+$ 330.16. $^1$H NMR (300 MHz, D$_2$O): 8.64 (d, 1H), 8.05 (s, 1H), 7.68 (d, 1H), 3.69 (d, 1H), 3.64 (d, 1H), 3.51 (s, 1H), 3.46 (s, 1H), 2.96 (br s, 2H), 2.80 (s, 3H), 1.78 (br d, 2H), 1.61-1.37 (m, 4H), 1.44 (s, 3H), 1.22-1.17 (m, 2H), 0.78-0.73 (m, 2H).
Compound 96

Synthesis of 4-((1R,5S,9r)-3-((1H-imidazol-5-yl)methyl)-9-methoxy-3-azabicyclo[3.3.1]nonan-9-yl)picolinamide Hydrochloride

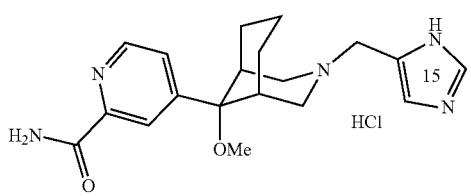 [SMILES: COC1(c2ccnc(C(N)=O)c2)C2CCCC1CN(Cc1cnc[nH]1)C2 ; Cl]

To a mixture of 4-((1R,5S,9r)-9-methoxy-3-azabicyclo[3.3.1]nonan-9-yl)picolinamide hydrochloride (150 mg, 0.48 mmol), acetic acid (0.055 mL, 0.96 mmol), 4-formylimidazole (190 mg, 1.92 mmol) and dichloromethane (15 mL) was added sodium triacetoxyborohydride (200 mg, 0.96 mmol). The reaction mixture was stirred for 4 h, diluted with dichloromethane and washed with saturated sodium hydrogen carbonate solution. The aqueous phase was extracted with dichloromethane and the combined organic phases dried over MgSO$_4$, filtered and evaporated. The residue was purified by silica flash chromatography eluting with 10-15% methanol/dichloromethane to give 4-((1R,5S,9r)-3-((1H-imidazol-5-yl)methyl)-9-methoxy-3-azabicyclo[3.3.1]nonan-9-yl)picolinamide (81 mg, 47% yield).

To a solution of 4-((1R,5S,9r)-3-((1H-imidazol-5-yl)methyl)-9-methoxy-3-azabicyclo[3.3.1]nonan-9-yl)picolinamide (81 mg, 0.23 mmol) in 9:1 dichloromethane/methanol (5 mL) was added 2.0 M HCl in diethyl ether (0.14 mL, 0.23 mmol). The volatiles were removed and the residue freeze-dried from water to give 4-((1R,5S,9r)-3-((1H-imidazol-5-yl)methyl)-9-methoxy-3-azabicyclo[3.3.1]nonan-9-yl)picolinamide hydrochloride (79 mg, 89% yield); [M+H]$^+$ 356.05. $^1$H NMR (300 MHz, D6-DMSO): 8.91 (NH), 8.66 (d, 1H), 8.15 (s, 1H), 8.02 (s, 1H), 7.80-7.60 (m, 3H), 3.55-3.05 (m, 6H), 2.85-2.72 (m, 2H), 2.68 (s, 3H), 2.40-2.20 (m, 1H), 1.81-1.68 (m, 2H), 1.50-1.35 (m, 2H), 1.28-1.15 (m, 1H).
Compound 120

4-((1R,5S,9r)-3-((6-hydroxypyridin-2-yl)methyl)-9-methoxy-3-azabicyclo[3.3.1]nonan-9-yl)picolinamide Hydrochloride

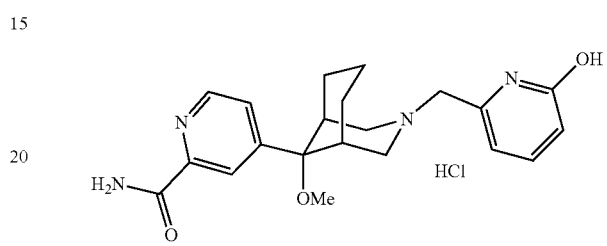

[M+H]$^+$ 383.2. $^1$H NMR (300 MHz, D6-DMSO): 9.25 (br s, 1H), 8.69 (d, 1H), 8.19 (br s, NH), 8.03 (s, 1H), 7.75 (s, 1H), 7.68 (d, 1H), 7.51 (dd, 1H), 6.68 (d, 1H), 6.48 (d, 1H), 4.24 (s, 2H), 3.55-3.35 (m, 4H), 2.97 (s, 2H), 2.72 (s, 3H), 2.25-2.10 (m, 1H), 1.90-1.78 (m, 2H), 1.55-1.25 (m, 3H).
Compound 77

4-((1R,5S,9r)-9-methoxy-3-(spiro[3.3]heptan-2-yl)-3-azabicyclo[3.3.1]nonan-9-yl)picolinamide Hydrochloride

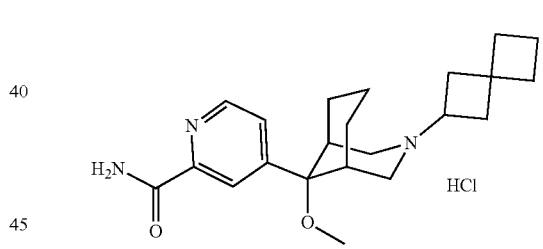

[M+H]$^+$ 370.20; $^1$H NMR (400 MHz, D$_2$O): 8.62 (d, 1H), 8.04 (s, 1H), 7.67 (d, 1H), 3.61-3.34 (m, 5H), 2.90-2.87 (m, 2H), 2.75 (s, 3H), 2.32-2.15 (m, 4H), 1.94-1.37 (m, 12H).
Compound 81

4-((1R,5S,9r)-9-methoxy-3-(2-oxaspiro[3.3]heptan-6-yl)-3-azabicyclo[3.3.1]nonan-9-yl)picolinamide (S)-2-hydroxysuccinate

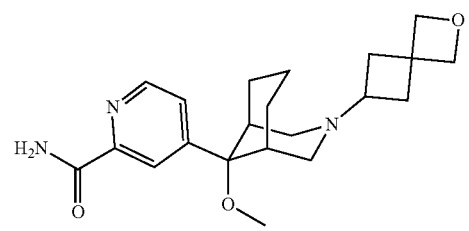

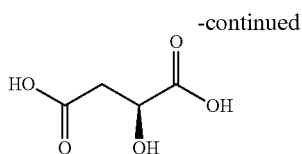

[M+H]⁺ 372.12; ¹H NMR (400 MHz, D₂O): 8.55 (d, 1H), 7.95 (s, 1H), 7.57 (d, 1H), 4.62 (s, 2H), 4.57 (s, 2H), 4.29-4.26 (m, 1H), 3.59-3.53 (m, 1H), 3.45-3.41 (m, 2H), 3.33-3.26 (m, 2H), 2.88-2.86 (m, 2H), 2.68-2.64 (m, 4H), 2.57-2.44 (m, 6H), 1.71-1.67 (m, 2H), 1.53-1.47 (m, 2H), 1.33-1.29 (m, 1H).

Compound 88

4-((1R,5S,9r)-3-(2-(1,1-dioxidoisothiazolidin-2-yl)ethyl)-9-methoxy-3-azabicyclo[3.3.1]nonan-9-yl)picolinamide Hydrochloride

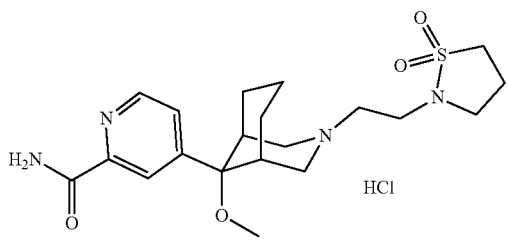 [SMILES: COC1(c2ccnc(C(N)=O)c2)C2CCCC1CN(CCN1CCCS1(=O)=O)C2 ; Cl]

[M+H]⁺ 423.02; ¹H NMR (300 MHz, D₂O): 8.63-8.57 (m, 1H), 8.02-7.96 (m, 1H), 7.64-7.59 (m, 1H), 3.77-3.25 (m, 12H), 2.89-2.88 (m, 2H), 2.75 (s, 3H), 2.38-2.25 (m, 2H), 1.90-1.77 (m, 2H), 1.72-1.39 (m, 4H).

Compounds 61 and 62

Synthesis of 4-((1R,5S,9S)-9-methoxy-3-((S)-1-methoxypropan-2-yl)-3-azabicyclo[3.3.1]nonan-9-yl)picolinamide hydrochloride and 4-((1R,5S,9R)-9-methoxy-3-((R)-1-methoxypropan-2-yl)-3-azabicyclo[3.3.1]nonan-9-yl)picolinamide Hydrochloride

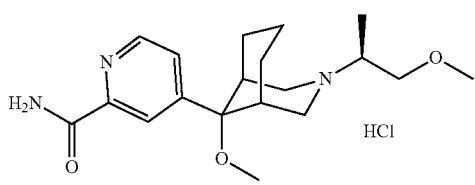

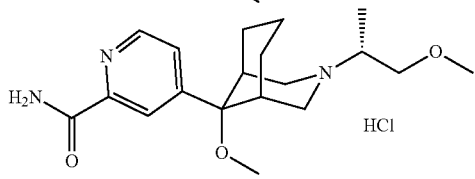

Methoxyacetone (0.15 mL, 1.60 mmol) was added to a suspension of 4-((1R,5S,9r)-9-methoxy-3-azabicyclo[3.3.1]nonan-9-yl)picolinamide hydrochloride (250 mg, 0.80 mmol) in dichloromethane (5 mL), followed by triethylamine (0.11 mL, 0.80 mmol). After stirring at room temperature for 15 minutes sodium triacetoxyborohydride (340 mg, 1.60 mmol) was added and the reaction mixture was stirred at room temperature for 16 hours. The mixture was quenched with aqueous sodium hydrogen carbonate solution and extracted with dichloromethane (×2). The combined organic phases were washed with brine, dried over MgSO₄, filtered and concentrated under reduced pressure. The residue was purified by silica chromatography eluting with 2-8% methanol in dichloromethane. The mixture of enantiomers were separated by chiral supercritical fluid chromatography and the stereochemistry arbitrarily assigned to give 4-((1R,5S,9S)-9-methoxy-3-((S)-1-methoxypropan-2-yl)-3-azabicyclo[3.3.1]nonan-9-yl)picolinamide (101 mg, 36% yield) and 4-((1R,5S,9R)-9-methoxy-3-((R)-1-methoxypropan-2-yl)-3-azabicyclo[3.3.1]nonan-9-yl)picolinamide (98 mg, 35% yield).

To a solution of 4-((1R,5S,9S)-9-methoxy-3-((S)-1-methoxypropan-2-yl)-3-azabicyclo[3.3.1]nonan-9-yl)picolinamide (101 mg, 0.29 mmol) in ethyl acetate (5 mL) was added 2 M hydrochloric acid in diethyl ether (0.17 mL, 0.35 mmol) and the reaction mixture was stirred for 15 minutes. The mixture was concentrated under reduced pressure and the residue freeze dried from water to give 4-((1R,5S,9S)-9-methoxy-3-((S)-1-methoxypropan-2-yl)-3-azabicyclo[3.3.1]nonan-9-yl)picolinamide hydrochloride (112 mg, 100% yield); [M+H]⁺ 348.14; ¹H NMR (300 MHz, D₂O): 8.64 (d, 1H), 8.06 (s, 1H), 7.69 (d, 1H), 3.79-3.33 (m, 10H), 2.98-2.94 (m, 2H), 2.79 (s, 3H), 1.92-1.45 (m, 6H), 1.23 (s, 3H).

To a solution of 4-((1R,5S,9R)-9-methoxy-3-((R)-1-methoxypropan-2-yl)-3-azabicyclo[3.3.1]nonan-9-yl)picolinamide (98 mg, 0.28 mmol) in ethyl acetate (5 mL) was added 2 M hydrochloric acid in diethyl ether (0.17 mL, 0.34 mmol) and the reaction mixture was stirred for 15 minutes. The mixture was concentrated under reduced pressure and the residue freeze dried from water to give 4-((1R,5S,9R)-9-methoxy-3-((R)-1-methoxypropan-2-yl)-3-azabicyclo[3.3.1]nonan-9-yl)picolinamide hydrochloride (110 mg, 100% yield); [M+H]⁺ 348.21; ¹H NMR (400 MHz, D₂O): 8.63 (d, 1H), 8.05 (s, 1H), 7.68 (d, 1H), 3.76-3.71 (m, 1H), 3.63-3.58 (m, 3H), 3.55-3.34 (m, 3H), 3.33 (s, 3H), 2.97-2.93 (m, 2H), 2.77 (s, 3H), 1.88-1.78 (m, 2H), 1.67-1.55 (m, 2H), 1.52-1.38 (m, 2H), 1.22 (d, 3H).

Compound 125

4-((1R,5S,9r)-9-methoxy-3-((1-methyl-1H-1,2,3-triazol-5-yl)methyl)-3-azabicyclo[3.3.1]nonan-9-yl)picolinamide Hydrochloride

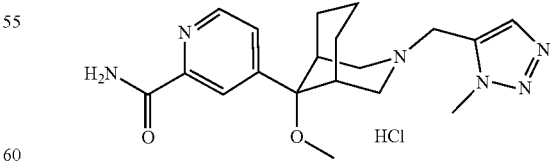

[M+H]⁺ 371.14; ¹H NMR (300 MHz, D₂O): 8.58 (d, 1H), 7.99-7.96 (m, 2H), 7.61-7.58 (m, 1H), 4.55 (s, 2H), 4.06 (s, 3H), 3.63-3.50 (m, 4H), 2.94-2.88 (m, 2H), 2.65 (s, 3H), 1.81-1.37 (m, 6H).

Compounds 135 and 136

Synthesis of 4-((1R,5S,9S)-9-methoxy-3-(((S)-tetrahydrofuran-2-yl)methyl)-3-azabicyclo[3.3.1]nonan-9-yl)picolinamide hydrochloride and 4-((1R,5S,9R)-9-methoxy-3-(((R)-tetrahydrofuran-2-yl)methyl)-3-azabicyclo[3.3.1]nonan-9-yl)picolinamide Hydrochloride

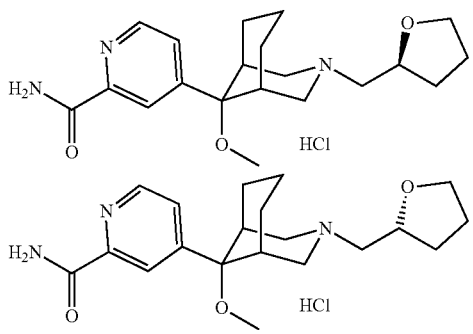

Dess-Martin periodinane (1.22 g, 2.89 mmol) was added to a solution of tetrahydrofurfuryl alcohol (0.28 mL, 2.89 mmol) in dichloromethane (8 mL) cooled in an ice bath. After stirring at room temperature for 2 hours the reaction mixture was filtered through celite, washing through with dichloromethane, and 4-((1R,5S,9r)-9-methoxy-3-azabicyclo[3.3.1]nonan-9-yl)picolinamide hydrochloride (300 mg, 0.96 mmol) and acetic acid (0.11 mL, 1.92 mmol) were added. After stirring at room temperature for 20 minutes, sodium triacetoxyborohydride (408 mg, 1.92 mmol) was added and the reaction mixture was stirred for 16 hours and then quenched with aqueous sodium hydrogen carbonate solution. The mixture was extracted with dichloromethane (×2) and the combined organic phases were washed with brine, dried over MgSO₄, filtered and concentrated under reduced pressure. The residue was purified by silica chromatography eluting with 2-8% methanol in dichloromethane. The mixture of enantiomers were separated by chiral supercritical fluid chromatography and then the enantiomers purified via preparative HPLC to give 4-((1R,5S,9S)-9-methoxy-3-(((S)-tetrahydrofuran-2-yl)methyl)-3-azabicyclo[3.3.1]nonan-9-yl)picolinamide (50 mg, 14% yield); and reverse phase chromatography (C18) to give 4-((1R,5S,9R)-9-methoxy-3-(((R)-tetrahydrofuran-2-yl)methyl)-3-azabicyclo[3.3.1]nonan-9-yl)picolinamide (48 mg, 14% yield). The stereochemistry of the enantiomers was arbitrarily assigned.

To a solution of 4-((1R,5S,9S)-9-methoxy-3-(((S)-tetrahydrofuran-2-yl)methyl)-3-azabicyclo[3.3.1]nonan-9-yl)picolinamide (50 mg, 0.14 mmol) in ethyl acetate (2 mL) was added 2 M hydrochloric acid in diethyl ether (0.07 mL, 0.15 mmol) and the reaction mixture was stirred for 15 minutes. The mixture was concentrated under reduced pressure and the residue freeze dried from water to give 4-((1R,5S,9S)-9-methoxy-3-(((S)-tetrahydrofuran-2-yl)methyl)-3-azabicyclo[3.3.1]nonan-9-yl)picolinamide hydrochloride (50 mg, 91% yield); [M+H]⁺ 360.17; ¹H NMR (300 MHz, D₂O): 8.66 (d, 1H), 8.09 (s, 1H), 7.72 (d, 1H), 4.35-4.30 (m, 1H), 3.85-3.56 (m, 6H), 3.23-3.11 (m, 2H), 2.96-2.91 (m, 2H), 2.76 (s, 3H), 2.12-2.01 (m, 1H), 1.90-1.79 (m, 4H), 1.68-1.47 (m, 5H).

To a solution of 4-((1R,5S,9R)-9-methoxy-3-(((R)-tetrahydrofuran-2-yl)methyl)-3-azabicyclo[3.3.1]nonan-9-yl)picolinamide (48 mg, 0.13 mmol) in ethyl acetate (4 mL) was added 2 M hydrochloric acid in diethyl ether (0.07 mL, 0.15 mmol) and the reaction mixture was stirred for 15 minutes. The mixture was concentrated under reduced pressure and the residue freeze dried from water to give 4-((1R,5S,9R)-9-methoxy-3-(((R)-tetrahydrofuran-2-yl)methyl)-3-azabicyclo[3.3.1]nonan-9-yl)picolinamide hydrochloride (48 mg, 90% yield); [M+H]⁺ 360.10; ¹H NMR (300 MHz, D₂O): 8.66 (d, 1H), 8.09 (s, 1H), 7.72 (d, 1H), 4.35-4.29 (m, 1H), 3.85-3.56 (m, 6H), 3.23-3.11 (m, 2H), 2.96-2.91 (m, 2H), 2.76 (s, 3H), 2.12-2.01 (m, 1H), 1.90-1.79 (m, 4H), 1.68-1.47 (m, 5H).

Compounds 2 and 5

4-((1R,5S,9R)-3-((1 s,3S)-3-fluorocyclobutyl)-9-methoxy-3-azabicyclo[3.3.1]nonan-9-yl)picolinamide hydrochloride and 4-((1R,5S,9R)-3-((1r,3R)-3-fluorocyclobutyl)-9-methoxy-3-azabicyclo[3.3.1]nonan-9-yl)picolinamide Hydrochloride

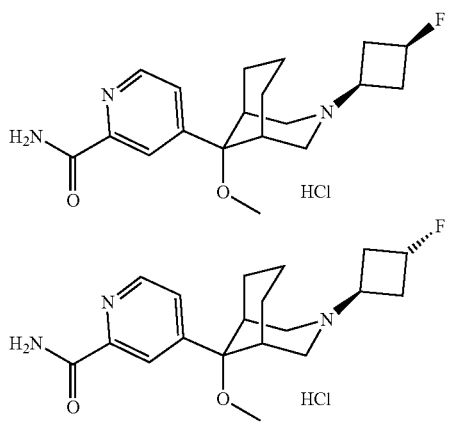

[M+H]⁺ 348.14; ¹H NMR (300 MHz, D₂O): 8.64 (d, 1H), 8.06 (s, 1H), 7.68 (d, 1H), 4.99-4.70 (d, 1H), 3.62-3.57 (m, 2H), 3.50-3.36 (m, 3H), 2.97-2.95 (m, 2H), 2.88-2.51 (m, 7H), 1.95-1.77 (m, 2H), 1.64-1.40 (m, 4H).

[M+H]⁺ 348.14; ¹H NMR (300 MHz, D₂O): 8.65 (d, 1H), 8.07 (s, 1H), 7.70 (d, 1H), 5.32-5.09 (m, 1H), 4.17-4.11 (m, 1H), 3.58-3.41 (m, 4H), 2.98-2.94 (m, 2H), 2.91-2.51 (m, 7H), 1.82-1.76 (m, 2H), 1.64-1.39 (m, 4H).

Compound 113

4-((1R,5S,9r)-9-methoxy-3-(oxazol-2-ylmethyl)-3-azabicyclo[3.3.1]nonan-9-yl)picolinamide Hydrochloride

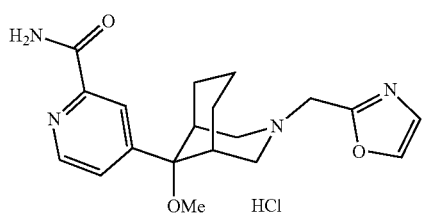 [SMILES: COC1(c2ccnc(C(N)=O)c2)C2CCCC1CN(Cc1ncco1)C2 ; Cl]

[M+H]⁺ 357.18. ¹H NMR (300 MHz, D₂O): 8.59 (s, 1H), 8.09-7.87 (m, 2H), 7.61 (s, 1H), 7.20 (s, 1H), 4.63-4.50 (m, 2H), 3.66-3.59 (m, 4H), 2.92 (br s, 2H), 2.66 (s, 3H), 1.80-1.55 (m, 6H).

Compound 123

Synthesis of 4-((1R,5S,9r)-9-methoxy-3-((1-methyl-1H-imidazol-4-yl)methyl)-3-azabicyclo[3.3.1]nonan-9-yl)picolinamide Hydrochloride

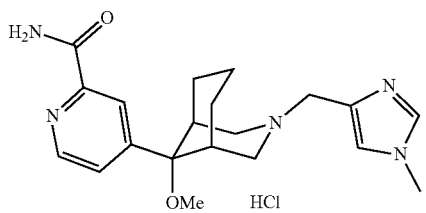 [SMILES: COC1(c2ccnc(C(N)=O)c2)C2CCCC1CN(Cc1cn(C)cn1)C2 ; Cl]

To a suspension of 4-((1R,5S,9r)-9-methoxy-3-azabicyclo[3.3.1]nonan-9-yl)picolinamide hydrochloride (100 mg, 0.32 mmol), 1-methyl-1H-imidazole-4-carboxaldehyde (70 mg, 0.64 mmol) and acetic acid (37 μL, 0.64 mmol) in dichloromethane (5 mL) was added sodium triacetoxyborohydride (203 mg, 0.96 mmol) at ambient temperature. After stirring for 16 hours, the reaction was quenched with saturated aqueous sodium hydrogen carbonate solution and extracted with dichloromethane (×3). The combined organic extracts were washed with brine, dried over magnesium sulfate, filtered and concentrated under reduced pressure. The residue was purified by silica column chromatography, eluting with 2-10% methanol in dichloromethane to yield 4-((1R,5S,9r)-9-methoxy-3-((1-methyl-1H-imidazol-4-yl)methyl)-3-azabicyclo[3.3.1]nonan-9-yl)picolinamide (84 mg, 71% yield).

To 4-((1R,5S,9r)-9-methoxy-3-((1-methyl-1H-imidazol-4-yl)methyl)-3-azabicyclo[3.3.1]nonan-9-yl)picolinamide (125 mg, 0.34 mmol) in ethyl acetate (10 mL) and dichloromethane (2 mL), was added 2M HCl in diethyl ether (0.17 mL, 0.34 mmol). The solvent was removed under reduced pressure. The resulting solid was triturated with diethyl ether and the liquors decanted. The solid was dried, dissolved in water and freeze-dried to yield 4-((1R,5S,9r)-9-methoxy-3-((1-methyl-1H-imidazol-4-yl)methyl)-3-azabicyclo[3.3.1]nonan-9-yl)picolinamide hydrochloride (83 mg, 60% yield). [M+H]$^+$ 370.15. $^1$H NMR (400 MHz, D$_2$O): 8.60 (d, 1H), 8.21 (s, 1H), 7.98 (s, 1H), 7.60 (d, 1H), 7.54 (s, 1H), 4.33 (s, 2H), 3.74 (s, 3H), 3.61 (d, 2H), 3.48 (d, 2H), 2.92 (s, 2H), 2.67 (s, 3H), 1.85-1.68 (m, 2H), 1.56-1.42 (m, 4H).

Compounds 139 and 179

4-((1R,5S,9R)-9-methoxy-3-((1 r,3R)-3-methoxycyclobutyl)-3-azabicyclo[3.3.1]nonan-9-yl)picolinamide hydrochloride and 4-((1R,5S,9R)-9-methoxy-3-((1s,3S)-3-methoxycyclobutyl)-3-azabicyclo[3.3.1]nonan-9-yl)picolinamide Hydrochloride

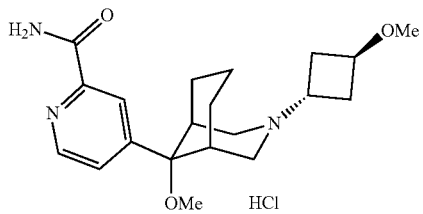

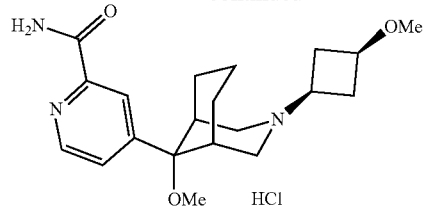

[M+H]$^+$ 360.17. $^1$H NMR (400 MHz, D$_2$O): 8.54 (d, 1H), 7.96 (s, 1H), 7.57 (d, 1H), 3.98 (t, 1H), 3.86 (quint, 1H), 3.47 (d, 2H), 3.34 (d, 2H), 3.11 (s, 3H), 2.86 (br s, 2H), 2.69 (s, 3H), 2.56-2.44 (m, 2H), 2.27 (dd, 2H), 1.69 (d, 2H), 1.49 (d, 3H), 1.31 (s, 1H).

[M+H]$^+$ 360.17. $^1$H NMR (400 MHz, D$_2$O): 8.35 (d, 1H), 7.95 (s, 1H), 7.56 (d, 1H), 3.65 (quint., 1H), 3.45 (d, 2H), 3.33 (d, 3H), 3.11 (s, 3H), 2.86 (br s, 2H), 2.69 (s, 3H), 2.65-2.55 (m, 2H), 2.31 (q, 2H), 1.70 (d, 2H), 1.52 (d, 3H), 1.30 (s, 1H).

Compound 8

4-((1R,5S,9r)-9-methoxy-3-(2-(methylsulfonyl)ethyl)-3-azabicyclo[3.3.1]nonan-9-yl)picolinamide Hydrochloride

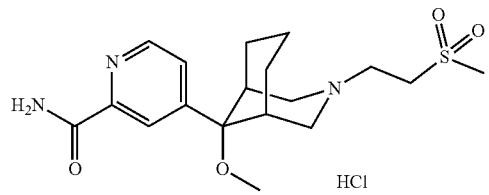 [SMILES: COC1(c2ccnc(C(N)=O)c2)C2CCCC1CN(CCS(C)(=O)=O)C2 ; Cl]

[M+H]$^+$ 382.18. $^1$H NMR (300 MHz, D$_2$O): 8.59 (d, 1H), 8.00 (s, 1H), 7.63 (s, 1H), 3.79-3.71 (m, 2H), 3.67-3.56 (m, 5H), 3.11 (s, 3H), 2.93 (br s, 2H), 2.73 (s, 3H), 1.79 (d, 2H), 1.65-1.42 (m, 5H).

Compound 86

4-((1R,5S,9r)-3-(2-cyclopropylethyl)-9-methoxy-3-azabicyclo[3.3.1]nonan-9-yl)picolinamide Hydrochloride

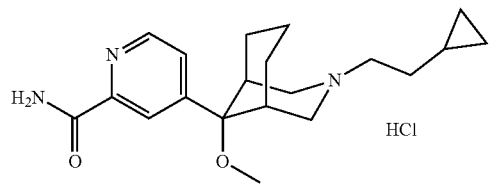 [SMILES: COC1(c2ccnc(C(N)=O)c2)C2CCCC1CN(CCC1CC1)C2 ; Cl]

[M+H]$^+$ 344.15. $^1$H NMR (300 MHz, DMSO-de): 8.73-8.60 (m, 2H), 8.17 (s, 1H), 8.04 (s, 1H), 7.76-7.66 (m, 2H), 3.58-3.47 (dd, 2H), 3.45-3.32 (m, 2H), 3.15-3.05 (m, 2H), 2.92 (s, 2H), 2.74 (s, 3H), 2.15-1.97 (m, 1H), 1.86-1.74 (dd, 2H), 1.74-1.63 (m, 2H), 1.54-1.36 (m, 2H), 1.34-1.18 (m, 1H), 0.72-0.59 (m, 1H), 0.47-0.38 (m, 2H), 0.17-0.09 (m, 2H).

Compound 83

4-((1R,5S,9r)-9-methoxy-3-(2-methoxyethyl)-3-azabicyclo[3.3.1]nonan-9-yl)picolinamide Hydrochloride

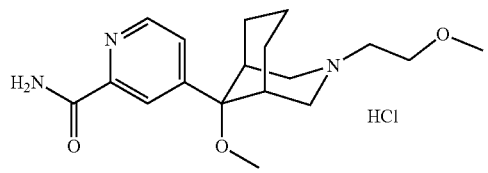 [SMILES: COCCN1CC2CCCC(C1)C2(OC)c1ccnc(C(N)=O)c1 ; Cl]

[M+H]+ 334.10. ¹H NMR (300 MHz, DMSO-d₆): 8.70 (d, 1H), 8.39 (br s, 1H), 8.17 (s, 1H), 8.04 (s, 1H), 7.73 (d, 1H), 7.70-7.66 (dd, 1H), 3.76 (t, 2H), 3.60-3.44 (m, 4H), 3.35-3.26 (m, 5H), 2.95 (s, 2H), 2.74 (s, 3H), 2.02-1.77 (m, 3H), 1.55-1.26 (m, 3H).

Compounds 144, 145, 146 and 147

Synthesis of 1-ethoxycyclopropanol

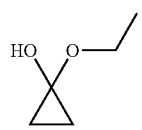

To a solution of (1-ethoxycyclopropoxy)trimethylsilane (17 mL, 84.6 mmol) in methanol (60 mL) was added 2 drops of 12M hydrochloric acid. The reaction was stirred at room temperature for 2 hours then the solvents were removed under reduced pressure at low temperature to afford 1-ethoxycyclopropanol (6.5 g, 75% yield). ¹H NMR (300 MHz, CDCl₃): 3.75 (q, 2H), 3.23 (br s, 1H), 1.21 (t, 3H), 0.96-0.90 (m, 4H).

Synthesis of 1-vinylcyclopropanol

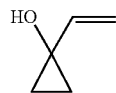

To vinyl magnesium bromide (29.4 mL, 1M in tetrahydrofuran, 29.4 mmol), at 0° C., was added a solution of 1-ethoxycyclopropanol (1.5 g, 14.7 mmol) in tetrahydrofuran (15 mL) over 15 minutes. The reaction was stirred at room temperature for 2 hours then at reflux for 3 hours before cooling to room temperature and quenching with water. The mixture was diluted with diethyl ether then filtered through celite. The phases were separated and the aqueous phase was extracted with diethyl ether. The organics were combined, dried over magnesium sulphate, filtered and the solvents removed under reduced pressure at low temperature to afford 1-vinylcyclopropanol (1 g, 81% yield). Material used crude in subsequent step. ¹H NMR (300 MHz, CDCl₃): 5.68-5.52 (m, 1H), 5.28 (d, 1H), 5.05 (d, 1H), 0.80-0.70 (m, 4H).

Synthesis of 4-((1R,5S,9S)-9-methoxy-3-((1S,2S)-2-methylcyclobutyl)-3-azabicyclo[3.3.1]nonan-9-yl)picolinamide, 4-((1R,5S,9S)-9-methoxy-3-((1S,2R)-2-methylcyclobutyl)-3-azabicyclo[3.3.1]nonan-9-yl)picolinamide, 4-((1R,5S,9R)-9-methoxy-3-((1R,2S)-2-methylcyclobutyl)-3-azabicyclo[3.3.1]nonan-9-yl)picolinamide and 4-((1R,5S,9R)-9-methoxy-3-((1R,2R)-2-methylcyclobutyl)-3-azabicyclo[3.3.1]nonan-9-yl)picolinamide

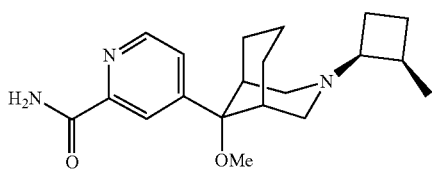

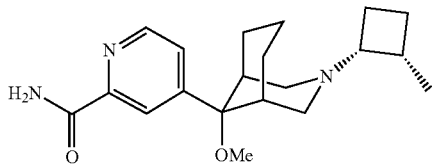

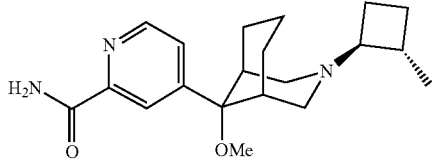 [SMILES: COC1(c2ccnc(C(N)=O)c2)C2CCCC1CN([C@H]1CC[C@@H]1C)C2 ; Cl]

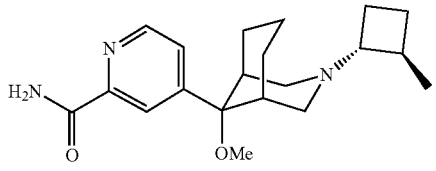

Hydrogen bromide gas was bubbled through a solution of 1-vinylcyclopropanol (1 g, 11.9 mmol) in dichloromethane (120 mL), at 0° C., for 2 minutes. The reaction was stirred at 0° C. for 5 minutes then quenched with saturated sodium hydrogen carbonate solution. The organic layer was dried over magnesium sulphate and filtered. Product stored as a solution in dichloromethane.

To a solution of 2-methylcyclobutanone (63 mL, 0.091M in dichloromethane, 5.77 mmol) was added 4-((1R,5S,9r)-9-methoxy-3-azabicyclo[3.3.1]nonan-9-yl)picolinamide hydrochloride (450 mg, 1.44 mmol), titanium (IV) isopropoxide (0.86 mL, 2.89 mmol), sodium triacetoxyborohydride (1.07 g, 5.05 mmol) and acetic acid (0.16 mL, 2.89 mmol). The reaction was stirred at room temperature for 16 hours then 2-methylcyclobutanone (30 mL, 0.091M in dichloromethane, 2.73 mmol) and sodium triacetoxyborohydride (1.07 g, 5.05 mmol) were added. The reaction was stirred at room temperature for 5 hours then quenched with saturated sodium hydrogen carbonate solution and filtered through celite. The phases were separated and the aqueous phase was extracted with dichloromethane. The combined organics were dried over magnesium sulphate, filtered and the solvents were removed under reduced pressure. The crude material was purified by C18 reverse chromatography then the enantiomers were separated by chiral SFC to afford 4-((1R,5S,9S)-9-methoxy-3-((1S,2S)-2-methylcyclobutyl)-3-azabicyclo[3.3.1]nonan-9-yl)picolinamide (75.4 mg, 15% yield); [M+H]+ 344.24, 4-((1R,5S,9S)-9-methoxy-3-((1

S,2R)-2-methylcyclobutyl)-3-azabicyclo[3.3.1]nonan-9-yl) picolinamide (9.3 mg, 2% yield); [M+H]+ 344.24, 4-((1R,5S,9R)-9-methoxy-3-((1R,2S)-2-methylcyclobutyl)-3-azabicyclo[3.3.1]nonan-9-yl)picolinamide (11.3 mg, 2% yield); [M+H]+ 344.24 and 4-((1R,5S,9R)-9-methoxy-3-((1R,2R)-2-methylcyclobutyl)-3-azabicyclo[3.3.1]nonan-9-yl)picolinamide (82.2 mg, 17% yield); [M+H]+ 344.24. Diastereomeric configuration determined by ¹H NMR, enantiomeric configuration arbitrarily assigned.

Compound 144

Synthesis of 4-((1R,5S,9S)-9-methoxy-3-((1 S,2S)-2-methylcyclobutyl)-3-azabicyclo[3.3.1]nonan-9-yl) picolinamide Hydrochloride

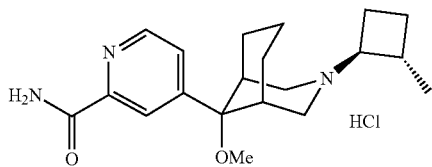

To a solution of 4-((1R,5S,9S)-9-methoxy-3-((1 S,2S)-2-methylcyclobutyl)-3-azabicyclo[3.3.1]nonan-9-yl)picolinamide (75.4 mg, 0.22 mmol) in ethyl acetate (0.3 mL) was added 2M HCl in diethyl ether (0.17 mL, 0.33 mmol) and the mixture was stirred at room temperature for 15 minutes. The solvents were removed under reduced pressure then the residue was dissolved in water and freeze dried to give 4-((1R,5S,9S)-9-methoxy-3-((1 S,2S)-2-methylcyclobutyl)-3-azabicyclo[3.3.1]nonan-9-yl)picolinamide hydrochloride (72.2 mg, 87% yield). [M+H]+ 344.18. ¹H NMR (300 MHz, D₂O): 8.64 (d, 1H), 8.08 (s, 1H), 7.72 (d, 1H), 3.64-3.56 (d, 1H), 3.53-3.46 (d, 1H), 3.43-3.25 (m, 3H), 2.92 (br s, 2H), 2.76 (s, 3H), 2.71-2.58 (m, 1H), 2.19-1.90 (m, 3H), 1.78 (d, 2H), 1.58 (d, 3H), 1.40-1.23 (m, 2H), 1.07 (d, 3H).

Compound 145

Synthesis of 4-((1R,5S,9S)-9-methoxy-3-((1 S,2R)-2-methylcyclobutyl)-3-azabicyclo[3.3.1]nonan-9-yl) picolinamide Hydrochloride

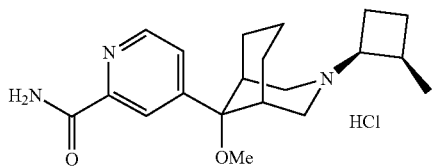 [SMILES: COC1(c2ccnc(C(N)=O)c2)C2CCCC1CN([C@H]1CC[C@H]1C)C2 ; Cl]

To a solution of 4-((1R,5S,9S)-9-methoxy-3-((1 S,2R)-2-methylcyclobutyl)-3-azabicyclo[3.3.1]nonan-9-yl)picolinamide (9.3 mg, 0.03 mmol) in ethyl acetate (0.10 mL) was added 2M HCl in diethyl ether (20 μL, 0.04 mmol) and the mixture was stirred at room temperature for 15 minutes. The solvents were removed under reduced pressure then the residue was dissolved in water and freeze dried to give 4-((1R,5S,9S)-9-methoxy-3-((1 S,2R)-2-methylcyclobutyl)-3-azabicyclo[3.3.1]nonan-9-yl)picolinamide hydrochloride (5.3 mg, 52% yield). [M+H]+ 344.18. ¹H NMR (300 MHz, D₂O): 8.67 (br s, 1H), 8.14 (s, 1H), 7.79 (d, 1H), 3.78-3.65 (m, 1H), 3.61-3.36 (m, 4H), 2.97 (s, 1H), 2.89 (s, 1H), 2.77 (s, 3H), 2.74-2.62 (m, 1H), 2.54-2.34 (m, 1H), 2.23-2.10 (m, 1H), 1.94-1.77 (m, 3H), 1.70-1.44 (m, 4H), 1.44-1.32 (t, 1H), 1.22 (d, 3H).

Compound 146

Synthesis of 4-((1R,5S,9R)-9-methoxy-3-((1R,2S)-2-methylcyclobutyl)-3-azabicyclo[3.3.1]nonan-9-yl) picolinamide Hydrochloride

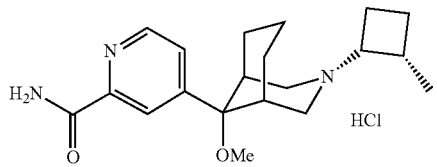

To a solution of 4-((1R,5S,9R)-9-methoxy-3-((1R,2S)-2-methylcyclobutyl)-3-azabicyclo[3.3.1]nonan-9-yl)picolinamide (11.3 mg, 0.03 mmol) in ethyl acetate (0.1 mL) was added 2M HCl in diethyl ether (25 μL, 0.05 mmol) and the mixture was stirred at room temperature for 15 minutes. The solvents were removed under reduced pressure then the residue was dissolved in water and freeze dried to afford 4-((1R,5S,9R)-9-methoxy-3-((1R,2S)-2-methylcyclobutyl)-3-azabicyclo[3.3.1]nonan-9-yl)picolinamide hydrochloride (6.5 mg, 52% yield). [M+H]+ 344.18. ¹H NMR (300 MHz, D₂O): 8.67 (br s, 1H), 8.14 (s, 1H), 7.79 (d, 1H), 3.78-3.65 (m, 1H), 3.61-3.36 (m, 4H), 2.97 (s, 1H), 2.89 (s, 1H), 2.77 (s, 3H), 2.74-2.62 (m, 1H), 2.54-2.34 (m, 1H), 2.23-2.10 (m, 1H), 1.94-1.77 (m, 3H), 1.70-1.44 (m, 4H), 1.44-1.32 (t, 1H), 1.22 (d, 3H).

Compound 147

Synthesis of 4-((1R,5S,9R)-9-methoxy-3-((1R,2R)-2-methylcyclobutyl)-3-azabicyclo[3.3.1]nonan-9-yl) picolinamide Hydrochloride

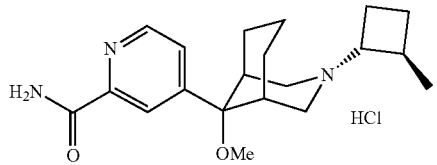

To a solution of 4-((1R,5S,9R)-9-methoxy-3-((1R,2R)-2-methylcyclobutyl)-3-azabicyclo[3.3.1]nonan-9-yl)picolinamide (82.2 mg, 0.24 mmol) in ethyl acetate (0.3 mL) was added 2M HCl in diethyl ether (0.18 mL, 0.36 mmol) and the mixture was stirred at room temperature for 15 minutes. The solvents were removed under reduced pressure then the residue was dissolved in water and freeze dried to afford 4-((1R,5S,9R)-9-methoxy-3-((1R,2R)-2-methylcyclobutyl)-3-azabicyclo[3.3.1]nonan-9-yl)picolinamide hydrochloride (89.5 mg, 98% yield). [M+H]+ 344.18. ¹H NMR (300 MHz, D₂O): 8.64 (d, 1H), 8.08 (s, 1H), 7.72 (d, 1H), 3.64-3.56 (d, 1H), 3.53-3.46 (d, 1H), 3.43-3.25 (m, 3H), 2.92 (br s, 2H), 2.76 (s, 3H), 2.71-2.58 (m, 1H), 2.19-1.90 (m, 3H), 1.78 (d, 2H), 1.58 (d, 3H), 1.40-1.23 (m, 2H), 1.07 (d, 3H).

Compound 118

Synthesis of 4-((1R,5S,9R)-9-methoxy-3-((R)-pentan-2-yl)-3-azabicyclo[3.3.1]nonan-9-yl)picolinamide and 4-((1R,5S,9S)-9-methoxy-3-((S)-pentan-2-yl)-3-azabicyclo[3.3.1]nonan-9-yl)picolinamide

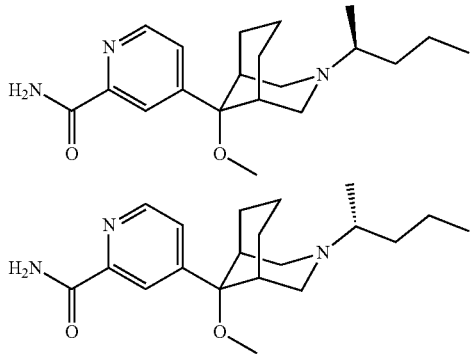

To a suspension of 4-((1R,5S,9r)-9-methoxy-3-azabicyclo[3.3.1]nonan-9-yl)picolinamide hydrochloride (600 mg, 1.92 mmol) in dichloromethane (12 mL) was added 2-pentanone (0.31 mL, 2.89 mmol), acetic acid (0.22 mL, 3.85 mmol) and sodium triacetoxyborohyride (1.22 g, 5.77 mmol). The reaction was stirred at room temperature for 20 hours then 2-pentanone (0.31 mL, 2.89 mmol) and sodium triacetoxyborohydride (1.22 g, 5.77 mmol) were added. The reaction was stirred at room temperature for 4 hours then was quenched with saturated sodium hydrogen carbonate solution. The organics were separated then dried over magnesium sulphate, filtered and the solvents removed under reduced pressure. The crude material was purified by C18 reverse phase chromatography to afford 4-((1R,5S,9R)-9-methoxy-3-((R)-pentan-2-yl)-3-azabicyclo[3.3.1]nonan-9-yl)picolinamide and 4-((1R,5S,9S)-9-methoxy-3-((S)-pentan-2-yl)-3-azabicyclo[3.3.1]nonan-9-yl)picolinamide (220 mg, 33% yield). The mixture (220 mg) was separated by chiral supercritical fluid chromatography to afford 4-((1R,5S,9R)-9-methoxy-3-((R)-pentan-2-yl)-3-azabicyclo[3.3.1]nonan-9-yl)picolinamide (70.3 mg, 11% yield); [M+H]$^+$ 346.23 and 4-((1R,5S,9S)-9-methoxy-3-((S)-pentan-2-yl)-3-azabicyclo[3.3.1]nonan-9-yl)picolinamide (67 mg, 10% yield); [M+H]$^+$ 346.23. The stereochemistry of the enantiomers was arbitrarily assigned.

Synthesis of 4-((1R,5S,9r)-9-methoxy-3-(pentan-2-yl)-3-azabicyclo[3.3.1]nonan-9-yl)picolinamide Hydrochloride

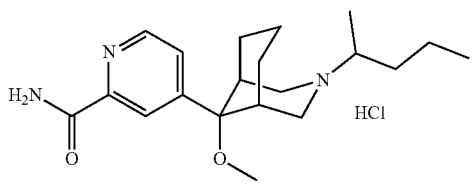 [SMILES: CCCC(C)N1CC2CCCC(C1)C2(OC)c1ccnc(C(N)=O)c1 ; Cl]

To 4-((1R,5S,9r)-9-methoxy-3-(pentan-2-yl)-3-azabicyclo[3.3.1]nonan-9-yl)picolinamide (20 mg, 0.06 mmol) in ethyl acetate (1 mL) was added 2M HCl in diethyl ether (44 µL, 0.09 mmol). After 10 minutes, the solvent was removed under reduced pressure. The product was dissolved in water and freeze dried to give 4-((1R,5S,9r)-9-methoxy-3-(pentan-2-yl)-3-azabicyclo[3.3.1]nonan-9-yl)picolinamide hydrochloride (13.86 mg, 63% yield); [M+H]$^+$ 346.16. $^1$H NMR (300 MHz, D$_2$O): 8.57 (d, 1H), 7.98 (s, 1H), 7.60 (d, 1H), 3.56 (d, 2H), 3.43-3.30 (t, 2H), 3.30-3.14 (m, 1H), 2.90 (s, 2H), 2.74 (s, 3H), 1.86-1.08 (m, 13H), 0.79 (t, 3H).

Compound 137

4-((1R,5S,9R)-9-methoxy-3-((R)-pentan-2-yl)-3-azabicyclo[3.3.1]nonan-9-yl)picolinamide Hydrochloride

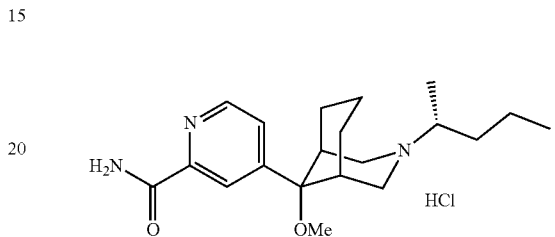

[M+H]$^+$ 346.23. $^1$H NMR (300 MHz, D$_2$O): 8.63 (d, 1H), 8.06 (s, 1H), 7.69 (d, 1H), 3.59 (d, 2H), 3.45-3.34 (t, 2H). 3.32-3.19 (m, 1H), 2.93 (s, 2H), 2.77 (s, 3H), 1.86-1.13 (m, 13H), 0.82 (t, 3H).

Compound 134

4-((1R,5S,9S)-9-methoxy-3-((S)-pentan-2-yl)-3-azabicyclo[3.3.1]nonan-9-yl)picolinamide Hydrochloride

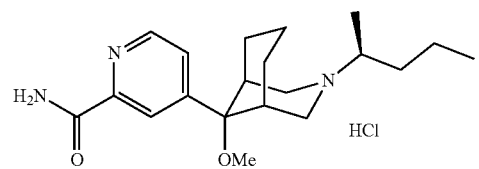 [SMILES: CCC[C@H](C)N1CC2CCCC(C1)C2(OC)c1ccnc(C(N)=O)c1 ; Cl]

[M+H]$^+$ 346.23. $^1$H NMR (300 MHz, D$_2$O): 8.64 (d, 1H), 8.08 (s, 1H), 7.72 (d, 1H), 3.58 (d, 2H), 3.45-3.33 (t, 2H), 3.32-3.18 (m, 1H), 2.93 (s, 2H), 2.76 (s, 3H), 1.85-1.11 (m, 13H), 0.81 (t, 3H).

Compound 121

4-((1R,5S,9r)-9-methoxy-3-((1-methyl-1H-imidazol-5-yl)methyl)-3-azabicyclo[3.3.1]nonan-9-yl)picolinamide Hydrochloride

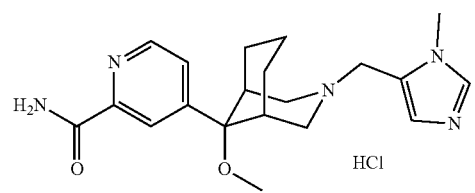 [SMILES: COC1(c2ccnc(C(N)=O)c2)C2CCCC1CN(Cc1cncn1C)C2 ; Cl]

[M+H]+ 370.15. ¹H NMR (300 MHz, DMSO-d6): 9.65 (br s, 1H), 9.23 (s, 1H), 8.69 (s, 1H), 8.19 (s, 1H), 8.04 (s, 1H), 7.78-7.65 (m, 2H), 4.51 (s, 3H), 3.97 (s, 3H), 3.70-3.58 (m, 2H), 3.55-3.41 (m, 2H), 2.96 (s, 1H), 2.72 (s, 4H), 2.33-2.19 (m, 1H), 1.87-1.63 (m, 2H), 1.51-1.35 (m, 2H), 1.26-1.13 (m, 1H).

Compound 158

Synthesis of 4-((1R,5S,9r)-9-methoxy-3-(2-oxaspiro[3.5]nonan-7-yl)-3-azabicyclo[3.3.1]nonan-9-yl)picolinamide (S)-2-hydroxysuccinate

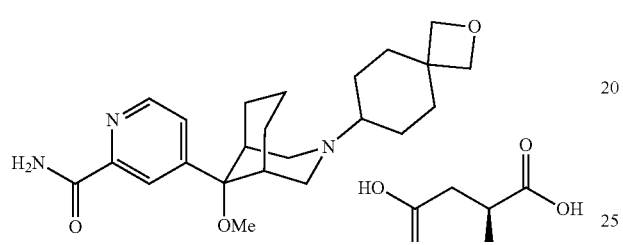

To a suspension of 4-((1R,5S,9r)-9-methoxy-3-azabicyclo[3.3.1]nonan-9-yl)picolinamide hydrochloride (250 mg, 0.80 mmol) in dichloromethane (6 mL) was added 2-oxaspiro[3.5]nonan-7-one (170 mg, 1.20 mmol), sodium triacetoxyborohydride (510 mg, 2.41 mmol) and acetic acid (92 µL, 1.60 mmol). The reaction was stirred at room temperature for 16 hours then 2-oxaspiro[3.5]nonan-7-one (100 mg, 0.71 mmol) and sodium triacetoxyborohydride (510 mg, 2.41 mmol) were added. The reaction was stirred at room temperature for 4 hours then quenched with saturated sodium hydrogen carbonate solution. The layers were separated and the aqueous phase was extracted with dichloromethane. The combined organics were washed with brine, dried over magnesium sulphate, filtered and the solvents removed under reduced pressure. The crude material was purified by C18 reverse phase chromatography then by preparative HPLC to afford 4-((1R,5S,9r)-9-methoxy-3-(2-oxaspiro[3.5]nonan-7-yl)-3-azabicyclo[3.3.1]nonan-9-yl)picolinamide (60 mg, 19% yield).

To a solution of 4-((1R,5S,9r)-9-methoxy-3-(2-oxaspiro[3.5]nonan-7-yl)-3-azabicyclo[3.3.1]nonan-9-yl)picolinamide (60 mg, 0.15 mmol) in ethyl acetate (0.5 mL) was added L-(−)-malic acid (20.5 mg, 0.15 mmol). The mixture was stirred at room temperature for 2 hours then the solvents were removed under reduced pressure. The residue was dissolved in water and freeze dried to afford 4-((1R,5S,9r)-9-methoxy-3-(2-oxaspiro[3.5]nonan-7-yl)-3-azabicyclo[3.3.1]nonan-9-yl)picolinamide (S)-2-hydroxysuccinate (77.7 mg, 97% yield). [M+H]+ 400.16. ¹H NMR (300 MHz, D₂O): 8.59 (d, 1H), 7.99 (s, 1H), 7.61 (d, 1H), 4.42 (s, 2H), 4.30 (s, 2H), 4.26-4.20 (m, 1H), 3.61-3.53 (m, 2H), 3.49-3.41 (d, 2H), 3.14-3.02 (m, 1H), 2.91 (br s, 2H), 2.74 (s, 3H), 2.71-2.63 (dd, 1H), 2.53-2.42 (dd, 1H), 2.23-2.17 (m, 2H), 2.08-1.99 (m, 2H), 1.82-1.71 (m, 2H), 1.63-1.36 (m, 8H).

Compounds 12 and 10

4-((1R,5S,9R)-3-((1R,3s,5S)-8-oxabicyclo[3.2.1]octan-3-yl)-9-methoxy-3-azabicyclo[3.3.1]nonan-9-yl)picolinamide hydrochloride and 4-((1R,5S,9R)-3-((1R,3r,5S)-8-oxabicyclo[3.2.1]octan-3-yl)-9-methoxy-3-azabicyclo[3.3.1]nonan-9-yl)picolinamide Hydrochloride

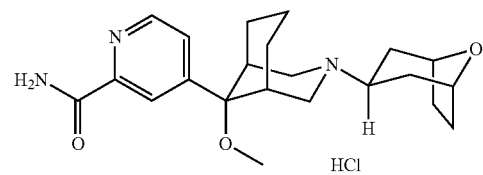

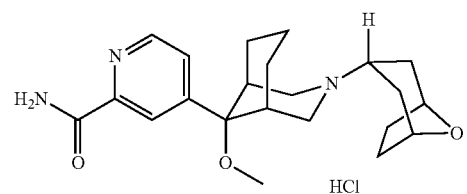

[M+H]+ 386.22. ¹H NMR (300 MHz, D₂O): 8.57 (d, 1H), 7.98 (s, 1H), 7.60 (d, 1H), 4.49-4.39 (m, 2H), 3.52-3.47 (m, 3H), 3.31-3.16 (m, 1H), 2.89 (s, 2H), 2.72 (s, 3H), 2.68-2.55 (m, 2H), 1.90-1.31 (m, 13H).

[M+H]+ 386.22. ¹H NMR (300 MHz, D₂O): 8.58 (d, 1H), 7.99 (s, 1H), 7.62 (d, 1H), 4.50-4.43 (m, 2H), 3.58-3.38 (m, 5H), 2.89 (s, 2H), 2.71 (s, 3H), 2.07-1.97 (dd, 2H), 1.90-1.78 (m, 4H), 1.75-1.62 (m, 4H), 1.56-1.48 (m, 3H), 1.31 (s, 1H).

Compound 115

4-((1R,5S,9r)-9-methoxy-3-((tetrahydro-2H-pyran-4-yl)methyl)-3-azabicyclo[3.3.1]nonan-9-yl)picolinamide Hydrochloride

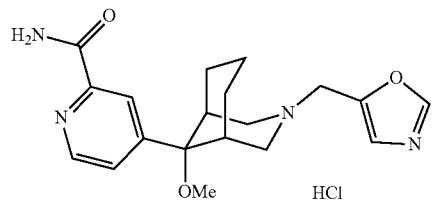 [SMILES: COC1(c2ccnc(C(N)=O)c2)C2CCCC1CN(Cc1cnco1)C2 ; Cl]

[M+H]+ 357.06. ¹H NMR (400 MHz, D₂O): 8.57 (d, 1H), 8.19 (s, 1H), 7.96 (s, 1H), 7.59 (s, 1H), 7.34 (s, 1H), 4.43 (s, 2H), 3.49-3.56 (m, 4H), 2.89 (s, 2H), 2.66 (s, 3H), 1.39-1.75 (m, 6H).

Compounds 131 and 130

4-((1R,5S,9R)-9-methoxy-3-((1 r,3R)-3-methylcyclobutyl)-3-azabicyclo[3.3.1]nonan-9-yl)picolinamide hydrochloride and 4-((1R,5S,9R)-9-methoxy-3-((1s,3S)-3-methylcyclobutyl)-3-azabicyclo[3.3.1]nonan-9-yl)picolinamide Hydrochloride

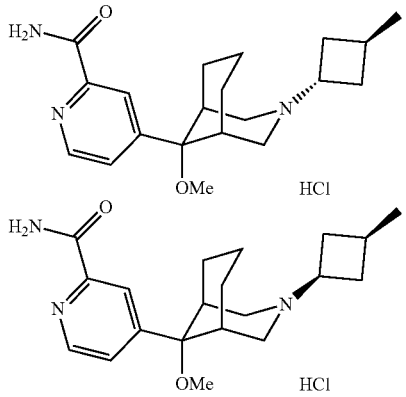

[M+H]$^+$ 344.18. $^1$H NMR (400 MHz, D$_2$O): 8.60 (dd, 1H), 8.02 (s, 1H), 7.65 (dd, 1H), 3.78-3.89 (m, 1H), 3.32-3.49 (m, 4H), 2.89 (s, 2H), 2.74 (s, 3H), 2.26-2.45 (m, 3H), 1.73-1.90 (m, 4H), 1.54 (d, 3H), 1.30 (s, 1H), 1.03 (d, 3H).
[M+H]$^+$ 344.18. $^1$H NMR (400 MHz, D$_2$O): 8.63 (d, 1H), 8.08 (s, 1H), 7.73 (d, 1H), 3.34-3.57 (m, 5H), 2.89 (s, 2H), 2.73 (s, 3H), 2.27-2.35 (m, 2H), 1.91-2.06 (m, 1H), 1.74-1.84 (m, 4H), 1.50-1.60 (m, 3H), 1.35 (s, 1H), 0.97 (d, 3H).

Compound 106

Synthesis of tert-butyl (3-phenylbicyclo[1.1.1]pentan-1-yl)carbamate

Diphenylphosphoryl azide (2.28 mL, 10.6 mmol) was added to a mixture of 3-Phenylbicyclo[1.1.1]pentane carboxylic acid (2.00 g, 10.6 mmol), triethylamine (1.48 mL, 10.6 mmol) and tert-butanol (30 mL) at room temperature and stirred for 6 hours. The mixture was then heated under reflux for 24 hours. The solvent was removed in vacuo, the residue was dissolved in a 1:1 mixture of ethyl acetate and tert-butylmethylether (≈50 mL) and washed with saturated sodium hydrogen carbonate solution. The aqueous phase was washed with ethyl acetate and the combined organics were dried over MgSO$_4$, filtered and the solvent removed under reduced pressure to yield tert-butyl (3-phenylbicyclo[1.1.1]pentan-1-yl)carbamate (2.73 g, 99% yield). $^1$H NMR (CDCl$_3$; 300 MHz): 7.35-7.15 (m, 5H), 4.98 (s, 1H), 2.27 (s, 6H), 1.46 (s, 9H).

Synthesis of 3-phenylbicyclo[1.1.1]pentan-1-amine

4M HCl in dioxane (15 mL, 60.0 mmol) was added to a solution of tert-Butyl (3-phenylbicyclo[1.1.1]pentan-1-yl)carbamate (2.73 g, 10.5 mmol) in ethyl acetate (15 mL) at room temperature and left to stir at room temperature for 20 hours. The resulting white suspension was concentrated under reduced pressure to ~⅓ of its original volume, filtered and the white solid was washed with diethyl ether. The white solid was added to saturated potassium carbonate solution, the aqueous phase was then extracted with ethyl acetate (×2), the solvent was removed under reduced pressure and the residue azeotroped with toluene to yield 3-phenylbicyclo[1.1.1]pentan-1-amine (1.25 g, 74% yield). $^1$H NMR (CDCl$_3$; 300 MHz): 7.38-7.15 (m, 5H), 2.11 (s, 6H).1.76 (s, br 2H).

Synthesis of 3-(3-phenylbicyclo[1.1.1]pentan-1-yl)-1,5,3-dioxazepane

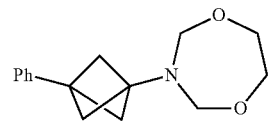 [SMILES: c1ccc(C23CC(N4COCCOC4)(C2)C3)cc1]

A mixture of 3-phenylbicyclo[1.1.1]pentan-1-amine (1.25 g, 7.9 mmol), paraformaldehyde (0.59 g, 19.6 mmol), ethylene glycol (0.53 mL, 9.4 mmol) and toluene (30 mL) were heated under reflux employing a Dean-Stark trap to remove the water. After 3 hours, additional paraformaldehyde (0.15 g, 4.9 mmol), ethylene glycol (0.13 mL, 2.3 mmol) were added and this was repeated every 3 hours until the reaction progressed to completion. The reaction mixture was cooled to room temperature, diluted with ethyl acetate and washed with brine then concentrated to yield 3-(3-phenylbicyclo[1.1.1]pentan-1-yl)-1,5,3-dioxazepane (2.04 g). $^1$H NMR (CDCl$_3$; 300 MHz) 7.35-7.15 (m, 5H), 4.59 (s, 4H), 3.38 (s, 4H), 2.20 (s, 6H).

Synthesis of (1R,5S)-3-(3-phenylbicyclo[1.1.1]pentan-1-yl)-3-azabicyclo[3.3.1]nonan-9-one

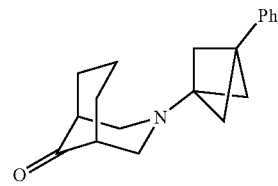 [SMILES: O=C1C2CCCC1CN(C13CC(c4ccccc4)(C1)C3)C2]

Acetyl chloride (1.67 mL, 23.55 mmol) was added dropwise over ~5 minutes to a solution of 3-(3-phenylbicyclo[1.1.1]pentan-1-yl)-1,5,3-dioxazepane (2.04 g, 7.85 mmol) in methanol (25 mL) cooled to 0° C., then cyclohexanone (0.77 g, 7.85 mmol) in methanol (5 mL) was added and the mixture was stirred for a further ~5 minutes before the ice/water bath was removed. The reaction mixture was allowed to warm to room temperature and stirred for a further 20 hours. The mixture was basified with concentrated aqueous ammonia and the cloudy aqueous mixture was extracted with ethyl acetate (×3). The combined organic fractions were washed with brine, concentrated under reduced pressure and azeotroped with toluene. The residue was dissolved in 4M HCl (aq) (20 mL) and heated at 50° C.

for 3 hours. The mixture was cooled, basified with concentrated aqueous ammonia and the cloudy aqueous mixture was extracted with ethyl acetate (×3). The combined organic fractions were washed with brine, concentrated under reduced pressure and azeotroped with toluene. Purification by silica column chromatography, eluted with 0-5% ethyl acetate in heptanes yielded (1R,5S)-3-(3-phenylbicyclo[1.1.1]pentan-1-yl)-3-azabicyclo[3.3.1]nonan-9-one (317 mg, 14% over 2 steps); [M+H]$^+$ 282.17.

Synthesis of (1R,5S,9r)-9-(2-chloropyridin-4-yl)-3-(3-phenylbicyclo[1.1.1]pentan-1-yl)-3-azabicyclo[3.3.1]nonan-9-ol and (1R,5S,9s)-9-(2-chloropyridin-4-yl)-3-(3-phenylbicyclo[1.1.1]pentan-1-yl)-3-azabicyclo[3.3.1]nonan-9-ol

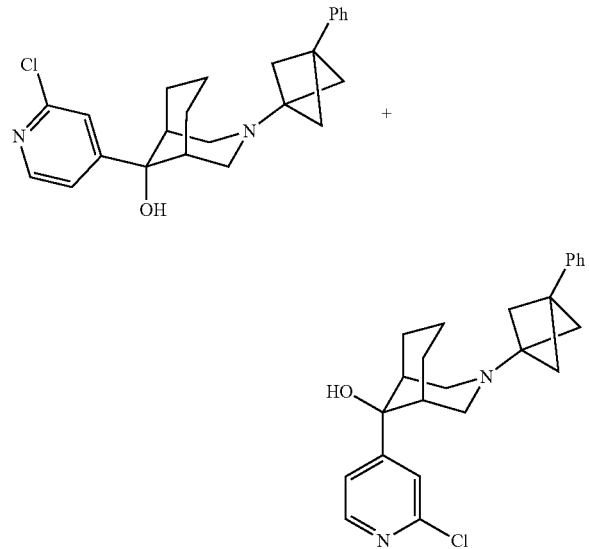

n-Butyl lithium (0.5 mL, 2.3 M solution in hexanes, 1.15 mmol) was added over ~10 minutes to a mixture of (1R,5S)-3-(3-phenylbicyclo[1.1.1]pentan-1-yl)-3-azabicyclo[3.3.1]nonan-9-one (271 mg, 0.96 mmol) and 4-iodo-2-chloropyridine (299 mg, 1.25 mmol) in diethyl ether (13.5 mL) cooled to ~78° C. The mixture was stirred for 15 minutes, the cooling bath was removed and the mixture was allowed to warm to room temperature. The mixture was quenched with water, the organics were removed under reduced pressure and the aqueous residue extracted with ethyl acetate (×2). The combined organics were dried over MgSO$_4$, filtered and the solvent removed under reduced pressure to yield a yellow solid. This material was combined with the crude from a trial reaction starting from (1R,5S)-3-(3-phenylbicyclo[1.1.1]pentan-1-yl)-3-azabicyclo[3.3.1]nonan-9-one (48 mg, 0.17 mmol) and purified by silica column chromatography, eluting with 0-15% ethyl acetate in dichloromethane to yield (1R,5S,9r)-9-(2-chloropyridin-4-yl)-3-(3-phenylbicyclo[1.1.1]pentan-1-yl)-3-azabicyclo[3.3.1]nonan-9-ol and (1R,5S,9s)-9-(2-chloropyridin-4-yl)-3-(3-phenylbicyclo[1.1.1]pentan-1-yl)-3-azabicyclo[3.3.1]nonan-9-ol (273 mg, 63% yield); [M+H]$^+$ 282.17.

Synthesis of (1R,5S,9r)-9-(2-chloropyridin-4-yl)-9-methoxy-3-(3-phenylbicyclo[1.1.1]pentan-1-yl)-3-azabicyclo[3.3.1]nonane and (1R,5S,9s)-9-(2-chloropyridin-4-yl)-9-methoxy-3-(3-phenylbicyclo[1.1.1]pentan-1-yl)-3-azabicyclo[3.3.1]nonane

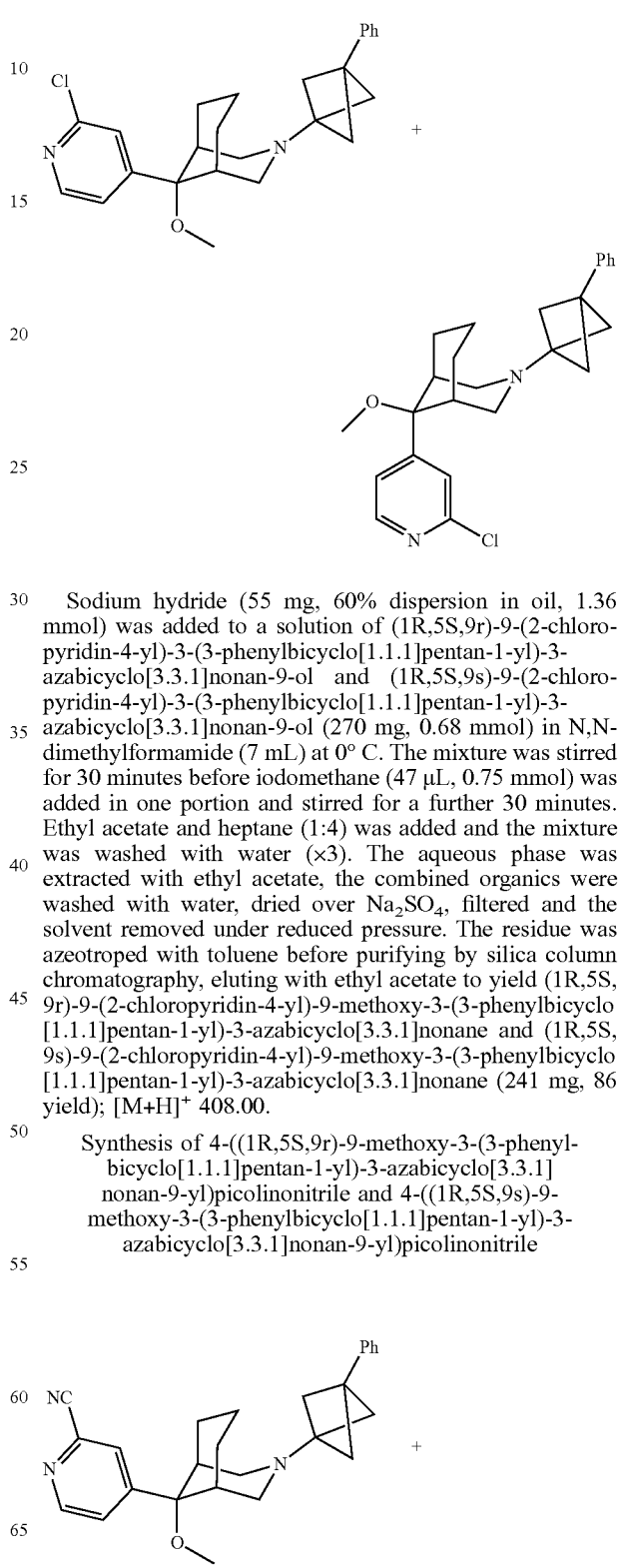

Sodium hydride (55 mg, 60% dispersion in oil, 1.36 mmol) was added to a solution of (1R,5S,9r)-9-(2-chloropyridin-4-yl)-3-(3-phenylbicyclo[1.1.1]pentan-1-yl)-3-azabicyclo[3.3.1]nonan-9-ol and (1R,5S,9s)-9-(2-chloropyridin-4-yl)-3-(3-phenylbicyclo[1.1.1]pentan-1-yl)-3-azabicyclo[3.3.1]nonan-9-ol (270 mg, 0.68 mmol) in N,N-dimethylformamide (7 mL) at 0° C. The mixture was stirred for 30 minutes before iodomethane (47 µL, 0.75 mmol) was added in one portion and stirred for a further 30 minutes. Ethyl acetate and heptane (1:4) was added and the mixture was washed with water (×3). The aqueous phase was extracted with ethyl acetate, the combined organics were washed with water, dried over Na$_2$SO$_4$, filtered and the solvent removed under reduced pressure. The residue was azeotroped with toluene before purifying by silica column chromatography, eluting with ethyl acetate to yield (1R,5S,9r)-9-(2-chloropyridin-4-yl)-9-methoxy-3-(3-phenylbicyclo[1.1.1]pentan-1-yl)-3-azabicyclo[3.3.1]nonane and (1R,5S,9s)-9-(2-chloropyridin-4-yl)-9-methoxy-3-(3-phenylbicyclo[1.1.1]pentan-1-yl)-3-azabicyclo[3.3.1]nonane (241 mg, 86 yield); [M+H]$^+$ 408.00.

Synthesis of 4-((1R,5S,9r)-9-methoxy-3-(3-phenylbicyclo[1.1.1]pentan-1-yl)-3-azabicyclo[3.3.1]nonan-9-yl)picolinonitrile and 4-((1R,5S,9s)-9-methoxy-3-(3-phenylbicyclo[1.1.1]pentan-1-yl)-3-azabicyclo[3.3.1]nonan-9-yl)picolinonitrile -continued

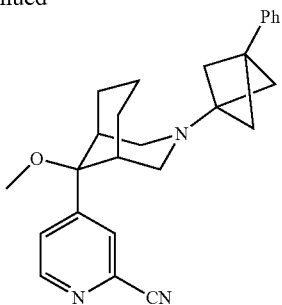

1,1'-Bis(diphenylphosphino)ferrocene (33 mg, 0.06 mmol) and tris(dibenzylideneacetone)dipalladium(0) (54 mg, 0.06 mmol) were added to a mixture of (1R,5S,9r)-9-(2-chloropyridin-4-yl)-9-methoxy-3-(3-phenylbicyclo[1.1.1]pentan-1-yl)-3-azabicyclo[3.3.1]nonane and (1R,5S,9s)-9-(2-chloropyridin-4-yl)-9-methoxy-3-(3-phenylbicyclo[1.1.1]pentan-1-yl)-3-azabicyclo[3.3.1]nonane (241 mg, 0.59 mmol) in N,N-dimethylformamide (5 mL) and heated to 60° C. Zinc cyanide (138 mg, 1.18 mmol) was added and the mixture was heated to 120° C. for 2.5 hours then left to cool to room temperature. Saturated sodium hydrogen carbonate solution was added and the mixture was extracted with ethyl acetate (×3). The organics were combined, concentrated under reduced pressure and azeotroped with toluene. The residue was purified by silica column chromatography, eluting with 5-20% ethyl acetate in heptane to give 4-((1R,5S,9r)-9-methoxy-3-(3-phenylbicyclo[1.1.1]pentan-1-yl)-3-azabicyclo[3.3.1]nonan-9-yl)picolinonitrile and 4-((1R,5S,9s)-9-methoxy-3-(3-phenylbicyclo[1.1.1]pentan-1-yl)-3-azabicyclo[3.3.1]nonan-9-yl)picolinonitrile (157 mg, 67% yield); [M+H]+ 399.00.

Synthesis of 4-((1R,5S,9r)-9-methoxy-3-(3-phenylbicyclo[1.1.1]pentan-1-yl)-3-azabicyclo[3.3.1]nonan-9-yl)picolinamide Hydrochloride

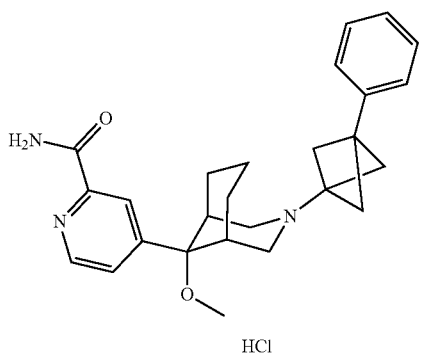 [SMILES: COC1(c2ccnc(C(N)=O)c2)C2CCCC1CN(C13CC(c4ccccc4)(C1)C3)C2 ; Cl]

To a solution of 4-((1R,5S,9r)-9-methoxy-3-(3-phenylbicyclo[1.1.1]pentan-1-yl)-3-azabicyclo[3.3.1]nonan-9-yl)picolinonitrile in tert-butanol is added potassium hydroxide and the mixture is heated under reflux for 30 minutes. The reaction mixture is cooled to room temperature, diluted with water and extracted with ethyl acetate (×3). The combined organics are washed with brine, dried over $Na_2SO_4$, filtered and the solvent is removed under reduced pressure. The residue is purified by silica column chromatography, eluting with 5% methanol in dichloromethane followed by purification using C18 reverse phase chromatography to yield 4-((1R,5S,9r)-9-methoxy-3-(3-phenylbicyclo[1.1.1]pentan-1-yl)-3-azabicyclo[3.3.1]nonan-9-yl)picolinamide.

To a solution of 4-((1R,5S,9r)-9-methoxy-3-(3-phenylbicyclo[1.1.1]pentan-1-yl)-3-azabicyclo[3.3.1]nonan-9-yl)picolinamide (15 mg, 0.04 mmol) in ethyl acetate (3 mL) and dichloromethane (0.1 mL) was added 2 M hydrochloric acid in diethyl ether (20 µL, 0.04 mmol). The mixture was concentrated under reduced pressure, triturated with diethyl ether, the supernatant removed and the residue concentrated under reduced pressure. The residue was dissolved in water and freeze dried to give 4-((1R,5S,9r)-9-methoxy-3-(3-phenylbicyclo[1.1.1]pentan-1-yl)-3-azabicyclo[3.3.1]nonan-9-yl)picolinamide hydrochloride (15 mg, 92% yield); [M+H]+ 418 0.28. H NMR (d6-DMSO; 300 MHz): 9.32 (s, br 1H), 8.74-8.65 (m, 1H), 8.14-8.22 (m, 1H), 8.06 (s, br 1H), 7.84-7.63 (m, 2H), 7.38-7.22 (m, 5H), 3.32-3.55 (m, 3H), 2.96-3.05 (m, 2H), 2.92-2.55 (m, 5H), 2.38 (s, 4H), 1.79-1.74 (m, 4H), 1.53-1.25 (m, 3H).
Compound 119

4-((1R,5S,9r)-3-((1H-indol-2-yl)methyl)-9-methoxy-3-azabicyclo[3.3.1]nonan-9-yl)picolinamide (S)-2-hydroxysuccinate

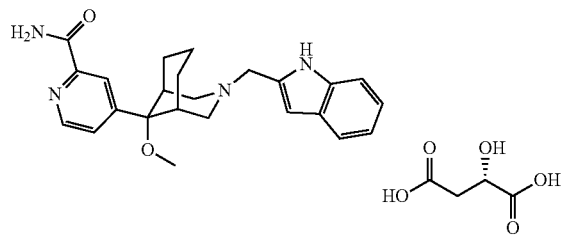 [SMILES: COC1(c2ccnc(C(N)=O)c2)C2CCCC1CN(Cc1cc3ccccc3[nH]1)C2 ; O=C(O)C[C@H](O)C(=O)O]

[M+H]+ 305.3; 1H NMR (400 MHz, d6-DMSO): 10.87 (s, 1H), 8.63 (d, 1H), 8.14 (s, 1H), 8.01 (s, 1H), 7.68 (s, 1H), 7.63 (d, 1H), 7.41 (d, 1H), 7.29 (d, 1H), 7.00-6.85 (m, 2H), 6.25 (s, 1H), 4.20 (s, 2H), 3.53 (s, 3H), 2.90-2.25 (m, 13H), 1.72-1.58 (m, 2H), 1.51-1.37 (m, 2H), 1.22-1.10 (m, 1H).
Compound 127

Synthesis of 4-((1R,5S,9r)-9-methoxy-3-((tetrahydro-2H-pyran-4-yl)methyl)-3-azabicyclo[3.3.1]nonan-9-yl)picolinamide Hydrochloride

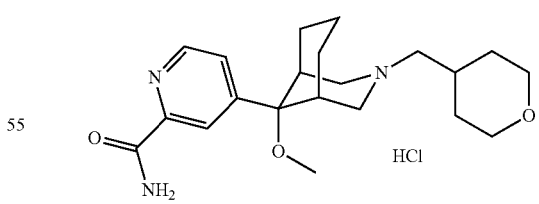

To a suspension of 4-((1R,5S,9r)-9-methoxy-3-azabicyclo[3.3.1]nonan-9-yl)picolinamide hydrochloride (250 mg, 0.80 mmol) in dichloromethane (11 mL) was added tetrahydro-2H-pyran-4-carbaldehyde (229 mg, 2.00 mmol) and acetic acid (0.09 mL, 0.16 mmol). The reaction was stirred for 20 minutes at ambient temperature before sodium triacetoxyborohydride (509 mg, 2.40 mmol) was added and the mixture was stirred for 18 hours at ambient temperature. The mixture was washed with saturated sodium hydrogen carbonate solution and the organics concentrated under reduced pressure. The residue was purified by silica column chromatography, eluting with 0-3% methanol in dichloromethane. The product was slurried in acetonitrile and filtered to yield 4-((1R,5S,9r)-9-methoxy-3-((tetrahydro-2H-pyran-4-yl)methyl)-3-azabicyclo[3.3.1]nonan-9-yl)picolinamide (108 mg, 39% yield).

To 4-((1R,5S,9r)-9-methoxy-3-((tetrahydro-2H-pyran-4-yl)methyl)-3-azabicyclo[3.3.1]nonan-9-yl)picolinamide (108 mg, 0.29 mmol) in ethyl acetate (40 mL) and dichloromethane (10 mL) was added 2M hydrochloric acid in diethyl ether (0.17 mL, 0.35 mmol) at room temperature. The cloudy mixture was concentrated under reduced pressure, triturated with diethyl ether, the supernatant removed and the residue concentrated under reduced pressure. The product was dissolved in water and freeze dried to yield 4-((1R,5S,9r)-9-methoxy-3-((tetrahydro-2H-pyran-4-yl)methyl)-3-azabicyclo[3.3.1]nonan-9-yl)picolinamide hydrochloride (118 mg, 100% yield); [M+H]+ 374.11. 1H NMR (300 MHz, D2O): 8.60 (d, 1H), 8.01 (s, 1H), 7.64 (d, 1H), 3.98-3.86 (m, 2H), 3.66-3.52 (m, 4H), 3.47-3.30 (m, 2H), 3.02 (d, 2H), 2.90 (br s, 2H), 2.74 (s, 3H), 2.33-2.11 (m, 1H), 1.91-1.78 (m, 2H), 1.65-1.23 (m, 8H).

Compound 153

Synthesis of 4-((1R,5S,9r)-9-methoxy-3-((5-methyl-1H-imidazol-2-yl)methyl)-3-azabicyclo[3.3.1]nonan-9-yl)picolinamide Hydrochloride

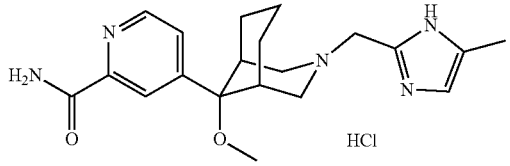 [SMILES: COC1(c2ccnc(C(N)=O)c2)C2CCCC1CN(Cc1ncc(C)[nH]1)C2 ; Cl]

To a suspension of 4-((1R,5S,9r)-9-methoxy-3-azabicyclo[3.3.1]nonan-9-yl)picolinamide hydrochloride (400 mg, 1.28 mmol) and 2-methylimidazole-4-carbaldehyde (282 mg, 2.56 mmol) in dichloromethane (15 mL) was added acetic acid (0.18 mL, 3.20 mmol) and the reaction mixture was stirred for 20 minutes. Sodium triacetoxyborohydride (816 mg, 3.84 mmol) was added and the reaction stirred for 1 hour at room temperature. The mixture was quenched with aqueous sodium hydrogen carbonate solution and extracted with dichloromethane (×3). The combined organic phases were washed with brine, dried over MgSO4, filtered and concentrated under reduced pressure. The residue was purified by C18 reverse phase column chromatography and preparative HPLC to give 4-((1R,5S,9r)-9-methoxy-3-((5-methyl-1H-imidazol-2-yl)methyl)-3-azabicyclo[3.3.1]nonan-9-yl)picolinamide (64 mg, 14% yield).

To 4-((1R,5S,9r)-9-methoxy-3-((5-methyl-1H-imidazol-2-yl)methyl)-3-azabicyclo[3.3.1]nonan-9-yl)picolinamide (64 mg, 0.17 mmol) in ethyl acetate (6 mL) was added 2 M HCl in diethyl ether (0.20 mL, 0.40 mmol) and the reaction mixture was stirred for 15 minutes. The mixture was concentrated under reduced pressure and the residue dissolved in water and freeze dried to give 4-((1R,5S,9r)-9-methoxy-3-((5-methyl-1H-imidazol-2-yl)methyl)-3-azabicyclo[3.3.1]nonan-9-yl)picolinamide hydrochloride (47 mg, 67% yield); [M+H]+ 370.20. 1H NMR (300 MHz, MeOD): 8.74 (d, 1H), 8.19 (s, 1H), 7.80 (s, 1H), 7.07 (dd, 1H), 4.50 (s, 2H), 3.86 (q, 4H), 3.02 (s, 2H), 2.85 (s, 3H), 2.69 (s, 3H), 2.12-1.88 (m, 3H), 1.79-1.61 (m, 2H), 1.57-1.44 (m, 1H).

Compound 99

4-((1R,5S,9r)-3-((1H-imidazol-2-yl)methyl)-9-methoxy-3-azabicyclo[3.3.1]nonan-9-yl)picolinamide Hydrochloride

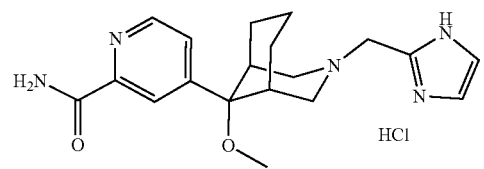 [SMILES: COC1(c2ccnc(C(N)=O)c2)C2CCCC1CN(Cc1ncc[nH]1)C2 ; Cl]

[M+H]+ 382.18. 1H NMR (300 MHz, D2O): 8.58 (br s, 1H), 7.98 (s, 1H), 7.61 (br s, 1H), 7.31 (s, 2H), 4.16 (s, 2H), 3.25-3.15 (m, 4H), 2.76 (s, 2H), 2.68 (s, 3H), 2.07-1.79 (m, 1H), 1.71 (br d, 2H), 1.61-1.40 (m, 2H), 1.36-1.20 (m, 1H).

Compound 80

4-((1R,5S,9r)-9-methoxy-3-(2-(2-oxooxazolidin-3-yl)ethyl)-3-azabicyclo[3.3.1]nonan-9-yl)picolinamide Hydrochloride

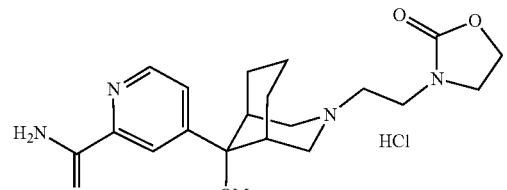

[M+H]+ 389.11. 1H NMR (300 MHz, de-DMSO): 8.70 (d, 1H), 8.26-8.09 (m, 2H), 8.02 (s, 1H), 7.73 (d, 1H), 7.69 (dd, 1H), 4.29 (t, 2H), 3.73 (dd, 2H), 3.66-3.56 (m, 4H), 3.45 (t, 2H), 3.31-3.24 (m, 2H), 2.97 (br s, 2H), 2.74 (s, 3H), 1.94-1.76 (m, 3H), 1.55-1.39 (m, 2H), 1.37-1.26 (m, 1H).

Compound 85

4-((1R,5S,9r)-9-methoxy-3-(2-(2-oxoimidazolidin-1-yl)ethyl)-3-azabicyclo[3.3.1]nonan-9-yl)picolinamide Hydrochloride

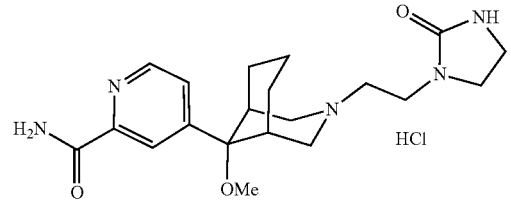 [SMILES: COC1(c2ccnc(C(N)=O)c2)C2CCCC1CN(CCN1CCNC1=O)C2 ; Cl]

[M+H]+ 373.19. 1H NMR (400 MHz, de-DMSO): 8.69 (d, 2H), 8.17 (s, 1H), 8.04 (s, 1H), 7.72 (br s, 1H), 7.69 (dd, 1H), 6.81 (br s, 1H), 3.76 (d, 2H), 3.48-3.36 (m, 6H), 3.32-3.23 (m, 4H), 2.96 (s, 2H), 2.74 (s, 3H), 1.98-1.75 (m, 3H), 1.55-1.40 (m, 2H), 1.36-1.23 (m, 1H).

Compound 76

4-((1R,5S,9r)-3-isopropyl-9-methoxy-3-azabicyclo[3.3.1]nonan-9-yl)picolinamide Hydrochloride

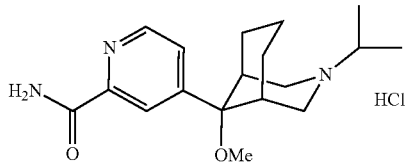 [SMILES: COC1(c2ccnc(C(N)=O)c2)C2CCCC1CN(C(C)C)C2 ; Cl]

[M+H]⁺ 318.11. ¹H NMR (300 MHz, d₆-DMSO): 8.69 (d, 1H), 8.66 (br s, 1H), 8.19 (s, 1H), 8.04 (s, 1H), 7.75 (s, 1H), 7.70 (dd, 1H), 3.48-3.34 (m, 5H), 2.95 (br s, 2H), 2.74 (s, 3H), 2.24-2.01 (m, 1H), 1.86-1.75 (m, 2H), 1.47-1.13 (m, 9H).

Compound 74

4-((1R,5S,9r)-9-methoxy-3-(tetrahydrofuran-3-yl)-3-azabicyclo[3.3.1]nonan-9-yl)picolinamide Hydrochloride

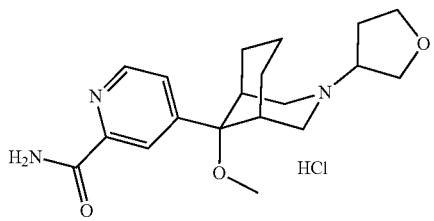 [SMILES: COC1(c2ccnc(C(N)=O)c2)C2CCCC1CN(C1CCOC1)C2 ; Cl]

[M+H]⁺ 346.14. ¹H NMR (300 MHz, d₆-DMSO): 9.47 (brs, 1H), 8.70 (d, 1H), 8.19 (brs, 1H), 8.05 (s, 1H), 7.80-7.67 (m, 2H), 4.18 (dd, 1H), 4.05-3.80 (m, 3H), 3.65-3.30 (m, 5H), 2.97 (s, 2H), 2.75 (s, 3H), 2.36-2.09 (m, 3H), 1.89-1.73 (m, 2H), 1.49-1.18 (m, 3H).

Compound 84

Synthesis of 4-((1R,5S,9r)-3-(azetidin-3-yl)-9-methoxy-3-azabicyclo[3.3.1]nonan-9-yl)picolinamide Dihydrochloride

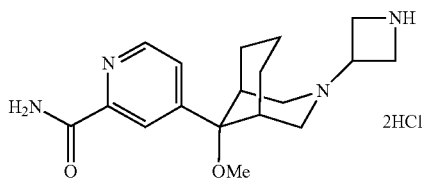 [SMILES: COC1(c2ccnc(C(N)=O)c2)C2CCCC1CN(C1CNC1)C2]

Tert-butyl 3-((1R,5S,9r)-9-(2-carbamoylpyridin-4-yl)-9-methoxy-3-azabicyclo[3.3.1]nonan-3-yl)azetidine-1-carboxylate (256 mg, 0.59 mmol) was stirred with 2M hydrochloric acid in diethyl ether (20 mL) for 18 hours. The solvent was decanted and the residue dried under reduced pressure giving 4-((1R,5S,9r)-3-(azetidin-3-yl)-9-methoxy-3-azabicyclo[3.3.1]nonan-9-yl)picolinamide dihydrochloride (320 mg); [M+H]⁺ 331.19.

Synthesis of 4-((1R,5S,9r)-3-(1-acetylazetidin-3-yl)-9-methoxy-3-azabicyclo[3.3.1]nonan-9-yl)picolinamide Hydrochloride

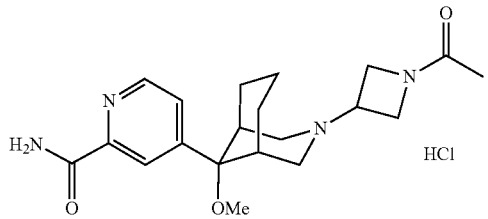 [SMILES: COC1(c2ccnc(C(N)=O)c2)C2CCCC1CN(C1CN(C(C)=O)C1)C2 ; Cl]

To a solution of 4-((1R,5S,9r)-3-(azetidin-3-yl)-9-methoxy-3-azabicyclo[3.3.1]nonan-9-yl)picolinamide dihydrochloride (130 mg, 0.32 mmol) in dichloromethane (20 mL) was added N,N-diisopropylethylamine (0.28 mL, 1.6 mmol) followed by acetyl chloride (0.02 mL, 0.36 mmol). After 45 minutes the reaction was quenched with water and extracted with dichloromethane (×2). The combined organic extracts were dried over MgSO₄, filtered and concentrated under reduced pressure. The crude product was purified by both C18 reverse phase chromatography and preparative HPLC to give 4-((1R,5S,9r)-3-(1-acetylazetidin-3-yl)-9-methoxy-3-azabicyclo[3.3.1]nonan-9-yl)picolinamide (56 mg, 47% yield).

To 4-((1R,5S,9r)-3-(1-acetylazetidin-3-yl)-9-methoxy-3-azabicyclo[3.3.1]nonan-9-yl)picolinamide (56 mg, 0.15 mmol) in ethyl acetate (15 mL) was added 2M HCl in diethyl ether (0.15 mL, 0.30 mmol). The solvent was removed under reduced pressure. The product was dissolved in water and freeze dried to give 4-((1R,5S,9r)-3-(1-acetylazetidin-3-yl)-9-methoxy-3-azabicyclo[3.3.1]nonan-9-yl)picolinamide hydrochloride (49 mg, 80% yield); [M+H]⁺ 373.19. ¹H NMR (300 MHz, d₆-DMSO): 9.57 (br s, 1H), 8.69 (d, 1H), 8.17 (br s, 1H), 8.05 (s, 1H), 7.76-7.64 (m, 2H), 4.29 (t, 1H), 4.25-4.06 (m, 2H), 4.00 (t, 1H), 3.67-3.55 (m, 2H), 3.37-3.24 (m, 2H), 2.00 (br s, 2H), 2.73 (s, 3H), 2.94-1.97 (m, 1H), 1.85-1.70 (m, 5H), 1.50-1.36 (m, 2H), 1.33-1.06 (m, 2H).

Compounds 79 and 78

Synthesis of (S)-tetrahydrofuran-3-yl trifluoromethanesulfonate

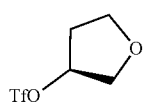

To diisopropylethylamine (0.74 mL, 4.26 mmol) in dichloromethane (10 mL) under argon at −78° C. was added trifluoromethanesulfonic anhydride (0.65 mL, 3.85 mmol). After 5 minutes, (S)-tetrahydrofuran-3-ol (250 mg, 2.84 mmol) was added. The reaction was stirred at −78° C. for 1 hour then 2 hours at room temperature. The reaction mixture was washed with saturated sodium hydrogen carbonate solution (×2), brine (×1), dried over MgSO₄, filtered and concentrated under reduced pressure to a minimum volume to give (S)-tetrahydrofuran-3-yl trifluoromethanesulfonate (assume quant.). ¹H NMR (400 MHz, CDCl₃): 5.52 (s, 1H), 4.10 (d, 1H), 4.02-3.89 (m, 3H), 2.33-2.22 (m, 2H).

Synthesis of 4-((1R,5S,9R)-9-methoxy-3-((R)-tetrahydrofuran-3-yl)-3-azabicyclo[3.3.1]nonan-9-yl)picolinamide hydrochloride and 4-((1R,5S,9S)-9-methoxy-3-((S)-tetrahydrofuran-3-yl)-3-azabicyclo[3.3.1]nonan-9-yl)picolinamide Hydrochloride

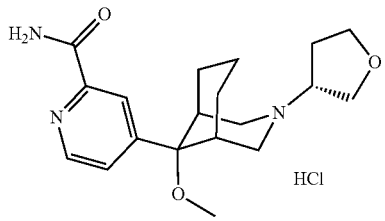

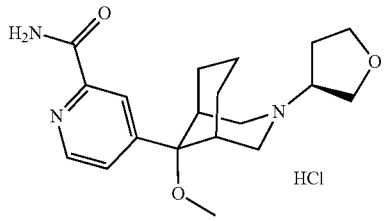

To 4-((1R,5S,9r)-9-methoxy-3-azabicyclo[3.3.1]nonan-9-yl)picolinamide hydrochloride (250 mg, 0.80 mmol) in acetonitrile (20 mL) was added diisopropylethylamine (0.56 mL, 3.20 mmol) followed by a solution of (S)-tetrahydrofuran-3-yl trifluoromethanesulfonate (568 mg, 2.84 mmol) in dichloromethane (2 mL). The reaction was stirred at room temperature overnight. The reaction was poured into 1M hydrochloric acid, diluted with dichloromethane and the phases separated. The dichloromethane phase was re-extracted with 1M hydrochloric acid. The acidic phases were combined, washed with dichloromethane before basifying with concentrated aqueous ammonia. The mixture was extracted with dichloromethane (×3). The dichloromethane phases were combined, washed (brine), dried over MgSO$_4$ and concentrated under reduced pressure. The residue was purified by silica chromatography, eluting with 0-10% methanol in dichloromethane. The enantiomers were separated by chiral preparative HPLC. Once separated, the enantiomers were purified further by C18 reverse phase chromatography to give 4-((1R,5S,9R)-9-methoxy-3-((R)-tetrahydrofuran-3-yl)-3-azabicyclo[3.3.1]nonan-9-yl)picolinamide (48 mg, 17% yield) and 4-((1R,5S,9S)-9-methoxy-3-((S)-tetrahydrofuran-3-yl)-3-azabicyclo[3.3.1]nonan-9-yl)picolinamide (48 mg, 17% yield).

To 4-((1R,5S,9R)-9-methoxy-3-((R)-tetrahydrofuran-3-yl)-3-azabicyclo[3.3.1]nonan-9-yl)picolinamide (48 mg, 0.14 mmol) in ethyl acetate (10 mL) was added 2M HCl in diethyl ether (0.08 mL, 0.15 mmol). After 10 minutes, the solvent was removed under reduced pressure. The product was dissolved in water and freeze dried to give 4-((1R,5S,9R)-9-methoxy-3-((R)-tetrahydrofuran-3-yl)-3-azabicyclo[3.3.1]nonan-9-yl)picolinamide hydrochloride (50 mg, 94% yield); [M+H]$^+$ 346.14. $^1$H NMR (400 MHz, D$_2$O): 8.57-8.55 (m, 1H), 7.98 (s, 1H), 7.62-7.59 (m, 1H), 4.11-4.07 (m, 1H), 4.02-3.94 (m, 2H), 3.77-3.72 (m, 1H), 3.60-3.54 (m, 1H), 3.51-3.39 (m, 4H), 2.90-2.87 (m, 2H), 2.71 (s, 3H), 2.34-2.27 (m, 1H), 2.15-2.08 (m, 1H), 1.73-1.68 (m, 2H), 1.51-1.47 (m, 3H), 1.36-1.31 (m, 1H).

To 4-((1R,5S,9S)-9-methoxy-3-((S)-tetrahydrofuran-3-yl)-3-azabicyclo[3.3.1]nonan-9-yl)picolinamide (48 mg, 0.14 mmol) in ethyl acetate (10 mL) was added 2M HCl in diethyl ether (0.08 mL, 0.15 mmol). After 10 minutes, the solvent was removed under reduced pressure. The product was dissolved in water and freeze dried to give 4-((1R,5S,9S)-9-methoxy-3-((S)-tetrahydrofuran-3-yl)-3-azabicyclo[3.3.1]nonan-9-yl)picolinamide hydrochloride (50 mg, 94% yield); [M+H]$^+$ 346.14. $^1$H NMR (400 MHz, D$_2$O): 8.57-8.55 (m, 1H), 7.98 (s, 1H), 7.62-7.59 (m, 1H), 4.11-4.07 (m, 1H), 4.02-3.94 (m, 2H), 3.77-3.72 (m, 1H), 3.60-3.54 (m, 1H), 3.51-3.39 (m, 4H), 2.90-2.87 (m, 2H), 2.71 (s, 3H), 2.34-2.27 (m, 1H), 2.15-2.08 (m, 1H), 1.73-1.68 (m, 2H), 1.51-1.47 (m, 3H), 1.36-1.31 (m, 1H).

Compound 82

4-((1R,5S,9r)-3-(3,3-difluorocyclobutyl)-9-methoxy-3-azabicyclo[3.3.1]nonan-9-yl)picolinamide Hydrochloride

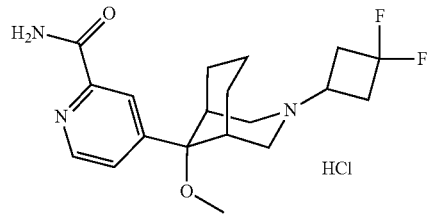 [SMILES: COC1(c2ccnc(C(N)=O)c2)C2CCCC1CN(C1CC(F)(F)C1)C2 ; Cl]

[M+H]$^+$ 366.20. $^1$H NMR (300 MHz, D$_2$O): 8.63 (s, 1H), 8.07 (br s, 1H), 7.71 (br s, 1H), 3.94-3.71 (m, 1H), 3.67-3.41 (m, 4H), 3.13-2.86 (m, 6H), 2.74 (s, 3H), 1.86-1.71 (m, 2H), 1.66-1.47 (m, 3H), 1.43-1.31 (m, 1H).

Compound 100

4-((1R,5S,9r)-3-((1H-pyrazol-5-yl)methyl)-9-methoxy-3-azabicyclo[3.3.1]nonan-9-yl)picolinamide Hydrochloride

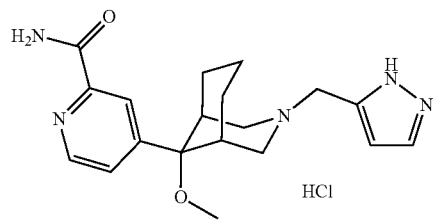 [SMILES: COC1(c2ccnc(C(N)=O)c2)C2CCCC1CN(Cc1ccn[nH]1)C2 ; Cl]

[M+H]$^+$ 356.19. $^1$H NMR (300 MHz, D$_2$O): 8.66 (br s, 1H), 8.11 (s, 1H), 7.78 (br s, 1H), 7.71 (s, 1H), 6.52 (s, 1H), 4.32 (s, 2H), 3.64 (d, 2H), 3.47 (d, 2H), 2.89 (s, 2H), 2.60 (s, 3H), 1.86-1.71 (m, 2H), 1.65-1.41 (m, 4H).

Compound 103

Synthesis of 3-(bicyclo[1.1.1]pentan-1-yl)-1,5,3-dioxazepane

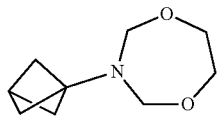 [SMILES: C1COCN(C23CC(C2)C3)CO1]

25 M Sodium hydroxide (4 mL) was added to a 1:1 mixture of bicyclo[1.1.1]pentan-1-amine hydrochloride and ammonium chloride (5.5 g, 45.9 mmol) and dichloromethane (15 mL) cooled in an ice bath. The mixture was warmed to ambient temperature, the dichloromethane was removed and washed with water. The combined aqueous fractions were extracted with dichloromethane. The dichloromethane fractions were combined then washed with water and concentrated under reduced pressure to give bicyclo[1.1.1]pentan-1-amine (10.46 g, 22.5% w/w solution in dichloromethane, 28.3 mmol). Toluene (40 mL), paraformaldehyde (2.1 g, 70.8 mmol) and ethylene glycol (1.9 mL, 34.0 mmol) were added and the mixture was stirred at ambient temperature for 10 minutes then heated under reflux with a Dean-Stark trap for 3 hours. The mixture was diluted with ethyl acetate, washed with brine and concentrated under reduced pressure to yield 3-(bicyclo[1.1.1]pentan-1-yl)-1,5,3-dioxazepane (4.3 g, 74% yield); $^1$H NMR (300 MHz, CDCl$_3$): 4.49 (s, 4H), 3.77 (s, 4H), 2.38 (s, 1H), 1.90 (s, 6H).

Synthesis of (1R,5S)-3-(bicyclo[1.1.1]pentan-1-yl)-3-azabicyclo[3.3.1]nonan-9-one

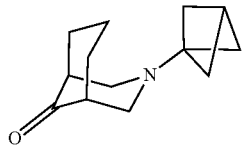 [SMILES: O=C1C2CCCC1CN(C13CC(C1)C3)C2]

Acetyl chloride (5.04 mL, 25.3 mmol) was added to a solution of 3-(bicyclo[1.1.1]pentan-1-yl)-1,5,3-dioxazepane (4.28 g, 25.3 mmol) in methanol (50 mL) at 0° C., then cyclohexanone (2.62 mL, 76 mmol) in methanol (10 mL) was added; the mixture was stirred for a further 15 minutes before the reaction mixture was allowed to warm to room temperature and stirred for a further 20 hours. The mixture was basified with concentrated aqueous ammonia and the cloudy aqueous mixture was extracted with ethyl acetate (×4), the combined organic fractions were washed with brine, concentrated under reduced pressure and azeotroped with toluene. The residue was dissolved in 4M hydrochloric acid (aq) (30 mL) and heated at 50° C. for 3 hours. The mixture was cooled, basified with concentrated aqueous ammonia and the cloudy aqueous mixture was extracted with ethyl acetate (×3), dried over magnesium sulphate and concentrated under reduced pressure and azeotroped with toluene. The residue was purified by column chromatography, eluting with 0.5-2% ethyl acetate in heptanes to give (1R,5S)-3-(bicyclo[1.1.1]pentan-1-yl)-3-azabicyclo[3.3.1]nonan-9-one (0.90 g, 21% yield over 2 steps); [M+H]$^+$ 206.18.

Synthesis of (1R,5S,9r)-3-(bicyclo[1.1.1]pentan-1-yl)-9-(2-chloropyridin-4-yl)-3-azabicyclo[3.3.1]nonan-9-ol and (1R,5S,9s)-3-(bicyclo[1.1.1]pentan-1-yl)-9-(2-chloropyridin-4-yl)-3-azabicyclo[3.3.1]nonan-9-ol

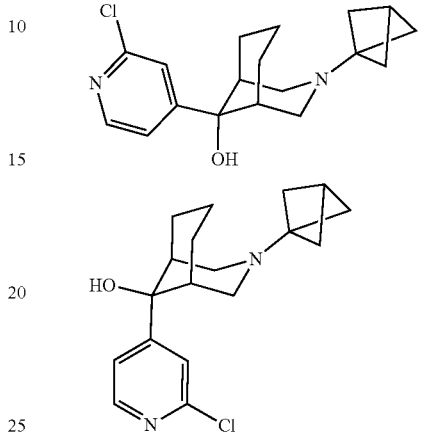

To (1R,5S)-3-(bicyclo[1.1.1]pentan-1-yl)-3-azabicyclo[3.3.1]nonan-9-one (0.71 g, 3.46 mmol) in diethyl ether (35 mL) under argon was added 2-chloro-4-iodopyridine (1.08 g, 4.50 mmol). The reaction was cooled to −78° C. and nButyl lithium (1.80 mL, 2.3 M in hexanes, 4.16 mmol) was added slowly. Once addition was complete, the reaction was allowed to warm to 0° C. and quenched with water. The reaction mixture was extracted with ethyl acetate (×3). The organic phases were combined, washed (brine), dried over MgSO$_4$ and concentrated under reduced pressure. The residue was combined with a trial batch on (1R,5S)-3-(bicyclo[1.1.1]pentan-1-yl)-3-azabicyclo[3.3.1]nonan-9-one (50 mg, 0.24 mmol). The material was purified by C18 reverse phase chromatography to give (1R,5S,9s)-3-(bicyclo[1.1.1]pentan-1-yl)-9-(2-chloropyridin-4-yl)-3-azabicyclo[3.3.1]nonan-9-ol (0.25 g, 20% yield) [M+H]$^+$ 319.12 and a mixture of (1R,5S,9r)-3-(bicyclo[1.1.1]pentan-1-yl)-9-(2-chloropyridin-4-yl)-3-azabicyclo[3.3.1]nonan-9-ol and (1R,5S,9s)-3-(bicyclo[1.1.1]pentan-1-yl)-9-(2-chloropyridin-4-yl)-3-azabicyclo[3.3.1]nonan-9-ol (0.98 g); [M+H]$^+$ 319.10.

Synthesis of (1R,5S,9r)-3-(bicyclo[1.1.1]pentan-1-yl)-9-(2-chloropyridin-4-yl)-9-methoxy-3-azabicyclo[3.3.1]nonane and (1R,5S,9s)-3-(bicyclo[1.1.1]pentan-1-yl)-9-(2-chloropyridin-4-yl)-9-methoxy-3-azabicyclo[3.3.1]nonane

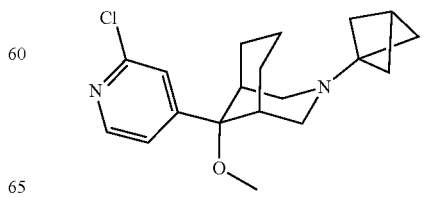

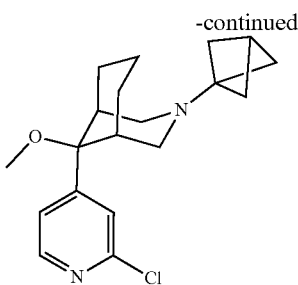

To (1R,5S,9r)-3-(bicyclo[1.1.1]pentan-1-yl)-9-(2-chloropyridin-4-yl)-3-azabicyclo[3.3.1]nonan-9-ol and (1R,5S,9s)-3-(bicyclo[1.1.1]pentan-1-yl)-9-(2-chloropyridin-4-yl)-3-azabicyclo[3.3.1]nonan-9-ol (0.98 g, 3.07 mmol) in N,N-dimethylformamide (30 mL) was added sodium hydride (0.25 g, 60% dispersion in oil, 6.15 mmol) followed by iodomethane (0.23 mL, 3.69 mmol) with water cooling. The reaction was allowed to warm to room temperature and stirred for 1.5 hours. The reaction was cooled to 0° C., quenched with water and extracted with ethyl acetate (×3). The organic phases were combined, washed (brine), dried over MgSO$_4$ and concentrated under reduced pressure. The residue was purified by silica column chromatography eluting with 20% ethyl acetate in heptane to give (1R,5S,9r)-3-(bicyclo[1.1.1]pentan-1-yl)-9-(2-chloropyridin-4-yl)-9-methoxy-3-azabicyclo[3.3.1]nonane and (1R,5S,9s)-3-(bicyclo[1.1.1]pentan-1-yl)-9-(2-chloropyridin-4-yl)-9-methoxy-3-azabicyclo[3.3.1]nonane (0.87 g, 90% yield over 2 steps); [M+H]$^+$ 333.16.

Synthesis of 4-((1R,5S,9r)-3-(bicyclo[1.1.1]pentan-1-yl)-9-methoxy-3-azabicyclo[3.3.1]nonan-9-yl) picolinonitrile and 4-((1R,5S,9s)-3-(bicyclo[1.1.1]pentan-1-yl)-9-methoxy-3-azabicyclo[3.3.1]nonan-9-yl) picolinonitrile

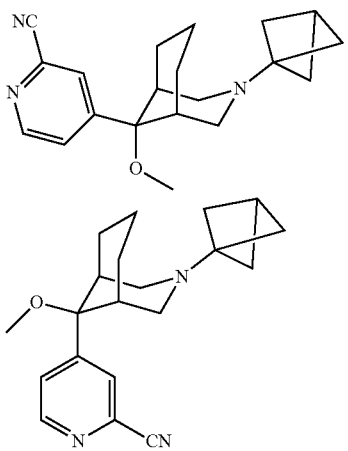

To (1R,5S,9r)-3-(bicyclo[1.1.1]pentan-1-yl)-9-(2-chloropyridin-4-yl)-9-methoxy-3-azabicyclo[3.3.1]nonane and (1R,5S,9s)-3-(bicyclo[1.1.1]pentan-1-yl)-9-(2-chloropyridin-4-yl)-9-methoxy-3-azabicyclo[3.3.1]nonane (0.87 g, 2.62 mmol) in degassed N,N-dimethylformamide (25 mL) under an atmosphere of argon was added tris(dibenzylideneacetone)dipalladium(0) (0.24 g, 0.26 mmol) and 1,1'-bis(diphenylphosphino)ferrocene (0.15 g, 0.26 mmol). The reaction was heated to 60° C. before zinc cyanide (0.62 g, 5.24 mmol) was added. The reaction was heated to 120° C. for 1.5 hours. The reaction was cooled to room temperature, quenched with saturated sodium hydrogen carbonate solution and diluted with ethyl acetate. The mixture was filtered through celite and the filtrate extracted with ethyl acetate (×3). The organic phases were combined, washed (water/brine×3), dried over MgSO$_4$ and concentrated under reduced pressure. The residue was purified by silica column chromatography, eluting with 10-20% ethyl acetate in heptane to give 4-((1R,5S,9r)-3-(bicyclo[1.1.1]pentan-1-yl)-9-methoxy-3-azabicyclo[3.3.1]nonan-9-yl)picolinonitrile and 4-((1R,5S,9s)-3-(bicyclo[1.1.1]pentan-1-yl)-9-methoxy-3-azabicyclo[3.3.1]nonan-9-yl)picolinonitrile (0.93 g); [M+H]$^+$ 324.20.

Synthesis of 4-((1R,5S,9r)-3-(bicyclo[1.1.1]pentan-1-yl)-9-methoxy-3-azabicyclo[3.3.1]nonan-9-yl) picolinamide

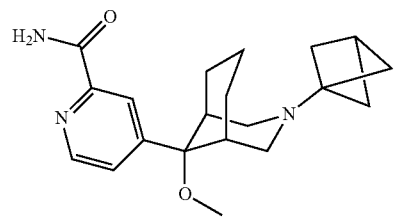 [SMILES: COC1(c2ccnc(C(N)=O)c2)C2CCCC1CN(C13CC(C1)C3)C2]

To 4-((1R,5S,9r)-3-(bicyclo[1.1.1]pentan-1-yl)-9-methoxy-3-azabicyclo[3.3.1]nonan-9-yl)picolinonitrile in tert-butanol is added potassium hydroxide and the reaction heated to reflux for 30 minutes. The reaction is cooled to room temperature, diluted with water and extracted with ethyl acetate (×3). The organic phases are combined, washed (brine), dried over MgSO$_4$ and concentrated under reduced pressure. The residue is purified by silica column chromatography, eluting with 0-50% ethyl acetate in heptane.

Synthesis of 4-((1R,5S,9r)-3-(bicyclo[1.1.1]pentan-1-yl)-9-methoxy-3-azabicyclo[3.3.1]nonan-9-yl) picolinamide Hydrochloride

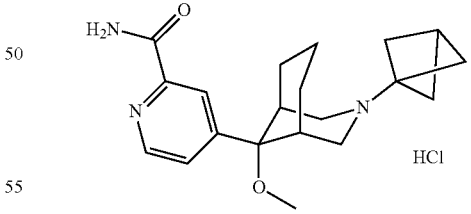

To 4-((1R,5S,9r)-3-(bicyclo[1.1.1]pentan-1-yl)-9-methoxy-3-azabicyclo[3.3.1]nonan-9-yl)picolinamide (84 mg, 0.25 mmol) in ethyl acetate (10 mL) was added 2M HCl in diethyl ether (0.15 mL, 0.30 mmol). After 10 minutes, the solvent was removed under reduced pressure. The solid was triturated with diethyl ether and the liquors decanted before drying under vacuum. The product was dissolved in water and freeze dried to give 4-((1R,5S,9r)-3-(bicyclo[1.1.1]pentan-1-yl)-9-methoxy-3-azabicyclo[3.3.1]nonan-9-yl)picolinamide hydrochloride (99 mg, 100% yield); [M+H]$^+$ 342.24. $^1$H NMR (300 MHz, D$_2$O): 8.67 (s, 1H), 8.11 (s, 1H), 7.76 (s, 1H), 3.56-3.39 (m, 4H), 2.95 (s, 2H), 2.78 (s, 3H), 2.71 (s, 1H), 2.07 (s, 6H), 1.85-1.70 (m, 2H), 1.66-1.46 (m, 3H), 1.44-1.32 (m, 1H).

Compound 15

4-((1R,5S,9r)-3-((4-fluorotetrahydro-2H-pyran-4-yl)methyl)-9-methoxy-3-azabicyclo[3.3.1]nonan-9-yl)picolinamide Hydrochloride

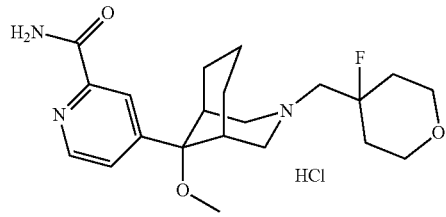 [SMILES: COC1(c2ccnc(C(N)=O)c2)C2CCCC1CN(CC1(F)CCOCC1)C2 ; Cl]

[M+H]$^+$ 392.23. $^1$H NMR (300 MHz, D$_2$O): 8.59 (d, 1H), 8.03 (s, 1H), 7.67 (d, 1H), 3.81-3.54 (m, 8H), 3.40 (d, 2H), 2.89 (s, 2H), 2.72 (s, 3H), 1.96-1.66 (m, 6H), 1.65-1.30 (m, 4H).

Compound 18

4-((1R,5S,9R)-3-((1R,3r,5S)-6,6-difluorobicyclo[3.1.0]hexan-3-yl)-9-methoxy-3-azabicyclo[3.3.1]nonan-9-yl)picolinamide Hydrochloride

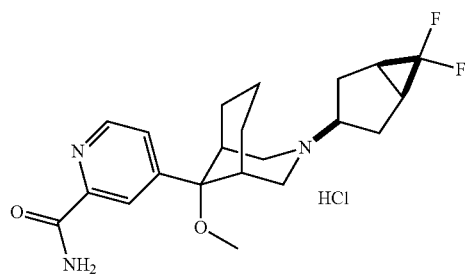

[M+H$^+$] 392.16. $^1$H NMR (400 MHz, d6-DMSO): 8.70 (d, 1H), 8.58 (br s, 1H), 8.18 (s, 1H), 8.03 (s, 1H), 7.74 (s, 1H), 7.70 (d, 1H), 3.55-3.41 (m, 5H), 2.93 (br s, 3H), 2.74 (s, 3H), 2.26-2.19 (m, 2H), 1.98-1.88 (m, 3H), 1.83-1.74 (m, 2H), 1.48-1.22 (m, 4H).

Compound 7

4-((1R,5S,9r)-3-(4,4-difluorocyclohexyl)-9-methoxy-3-azabicyclo[3.3.1]nonan-9-yl)picolinamide Hydrochloride

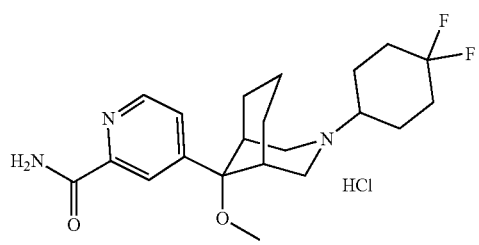 [SMILES: COC1(c2ccnc(C(N)=O)c2)C2CCCC1CN(C1CCC(F)(F)CC1)C2 ; Cl]

[M+H]$^+$ 394.22; $^1$H NMR (300 MHz, d6-DMSO): 8.77 (br s, 1H), 8.70 (d, 1H), 8.20 (s, 1H), 8.05 (s, 1H), 7.76 (s, 1H), 7.71 (dd, 1H), 3.64-3.43 (m, 4H), 3.27 (br s, 1H), 2.97 (s, 2H), 2.75 (s, 3H), 2.38-2.22 (m, 2H), 2.21-2.01 (m, 3H), 2.00-1.74 (m, 6H), 1.51-1.16 (m, 3H).

Compound 13

4-((1R,5S,9r)-9-methoxy-3-(7-oxaspiro[3.5]nonan-2-yl)-3-azabicyclo[3.3.1]nonan-9-yl)picolinamide Hydrochloride

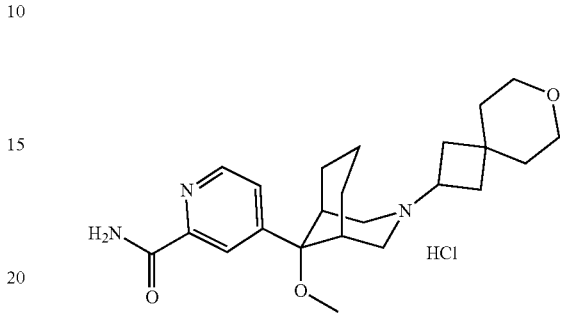

[M+H]$^+$ 400.16; $^1$H NMR (300 MHz, d6-DMSO): 9.31 (br s, 1H), 8.70 (d, 1H), 8.19 (s, 1H), 8.05 (s, 1H), 7.75 (s, 1H), 7.70 (dd, 1H), 3.82-3.60 (m, 1H), 3.57-3.39 (m, 6H), 3.32-3.16 (m, 2H), 2.95 (s, 2H), 2.74 (s, 3H), 2.42 (t, 2H), 2.35-2.18 (m, 1H), 2.11 (t, 2H), 1.86-1.73 (m, 2H), 1.57 (dt, 4H), 1.50-1.31 (m, 2H), 1.30-1.16 (m, 1H).

Compound 124

4-((1R,5S,9r)-3-(isoxazol-5-ylmethyl)-9-methoxy-3-azabicyclo[3.3.1]nonan-9-yl)picolinamide Hydrochloride

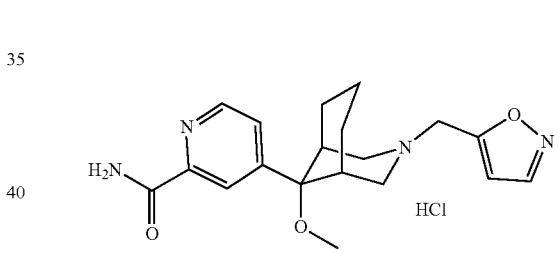

[M+H]$^+$ 357.06; $^1$H NMR (400 MHz, d6-DMSO): 9.68 (br s, 1H), 8.72 (s, 1H), 8.67 (d, 1H), 8.19 (s, 1H), 8.00 (s, 1H), 7.75 (s, 1H), 7.65 (dd, 1H), 6.97 (s, 1H), 4.61 (s, 2H), 3.50 (s, 4H), 2.97 (s, 2H), 2.60 (s, 3H), 2.23-2.03 (m, 1H), 1.88-1.64 (m, 2H), 1.49-1.19 (m, 3H).

Compounds 94 and 93

4-((1R,5S,9R)-3-((1R,3s,5S)-bicyclo[3.1.0]hexan-3-yl)-9-methoxy-3-azabicyclo[3.3.1]nonan-9-yl)picolinamide hydrochloride and 4-((1R,5S,9R)-3-((1R,3r,5S)-bicyclo[3.1.0]hexan-3-yl)-9-methoxy-3-azabicyclo[3.3.1]nonan-9-yl)picolinamide Hydrochloride

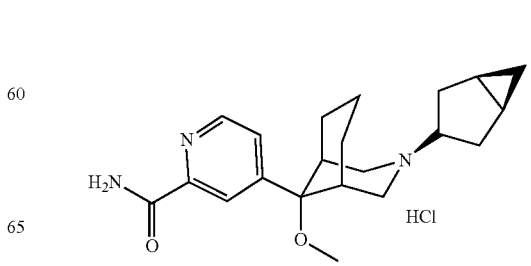

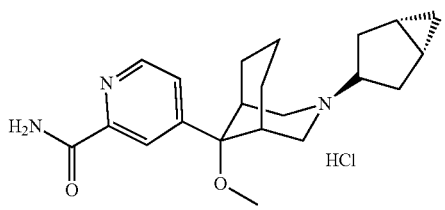

[M+H]+ 356.19; 1H NMR (400 MHz, d6-DMSO): 8.68 (d, 1H), 8.47 (brs, 1H), 8.18 (d, 1H), 8.02 (s, 1H), 7.74 (d, 1H), 7.68 (dd, 1H), 3.78 (q, 1H), 3.40 (d, 4H), 2.90 (s, 2H), 2.73 (s, 3H), 2.43-2.31 (m, 1H), 2.08-1.90 (m, 1H), 1.82-1.64 (m, 4H), 1.46-1.15 (m, 6H), 0.84 (sex, 1H), 0.46 (q, 1H).

[M+H]+ 356.12; 1H NMR (400 MHz, d6-DMSO): 8.68 (d, 1H), 8.23-8.06 (m, 2H), 8.01 (br s, 1H), 7.76-7.71 (m, 1H), 7.68 (dd, 1H), 3.53-3.46 (m, 2H), 3.43-3.34 (m, 2H), 3.27-3.17 (m, 1H), 2.90 (br s, 2H), 2.73 (s, 3H), 2.24-2.09 (m, 3H), 2.06-1.88 (m, 1H), 1.83-1.74 (m, 2H), 1.49-1.09 (m, 6H), 0.40-0.29 (m, 1H), 0.21-0.15 (m, 1H).

Compound 105

4-((1R,5S,9r)-9-methoxy-3-neopentyl-3-azabicyclo[3.3.1]nonan-9-yl)picolinamide Hydrochloride

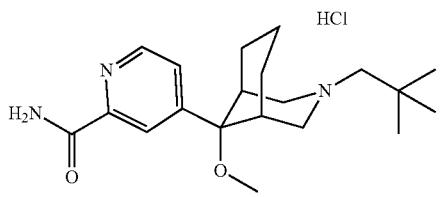 [SMILES: Cl ; COC1(c2ccnc(C(N)=O)c2)C2CCCC1CN(CC(C)(C)C)C2]

[M+H]+ 346.35; 1H NMR (400 MHz, d6-DMSO): 8.70 (d, 1H), 8.19 (s, 1H), 8.03 (s, 1H), 7.74 (s, 1H), 7.67 (dd, 1H), 7.30-7.12 (br s, 1H), 3.72 (dd, 2H), 3.46 (t, 2H), 3.05 (d, 2H), 2.95 (s, 2H), 2.74 (s, 3H), 2.00-1.88 (m, 2H), 1.83-1.64 (m, 1H), 1.51-1.33 (m, 3H), 1.10 (s, 9H).

Compounds 104 and 102

Synthesis of 4-((1R,5S,9R)-3-((1R,3s,5S)-bicyclo[3.1.0]hexan-3-ylmethyl)-9-methoxy-3-azabicyclo[3.3.1]nonan-9-yl)picolinamide hydrochloride and 4-((1R,5S,9R)-3-((1R,3r,5S)-bicyclo[3.1.0]hexan-3-ylmethyl)-9-methoxy-3-azabicyclo[3.3.1]nonan-9-yl)picolinamide Hydrochloride

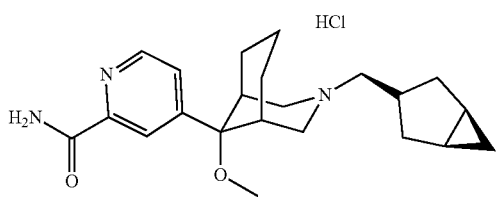

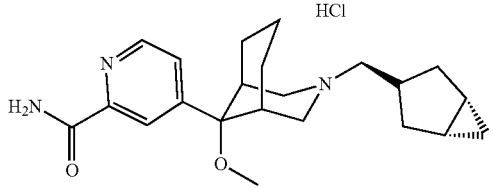

To a suspension of 4-((1R,5S,9r)-9-methoxy-3-azabicyclo[3.3.1]nonan-9-yl)picolinamide hydrochloride (143 mg, 0.46 mmol) and (1R,5S)-bicyclo[3.1.0]hexane-3-carbaldehyde (79 mg, 0.72 mmol) in dichloromethane (15 mL) was added acetic acid (0.06 mL, 0.95 mmol) followed by sodium triacetoxyborohydride (306 mg, 1.44 mmol). The reaction was stirred for 1 hour at room temperature. The reaction mixture was quenched with aqueous sodium hydrogen carbonate solution and extracted with dichloromethane (×3). The combined organic phases were dried over MgSO4, filtered and concentrated under reduced pressure. The diastereoisomers were separated by chiral preparative HPLC and then purified by C18 reverse phase chromatography to give 4-((1R,5S,9R)-3-((1R,3s,5S)-bicyclo[3.1.0]hexan-3-ylmethyl)-9-methoxy-3-azabicyclo[3.3.1]nonan-9-yl)picolinamide (85 mg, 50% yield) and 4-((1R,5S,9R)-3-((1R,3r,5S)-bicyclo[3.1.0]hexan-3-ylmethyl)-9-methoxy-3-azabicyclo[3.3.1]nonan-9-yl)picolinamide (15 mg, 9% yield). Stereochemistry of diastereoisomers inferred based on steric hindrance and previous trends.

To a mixture of 4-((1R,5S,9R)-3-((1R,3s,5S)-bicyclo[3.1.0]hexan-3-ylmethyl)-9-methoxy-3-azabicyclo[3.3.1]nonan-9-yl)picolinamide (85 mg, 0.23 mmol) in dichloromethane (20 mL) was added 2 M hydrochloric acid in diethyl ether (0.20 mL, 0.40 mmol). The mixture was stirred for 5 minutes and then concentrated under reduced pressure and the residue freeze dried from water to give 4-((1R,5S,9R)-3-((1R,3s,5S)-bicyclo[3.1.0]hexan-3-ylmethyl)-9-methoxy-3-azabicyclo[3.3.1]nonan-9-yl)picolinamide hydrochloride (94 mg, 100% yield); [M+H]+ 370.35; 1H NMR (400 MHz, d6-DMSO): 8.69 (d, 1H), 8.17 (s, 1H), 8.10-7.90 (m, 2H), 7.72 (d, 1H), 7.67 (dd, 1H), 3.56-3.44 (m, 2H), 3.38-3.25 (m, 2H), 2.99-2.86 (m, 4H), 2.77-2.64 (m, 4H), 2.26-2.12 (m, 2H), 1.96-1.74 (m, 3H), 1.52-1.37 (m, 4H), 1.35-1.21 (m, 3H), 0.63-0.53 (m, 1H), −0.04 (q, 1H).

To 4-((1R,5S,9R)-3-((1R,3r,5S)-bicyclo[3.1.0]hexan-3-ylmethyl)-9-methoxy-3-azabicyclo[3.3.1]nonan-9-yl)picolinamide (15 mg, 0.04 mmol) in ethyl acetate (10 mL) was added 2 M hydrochloric acid in diethyl ether (0.03 mL, 0.06 mmol). The mixture was stirred for 5 minutes and then concentrated under reduced pressure and the residue freeze dried from water to give 4-((1R,5S,9R)-3-((1R,3r,5S)-bicyclo[3.1.0]hexan-3-ylmethyl)-9-methoxy-3-azabicyclo[3.3.1]nonan-9-yl)picolinamide hydrochloride (15 mg, 90% yield); [M+H]+ 370.35; 1H NMR (400 MHz, d6-DMSO): 8.69 (d, 1H), 8.24-8.06 (m, 2H), 8.02 (s, 1H), 7.73 (s, 1H), 7.67 (d, 1H), 3.57 (d, 2H), 3.32 (t, 2H), 3.09-3.00 (m, 2H), 2.92 (br s, 2H), 2.72 (s, 3H), 2.13-2.01 (m, 1H), 1.99-1.78 (m, 5H), 1.56-1.35 (m, 4H), 1.34-1.17 (m, 3H), 0.32-0.24 (m, 1H), 0.21-0.15 (m, 1H).

Compound 108

Synthesis of 4-((1R,5S,9r)-3-((1H-1,2,3-triazol-5-yl)methyl)-9-methoxy-3-azabicyclo[3.3.1]nonan-9-yl)picolinamide Hydrochloride

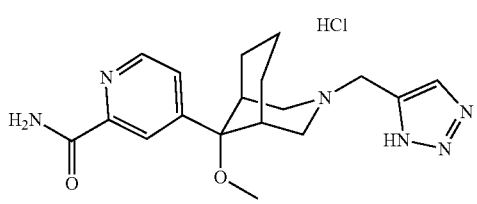 [SMILES: Cl ; COC1(c2ccnc(C(N)=O)c2)C2CCCC1CN(Cc1cnn[nH]1)C2]

To a suspension of 4-((1R,5S,9r)-9-methoxy-3-azabicyclo[3.3.1]nonan-9-yl)picolinamide hydrochloride (150 mg, 0.48 mmol) and 1H-1,2,3-triazole-5-carbaldehyde (69 mg, 0.72 mmol) in dichloromethane (15 mL) was added acetic acid (0.10 mL, 1.92 mmol) followed by sodium triacetoxyborohydride (308 mg, 1.44 mmol). The reaction was stirred for 30 minutes at room temperature. The reaction mixture was quenched with aqueous sodium hydrogen carbonate solution and extracted with dichloromethane (×3). The combined organic phases were dried over MgSO$_4$, filtered and concentrated under reduced pressure. The residue was purified by C18 reverse phase chromatography to give 4-((1R,5S,9r)-3-((1H-1,2,3-triazol-5-yl)methyl)-9-methoxy-3-azabicyclo[3.3.1]nonan-9-yl)picolinamide (110 mg, 64% yield).

To a solution of 4-((1R,5S,9r)-3-((1H-1,2,3-triazol-5-yl)methyl)-9-methoxy-3-azabicyclo[3.3.1]nonan-9-yl)picolinamide (110 mg, 0.31 mmol) in ethyl acetate (25 mL) was added 2 M hydrochloric acid in diethyl ether (0.20 mL, 0.40 mmol). The mixture was stirred for 5 minutes and then concentrated under reduced pressure and the residue freeze dried from water to give 4-((1R,5S,9r)-3-((1H-1,2,3-triazol-5-yl)methyl)-9-methoxy-3-azabicyclo[3.3.1]nonan-9-yl)picolinamide hydrochloride (109 mg, 89% yield); [M+H]$^+$ 357.13; $^1$H NMR (300 MHz, d6-DMSO): 9.30 (br s, 1H), 8.67 (d, 1H), 8.24 (s, 1H), 8.15 (s, 1H), 8.00 (s, 1H), 7.71 (s, 1H), 7.64 (d, 1H), 4.94 (br s, 1H), 4.43 (s, 2H), 3.59-3.37 (m, 4H), 2.93 (s, 2H), 2.55 (s, 3H), 2.20-1.93 (m, 1H), 1.88-1.70 (m, 2H), 1.52-1.07 (m, 3H).

Compound 23

Synthesis of 3-((1R,5S,9r)-9-methoxy-3-methyl-3-azabicyclo[3.3.1]nonan-9-yl)benzonitrile

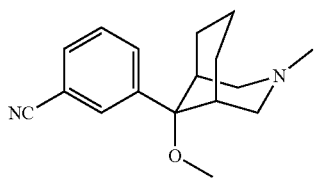 [SMILES: COC1(c2cccc(C#N)c2)C2CCCC1CN(C)C2]

To a solution of (1R,5S,9r)-9-(3-iodophenyl)-9-methoxy-3-methyl-3-azabicyclo[3.3.1]nonane (1.80 g, 4.85 mmol) in degassed N,N-dimethylformamide (25 mL) was added tetrakis(triphenylphosphine)palladium(0) (0.56 g, 0.49 mmol) and the mixture was heated to 50° C., then zinc cyanide (0.34 g, 2.91 mmol) was added. The reaction mixture was heated at 110° C. for 4 hours, cooled to room temperature and quenched with aqueous sodium hydrogen carbonate solution. The mixture was diluted with ethyl acetate and filtered through a pad of Celite, and extracted with ethyl acetate (×3). The combined organic phases were washed with water (×2), then brine, dried over MgSO$_4$, filtered and concentrated under reduced pressure. The residue was purified by silica chromatography, eluting with 50-100% ethyl acetate in heptane, to give 3-((1R,5S,9r)-9-methoxy-3-methyl-3-azabicyclo[3.3.1]nonan-9-yl)benzonitrile (0.63 g, 48% yield); [M+H]$^+$ 271.19.

Synthesis of 3-((1R,5S,9r)-9-methoxy-3-methyl-3-azabicyclo[3.3.1]nonan-9-yl)benzamide Hydrochloride

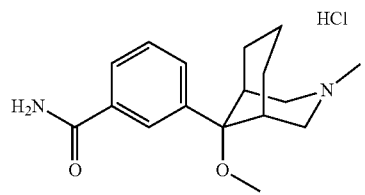 [SMILES: Cl ; COC1(c2cccc(C(N)=O)c2)C2CCCC1CN(C)C2]

To a solution of 3-((1R,5S,9r)-9-methoxy-3-methyl-3-azabicyclo[3.3.1]nonan-9-yl)benzonitrile (632 mg, 2.19 mmol) in tert-butanol (17 mL) was added potassium hydroxide (655 mg, 11.67 mmol) and the reaction mixture was heated at reflux for 2 hours. The mixture was quenched with water and extracted with ethyl acetate (×3). The combined organic phases were washed with water (×2), then brine, dried over MgSO$_4$, filtered and concentrated under reduced pressure. The residue was purified by reverse phase chromatography (C18) to give 3-((1R,5S,9r)-9-methoxy-3-methyl-3-azabicyclo[3.3.1]nonan-9-yl)benzamide (359 mg, 57% yield).

To a solution of 3-((1R,5S,9r)-9-methoxy-3-methyl-3-azabicyclo[3.3.1]nonan-9-yl)benzamide (359 mg, 1.24 mmol) in ethyl acetate (10 mL) and dichloromethane (10 mL) was added 2 M hydrochloric acid in diethyl ether (0.68 mL, 1.36 mmol) and the reaction stirred for 10 minutes at room temperature. The mixture was concentrated under reduced pressure and the residue freeze dried from water to give 3-((1R,5S,9r)-9-methoxy-3-methyl-3-azabicyclo[3.3.1]nonan-9-yl)benzamide hydrochloride (406 mg, quant.); [M+H]$^+$ 289.13; $^1$H NMR (300 MHz, d$_3$-MeOD): 8.03-7.98 (m, 1H), 7.89 (d, 1H), 7.70 (d, 1H), 7.56 (t, 1H), 3.73-3.57 (m, 4H), 2.97 (br s, 2H), 2.92 (s, 3H), 2.82 (s, 3H), 2.02-1.67 (m, 5H), 1.63-1.48 (m, 1H).

Compound 75

3-((1R,5S,9r)-3-((1H-1,2,3-triazol-5-yl)methyl)-9-methoxy-3-azabicyclo[3.3.1]nonan-9-yl)benzamide Hydrochloride

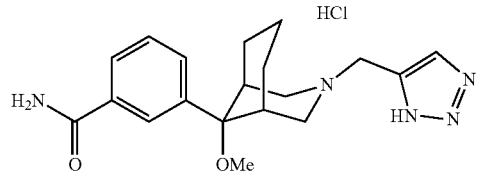 [SMILES: Cl ; COC1(c2cccc(C(N)=O)c2)C2CCCC1CN(Cc1cnn[nH]1)C2]

[M+H]+ 356.09. ¹H NMR (300 MHz, D₂O) 8.07 (s, 1H), 7.70 (s, 1H), 7.66 (d, 1H), 7.54 (d, 1H), 7.44 (t, 1H), 4.41 (s, 2H), 3.57 (d, 2H), 3.44 (d, 2H), 2.86 (br, 2H), 2.53 (s, 3H), 1.76-1.31 (m, 6H).

Compound 6

3-((1R,5S,9r)-9-methoxy-3-(7-oxaspiro[3.5]nonan-2-yl)-3-azabicyclo[3.3.1]nonan-9-yl)benzamide Hydrochloride

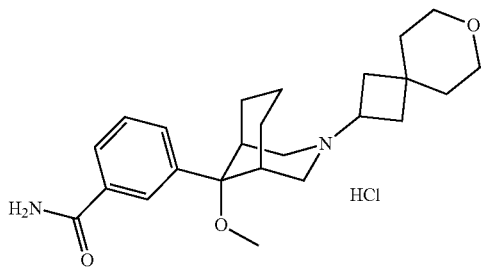 [SMILES: COC1(c2cccc(C(N)=O)c2)C2CCCC1CN(C1CC3(CCOCC3)C1)C2 ; Cl]

[M+H]+ 399.24. ¹H NMR (300 MHz, D₂O) 7.74 (s, 1H), 7.68 (d, 1H), 7.59 (d, 1H), 7.46 (t, 1H), 3.70 (quintuplet, 1H), 3.55-3.42 (m, 6H), 3.34 (br, 1H), 3.30 (br, 1H), 2.88 (br, 2H), 2.68 (s, 3H), 2.23-2.16 (m, 2H), 2.08-2.01 (m, 2H), 1.72-1.50 (m, 9H), 1.36-1.30 (m, 1H).

Compound 122

Synthesis of 3-((1R,5S,9r)-9-methoxy-3-((tetrahydro-2H-pyran-4-yl)methyl)-3-azabicyclo[3.3.1]nonan-9-yl)benzamide Hydrochloride

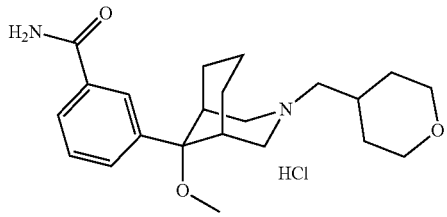 [SMILES: COC1(c2cccc(C(N)=O)c2)C2CCCC1CN(CC1CCOCC1)C2 ; Cl]

To 3-((1R,5S,9r)-9-methoxy-3-azabicyclo[3.3.1]nonan-9-yl)benzamide hydrochloride (200 mg, 0.64 mmol) in dichloromethane (10 mL) was added tetrahydro-2H-pyran-4-carbaldehyde (147 mg, 1.29 mmol) followed by triethylamine (0.27 ml, 1.93 mmol). The reaction was stirred at room temperature for 15 minutes before the addition of sodium triacetoxyborohydride (409 mg, 1.93 mmol) and further dichloromethane (10 mL). The reaction was stirred at room temperature overnight. The reaction was quenched with saturated sodium hydrogen carbonate solution and extracted with dichloromethane (×3). The dichloromethane phases were combined, washed (brine), dried over MgSO₄, filtered and concentrated under reduced pressure. The residue was purified by C18 reverse phase chromatography to give 3-((1R,5S,9r)-9-methoxy-3-((tetrahydro-2H-pyran-4-yl)methyl)-3-azabicyclo[3.3.1]nonan-9-yl)benzamide (232 mg, 97% yield).

To 3-((1R,5S,9r)-9-methoxy-3-((tetrahydro-2H-pyran-4-yl)methyl)-3-azabicyclo[3.3.1]nonan-9-yl)benzamide (232 mg, 0.62 mmol) in ethyl acetate (100 mL) was added 2M HCl in diethyl ether (0.34 mL, 0.69 mmol). After 10 minutes, the solvent was removed under reduced pressure. The product was dissolved in water and freeze dried to give 3-((1R,5S,9r)-9-methoxy-3-((tetrahydro-2H-pyran-4-yl)methyl)-3-azabicyclo[3.3.1]nonan-9-yl)benzamide hydrochloride (233 mg, 92% yield); [M+H]+ 373.12. ¹H NMR (300 MHz, D₂O): 7.75 (s, 1H), 7.69 (d, 1H), 7.60 (d, 1H), 7.47 (dd, 1H), 3.86 (dd, 2H), 3.63-3.44 (m, 4H), 3.37 (t, 2H), 2.97 (d, 2H), 2.89 (s, 2H), 2.70 (s, 3H), 2.24-2.05 (m, 1H), 1.84-1.52 (m, 6H), 1.49-1.21 (m, 4H).

Compound 129

3-((1R,5S,9r)-9-methoxy-3-(spiro[3.3]heptan-2-yl)-3-azabicyclo[3.3.1]nonan-9-yl)benzamide Hydrochloride

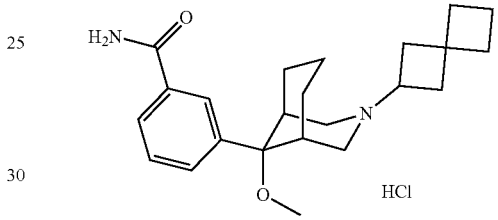

[M+H]+ 369.16. ¹H NMR (300 MHz, D₂O): 7.77 (s, 1H), 7.71 (d, 1H), 7.61 (d, 1H), 7.49 (dd, 1H), 3.62-3.48 (m, 1H), 3.47-3.27 (m, 4H), 2.89 (br s, 2H), 2.70 (s, 3H), 2.33-2.22 (m, 2H), 2.22-2.11 (m, 2H), 1.97-1.82 (m, 4H), 1.79-1.30 (m, 8H).

Compound 3

3-((1R,5S,9r)-9-methoxy-3-(2-oxaspiro[3.5]nonan-7-yl)-3-azabicyclo[3.3.1]nonan-9-yl)benzamide (S)-2-hydroxysuccinate

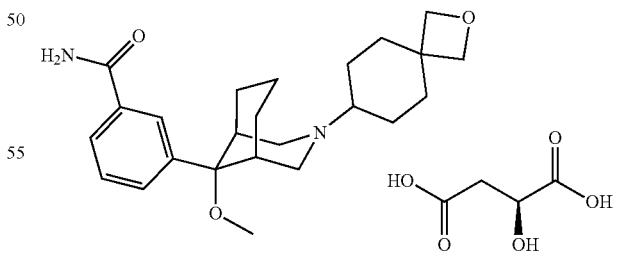

[M+H]+ 399.24. ¹H NMR (300 MHz, D₂O): 7.70 (s, 1H), 7.63 (d, 1H), 7.54 (d, 1H), 7.42 (dd, 1H), 4.36 (s, 2H), 4.24 (s, 2H), 4.18 (dd, 1H), 3.50 (d, 2H), 3.36 (d, 2H), 3.00 (br s, 1H), 2.85 (s, 2H), 2.64 (s, 3H), 2.58 (d, 1H), 2.43 (dd, 1H), 2.13 (br d, 2H), 1.96 (s, 2H), 1.72-1.24 (m, 10H).

Compound 1

3-((1R,5S,9r)-3-((1,1-dioxidotetrahydro-2H-thiopyran-4-yl)methyl)-9-methoxy-3-azabicyclo[3.3.1]nonan-9-yl)benzamide Hydrochloride

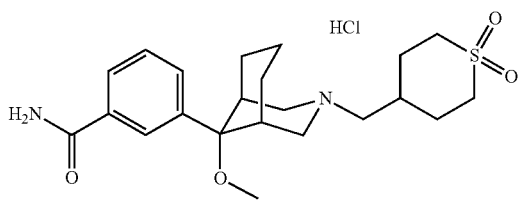 [SMILES: COC1(c2cccc(C(N)=O)c2)C2CCCC1CN(CC1CCS(=O)(=O)CC1)C2 ; Cl]

[M+H]⁺ 421.11; ¹H NMR (300 MHz, d6-DMSO): 8.08 (s, 1H), 8.03 (br, 1H), 7.94 (s, 1H), 7.87 (d, 1H), 7.63 (d, 1H), 7.51 (t, 1H), 7.44 (s, 1H), 3.64 (d, 2H), 3.45-3.38 (m, 2H), 3.13-3.07 (m, 6H), 2.96 (s, 2H), 2.71 (s, 3H), 2.25-2.13 (m, 3H), 1.86-1.69 (m, 5H), 1.54 (bs, 2H), 1.38-1.31 (m, 1H).

Compound 138

Synthesis of 3-((1R,5S,9r)-3-(2-cyclopropylethyl)-9-methoxy-3-azabicyclo[3.3.1]nonan-9-yl)benzamide Hydrochloride

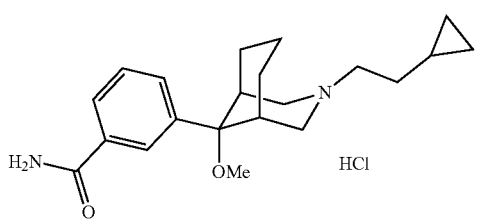 [SMILES: COC1(c2cccc(C(N)=O)c2)C2CCCC1CN(CCC1CC1)C2 ; Cl]

To a solution of 2-cyclopropylethanol (0.21 g, 2.41 mmol) in dichloromethane (40 mL) was added silica (3 g), followed by pyridinium chlorochromate (0.52 g, 2.41 mmol). After 2 h of stirring the reaction mixture was filtered through a plug of silica and the desired aldehyde eluted with dichloromethane. The collected dichloromethane solution was concentrated to 30 mL and 3-((1R,5S,9r)-9-methoxy-3-azabicyclo[3.3.1]nonan-9-yl)benzamide hydrochloride (0.25 g, 0.80 mmol) added. To the resulting suspension was then added triethylamine (0.33 mL, 2.41 mmol) and sodium triacetoxyborohydride (0.51 g, 2.41 mmol) and the reaction mixture stirred for 3 hours. Concentrated aqueous ammonia was added and the mixture was extracted with dichloromethane (×3). The combined organic phases were concentrated and purified by reverse phase chromatography (C18) to give 3-((1R,5S,9r)-3-(2-cyclopropylethyl)-9-methoxy-3-azabicyclo[3.3.1]nonan-9-yl)benzamide (0.17 g, 62% yield).

2.0 M HCl in diethyl ether (0.25 mL, 0.50 mmol) was added to a solution of 3-((1R,5S,9r)-3-(2-cyclopropylethyl)-9-methoxy-3-azabicyclo[3.3.1]nonan-9-yl)benzamide (0.17 g, 0.50 mmol) in dichloromethane (5 mL) and then the volatiles removed. The residue was freeze-dried from water to give 3-((1R,5S,9r)-3-(2-cyclopropylethyl)-9-methoxy-3-azabicyclo[3.3.1]nonan-9-yl)benzamide hydrochloride (0.10 g, 55%); [M+H]⁺ 343.19. ¹H NMR (300 MHz, D₂O): 7.76 (s, 1H), 7.70 (d, 1H), 7.61 (d, 1H), 7.49 (t, 1H), 3.63-3.42 (m, 4H), 3.20-3.11 (m, 2H), 2.89 (br, 2H), 2.71 (s, 3H), 1.80-1.50 (m, 4H), 0.65-0.55 (m, 1H), 0.50-0.38 (m, 2H), 0.42-0.35 (m, 2H), 0.05-0.00 (m, 2H).

Compound 154

3-((1R,5S,9r)-3-((1H-indazol-3-yl)methyl)-9-methoxy-3-azabicyclo[3.3.1]nonan-9-yl)benzamide Hydrochloride

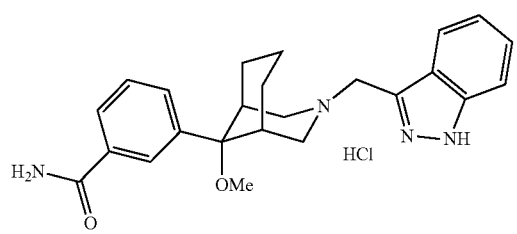 [SMILES: COC1(c2cccc(C(N)=O)c2)C2CCCC1CN(Cc1n[nH]c3ccccc13)C2 ; Cl]

[M+H]⁺ 405.12. ¹H NMR (300 MHz, D6-DMSO): 9.10 (br, 1H), 8.04-7.95 (m, 2H), 7.88-7.77 (m, 2H), 7.15-7.33 (m, 6H), 7.24 (t, 1H), 4.69 (s, 2H), 3.77-3.55 (m, 4H), 2.90 (s, 2H), 2.30 (s, 3H), 2.14-1.90 (m, 1H), 1.88-1.69 (m, 2H), 1.63-1.26 (m, 3H).

Compound 11

3-((1R,5S,9r)-3-(bicyclo[3.1.0]hexan-3-yl)-9-methoxy-3-azabicyclo[3.3.1]nonan-9-yl)benzamide Hydrochloride

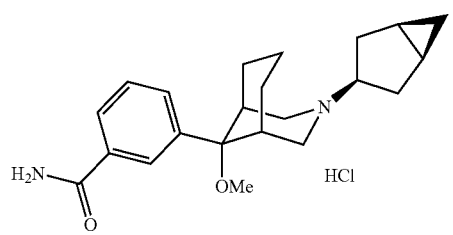 [SMILES: COC1(c2cccc(C(N)=O)c2)C2CCCC1CN([C@H]1C[C@H]3C[C@H]3C1)C2 ; Cl]

[M+H]⁺ 355.22. ¹H NMR (300 MHz, D₂O): 7.71 (s, 1H), 7.65 (d, 1H), 7.55 (d, 1H), 7.43 (t, 1H), 3.81-3.73 (m, 1H), 3.42-3.38 (m, 4H), 2.82 (br, 2H), 2.66 (s, 3H), 2.41-2.32 (m, 2H), 1.69-1.46 (m, 10H), 1.45-1.35 (m, 1H), 1.30-1.19 (m, 1H).

Compound 64

3-((1R,5S,9r)-3-((1H-benzo[d]imidazol-2-yl)methyl)-9-methoxy-3-azabicyclo[3.3.1]nonan-9-yl)benzamide Hydrochloride

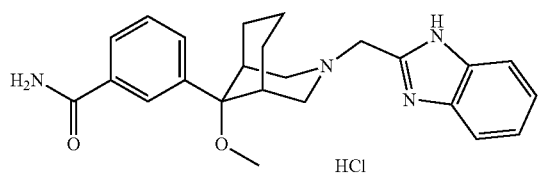 [SMILES: COC1(c2cccc(C(N)=O)c2)C2CCCC1CN(Cc1nc3ccccc3[nH]1)C2 ; Cl]

[M+H]+ 405.12. ¹H NMR (300 MHz, d6-DMSO): 8.05 (s, 1H), 7.91 (s, 1H), 7.83 (d, 1H), 7.80-7.71 (m, 2H), 7.58 (d, 1H), 7.51-7.36 (m, 4H), 4.73 (br, 1H), 4.24 (br, 1H), 2.85-2.73 (m, 2H), 2.60 (s, 2H), 2.53-2.41 (m, 8H), 1.80-1.66 (m, 2H), 1.61-1.45 (m, 2H), 1.31-1.18 (m, 1H).

Compound 157

3-((1R,5S,9r)-3-(3-fluoropropyl)-9-methoxy-3-azabicyclo[3.3.1]nonan-9-yl)benzamide Hydrochloride

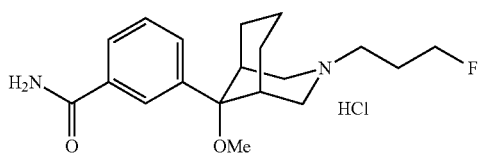 [SMILES: COC1(c2cccc(C(N)=O)c2)C2CCCC1CN(CCCF)C2 ; Cl]

[M+H]+ 335.12. ¹H NMR (300 MHz, D₂O): 7.78 (s, 1H), 7.71 (d, 1H), 7.62 (d, 1H), 7.50 (t, 1H), 4.61 (t, 1H), 4.45 (t, 1H), 3.62 (d, 2H), 3.51 (d, 2H), 3.25 (t, 2H), 2.92 (br s, 2H), 2.72 (s, 3H), 2.23-2.13 (m, 1H), 2.13-2.03 (m, 1H), 1.83-1.58 (m, 4H), 1.50-1.38 (m, 2H).

Compounds 16 and 14

3-((1R,5S,9R)-3-((1R,3s,5S)-8-oxabicyclo[3.2.1]octan-3-yl)-9-methoxy-3-azabicyclo[3.3.1]nonan-9-yl)benzamide hydrochloride and 3-((1R,5S,9R)-3-((1R,3r,5S)-8-oxabicyclo[3.2.1]octan-3-yl)-9-methoxy-3-azabicyclo[3.3.1]nonan-9-yl)benzamide Hydrochloride

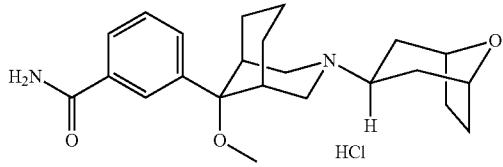

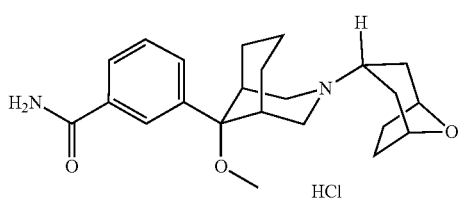

[M+H]+ 385.23, 99.66% de. ¹H NMR (300 MHz, D₂O): 7.77 (s, 1H), 7.72 (d, 1H), 7.62 (d, 1H), 7.50 (t, 1H), 4.51-4.43 (m, 2H), 3.51 (s, 3H), 3.33-3.18 (m, 1H), 2.92 (s, 2H), 2.72 (s, 3H), 2.70-2.59 (m, 2H), 1.94-1.86 (m, 2H), 1.79-1.29 (m, 11H).

[M+H]+ 385.23, 99.53% de. ¹H NMR (300 MHz, D₂O): 7.78 (s, 1H), 7.72 (d, 1H), 7.62 (d, 1H), 7.50 (t, 1H), 4.54-4.47 (m, 2H), 3.59-3.39 (m, 5H), 2.94 (s, 2H), 2.72 (s, 3H), 2.10-2.01 (m, 2H), 1.95-1.82 (m, 4H), 1.75-1.49 (m, 8H).

Compounds 148 and 143

Synthesis of 3-((1R,5S,9S)-9-methoxy-3-(((S)-tetrahydrofuran-3-yl)methyl)-3-azabicyclo[3.3.1]nonan-9-yl)benzamide hydrochloride and 3-((1R,5S,9R)-9-methoxy-3-(((R)-tetrahydrofuran-3-yl)methyl)-3-azabicyclo[3.3.1]nonan-9-yl)benzamide Hydrochloride

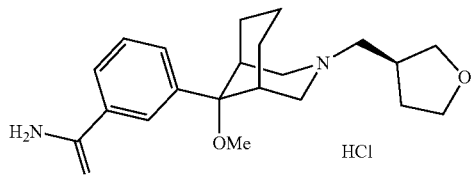

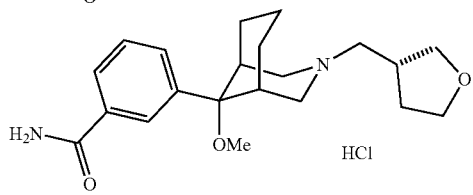

To a suspension of 3-((1R,5S,9r)-9-methoxy-3-azabicyclo[3.3.1]nonan-9-yl)benzamide hydrochloride (200 mg, 0.64 mmol), tetrahydrofuran-3-carboxaldehyde (240 μl, 1.28 mmol) in tetrahydrofuran (16 ml) was added triethylamine (225 μl, 1.61 mmol) and the reaction mixture was stirred at room temperature for 20 minutes. Sodium triacetoxyborohydride (408 mg, 1.92 mmol) was added and the mixture stirred at room temperature overnight. The reaction was quenched with aqueous solution of sodium hydrogen carbonate and extracted with dichloromethane (×3). The combined organics were washed with brine, dried over MgSO₄, filtered and concentrated under reduced pressure. The crude product was purified by silica chromatography eluting with 1-5% methanol in dichloromethane then the enantiomers were separated by chiral supercritical fluid chromatography. The individual enantiomers were purified by silica chromatography eluting with 0 to 8% methanol/ammonia in dichloromethane and then reverse phase chromatography (C18) to give 3-((1R,5S,9S)-9-methoxy-3-(((S)-tetrahydrofuran-3-yl)methyl)-3-azabicyclo[3.3.1]nonan-9-yl)benzamide (57 mg, 25% yield) and 3-((1R,5S,9R)-9-methoxy-3-(((R)-tetrahydrofuran-3-yl)methyl)-3-azabicyclo[3.3.1]nonan-9-yl)benzamide (30 mg, 13% yield). The stereochemistry was arbitrarily assigned.

To a solution of 3-((1R,5S,9S)-9-methoxy-3-(((S)-tetrahydrofuran-3-yl)methyl)-3-azabicyclo[3.3.1]nonan-9-yl)benzamide (57 mg, 0.16 mmol) in diethyl ether (15 ml) was added 2M hydrogen chloride solution in diethyl ether (0.12 ml, 0.24 mmol). The suspension was stirred at room temperature for 15 minutes then concentrated under reduced pressure and the residue dissolved in water and freeze dried to give 3-((1R,5S,9S)-9-methoxy-3-(((S)-tetrahydrofuran-3-yl)methyl)-3-azabicyclo[3.3.1]nonan-9-yl)benzamide hydrochloride (48 mg, 76% yield); [M+H]+ 359.18. ¹H NMR (300 MHz, D₂O): 7.76 (s, 1H), 7.69 (d, 1H), 7.58 (d, 1H), 7.48 (dd, 1H), 3.93 (dd, 1H), 3.75-3.85 (m, 1H), 3.68 (dd, 1H), 3.40-3.64 (m, 5H), 3.19 (t, 2H), 2.91 (s, 2H), 2.65-2.71 (m, 4H), 2.10-2.20 (m, 1H), 1.40-1.80 (m, 7H).

To a solution of 3-((1R,5S,9R)-9-methoxy-3-(((R)-tetrahydrofuran-3-yl)methyl)-3-azabicyclo[3.3.1]nonan-9-yl)

benzamide (30 mg, 0.08 mmol) in diethyl ether (8 ml) was added 2M hydrogen chloride solution in diethyl ether (0.06 ml, 0.13 mmol). The suspension was stirred at room temperature for 15 minutes then concentrated under reduced pressure and the residue dissolved in water and freeze dried to give 3-((1R,5S,9R)-9-methoxy-3-(((R)-tetrahydrofuran-3-yl)methyl)-3-azabicyclo[3.3.1]nonan-9-yl)benzamide hydrochloride (29 mg, 86% yield); [M+H]$^+$ 359.18. $^1$H NMR (300 MHz, d6-DMSO): 8.60 (s, 1H), 8.04-8.10 (m, 1H), 7.79-7.88 (m, 2H), 7.36-7.62 (m, 3H), 3.90 (dd, 1H), 3.62-3.72 (m, 3H), 3.23-3.43 (m, 2H), 3.16 (s, 1H), 2.95 (s, 1H), 2.64-2.78 (m, 5H), 2.11-2.19 (m, 2H), 1.52-1.85 (m, 5H), 1.14-1.27 (m, 2H), 0.97-1.01 (m, 1H), 0.77-0.86 (m, 1H).

Compounds 140 and 141

Synthesis of 3-((1R,5S,9S)-9-methoxy-3-((S)-tetrahydro-2H-pyran-3-yl)-3-azabicyclo[3.3.1]nonan-9-yl)benzamide hydrochloride and 3-((1R,5S,9R)-9-methoxy-3-((R)-tetrahydro-2H-pyran-3-yl)-3-azabicyclo[3.3.1]nonan-9-yl)benzamide Hydrochloride

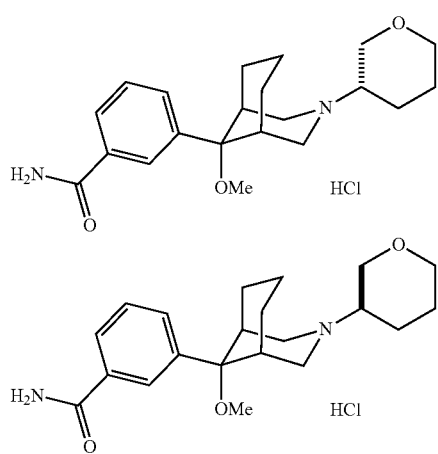

To a suspension of 3-((1R,5S,9r)-9-methoxy-3-azabicyclo[3.3.1]nonan-9-yl)benzamide hydrochloride (300 mg, 0.97 mmol), dihydro-2H-pyran-3(4)-one (194 mg, 1.93 mmol) in tetrahydrofuran (16 ml) was added triethylamine (0.34 ml, 2.50 mmol) and the reaction mixture was stirred at room temperature for 20 minutes. Sodium triacetoxyborohydride (614 mg, 2.89 mmol) was added and the mixture stirred at room temperature overnight. The reaction was quenched with aqueous solution of sodium hydrogen carbonate and extracted with dichloromethane (×3). The combined organics were washed with brine, dried over MgSO$_4$, filtered and concentrated under reduced pressure. The crude product was purified by silica chromatography eluting with 1-5% methanol in dichloromethane. The enantiomers were separated by chiral supercritical fluid chromatography to give 3-((1R,5S,9S)-9-methoxy-3-((S)-tetrahydro-2H-pyran-3-yl)-3-azabicyclo[3.3.1]nonan-9-yl)benzamide (81 mg, 25% yield) and 3-((1R,5S,9R)-9-methoxy-3-((R)-tetrahydro-2H-pyran-3-yl)-3-azabicyclo[3.3.1]nonan-9-yl)benzamide (71 mg, 19% yield). The stereochemistry was arbitrarily assigned.

To a solution of 3-((1R,5S,9S)-9-methoxy-3-((S)-tetrahydro-2H-pyran-3-yl)-3-azabicyclo[3.3.1]nonan-9-yl)benzamide (81 mg, 0.26 mmol) in ethyl acetate (3 ml) was added 2M hydrogen chloride solution in diethyl ether (124 µl, 0.25 mmol). The suspension was stirred at room temperature for 15 minutes then concentrated under reduced pressure and the residue dissolved in water and freeze dried to give 3-((1R,5S,9S)-9-methoxy-3-((S)-tetrahydro-2H-pyran-3-yl)-3-azabicyclo[3.3.1]nonan-9-yl)benzamide hydrochloride (90 mg, 100% yield); [M+H$^+$] 359.18. $^1$H NMR (300 MHz, D$_2$O): 7.78 (s, 1H), 7.71 (d, 1H), 7.61 (d, 1H), 7.52 (t, 1H), 4.15-4.20 (m, 1H), 3.76-3.82 (m, 1H), 3.48-3.69 (m, 5H), 3.25-3.44 (m, 2H), 2.93-2.98 (m, 2H), 2.73 (s, 3H), 2.23-2.29 (m, 1H), 1.38-1.83 (m, 9H).

To a solution of 3-((1R,5S,9R)-9-methoxy-3-((R)-tetrahydro-2H-pyran-3-yl)-3-azabicyclo[3.3.1]nonan-9-yl)benzamide (71 mg, 0.20 mmol) in ethyl acetate (3 ml) was added 2M hydrogen chloride solution in diethyl ether (109 µl, 0.22 mmol). The suspension was stirred at room temperature for 15 minutes then concentrated under reduced pressure and the residue dissolved in water and freeze dried to give 3-((1R,5S,9R)-9-methoxy-3-((R)-tetrahydro-2H-pyran-3-yl)-3-azabicyclo[3.3.1]nonan-9-yl)benzamide hydrochloride (78 mg, 99% yield); [M+H]$^+$ 359.18. $^1$H NMR (300 MHz, D$_2$O): 7.78 (s, 1H), 7.73 (d, 1H), 7.62 (d, 1H), 7.50 (t, 1H), 4.15-4.19 (m, 1H), 3.76-3.81 (m, 1H), 3.48-3.67 (m, 5H), 3.25-3.44 (m, 2H), 2.93-2.97 (m, 2H), 2.73 (s, 3H), 2.22-2.27 (m, 1H), 1.40-1.43 (m, 9H).

Compound 149

3-((1R,5S,9r)-9-methoxy-3-((2-methyl-1H-imidazol-4-yl)methyl)-3-azabicyclo[3.3.1]nonan-9-yl)benzamide Hydrochloride

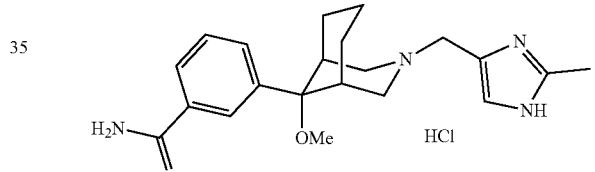

[M+H]$^+$ 369.16. $^1$H NMR (300 MHz, MeOD): 7.99 (s, 1H), 7.86 (d, 1H), 7.68 (d, 1H), 7.59-7.62 (m 1H), 7.53 (dd, 1H), 7.46 (s, 1H), 4.23-4.30 (m, 1H), 3.44-3.48 (m, 2H), 2.88 (s, 2H), 2.76 (s, 3H), 2.53 (s, 3H), 2.14-2.26 (m, 1H), 1.74-1.83 (m, 4H), 1.27-1.43 (m, 2H), 0.73-0.98 (m, 2H).

Compound 128

Synthesis of 3-((1R,5S,9r)-9-methoxy-3-(2-methoxyethyl)-3-azabicyclo[3.3.1]nonan-9-yl)benzamide Hydrochloride

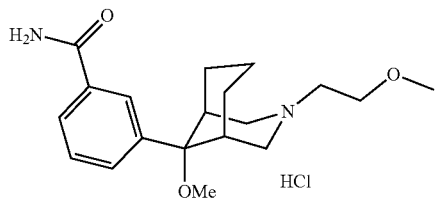 [SMILES: COCCN1CC2CCCC(C1)C2(OC)c1cccc(C(N)=O)c1 ; Cl]

A suspension of 3-((1R,5S,9r)-9-methoxy-3-azabicyclo[3.3.1]nonan-9-yl)benzamide hydrochloride (200 mg, 0.64 mmol), 2-bromoethylmethyl ether (134 mg, 0.97 mmol) and potassium carbonate (267 mg, 1.93 mmol) in N,N-dimethylformamide (5 mL) was stirred at 50° C. After 16 h, the reaction was cooled to ambient temperature and diluted with water. The solution was extracted with ethyl acetate (×3) and the combined organic extracts washed with water (×3), brine, dried over MgSO$_4$, filtered and concentrated under reduced pressure. The residue was purified by reverse phase chromatography (C18) to give 3-((1R,5S,9r)-9-methoxy-3-(2-methoxyethyl)-3-azabicyclo[3.3.1]nonan-9-yl)benzamide (109 mg, 51% yield). This was combined with a previous batch (54 mg) and purified by reverse phase preparative HPLC to give 3-((1R,5S,9r)-9-methoxy-3-(2-methoxyethyl)-3-azabicyclo[3.3.1]nonan-9-yl)benzamide (94 mg, 30% yield).

To a solution of 3-((1R,5S,9r)-9-methoxy-3-(2-methoxyethyl)-3-azabicyclo[3.3.1]nonan-9-yl)benzamide (94 mg, 0.28 mmol) in ethyl acetate (5 mL) was added 2M HCl in diethyl ether (210 µL, 0.42 mmol), the resulting suspension was concentrated under vacuum and the resulting solid dissolved in water and freeze dried to give 3-((1R,5S,9r)-9-methoxy-3-(2-methoxyethyl)-3-azabicyclo[3.3.1]nonan-9-yl)benzamide hydrochloride (91 mg, 87% yield); [M+H]$^+$ 333.07. $^1$H NMR (300 MHz, D$_2$O) 7.78 (1H, s), 7.70-7.75 (m, 1H), 7.60-7.66 (m, 1H), 7.47-7.55 (m, 1H), 3.68-3.74 (m, 2H), 3.58 (s, 4H), 3.31 (s, 5H), 2.92 (br s, 2H), 2.73 (s, 3H), 1.61-1.85 (m, 4H), 1.40-1.52 (m, 2H).

Compound 151

3-((1R,5S,9r)-9-methoxy-3-(1-phenylazetidin-3-yl)-3-azabicyclo[3.3.1]nonan-9-yl)benzamide (S)-2-hydroxysuccinate

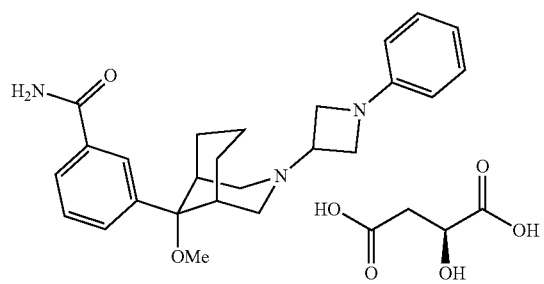 [SMILES: COC1(c2cccc(C(N)=O)c2)C2CCCC1CN(C1CN(c3ccccc3)C1)C2 ; O=C(O)C[C@H](O)C(=O)O]

[M+H]$^+$ 406.18. $^1$H NMR (300 MHz, d6-DMSO): 8.03 (br s, 1H), 7.93 (s, 1H), 7.78 (d, 1H), 7.58 (d, 1H), 7.44 (t, 1H), 7.36 (br s, 1H), 7.14 (t, 2H), 6.60 (t, 1H), 6.42 (d, 2H), 5.44 (br s, 1H), 4.21 (dd, 2H), 3.92 (t, 2H), 3.53 (t, 2H), 3.13 (d, 2H), 2.65-2.76 (m, 10H), 2.59 (dd, 1H), 2.40 (dd, 1H), 1.71-1.63 (m, 2H), 1.61-1.45 (m, 2H), 1.20 (br s, 2H).

Compound 150

Synthesis of 3-((1R,5S,9r)-9-methoxy-3-(2-(methylsulfonyl)ethyl)-3-azabicyclo[3.3.1]nonan-9-yl)benzamide Hydrochloride

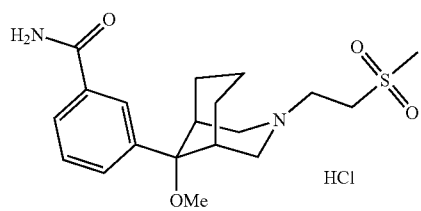 [SMILES: COC1(c2cccc(C(N)=O)c2)C2CCCC1CN(CCS(C)(=O)=O)C2 ; Cl]

To a suspension of 3-((1R,5S,9r)-9-methoxy-3-azabicyclo[3.3.1]nonan-9-yl)benzamide hydrochloride (150 mg, 0.48 mmol) and Hünig's base (0.25 mL, 1.45 mmol) in acetonitrile (5 mL) was added 2-(methylsulfonyl)ethyl methanesulfonate (195 mg, 0.97 mmol). After stirring for 16 h, 2-(methylsulfonyl)ethyl methanesulfonate (54 mg, 0.26 mmol) was added followed by N,N-dimethylformamide (2 mL). After 4 h the reaction was quenched with aqueous saturated sodium hydrogen carbonate and extracted with dichloromethane (×3). The combined organic extracts were then washed with brine, dried over MgSO$_4$, filtered and concentrated. The crude material was purified by silica chromatography, eluting with 0-5% methanol in dichloromethane to give a white solid, which was triturated with diethyl ether and dried. The product was further purified by preparative HPLC to give 3-((1R,5S,9r)-9-methoxy-3-(2-(methylsulfonyl)ethyl)-3-azabicyclo[3.3.1]nonan-9-yl)benzamide (28 mg, 15% yield).

To a solution of methoxy-3-(2-(methylsulfonyl)ethyl)-3-azabicyclo[3.3.1]nonan-9-yl)benzamide (28 mg, 0.07 mmol) in ethyl acetate (5 mL) was added 2M HCl in diethyl ether (50 µL, 0.10 mmol), the resulting suspension was stirred at room temperature for 30 minutes, concentrated under vacuum and the resulting solid dissolved in water and freeze dried to give 3-((1R,5S,9r)-9-methoxy-3-(2-(methylsulfonyl)ethyl)-3-azabicyclo[3.3.1]nonan-9-yl)benzamide hydrochloride (23 mg, 74% yield); [M+H]$^+$ 381.12. $^1$H NMR (300 MHz, d$_6$-DMSO): 8.58 (br s, 1H), 8.07 (s, 1H), 7.94 (s, 1H), 7.90-7.77 (m, 1H), 7.64 (d, 1H), 7.55-7.39 (m, 2H), 3.88-3.72 (m, 2H), 3.70-3.58 (m, 2H), 3.57-3.42 (m, 4H), 3.12 (s, 3H), 2.98 (br s, 3H), 2.73-2.63 (m, 3H), 1.90-1.71 (m, 2H), 1.63-1.44 (m, 2H), 1.41-1.20 (m, 1H).

Compound 133

Synthesis of 3-((1R,5S,9r)-9-methoxy-3-(2-oxaspiro[3.3]heptan-6-yl)-3-azabicyclo[3.3.1]nonan-9-yl)benzamide (S)-2-hydroxysuccinate

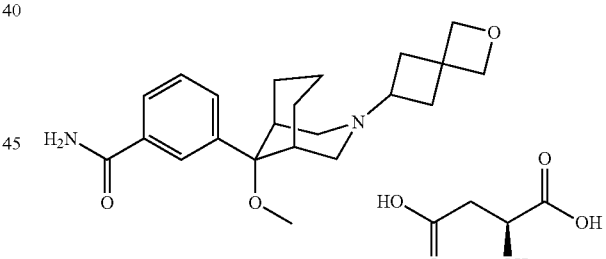

Dess-Martin periodinane (557 mg, 1.31 mmol) was added to a solution of 2-oxaspiro[3.3]heptan-6-ol (150 mg, 1.31 mmol) in dichloromethane (10 mL) cooled in an ice bath. After stirring at room temperature for 2 hours, the reaction mixture was filtered through celite, washing through with dichloromethane, and 3-((1R,5S,9r)-9-methoxy-3-azabicyclo[3.3.1]nonan-9-yl)benzamide hydrochloride (204 mg, 0.66 mmol) and acetic acid (0.08 mL, 1.32 mmol) were added. After stirring at room temperature for 30 minutes, sodium triacetoxyborohydride (418 mg, 1.97 mmol) was added and the reaction mixture was stirred for 16 hours and then quenched with aqueous sodium hydrogen carbonate solution. The mixture was extracted with dichloromethane (×2) and the combined organic phases were washed with brine, dried over MgSO$_4$, filtered and concentrated under reduced pressure. The residue was purified by silica chromatography eluting with 5-8% methanol in dichloromethane, recrystallised from isopropyl alcohol and the filtrate re-purified via preparative HPLC and combined to give 3-((1R,5S,9r)-9-methoxy-3-(2-oxaspiro[3.3]heptan-6-yl)-3-azabicyclo[3.3.1]nonan-9-yl)benzamide (100 mg, 41% yield).

To a solution of 3-((1R,5S,9r)-9-methoxy-3-(2-oxaspiro[3.3]heptan-6-yl)-3-azabicyclo[3.3.1]nonan-9-yl)benzamide (100 mg, 0.27 mmol) in ethyl acetate (8 mL) was added L-malic acid (36 mg, 0.27 mmol) and the reaction mixture was stirred for 20 minutes. The mixture was concentrated under reduced pressure and the residue freeze dried from water to give 3-((1R,5S,9r)-9-methoxy-3-(2-oxaspiro[3.3]heptan-6-yl)-3-azabicyclo[3.3.1]nonan-9-yl)benzamide (S)-2-hydroxysuccinate (131 mg, 96% yield); [M+H]$^+$ 371.14; $^1$H NMR (300 MHz, D$_2$O): 7.76 (s, 1H), 7.69 (d, 1H), 7.59 (d, 1H), 7.48 (t, 1H), 4.67 (s, 2H), 3.59 (s, 2H), 4.26-4.21 (m, 1H), 3.62-3.54 (m, 1H), 3.48-3.28 (m, 4H), 2.91-2.88 (m, 2H), 2.70 (s, 3H), 2.68-2.47 (m, 6H), 1.71-1.57 (m, 5H), 1.34-1.30 (m, 1H).

Compound 155

Synthesis of 3-((1R,5S,9r)-3-(but-3-yn-1-yl)-9-methoxy-3-azabicyclo[3.3.1]nonan-9-yl)benzamide

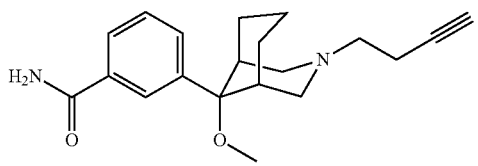 [SMILES: C#CCCN1CC2CCCC(C1)C2(OC)c1cccc(C(N)=O)c1]

4-Bromo-1-butyne (0.09 mL, 0.97 mmol) and potassium carbonate (200 mg, 1.45 mmol) were added to a solution of 3-((1R,5S,9r)-9-methoxy-3-azabicyclo[3.3.1]nonan-9-yl)benzamide hydrochloride (150 mg, 0.48 mmol) in acetonitrile (5 mL). The reaction mixture was heated to 60° C. and after three hours additional 4-bromo-1-butyne (0.09 mL, 0.97 mmol) and potassium carbonate (200 mg, 1.45 mmol) were added. After a further two hours at 60° C., the reaction mixture was cooled to room temperature and partitioned between water and ethyl acetate. The aqueous phase was extracted with ethyl acetate (×2) and the combined organics were washed with brine, dried over MgSO$_4$, filtered and concentrated under reduced pressure. The residue was purified by silica column chromatography, eluting with 0-10% methanol in dichloromethane to give 3-((1R,5S,9r)-3-(but-3-yn-1-yl)-9-methoxy-3-azabicyclo[3.3.1]nonan-9-yl)benzamide (122 mg, 77% yield); [M+H]$^+$ 327.21.

Synthesis of 3-((1R,5S,9r)-3-(2-(1H-1,2,3-triazol-4-yl)ethyl)-9-methoxy-3-azabicyclo[3.3.1]nonan-9-yl)benzamide Hydrochloride

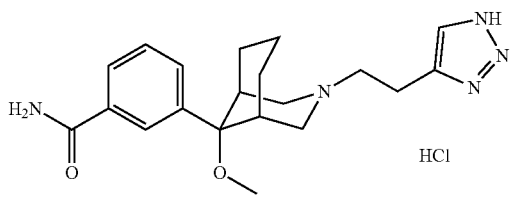 [SMILES: COC1(c2cccc(C(N)=O)c2)C2CCCC1CN(CCc1c[nH]nn1)C2 ; Cl]

To a solution of 3-((1R,5S,9r)-3-(but-3-yn-1-yl)-9-methoxy-3-azabicyclo[3.3.1]nonan-9-yl)benzamide (122 mg, 0.37 mmol) in degassed N,N-dimethylformamide (3 mL) and water (0.4 mL) was added copper sulphate pentahydrate (5 mg, 0.02 mmol), sodium ascorbate (30 mg, 0.15 mmol) and sodium azide (73 mg, 1.12 mmol). The reaction mixture was heated in a microwave reactor at 120° C. for 5 hours and then partitioned between water and ethyl acetate. The aqueous phase was extracted with ethyl acetate and the combined organic phases were washed with water (×2), brine (×2), dried over MgSO$_4$, filtered and concentrated under reduced pressure. The residue was purified by silica column chromatography, eluting with 5-10% NH$_3$/methanol in dichloromethane, then by reverse phase chromatography (C18) then by preparative HPLC to give 3-((1R,5S,9r)-3-(2-(1H-1,2,3-triazol-4-yl)ethyl)-9-methoxy-3-azabicyclo[3.3.1]nonan-9-yl)benzamide (51 mg, 37% yield).

To a suspension of 3-((1R,5S,9r)-3-(2-(1H-1,2,3-triazol-4-yl)ethyl)-9-methoxy-3-azabicyclo[3.3.1]nonan-9-yl)benzamide (51 mg, 0.14 mmol) in ethyl acetate (3 mL) was added 2 M hydrochloric acid in diethyl ether (0.08 mL, 0.15 mmol) and the reaction mixture was stirred for 30 minutes. The mixture was concentrated under reduced pressure and the residue freeze dried from water to give 3-((1R,5S,9r)-3-(2-(1H-1,2,3-triazol-4-yl)ethyl)-9-methoxy-3-azabicyclo[3.3.1]nonan-9-yl)benzamide hydrochloride (48 mg, 86% yield); [M+H]$^+$ 370.15; $^1$H NMR (300 MHz, D$_2$O): 7.79 (s, 1H), 7.76-7.71 (m, 2H), 7.64 (d, 1H), 7.53 (t, 1H), 3.71-3.57 (m, 4H), 3.45-3.40 (m, 2H), 3.23-3.17 (m, 2H), 2.97-2.94 (m, 2H), 2.74 (s, 3H), 1.85-1.43 (m, 6H).

Compounds 156 and 152

3-((1R,5S,9R)-3-((1R,3r,5S)-bicyclo[3.1.0]hexan-3-ylmethyl)-9-methoxy-3-azabicyclo[3.3.1]nonan-9-yl)benzamide hydrochloride and 3-((1R,5s,9R)-3-((1R,3s,5S)-bicyclo[3.1.0]hexan-3-ylmethyl)-9-methoxy-3-azabicyclo[3.3.1]nonan-9-yl)benzamide Hydrochloride

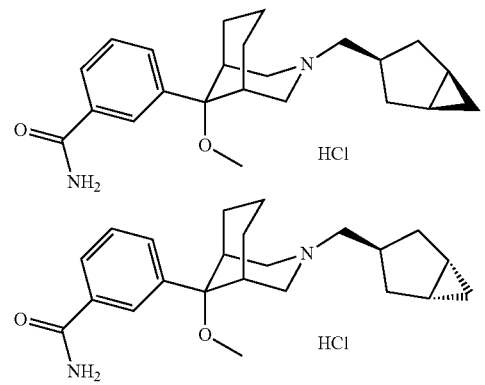

[M+H]$^+$ 369.16; $^1$H NMR (300 MHz, D$_2$O): 7.75 (s, 1H), 7.65-7.72 (m, 1H), 7.57-7.63 (m, 1H), 7.42-7.52 (m, 1H), 3.40-3.58 (m, 4H), 3.05 (d, 2H), 2.75-2.92 (m, 2H), 2.69 (s, 3H), 1.37-1.98 (m, 11H), 1.19 (d, 2H), 0.15-0.28 (m, 1H), 0.05-0.11 (m, 1H).

[M+H]$^+$ 369.16; $^1$H NMR (300 MHz, D$_2$O): 7.76 (s, 1H), 7.69-7.78 (m, 1H), 7.59-7.67 (m, 1H), 7.46-7.54 (m, 1H), 3.41-3.55 (m, 4H), 2.96 (d, 2H), 2.89 (s, 2H), 2.71 (s, 3H), 2.55-2.71 (m, 1H), 2.12-2.18 (m, 2H), 1.60-1.85 (m, 4H), 1.39-1.53 (m, 2H), 1.20-1.38 (m, 4H), 0.50-0.60 (m, 1H), 0.13-0.22 (m, 1H).

Compound 9

3-((1R,5S,9r)-3-(4,4-difluorocyclohexyl)-9-methoxy-3-azabicyclo[3.3.1]nonan-9-yl)benzamide Hydrochloride

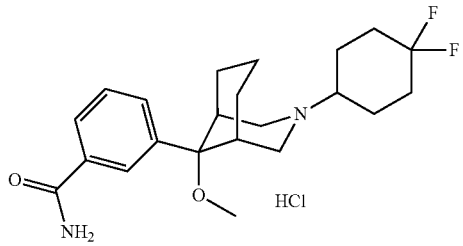 [SMILES: COC1(c2cccc(C(N)=O)c2)C2CCCC1CN(C1CCC(F)(F)CC1)C2 ; Cl]

[M+H]+ 393.15; ¹H NMR (300 MHz, D₂O): 7.74 (s, 1H), 7.67 (d, 1H), 7.58 (d, 1H), 7.45 (dd, 1H), 3.57 (d, 2H), 3.49 (d, 2H), 3.17-3.25 (m, 1H), 2.91 (s, 2H), 2.69 (s, 3H), 2.05-2.18 (m, 4H), 1.66-1.84 (m, 6H), 1.40-1.61 (m, 3H), 1.28-1.38 (m, 1H).

Compound 17

3-((1R,5S,9R)-3-((1R,3r,5S)-6,6-difluorobicyclo[3.1.0]hexan-3-yl)-9-methoxy-3-azabicyclo[3.3.1]nonan-9-yl)benzamide Hydrochloride

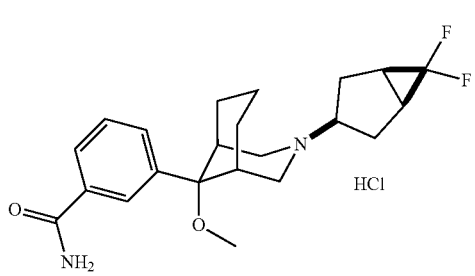

[M+H]+ 391.17. ¹H NMR (400 MHZ, de-DMSO): 8.65 (br s, 1H), 8.08 (s, 1H), 7.92 (s, 1H), 7.86 (d, 1H), 7.61 (d, 1H), 7.49 (t, 1H), 7.43 (s, 1H), 3.85-3.74 (m, 1H), 3.52-3.41 (m, 5H), 2.92 (s, 2H), 2.70 (s, 3H), 2.54-2.48 (m, 1H), 2.25-2.18 (m, 2H), 2.02-1.88 (m, 3H), 1.77-1.70 (m, 2H), 1.52-1.40 (m, 2H), 1.28-1.20 (m, 1H).

Compounds 19 and 20

3-((1R,5S,9S)-3-((S)-1-(1H-imidazol-5-yl)ethyl)-9-methoxy-3-azabicyclo[3.3.1]nonan-9-yl)benzamide hydrochloride and 3-((1R,5S,9R)-3-((R)-1-(1H-imidazol-5-yl)ethyl)-9-methoxy-3-azabicyclo[3.3.1]nonan-9-yl)benzamide Hydrochloride

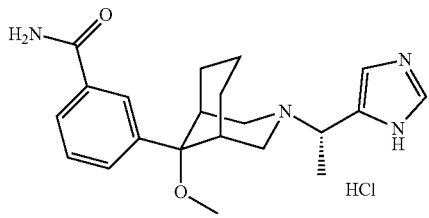

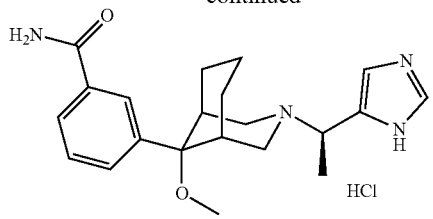

[M+H]+ 369.23. ¹H NMR (300 MHz, D₂O): 8.68-8.65 (m, 1H), 7.78-7.66 (m, 3H), 7.57-7.53 (m, 1H), 7.47-7.42 (m, 1H), 3.54-3.44 (m, 4H), 2.92-2.89 (m, 2H), 2.49 (s, 3H), 1.77-1.37 (m, 10H).

[M+H]+ 369.23. ¹H NMR (300 MHz, D₂O): 8.36-8.32 (m, 1H), 7.69-7.62 (m, 3H), 7.51 (d, 1H), 7.44 (t, 1H), 3.57-3.44 (m, 4H), 2.87 (br s, 2H), 2.46 (s, 3H), 1.74-1.36 (m, 10H).

Compound 63

Synthesis of 3-((1R,5S,9r)-9-methoxy-3-(2-(2-oxoimidazolidin-1-yl)ethyl)-3-azabicyclo[3.3.1]nonan-9-yl)benzamide Hydrochloride

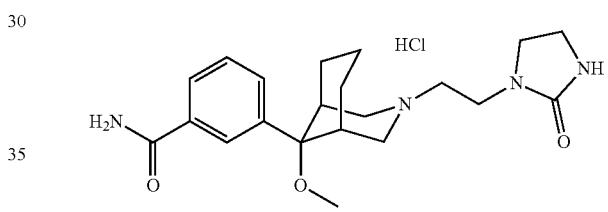

A mixture of 3-((1R,5S,9r)-9-methoxy-3-azabicyclo[3.3.1]nonan-9-yl)benzamide hydrochloride (175 mg, 0.56 mmol), 2-(2-oxoimidazolidin-1-yl)ethyl methanesulfonate (294 mg, 1.41 mmol) and N,N-diisopropylethylamine (0.39 mL, 2.24 mmol) in acetonitrile (15 mL) was heated at 50° C. for 16 hours. The reaction was partitioned between ethyl acetate and water. The organic phase was separated and the aqueous phase extracted twice more with dichloromethane. The combined organic phases were dried over MgSO₄, filtered and concentrated under reduced pressure. The residue was purified by prep-HPLC to give 3-((1R,5S,9r)-9-methoxy-3-(2-(2-oxoimidazolidin-1-yl)ethyl)-3-azabicyclo[3.3.1]nonan-9-yl)benzamide (25 mg, 12% yield).

To a mixture of 3-((1R,5S,9r)-9-methoxy-3-(2-(2-oxoimidazolidin-1-yl)ethyl)-3-azabicyclo[3.3.1]nonan-9-yl)benzamide (25 mg, 0.06 mmol) in ethyl acetate (10 mL) was added 2 M hydrochloric acid in diethyl ether (0.05 mL, 0.10 mmol). The mixture was stirred for 5 minutes and then concentrated under reduced pressure and the residue freeze dried from water to give 3-((1R,5S,9r)-9-methoxy-3-(2-(2-oxoimidazolidin-1-yl)ethyl)-3-azabicyclo[3.3.1]nonan-9-yl)benzamide hydrochloride (25 mg, 93% yield); [M+H]+ 387.14; ¹H NMR (300 MHz, D₂O): 7.79 (s, 1H), 7.73 (d, 1H), 7.64 (d, 1H), 7.51 (t, 1H), 3.75 (d, 2H), 3.59-3.44 (m, 6H), 3.40-3.25 (m, 4H), 2.93 (s, 2H), 2.74 (s, 3H), 1.86-1.69 (m, 4H), 1.56-1.34 (m, 2H).

Compound 29

3-((1R,5S,9r)-3-butyl-9-methoxy-3-azabicyclo[3.3.1]nonan-9-yl)benzamide Hydrochloride

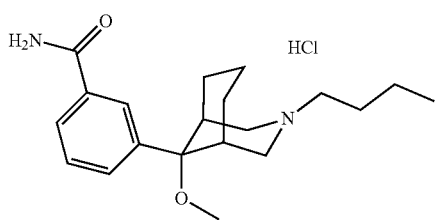 [SMILES: CCCCN1CC2CCCC(C1)C2(OC)c1cccc(C(N)=O)c1 ; Cl]

[M+H]⁺ 331.18; ¹H NMR (300 MHz, D₂O): 7.73 (s, 1H), 7.67 (d, 1H), 7.58 (d, 1H), 7.45 (t, 1H), 3.52 (d, 2H), 3.43 (d, 2H), 3.04-2.94 (m, 2H), 2.86 (br s, 2H), 2.67 (s, 3H), 1.83-1.31 (m, 8H), 1.21 (sextet. 2H), 0.77 (t, 3H).

Compound 71

5-((1R,5S,9r)-9-methoxy-3-(tetrahydro-2H-pyran-4-yl)-3-azabicyclo[3.3.1]nonan-9-yl)thiophene-2-carboxamide Hydrochloride

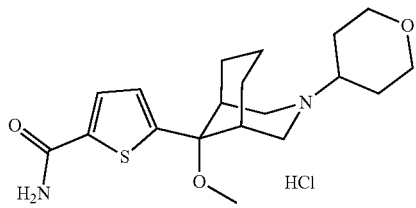 [SMILES: COC1(c2ccc(C(N)=O)s2)C2CCCC1CN(C1CCOCC1)C2 ; Cl]

[M+H]⁺ 365.15; ¹H NMR (300 MHz, D₂O): 7.51 (d, 1H), 7.15 (d, 1H), 3.96 (dd, 2H), 3.48 (br s, 4H), 3.36-3.29 (m, 3H), 2.82 (s, 3H), 2.69 (br s, 2H), 2.01 (d, 2H), 1.89-1.69 (m, 6H), 1.60-1.42 (m, 2H).

Compound 114

Synthesis of 5-((1R,5S,9r)-3-(azetidin-3-yl)-9-methoxy-3-azabicyclo[3.3.1]nonan-9-yl)thiophene-2-carboxamide Dihydrochloride

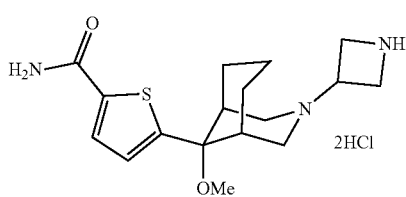 [SMILES: COC1(c2ccc(C(N)=O)s2)C2CCCC1CN(C1CNC1)C2]

Tert-butyl 3-((1R,5S,9r)-9-(5-carbamoylthiophen-2-yl)-9-methoxy-3-azabicyclo[3.3.1]nonan-3-yl)azetidine-1-carboxylate (51 mg, 0.12 mmol) was stirred in a solution of 2M HCl in diethyl ether (5 mL) at ambient temperature. After 1 hour the solvent was removed under reduced pressure to give 5-((1R,5S,9r)-3-(azetidin-3-yl)-9-methoxy-3-azabicyclo[3.3.1]nonan-9-yl)thiophene-2-carboxamide dihydrochloride (48 mg, 100% yield); [M-OMe]+304.09.

Synthesis of 5-((1R,5S,9r)-3-(1-acetylazetidin-3-yl)-9-methoxy-3-azabicyclo[3.3.1]nonan-9-yl)thiophene-2-carboxamide Hydrochloride

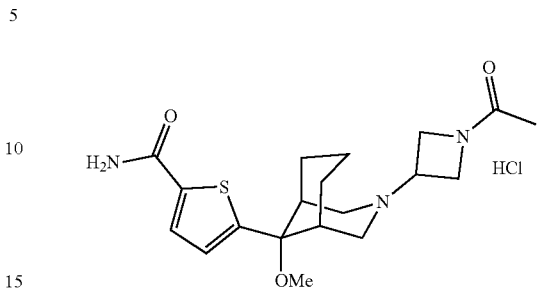

To a solution of 5-((1R,5S,9r)-3-(azetidin-3-yl)-9-methoxy-3-azabicyclo[3.3.1]nonan-9-yl)thiophene-2-carboxamide dihydrochloride (50 mg, 0.12 mmol) and Hünig's base (100 μL, 0.59 mmol) in dichloromethane (5 mL) was added acetyl chloride (20 μL, 0.28 mmol) at ambient temperature. After 1 hour the reaction was quenched with saturated aqueous sodium hydrogen carbonate solution and extracted with dichloromethane. The organic extract was dried over MgSO₄, filtered and concentrated under reduced pressure. The crude product was combined with a previous batch and purified by silica chromatography, eluted with 5% methanol in dichloromethane to give 5-((1R,5S,9r)-3-(1-acetylazetidin-3-yl)-9-methoxy-3-azabicyclo[3.3.1]nonan-9-yl)thiophene-2-carboxamide (40 mg, 44% yield).

To 5-((1R,5S,9r)-3-(1-acetylazetidin-3-yl)-9-methoxy-3-azabicyclo[3.3.1]nonan-9-yl)thiophene-2-carboxamide (40 mg, 0.10 mmol) in ethyl acetate (2 mL) was added 2M HCl in diethyl ether (60 μL, 0.11 mmol). After 10 minutes the solvent was removed under reduced pressure and the residue washed with diethyl ether, the liquors were decanted off and the solid dried under reduced pressure. The product was dissolved in water and freeze-dried to give 5-((1R,5S,9r)-3-(1-acetylazetidin-3-yl)-9-methoxy-3-azabicyclo[3.3.1]nonan-9-yl)thiophene-2-carboxamide hydrochloride (10 mg, 10% yield); [M+H]⁺ 378.06, ¹H NMR (400 MHz, D₂O) 7.53 (s, 1H), 7.17 (s, 1H), 4.72-4.63 (m, 5H), 4.35-4.18 (m, 2H), 4.15-3.95 (m, 2H), 2.83 (s, 3H), 2.65-2.49 (m, 2H), 1.77 (br s, 8H), 1.39-1.23 (m, 1H).

Compound 98

5-((1R,5S,9r)-9-methoxy-3-(2-(2-oxooxazolidin-3-yl)ethyl)-3-azabicyclo[3.3.1]nonan-9-yl)thiophene-2-carboxamide (S)-2-hydroxysuccinate

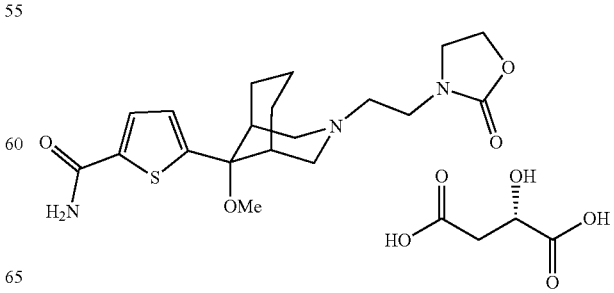

[M+H]+ 394.08. 1H NMR (300 MHz, MeOD): 7.60 (d, 1H), 7.17 (d, 1H), 4.42-4.31 (m, 4H), 3.66 (t, 2H), 3.50 (t, 2H), 3.12 (dd, 2H), 2.91 (s, 3H), 2.81-2.71 (m, 2H), 2.59 (dd, 1H), 2.50 (bs, 2H), 2.32-2.15 (m, 1H), 2.00-1.80 (m, 4H), 1.41-1.31 (m, 1H).

Compound 95

5-((1R,5S,9r)-9-methoxy-3-(2-(2-oxoimidazolidin-1-yl)ethyl)-3-azabicyclo[3.3.1]nonan-9-yl)thiophene-2-carboxamide (S)-2-hydroxysuccinate

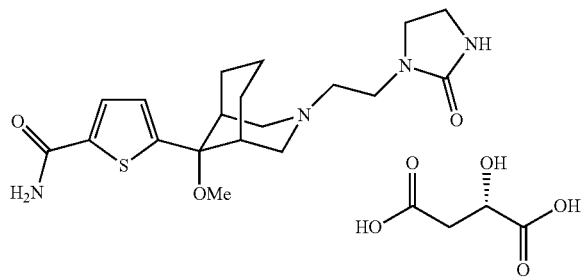

[M+H]+ 393.07. 1H NMR (300 MHz, D2O): 7.92 (bs, 1H), 7.59 (d, 1H), 7.35 (bs, 1H), 7.14 (d, 1H), 6.20 (bs, 1H), 4.19 (dd, 1H), 3.36-3.25 (m, 2H), 3.21-3.12 (m, 4H), 2.86-2.66 (m, 7H), 2.58 (dd, 1H), 2.48-2.28 (m, 6H), 1.75-1.65 (m, 4H), 1.22-1.10 (m, 1H).

Compound 97

5-((1R,5S,9r)-3-(2-(1,1-dioxidoisothiazolidin-2-yl)ethyl)-9-methoxy-3-azabicyclo[3.3.1]nonan-9-yl)thiophene-2-carboxamide (S)-2-hydroxysuccinate

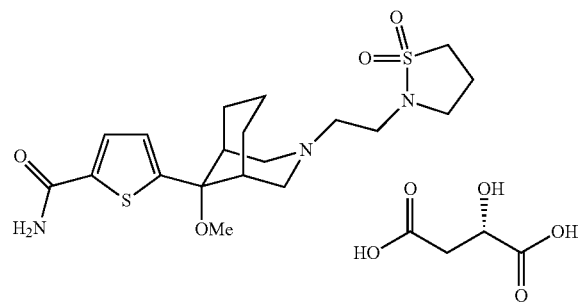 [SMILES: COC1(c2ccc(C(N)=O)s2)C2CCCC1CN(CCN1CCCS1(=O)=O)C2 ; O=C(O)C[C@H](O)C(=O)O]

[M+H]+ 427.98. 1H NMR (300 MHz, MeOD): 7.61 (d, 1H), 7.20 (d, 1H), 4.41-4.31 (m, 2H), 3.40-3.15 (m, 8H), 3.01-2.89 (m, 5H), 2.79 (dd, 1H), 2.65-2.55 (m, 3H), 2.40-2.30 (m, 2H), 2.00-1.87 (m, 4H), 1.50-1.40 (m, 1H), 1.35-1.25 (m, 2H).

Compound 101

5-((1R,5S,9r)-3-cyclohexyl-9-methoxy-3-azabicyclo[3.3.1]nonan-9-yl)thiophene-2-carboxamide Hydrochloride

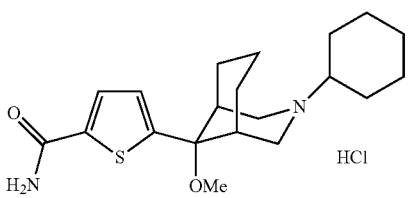 [SMILES: COC1(c2ccc(C(N)=O)s2)C2CCCC1CN(C1CCCCC1)C2 ; Cl]

[M+H]+ 363.2. 1H NMR (300 MHz, d6-DMSO): 8.23 (s, 1H), 8.00 (s, 1H), 7.65 (d, 1H), 7.44 (s, 1H), 7.26 (d, 1H), 3.56-3.33 (m, 5H), 3.09-2.94 (m, 1H), 2.82 (s, 3H), 2.65 (s, 1H), 2.18-1.91 (m, 3H), 1.86-1.62 (m, 6H), 1.16-1.45 (m, 3H), 1.37-1.03 (m, 4H).

Compound 112

Synthesis of (1R,5S,9r)-3-(bicyclo[1.1.1]pentan-1-yl)-9-(5-bromothiophen-2-yl)-3-azabicyclo[3.3.1]nonan-9-ol and (1R,5S,9s)-3-(bicyclo[1.1.1]pentan-1-yl)-9-(5-bromothiophen-2-yl)-3-azabicyclo[3.3.1]nonan-9-ol

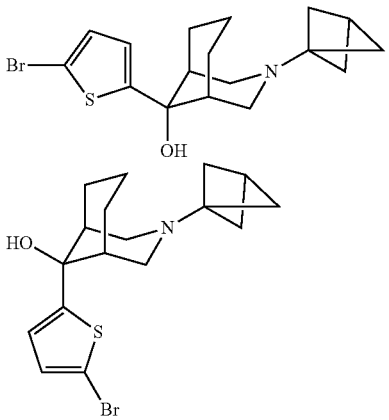

A solution of (1R,5S)-3-(bicyclo[1.1.1]pentan-1-yl)-3-azabicyclo[3.3.1]nonan-9-one (98 mg, 0.47 mmol), 2,5-dibromothiophene (150 mg, 0.62 mmol) in tetrahydrofuran (4 mL) was cooled to −78° C. under argon. Then n-butyl lithium (0.64 mL, 2.5 M solution in hexane, 1.60 mmol) was added dropwise and reaction stirred at −78° C. for 10 minutes, before warming slowly to 0° C. The reaction was quenched into ice/water and stirred for a further 15 minutes before the reaction was extracted with ethyl acetate (×3). The organics were combined, washed with brine, dried over MgSO4, filtered and concentrated under reduced pressure. The residue was purified by silica column chromatography, eluting with 6:1 heptane:ethyl acetate to give (1R,5S,9r)-3-(bicyclo[1.1.1]pentan-1-yl)-9-(5-bromothiophen-2-yl)-3-azabicyclo[3.3.1]nonan-9-ol and (1R,5S,9s)-3-(bicyclo[1.1.1]pentan-1-yl)-9-(5-bromothiophen-2-yl)-3-azabicyclo[3.3.1]nonan-9-ol (100 mg, 56% yield); [M+H]+ 368.05, 370.04.

Synthesis of (1R,5S,9r)-3-(bicyclo[1.1.1]pentan-1-yl)-9-(5-bromothiophen-2-yl)-9-methoxy-3-azabicyclo[3.3.1]nonane

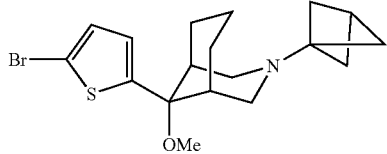 [SMILES: COC1(c2ccc(Br)s2)C2CCCC1CN(C13CC(C1)C3)C2]

To a solution of (1R,5S,9r)-3-(bicyclo[1.1.1]pentan-1-yl)-9-(5-bromothiophen-2-yl)-3-azabicyclo[3.3.1]nonan-9-ol and (1R,5S,9s)-3-(bicyclo[1.1.1]pentan-1-yl)-9-(5-bromothiophen-2-yl)-3-azabicyclo[3.3.1]nonan-9-ol (100 mg, 0.27 mmol) in methanol (2.6 mL) was added sulfuric acid (2.6 mL, 6 M in methanol 15.60 mmol) and the reaction was stirred at room temperature overnight. The reaction mixture was poured onto concentrated aqueous ammonia/ice and extracted with ethyl acetate (×3). The organics were combined, washed with brine, dried over MgSO$_4$, filtered and concentrated under reduced pressure. The residue was purified by silica column chromatography, eluting with 10:1 heptane:ethyl acetate to give (1R,5S,9r)-3-(bicyclo[1.1.1]pentan-1-yl)-9-(5-bromothiophen-2-yl)-9-methoxy-3-azabicyclo[3.3.1]nonane (69 mg, 67% yield); [M+H]$^+$ 382.08, 384.07.

Synthesis of 5-((1R,5S,9r)-3-(bicyclo[1.1.1]pentan-1-yl)-9-methoxy-3-azabicyclo[3.3.1]nonan-9-yl)thiophene-2-carbonitrile

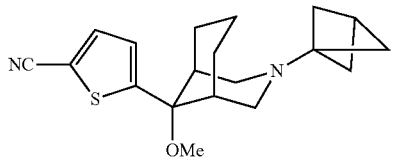

To a solution of (1R,5S,9r)-3-(bicyclo[1.1.1]pentan-1-yl)-9-(5-bromothiophen-2-yl)-9-methoxy-3-azabicyclo[3.3.1]nonane (87 mg, 0.23 mmol) in degassed N,N-dimethylformamide (3 mL) was added tetrakis(triphenylphosphine)palladium(0) (53 mg, 0.05 mmol). The resulting suspension was heated at 50° C., then zinc cyanide (53 mg, 0.46 mmol) was added. This suspension was heated at 120° C. for 4 hours. After cooling to room temperature, the reaction was quenched with saturated sodium hydrogen carbonate solution, filtered through celite, washing through with ethyl acetate. The phases were separated and the organic phase washed with brine, dried over MgSO$_4$, filtered and concentrated under reduced pressure. The resultant residue was purified by silica column chromatography, eluting with 10:1 heptane:ethyl acetate to afford 5-((1R,5S,9r)-3-(bicyclo[1.1.1]pentan-1-yl)-9-methoxy-3-azabicyclo[3.3.1]nonan-9-yl)thiophene-2-carbonitrile (40 mg, 54% yield); [M+H]$^+$ 329.16.

Synthesis of 5-((1R,5S,9r)-3-(bicyclo[1.1.1]pentan-1-yl)-9-methoxy-3-azabicyclo[3.3.1]nonan-9-yl)thiophene-2-carboxamide Hydrochloride

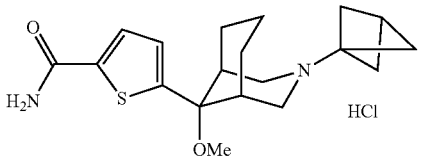 [SMILES: COC1(c2ccc(C(N)=O)s2)C2CCCC1CN(C13CC(C1)C3)C2 ; Cl]

To a solution of 5-((1R,5S,9r)-3-(bicyclo[1.1.1]pentan-1-yl)-9-methoxy-3-azabicyclo[3.3.1]nonan-9-yl)thiophene-2-carbonitrile (40 mg, 0.12 mmol) in tert-butanol (3 mL) was added potassium hydroxide (70 mg, 1.24 mmol). The mixture was heated at reflux for 1.5 hours, then cooled to room temperature and diluted in water. The mixture was extracted with ethyl acetate (×3), the organics combined and washed with brine, dried over MgSO$_4$, filtered and concentrated under reduced pressure. The resultant residue was purified by reverse phase chromatography (C18) to afford 5-((1R,5S,9r)-3-(bicyclo[1.1.1]pentan-1-yl)-9-methoxy-3-azabicyclo[3.3.1]nonan-9-yl)thiophene-2-carboxamide (25 mg, 33% yield).

To a solution of 5-((1R,5S,9r)-3-(bicyclo[1.1.1]pentan-1-yl)-9-methoxy-3-azabicyclo[3.3.1]nonan-9-yl)thiophene-2-carboxamide (22 mg, 0.06 mmol) in diethyl ether (10 mL) was added 2M HCl in diethyl ether (50 µl, 0.10 mmol). The resulting suspension was stirred at room temperature for 15 minutes, before decanting off the solvent and drying the precipitate under vacuum. The solid was dissolved in water and freeze dried overnight to afford 5-((1R,5S,9r)-3-(bicyclo[1.1.1]pentan-1-yl)-9-methoxy-3-azabicyclo[3.3.1]nonan-9-yl)thiophene-2-carboxamide hydrochloride (13 mg, 54% yield); [M+H]$^+$ 347.08. $^1$H NMR (300 MHz, de-DMSO): 10.05 (br s, 1H), 8.04 (br s, 1H), 7.60-7.68 (m, 1H), 7.44 (br s, 1H), 7.15-7.28 (m, 1H), 3.25-3.42 (m, 4H), 2.66-2.81 (m, 6H), 2.09-2.35 (m, 5H), 1.67-1.77 (m, 4H), 1.16-1.31 (m, 2H), 0.75-0.85 (m, 1H).

Compound 21

3-((1R,5S,9r)-3-benzyl-9-methoxy-3-azabicyclo[3.3.1]nonan-9-yl)benzamide Hydrochloride

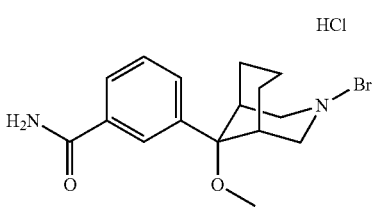 [SMILES: Cl ; COC1(c2cccc(C(N)=O)c2)C2CCCC1CN(Br)C2]

[M+H]$^+$ 365.38. $^1$H NMR (300 MHz, D$_2$O) 7.66 (2H, m), 7.54 (1H, m), 7.40 (6H, m), 4.25 (2H, s), 3.55 (2H, d), 3.40 (2H, d), 2.84 (2H, s), 2.55 (3H, s), 1.77-1.24 (6H, m).

Compound 22

Synthesis of 3-((1R,5S,9r)-9-methoxy-3-azabicyclo[3.3.1]nonan-9-yl)benzamide

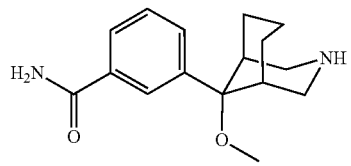 [SMILES: COC1(c2cccc(C(N)=O)c2)C2CCCC1CNC2]

To a solution of 3-((1R,5S,9r)-3-benzyl-9-methoxy-3-azabicyclo[3.3.1]nonan-9-yl)benzamide (0.66 g, 1.81 mmol) in methanol (20 mL) was added ammonium formate (1.14 g, 18.08 mmol) and palladium hydroxide on carbon (20% wt loading, 66 mg, 0.1 wt %). The reaction was heated to reflux for 1 hour. Reaction was incomplete so a further portion of ammonium formate (1.14 g, 18.08 mmol) was added and the reaction heated for a further 1.5 hours at reflux. The reaction was filtered through celite and concentrated under reduced pressure. The residue was taken up in dichloromethane and stirred for 1 hour. The resulting solid was collected by filtration and taken up in water. The mixture was basified with ammonia (aq) and extracted with 2-methyl tetrahydrofuran (×3). The organic phases were combined, washed with brine, dried (MgSO$_4$), filtered and concentrated to give 3-((1R,5S,9r)-9-methoxy-3-azabicyclo[3.3.1]nonan-9-yl)benzamide (190 mg, 38% yield); [M+H]$^+$ 275.28.

Synthesis of 3-((1R,5S,9r)-3-(cyclopropylmethyl)-9-methoxy-3-azabicyclo[3.3.1]nonan-9-yl)benzamide Hydrochloride

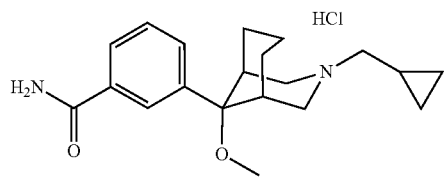 [SMILES: Cl ; COC1(c2cccc(C(N)=O)c2)C2CCCC1CN(CC1CC1)C2]

To a solution of 3-((1R,5S,9r)-9-methoxy-3-azabicyclo[3.3.1]nonan-9-yl)benzamide (248 mg, 0.91 mmol) in dichloromethane (18 mL) was added cyclopropyl carboxaldehyde (0.14 mL, 1.81 mmol) followed by sodium triacetoxyborohydride (384 mg, 1.81 mmol). The reaction was stirred at room temperature for 3 hours. The reaction was quenched with aqueous saturated sodium hydrogen carbonate solution and extracted with dichloromethane (×3). The dichloromethane phases were combined, washed with brine, dried (MgSO$_4$), filtered and concentrated. The crude material was purified by prep HPLC to give 3-((1R,5S,9r)-3-(cyclopropylmethyl)-9-methoxy-3-azabicyclo[3.3.1]nonan-9-yl)benzamide (175 mg, 59% yield).

To a solution of 3-((1R,5S,9r)-3-(cyclopropylmethyl)-9-methoxy-3-azabicyclo[3.3.1]nonan-9-yl)benzamide (175 mg, 0.50 mmol) in ethyl acetate (6 mL) and dichloromethane (3 mL) was added 2M HCl in diethyl ether (0.27 mL, 0.55 mmol). The product precipitated from solution and the liquors were concentrated under reduced pressure. The product was dissolved in water and freeze dried to give 3-((1R,5S,9r)-3-(cyclopropylmethyl)-9-methoxy-3-azabicyclo[3.3.1]nonan-9-yl)benzamide hydrochloride (195 mg, 100% yield); [M+H]$^+$ 329.35. $^1$H NMR (300 MHz, D$_2$O) 7.75 (1H, s), 7.67 (1H, d), 7.59 (1H, d), 7.46 (1H, t), 3.62 (2H, d), 3.50 (2H, d), 2.96 (2H, d), 2.88 (2H, s), 2.68 (3H, s), 1.83-1.27 (6H, m), 1.05-0.92 (1H, m), 0.61 (2H, q), 0.28 (2H, q).

Compound 160

Synthesis of (1R,5S,9r)-3-benzyl-9-(3-iodophenyl)-9-ethoxy-3-azabicyclo[3.3.1]nonane

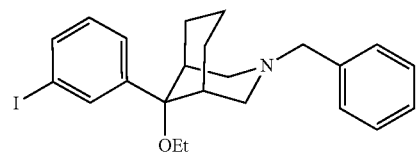 [SMILES: CCOC1(c2cccc(I)c2)C2CCCC1CN(Cc1ccccc1)C2]

To an ice cold solution of (1R,5S,9r)-3-benzyl-9-(3-iodophenyl)-3-azabicyclo[3.3.1]nonan-9-ol (3.99 g, 9.21 mmol) in dimethyl sulfoxide (20 mL) was added sodium hydride (60% dispersion in oil, 0.66 g, 16.58 mmol) portion wise. After 10 minutes, iodoethane (0.86 mL, 13.81 mmol) was added. The reaction mixture was allowed to warm to room temperature, and stirred for 1 hour. A further portion of sodium hydride (60% dispersion in oil, 110 mg, 2.75 mmol) was added, followed by iodomethane (0.17 mL, 2.75 mmol) and the reaction mixture was stirred for 1 hour. The reaction was quenched by pouring into ice/water and extracted with ethyl acetate (×3). The combined organic phases were washed with brine, dried over MgSO$_4$, filtered and concentrated under reduced pressure. The crude material was purified by silica chromatography, eluting with 5-7% ethyl acetate in heptane, to give (1R,5S,9r)-3-benzyl-9-(3-iodophenyl)-9-ethoxy-3-azabicyclo[3.3.1]nonane (3.24 g, 78% yield); [M+H]$^+$ 448.30.

Synthesis of 3-((1R,5S,9r)-3-benzyl-9-ethoxy-3-azabicyclo[3.3.1]nonan-9-yl)benzonitrile

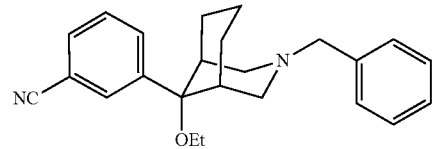 [SMILES: CCOC1(c2cccc(C#N)c2)C2CCCC1CN(Cc1ccccc1)C2]

To a solution of (1R,5S,9r)-3-benzyl-9-(3-iodophenyl)-9-ethoxy-3-azabicyclo[3.3.1]nonane (3.24 g, 7.20 mmol) in degassed N,N-dimethylformamide (35 mL) was added tris(dibenzylideneacetone)dipalladium (0) (0.66 g, 0.72 mmol) and 1,1'-bis(diphenylphosphino)ferrocene (0.80 g, 1.50 mmol). After heating to 50° C., zinc cyanide (0.51 g, 4.34 mmol) was added and the reaction mixture heated at 110° C. for 2 hours. The reaction mixture was cooled to room temperature, quenched with sodium hydrogen carbonate solution, diluted with ethyl acetate and filtered through a pad of Celite. The product was extracted with ethyl acetate (×3). The combined organic phases were washed with water (×2), brine (×1), dried over MgSO$_4$, filtered and concentrated under reduced pressure. The crude material was purified by silica chromatography, eluting with 0-20% ethyl acetate in heptane, to give 3-((1R,5S,9r)-3-benzyl-9-ethoxy-3-azabicyclo[3.3.1]nonan-9-yl)benzonitrile (1.89 g); [M+H]+ 347.36.

Synthesis of 3-((1R,5S,9r)-3-benzyl-9-ethoxy-3-azabicyclo[3.3.1]nonan-9-yl)benzamide

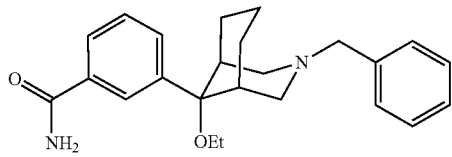 [SMILES: CCOC1(c2cccc(C(N)=O)c2)C2CCCC1CN(Cc1ccccc1)C2]

To 3-((1R,5S,9r)-3-benzyl-9-ethoxy-3-azabicyclo[3.3.1]nonan-9-yl)benzonitrile (1.89 g, 5.50 mmol) was added tert-butanol (55 mL), followed by potassium hydroxide (1.53 g, 27.3 mmol) and the reaction was heated at reflux for 2 hours. The mixture was cooled to room temperature, diluted with water and extracted with ethyl acetate (×3). The combined organic phases were washed with water (×2), then brine (×1), dried over MgSO₄, filtered and concentrated under reduced pressure. The crude material was purified by silica chromatography, eluting with 50-66% ethyl acetate in heptane, to give 3-((1R,5S,9r)-3-benzyl-9-ethoxy-3-azabicyclo[3.3.1]nonan-9-yl)benzamide (1.03 g, 39% yield over 2 steps); [M+H]+ 365.38.

Synthesis of 3-((1R,5S,9r)-9-ethoxy-3-azabicyclo[3.3.1]nonan-9-yl)benzamide

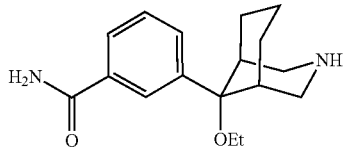 [SMILES: CCOC1(c2cccc(C(N)=O)c2)C2CCCC1CNC2]

A mixture of 3-((1R,5S,9r)-3-benzyl-9-ethoxy-3-azabicyclo[3.3.1]nonan-9-yl)benzamide (980 mg, 2.70 mmol), 20% palladium hydroxide on carbon (98 mg), and ammonium formate (1.70 g, 27.00 mmol) in methanol (25 mL) was heated at reflux for 30 minutes. Further ammonium formate (1.70 g, 27.00 mmol) and 20% palladium hydroxide on carbon (49 mg) were added and the mixture heated at reflux for 30 minutes. The mixture was cooled to room temperature and filtered through a pad of Celite washing thoroughly with methanol. The filtrate was concentrated under reduced pressure. The residue was taken up in dichloromethane and concentrated aqueous ammonia/water (1:1) and extracted with dichloromethane (×3). The combined organic phases were washed with brine, dried over MgSO₄, filtered and concentrated under reduced pressure. The residue was purified by reverse phase chromatography (C18) to give 3-((1R,5S,9r)-9-ethoxy-3-azabicyclo[3.3.1]nonan-9-yl)benzamide (273 mg, 37% yield); [M+H]+ 275.18.

In Vitro Characterization

Receptor Binding

The $K_i$ (binding affinity) for μ-receptor was determined with a previously described method using a competitive displacement assay (Neumeyer et al., J. Med. Chem., v. 46, p. 5162-5170, 2003). Membrane protein from CHO (Chinese Hamster Ovarian) cells that stably expressed one type of the cloned human opioid receptor were incubated with 12 different concentrations of the compound in the presence of 0.25 nM [3H]DAMGO, 0.2 nM [3H]naltrindole or 1 nM [3H]U69,593 in a final volume of 1 mL of 50 mM Tris-HCl, pH 7.5 at 25° C. Incubation times of 60 min were used for [3H]DAMGO and [3H]U69,593. Because of a slower association of [3H]naltrindole with the receptor, a 3 h incubation was used with this radioligand. Samples incubated with [3H]naltrindole also contained 10 mM MgCl2 and 0.5 mM phenylmethylsulfonyl fluoride. Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. For [3H] naltrindole and [3H]U69,593 binding, the filters were soaked in 0.1% polyethylenimine for at least 60 min before use. IC50 values will be calculated by least squares fit to a logarithm-probit analysis. Ki values of unlabelled compounds were calculated from the equation Ki=(IC50)/1+S where S=(concentration of radioligand)/(Kd of radioligand) (Cheng and Prusoff, Biochemical Pharmacology, v. 22, p. 3099-3108, 1973). $K_i$ values (nM) for compounds of the invention are shown in Table 1. All $K_i$ values reported in Table 1 were measured using this assay, with the exception of those compounds specifically noted in the alternate receptor binding assay described below.

Alternate Receptor Binding Assay

The $K_i$ (binding affinity) for μ-receptor was determined with a previously described method using a competitive displacement assay (Neumeyer et al., J. Med. Chem., v. 46, p. 5162-5170, 2003). Membrane protein from CHO (Chinese Hamster Ovarian) cells that stably expressed one type of the cloned human opioid receptor were incubated with 10 different concentrations of the compound in the presence of 0.8 nM [3H]DAMGO, 1 nM [3H]naltrindole or 1 nM [3H]U69,593 in a final volume of 1 mL of 5 mM MgCl₂, 50 mM Tris-HCl, pH 7.5 at 25° C. Incubation times of 120 min were used for [3H]DAMGO and [3H]U69,593. Because of a slower association of [3H]naltrindole with the receptor, a 3 h incubation was used with this radioligand. Samples incubated with [3H]naltrindole also contained 10 mM MgCl₂ and 0.5 mM phenylmethylsulfonyl fluoride. Nonspecific binding was measured by inclusion of 10 μM naloxone. The binding was terminated by filtering the samples through glass fiber filters, pre-soaked in 0.1% polyethylenimine for at least 60 min, using a 96-well PerkinElmer® cell harvester. The filters were subsequently washed three times with 0.3 mL of cold 50 mM Tris-HCl, pH 7.5, and air dried. The dried filters were treated with MeltiLex® B solid scintillant and counted using the MicroBeta (PerkinElmer®). IC₅₀ values were calculated by least squares fit to a logarithm-probit analysis. K_i values of unlabelled compounds were calculated from the equation Ki=(IC50)/1+S where S=(concentration of radioligand)/(Kd of radioligand) (Cheng and Prusoff, Biochemical Pharmacology, v. 22, p. 3099-3108, 1973). $K_i$ values (nM) for compounds 12, 16, 19, 20, 149, 151, 152, 157, 160, 180, 182, 183, 187, 188, 195-200, 202, and 203 are shown in Table 1.

Functional Activity (GTPγS Binding)

The [35S]GTPγS assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed one type of the cloned human opioid receptor human were used in the experiments. In a final volume of 0.5 mL, 12 different concentrations of each test compound were incubated with 7.5 µg of CHO cell membranes that stably expressed the human p opioid receptor. The assay buffer consisted of 50 mM Tris-HCl, pH 7.4, 3 mM MgCl2, 0.2 mM EGTA, 3 µM GDP, and 100 mM NaCl. The final concentration of [35S]GTPγS was 0.080 nM. Nonspecific binding was measured by inclusion of 10 µM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean $EC_{50}$ values±S.E.M. $EC_{50}$ values (nM) for compounds of the invention are shown in Table 1. All $EC_{50}$ values reported in Table 1 were measured using this assay, with the exception of those compounds specifically noted in the alternate functional activity assay described below.

Alternate Functional Activity (GTPγS Binding) Assay

The [$^{35}$S]GTPγS assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed one type of the cloned human opioid receptor human were used in the experiments. The assay buffer consisted of 50 mM Tris-HCl, pH 7.4, 3 mM $MgCl_2$, 0.2 mM EGTA, 5 µM GDP, and 100 mM NaCl. CHO cell membranes stably expressing the human p opioid receptor were pre-incubated with scintillation proximity assay beads from PerkinElmer® (WGA PVT SPA) for 30 minutes, at 8 □g membrane and 350 □g beads in a volume of 0.1 mL per reaction. In a final volume of 0.2 mL, 11 different concentrations of each test compound were incubated with the membrane-SPA bead mixture and a final concentration of 0.020 nM [35S]GTPγS for 1.5 hours with gentle shaking. Reactions were then incubated for 5 hours. Data are the mean $EC_{50}$ values±S.E.M. $EC_{50}$ values (nM) for compounds 12, 16, 19, 20, 149, 151, 152, 157, 160, 161, 164-169, 172, 173, 180-197, and 199-207 are shown in Table 1.

In Vivo Characterization

CFA Assay

Introduction

Administration of Complete Freund's Adjuvant (CFA), containing *Mycobacterium tuberculosis*, to a single hind paw of a rat produces inflammatory pain which can be accessed by measuring the amount of weight placed on the ipsi-vs. contra-lateral hind paw. This assay was used to assess the antinociceptive effect of subcutaneously administered test articles.

Procedure

Male Sprague-Dawley rats (approximately 200 g at time of test) were used for all studies. Rats were housed 2/cage and are given food and water ad libitum.

The weight bearing apparatus used was an incapacitance analgesia meter (Stoelting). Animals were habituated to the weight bearing test apparatus for 2 days prior to the start of the experiment. Raw data were reported as left and right-foot weight bearing in grams. Two separate measurements of hind-paw weight bearing were taken at each time point. The percentage of left hind-paw weight bearing was calculated for each individual measure (left paw weight bearing, g/right paw weight bearing, g*100). The average percentage change in weight bearing was calculated for the replicate measures and was the value used in all data analysis. Graphs depicting percentage change in weight bearing vs. time were generated using GraphPad Prizm 6.0.

On Day 0, baseline weight bearing of the rats was measured. Following baseline testing, rats were administered CFA. Rats were given a single intra-plantar administration of 100 µL of 100% CFA (1.0 mg/ml Complete Freund's Adjuvant Sigma F5881) in the left rear hind-paw while under light isofluorane anesthesia. This process took no longer than 90 seconds. No treatment was administered to the right, rear, contra-lateral paw.

On Day 1 (24 hrs post CFA), rats were 1$^{st}$ tested in the weight bearing apparatus in order to measure CFA-induced changes in weight bearing. A robust decrease in left hind paw weight bearing was observed at this time point. Animals were then randomized to treatment group and injected with test compound or vehicle via subcutaneous injection. Following test compound administration, animals were retested in the weight bearing apparatus at the following time points: 15, 30, 60, 120 and 240 minutes following test compound administration. Depending upon the duration of action of the test article, weight bearing measurements were also taken at 360 and 480 minutes post test compound administration.

Maximal reversal of hind paw weight bearing in the CFA assay occurs when a dose of test article reverses weight bearing to 50±0.5% at any measured time point.

Table 2 reports the minimum dose at which maximal reversal (MEMD) was achieved following subcutaneous administration (unless indicated otherwise) of test compound.

TABLE 2

| Compound No. | MEMO SC CFA (mg/kg) |
| --- | --- |
| 43 | 0.1 |
| 22 | 0.1 |
| 27 | 0.01 |
| 23 | 0.1 |
| 46 | 1 |
| 70 | 1 |
| 56 | 3 |
| 65 | 0.1 |
| 79 | 0.3 |
| 108 | 0.3 |
| 61 | 0.3 |
| 138 | 0.3 |
| 133 | 1 |
| 128 | 1 |
| 143 | 1 |
| 63 | >1 |
| 123 | 1 |
| 126 | 0.1 |
| 136 | 0.3 |
| 127 | 0.1 |
| 122 | 0.3 |
| 60 | 0.3 |
| 140 | 0.1 |
| 155 | 1 |
| 153 | 1 |
| 158 | 0.1 |
| 48 | 0.1 |
| 104 | ≤0.1 (dosed orally) |
| 91 | 3 (dosed orally) |
| 96 | 1 |
| 176 | 0.1 |
| 161 | 0.3 |
| 160 | 0.1 |
| Buprenorphine | 0.1 |
| Fentanyl | 0.01 |
| Morphine | 3 |
| Nalbuphine | >10 |
| Oxycodone | 3 |

Arterial Blood Gas (ABG) Assay

Introduction

The arterial blood gas (ABG) test is a blood test that measures the amounts of certain gases (such as oxygen and carbon dioxide) dissolved in arterial blood. An ABG test measures the blood gas tension values of arterial oxygen tension ($pO_2$), arterial carbon dioxide tension ($pCO_2$), and acidity (pH). Increase in $pCO_2$ and/or decrease in $pO_2$ and pH is indicative of respiratory dysfunction and depression (e.g., hypoventilation, hypercapnia, or hypoxemia). Full opioid agonists such as morphine and fentanyl can produce respiratory depression in nonclinical species and in man.

Procedure

Male Sprague-Dawley rats (approximately 250 g at time of test) were used for all studies. Rats were surgically implanted with indwelling cannula into the carotid artery approximately 7 days prior to ABG tests. Rats were single housed following surgery and were given food and water ad libitum.

On the day of the ABG experiment animals were housed on wire mesh grids beginning 1-hour prior to baseline blood sampling and for the duration of the experiment to prevent pica behavior. The Vet Stat Blood Gas Analyzer (IDEXX, USA) was calibrated daily prior to use and vet stat respiratory/blood gas cartridges (IDEXX, USA) were used to measure $pCO_2$, $pO_2$ and pH of arterial blood samples. Prior to test article administration, the block on the arterial cannula was removed and the cannula flushed with 0.1 mL of 100 U/mL heparinized saline. Immediately prior to dosing, a 300 μL whole blood sample was withdrawn from the arterial cannula using a 1 mL lithium-heparin containing blood gas syringe (Portex pro-vent arterial blood sampling syringe, Smiths Medical, USA) fitted with a 23 gauge luer stub needle. 100 μL of this sample was used immediately for the T=0 blood gas measurement by removing the needle and inserting the syringe into the analysis cartridge. Blood gas analysis was performed within 5 minutes of blood sampling. Cannula were then flushed with 0.1 mL of 100 U/mL heparinized saline.

Following baseline (T=0) ABG measurement, animals were injected subcutaneously with test article in a final dose volume of 1-5 mL/kg. At T=15, 30, 60 and 120 minutes after test compound administration, ~300 μL of arterial blood was taken from the catheter using a new blood gas syringe and analyzed immediately for blood gas content. About 100 μL of this sample was used immediately for blood gas measurement and the remaining blood prepared for pharmacokinetic analysis. $pCO_2$, $pO_2$ and pH in each sample were analyzed using the vet stat blood gas analyzer and the acquired values were analyzed in Graphpad Prism 6.0 (USA). Cmax $pCO_2$ levels above 60 mmHg were considered indicative of clinically meaningful negative change in respiration.

Table 3 reports the maximum respiratory effect on $pCO_2$ within 2 hours of test compound administration. Test compounds were dosed at one or both of 10× and 100× dose multiples of the CFA MEMD dose as reported in Table 2. Compounds denoted with a "−" resulted in a maximum $pCO_2$ value of greater than 60 mmHg within 2 hours of administration. Compounds denoted with a "+" resulted in a maximum $pCO_2$ value of less than 60 mmHg within 2 hours of administration. NT=not tested.

TABLE 3

| Compound No. | <60 mmHg @ 10X CFA MEMD | <60 mmHg @ 100X CFA MEMD |
|---|---|---|
| 43 | + | + |
| 70 | + | + |
| 79 | + | − |
| 91 | NT | + (dosed at 10 mg/kg) |
| 108 | + | + |
| 61 | + | + |
| 133 | + | NT |
| 123 | + | NT |
| 127 | + | + |
| 122 | + | NT |
| 60 | + | + |
| 140 | + | NT |
| 158 | + | + |
| 22 | + | − |
| 27 | NT | + |
| 23 | + | + |
| 46 | + | NT |
| 126 | − | NT |
| 160 | + | + |
| Morphine | − | NT |
| Fentanyl | − | NT |
| Oxycodone | − | NT |

The invention claimed is:

1. A compound of Formula IV:

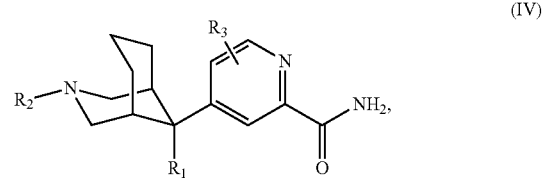

or a pharmaceutically acceptable salt thereof, wherein:
$R_1$ is $C_{1-2}$ alkoxy, wherein the $C_{1-2}$ alkoxy is optionally substituted with 1, 2, or 3 halo substituents;
$R_2$ is hydrogen, $C_{1-6}$ alkyl, $C_{3-10}$ cycloalkyl, 4- to 12-membered heterocycloalkyl, $C_{1-4}$ alkylene-$CF_3$, $C_{1-4}$ alkylene-($C_{3-10}$ cycloalkyl), $C_{1-4}$ alkylene-(4- to 12-membered heterocycloalkyl), $C_{1-4}$ alkylene-(5- to 14-membered heteroaryl), or ($C_{3-10}$ cycloalkylene)-($C_{6-14}$ aryl);
wherein each of the $C_{1-6}$ alkyl, $C_{3-10}$ cycloalkyl, 4- to 12-membered heterocycloalkyl, $C_{1-4}$ alkylene, $C_{3-10}$ cycloalkylene, $C_{6-14}$ aryl, and 5- to 14-membered heteroaryl of $R_2$ is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), and —S(=O)$_2$—($C_{1-4}$ alkyl); or
wherein the $C_{3-10}$ cycloalkyl, 5- to 14-membered heteroaryl, or 4- to 12-membered heterocycloalkyl of $R_2$ is optionally substituted with 1, 2, or 3 oxo moieties; and
$R_3$ is hydrogen, OH, halo, $C_{1-4}$ alkyl, or $C_{1-4}$ alkoxy.

2. The compound of claim 1, wherein $R_2$ is $C_{3-10}$ cycloalkyl or 4- to 12-membered heterocycloalkyl, wherein $C_{3-10}$ cycloalkyl, 4- to 12-membered heterocycloalkyl is unsubstituted or substituted with 1 or 2 substituents independently selected from the group consisting of —OH, halo, $C_{1-4}$ alkyl, $C_{1-4}$ alkoxy, —C(=O)—($C_{1-4}$ alkyl), and —S(=O)$_2$—($C_{1-4}$ alkyl).

3. The compound of claim 1, wherein $R_2$ is $C_{1-6}$ alkyl or $C_{1-4}$ alkylene-$CF_3$.

4. The compound of claim 3, wherein $R_2$ is $C_{1-6}$ alkyl.

5. The compound claim 1, wherein $R_1$ is unsubstituted $C_{1-2}$ alkoxy.
6. The compound of claim 1, wherein $R_1$ is —$OCH_3$.
7. The compound of claim 1, selected from the group consisting of:
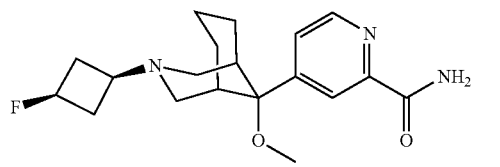
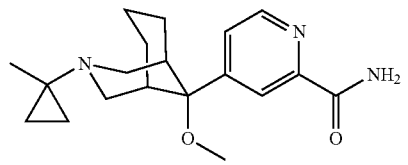
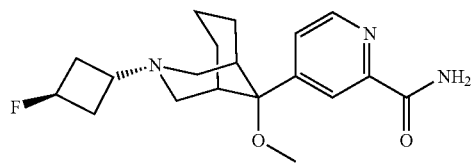
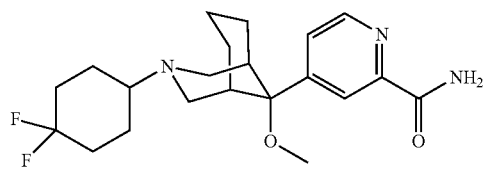
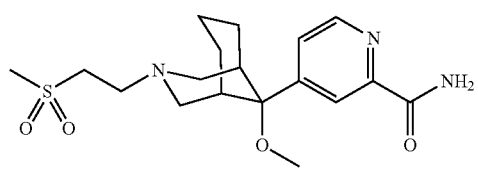
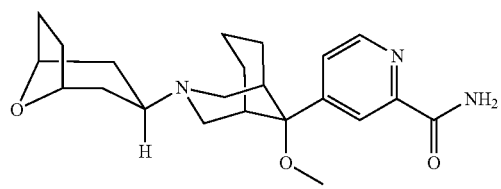
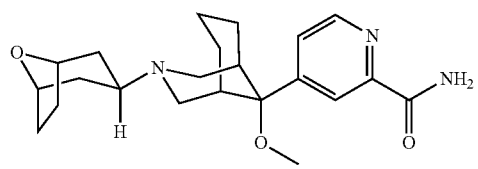
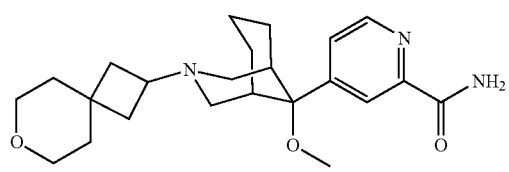
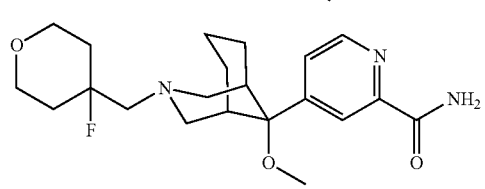
-continued
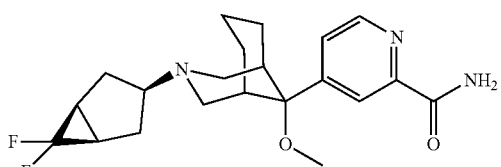
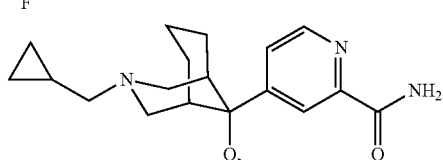
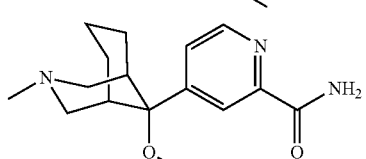
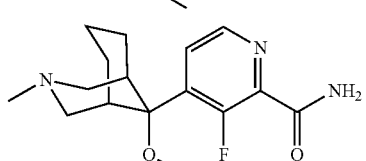
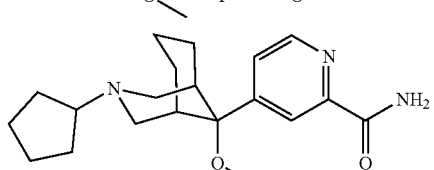
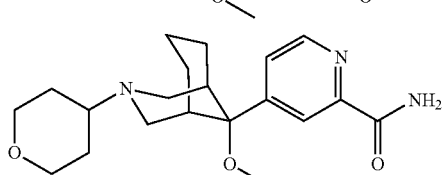
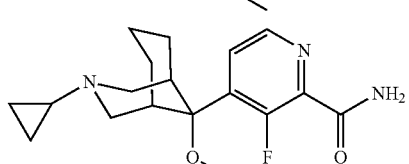
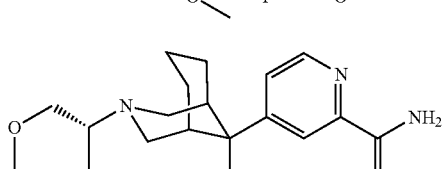
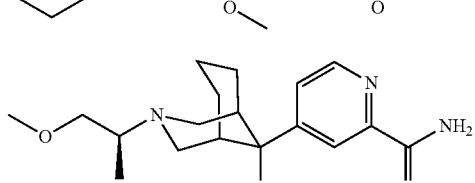
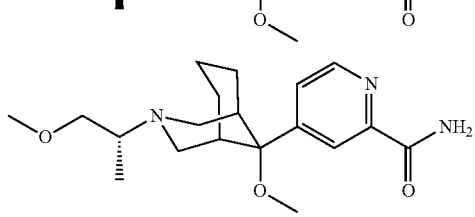

317
-continued
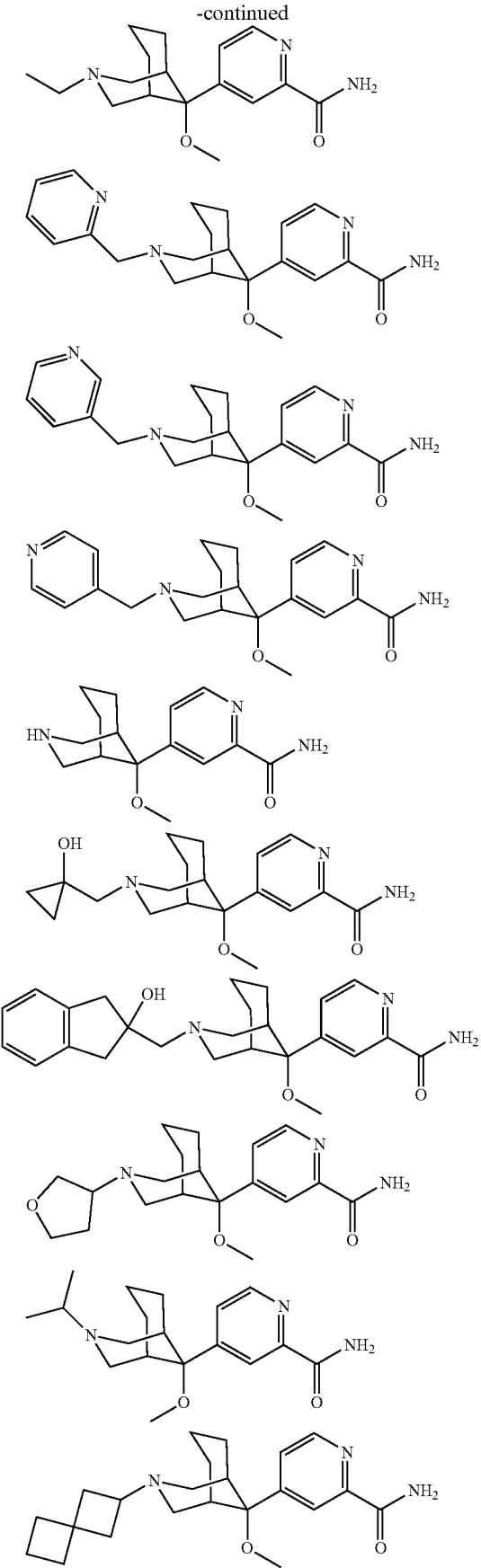
318
-continued
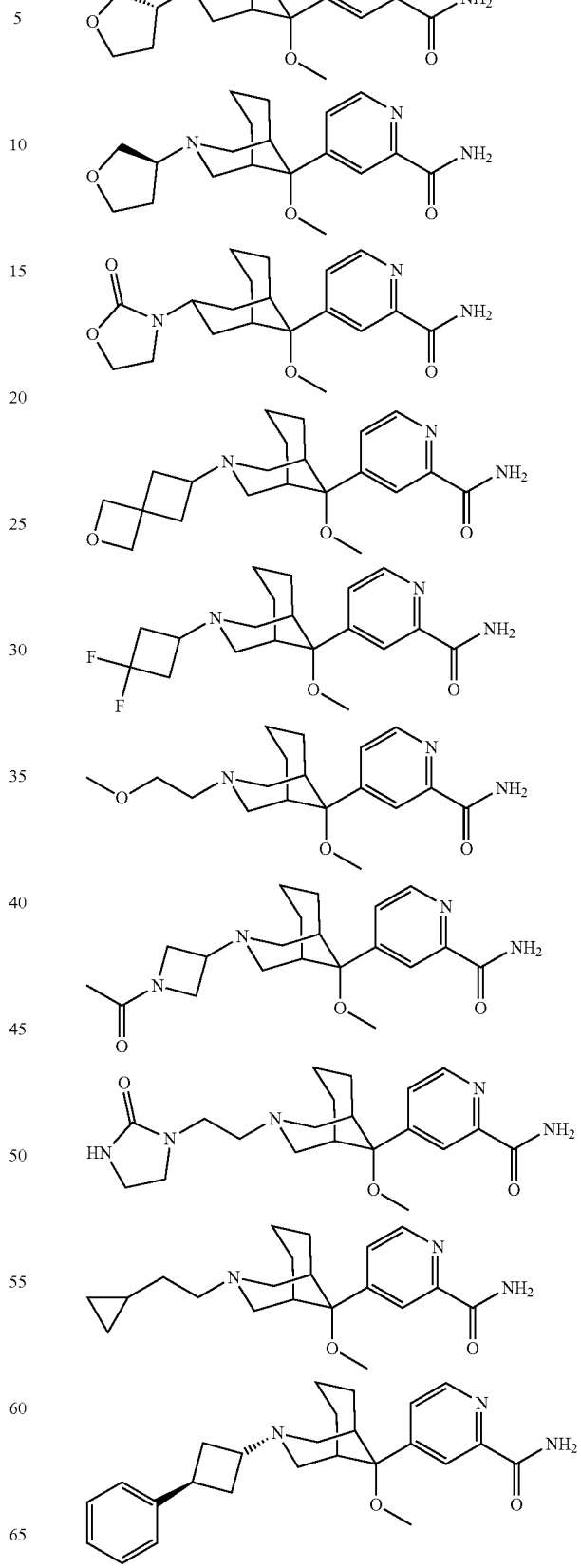

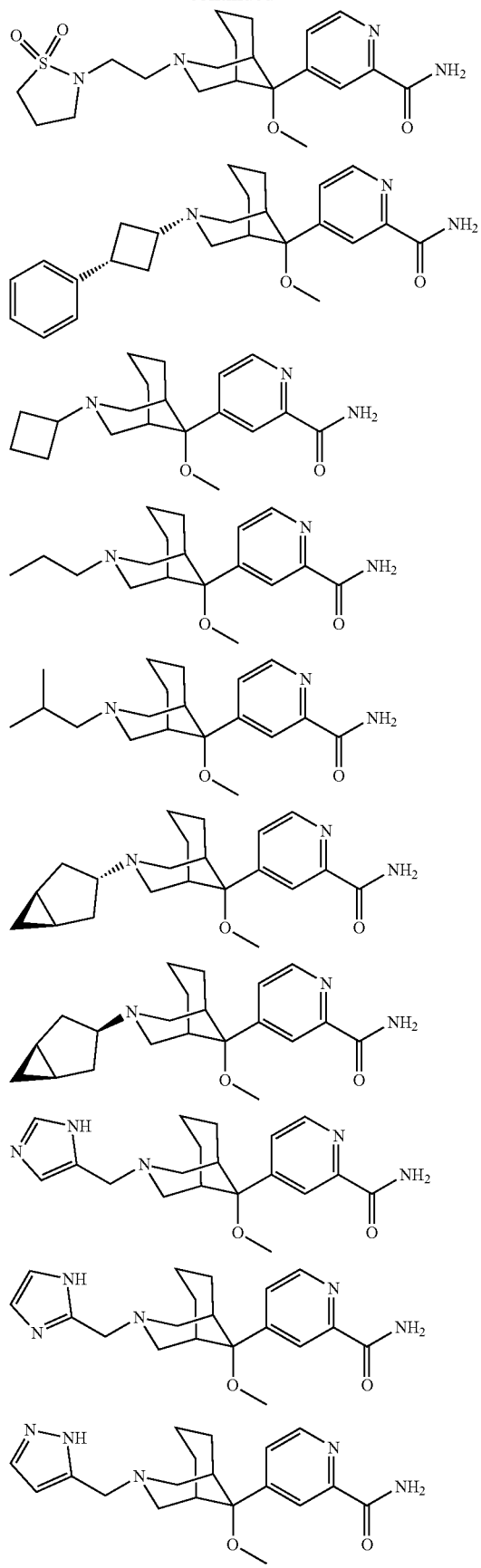
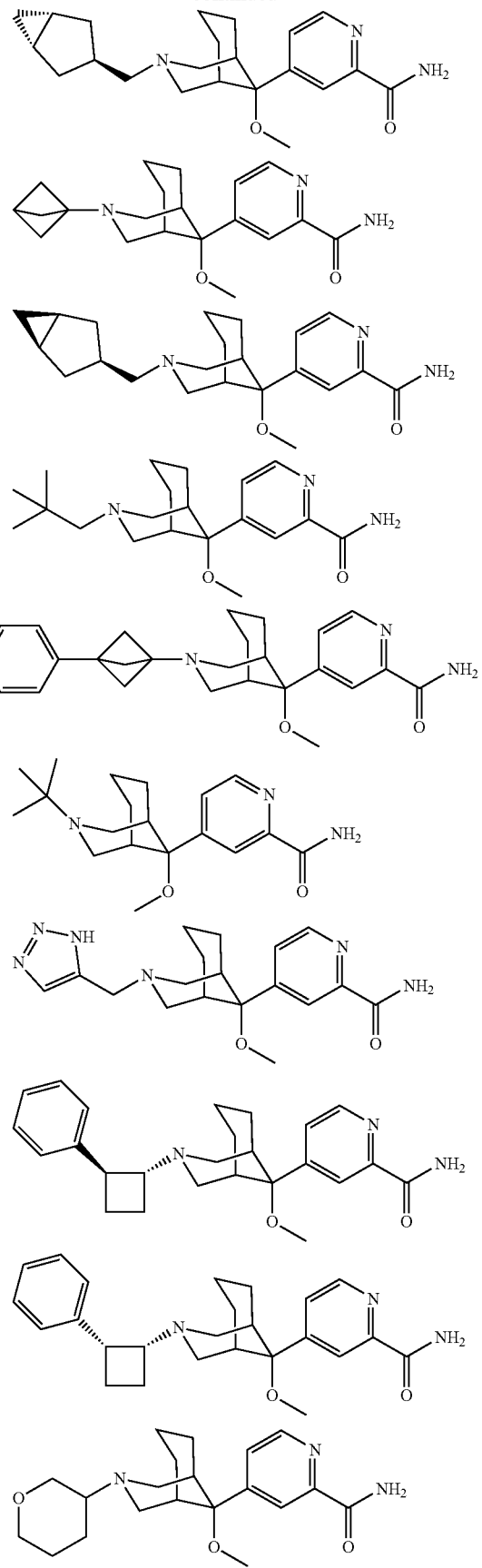

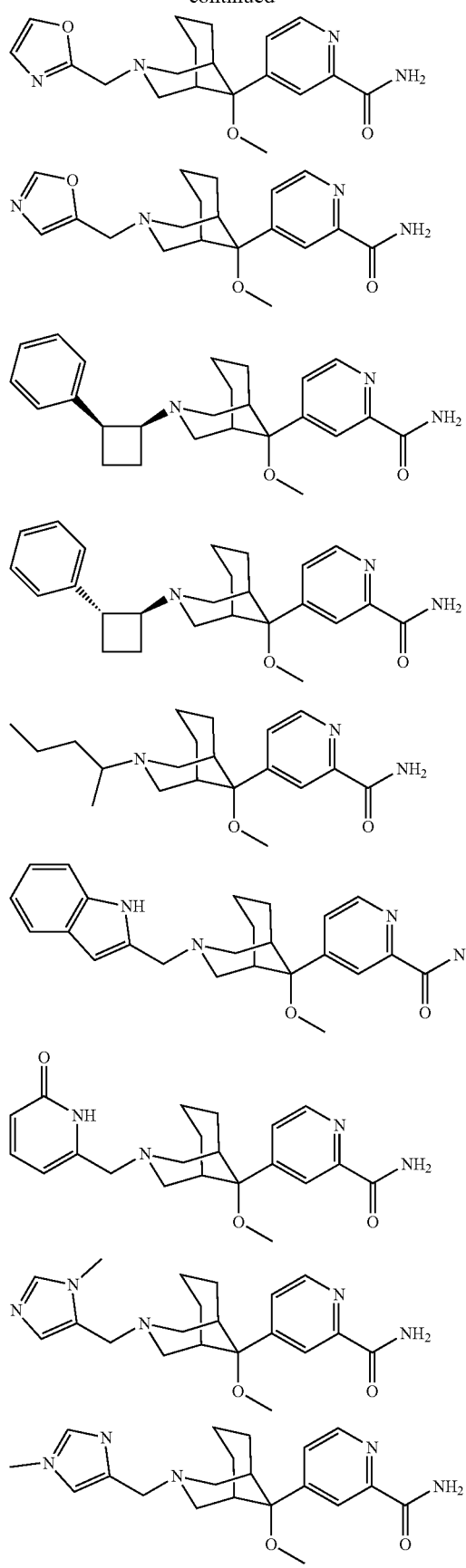
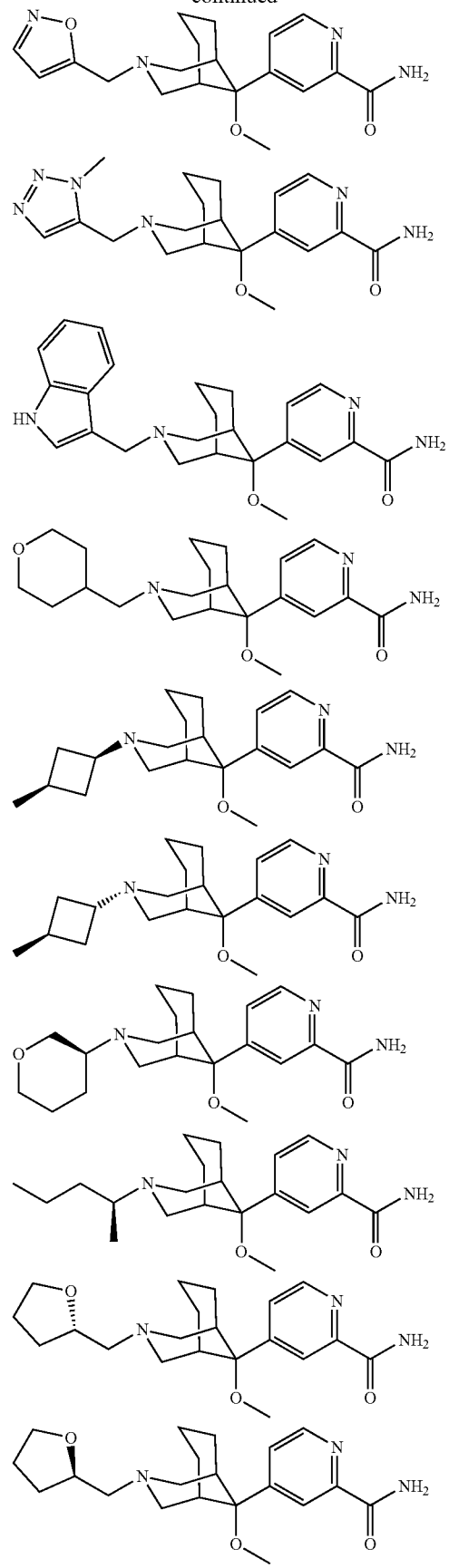

-continued
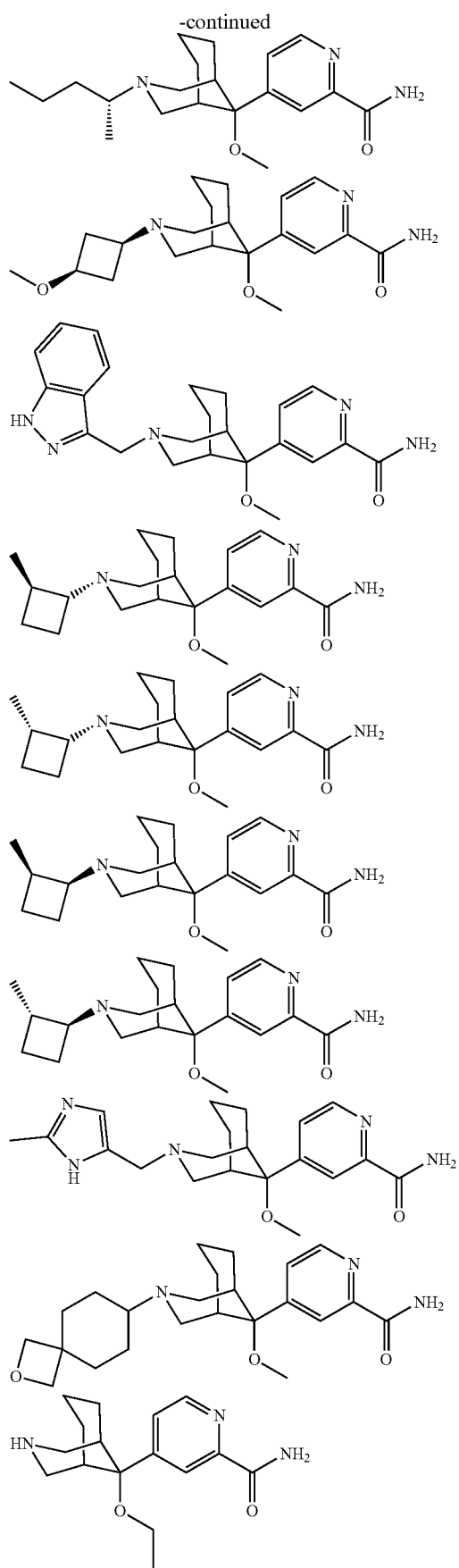
-continued
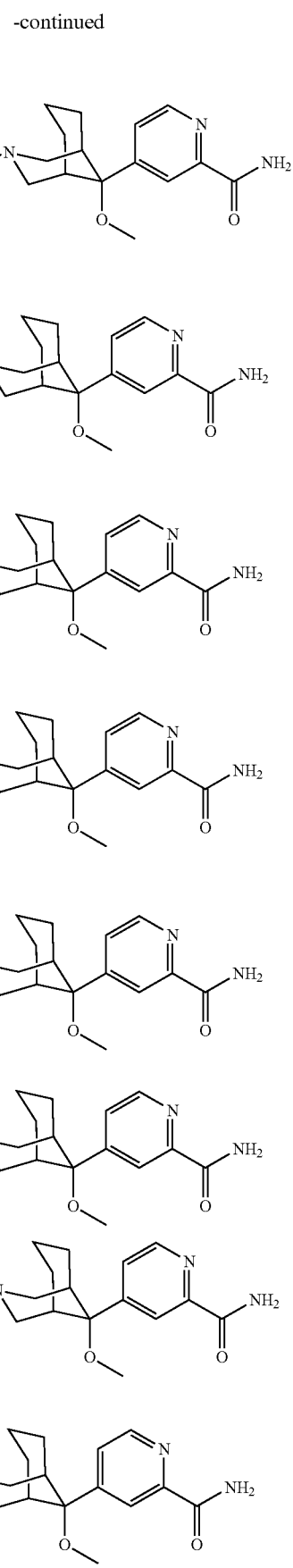

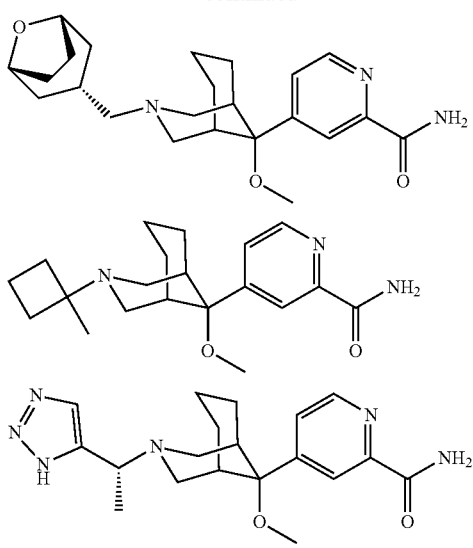
or a pharmaceutically acceptable salt thereof.
8. The compound of claim 7, selected from the group consisting of:
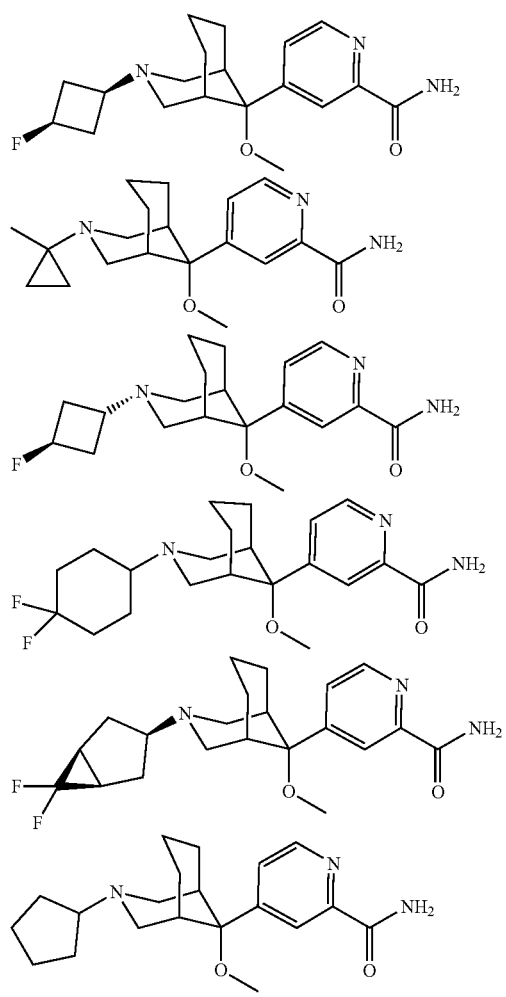
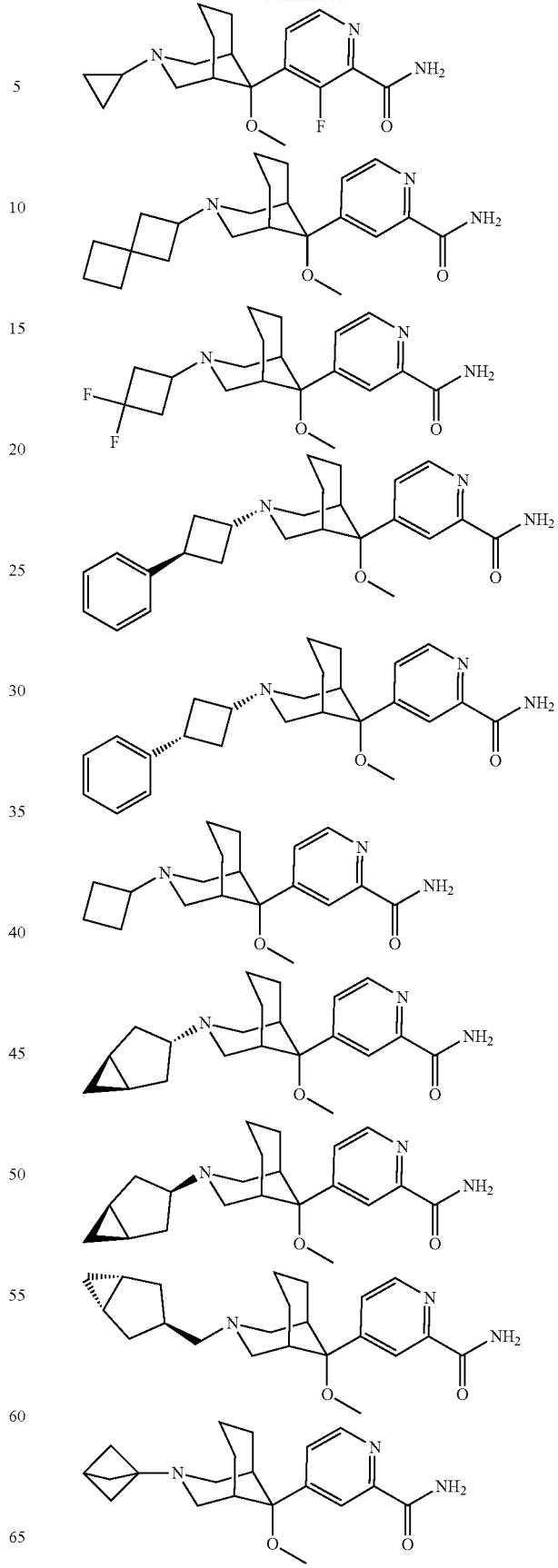

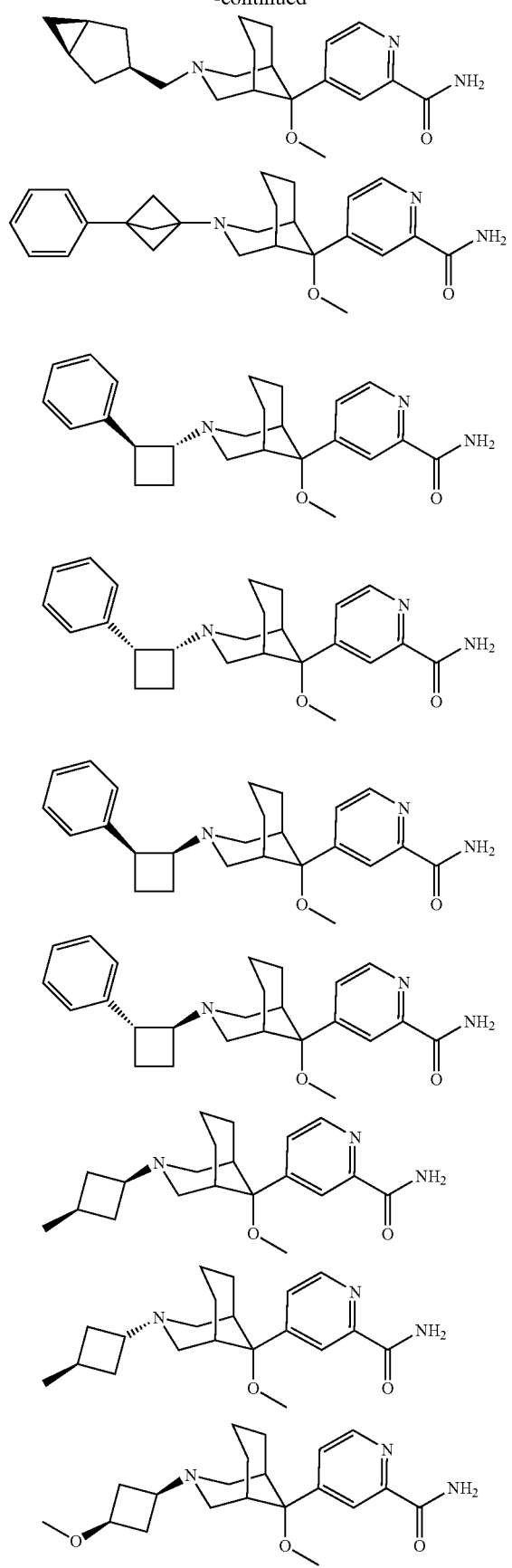
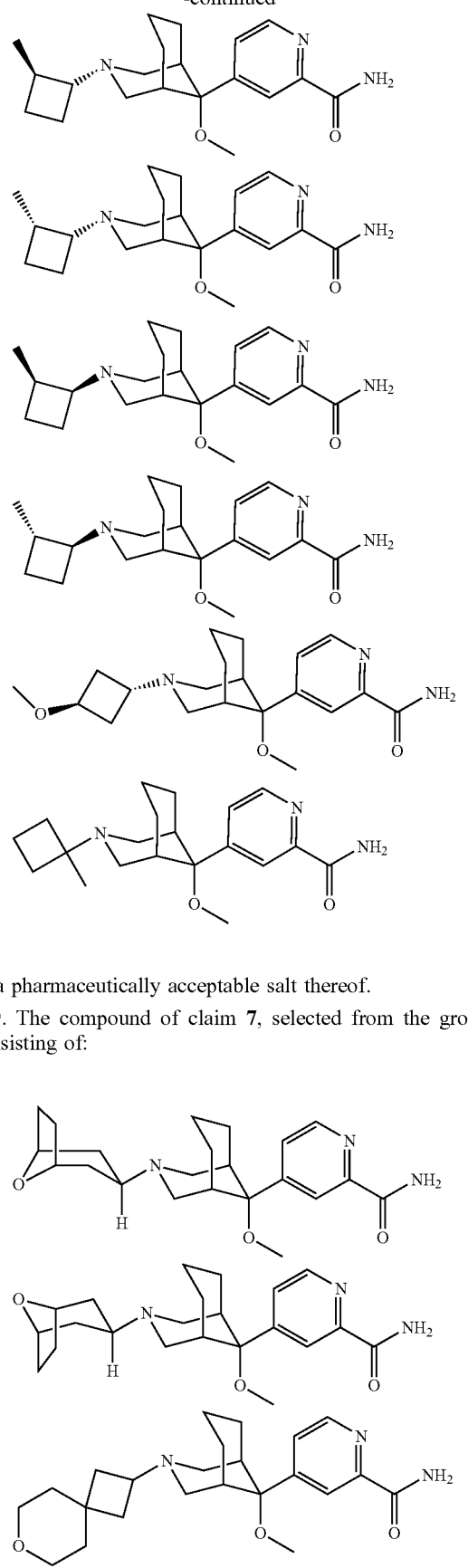
or a pharmaceutically acceptable salt thereof.
9. The compound of claim 7, selected from the group consisting of:
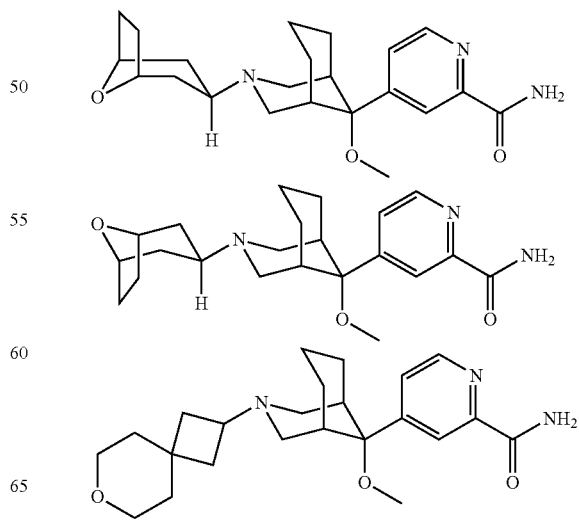

-continued
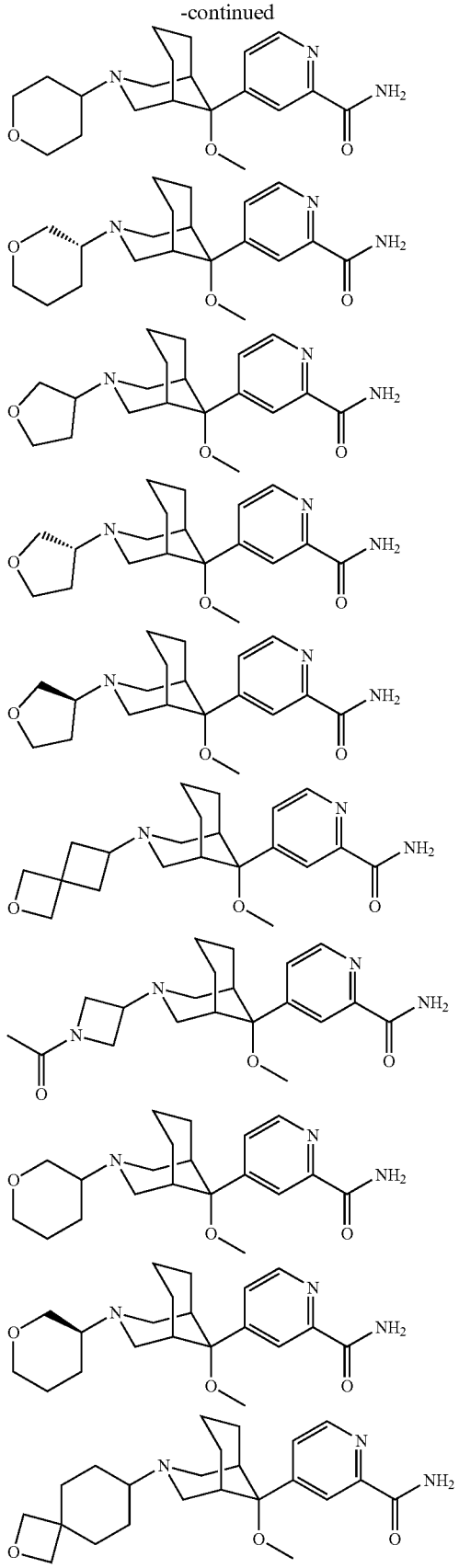
or a pharmaceutically acceptable salt thereof.
10. The compound of claim 7, selected from the group consisting of:
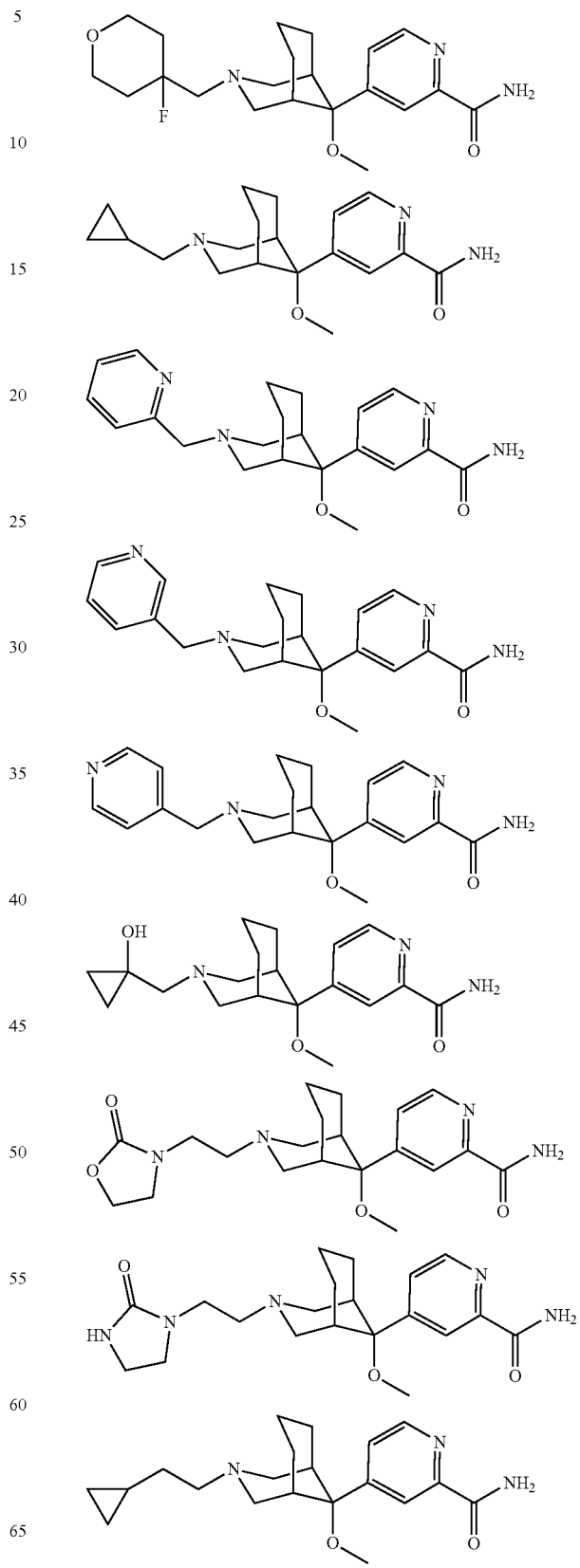

331
-continued
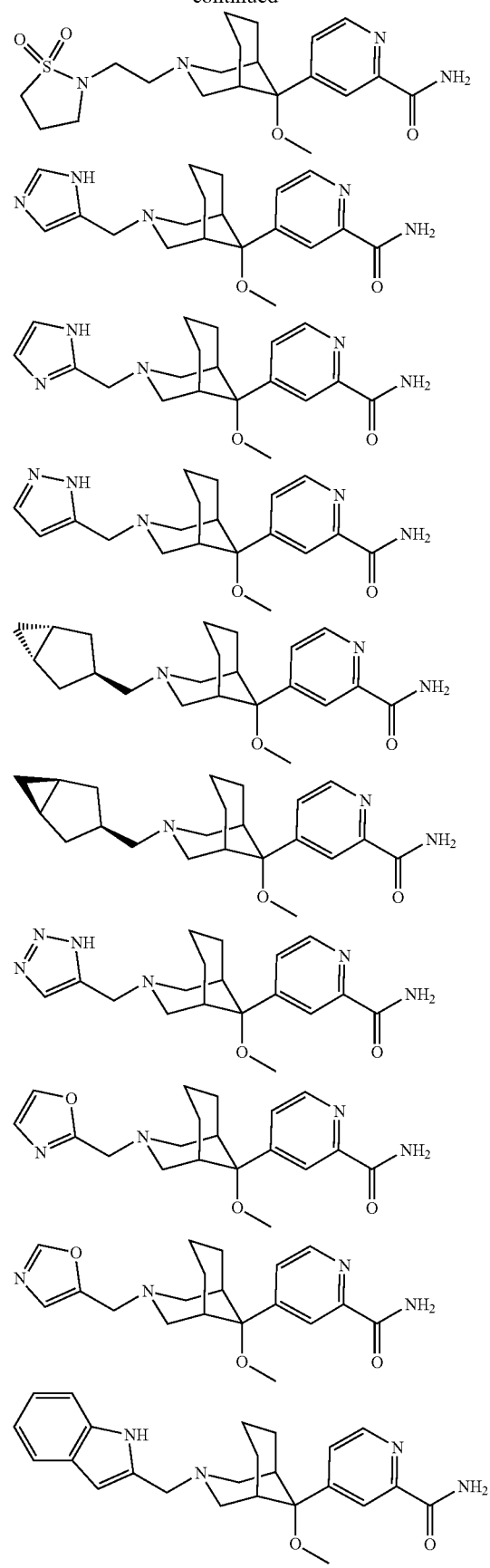
332
-continued
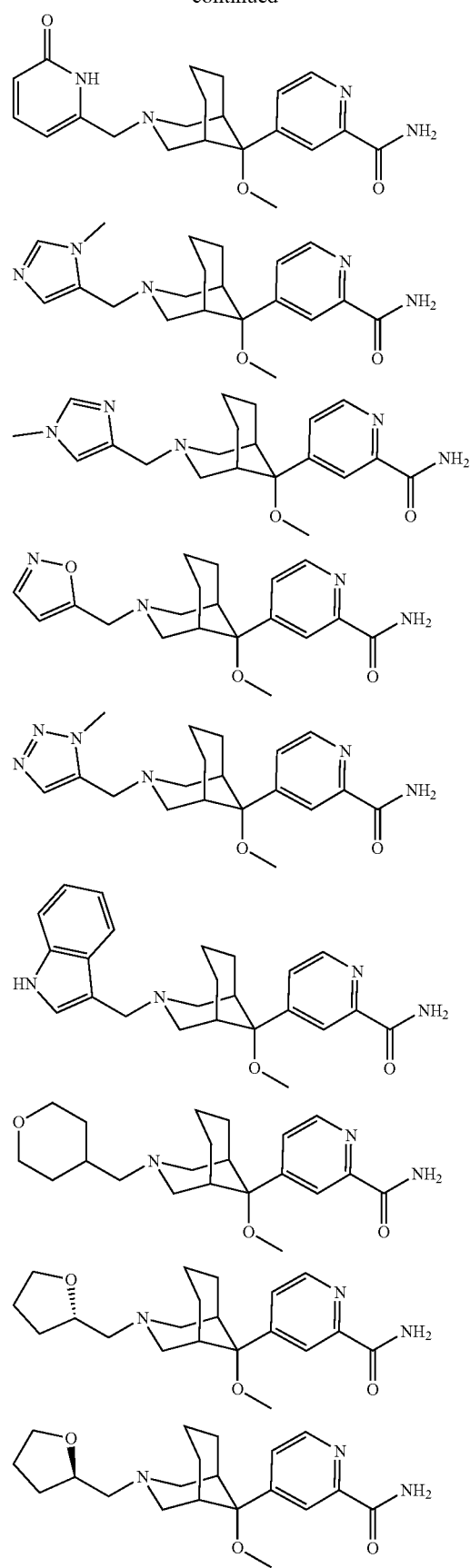

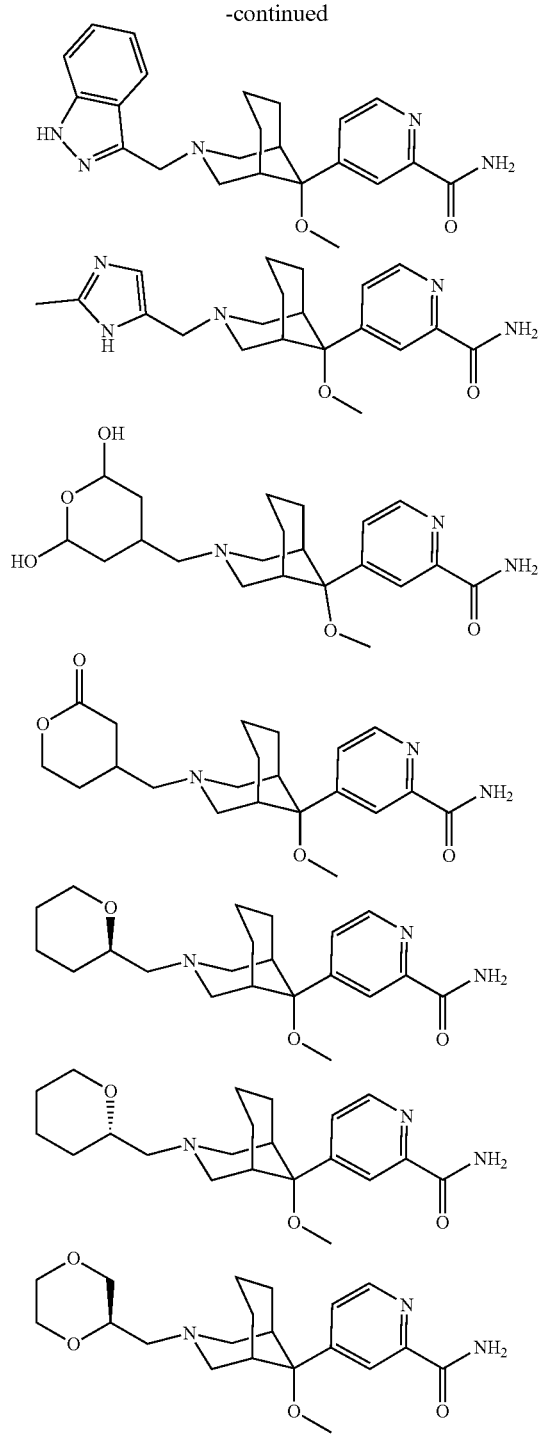

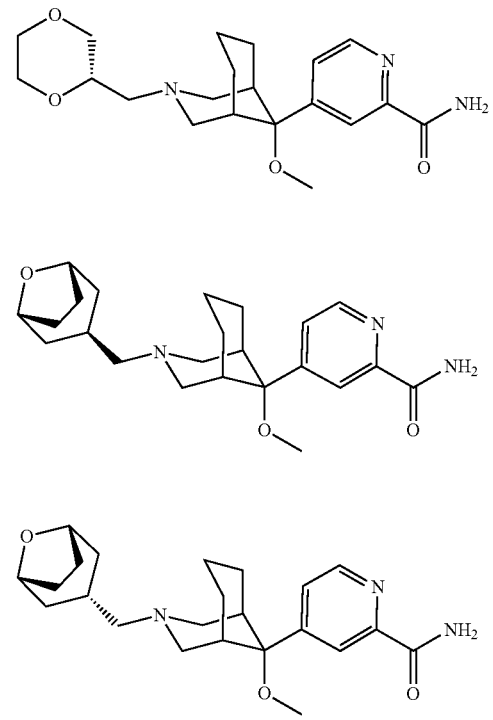

or a pharmaceutically acceptable salt thereof.

11. A pharmaceutical composition comprising the compound of claim 1 and a pharmaceutically acceptable carrier.

12. A method of treating pain in a subject in need thereof comprising administering to the subject the compound of claim 1.

13. The method of claim 12, wherein the pain is inflammatory pain, thermal pain, acute pain, chronic pain, traumatic pain, chemical pain, ischemic pain, centrally mediated pain, peripherally mediated pain, prickling pain, visceral pain, progressive disease pain, musculoskeletal pain and neuropathic pain.

14. The method of claim 12, wherein the pain is inflammatory pain, thermal pain, acute pain, chronic pain, musculoskeletal pain, and neuropathic pain.

15. The method of claim 12, wherein the pain is chronic pain.

16. The method of claim 12, wherein the pain is musculoskeletal pain.

\* \* \* \* \*